United States Patent
Stansfield et al.

(10) Patent No.: US 11,180,487 B2
(45) Date of Patent: Nov. 23, 2021

(54) SUBSTITUTED CYANOINDOLINE DERIVATIVES AS NIK INHIBITORS

(71) Applicant: Janssen Pharmaceutica NV, Beerse (BE)

(72) Inventors: Ian Stansfield, Issy-les Moulineaux (FR); Olivier Alexis Georges Querolle, Issy-les Moulineaux (FR); Virginie Sophie Poncelet, Issy-les Moulineaux (FR); Gerhard Max Gross, Beerse (BE); Edgar Jacoby, Beerse (BE); Lieven Meerpoel, Beerse (BE); Janusz Jozef Kulagowski, Harlow (GB); Calum Macleod, Harlow (GB); Samuel Edward Mann, Harlow (GB); Simon Richard Green, Harlow (GB); George Hynd, Harlow (GB)

(73) Assignee: Janssen Pharmaceutica NV, Beerse (BE)

(*) Notice: Subject to any disclaimer, the term of this patent is extended or adjusted under 35 U.S.C. 154(b) by 267 days.

(21) Appl. No.: 16/071,192

(22) PCT Filed: Jan. 20, 2017

(86) PCT No.: PCT/EP2017/051150
§ 371 (c)(1),
(2) Date: Jul. 19, 2018

(87) PCT Pub. No.: WO2017/125530
PCT Pub. Date: Jul. 27, 2017

(65) Prior Publication Data
US 2021/0087182 A1 Mar. 25, 2021

(30) Foreign Application Priority Data
Jan. 22, 2016 (EP) .................................... 16152416
Mar. 10, 2016 (EP) .................................... 16159651

(51) Int. Cl.
| | |
|---|---|
| *C07D 405/14* | (2006.01) |
| *C07D 403/10* | (2006.01) |
| *C07D 403/14* | (2006.01) |
| *C07D 413/14* | (2006.01) |
| *C07D 401/14* | (2006.01) |
| *C07F 9/535* | (2006.01) |
| *A61P 35/00* | (2006.01) |

(52) U.S. Cl.
CPC ............ *C07D 405/14* (2013.01); *A61P 35/00* (2018.01); *C07D 401/14* (2013.01); *C07D 403/10* (2013.01); *C07D 403/14* (2013.01); *C07D 413/14* (2013.01); *C07F 9/535* (2013.01)

(58) Field of Classification Search
CPC .. C07D 405/14; C07D 403/10; C07D 403/14; C07D 413/14; C07D 401/14; C07F 9/535; A61P 35/00
See application file for complete search history.

(56) References Cited

U.S. PATENT DOCUMENTS

2019/0119299 A1    4/2019    Stansfield et al.

FOREIGN PATENT DOCUMENTS

| JP | 2003511378 A | 3/2003 | |
|---|---|---|---|
| JP | 2014510794 A | 5/2014 | |
| WO | WO 2001/025220 A1 | 4/2001 | |
| WO | WO-0160816 A1 | 8/2001 | |
| WO | WO-0164643 A2 | 9/2001 | |
| WO | WO-02079197 A1 | 10/2002 | |
| WO | WO-02102313 A2 | 12/2002 | |
| WO | WO-03030909 A1 | 4/2003 | |
| WO | WO-2009158011 A1 | 12/2009 | |
| WO | WO-2009158571 A1 | 12/2009 | |
| WO | WO 2010/042337 * | 4/2010 | ............. A01N 43/54 |

(Continued)

OTHER PUBLICATIONS

Allen et al. NLRP12 suppresses colon inflammation and tumorigenesis through the negative regulation of noncanonical NF-kB signaling. Immunity. 36: 742-754 (2012).

Annuziata et al. Frequent engagement of the classical and alternative NF-kB pathways by diverse genetic abnormalities in multiple myeloma. Cancer Cell. 12: 115-130 (2007).

Aya et al. NF-κb-inducing kinase controls lymphocyte and osteoclast activities in inflammatory arthritis. J. Clin. Invest. 115: 1848-1854 (2005).

Bhattacharyya et al. Tumor necrosis factor-induced inflammation is increased but apoptosis is inhibited by common food additive carrageenan. J Biol. Chem. 285: 39511-39522 (2011).

(Continued)

*Primary Examiner* — Erich A Leeser

(57) ABSTRACT

The present invention relates to pharmaceutical agents of formula (I) useful for therapy and/or prophylaxis in a mammal, and in particular to inhibitors of NF-$_\kappa$B-inducing kinase (NIK—also known as MAP3K14) useful for treating diseases such as cancer, inflammatory disorders, metabolic disorders and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

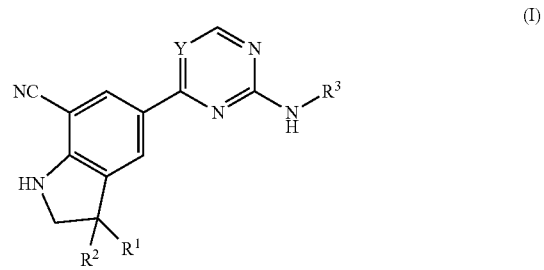

15 Claims, No Drawings

(56) References Cited

FOREIGN PATENT DOCUMENTS

| WO | WO-2010042337 A1 | 4/2010 |
|----|------------------|--------|
| WO | WO-2011022440 A2 | 2/2011 |
| WO | WO-2011153553 A2 | 12/2011 |
| WO | WO-2012016217 A1 | 2/2012 |
| WO | WO 2012/142329 A1 | 10/2012 |
| WO | WO-2014174021 A1 | 10/2014 |
| WO | WO-2015030847 A1 | 3/2015 |
| WO | WO-2015044267 A1 | 4/2015 |
| WO | WO-2015044269 A1 | 4/2015 |
| WO | WO-2015154039 A2 | 10/2015 |
| WO | WO-2015176135 A1 | 11/2015 |
| WO | WO-2016022645 A1 | 2/2016 |
| WO | WO 2016/049211 A1 | 3/2016 |
| WO | WO-2017114510 A1 | 7/2017 |
| WO | WO-2017125530 A1 | 7/2017 |
| WO | WO-2017125534 A1 | 7/2017 |
| WO | WO-2017161028 A1 | 9/2017 |
| WO | WO-2018002217 A1 | 1/2018 |
| WO | WO-2018002219 A1 | 1/2018 |

OTHER PUBLICATIONS

Bitar et al. Inflammation and apoptosis in aortic tissues of aged type II diabetes: Amelioration with α-lipoic acid through phosphatidylinositol 3-kinase/Akt-dependent mechanism. Life Sci. 86: 844-853 (2010).

Bushell et al., Genetic inactivation of TRAF3 in canine and human B-cell lymphoma. Blood. 125: 999-1005 (2015).

Choudhary et al. NF-B-Inducing Kinase (NIK) mediates skeletal muscle insulin resistance: blockade by adiponectin. Endocrinology. 152: 3622-3627 (2011).

Chung et al. NF-kB Inducing Kinase, NIK mediates cigarette smoke/ TNFa-induced histone acetylation and inflammation through differential activation of IKKs. PLoS ONE. 6(8): e23488. doi:10.1371/journal.pone.0023488 (2011).

Demchenko et al. Classical and/or alternative NF-κb pathway activation in multiple myeloma. Blood. 115: 3541-3552 (2010).

Gennaro et al. Remington's Pharmaceutical Sciences (18th ed., Mack Publishing Company, 1990, see especially Part 8 : Pharmaceutical preparations and their Manufacture (1990).

Hughes et al., 4-Aryl-5-cyano-2-aminopyrimidines as VEGF-R2 inhibitors: synthesis and biological evaluation.Bioorg Med Chem Lett. 17(12):3266-3270 (2007).

Keats et al. Promiscuous mutations activate the noncanonical NF-kB pathway in multiple myeloma. Cancer Cell. 12: 131-144 (2007).

Nishina et al. Biochem. Bioph. Res. Co. NIK is involved in constitutive activation of the alternative NF-jB pathway and proliferation of pancreatic cancer cells. 388: 96-101 (2009).

Pham et al. Constitutive BR3 receptor signaling in diffuse, large B-cell lymphomas stabilizes nuclear factor-B-inducing kinase while activating both canonical and alternative nuclear factor-B pathways. Blood. 117: 200-210 (2011).

Rahal et al., Pharmacological and genomic profiling identifies NF-κb-targeted treatment strategies for mantle cell lymphoma. Nature Med. 1: 87-92 (2014).

Ranuncolo et al. Hodgkin lymphoma requires stabilized NIK and constitutive ReIB expression for survival. Blood First Edition Paper. DOI 10.1182/blood-2012-01-405951 (2012).

Rosebeck et al. Cleavage of NIK by the API2-MALT1 fusion oncoprotein leads to noncanonical NF-kB activation. Science. 331: 468-472 (2011).

Saitoh et al. Overexpressed NF-B-inducing kinase contributes to the tumorigenesis of adult T-cell leukemia and Hodgkin Reed-Sternberg cells. Blood. 111: 5118-5129 (2008).

Shuto et al. Activation of NF-kB by nontypeable Hemophilus influenzae is mediated by toll-like receptor 2-TAK1-dependent NIK-IKKayb-IkBa and MKK3y6-p38 MAP kinase signaling pathways in epithelial cells. PNAS. 98: 8774-8779 (2001).

PCT/EP2017/066125 International Search Report and Written Opinion dated Jul. 27, 2017.

PCT/EP2017/051150 International Preliminary Report on Patentability dated Jul. 24, 2018.

PCT/EP2017/051150 International Search Report and Written Opinion dated Mar. 2, 2017.

PCT/EP2017/051160 International Preliminary Report on Patentability dated Jul. 24, 2018.

PCT/EP2017/051160 International Search Report and Written Opinion dated Sep. 3, 2017.

PCT/EP2017/066120 International Search Report and Written Opinion dated Aug. 23, 2017.

T. W. Greene and P. G. M. Wuts, Protective Groups in Organic Synthesis, 4th ed., Wiley, Hoboken, New Jersey, 2007.

Thu and Richmond, NF-κb inducing kinase: a key regulator in the immune system and in cancer. Cytokine Growth F. R. 21: 213-226 (2010).

Thu et al. NF-jB inducing kinase (NIK) modulates melanoma tumorigenesis by regulating expression of pro-survival factors through the b-catenin pathway. Oncogene. 31(20), 2580-2592 (2012).

Wixted et al. A model to identify novel targets involved in oxidative stress-induced apoptosis in human lung epithelial cells by RNA interferenceToxicol. In Vitro. 24: 310-318 (2010).

Yamamoto et al. Epigenetic alteration of the NF-jB-inducing kinase (NIK) gene is involved in enhanced NIK expression in basal-like breast cancer. Cancer Sci. 101: 2391-2397 (2010).

Yang et al. NIK stabilization in osteoclasts results in osteoporosis and enhanced inflammatoryosteolysis. PLoS ONE. 5(11): e15383. doi:10.1371/journal.pone.0015383 (2010).

Zhao et al. NF-κb-Inducing kinase increases renal tubule epithelial inflammation associated with diabetes. Exp. Diabetes Res. 2011: 1-9 (2011).

F. Herrington, et al., "Modulation of NF-κb Signaling as a Therapeutic Target in Autoimmunity", Journal of Biomolecular Screening, (2016), vol. 21, No. 3, pp. 223-242.

G. McMahon, "VEGF Receptor Signaling in Tumor Angiogenesis", The Oncologist, (2000), vol. 5, suppl. 1, pp. 3-10.

H.M. Pinedo, et al., "Translational Research: The Role of VEGF in Tumor Angiogenesis", The Oncologist, (2000), vol. 5, suppl. 1, pp. 1-2.

D. Vrabel, et al., "The impact of NF-κb signaling on pathogenesis and current treatment strategies in multiple myeloma", Blood Reviews, (2019), vol. 34, pp. 56-66.

Cancer [online]; Retrieved from the Internet, URL: http://www.nim.nih.gov/medlineplus/cancer.html (2007).

Golub et al.: Molecular Classification of Cancer: Class Discovery and Class Prediction by Gene Expression Monitoring; Science 286; 531-537 (1999).

International Application No. PCT/EP2017/066120 International Preliminary Report on Patentability dated Jan. 1, 2019.

Lala et al.: Role of nitric oxide in tumor progression: Lessons from experimental tumors; Cancer and Metastasis Reviews; 17; 91-106 (1999).

International Application No. PCT/EP2017/066125 International Preliminary Report on Patentability dated Jan. 1, 2019.

U.S. Appl. No. 16/309,080 Office Action dated May 29, 2019.

* cited by examiner

US 11,180,487 B2

SUBSTITUTED CYANOINDOLINE DERIVATIVES AS NIK INHIBITORS

FIELD OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer (in particular B-cell malignancies including leukemias, lymphomas and myeloma), inflammatory disorders, metabolic disorders including obesity and diabetes, and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer and inflammatory disorders. Nuclear factor-kappa B (NF-κB) is a transcription factor regulating the expression of various genes involved in the immune response, cell proliferation, adhesion, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK is indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF2 and TRAF3), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226) Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. *Cancer Cell* 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129). It has been demonstrated that the API2-MALT1 fusion oncoprotein created by the recurrent translocation t(11;18)(q21;q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11;18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210). More recently, also loss-of-function mutations in TRAF3 have been characterized in human and canine DLBCL (Bushell et al., *Blood* 2015, 125, 999-1005).

Recently, similar mutations in the non-cannonical NFkB signaling pathway (TRAF2, TRAF3, NIK, BIRC3) were found in ibrutinib-refractory mantle cell lymphoma cell lines (Rahal et al., *Nat Med* 2014, 1, 87-92).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010, 101, 2391-2397). In melanoma tumours, tissue microarray analysis of NIK expression revealed that there was a statistically significant elevation in NIK expression when compared with benign tissue. Moreover, shRNA techniques were used to knock-down NIK, the resultant NIK-depleted melanoma cell lines exhibited decreased proliferation, increased apoptosis, delayed cell cycle progression and reduced tumor growth in a mouse xenograft model (Thu et al. *Oncogene* 2012, 31(20), 2580-92). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signalling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium non-typeable *Hemophilus influenza* (Shuto et al. *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al. *PLoS ONE* 2011, 6(8): e23488. doi:10.1371/journal.pone.0023488). A shRNA screen was used in an in vitro model of oxidative stress induced cell death (as a model of COPD) to interrogate a human druggable genome siRNA library in order to identify genes that modulate the cellular response to stress. NIK was one of the genes identified in this screen as a potential new therapeutic target to modulate epithelial apoptosis in chronic lung diseases (Wixted et al. *Toxicol. In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9). The same group has shown that NIK plays a critical role in noncanonical NF-κB pathway activation, induced skeletal muscle insulin resistance in vitro, suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand-stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2 g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS ONE* 2010, 5(11): e15383. doi:10.1371/journal.pone.0015383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune responses and alloresponses, like GVHD (Graft Versus Host Disease) and transplant rejection, without crippling the immune system as severely as do inhibitors of canonical NF-κB activation.

WO2003030909 describes the preparation of 2- and 4-aminopyrimidines N-substituted by a bicyclic ring for use as kinase inhibitors in the treatment of cancer. WO2002079197 describes 4-aryl-substituted 2-pyrimidinamines and 2-pyridinamines, useful as inhibitors of c-Jun N-terminal kinases (JNK) and other protein kinases.

DESCRIPTION OF THE INVENTION

The present invention concerns novel compounds of Formula (I):

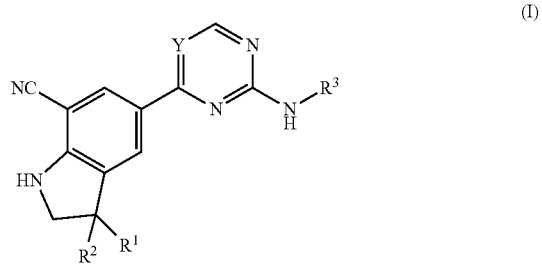

tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$ or N;
R$^4$ represents hydrogen or halo;
R$^5$ represents halo, Het$^{3a}$, —NR$^{6a}$R$^{6b}$, or —OR$^7$;
R$^{6a}$ represents hydrogen or C$_{1-4}$alkyl;
R$^{6b}$ represents hydrogen; C$_{1-4}$alkyl; C$_{3-6}$cycloalkyl; —C(=O)—C$_{1-4}$alkyl; —C(=O)—Het$^4$; —S(=O)$_2$—C$_{1-4}$alkyl; —C(=O)—C$_{1-4}$alkyl substituted with one substituent selected from the group consisting of —OH and —NR$^{16a}$R$^{16b}$; or C$_{1-4}$alkyl substituted with one substituent selected from the group consisting of —OH and —S(=O)$_2$—C$_{1-4}$alkyl;
R$^7$ represents hydrogen, C$_{1-4}$alkyl, —C$_{1-4}$alkyl-NR$^{8a}$R$^{8b}$, —C(=O)—R$^9$, —S(=O)$_2$OH, —P(=O)$_2$—OH, —(C=O)—CH(NH$_2$)—C$_{1-4}$alkyl-Ar$^1$, or —C$_{1-4}$alkyl-Het$^{3b}$;
R$^{8a}$ represents hydrogen or C$_{1-4}$alkyl;
R$^{8b}$ represents hydrogen, C$_{1-4}$alkyl, or C$_{3-6}$cycloalkyl;
R$^9$ represents C$_{1-6}$alkyl, or C$_{1-6}$alkyl substituted with one substituent selected from the group consisting of —NH$_2$, —COOH, and Het$^6$;
R$^{16a}$ and R$^{16b}$ each independently represents hydrogen, C$_{1-4}$alkyl or C$_{3-6}$cycloalkyl;
R$^3$ represents phenyl optionally substituted with one, two or three substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; R$^{21}$; P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; C$_{2-6}$alkenyl substituted with one R$^{13}$; C$_{2-6}$alkynyl; and C$_{2-6}$alkynyl substituted with one R$^{13}$;
R$^{10}$, represents —OH, —O—C$_{1-4}$alkyl, —NR$^{11a}$R$^{11b}$ or Het$^2$;
R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;
R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$ alkyl or C$_{3-6}$cycloalkyl;
Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;
wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, C$_{1-4}$ alkyl, cyano, —C(=O)—C$_{1-4}$ alkyl, —O—C$_{1-4}$alkyl, —NH$_2$, —NH(C$_{1-4}$alkyl), and —N(C$_{1-4}$alkyl)$_2$;
Het$^{1b}$, Het$^{1e}$, Het$^{1g}$, Het$^4$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^4$, Het$^7$ and Het$^8$ containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and
wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;
Het$^2$ represents a heterocyclyl of formula (b-1):

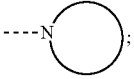

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with a substituent each independently selected from the group consisting of C$_{1-4}$alkyl, C$_{3-6}$cycloalkyl and Het$^7$; and
wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;
R$^{11b}$ represents hydrogen; Het$^{1e}$; C$_{1-4}$alkyl; —C$_{1-4}$alkyl-Het$^5$; —C$_{1-4}$alkyl-Het$^8$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;
R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, or —C(=O)—Het$^{1f}$;
R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, —S(=O)(=N—R$^{20b}$))—C$_{1-4}$alkyl, C$_{3-6}$cycloalkyl, Ar$^2$, or Het$^{1c}$;
Ar$^1$ represents phenyl optionally substituted with one hydroxy;
Ar$^2$ represents phenyl optionally substituted with one C$_{1-4}$alkyl;

Het$^{3a}$, Het$^{3b}$, Het$^5$, Het$^6$ and Het$^{1f}$ each independently represents a heterocyclyl of formula (c-1):

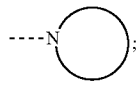

(c-1)

(c-1) represents a N-linked 4- to 7-membered monocyclic saturated heterocyclyl optionally containing one additional heteroatom selected from O, S, S(=O)$_p$ and N;
wherein in case (c-1) contains one additional N-atom, said additional N-atom may optionally be substituted with C$_{1-4}$alkyl or C$_{3-6}$cycloalkyl; and
wherein (c-1) may optionally be substituted on one or two ring C-atoms atoms with one or two substituents each independently selected from the group consisting of halo, C$_{1-4}$alkyl, and C$_{3-6}$cycloalkyl;
R$^{11a}$, R$^{14a}$, R$^{14c}$, R$^{15a}$, R$^{17a}$ and R$^{19a}$ each independently represents hydrogen or C$_{1-4}$alkyl;
R$^{14b}$, R$^{14d}$, R$^{15b}$, R$^{17b}$ and R$^{19b}$ each independently represents hydrogen; C$_{1-4}$alkyl; C$_{3-6}$cycloalkyl; —C(=O)—C$_{1-4}$alkyl; C$_{1-4}$alkyl substituted with one substituent selected from the group consisting of halo, —OH and —O—C$_{1-4}$alkyl; —C(=O)—C$_{1-4}$alkyl substituted with one substituent selected from the group consisting of halo, —OH and —O—C$_{1-4}$alkyl; or —S(=O)$_2$—C$_{1-4}$alkyl;
R$^{20a}$ and R$^{20b}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$alkyl;
p represents 1 or 2;
and the pharmaceutically acceptable addition salts, and the solvates thereof.

The present invention also relates to a pharmaceutical composition comprising a therapeutically effective amount of a compound of Formula (I), a pharmaceutically acceptable addition salt, or a solvate thereof, and a pharmaceutically acceptable carrier or excipient.

Additionally, the invention relates to a compound of Formula (I), a pharmaceutically acceptable addition salt, or a solvate thereof, for use as a medicament, and to a compound of Formula (I), a pharmaceutically acceptable addition salt, or a solvate thereof, for use in the treatment or in the prevention of cancer, inflammatory disorders, autoimmune disorders, and metabolic disorders such as diabetes and obesity.

In a particular embodiment, the invention relates to a compound of Formula (I), a pharmaceutically acceptable addition salt, or a solvate thereof, for use in the treatment or in the prevention of a haematological malignancy or solid tumour.

In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

The invention also relates to the use of a compound of Formula (I), a pharmaceutically acceptable addition salt, or a solvate thereof, in combination with an additional pharmaceutical agent for use in the treatment or prevention of cancer, inflammatory disorders, autoimmune disorders, and metabolic disorders such as diabetes and obesity. Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable addition salt, or a solvate thereof.

The invention also relates to a product comprising a compound of Formula (I), a pharmaceutically acceptable addition salt, or a solvate thereof, and an additional pharmaceutical agent, as a combined preparation for simultaneous, separate or sequential use in the treatment or prevention of cancer, inflammatory disorders, autoimmune disorders, and metabolic disorders such as diabetes and obesity. Additionally, the invention relates to a method of treating or preventing a cell proliferative disease in a warm-blooded animal which comprises administering to the said animal an effective amount of a compound of Formula (I), a pharmaceutically acceptable addition salt, or a solvate thereof, as defined herein, or a pharmaceutical composition or combination as defined herein.

Some of the compounds of the present invention may undergo metabolism to a more active form in vivo (prodrugs).

DETAILED DESCRIPTION OF THE INVENTION

The term 'halo' or 'halogen' as used herein represents fluoro, chloro, bromo and iodo.

The prefix 'C$_{x-y}$' (where x and y are integers) as used herein refers to the number of carbon atoms in a given group. Thus, a C$_{1-6}$alkyl group contains from 1 to 6 carbon atoms, a C$_{3-6}$cycloalkyl group contains from 3 to 6 carbon atoms, and so on.

The term 'C$_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term 'C$_{1-6}$alkyl' as used herein as a group or part of a group represents a straight or branched chain saturated hydrocarbon radical having from 1 to 6 carbon atoms such as the groups defined for C$_{1-4}$alkyl and n-pentyl, n-hexyl, 2-methylbutyl and the like.

The term "C$_{2-6}$alkenyl" as used herein as a group or part of a group represents a straight or branched chain hydrocarbon group containing from 2 to 6 carbon atoms and containing a carbon carbon double bond such as, but not limited to, ethenyl, propenyl, butenyl, pentenyl, 1-propen-2-yl, hexenyl and the like.

The term "C$_{2-6}$alkynyl" as used herein as a group or part of a group represents a straight or branched chain hydrocarbon group having from 2 to 6 carbon atoms and containing a carbon carbon triple bond.

The term 'C$_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

In general, whenever the term "substituted" is used in the present invention, it is meant, unless otherwise is indicated or is clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

The skilled person will understand that the term "optionally substituted" means that the atom or radical indicated in the expression using "optionally substituted" may or may not be substituted (this means substituted or unsubstituted respectively).

When two or more substituents are present on a moiety they may, where possible and unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent), for example in saturated heterocyclyl groups or 5-membered aromatic rings as used in the definition of $R^{18}$.

C(O) or C(=O) represents a carbonyl moiety.

$S(=O)_2$ or $SO_2$ represents a sulfonyl moiety.

The skilled person will understand that —S(=O)(=N—$R^{20a}$)—$C_{1-4}$alkyl corresponds with

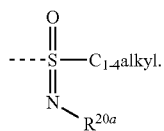

Within the context of this invention 'saturated' means 'fully saturated', if not otherwise specified.

$Het^{1a}$, $Het^{1c}$ and $Het^{1d}$, may be attached to the remainder of the molecule of Formula (I) through any available ring carbon or nitrogen atom as appropriate, if not otherwise specified.

The 5-membered aromatic ring containing one, two or three N-atoms as referred to in the definition of $R^{18}$, may be attached to the remainder of the molecule of Formula (I) through any available ring carbon or nitrogen atom as, if not otherwise specified.

It will be clear that in case a saturated cyclic moiety is substituted on two ring carbon atoms with one substituent, in total two carbon-linked substituents are present on the saturated cyclic moiety (one substituent on each carbon atom).

It will be clear that in case a saturated cyclic moiety is substituted on two ring carbon atoms with two substituents, in total four carbon-linked substituents are present on the saturated cyclic moiety (two substituents on each carbon atom).

It will be clear that in case a saturated cyclic moiety is substituted on three ring carbon atoms with two substituents, in total six carbon-linked substituents are present on the saturated cyclic moiety (two substituents on each carbon atom).

It will be clear that in case a saturated cyclic moiety is substituted on two ring N-atoms with a substituent, in total two N-linked substituents are present on the saturated cyclic moiety (a substituent on each N-atom).

It will be clear that a saturated cyclic moiety may, where possible, have substituents on both carbon and N-atoms, unless otherwise is indicated or is clear from the context.

Within the context of this invention, bicyclic saturated heterocyclyl groups include fused, Spiro and bridged saturated heterocycles.

Fused bicyclic groups are two cycles that share two atoms and the bond between these atoms.

Spiro bicyclic groups are two cycles that are joined at a single atom.

Bridged bicyclic groups are two cycles that share more than two atoms.

Examples of N-linked 6- to 11-membered fused bicyclic saturated heterocyclyl groups, include, but are not limited to

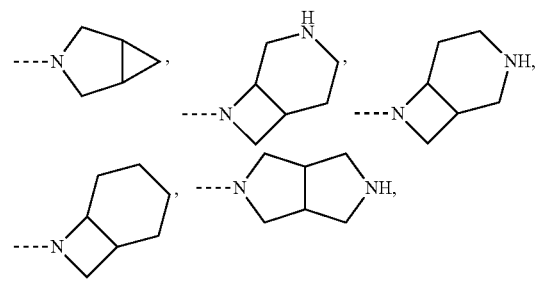

and the like.

Examples of N-linked 6- to 11-membered spiro bicyclic saturated heterocyclyl groups, include, but are not limited to

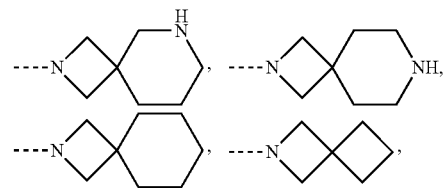

and the like.

Examples of N-linked 6- to 11-membered bridged bicyclic saturated heterocyclyl groups, include, but are not limited to

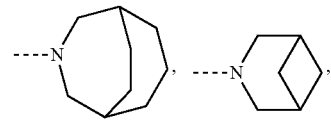

and the like.

The skilled person will realize that the definition of $Het^{1a}$, $Het^{1c}$ and $Het^{1d}$ also includes C-linked bicycles (attached to the remainder of the molecule of Formula (I) through any available ring carbon atom).

It should be understood that the exemplified bicyclic saturated heterocyclyl groups referred to above may optionally be substituted, where possible, on carbon and/or nitrogen atoms according to any of the embodiments.

Non-limiting examples of 4- to 7-membered monocyclic saturated heterocyclyl moieties containing one or two heteroatoms each independently selected from O, S, S($=$O)$_p$ and N (as in the definition of Het$^{1a}$, Het$^{1c}$, and Het$^{1d}$) are shown below:

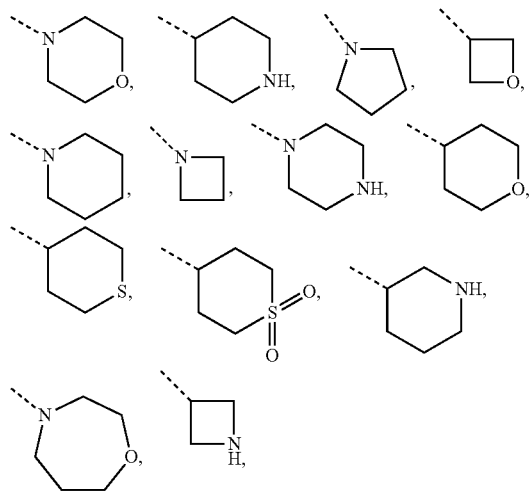

and the like.

Each of which may optionally be substituted, where possible, on carbon and/or nitrogen atoms according to any of the embodiments.

Non-limiting examples of 4- to 7-membered monocyclic saturated heterocyclyl moieties, attached to the remainder of the molecule of Formula (I) through any available ring carbon atom (C-linked), and containing one or two heteroatoms each independently selected from O, S, S($=$O)$_p$ and N (as in the definition of Het$^{1b}$, Het$^{1e}$, Het$^{1g}$, Het$^4$, Het$^7$ and Het$^8$) are shown below:

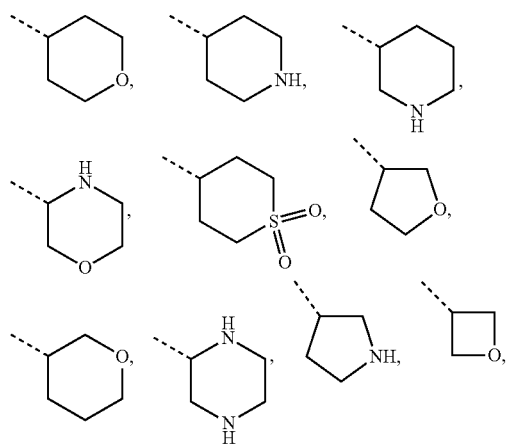

and the like.

Each of which may optionally be substituted, where possible, on carbon and/or nitrogen atoms according to any of the embodiments.

Non-limiting examples of N-linked 4- to 7-membered monocyclic saturated heterocyclyl moieties optionally containing one additional heteroatom selected from O, S, S($=$O)$_p$ and N (as in the definition of (b-1) and (c-1)) are shown below:

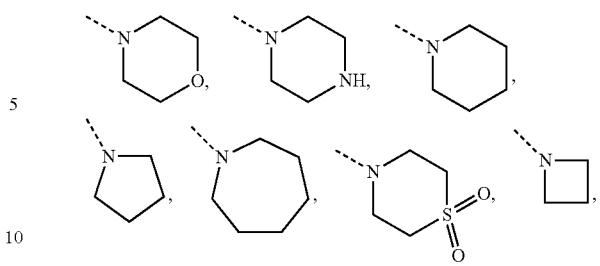

and the like.

Each of which may optionally be substituted, where possible, on carbon and/or nitrogen atoms according to any of the embodiments.

Non-limiting examples of 5-membered aromatic ring containing one, two or three N-atoms as referred to in the definition of R$^{18}$ are shown below:

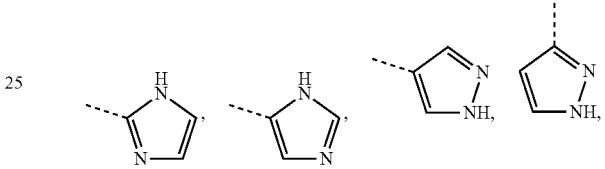

and the like.

Each of which may optionally be substituted, where possible, on carbon and/or nitrogen atoms according to any of the embodiments.

Whenever substituents are represented by chemical structure, "---" represents the bond of attachment to the remainder of the molecule of Formula (I).

Lines (such as "---") drawn into ring systems indicate that the bond may be attached to any of the suitable ring atoms.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable addition salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

Pharmaceutically-acceptable addition salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$ $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy.

The present invention relates in particular to compounds of Formula (I) as defined herein, tautomers and stereoisomeric forms thereof, wherein $R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents $Het^{3a}$, —$NR^{6a}R^{6b}$, or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$; C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —NH$_2$, —COOH, and $Het^6$;
$R^{16a}$ and $R^{16b}$ each independently represents hydrogen, $C_{1-4}$alkyl or $C_{3-6}$cycloalkyl;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—$(C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;
$R^{10}$ represents —OH, —O—$C_{1-4}$alkyl, —$NR^{11a}R^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;
$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;
$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het² represents a heterocyclyl of formula (b-1):

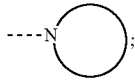

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with C$_{1-4}$alkyl; and wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;
R$^{11b}$ represents hydrogen; Het$^{1e}$; C$_{1-4}$alkyl; —C$_{1-4}$alkyl-Het$^5$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;
R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, or —C(=O)—Het$^{1f}$;
R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, —S(=O)(=N—R$^{20b}$)—C$_{1-4}$alkyl, C$_{3-6}$cycloalkyl, Ar$^2$, or Het$^{1c}$;
Ar$^1$ represents phenyl optionally substituted with one hydroxy;
Ar$^2$ represents phenyl optionally substituted with one C$_{1-4}$alkyl;
Het$^{3a}$, Het$^{3b}$, Het$^5$, Het$^6$ and Het$^{1f}$ each independently represents a heterocyclyl of formula (c-1):

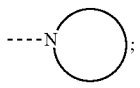

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with C$_{1-4}$alkyl or C$_{3-6}$cycloalkyl; and
wherein (c-1) may optionally be substituted on one or two ring C-atoms atoms with one or two substituents each independently selected from the group consisting of halo, C$_{1-4}$alkyl, and C$_{3-6}$cycloalkyl;
R$^{11a}$, R$^{14a}$, R$^{14c}$, R$^{15a}$, R$^{17a}$ and R$^{19a}$ each independently represents hydrogen or C$_{1-4}$ alkyl;
R$^{14b}$, R$^{14d}$, R$^{15b}$, R$^{17b}$ and R$^{19b}$ each independently represents hydrogen; C$_{1-4}$alkyl; C$_{3-6}$cycloalkyl; or C$_{1-4}$alkyl substituted with one substituent selected from the group consisting of halo, —OH and —O—C$_{1-4}$alkyl;
R$^{20a}$ and R$^{20b}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$alkyl;

p represents 1 or 2;
and the pharmaceutically acceptable addition salts, and the solvates thereof.

The present invention relates in particular to compounds of Formula (I) as defined herein, tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$ or N;
R$^4$ represents hydrogen or halo;
R$^5$ represents halo, Het$^{3a}$, —NR$^{6a}$R$^{6b}$; or —OR$^7$;
R$^{6a}$ represents hydrogen or C$_{1-4}$alkyl;
R$^{6b}$ represents hydrogen; C$_{1-4}$alkyl; C$_{3-6}$cycloalkyl; —C(=O)—C$_{1-4}$alkyl; —S(=O)$_2$—C$_{1-4}$alkyl; —C(=O)—C$_{1-4}$alkyl substituted with one substituent selected from the group consisting of —OH and —NR$^{16a}$R$^{16b}$; or C$_{1-4}$alkyl substituted with one substituent selected from the group consisting of —OH and —S(=O)$_2$—C$_{1-4}$alkyl;
R$^7$ represents hydrogen, C$_{1-4}$alkyl, —C$_{1-4}$alkyl-NR$^{8a}$R$^{8b}$(=O)—R$^9$, —S(=O)$_2$—OH, —P(=O)$_2$—OH, —(C=O)—CH(NH$_2$)—C$_{1-4}$alkyl-Ar$^1$, or —C$_{1-4}$alkyl-Het$^{3b}$;
R$^{8a}$ represents hydrogen or C$_{1-4}$alkyl;
R$^{8b}$ represents hydrogen, C$_{1-4}$alkyl, or C$_{3-6}$cycloalkyl;
R$^9$ represents C$_{1-4}$alkyl, or C$_{1-4}$alkyl substituted with one substituent selected from the group consisting of —NH$_2$, —COOH, and Het$^6$;
R$^{16a}$ and R$^{16b}$ each independently represents hydrogen, C$_{1-4}$alkyl or C$_{3-6}$cycloalkyl;
R$^3$ represents phenyl optionally substituted with one, two or three substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O—Het$^{1b}$; R$^{18}$; R$^{21}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; C$_{2-6}$alkenyl substituted with one R$^{13}$; C$_{2-6}$alkynyl; and C$_{2-6}$alkynyl substituted with one R$^{13}$;
R$^{10}$ represents —OH, —O—C$_{1-4}$alkyl, —NR$^{11a}$R$^{11b}$ or Het$^2$;
R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;
R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;
Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^{1b}$, $Het^{1e}$, $Het^{1g}$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^7$ and $Het^8$ containing one or two heteroatoms each independently selected from O, S, S(=O)$_p$ and N; wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^2$ represents a heterocyclyl of formula (b-1):

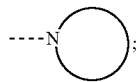

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and wherein (b-1) may optionally be substituted on one, two or three ring C-atoms with one or two substituents each independently selected from the group consisting of halo, —OH, cyano, $C_{1-4}$ alkyl, —O—$C_{1-4}$ alkyl, —$NH_2$, —NH($C_{1-4}$ alkyl), —N($C_{1-4}$ alkyl)$_2$, and —$C_{1-4}$ alkyl-OH;

$R^{11b}$ represents hydrogen; $Het^{1e}$; $C_{1-4}$alkyl; —$C_{1-4}$alkyl-$Het^5$; —$C_{1-4}$alkyl-$Het^8$; substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)N$R^{15a}R^{15b}$, —N$R^{19a}R^{19b}$, $C_{3-6}$cycloalkyl, $Het^{1d}$, or —C(=O)—$Het^{1f}$;

$R^{12}$ represents —OH, —N$R^{14a}R^{14b}$, —C(=O)N$R^{14c}R^{14d}$, —S(=O)$_2$—$C_{1-4}$alkyl, —S(=O)(=N—$R^{20b}$)—$C_{1-4}$alkyl, $C_{3-6}$cycloalkyl, $Ar^2$, or $Het^{1c}$;

$Ar^1$ represents phenyl optionally substituted with one hydroxy;

$Ar^2$ represents phenyl optionally substituted with one $C_{1-4}$alkyl;

$Het^{3a}$, $Het^{3b}$, $Het^5$, $Het^6$ and $Het^{1f}$ each independently represents a heterocyclyl of formula (c-1):

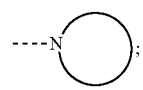

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R_{17a}$ and $R^{19a}$ each independently represents hydrogen or $C_{1-4}$alkyl;

$R^{14b}$, $R^{14d}$, $R^{15b}$, $R_{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents $Het^{3a}$, —N$R^{6a}R^{6b}$, or —O$R^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —N$R^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-N$R^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —$NH_2$, —COOH, and $Het^6$;

$R^{16a}$ and $R^{16b}$ each independently represents hydrogen, $C_{1-4}$alkyl or $C_{3-6}$cycloalkyl;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; Het$^{1a}$, —O-Het$^{1b}$, $R^{18}$; $R^{21}$; P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$R^{10}$ represents —OH, —O—$C_{1-4}$alkyl, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^{1b}$, Het$^{1e}$, and Het$^{1g}$ each independently represents a 4- to 7-membered monocyclic saturated heterocyclyl, attached to the remainder of the molecule of Formula (I) through any available ring carbon atom, said Het$^{1b}$, Het$^{1e}$, and Het$^{1g}$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$,
—NH($C_{1-4}$alkyl), and —N($C_{1-4}$alkyl)$_2$;

Het$^2$ represents a heterocyclyl of formula (b-1):

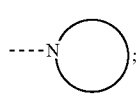

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; Het$^{1e}$; $C_{1-4}$alkyl; —$C_{1-4}$alkyl-Het$^5$; $C_{1-4}$alkyl substituted with one, two or three substituents each independently selected from the group consisting of halo, —OH and –O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

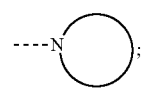

(c-1)

(c-1) represents a N-linked 4- to 7-membered monocyclic saturated heterocyclyl optionally containing one additional heteroatom selected from O, S, S(=O)$_p$ and N;

wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;
$R^2$ represents $C_{1-6}$alkyl, or $C_{1-6}$alkyl substituted with one $R^5$;
Y represents $CR^4$ or N;
$R^4$ represents hydrogen or halo;
$R^5$ represents halo, $Het^{3a}$, —$NR^{6a}R^{6b}$; or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-4}$alkyl, or $C_{1-4}$alkyl substituted with one substituent selected from the group consisting of —NH$_2$, —COOH, and $Het^6$;
$R^{16a}$ and $R^{16b}$ each independently represents hydrogen, $C_{1-4}$alkyl or $C_{3-6}$cycloalkyl;
$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; $C_{2-6}$alkenyl substituted with one $R^{13}$; $C_{2-6}$alkynyl; and $C_{2-6}$alkynyl substituted with one $R^{13}$;
$R^{10}$ represents —OH, —O—$C_{1-4}$alkyl, —$NR^{11a}R^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;
$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;
wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and O—$C_{1-4}$alkyl; and
wherein said 4- to 7-membered monocyclic saturated heterocyclyl or said 6- to 11-membered bicyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;
$Het^{1b}$, $Het^{1e}$, $Het^{1g}$, $Het^4$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^4$, $Het^7$ and $Het^8$ containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;
$Het^2$ represents a heterocyclyl of formula (b-1):

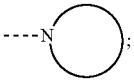

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and
wherein (b-1) may optionally be substituted on one, two or three ring C-atoms with one substituent each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;
$R^{11b}$ represents hydrogen; $Het^{1e}$; $C_{1-4}$alkyl; —$C_{1-4}$alkyl-$Het^5$; —$C_{1-4}$alkyl-$Het^8$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;
$R^{16}$ represents —OH, —$NR^{14a}R^{14b}$, —C(=O)$NR^{14c}R^{14d}$, —S(=O)$_2$—$C_{1-4}$alkyl, —S(=O)(=N—$R^{20b}$)—$C_{1-4}$alkyl, $C_{3-6}$cycloalkyl, $Ar^2$, or $Het^{1c}$;
$Ar^1$ represents phenyl optionally substituted with one hydroxy;
$Ar^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

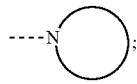

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with C$_{1-4}$alkyl or C$_{3-6}$cycloalkyl; and wherein (c-1) may optionally be substituted on one or two ring C-atoms atoms with one substituent each independently selected from the group consisting of halo, C$_{1-4}$alkyl, and C$_{3-6}$cycloalkyl;

R$^{11a}$, R$^{14a}$, R$^{14c}$, R$^{15a}$, R$^{17a}$ and R$^{19a}$ each independently represents hydrogen or C$_{1-4}$alkyl;

R$^{14b}$, R$^{14d}$, R$^{15b}$, R$^{17b}$ and R$^{19b}$ each independently represents hydrogen; C$_{1-4}$alkyl; C$_{3-6}$cycloalkyl; —C(=O)—C$_{1-4}$alkyl; C$_{1-4}$alkyl substituted with one substituent selected from the group consisting of halo, —OH and —O—C$_{1-4}$alkyl; —C(=O)—C$_{1-4}$alkyl substituted with one substituent selected from the group consisting of halo, —OH and —O—C$_{1-4}$alkyl; or —S(=O)$_2$—C$_{1-4}$alkyl;

R$^{20a}$ and R$^{20b}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein R$^1$ represents C$_{1-4}$alkyl;

R$^2$ represents C$_{1-6}$alkyl, or C$_{1-6}$alkyl substituted with one R$^5$;

Y represents CR$^4$;

R$^4$ represents hydrogen or halo;

R$^5$ represents Het$^{3a}$, —NR$^{6a}$R$^{6b}$, or —OR$^7$;

R$^{6a}$ represents hydrogen or C$_{1-4}$alkyl;

R$^{6b}$ represents hydrogen; C$_{1-4}$alkyl; C$_{3-6}$cycloalkyl; —C(=O)—C$_{1-4}$alkyl; —C(=O)—Het$^4$; —S(=O)$_2$—C$_{1-4}$ alkyl; —C(=O)—C$_{1-4}$alkyl substituted with one substituent selected from the group consisting of —OH and —NR$^{16a}$R$^{16b}$; or C$_{1-4}$alkyl substituted with one substituent selected from the group consisting of —OH and —S(=O)$_2$—C$_{1-4}$alkyl;

R$^7$ represents hydrogen, C$_{1-4}$alkyl, —C$_{1-4}$alkyl-NR$^{8a}$R$^{8b}$; C(=O)—R$^9$, —S(=O)$_2$—OH, —P(=O)$_2$—OH, —(C=O)—CH(NH$_2$)—C$_{1-4}$alkyl-Ar$^1$, or —C$_{1-4}$alkyl-Het$^{3b}$;

R$^{8a}$ represents hydrogen or C$_{1-4}$alkyl;

R$^{8b}$ represents hydrogen, C$_{1-4}$alkyl, or C$_{3-6}$cycloalkyl;

R$^9$ represents C$_{1-4}$alkyl, or C$_{1-4}$alkyl substituted with one substituent selected from the group consisting of —NH$_2$, —COOH, and Het$^6$;

R$^{16a}$ and R$^{16b}$ each independently represents hydrogen, C$_{1-4}$alkyl or C$_{3-6}$cycloalkyl;

R$^3$ represents phenyl optionally substituted with one, two or three substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; R$^{21}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$;

R$^{10}$ represents —OH, —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{12}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one substituent each independently selected from the group consisting of —OH, halo, C$_{1-4}$alkyl, cyano, —C(=O)—C$_{1-4}$alkyl, —O—C$_{1-4}$ alkyl, —NH$_2$, —NH(C$_{1-4}$alkyl), and —N(C$_{1-4}$alkyl)$_2$;

Het$^{1b}$, Het$^{1e}$, Het$^{1g}$ and Het$^4$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$ and Het$^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one substituent each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het² represents a heterocyclyl of formula (b-1):

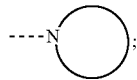

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with $C_{1-4}$alkyl; and
wherein (b-1) may optionally be substituted on one, two or three ring C-atoms with one substituent each independently selected from the group consisting of halo, —OH, cyano, $C_{1-4}$ alkyl, —O—$C_{1-4}$alkyl, —NH$_2$, —NH($C_{1-4}$alkyl), —N($C_{1-4}$alkyl)$_2$, and $C_{1-4}$alkyl-OH;
$R^{11b}$ represents hydrogen; Het$^{1e}$; $C_{1-4}$alkyl; $C_{1-4}$alkyl-Het$^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;
$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;
Ar$^1$ represents phenyl optionally substituted with one hydroxy;
Ar$^2$ represents phenyl optionally substituted with one $C_{1-4}$alkyl;
Het$^{3a}$, Het$^{3b}$, Het$^5$, Het$^6$ and Het$^{1f}$ each independently represents a heterocyclyl of formula (c-1):

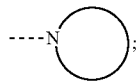

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and
wherein (c-1) may optionally be substituted on one or two ring C-atoms atoms with one substituent each independently selected from the group consisting of halo, $C_{1-4}$alkyl, and $C_{3-6}$cycloalkyl;
$R^{11a}$, $R^{14a}$, $R^{14c}$, $R^{15a}$, $R^{17a}$ and $R^{19a}$ each independently represents hydrogen or $C_{1-4}$alkyl;
$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents CR$^4$ or N;
$R^4$ represents hydrogen or halo;
$R^5$ represents halo, —NR$^{6a}$R$^{6b}$, or —OR$^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-NR$^{8a}$R$^{8b}$; C(=O)—R$^9$, —S(=O)$_2$—OH, —P(=O)$_2$—OH, or —(C=O)—CH(NH$_2$)—$C_{1-4}$alkyl-Ar$^1$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-4}$alkyl, or $C_{1-4}$alkyl substituted with one substituent selected from the group consisting of —NH$_2$ and —COOH;
$R^{16a}$ and $R^{16b}$ each independently represents hydrogen, $C_{1-4}$alkyl or $C_{3-6}$cycloalkyl;
$R^3$ represents phenyl optionally substituted with one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; —P(=O)—($C_{1-4}$ alkyl)$_2$; —NH—C(=O)—$C_{1-4}$alkyl; —NR$^{17a}$R$^{17b}$; $C_{1-4}$ alkyl substituted with one, two or three halo atoms; $C_{1-4}$alkyl substituted with one, two or three —OH substituents; $C_{1-4}$alkyl substituted with one R$^{13}$; $C_{2-6}$alkenyl; $C_{2-6}$alkenyl substituted with one R$^{13}$; $C_{2-6}$alkynyl; and $C_{2-6}$alkynyl substituted with one R$^{13}$;
$R^{10}$ represents —OH, —O—$C_{1-4}$alkyl, or —NR$^{11a}$R$^{11b}$;
$R^{11b}$ represents hydrogen; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)NR$^{15a}$R$^{15b}$, —NR$^{19a}$R$^{19b}$, or $C_{3-6}$cycloalkyl;
$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$ alkyl, $C_{3-6}$cycloalkyl, or Ar$^2$;
Ar$^1$ represents phenyl optionally substituted with one hydroxy;
Ar$^2$ represents phenyl optionally substituted with one $C_{1-4}$alkyl;
$R^{11a}$, $R^{14a}$, $R^{14c}$, $R^{15a}$, $R^{17a}$ and $R^{19a}$ each independently represents hydrogen or $C_{1-4}$alkyl;
$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$ alkyl; $C_{1-4}$alkyl substituted with one substituent selected from the group consisting of halo, —OH and —O—$C_{1-4}$ alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, or —(C=O)—CH(NH$_2$)—$C_{1-4}$alkyl-$Ar^1$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —NH$_2$ and —COOH;

$R^{16a}$ and $R^{16b}$ each independently represents hydrogen, $C_{1-4}$alkyl or $C_{3-6}$cycloalkyl;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; —P(=O)—($C_{1-4}$alkyl)$_2$; —NH—C(=O)—$C_{1-4}$alkyl; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$;

$R^{10}$ represents —OH, —O—$C_{1-4}$alkyl, or —$NR^{11a}R^{11b}$;

$R^{11b}$ represents hydrogen; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)$NR^{15a}R^{15b}$, —$NR^{19a}R^{19b}$, or $C_{3-6}$cycloalkyl;

$R^{12}$ represents —OH, —O—$C_{1-4}$alkyl, —$NR^{14a}R_{14b}$, —C(=O)$NR^{14c}R^{14d}$, —S(=O)$_2$—$C_{1-4}$alkyl, —S(=O)(=N—$R^{20b}$)—$C_{1-4}$alkyl, $C_{3-6}$cycloalkyl, or $Ar^2$;

$Ar^1$ represents phenyl optionally substituted with one hydroxy;

$Ar^2$ represents phenyl optionally substituted with one $C_{1-4}$alkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$ or N;

$R^4$ represents hydrogen or halo;

$R^5$ represents halo, —$NR^{6a}R^{6b}$, or —$OR^7$;

$R^{6a}$ represents hydrogen;

$R^{6b}$ represents —C(=O)—$C_{1-4}$alkyl; or —S(=O)$_2$—$C_{1-4}$alkyl;

$R^7$ represents hydrogen, —$C_{1-4}$alkyl-$NR^{8a}R^{8b}$, —C(=O)—$R^9$, —S(=O)$_2$—OH, or —(C=O)—CH(NH$_2$)—$C_{1-4}$alkyl-$Ar^1$;

$R^{8a}$ represents hydrogen;

$R^{8b}$ represents $C_{3-6}$cycloalkyl;

$R^9$ represents $C_{1-6}$alkyl, or $C_{1-6}$alkyl substituted with one substituent selected from the group consisting of —NH$_2$, —COOH, and $Het^6$;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl substituted with one $R^{13}$; and $C_{2-6}$alkynyl substituted with one $R^{13}$;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl;

$Het^{1a}$, $Het^{1c}$ and $Het^{1d}$ each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, —O—$C_{1-4}$alkyl, and —N($C_{1-4}$alkyl)$_2$;

$Het^{1b}$, $Het^{1e}$, $Het^{1g}$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^7$ and $Het^8$ containing one or two heteroatoms each independently selected from O and N; wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and
wherein said 4- to 7-membered monocyclic saturated heterocyclyl may optionally be substituted on one, two or three ring C-atoms with one or two substituents each independently selected from the group consisting of —OH, and halo;
$Het^2$ represents a heterocyclyl of formula (b-1):

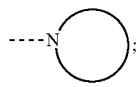

(b-1)

(b-1) represents a N-linked 4- to 7-membered monocyclic saturated heterocyclyl optionally containing one additional heteroatom selected from O and N, or a N-linked 6- to 11-membered bicyclic saturated heterocyclyl, including fused, spiro and bridged cycles, optionally containing one or two additional N-atoms;
wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and
wherein (b-1) may optionally be substituted on one, two or three ring C-atoms with one or two substituents each independently selected from the group consisting of —OH, cyano, $C_{1-4}$alkyl, and $C_{1-4}$alkyl-OH;
$R^{11b}$ represents $Het^{1e}$; $C_{1-4}$alkyl; —$C_{1-4}$alkyl-$Het^5$; —$C_{1-4}$alkyl-$Het^8$, $C_{1-4}$alkyl substituted with one, two or three OH substituents; or $C_{3-6}$cycloalkyl substituted with one, two or three substituents each independently selected from the group consisting of halo and —OH;
$R^{13}$ represents —O—$C_{1-4}$alkyl, —C(=O)NR$^{15a}$R$^{15b}$, —NR$^{19a}$R$^{19b}$, $C_{3-6}$cycloalkyl, $Het^{1d}$, or —C(=O)—$Het^{1f}$;
$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, $C_{3-6}$cycloalkyl, $Ar^2$, or $Het^{1c}$;
$Ar^1$ represents phenyl;
$Ar^2$ represents phenyl optionally substituted with one $C_{1-4}$alkyl;
$Het^5$, $Het^6$ and $Het^{1f}$ each independently represents a heterocyclyl of formula (c-1):

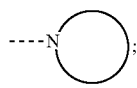

(c-1)

(c-1) represents a N-linked 4- to 7-membered monocyclic saturated heterocyclyl optionally containing one additional heteroatom selected from O and N;
wherein in case (c-1) contains one additional N-atom, said additional N-atom may optionally be substituted with $C_{1-4}$alkyl;
$R^{11a}$, $R^{14a}$, $R^{14c}$, $R^{15a}$, $R^{17a}$ and $R^{19a}$ each independently represents hydrogen or $C_{1-4}$alkyl;
$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of —OH and —O—$C_{1-4}$alkyl; or —S(=O)$_2$—$C_{1-4}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents —NR$^{6a}$R$^{6b}$, or —OR$^7$;
$R^{6a}$ represents hydrogen;
$R^{6b}$ represents —C(=O)—$C_{1-4}$alkyl; or —S(=O)$_2$—$C_{1-4}$alkyl;
$R^7$ represents hydrogen, —C(=O)—$R^9$, —S(=O)$_2$—OH, or —(C=O)—CH(NH$_2$)—$C_{1-4}$alkyl-$Ar^1$;
$R^9$ represents $C_{1-4}$alkyl, or $C_{1-4}$alkyl substituted with one substituent selected from the group consisting of —NH$_2$, —COOH, and $Het^6$;
$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; $C_{3-6}$cycloalkyl; —O—$C_{3-6}$cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^{1g}$; $C_{1-4}$alkyl substituted with one, two or three halo atoms; $C_{1-4}$alkyl substituted with one, two or three —OH substituents; and $C_{1-4}$alkyl substituted with one $R^{13}$;
$R^{10}$ represents —OH, —O—$C_{1-4}$alkyl, —NR$^{11a}$R$^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl;
$Het^{1a}$, $Het^{1c}$ and $Het^{1d}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, —O—$C_{1-4}$alkyl, and —N($C_{1-4}$alkyl)$_2$;
$Het^{1b}$, $Het^{1e}$, and $Het^{1g}$ each independently represents a 4- to 7-membered monocyclic saturated heterocyclyl, attached to the remainder of the molecule of Formula (I) through any available ring carbon atom, said $Het^{1b}$, $Het^{1e}$ and $Het^{1g}$ containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two —OH substituents;

Het² represents a heterocyclyl of formula (b-1):

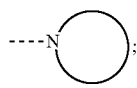

(b-1)

(b-1) represents a N-linked 4- to 7-membered monocyclic saturated heterocyclyl optionally containing one additional N-atom, or a N-linked 6- to 11-membered bicyclic saturated heterocyclyl, including fused, spiro and bridged cycles, optionally containing one or two additional N-atoms;
wherein in case (b-1) contains one or two additional N-atoms, said one or two N-atoms may optionally be substituted with $C_{1-4}$alkyl; and
wherein (b-1) may optionally be substituted on one, two or three ring C-atoms with one or two substituents each independently selected from the group consisting of —OH, cyano, and $C_{1-4}$alkyl-OH;
$R^{11b}$ represents $Het^{1e}$; $C_{1-4}$alkyl; —$C_{1-4}$alkyl-$Het^5$; $C_{1-4}$alkyl substituted with one, two or three OH substituents; or $C_{3-6}$cycloalkyl substituted with one, two or three substituents each independently selected from the group consisting of halo and —OH;
$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;
$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, $C_{3-6}$cycloalkyl, $Ar^2$, or $Het^{1c}$;
$Ar^1$ represents phenyl;
$Ar^2$ represents phenyl optionally substituted with one $C_{1-4}$alkyl;
$Het^5$, $Het^6$ and $Het^{1f}$ each independently represents a heterocyclyl of formula (c-1):

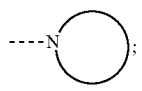

(c-1)

(c-1) represents a N-linked 4- to 7-membered monocyclic saturated heterocyclyl optionally containing one additional heteroatom selected from O and N;
wherein in case (c-1) contains one additional N-atom, said additional N-atom may optionally be substituted with $C_{1-4}$alkyl;
$R^{11a}$, $R^{14a}$, $R^{14c}$, $R^{15a}$, $R^{17a}$ and $R^{19a}$ each independently represents hydrogen or $C_{1-4}$alkyl;
$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one —O—$C_{1-4}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents —$OR^7$;
$R^7$ represents hydrogen or —C(=O)—$R^9$;
$R^9$ represents $C_{1-4}$alkyl;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; $Het^{1a}$; —O-$Het^{1b}$; —P(=O)—($C_{1-4}$alkyl)$_2$; —NH—C(=O)—$C_{1-4}$alkyl; —NH—C(=O)-$Het^{1g}$; $C_{1-4}$alkyl substituted with one, two or three halo atoms; $C_{1-4}$alkyl substituted with one, two or three —OH substituents; and $C_{1-4}$alkyl substituted with one $R^{13}$;
$R^{10}$ represents —O—$C_{1-4}$alkyl, $R^{11a}R^{11b}$ or $Het^2$;
$Het^{1a}$, $Het^{1c}$ and $Het^{1d}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, —O—$C_{1-4}$alkyl, and —N($C_{1-4}$alkyl)$_2$;
$Het^{1b}$, $Het^{1e}$, and $Het^{1g}$ each independently represents a 4- to 7-membered monocyclic saturated heterocyclyl, attached to the remainder of the molecule of Formula (I) through any available ring carbon atom, said $Het^{1b}$, $Het^{1e}$ and $Het^{1g}$ containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and
wherein said 4- to 7-membered monocyclic saturated heterocyclyl may optionally be substituted on one, two or three ring C-atoms with one or two —OH substituents;
Het² represents a heterocyclyl of formula (b-1):

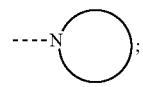

(b-1)

(b-1) represents a N-linked 4- to 7-membered monocyclic saturated heterocyclyl optionally containing one additional N-atom, or a N-linked 6- to 11-membered bicyclic saturated heterocyclyl, including fused, spiro and bridged cycles, optionally containing one or two additional N-atoms;
wherein in case (b-1) contains one or two additional N-atoms, said one or two N-atoms may optionally be substituted with $C_{1-4}$alkyl; and
wherein (b-1) may optionally be substituted on one, two or three ring C-atoms with one or two substituents each independently selected from the group consisting of —OH, cyano, and $C_{1-4}$alkyl-OH;
$R^{11b}$ represents $Het^{1e}$; $C_{1-4}$alkyl; $C_{1-4}$alkyl substituted with one, two or three OH substituents; or $C_{3-6}$cycloalkyl substituted with one, two or three substituents each independently selected from the group consisting of halo and —OH;
$R^{13}$ represents —O—$C_{1-4}$alkyl, —C(=O)$NR^{15a}R^{15b}$, $C_{3-6}$cycloalkyl, $Het^{1d}$, or —C(=O)—$Het^{1f}$;

$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, $C_{3-6}$cycloalkyl, $Ar^2$, or $Het^{1c}$;

$Ar^2$ represents phenyl optionally substituted with one $C_{1-4}$alkyl;

$Het^{1f}$ represents a heterocyclyl of formula (c-1):

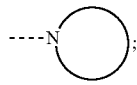
(c-1)

(c-1) represents a N-linked 4- to 7-membered monocyclic saturated heterocyclyl optionally containing one additional heteroatom selected from O and N;

wherein in case (c-1) contains one additional N-atom, said additional N-atom may optionally be substituted with $C_{1-4}$alkyl;

$R^{11a}$, $R^{14a}$, $R^{14c}$, and $R^{15a}$ each independently represents hydrogen or $C_{1-4}$alkyl;

$R^{14b}$, $R^{14d}$, and $R^{15b}$ each independently represents hydrogen; $C_{1-4}$alkyl; or $C_{3-6}$ cycloalkyl;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen;

$R^5$ represents —$OR^7$;

$R^7$ represents hydrogen or —C(=O)—$R^9$;

$R^9$ represents $C_{1-4}$alkyl; or $C_{1-4}$alkyl substituted with one —$NH_2$ substituent;

$R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; —O—$C_{3-6}$cycloalkyl; —O-$Het^{1b}$; —NH—C(=O)—$Het^{1g}$; and $C_{1-4}$alkyl substituted with one $R^{13}$;

$R^{10}$ represents —$NR^{11a}R^{11b}$ or $Het^2$;

$Het^{1g}$ represents a 4- to 7-membered monocyclic saturated heterocyclyl, attached to the remainder of the molecule of Formula (I) through any available ring carbon atom, said $Het^{1g}$ containing one or two N-atoms;

wherein said 4- to 7-membered monocyclic saturated heterocyclyl may optionally be substituted, where possible, on one or two ring N-atoms with a $C_{1-4}$alkyl substituent;

$Het^{1b}$ represents a 4- to 7-membered monocyclic saturated heterocyclyl, attached to the remainder of the molecule of Formula (I) through any available ring carbon atom, said $Het^{1b}$ containing one or two N-atoms;

wherein said 4- to 7-membered monocyclic saturated heterocyclyl may optionally be substituted, where possible, on one or two ring N-atoms with a $C_{1-4}$alkyl substituent; and wherein said 4- to 7-membered monocyclic saturated heterocyclyl may optionally be substituted on one ring C-atom with one halo substituent;

$Het^2$ represents a heterocyclyl of formula (b-1):

(b-1)

(b-1) represents a N-linked 4- to 7-membered monocyclic saturated heterocyclyl wherein (b-1) may optionally be substituted on one C-atom with one —OH substituent;

$R^{11b}$ represents $C_{1-4}$alkyl;

$R^{13}$ represents —O—$C_{1-4}$alkyl;

$R^{12}$ represents —O—$C_{1-4}$alkyl;

$R^{11a}$ represents hydrogen;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen;

$R^5$ represents —$OR^7$;

$R^7$ represents hydrogen or —C(=O)—$R^9$;

$R^9$ represents $C_{1-4}$alkyl;

$R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; —NH—C(=O)—$Het^{1g}$; and $C_{1-4}$alkyl substituted with one $R^{13}$;

$R^{10}$ represents —$NR^{11a}R^{11b}$ or $Het^2$;

$Het^{1g}$ represents a 4- to 7-membered monocyclic saturated heterocyclyl, attached to the remainder of the molecule of Formula (I) through any available ring carbon atom, said $Het^{1g}$ containing one or two N-atoms;

wherein said 4- to 7-membered monocyclic saturated heterocyclyl may optionally be substituted, where possible, on one or two ring N-atoms with a $C_{1-4}$alkyl substituent;

$Het^2$ represents a heterocyclyl of formula (b-1):

(b-1)

(b-1) represents a N-linked 4- to 7-membered monocyclic saturated heterocyclyl wherein (b-1) may optionally be substituted on one C-atom with one —OH substituent;

$R^{11b}$ represents $C_{1-4}$alkyl;

$R^{13}$ represents —O—$C_{1-4}$alkyl;

$R^{12}$ represents —O—$C_{1-4}$alkyl;

$R^{11a}$ represents hydrogen;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen;

$R^5$ represents —$OR^7$;

$R^7$ represents hydrogen or $-C(=O)-R^9$;
$R^9$ represents $C_{1-4}$alkyl; or $C_{1-4}$alkyl substituted with one $-NH_2$ substituent;
$R^3$ represents phenyl substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-O-C_{1-4}$alkyl-$R^{12}$; $-O-C_{3-6}$cycloalkyl; and $C_{1-4}$alkyl substituted with one $R^{13}$;
$R^{10}$ represents $-NR^{11a}R^{11b}$;
$R^{11b}$ represents $C_{1-4}$alkyl;
$R^{13}$ represents $-O-C_{1-4}$alkyl;
$R^{12}$ represents $-O-C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen;
$R^5$ represents $-OR^7$;
$R^7$ represents hydrogen or $-C(=O)-R^9$;
$R^9$ represents $C_{1-4}$alkyl;
$R^3$ represents phenyl substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$ alkyl; $-O-C_{1-4}$alkyl-$R^{12}$; $-O-C_{3-6}$cycloalkyl; and $C_{1-4}$alkyl substituted with one $R^{13}$;
$R^{10}$ represents $-NR^{11a}R^{11b}$;
$R^{11b}$ represents $C_{1-4}$alkyl;
$R^{13}$ represents $-O-C_{1-4}$alkyl;
$R^{12}$ represents $-O-C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents $-OR^7$;
$R^7$ represents hydrogen or $-C(=O)-R^9$;
$R^9$ represents $C_{1-4}$alkyl; or $C_{1-4}$alkyl substituted with one $-NH_2$ substituent;
$R^3$ represents phenyl substituted with one, two or three substituents each independently selected from the group consisting of halo; cyano; $C_{1-6}$alkyl; $-O-C_{1-4}$alkyl; $-C(=O)-R^{10}$; $-O-C_{3-6}$cycloalkyl; and $-O-Het^{1b}$;
$R^{10}$ represents $-NR^{11a}R^{11b}$;
$Het^{1b}$ represents a 4- to 7-membered monocyclic saturated heterocyclyl, attached to the remainder of the molecule of Formula (I) through any available ring carbon atom, said $Het^{1b}$ containing one or two N-atoms;
wherein said 4- to 7-membered monocyclic saturated heterocyclyl may optionally be substituted, where possible, on one or two ring N-atoms with a $C_{1-4}$alkyl substituent; and wherein said 4- to 7-membered monocyclic saturated heterocyclyl may optionally be substituted on one ring C-atom with one halo substituent;

$R^{11b}$ represents $C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-4}$alkyl substituted with one $R^5$;
Y represents $CR^4$;
$R^4$ represents hydrogen;
$R^5$ represents $-OR^7$;
$R^7$ represents hydrogen;
$R^3$ represents phenyl substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-O-C_{1-4}$alkyl-$R^{12}$; $-O-C_{3-6}$cycloalkyl; $-O-Het^{1b}$; $-NH-C(=O)-Het^{1g}$; and $C_{1-4}$alkyl substituted with one $R^{13}$;
$R^{10}$ represents $-NR^{11a}R^{11b}$;
$Het^{1b}$ represents a pyrrolidine attached to the remainder of the molecule of Formula (I) through any available ring carbon atom, wherein the N-atom is substituted with methyl and one ring C-atom is substituted with one halo substituent;
$Het^{1g}$ represents 4-piperidinyl wherein the N-atom is substituted with methyl;
$R^{11b}$ represents $C_{1-4}$alkyl;
$R^{13}$ represents $-O-C_{1-4}$alkyl;
$R^{12}$ represents $-O-C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-4}$alkyl substituted with one $R^5$;
Y represents $CR^4$;
$R^4$ represents hydrogen;
$R^5$ represents $-OR^7$;
$R^7$ represents hydrogen;
$R^3$ represents phenyl substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-O-C_{1-4}$alkyl-$R^{12}$; $-NH-C(=O)-Het^{1g}$; and $C_{1-4}$ alkyl substituted with one $R^{13}$;
in particular $R^3$ represents phenyl substituted with one, two or three substituents each independently selected from the group consisting of halo; cyano; $C_{1-6}$alkyl; $-O-C_{1-4}$alkyl, $-C(=O)-R^{10}$; $-S(=O)_2-C_{1-4}$alkyl; $-O-C_{1-4}$alkyl-$R^{12}$; and
$C_{1-4}$alkyl substituted with one $R^{13}$;
$R^{10}$ represents $-NR^{11a}R^{11b}$;
$Het^{1g}$ represents 4-piperidinyl wherein the N-atom is substituted with methyl;
$R^{11b}$ represents $C_{1-4}$alkyl;
$R^{13}$ represents $-O-C_{1-4}$alkyl;
$R^{12}$ represents $-O-C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;

$R^4$ represents hydrogen;
$R^5$ represents —$OR^7$;
$R^7$ represents hydrogen or —C(=O)—$R^9$;
$R^9$ represents $C_{1-4}$alkyl; or $C_{1-4}$alkyl substituted with one substituent selected from the group consisting of —$NH_2$ and —COOH;
$R^3$ represents phenyl substituted with one, two or three substituents each independently selected from the group consisting of halo; cyano; and $C_{1-6}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents phenyl substituted with one, two or three substituents each independently selected from the group consisting of halo; cyano; and $C_{1-6}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents methyl;
$R^2$ represents methyl substituted with one $R^5$;
Y represents $CR^4$;
$R^4$ represents hydrogen;
$R^5$ represents —$OR^7$;
$R^7$ represents hydrogen or —C(=O)—$R^9$;
$R^9$ represents $C_{1-4}$alkyl substituted with one —$NH_2$ substituent;
$R^3$ represents phenyl substituted with one, two or three substituents each independently selected from the group consisting of cyano; and $C_{1-6}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents methyl;
$R^2$ represents methyl substituted with one $R^5$;
Y represents $CR^4$;
$R^4$ represents hydrogen;
$R^5$ represents —$OR^7$;
$R^7$ represents hydrogen;
$R^3$ represents phenyl substituted with one, two or three substituents each independently selected from the group consisting of cyano; and $C_{1-6}$alkyl;
and the pharmaceutically acceptable addition salts, and the solvates thereof.

In an embodiment, the present invention relates to those compounds of Formula (I) and the pharmaceutically acceptable addition salts, and the solvates thereof, or any subgroup thereof as mentioned in any of the other embodiments, wherein
$R^5$ represents —$NR^{6a}R^{6b}$, or —$OR^7$;
$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, or —(C=O)—CH($NH_2$)—$C_{1-4}$alkyl-$Ar^1$.

Another embodiment of the present invention relates to those compounds of Formula (I) and the pharmaceutically acceptable addition salts, and the solvates thereof, or any subgroup thereof as mentioned in any of the other embodiments wherein Y represents $CR^4$ or N, in particular wherein Y represents $CR^4$; and wherein one or more of the following restrictions apply:

(a) $R^5$ represents halo, —$NR^{6a}R_{6b}$, or —$OR^7$; in particular $R^5$ represents —$NR^{6a}R^{6b}$, or —$OR^7$;
(b) $R^{6a}$ represents hydrogen;
(c) $R^{6b}$ represents —C(=O)—$C_{1-4}$alkyl; or —S(=O)$_2$—$C_{1-4}$alkyl;
(d) $R^7$ represents hydrogen, —$C_{1-4}$alkyl-$NR^{8a}R^{8b}$, —C(=O)—$R^9$, —S(=O)$_2$—OH, or —(C=O)—CH($NH_2$)—$C_{1-4}$alkyl-$Ar^1$; in particular $R^7$ represents hydrogen, —C(=O)—$R^9$, —S(=O)$_2$—OH, or —(C=O)—CH($NH_2$)—$C_{1-4}$alkyl-$Ar^1$;
(e) $R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl substituted with one $R^{13}$; and $C_{2-6}$alkynyl substituted with one $R^{13}$;

in particular $R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^{1g}$; $C_{1-4}$alkyl substituted with one, two or three halo atoms; $C_{1-4}$alkyl substituted with one, two or three —OH substituents; and $C_{1-4}$alkyl substituted with one $R^{13}$;
(f) $R^{18}$ represents a 5-membered aromatic ring containing one, two or three N-atoms; wherein said 5-membered aromatic ring may optionally be substituted with one substituent selected from the group consisting of $C_{1-4}$alkyl;
(g) Het$^{1a}$, Het$^{1c}$ and Het$^{1d}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, —O—$C_{1-4}$alkyl, and —N($C_{1-4}$alkyl)$_2$;
(h) Het$^{1b}$, Het$^{1e}$, Het$^{1g}$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^7$ and Het$^8$ containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two substituents each independently selected from the group consisting of —OH, and halo; in particular $Het^{1b}$, $Het^{1e}$, and $Het^{1g}$ each independently represents a 4- to 7-membered monocyclic saturated heterocyclyl, attached to the remainder of the molecule of Formula (I) through any available ring carbon atom, said $Het^{1b}$, $Het^{1e}$ and $Het^{1g}$ containing one or two heteroatoms each independently selected from O and N; wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two —OH substituents;

(i) $Het^2$ represents a heterocyclyl of formula (b-1):

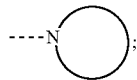

(b-1)

(b-1) represents a N-linked 4- to 7-membered monocyclic saturated heterocyclyl optionally containing one additional heteroatom selected from O and N, or a N-linked 6- to 11-membered bicyclic saturated heterocyclyl, including fused, spiro and bridged cycles, optionally containing one or two additional N-atoms;
wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and wherein (b-1) may optionally be substituted on one, two or three ring C-atoms with one or two substituents each independently selected from the group consisting of —OH, cyano, $C_{1-4}$alkyl, and $C_{1-4}$alkyl-OH;
in particular $Het^2$ represents a heterocyclyl of formula (b-1):

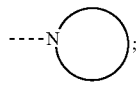

(b-1)

(b-1) represents a N-linked 4- to 7-membered monocyclic saturated heterocyclyl optionally containing one additional N-atom, or a N-linked 6- to 11-membered bicyclic saturated heterocyclyl, including fused, spiro and bridged cycles, optionally containing one or two additional N-atoms;
wherein in case (b-1) contains one or two additional N-atoms, said one or two N-atoms may optionally be substituted with $C_{1-4}$alkyl; and
wherein (b-1) may optionally be substituted on one, two or three ring C-atoms with one or two substituents each independently selected from the group consisting of —OH, cyano, and $C_{1-4}$alkyl-OH;

(j) $R^{11b}$ represents $Het^{1e}$; $C_{1-4}$alkyl; —$C_{1-4}$alkyl-$Het^5$; —$C_{1-4}$alkyl-$Het^8$, $C_{1-4}$alkyl substituted with one, two or three OH substituents; or $C_{3-6}$cycloalkyl substituted with one, two or three substituents each independently selected from the group consisting of halo and —OH; in particular $R^{11b}$ represents $Het^{1e}$; $C_{1-4}$alkyl; —$C_{1-4}$alkyl-$Het^5$; $C_{1-4}$alkyl substituted with one, two or three OH substituents; or $C_{3-6}$cycloalkyl substituted with one, two or three substituents each independently selected from the group consisting of halo and —OH;

(k) $R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;

(l) $R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, $C_{3-6}$cycloalkyl, $Ar^2$, or $Het^{1c}$;

(m) $Ar^1$ represents phenyl;

(n) $Het^5$, $Het^6$ and $Het^{1f}$ each independently represents a heterocyclyl of formula (c-1):

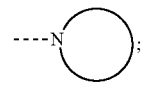

(c-1)

(c-1) represents a N-linked 4- to 7-membered monocyclic saturated heterocyclyl optionally containing one additional heteroatom selected from O and N;
wherein in case (c-1) contains one additional N-atom, said additional N-atom may optionally be substituted with $C_{1-4}$alkyl;

(o) $R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of —OH and —O—$C_{1-4}$alkyl; or —S(=O)$_2$—$C_{1-4}$alkyl; in particular $R^{14b}$, $R^{14d}$, $R^{15b}$, and $R^{19b}$ each independently represents hydrogen; $C_{1-4}$alkyl; $C_{3-6}$cycloalkyl; or $C_{1-4}$alkyl substituted with one —O—$C_{1-4}$alkyl.

Another embodiment of the present invention relates to those compounds of Formula (I) and the pharmaceutically acceptable addition salts, and the solvates thereof, or any subgroup thereof as mentioned in any of the other embodiments wherein Y represents $CR^4$ or N, in particular wherein Y represents $CR^4$; and wherein one or more of the following restrictions apply:

(a) $R^4$ represents hydrogen;

(b) $R^5$ represents —$OR^7$;

(c) $R^7$ represents hydrogen or —C(=O)—$R^9$;

(d) $R^9$ represents $C_{1-4}$alkyl;

(e) $R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; —NH—C(=O)—$Het^{1g}$; and $C_{1-4}$alkyl substituted with one $R^{13}$;

(g) $Het^{1g}$ represents a 4- to 7-membered monocyclic saturated heterocyclyl, attached to the remainder of the molecule of Formula (I) through any available ring carbon atom, said $Het^{1g}$ containing one or two N-atoms;
wherein said 4- to 7-membered monocyclic saturated heterocyclyl may optionally be substituted, where possible, on one or two ring N-atoms with a $C_{1-4}$alkyl substituent;

(h) Het² represents a heterocyclyl of formula (b-1):

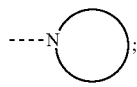

(b-1) represents a N-linked 4- to 7-membered monocyclic saturated heterocyclyl wherein (b-1) may optionally be substituted on one C-atom with one —OH substituent;
(i) $R^{11b}$ represents $C_{1-4}$alkyl;
(j) $R^{13}$ represents —O—$C_{1-4}$alkyl;
(k) $R^{12}$ represents —O—$C_{1-4}$alkyl;
(l) $R^{11a}$ represents hydrogen.

In an embodiment, the present invention relates to a subgroup of Formula (I), hereby named compounds of Formula (I'), and the pharmaceutically acceptable addition salts, and the solvates thereof:

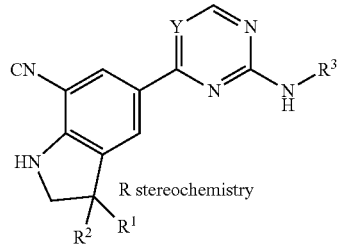

(I')

wherein $R^1$ represents $C_{1-4}$alkyl;
$R^2$ represents $C_{1-6}$alkyl substituted with one $R^5$;
in particular wherein $R^1$ represents $C_{1-4}$alkyl;
$R^2$ represents $C_{1-6}$alkyl substituted with one $R^5$;
$R^5$ represents —$OR^7$;
more in particular wherein $R^1$ represents $C_{1-4}$alkyl;
$R^2$ represents $C_{1-6}$alkyl substituted with one $R^5$;
$R^5$ represents —$OR^7$;
$R^7$ represents hydrogen;
and wherein all other variables are defined according to any of the other embodiments.

In an embodiment, the present invention relates to a subgroup of Formula (I), hereby named compounds of Formula (I''), and the pharmaceutically acceptable addition salts, and the solvates thereof:

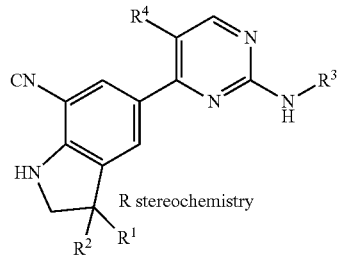

(I'')

wherein $R^1$ represents $C_{1-4}$alkyl;
$R^2$ represents $C_{1-6}$alkyl substituted with one $R^5$;
in particular wherein $R^1$ represents $C_{1-4}$alkyl;
$R^2$ represents $C_{1-6}$alkyl substituted with one $R^5$;
$R^5$ represents —$OR^7$;
more in particular wherein $R^1$ represents $C_{1-4}$alkyl;
$R^2$ represents $C_{1-6}$alkyl substituted with one $R^5$;
$R^5$ represents —$OR^7$;
$R^7$ represents hydrogen;
and wherein all other variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents methyl;
$R^2$ represents methyl or —$CH_2$—OH.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents methyl; $R^2$ represents —$CH_2$—OH.

In an embodiment, the present invention relates to those compounds of Formula (I) and the pharmaceutically acceptable addition salts, and the solvates thereof, or any subgroup thereof as mentioned in any of the other embodiments, wherein $R^3$ represents phenyl which is substituted with one, two or three substituents according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
$R^3$ represents phenyl optionally substituted with one, two or three substituents according to any of the other embodiments, provided however that the substituents are not selected from the group consisting of —S($=$O)$_2$—$C_{1-4}$alkyl; —S($=$O)($=$N—$R^{20a}$)—$C_{1-4}$alkyl; and —P($=$O)—($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein $R^4$ is hydrogen or fluoro.

In an embodiment, the present invention relates to those compounds of Formula (I) and the pharmaceutically acceptable addition salts, and the solvates thereof, or any subgroup thereof as mentioned in any of the other embodiments, wherein $R^4$ is hydrogen.

In an embodiment, the present invention relates to those compounds of Formula (I) and the pharmaceutically acceptable addition salts, and the solvates thereof, or any subgroup thereof as mentioned in any of the other embodiments, wherein $R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^5$ represents —$OR^7$; and
$R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^9$ represents $C_{1-4}$alkyl, or $C_{1-4}$alkyl substituted with one substituent selected from the group consisting of —$NH_2$, —COOH, and Het⁶.

In an embodiment, the present invention relates to those compounds of Formula (I) and the pharmaceutically acceptable addition salts, and the solvates thereof, or any subgroup thereof as mentioned in any of the other embodiments, wherein $R^{18}$ is attached to the remainder of the molecule of Formula (I) via a carbon atom.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

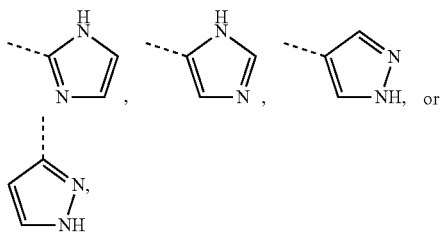

in particular

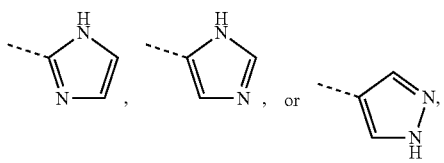

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

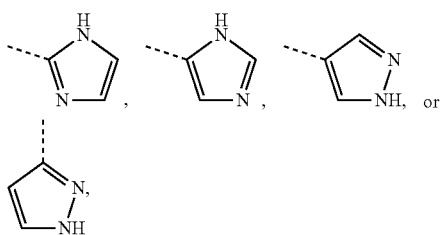

in particular

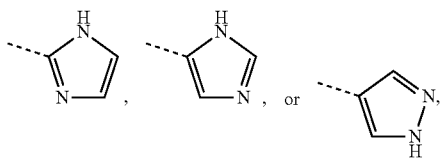

each substituted on the NH with $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents morpholinyl, piperidinyl, pyrrolidinyl, oxetanyl, azetidinyl, piperazinyl, tetrahydro-2H-pyranyl, or hexahydro-1,4-oxazepinyl, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents

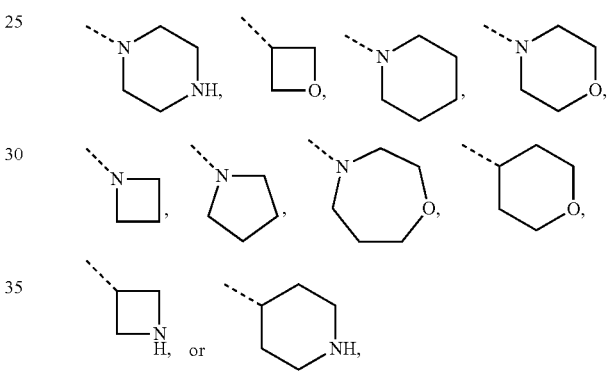

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$ represents

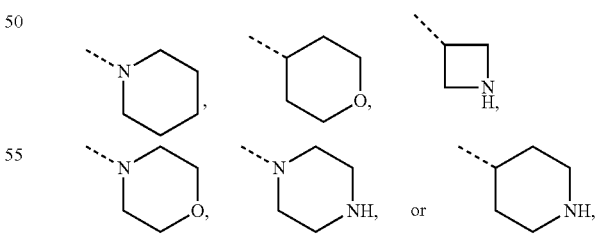

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1c}$ represents

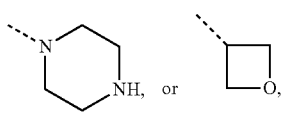

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1d}$ represents

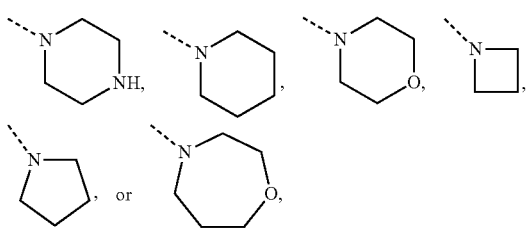

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, attached to the remainder of the molecule of Formula (I) through any available ring carbon atom,
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents piperidinyl, tetrahydro-2H-pyranyl, or pyrrolidinyl, attached to the remainder of the molecule of Formula (I) through any available ring carbon atom,
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents

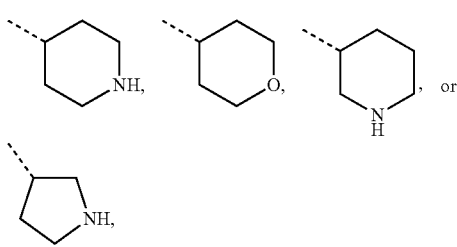

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1g}$ represents

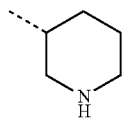

optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1e}$ represents

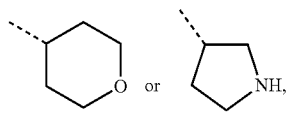

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$ represents

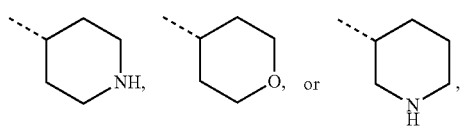

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^2$ represents

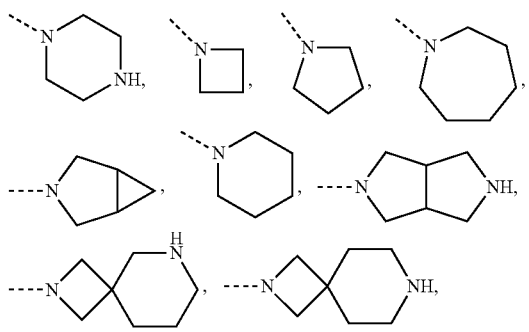

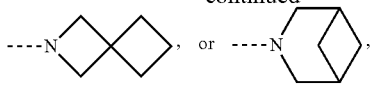

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{3a}$, $Het^{3b}$, $Het^5$, $Het^6$ and $Het^{1f}$ each independently represents

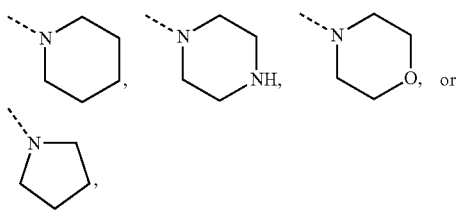

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^4$ represents pyrrolidinyl, piperidinyl, tetrahydropyranyl, azetidinyl, or 1,1-dioxidethiopyranyl;
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^5$ represents

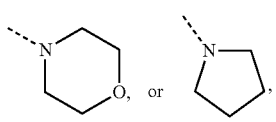

each optionally substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^6$ represents

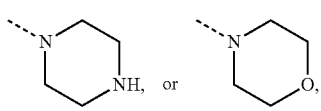

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1f}$ represents

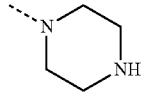

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^7$ and $Het^8$ each independently represent

optionally substituted on carbon atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein $Het^2$ represents a heterocyclyl of formula (b-1):

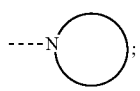

(b-1)

(b-1) represents a N-linked 4- to 7-membered monocyclic saturated heterocyclyl optionally containing one additional heteroatom selected from O, S, $S(=O)_p$ and N; wherein in case (b-1) contains one additional N-atom, said N-atom may optionally be substituted with $C_{1-4}$alkyl; and
wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —$NH_2$, —NH($C_{1-4}$alkyl), —N($C_{1-4}$alkyl)$_2$, and $C_{1-4}$alkyl-OH.

In an embodiment, the present invention relates to those compounds of Formula (I) and the pharmaceutically acceptable addition salts, and the solvates thereof, or any subgroup thereof as mentioned in any of the other embodiments, wherein Het$^{1a}$ represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;
wherein said 4- to 7-membered monocyclic saturated heterocyclyl or said 6- to 11-membered bicyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1c}$ and Het$^{1d}$ each independently represents a 4- to 7-membered monocyclic saturated heterocyclyl containing one or two heteroatoms each independently selected from O, S, S(=O)$_p$ and N; or in case Het$^{1c}$ and Het$^{1d}$ are attached to the remainder of the molecule of Formula (I) through an N-atom, Het$^{1c}$ and Het$^{1d}$ may also represent a N-linked 6- to 11-membered bicyclic saturated heterocyclyl, including fused, spiro and bridged cycles, optionally containing one or two additional heteroatoms each independently selected from O, S, S(=O)$_p$ and N;
wherein said 4- to 7-membered monocyclic saturated heterocyclyl or said N-linked 6- to 11-membered bicyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said N-linked 6- to 11-membered bicyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$ alkyl, —O—C$_{1-4}$alkyl, —NH$_2$, —NH(C$_{1-4}$alkyl), and —N(C$_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein Y represents CR$^4$.

In an embodiment, the present invention relates to a subgroup of Formula (I), hereby named compounds of Formula (I-x), and the pharmaceutically acceptable addition salts, and the solvates thereof:

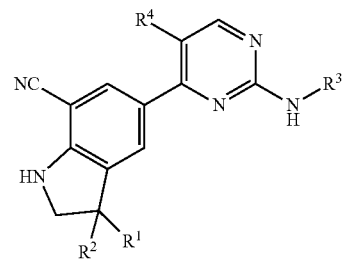

(I-x)

wherein all variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Y represents N.

In an embodiment, the present invention relates to a subgroup of Formula (I), hereby named compounds of Formula (I-y), and the pharmaceutically acceptable addition salts, and the solvates thereof:

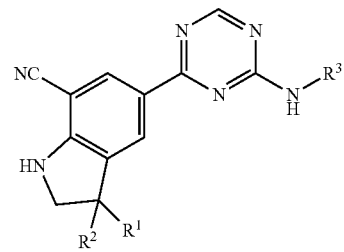

(I-y)

wherein all variables are defined according to any of the other embodiments.

In an embodiment, the present invention relates to a subgroup of Formula (I) as defined in the general reaction schemes.

In an embodiment the compound of Formula (I) is selected from the group consisting of compounds 1, 4, 45, 66, 68, 73, 74, 110, 125, 138, 155, 156 and 232, tautomers and stereoisomeric forms thereof,
and the free bases, any pharmaceutically acceptable addition salts, and the solvates thereof.

In an embodiment the compound of Formula (I) is selected from the group consisting of compounds 1, 4, 45, 66, 68, 73, 74, 110, 125, 138, 155, 156 and 232.

In an embodiment the compound of Formula (I) is selected from the group consisting of compounds 1, 138, 155, 156 and 232, tautomers and stereoisomeric forms thereof, and the free bases, any pharmaceutically acceptable addition salts, and the solvates thereof.

In an embodiment the compound of Formula (I) is selected from the group consisting of compounds 1, 138, 155, 156 and 232.

In an embodiment the compound of Formula (I) is selected from the group consisting of compounds 1, 4, 45, 66, 68, 73, 74, 110, and 125, tautomers and stereoisomeric forms thereof,
and the pharmaceutically acceptable addition salts, and the solvates thereof.

In an embodiment the compound of Formula (I) is selected from the group consisting of compounds 1, 4, 45, 66, 68, 73, 74, 110, and 125.

In an embodiment the compound of Formula (I) is selected from the group consisting of any of the exemplified compounds, tautomers and stereoisomeric forms thereof, and the free bases, any pharmaceutically acceptable addition salts, and the solvates thereof.

In an embodiment the compound of Formula (I) is selected from the group consisting of

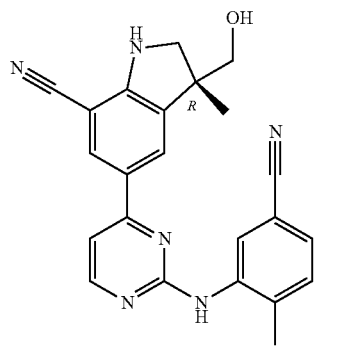

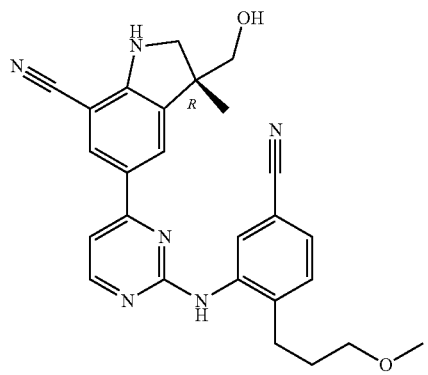

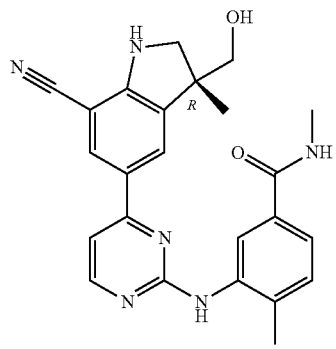

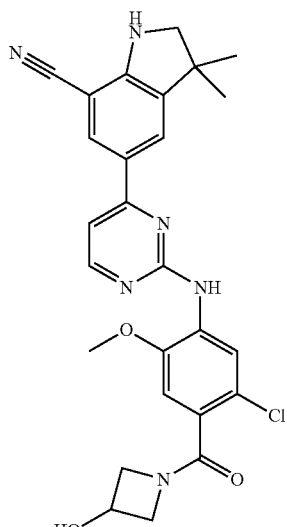

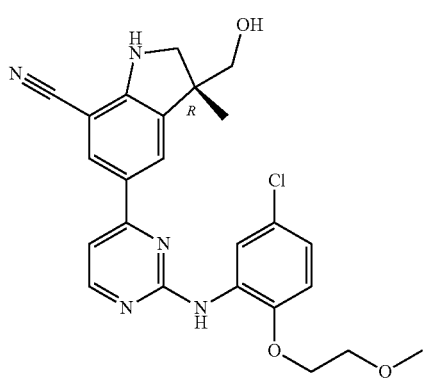

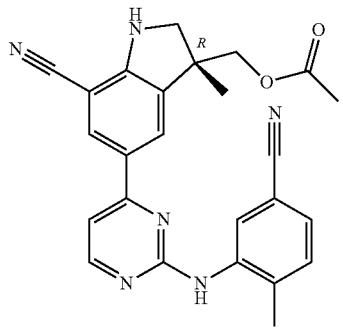

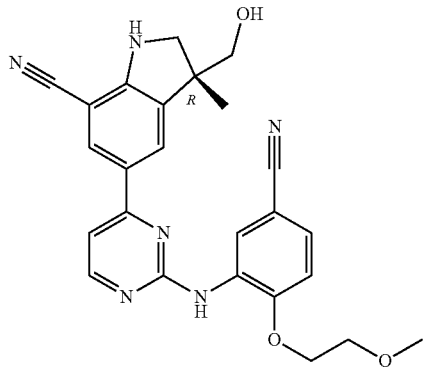

-continued

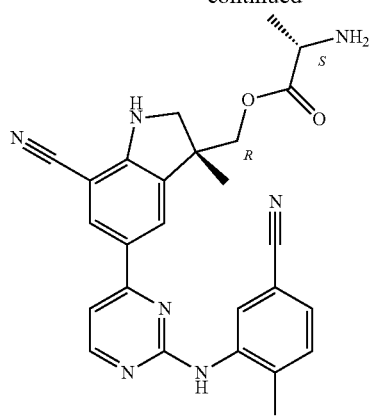

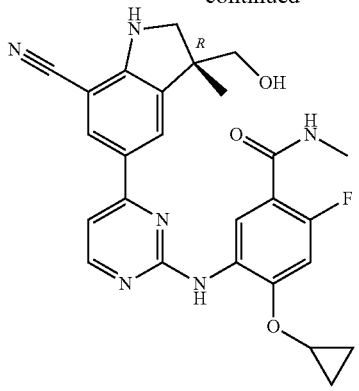

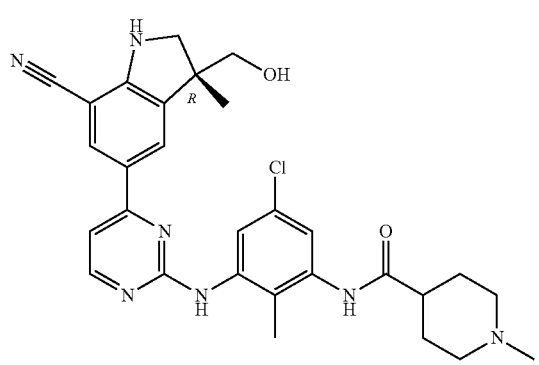

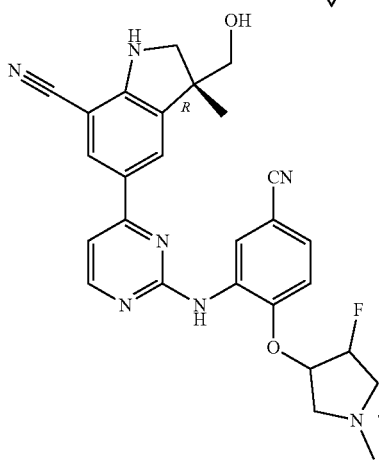

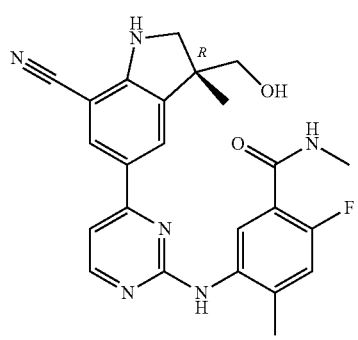

tautomers and stereoisomeric forms thereof,
and the pharmaceutically acceptable addition salts, and the solvates thereof.

In an embodiment the compound of Formula (I) is selected from the group consisting of

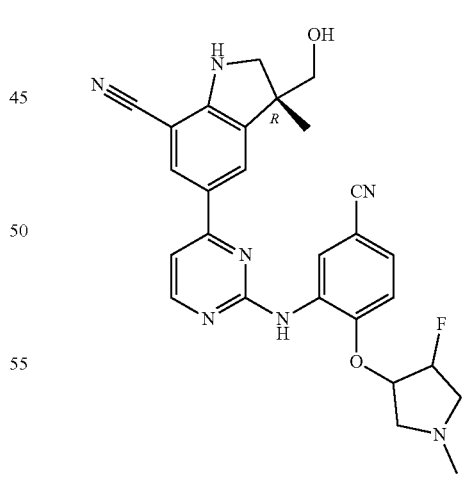

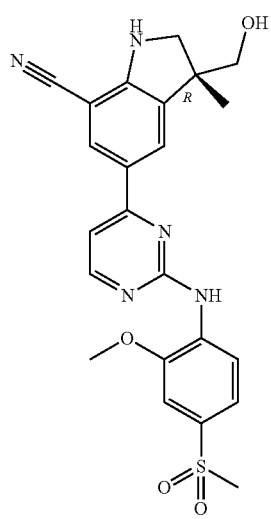

tautomers and stereoisomeric forms thereof,
and the pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realise that functionalization reactions illustrated in the Schemes below for compounds of Formula (I) wherein Y is $CR^4$, may also be carried out for compounds wherein Y is N. The skilled person will realise this applies, for example and without limitation, to steps 3 and 4 of scheme 2 and scheme 18.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 6, the NH moiety on the pyrimidinyl can be protected with a t-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of formula (I).

The skilled person will realize that intermediates and final compounds shown in the schemes below may be further functionalized according to methods well-known by the person skilled in the art.

Scheme 1

In general, compounds of Formula (I) wherein $R^2$ is $R^{2a}$ being $C_{1-6}$alkyl, Y is $CR^4$, and wherein all the other variables are defined according to the scope of the present invention, hereby named compounds of Formula (Ia), can be prepared according to the following reaction Scheme 1. In Scheme 1 halo$^1$ is defined as Cl, Br or I; and PG$^1$ represents a suitable protecting group, such as for example tert-(butoxycarbonyl). All other variables in Scheme 1 are defined according to the scope of the present invention.

In Scheme 1, the following reaction conditions apply:

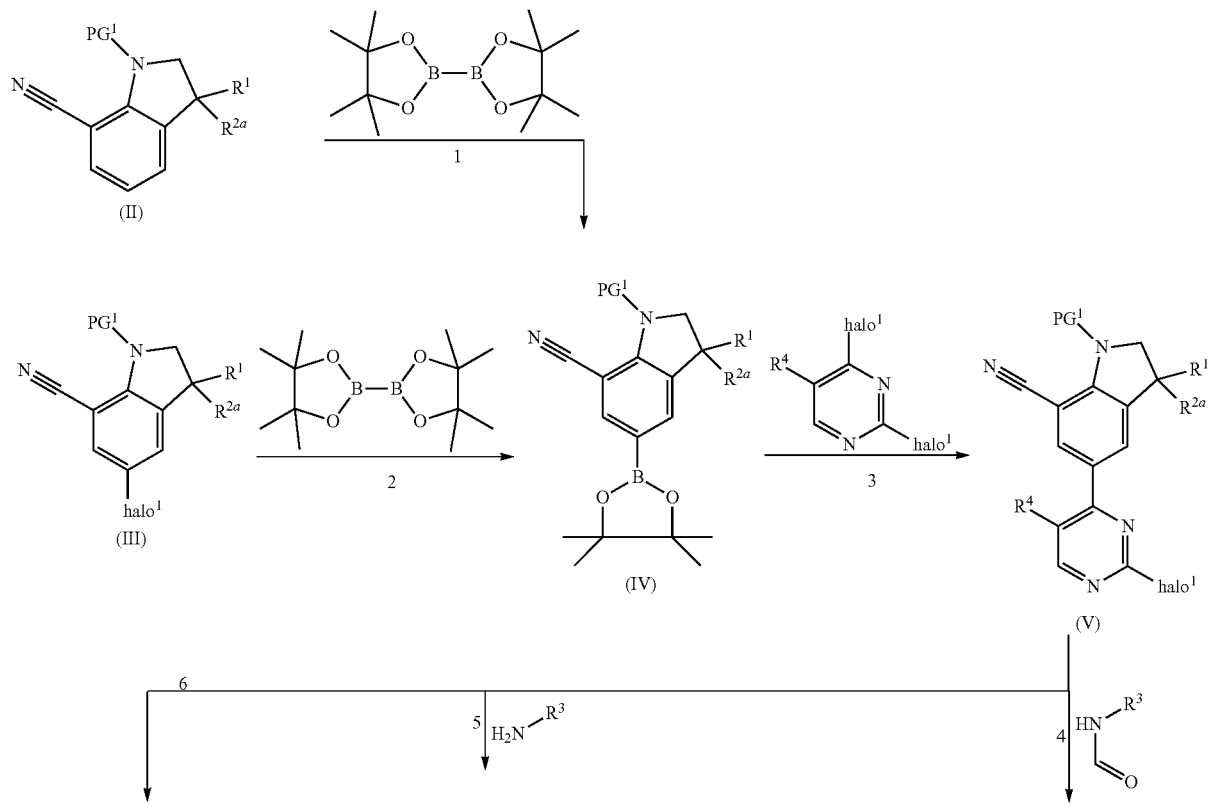

-continued

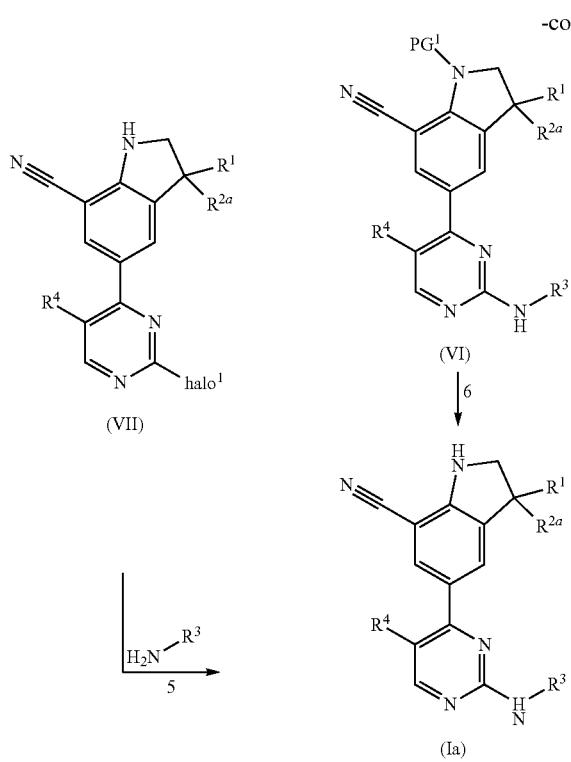

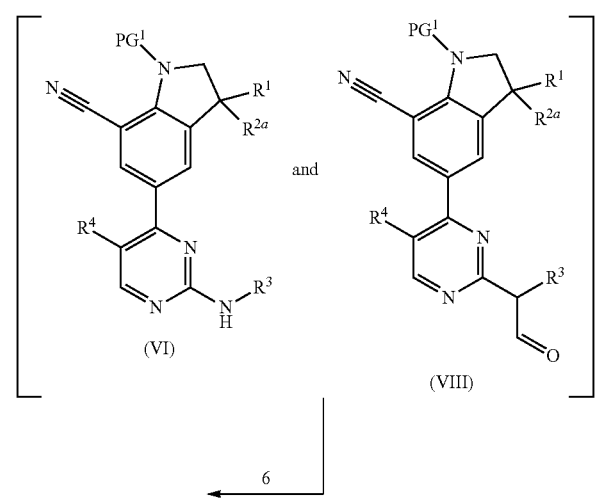

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-μ-methoxydiiridium (I) ([Ir(OCH$_3$)(C$_8$H$_{12}$)]$_2$), and a suitable solvent such as for example heptane;

2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

3: at a suitable temperature such as for example 85° C., in the presence of a suitable catalyst such as for example palladium tetrakis (Pd(PPh$_3$)$_4$), a suitable base such as for example sodium carbonate, and a suitable solvent such as for example 1,4-dioxane;

4: at a suitable temperature such as for example room temperature, in presence of a suitable base such as for example sodium hydride, and a suitable solvent such as for example dimethylformamide;

5: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BI-NAP), a suitable base such as for example cesium carbonate, and a suitable solvent such as for example 1,4-dioxane, optionally under microwave activation;

or alternatively at a suitable temperature such as for example 95° C., in the presence of a suitable acid such as for example p-toluenesulfonic acid and a suitable solvent such as for example 1,4-dioxane;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

Scheme 2

In general, compounds of Formula (I) wherein $R^2$ is $R^{2a}$ being $C_{1-6}$alkyl, $R^3$ is phenyl substituted with —C(=O)—$R^{10}$ and optionally substituted with other substituents according to the scope of the present invention, Y is $CR^4$, and wherein all the other variables are as defined according to the scope of the present invention, hereby named compounds of Formula (Ib), can be prepared according to the following reaction Scheme 2. In Scheme 2 halo$^1$ is defined as Cl, Br or I; $PG^1$ represents a suitable protecting group, such as for example tert-(butoxycarbonyl). All other variables in Scheme 2 are defined according to the scope of the present invention.

In Scheme 2, the following reaction conditions apply:

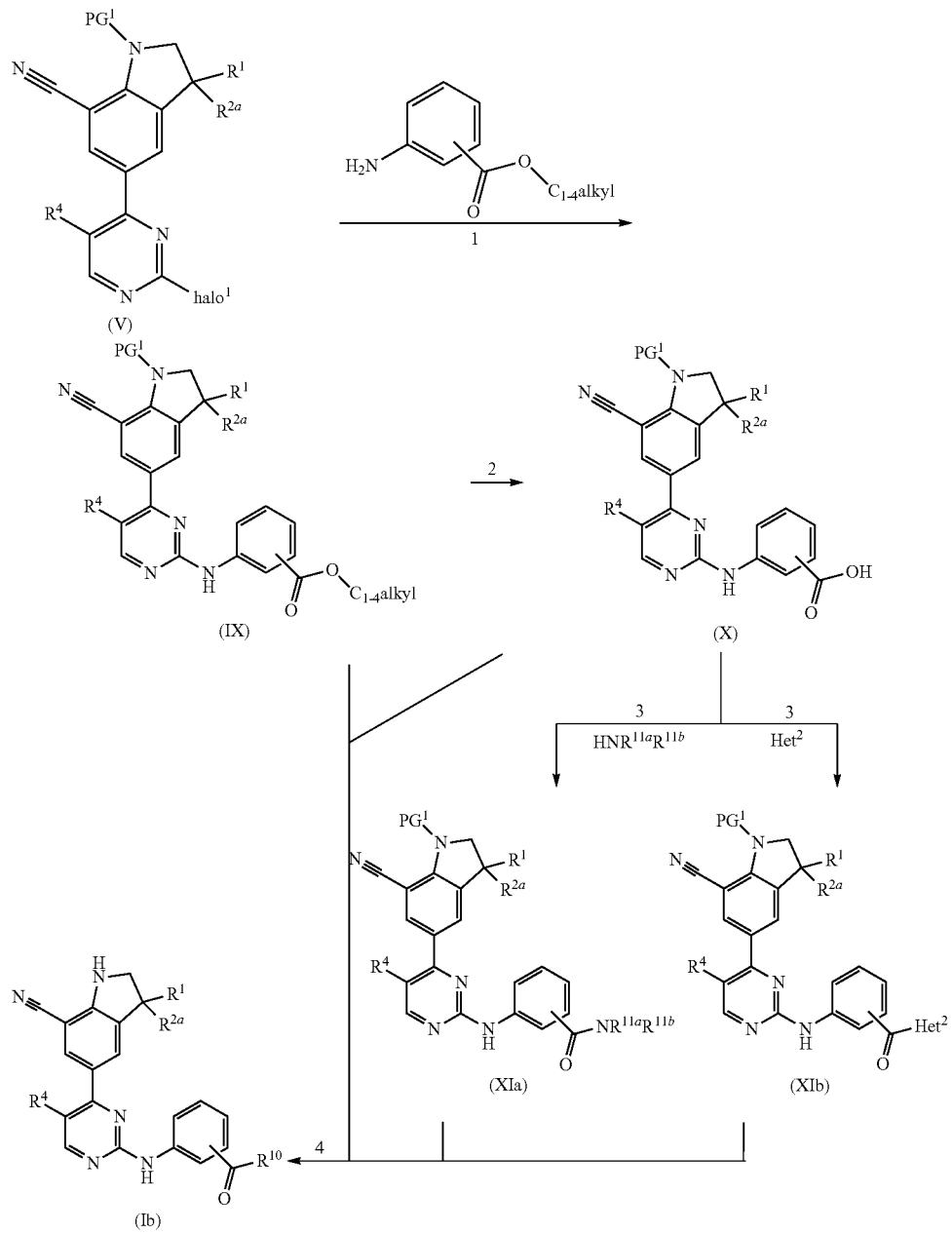

1: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BI-NAP), a suitable base such as for example cesium carbonate, and a suitable solvent such as for example 1,4-dioxane, optionally under microwave activation;
2: at a suitable temperature such as for example 70° C., in presence of a suitable base such as for example lithium hydroxide, and a suitable solvent such as for example a mixture of tetrahydrofuran and water;
3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethylacetate, or 1,4-dioxane, and a suitable time such as for example 3 hours.

Scheme 3

In general, compounds of Formula (I) wherein $R^2$ is $R^{2b}$ being $C_{1-6}$alkyl substituted with one OH, Y is $CR^4$, and wherein all the other variables are as defined according to the scope of the present invention, hereby named compounds of Formula (Ic), can be prepared according to the following reaction Scheme 3. In Scheme 3 halo$^1$ is defined as Cl, Br or I; PG$^1$ represents a suitable protecting group, such as for example tert-(butoxycarbonyl) and PG$^2$ represents a suitable protecting group, such as for example tert-butyl-dimethylsilyl. All other variables in Scheme 3 are defined according to the scope of the present invention.
In Scheme 3, the following reaction conditions apply:
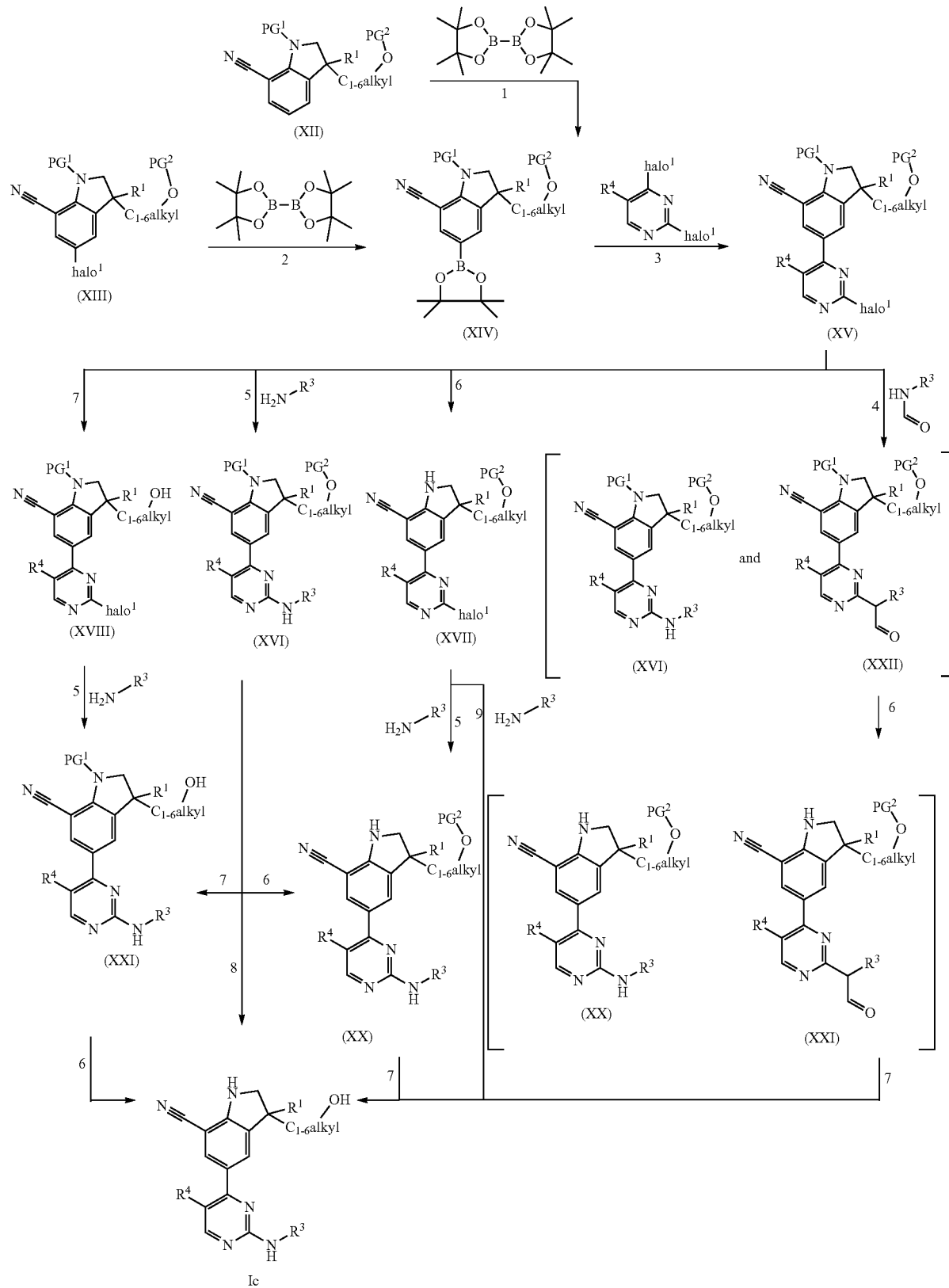

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-µ-methoxydiiridium (I) ([Ir(OCH$_3$)(C$_8$H$_{12}$)]$_2$), and a suitable solvent such as for example heptane;

2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

3: at a suitable temperature such as for example 85° C., in the presence of a suitable catalyst such as for example palladium tetrakis (Pd(PPh$_3$)$_4$), a suitable base such as for example sodium carbonate, and a suitable solvent such as for example 1,4-dioxane;

4: at a suitable temperature such as for example room temperature, in presence of a suitable base such as for example sodium hydride, and a suitable solvent such as for example dimethylformamide;

5: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BI-NAP), a suitable base such as for example cesium carbonate, and a suitable solvent such as for example 1,4-dioxane, optionally under microwave activation;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;

7: at a suitable temperature such as for example room temperature, in presence of a suitable desilylating agent such as for example tetra-n-butylammonium fluoride and a suitable solvent such as for example 2-methyltetrahydrofuran or tetrahydrofuran;

8: at a suitable temperature such as for example reflux, in presence of a suitable acid such as for example aqueous hydrochloric acid with a suitable solvent such as for example dichloromethane, methanol, ethyl acetate or 1,4-dioxane, and a suitable time such as for example 6 hours;

9: at a suitable temperature such as for example 95° C., in the presence of a suitable acid such as for example p-toluenesulfonic acid and a suitable solvent such as for example 1,4-dioxane.

Scheme 4

In general, compounds of Formula (I) wherein $R^2$ is $R^{2b}$ being $C_{1-6}$alkyl substituted with one OH, $R^3$ is phenyl substituted with —C(=O)—$R^{10}$ and optionally substituted with other substituents according to the scope of the present invention, Y is $CR^4$, and wherein all the other variables are as defined according to the scope of the present invention, hereby named compounds of Formula (Id), can be prepared according to the following reaction Scheme 4. In Scheme 4 halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 4 are defined according to the scope of the present invention.

In Scheme 4, the following reaction conditions apply:

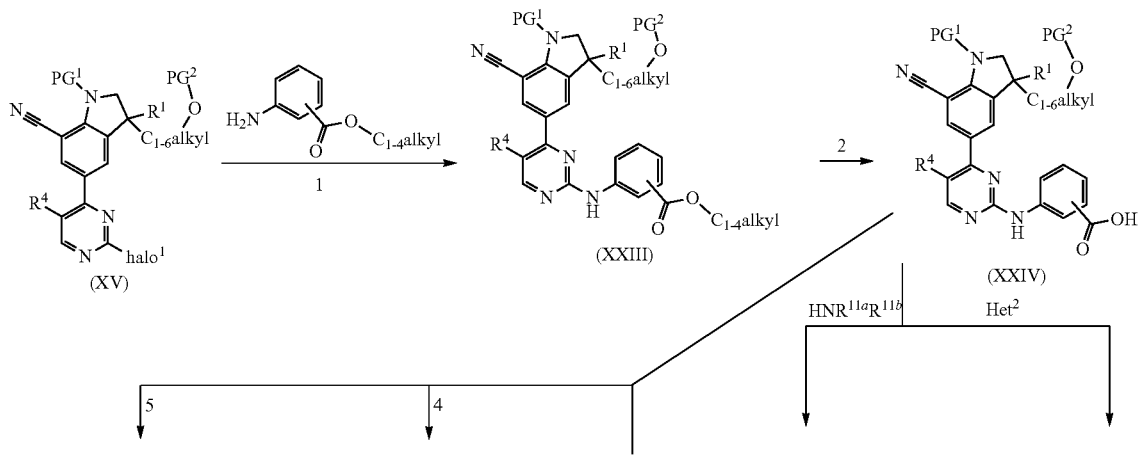

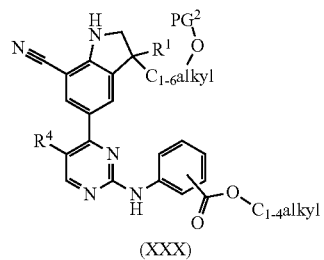
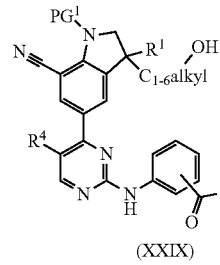
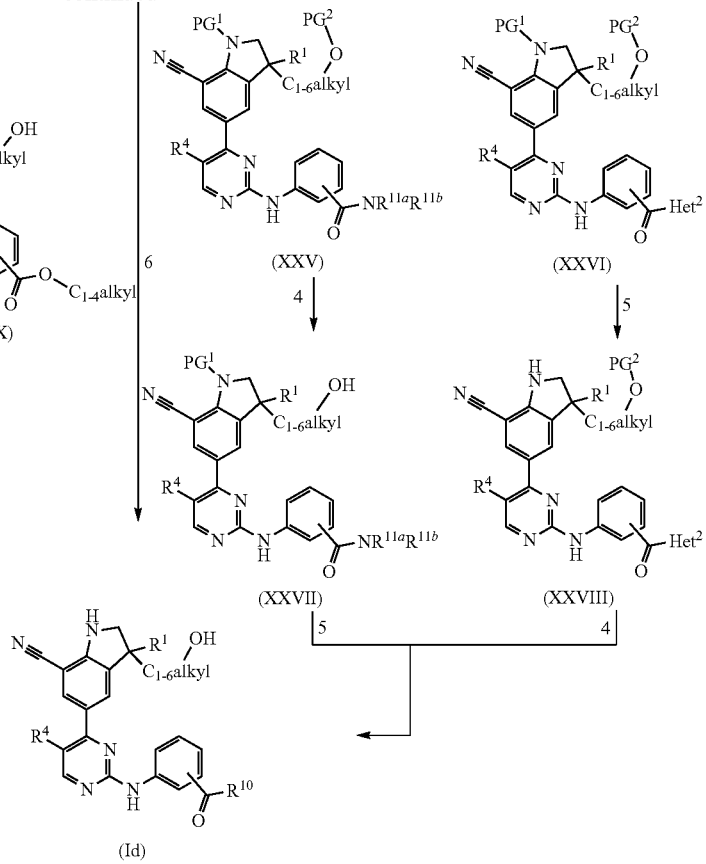

1: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;
2: at a suitable temperature such as for example 70° C., in presence of a suitable base such as for example lithium hydroxide, and a suitable solvent such as for example a mixture of tetrahydrofuran and water;
3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;
4: at a suitable temperature such as for example room temperature, in presence of a suitable desilylating agent such as for example tetra-n-butylammonium fluoride and a suitable solvent such as for example 2-methyltetrahydrofuran or tetrahydrofuran;
5: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.
6: at a suitable temperature such as for example reflux, in presence of a suitable acid such as for example aqueous hydrochloric acid with a suitable solvent such as for example dichloromethane, methanol, ethyl acetate or 1,4-dioxane, and a suitable time such as for example 6 hours.

Scheme 5

In general, compounds of Formula (I) wherein $R^2$ is $R^{2c}$ being $C_{1-6}$alkyl substituted with one $Het^{3a}$ or —$NR^{6a}R^{6b}$, wherein $R^{6b}$ is $R^{6ba}$ being H, $C_{1-4}$alkyl and $C_{3-6}$cycloalkyl, Y is $CR^4$, and wherein all the other variables are as defined according to the scope of the present invention, hereby named compounds of Formula (Ie) and Formula (If), can be prepared according to the following reaction Scheme 5. In Scheme 5 $PG^1$ represents a suitable protecting group, such as for example tert-(butoxycarbonyl). All other variables in Scheme 5 are defined according to the scope of the present invention.

In Scheme 5, the following reaction conditions apply:

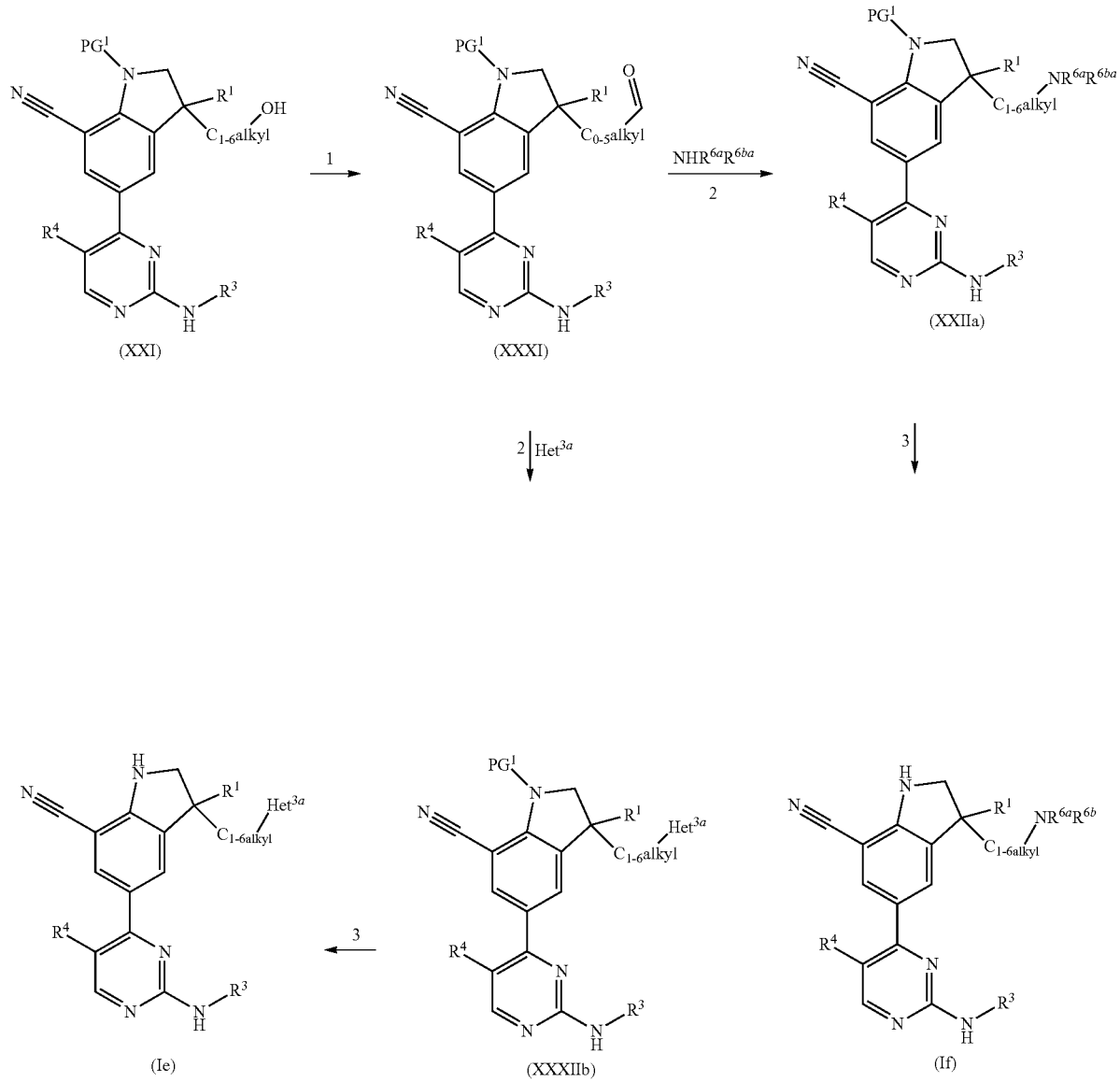

1: at a suitable temperature such as for example −78° C., in the presence of oxalyl chloride and dimethyl sulfoxide as reagents, a suitable base such as for example N,N-diisopropylethylamine, and a suitable solvent such as for example dichloromethane;

2: at a suitable temperature such as for example room temperature, in the presence of a suitable acid such as for example acetic acid, a suitable reducing agent such as for example sodium triacetoxyborohydride, and a suitable solvent such as for example dichloroethane;

3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

Scheme 6

In general, compounds of Formula (I) wherein $R^2$ is $C_{1-6}$alkyl substituted with one $OR^{7a}$, $R^{7a}$ being —C(=O)—$R^9$ or —(C=O)—CH(NH$_2$)—C$_{1-4}$alkyl-Ar$^1$), Y is CR$^4$, and wherein all the other variables are as defined according to the scope of the present invention, hereby named compounds of Formula (Ig), can be prepared according to the following reaction Scheme 6. In Scheme 6 PG$^3$ represents a suitable protecting group, such as for example a tert-(butoxycarbonyl), a tert-butyl or a benzyl. All other variables in Scheme 6 are defined according to the scope of the present invention.

In Scheme 6, the following reaction conditions apply:

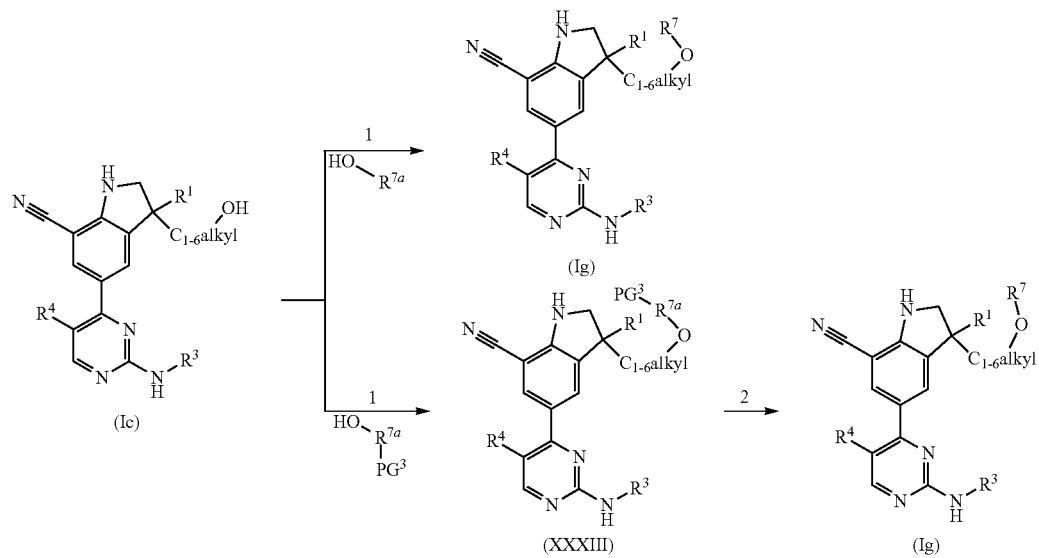

1: at a suitable temperature such as for example room temperature, in the presence of a suitable coupling reagent such as for example 1-[bis(dimethylamino)methylene]-1H-1,2,3-triazolo[4,5-b]pyridinium 3-oxid hexafluorophosphate (HATU), in the presence of a suitable base as for example N,N-diisopropylethylamine, and a suitable solvent such as for example a mixture of tetrahydrofuran and dimethylformamide, and optionally followed by a deprotection step using a suitable acid such as for example hydrochloric acid in a suitable solvent such as for example 1,4-dioxane;
2: at a suitable temperature such as for example 0° C. or room temperature, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

Scheme 7

In general, compounds of Formula (I) wherein $R^2$ is $C_{1-6}$alkyl substituted with one $OR^{7b}$, $R^{7b}$ being $C_{1-4}$alkyl, Y is $CR^4$, and wherein all the other variables are as defined according to the scope of the present invention, hereby named compounds of Formula (Ih), can be prepared according to the following reaction Scheme 7. In Scheme 7 $halo^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl; W represents a leaving group, such as for example a methane sulfonate or toluene sulfonate or an halogen (Cl, Br or I). All other variables in Scheme 7 are defined according to the scope of the present invention.

In Scheme 7, the following reaction conditions apply:

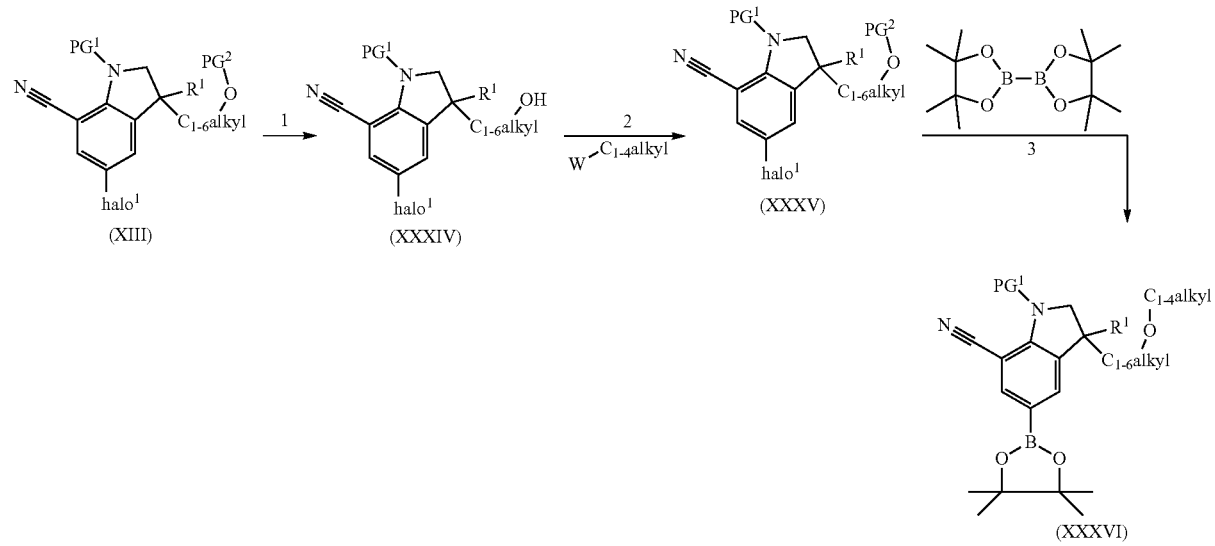

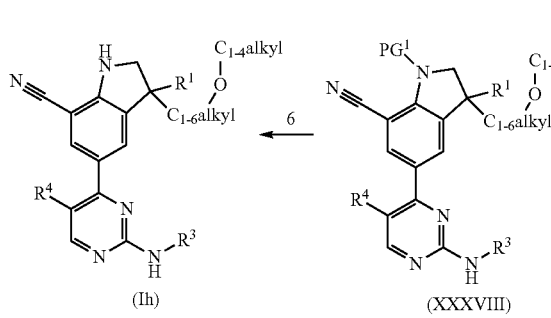
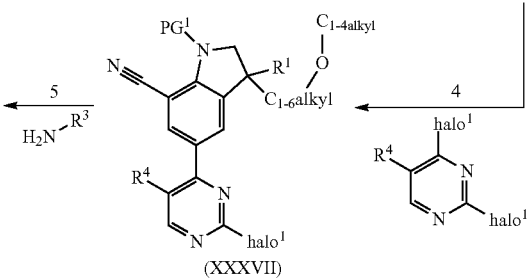

1: at a suitable temperature such as for example room temperature, in presence of a suitable desilylating agent such as for example tetra-n-butylammonium fluoride and a suitable solvent such as for example 2-methyltetrahydrofuran or tetrahydrofuran;
2: at a suitable temperature such as for example room temperature, in the presence of a suitable base as for example sodium hydride, and a suitable solvent such as for example dimethylformamide;
3: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;
4: at a suitable temperature such as for example 80° C., in the presence of a suitable catalyst such as for example palladium tetrakis (Pd(PPh$_3$)$_4$), a suitable base such as for example sodium carbonate, and a suitable solvent such as for example 1,4-dioxane;
5: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

Scheme 8

In general, compounds of Formula (I) wherein R$^2$ is C$_{1-6}$alkyl substituted with one OR$^{7c}$, R$^{7c}$ being C$_{1-4}$alkyl-NR$^{8a}$R$^{8b}$ or C$_{1-4}$alkyl-Het$^{3b}$, Y is CR$^4$, and wherein all the other variables are as defined according to the scope of the present invention, hereby named compounds of Formula (Ii) and Formula (Ij), can be prepared according to the following reaction Scheme 8. In Scheme 8 halo$^1$ is defined as Cl, Br or I; PG$^1$ represents a suitable protecting group, such as for example tert-(butoxycarbonyl); W$^1$ represents a leaving group, such as for example a methane sulfonate or toluene sulfonate or an halogen (Cl, Br or I); W$^2$ represents a leaving group, such as for example a mesyl or a tosyl. All other variables in Scheme 8 are defined according to the scope of the present invention.

In Scheme 8, the following reaction conditions apply:

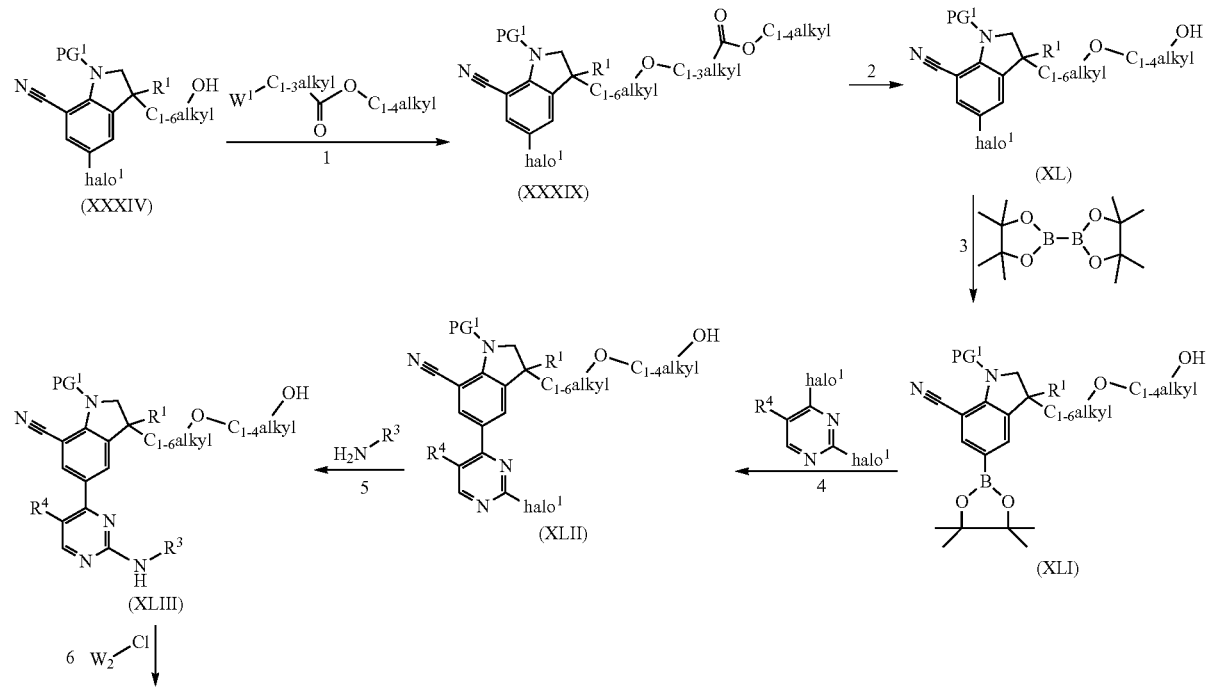

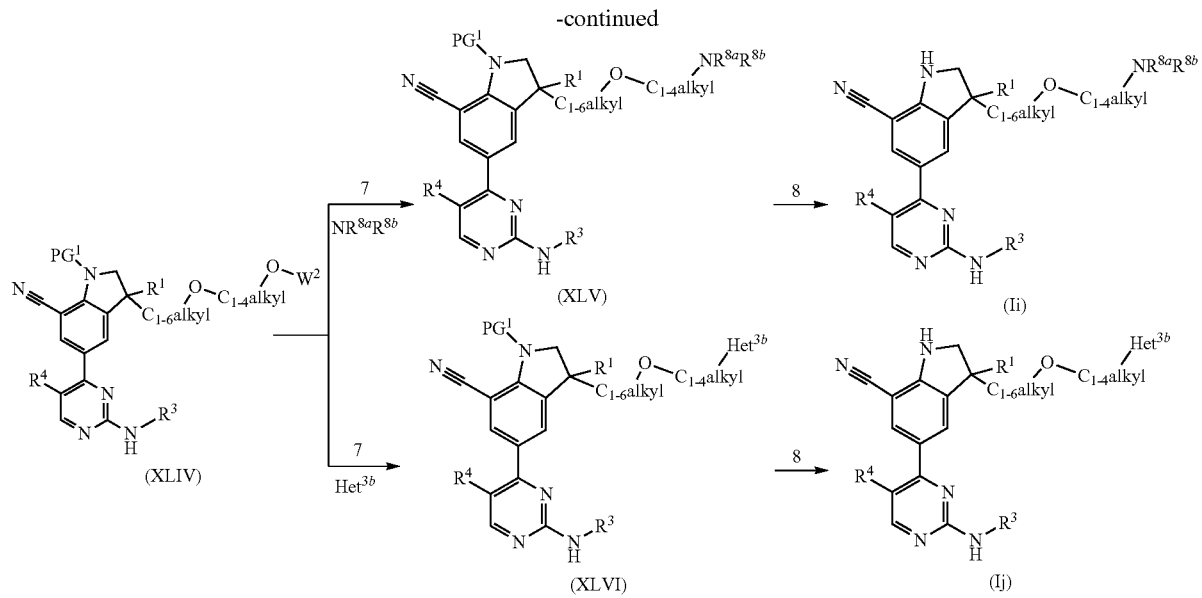

1: at a suitable temperature such as for example room temperature, in the presence of a suitable base as for example sodium hydride, and a suitable solvent such as for example dimethylformamide;
2: at a suitable temperature such as for example 55° C., in presence of reducing agent such as for example sodium borohydride and a suitable solvent such as for example a mixture of tetrahydrofuran and methanol;
3: at a suitable temperature such as for example 100° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;
4: at a suitable temperature such as for example 85° C., in the presence of a suitable catalyst such as for example palladium tetrakis ($Pd(PPh_3)_4$), a suitable base such as for example sodium carbonate, and a suitable solvent such as for example 1,4-dioxane;
5: at a suitable temperature such as for example 120° C., in the presence of a suitable catalyst such as for example palladium acetate ($Pd(OAc)_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;

6: at a suitable temperature such as for example 5° C., in the presence of a suitable base such as for example triethylamine, and a suitable solvent such as for example dichloromethane;
7: at a suitable temperature such as for example 80° C., and a suitable solvent such as for example acetonitrile;
8: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

Scheme 9

In general, intermediates of Formula (II) and (III) wherein $R^2$ is $R^{2a}$ being $C_{1-6}$alkyl, and wherein all the other variables are as defined according to the scope of the present invention, hereby named compounds of Formula (II) and (III), can be prepared according to the following reaction Scheme 9. In Scheme 9 halo$^1$ is defined as Cl, Br, I; halo$^2$ is defined as Cl, Br, I; $PG^1$ represents a suitable protecting group, such as for example tert-(butoxycarbonyl); $W^1$ represents a leaving group, such as for example a methane sulfonate or toluene sulfonate or an halogen (Cl, Br or I). All other variables in Scheme 9 are defined according to the scope of the present invention.

In Scheme 9, the following reaction conditions apply:

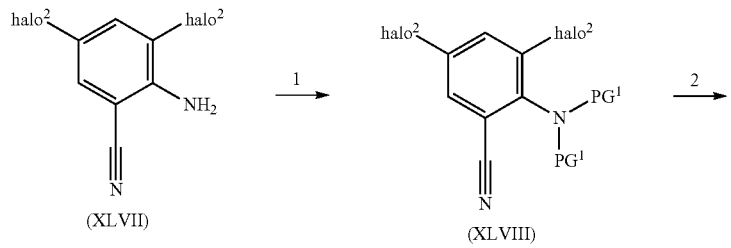

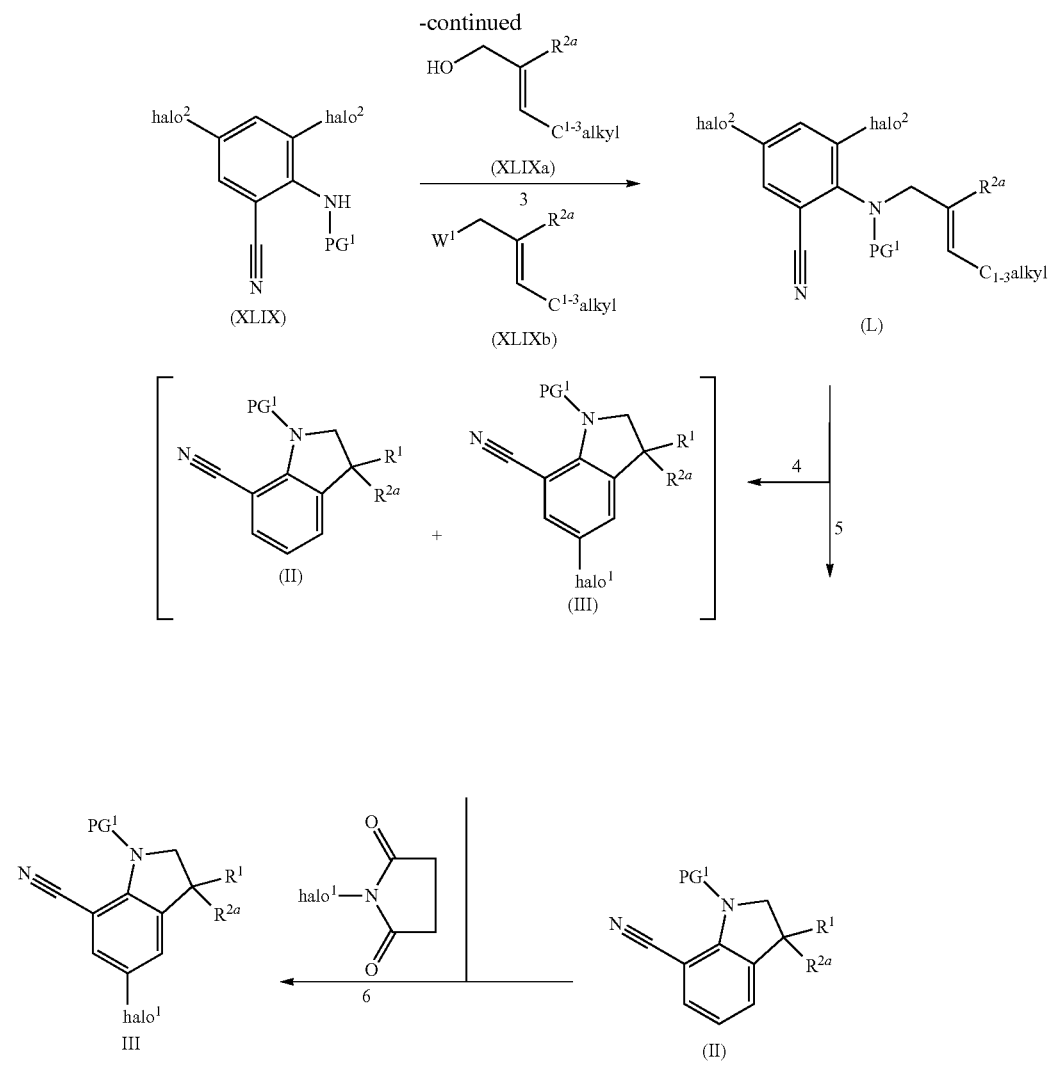

1: at a suitable temperature such as for example 45° C., in the presence of a suitable reagent such as for example di-tert-butyl dicarbonate, in the presence of a suitable catalyst such as for example 4-dimethylaminopyridine (DMAP), and a suitable solvent such as for example dichloromethane;
2: at a suitable temperature such as for example 65° C. and a suitable solvent such as for example methanol;
3: in case of (XLIXa), at a suitable temperature such as for example at room temperature, in the presence of tri-n-butylphosphine and 1,1'-(azodicarbonyl)piperidine and a suitable solvent such as for example 2-methyltetrahydrofuran;
In case of (XLIXb), at a suitable temperature such as for example 80° C., in the presence of a suitable base such as for example potassium carbonate, a suitable additive such as for example sodium iodide, in a suitable solvent such as for example acetonitrile;
4: at a suitable temperature such as for example 85° C., in the presence of sodium acetate, sodium formate and tetraethylammonium chloride, a suitable catalyst such as for example palladium acetate (Pd(OAc)$_2$), and a suitable solvent such as for example dimethylformamide;
5: at a suitable temperature such as for example 60° C., in the presence of sodium acetate, sodium formate dehydrate and tetraethylammonium chloride, a suitable catalyst such as for example [1,1'-bis(diphenylphosphino) ferrocene] palladium, (II) chloride optionally with dichloromethane complex, and a suitable solvent such as for example dimethylformamide;
6: at a suitable temperature such as for example 40° C., in the presence of N-halogeno-succinimide, and a suitable solvent such as for example acetonitrile. Alternatively, in the presence of a suitable reagent such as for example 1,3-dibromo-5,5-dimethylhydantoin, in a suitable solvent such as for example acetonitrile.

Scheme 10

In general, intermediates of Formula (XII) and (XIII) wherein $R^2$ is $R^{2b}$ being $C_{1-6}$alkyl substituted with one OH, and wherein all the other variables are as defined according to the scope of the present invention, hereby named compounds of Formula (XII) and (XIII), can be prepared according to the following reaction Scheme 10. In Scheme 10 halo$^1$ is defined as Cl, Br, I; halo$^2$ is defined as Cl, Br, I; PG$^1$ represents a suitable protecting group, such as for example tert-(butoxycarbonyl) and PG$^2$ represents a suitable protecting group, such as for example tert-butyl-dimethylsilyl. All other variables in Scheme 10 are defined according to the scope of the present invention.

In Scheme 10, the following reaction conditions apply:

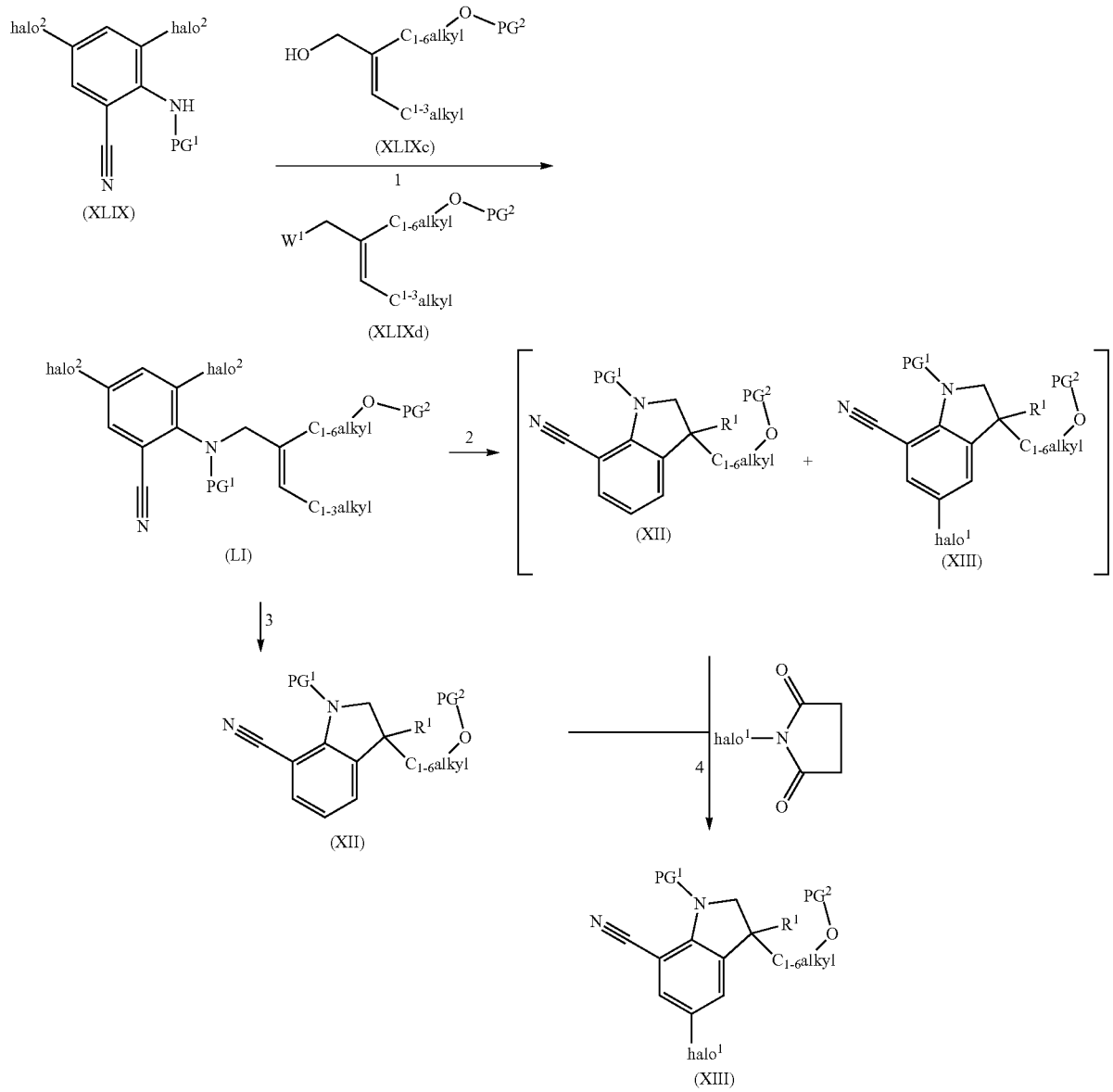

1: in case of (XLIXc), at a suitable temperature such as for example at room temperature, in the presence of tri-n-butylphosphine and 1,1'-(azodicarbonyl)piperidine and a suitable solvent such as for example 2-methyltetrahydrofuran;
In case of (XLIXd), at a suitable temperature such as for example 80° C., in the presence of a suitable base such as for example potassium carbonate, a suitable additive such as for example sodium iodide, in a suitable solvent such as for example acetonitrile;
2: at a suitable temperature such as for example 85° C., in the presence of sodium acetate, sodium formate and tetraethylammonium chloride, a suitable catalyst such as for example palladium acetate (Pd(OAc)$_2$), and a suitable solvent such as for example dimethylformamide;
3: at a suitable temperature such as for example 60° C., in the presence of sodium acetate, sodium formate dehydrate and tetraethylammonium chloride, a suitable catalyst such as for example [1,1'-bis(diphenylphosphino) ferrocene] palladium, (II) chloride optionally with dichloromethane complex, and a suitable solvent such as for example dimethylformamide;
4: at a suitable temperature such as for example 40° C., in the presence of N-halogeno-succinimide, and a suitable solvent such as for example acetonitrile. Alternatively, in the presence of a suitable reagent such as for example 1,3-dibromo-5,5-dimethylhydantoin, in a suitable solvent such as for example acetonitrile.

Scheme 11

In general, compounds of Formula (I) wherein $R^2$ is as shown in the scheme 11, Y is $CR^4$, and wherein all the other variables are as defined according to the scope of the present invention, hereby named compounds of Formula (Ik) can be prepared according to the following reaction Scheme 11. In Scheme 11 PG¹ represents a suitable protecting group, such as for example tert-(butoxycarbonyl). All other variables in Scheme 11 are defined according to the scope of the present invention.

In Scheme 11, the following reaction conditions apply:

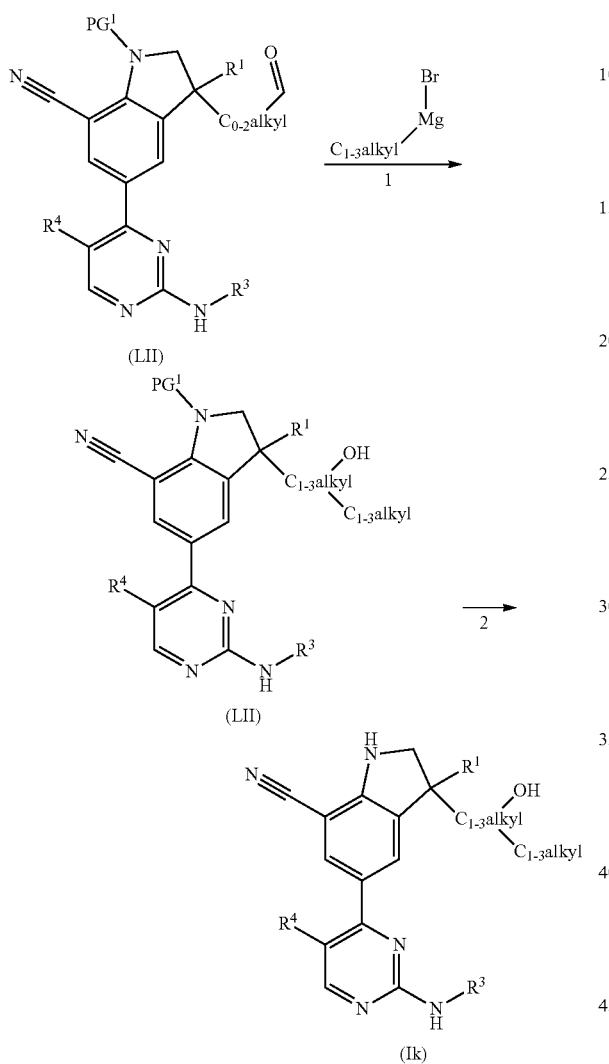

1: at a suitable temperature such as for example at room temperature, and a suitable solvent such as for example tetrahydrofuran;
2: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

Scheme 12

In general, compounds of Formula (I) wherein R² is as shown in the scheme 12, Y is CR⁴, and wherein all the other variables are as defined according to the scope of the present invention, hereby named compounds of Formula (Il) can be prepared according to the following reaction Scheme 12. In Scheme 12 PG¹ represents a suitable protecting group, such as for example tert-(butoxycarbonyl). All other variables in Scheme 12 are defined according to the scope of the present invention.

In Scheme 12, the following reaction conditions apply:

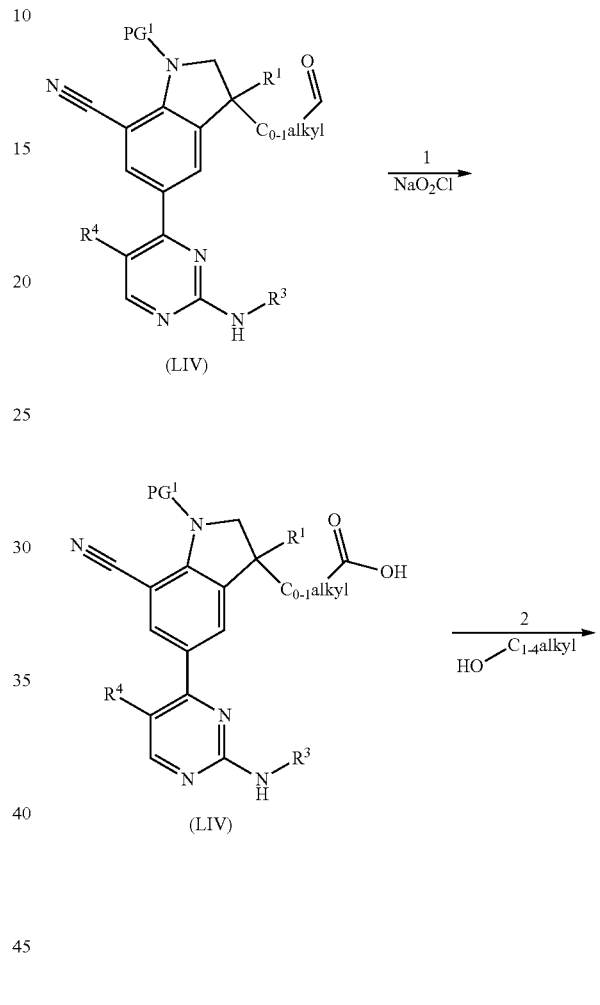

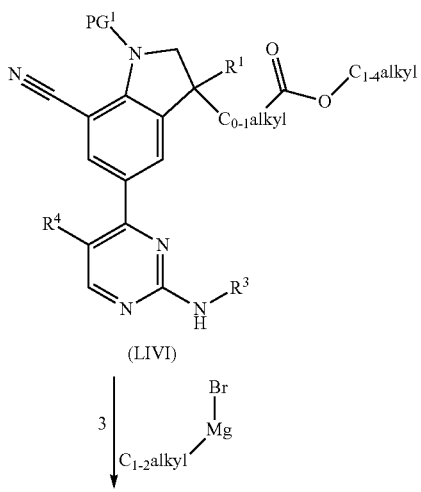

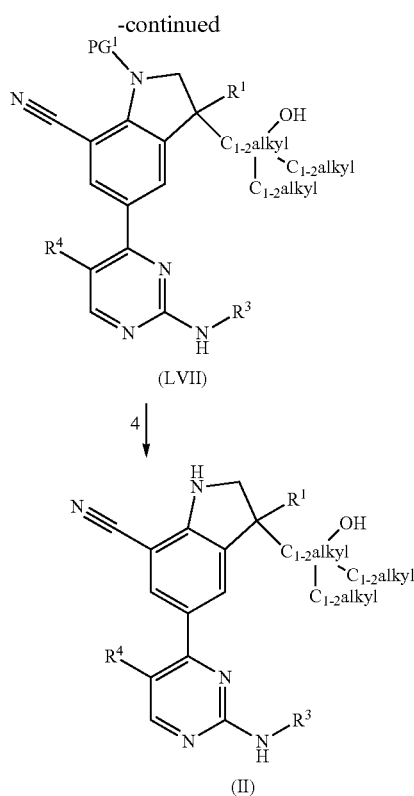

(LVII)

↓ 4

(II)

1: at a suitable temperature such as for example at room temperature, in the presence of tert-butyl alcohol, 2-methyl-2-butene, sodium dihydrogenophosphate and distilled water;
2: at a suitable temperature such as for example at room temperature, in presence of 1-[bis(dimethylamino)methyl-ene]-1H-1,2,3-triazolo[4,5-b]pyridinium 3-oxid hexafluoro-phosphate (HATU) and dimethyl aminopyridine (DMAP), a suitable base such as for example DIPEA and a suitable solvent such as for example dimethylformamide;
3: at a suitable temperature such as for example at room temperature, and a suitable solvent such as for example tetrahydrofuran;
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

Scheme 13

In general, compounds of Formula (I) wherein $R^2$ is as shown in the scheme 13, Y is $CR^4$, and wherein all the other variables are as defined according to the scope of the present invention, hereby named compounds of Formula (Im) can be prepared according to the following reaction Scheme 13. In Scheme 13 $PG^1$ represents a suitable protecting group, such as for example tert-(butoxycarbonyl). All other variables in Scheme 13 are defined according to the scope of the present invention.

In Scheme 13, the following reaction conditions apply:

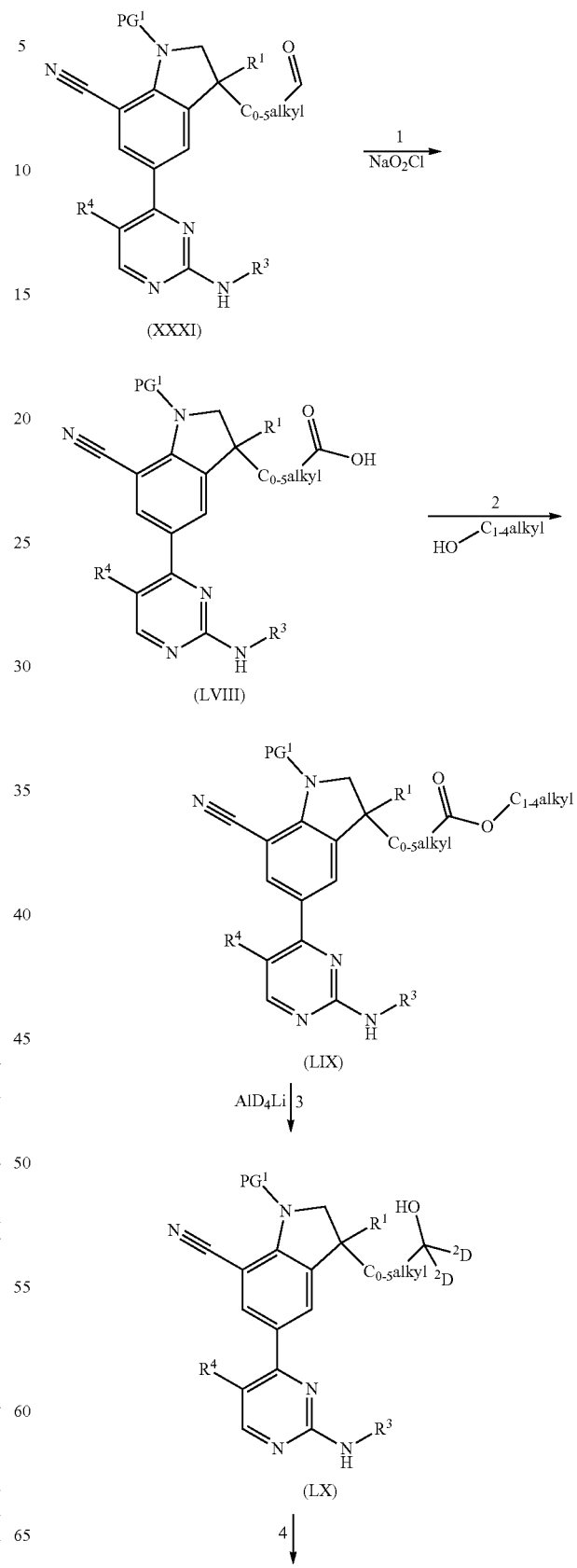

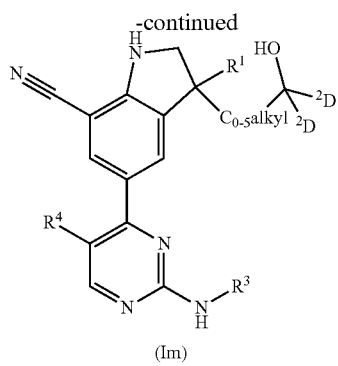

(Im)

1: at a suitable temperature such as for example at room temperature, in the presence of tert-butyl alcohol, 2-methyl-2-butene, sodium dihydrogenophosphate and distilled water;
2: at a suitable temperature such as for example at room temperature, in presence of 1-[bis(dimethylamino)methylene]-1H-1,2,3-triazolo[4,5-b]pyridinium 3-oxid hexafluorophosphate (HATU) and dimethyl aminopyridine (DMAP), a suitable base such as for example DIPEA and a suitable solvent such as for example dimethylformamide;
3: at a suitable temperature such as for example at 0° C., and a suitable solvent such as for example tetrahydrofuran ("AlD$_4$Li" means lithium aluminium deuteride);
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

Scheme 14

In general, compounds of Formula (I) wherein $R^2$ is being $C_{1-6}$alkyl substituted with one $Het^{3a}$ or $—NR^{6a}R^{6b}$, wherein $R^{6a}$ is being H, $R^{6b}$ is being $—C(=O)—C_{1-4}$alkyl; $—C(=O)-Het^4$; $—S(=O)_2—C_{1-4}$alkyl, Y is $CR^4$, and wherein all the other variables are as defined according to the scope of the present invention, hereby named compounds of Formula (In), Formula (Io) and Formula (Ip), can be prepared according to the following reaction Scheme 14. In Scheme 14, $PG^1$ represents a suitable protecting group, such as for example tert-(butoxycarbonyl). All other variables in Scheme 14 are defined according to the scope of the present invention.

In Scheme 14, the following reaction conditions apply:

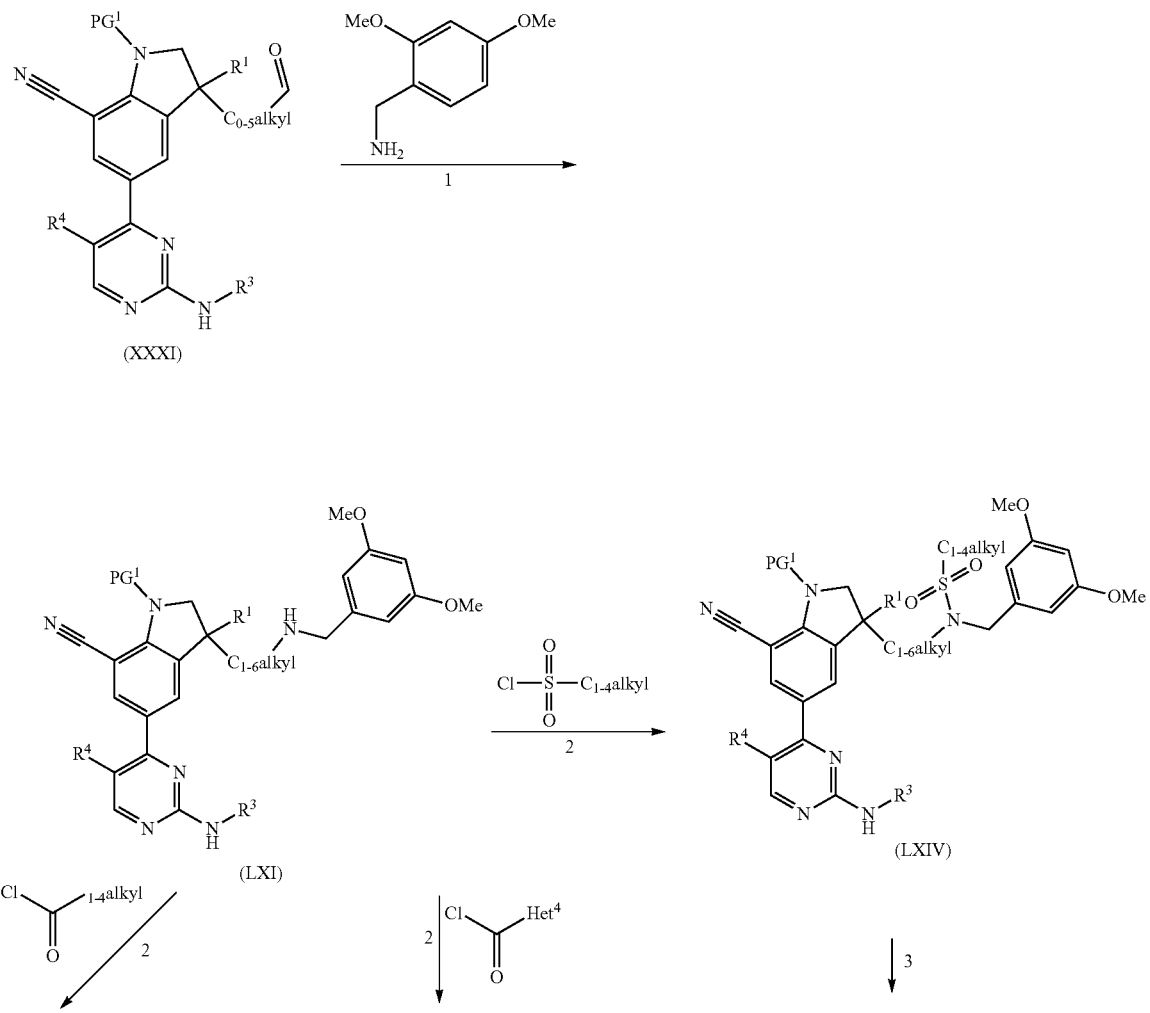

-continued

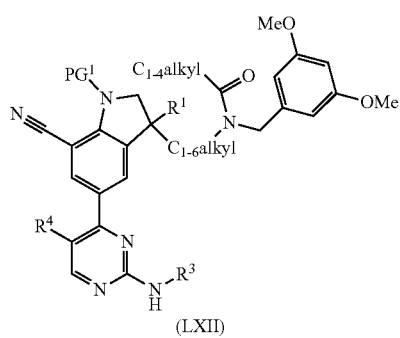
(LXII)

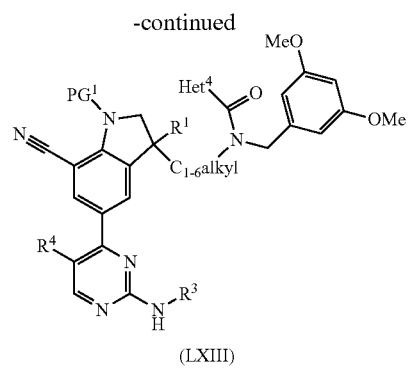
(LXIII)

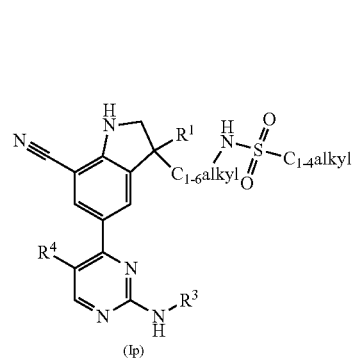
(Ip)

↓3      ↓3

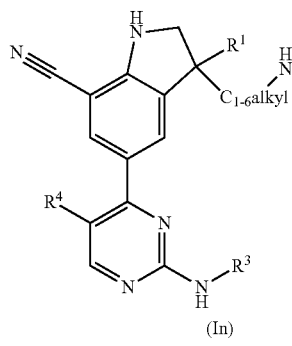
(In)

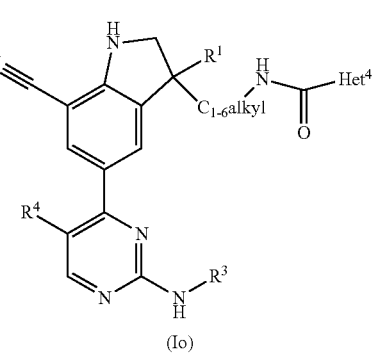
(Io)

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;

2: at a suitable temperature such as for example at room temperature, in the presence of a suitable base such as for example triethylamine, in a suitable solvent such as for example tetrahydrofuran;

3: at a suitable temperature such as for example at room temperature, in the presence of a suitable acid such as for example trifluoroacetic acid, in a suitable solvent such as for example dichloromethane.

Scheme 15

In general, compounds of Formula (I) wherein $R^2$ is being $C_{1-6}$alkyl substituted with one $Het^{3a}$ or $-NR^{6a}R^{6b}$, wherein $R^{6a}$ is being $C_{1-4}$alkyl, $R^{6b}$ is being $-C(=O)-C_{1-4}$alkyl; $-C(=O)-Het^4$; $-S(=O)_2-C_{1-4}$alkyl, Y is $CR^4$, and wherein all the other variables are as defined according to the scope of the present invention, hereby named compounds of Formula (Iq), Formula (Ir) and Formula (Is), can be prepared according to the following reaction Scheme 15. In Scheme 15, $PG^1$ represents a suitable protecting group, such as for example tert-(butoxycarbonyl). All other variables in Scheme 15 are defined according to the scope of the present invention.

In Scheme 15, the following reaction conditions apply:

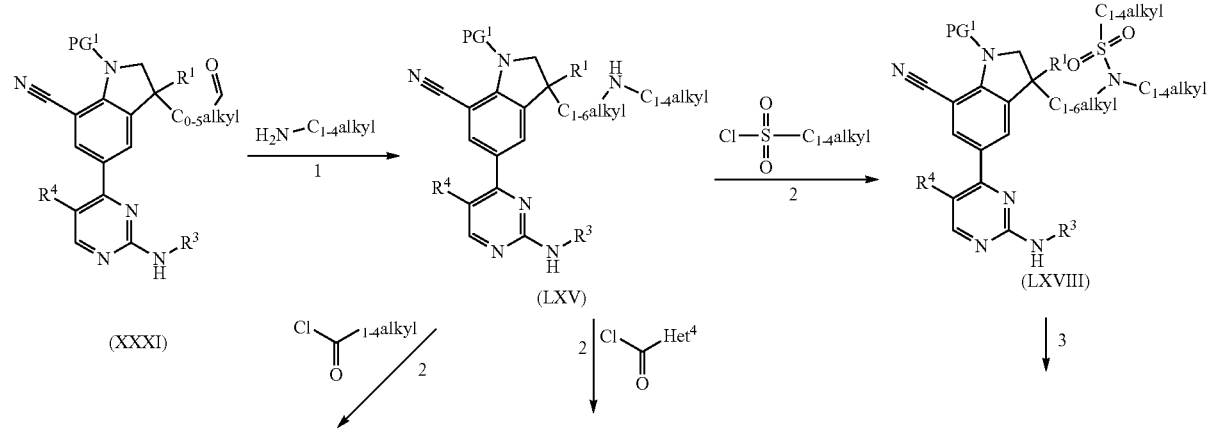

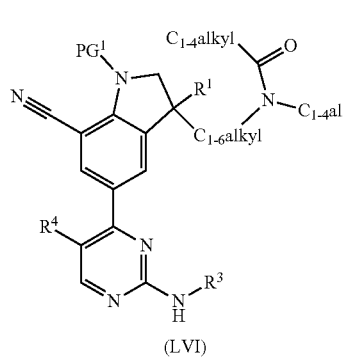
(LVI)

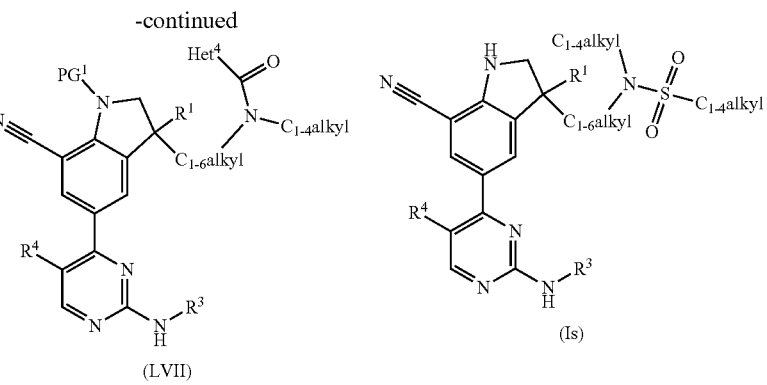
(LVII)    (Is)

↓3    ↓3

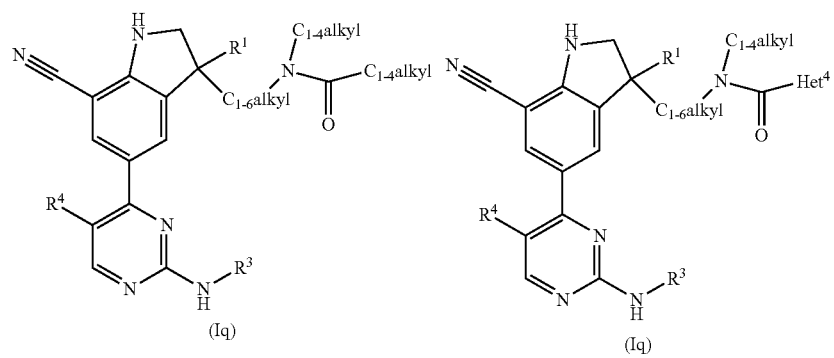
(Iq)    (Iq)

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;

2: at a suitable temperature such as for example at room temperature, in the presence of a suitable base such as for example triethylamine, in a suitable solvent such as for example tetrahydrofuran;

3: at a suitable temperature such as for example at room temperature, in the presence of a suitable acid such as for example trifluoroacetic acid, in a suitable solvent such as for example dichloromethane.

Scheme 16

In general, compounds of Formula (I) wherein $R^2$ is $C_{1-6}$alkyl substituted with one $OR^{7d}$, $R^{7d}$ being —S(=O)$_2$—OH or —P(=O)—(OH)$_2$, Y is $CR^4$, and wherein all the other variables are as defined according to the scope of the present invention, hereby named compounds of Formula (It) and Formula (Iu), can be prepared according to the following reaction Scheme 16. All other variables in Scheme 16 are defined according to the scope of the present invention.

In Scheme 16, the following reaction conditions apply:

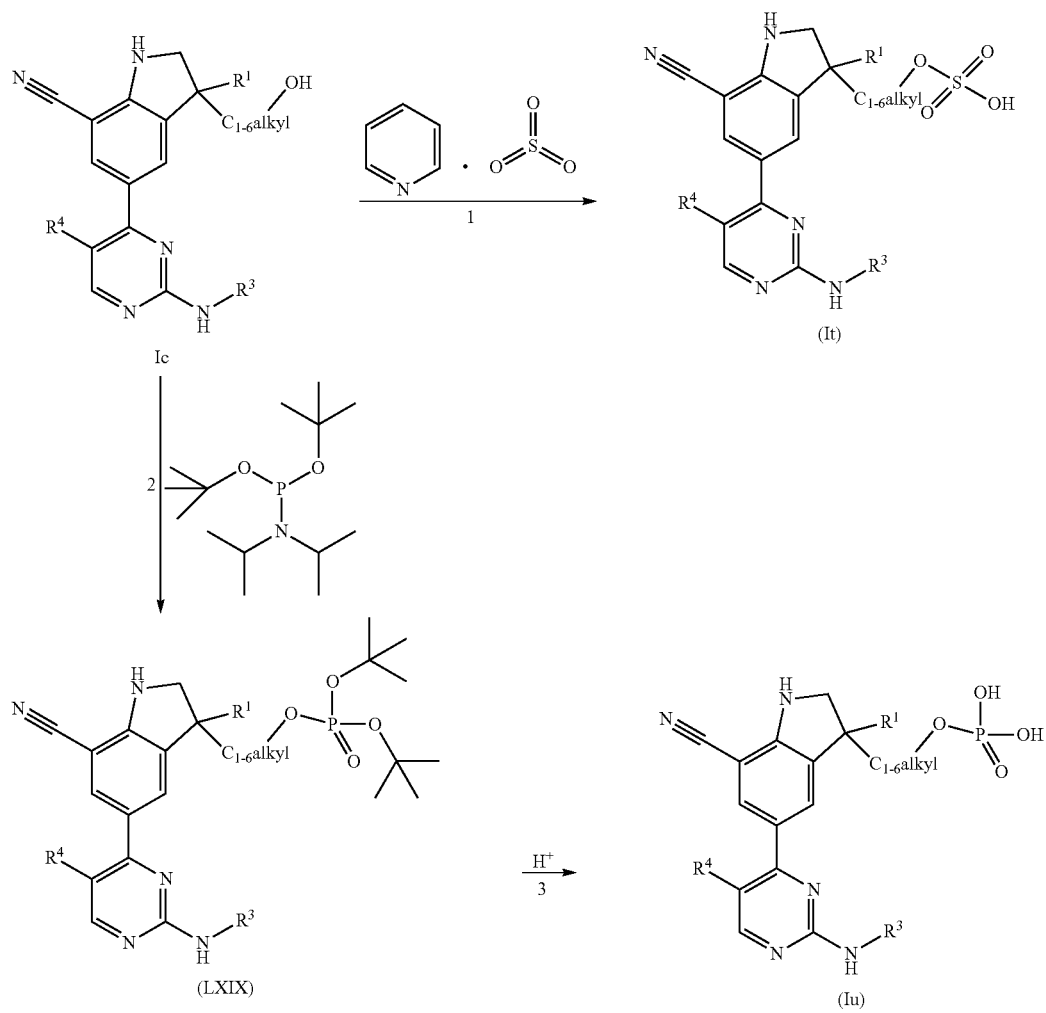

1: at a suitable temperature such as for example at room temperature, in a suitable solvent such as for example tetrahydrofuran, in the presence of a suitable base such as for example sodium hydroxide;

2: in the presence of a suitable reagent such as for example tetrazole, in the presence of a suitable oxidizing agent such as for example meta-chloroperbenzoic acid, in a suitable solvent such as for example acetonitrile;

3: at a suitable temperature such as for example at room temperature, in the presence of a suitable acid such as for example hydrochloric acid, in a suitable solvent such as for example acetonitrile.

Scheme 17

In general, intermediates of Formula (XII) wherein all the variables are as defined according to the scope of the present invention can be prepared according to the following reaction Scheme 17.

In Scheme 17, the following reaction conditions apply:

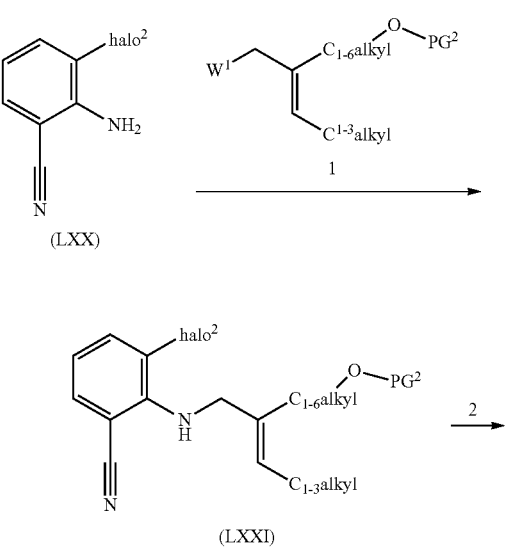

-continued

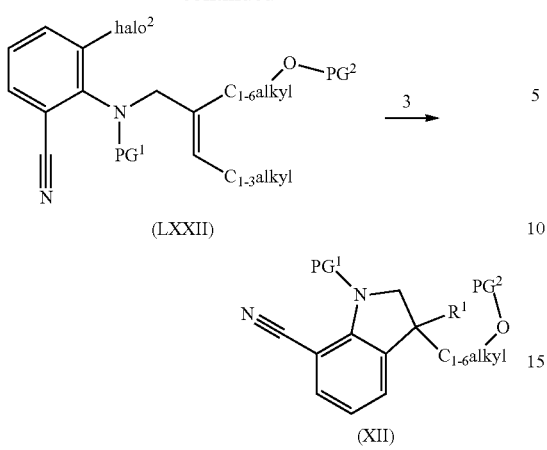

(LXXII)

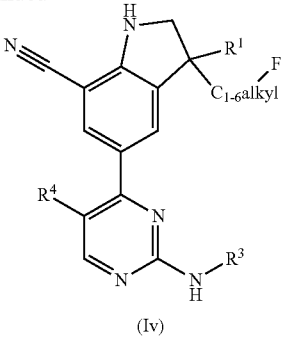

(Iv)

1: in the presence of a suitable fluorinating reagent such as for example diethylaminosulfur trifluoride, a suitable solvent such as for example dichloromethane, at a suitable temperature such as for example room temperature.

Scheme 19

In general, compounds of Formula (I) wherein $R^2$ is $R^{2b}$ being $C_{1-6}$alkyl substituted with one OH, Y is N, and wherein all the other variables are as defined according to the scope of the present invention, hereby named compounds of Formula (Iw), can be prepared according to the following reaction Scheme 19. In Scheme 19, halo$^1$ is defined as Cl, Br or I; PG$^1$ represents a suitable protecting group, such as for example tert-(butoxycarbonyl) and PG$^2$ represents a suitable protecting group, such as for example tert-butyl-dimethylsilyl. All other variables in Scheme 19 are defined according to the scope of the present invention.

In Scheme 19, the following reaction conditions apply:

(XII)

1: At a suitable temperature range between −5° C. and 5° C., in the presence of a suitable base such as for example sodium tert-butoxide in a suitable solvent such as for example tetrahydrofuran;
2: at a suitable temperature ranged between 65 and 70° C., in to presence of a suitable reagent such as for example di-tert-butyl dicarbonate, in the presence of a suitable catalyst such as for example 4-dimethylaminopyridine (DMAP), and a suitable solvent such as for example tetrahydrofuran;
3: at a suitable temperature ranged between 45 and 50° C., in the presence of sodium acetate, sodium formate dehydrate and tetraethylammonium chloride, a suitable catalyst such as for example palladium acetate or [1,1'-bis(diphenylphosphino) ferrocene] palladium, (II) chloride optionally with dichloromethane complex, and a suitable solvent such as for example dimethylformamide.

Scheme 18

In general, compounds of Formula (I) wherein $R^2$ is $C_{1-6}$alkyl substituted with one $R^5$, $R^5$ being a fluorine, Y is $CR^4$, and wherein all the other variables are as defined according to the scope of the present invention, hereby named compounds of Formula (Iv), can be prepared according to the following reaction Scheme 18. All other variables in Scheme 18 are defined according to the scope of the present invention.

In Scheme 18, the following reaction conditions apply:

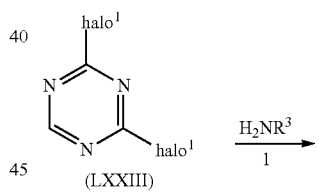

(LXXIII)

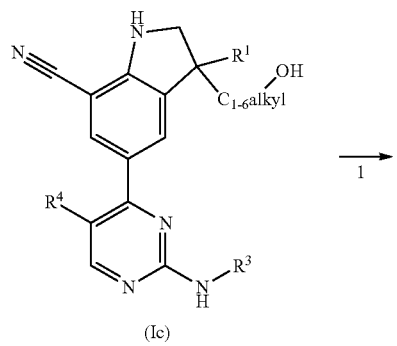

(Ic)

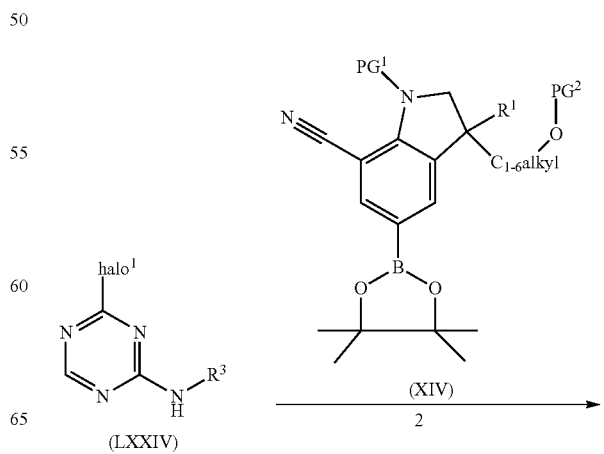

(LXXIV)

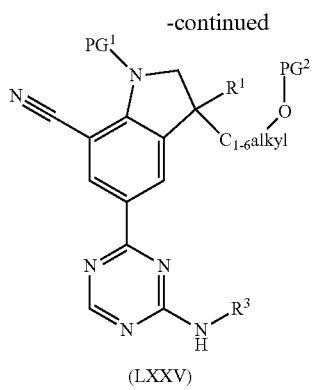

(LXXV)

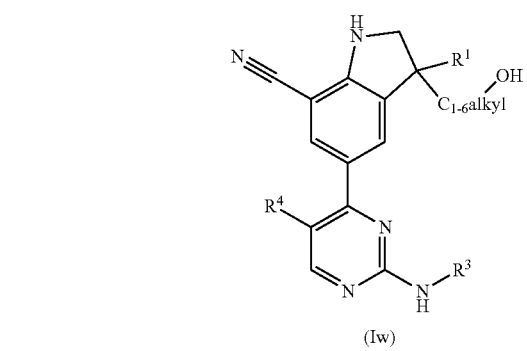

(LXXVI)

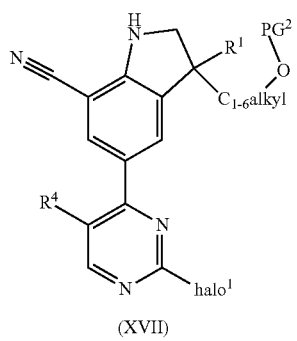

(Iw)

1: in the presence of a suitable base such as for example diisopropylethylamine, in a suitable solvent such as for example acetonitrile;

2: in the presence of a suitable catalyst such as for example [1,1'-bis(diphenylphosphino)ferrocene] dichloropalladium (II), optionally with dichloromethane complex, a suitable base such as an aqueous solution of hydrogenocarbonate at a suitable temperature such as 80° C.;

3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;

4: at a suitable temperature such as for example room temperature, in presence of a suitable desilylating agent such as for example tetra-n-butylammonium fluoride and a suitable solvent such as for example 2-methyltetrahydrofuran or tetrahydrofuran.

Scheme 20

In general, compounds of Formula (I) wherein $R^2$ is $R^{2b}$ being $C_{1-6}$alkyl substituted with one OH, $R^3$ is phenyl substituted with —C(=O)—$R^{10}$ and optionally substituted with other substituents according to the scope of the present invention, Y is $CR^4$, and wherein all the other variables are as defined according to the scope of the present invention, hereby named compounds of Formula (Ida), (Idb) and (Idc) can be prepared according to the following reaction Scheme 20. In Scheme 20, $halo^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 20 are defined according to the scope of the present invention.

In Scheme 20, the following reaction conditions apply:

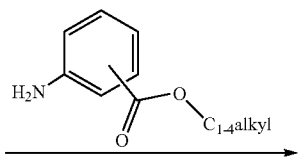

(XVII)

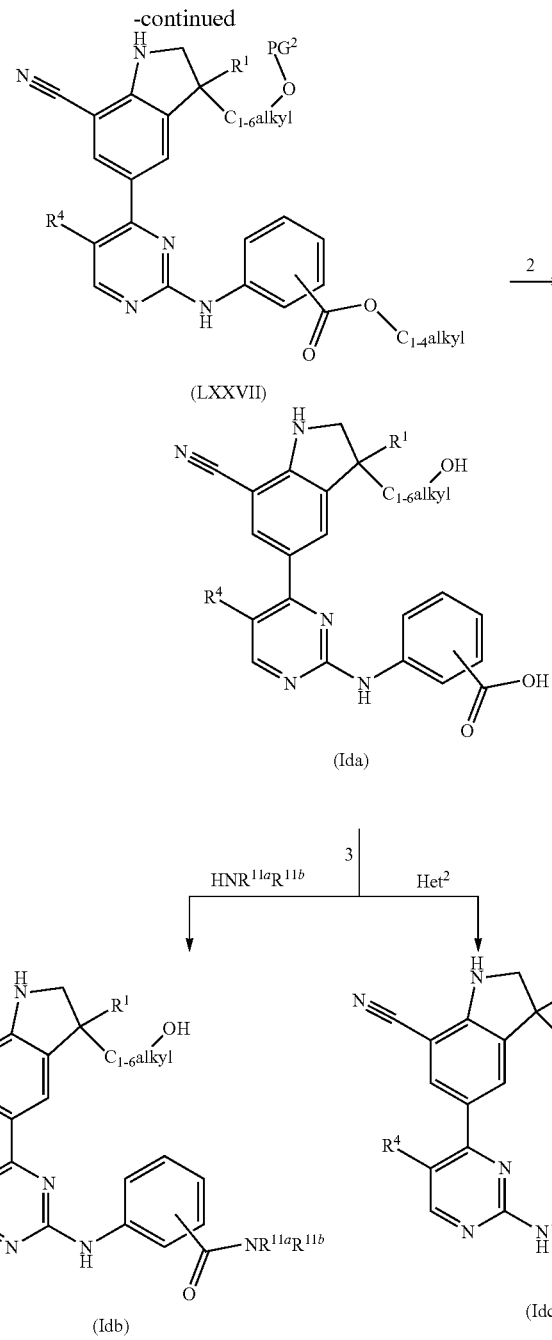

1: at a suitable temperature such as for example 120° C., in the presence of a suitable catalyst such as for example palladium acetate (Pd(OAc)$_2$), a suitable ligand such as for example 2,2'-bis(diphenylphosphino)-1,1'-binaphthyl (BI-NAP), a suitable base such as for example cesium carbonate, and a suitable solvent such as for example 1,4-dioxane, optionally under microwave activation;

2: at a suitable temperature such as for example 60° C., in presence of a suitable base such as for example lithium hydroxide, and a suitable solvent such as for example a mixture of tetrahydrofuran and water;

3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide or dichloromethane.

Scheme 21

In general, compounds of Formula (I) wherein $R^2$ is $R^{2b}$ being $C_{1-6}$alkyl substituted with one OH, Y is $CR^4$, and wherein all the other variables are as defined according to the scope of the present invention, hereby named compounds of Formula (Ic), can be prepared according to the following reaction Scheme 21. All other variables in Scheme 21 are defined according to the scope of the present invention or as above.

In Scheme 21, the following reaction conditions apply:

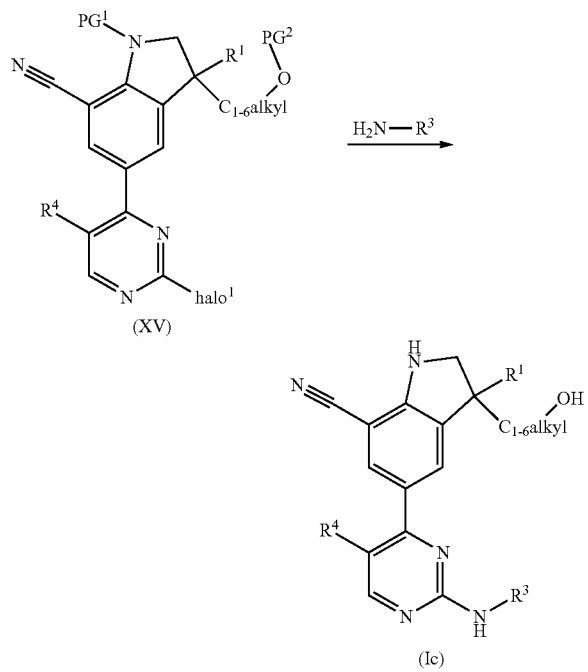

1: at a suitable temperature such as for example 90° C., in the presence of a suitable acid such as for example p-toluenesulfonic acid and a suitable solvent such as for example 1,4-dioxane.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention inhibit NF-κB-inducing kinase (NIK—also known as MAP3K14). Some of the compounds of the present invention may undergo metabolism to a more active form in vivo (prodrugs). Therefore the compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, non-Hodgkin's lymphoma, Hodgkin lymphoma, T-cell leukaemia, mucosa-associated lymphoid tissue lymphoma, diffuse large B-cell lymphoma and mantle cell lymphoma, in a particular embodiment mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Particular examples of cancers which may be treated (or inhibited) include B-cell malignancies, such as multiple myeloma, hodgkins lymphoma, mantle cell lymphoma, diffuse large B-cell lymphoma or chronic lymphocytic leukemia, with mutations in the non-canonical NFkB signalling pathway (eg in NIK (MAP3K14), TRAF3, TRAF2, BIRC2 or BIRC3 genes).

Hence, the invention relates to compounds of Formula (I), the tautomers and the stereoisomeric forms thereof, and the pharmaceutically acceptable addition salts, and the solvates thereof, for use as a medicament.

The invention also relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable addition salt, or a solvate thereof, or a pharmaceutical composition according to the invention, for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase.

Also, the present invention relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), a tautomer or a stereoisomeric form thereof, or a pharmaceutically acceptable addition salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable addition salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable addition salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), a tautomer or a stereoisomeric form thereof, or a pharmaceutically acceptable addition salt, or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable addition salt, or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 10 mg/kg body weight to 40 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable addition salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more medicinal agent, more particularly, with one or more anticancer agent or adjuvant, as a combined preparation for simultaneous, separate or sequential use in the treatment of patients suffering from cancer.

Accordingly, for the treatment of the conditions mentioned hereinbefore, the compounds of the invention may be advantageously employed in combination with one or more other medicinal agents (also referred to as therapeutic agents), more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetracarcin A;

glucocorticoIden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacytidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;

Inhibitors of the ubiquitin-proteasome pathway for example PS-341, Velcade (MLN-341) or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-199;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment.

The taxane compound is advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

The camptothecin compound is advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

The anti-tumour podophyllotoxin derivative is advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

The anti-tumour vinca alkaloid is advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m2) of body surface area, for example 700 to 1500 mg/m2, particularly for 5-FU in a dosage of 200 to 500 mg/m2, for gemcitabine in a dosage of about 800 to 1200 mg/m2 and for capecitabine in about 1000 to 2500 mg/m2 per course of treatment.

The alkylating agents such as nitrogen mustard or nitrosourea is advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg, for carmustine in a dosage of about 150 to 200 mg/m2, and for lomustine in a dosage of about 100 to 150 mg/m2 per course of treatment.

The anti-tumour anthracycline derivative is advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m2) of body surface area, or as known in the art, if different. Trastuzumab is advantageously administered in a dosage of 1 to 5 mg per square meter (mg/m2) of body surface area, particularly 2 to 4 mg/m2 per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. Unless otherwise noted, all starting materials were obtained from commercial suppliers and used without further purification.

Hereinafter, the terms: 'ACN' means acetonitrile, 'AcOH' means acetic acid, 'AcCl' means acetyl chloride, 'Ar' means argon, 'BINAP' means 2,2'-bis(diphenylphosphino)-1,1'-binaphthyl, 'BOC' or 'Boc' means tert-butyloxycarbonyl, 'Boc$_2$O' means di-tert-butyl dicarbonate, Celite® means diatomaceous earth, 'DCM' means dichloromethane, 'DIEA' or 'DIPEA' means diisopropylethylamine, 'DiPE' means diisopropylether, 'h' means hours(s), 'min' means minute(s), 'DMAP' means dimethylaminopyridine, 'DMF' means dimethylformamide, 'Et$_2$O' means diethylether, 'EtOAc' or 'AcOEt' means ethyl acetate, 'HPLC' means High-performance Liquid Chromatography, 'IPrNH$_2$' means isopropylamine, 'iPrOH' means isopropyl alcohol, 'KHMDS' means potassium bis(trimethylsilyl)amide, 'HATU' means 1-[bis(dimethylamino)methylene]-1H-[1,2,3]triazolo[4,5-b]pyridin-1-ium 3-oxide hexafluorophosphate, 'LC/MS' means Liquid Chromatography/Mass Spectrometry, 'LiHMDS' means Lithium bis(trimethylsilyl)amide, 'Me' means methyl, 'Me-THF' means 2-methyltetrahydrofuran, 'MeOH' means methanol, 'NIBS' means N-bromosuccinimide, 'NCS' means N-chlorosuccinimide, 'NMR' means Nuclear Magnetic Resonance, 'Pd/C 10%' means palladium on carbon loading 10%, 'Pd(OAc)$_2$' means palladium (II) acetate, 'Pd(PPh$_3$)$_2$Cl$_2$' means bis(triphenylphosphine)palladium(II) chloride 'Pd(PPh$_3$)$_4$' means tetrakis(triphenylphosphine)palladium (0), 'Pd(dppf)Cl$_2$' or 'PdCl$_2$dppf means [1,1'-Bis(diphenylphosphino)ferrocene]dichloropalladium(II), 'Pd(t-Bu$_3$P)$_2$' means bis(tri-tert-butyl-phosphine) palladium (0), 'rt' means room temperature, 'SFC' means supercritical fluid chromatography, 'ee' means enantiomeric excess, 'TBAF' means tetrabutylammonium fluoride, 'tBDMS', 'TBDMS' or 'SMDBT' means tert-butyldimethylsilyl, 'TEA' or 'Et$_3$N' means triethylamine, 'TFA' means trifluoroacetic acid, 'THF' means tetrahydrofuran, 'CV' means column volumes, 'Quant.' means quantitative, 'o/n' means overnight, '@' means at, 'eq.' or 'equiv.' means equivalent(s), 'Psi' means Pounds per Square Inch (pressure), 'M.P.', 'MP' or 'm.p.' means melting point, 'OR' means optical rotation, 'DSC' means Differential Scanning calorimetry.

When a stereocenter is indicated with 'RS' this means that a racemic mixture was obtained. Compounds like compound 39 and compound 124 which have two stereocenters indicated with 'RS' were obtained as a mixture of diastereoisomers.

It is well known to one skilled in the art that protecting groups such as TBDMS can routinely be removed with TBAF in a variety of solvents such as for example THF. Similarly, conditions for removal of BOC protecting groups are well known to one skilled in the art, commonly including for example TFA in a solvent such as for example DCM, or HCl in a solvent such as for example dioxane.

The skilled person will realize that in some cases where an organic layer was obtained at the end of an experimental protocol, it was necessary to dry the organic layer with a typical drying agent such as for example MgSO$_4$, or by azeotropic distillation, and to evaporate the solvent before using the product as a starting material in the next reaction step.

A. PREPARATION OF THE INTERMEDIATES

Example A1

Preparation of Intermediate 1:

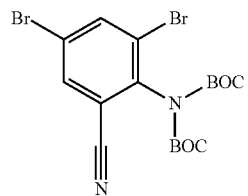 [SMILES: CC(C)(C)OC(=O)N(C(=O)OC(C)(C)C)c1c(Br)cc(Br)cc1C#N]

To a solution of 2,4-dibromo-6-cyanoaniline (200.00 g, 724.82 mmol) and DMAP (17.71 g, 144.96 mmol) in DCM (3 L), Boc$_2$O (474.58 g, 2.17 mol) was added and the reaction mixture was stirred at 45° C. for 4 h. The crude mixture was successively washed with saturated NaHCO$_3$ (2×1 L) and brine (2×1 L), dried over MgSO$_4$, filtered and concentrated under vacuum to give 323 g of intermediate 1 (56% yield, yellow solid, 86% purity evaluated by LC/MS). The product was used in the next step without any further purification.

Preparation of Intermediate 2.

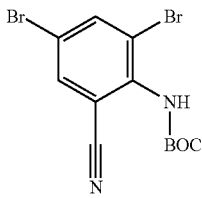 [SMILES: CC(C)(C)OC(=O)Nc1c(Br)cc(Br)cc1C#N]

A mixture of intermediate 1 (620.00 g, 1.30 mol) and K$_2$CO$_3$ (539.02 g, 3.90 mol) in MeOH (6 L) was stirred at 65° C. for 3 h. The reaction mixture was cooled to 25° C. filtered and concentrated under vacuum. Then, the residue was dissolved in EtOAc (4 L) and the organic layer was washed with brine (2 L), dried over MgSO$_4$, and filtered. The filtrate was evaporated under vacuum to 1/8 solvent, filtered to collect the solid and dried under reduced pressure to give 300 g of intermediate 2 (60% yield, yellow solid). The product was used in the next step without any further purification.

Preparation of Intermediate 3:

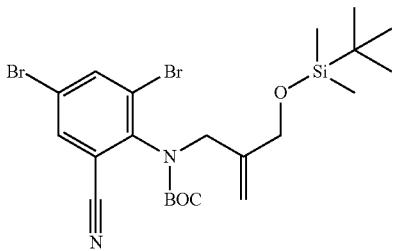 [SMILES: C=C(CO[Si](C)(C)C(C)(C)C)CN(C(=O)OC(C)(C)C)c1c(Br)cc(Br)cc1C#N]

Intermediate 2 (100.00 g, 265.93 mmol), 2-(((tert-butyl-dimethyl-silanyl)oxy) methyl) prop-2-en-1-ol (80.72 g, 398.90 mmol) and tributylphosphane (107.61 g, 531.86 mmol) were dissolved in THF (2 L) and cooled to 0° C. A solution of 1,1'-(azodicarbonyl)-dipiperidine (147.61 g, 585.05 mmol) in THF (50 mL) was added dropwise under N$_2$ and stirred at 0° C. for 1 h, then 25° C. for 12 h. The resulting mixture was triturated with petroleum ether (3 L), filtered and concentrated under vacuum. Then, the residue was dissolved in EtOAc (6 L), washed successively with water (2×2 L) and brine (2×2 L), dried over MgSO$_4$, filtered and concentrated under vacuum. Three reactions (each 100 g) were carried out in parallel. The resulting residues were purified by column chromatography on silica gel (SiO$_2$, mobile phase: petroleum ether/EtOAc, 10:1). The desired fractions were collected and the solvent was concentrated to dryness under vacuum to give 350 g of intermediate 3 (78% yield, yellow oil).

Preparation of Intermediate 3a:

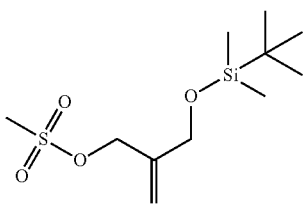 [SMILES: C=C(CO[Si](C)(C)C(C)(C)C)COS(C)(=O)=O]

Triethylamine (196.3 mL; 1.408 mol) was added to a solution of 2-(((tert-butyl-dimethyl-silanyl)oxy) methyl) prop-2-en-1-ol (114 g, 563.3 mmol) in DCM (1 L) at 0° C. Methanesulfonylchloride (56.0 mL; 704.2 mmol) was added slowly to the mixture and this mixture was stirred for 2 h at 0° C. The reaction was quenched with saturated aqueous solution of NaHCO$_3$ (100 ml) and extracted with DCM (500 ml*2). The organic layer was dried over MgSO$_4$, filtered, and concentrated under vacuum. The residue was purified by silica gel chromatography (Petroleum ether/ethyl acetate from 0/100 to 5/1) to give 50 g (32%; light yellow oil) of intermediate 3a.

Alternative Preparation of Intermediate 3a:

A solution of 1,3-Hydroxy-2-methylenepropane (100 g) in dry THF (200 mL) was added dropwise at 0° C. to a suspension of sodium hydride (0.95 eq.) in dry THF (600 mL). After 30 min a solution of tert-butyldimethylsilylchloride (0.95 eq.) in dry THF (200 mL) was added dropwise to the mixture. After approximately 18 hours at 0-5° C. the reaction was complete by GC and water (500 mL) was added slowly keeping the temperature between 0-5° C. After phase separation, the aqueous layer was back-extracted with ethyl acetate (500 mL) and the combined organic layers were washed with water (500 mL). The organic phase was concentrated to a residue which was azeotropically dried by co-evaporation with THF affording 252.7 g of the crude monoTBDMS-protected diol. A portion of the crude monoTBDMS-protected diol (152.4 g) was dissolved in dry dichloromethane (610 mL) and triethylamine (1.4 eq.) was added. The mixture was then stirred at 0° C. for 30 min and methanesulfonic anhydride (1.2 eq.) was added as a solution in dichloromethane (950 mL) and the mixture was stirred for 1 h between −5 and 5° C. An additional aliquot of methanesulfonic anhydride (0.1 eq.) and triethylamine (0.2 eq.) were added and, after 1 additional hour, water (500 mL) was added. After phase separation, the organic layer was washed twice with water (500 mL) and concentrated to a residue, which was re-diluted with THF and partially concentrated to obtain a solution of intermediate 3a (311.1 g, 57 weight % intermediate 3a in the solution).

Alternative Preparation of Intermediate 3:

Intermediate 2 (140 g; 372.3 mmol) was dissolved in acetonitrile (1.3 L). Intermediate 3a (104.4 g; 372.3 mmol), potassium carbonate (128.6 g; 930.7 mmol), and sodium iodide (5.58 g; 37.2 mmol) were added. The mixture was stirred at 80° C. for 12 h, cooled and concentrated under reduced pressure. The residue was dissolved in water (1 L) and extracted with ethyl acetate (1 L×2). The combined organic phase was washed with brine (1 L), dried over Na$_2$SO$_4$ and filtered. The filtrate was concentrated under vacuum to give a crude product. The residue was purified by silica gel chromatography (Petroleum ether/ethyl acetate from 100/0 to 40/1) to give 180 g (86%; clear oil) of intermediate 3.

Preparation of Intermediate 4 and Intermediate 4':

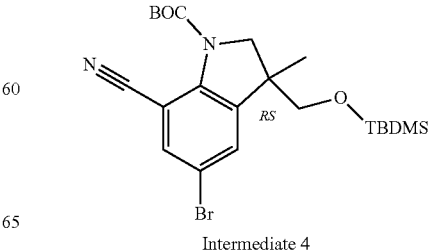

Intermediate 4

-continued

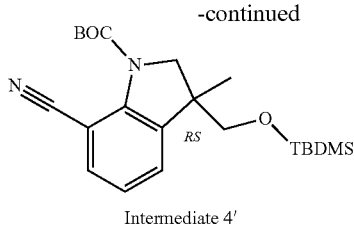

Intermediate 4'

A suspension of intermediate 3 (120.00 g, 214.14 mmol), sodium acetate (45.67 g, 556.76 mmol), sodium formate (37.86 g, 556.76 mmol), Pd(OAc)$_2$ (4.81 g, 21.41 mmol) and tetraethylammonium chloride (44.35 g, 267.67 mmol) in DMF (1.26 L) was degassed under vacuum, purged with Ar three times, and stirred at 85° C. for 2 h. The resulting mixture was filtered through a pad of Celite® and the solid was washed with DCM (2 L). The filtrate was concentrated under vacuum. The residue was dissolved in ethyl acetate (4 L), washed successively with water (2×2 L) and brine (2×2 L), dried over MgSO$_4$, filtered and concentrated under vacuum. Then, the residue was purified by column chromatography on silica gel (SiO$_2$, mobile phase: petroleum ether/EtOAc, 15:1). The desired fractions were collected and the solvent was concentrated to dryness under vacuum to give a mixture of intermediates 5 and 5'. Three reactions (each on 100-120 g of intermediate 3) were carried out in parallel which gave in total 160 g of a mixture of intermediates 4 and 4' containing 38% of intermediate 4 (evaluated by LC/MS).
Alternative Preparation of Intermediate 4.

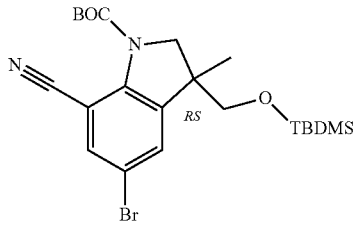

To a mixture of intermediates 4 and 4' in CH$_3$CN (1.60 L), 1-bromopyrrolidine-2,5-dione (212.20 g, 1.19 mol) was added and stirred at 40° C. for 16 h. The solvent was removed by evaporation under reduced pressure. The residue was dissolved in ethyl acetate (2 L), washed successively with NaHCO$_3$ (2×1 L) and brine (2×1 L), dried over MgSO$_4$ and filtered. The filtrate was evaporated under vacuum and purified by column chromatography on silica gel (SiO$_2$, mobile phase: petroleum ether/EtOAc, 50:1). The desired fractions were collected and the solvent was concentrated to dryness under vacuum to give 110.00 g of intermediate 4 (56% yield, yellow oil, 97% purity evaluated by LC/MS).
Alternative Preparation a of Intermediate 4':

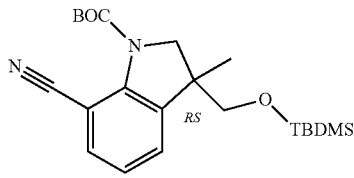

To a solution of intermediate 3 (295.00 g, 473.70 mmol), sodium acetate (101.05 g, 1.23 mol), sodium formate dihydrate (128.15 g, 1.23 mol) and [1,1'-bis(diphenylphosphino)ferrocene] palladium, (II) chloride complex with dichloromethane (19.34 g, 23.70 mmol) in DMF (2 L), tetra-N-butylammonium chloride (164.60 g, 592.20 mmol) was added under N$_2$ at rt. The reaction mixture was stirred overnight at 60° C., then, filtered through a pad of Celite® and the solid was washed with DCM (400 mL). The filtrate was concentrated under vacuum. The resulting residue was dissolved in EtOAc (4 L) and the organic layer was washed successively with water (2 L) and brine (2 L), dried over Na$_2$SO$_4$, filtered and concentrated to give the crude product as black oil. This residue was purified by column chromatography on silica gel (SiO$_2$, mobile phase: petroleum ether/EtOAc, gradient from 100:0 to 10:1). The desired fractions were collected and the solvent was concentrated to dryness under vacuum to give 155 g of intermediate 4' (70% yield, yellow oil).
Alternative Preparation B of Intermediate 4':

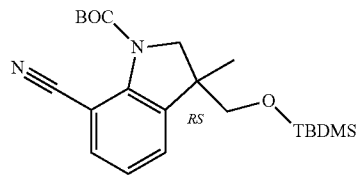

Intermediate 550 (50.0 g) was dissolved in DMF (250 mL). Sodium formate dehydrate (2.6 eq.), sodium acetate (2.6 eq.), tetraethylammonium chloride (1.25 eq.) and palladium acetate (0.05 eq.) were added. The mixture was degassed with nitrogen (3 times) and was then warmed at 45-50° C. until complete conversion (typically 24 hours monitored by HPLC). Water (350 mL) was then added followed by heptane (350 mL). The mixture was filtered and, after phase separation, the aqueous layer was extracted with heptane (350 mL). The combined organic layers were washed with water (250 mL) and then filtered on a diatomite pad (25 g; diatomaceous earth). The filtrate was concentrated to 100-150 mL, cooled to −10 to −5° C. for 2 hours and filtered to afford 37.6 g of intermediate 4'. An additional amount of intermediate 4' could be recovered by filtering the mother liquors on a silica gel pad to remove impurities, and subsequently cool down the filtrate to −10° C. to crystallize out an additional amount of intermediate 4'.
Preparation of Intermediate 4'R

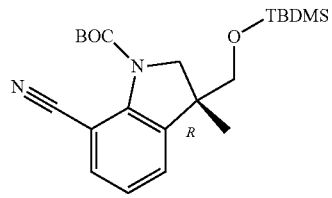

Intermediate 4'R

Intermediates 4'R was obtained from a chiral chromatography separation of intermediate 4' (column CHIRALPAK IC 5 cm*25 cm; mobile phase: hexane/EtOH:80/20; Flow rate: 60.0 mL/min; Wavelength: UV 254 nm; Temperature: 35° C.).

Preparation of Intermediate 4R and Intermediate 4S:

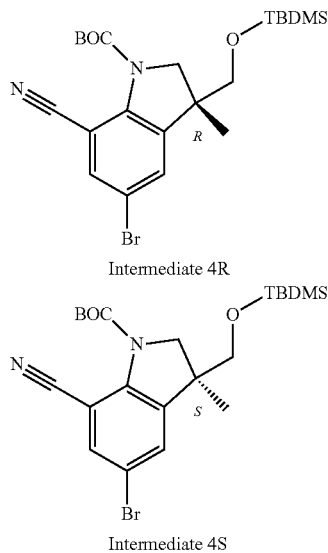

Intermediate 4R

Intermediate 4S

Intermediate 4 (500 g) was purified via Normal Phase Chiral separation (Stationary phase: Daicel Chiralpak IC 2000 gram 10 microhm, mobile phase: heptane/EtOH, Isocratic 80% heptane, 20% EtOH). The fractions containing the products were mixed and concentrated to afford 266 g of intermediate 4R (53% yield, ee>98%) and 225 g of intermediate 4S (45% yield, ee >98%).

Alternatively, intermediate 4 (10 g) was purified by chiral SFC (Stationary phase: CHIRALPAK IC 5 μm 250×30 mm, mobile phase: 85% $CO_2$, 15% iPrOH). The pure fractions were collected and evaporated to dryness yielding 4.3 g of intermediate 4R (43% yield, ee=100%) and 4.5 g of intermediate 4S (45% yield, ee=100%). Alternative preparation of intermediate 4R:

To a solution of intermediate 4'R (10.0 g) in ACN (100 mL) 1,3-dibromo-5,5-dimethylhydantoin (0.75 eq.) was added and the mixture was stirred at 20° C. for 24-28 hours, monitoring the conversion by HPLC. After complete conversion aqueous 5% $NaHCO_3$ was added (250 mL) and the mixture was stirred for 30 minutes. Toluene (250 mL) was then added and, after 30 min stirring at room temperature, the mixture was allowed to settle and the layers were separated. The organic layer was washed twice with water (100 mL) and used directly in the next step (conversion 99.6%).

Example A2

Preparation of Intermediate 5:

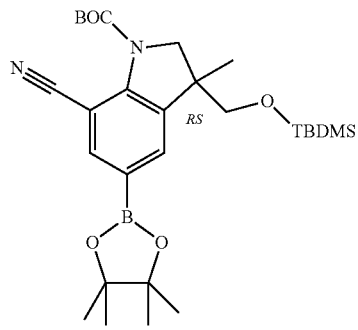

To a solution of intermediate 4 (127.00 g, 234.70 mmol) in 1,4-dioxane (1.2 L), bis(pinacolato)diboron (74.50 g, 293.40 mmol) and potassium acetate (69.11 g, 704.24 mmol) were added. Then, [1,1'-bis(diphenylphosphino) ferrocene] palladium, (II) chloride (8.59 g, 11.74 mmol) was added and stirred for 4 h at 85° C. under $N_2$ atmosphere. The mixture was cooled, partitioned between EtOAc (2 L) and water (500 mL) and filtered through a pad of Celite®. The organic and aqueous layers were separated. The organic layer was washed successively with water (300 mL), brine (300 mL), dried over $Na_2SO_4$ and concentrated under vacuum. The residue was dissolved in a mixture of DCM/EtOAc (90:10, 600 mL), filtered through a plug of flash silica gel, washed with DCM/EtOAc (90:10, 3 L). The filtrate was evaporated to give 125 g of crude intermediate 5 (brown oil) which was directly engaged in the next step.

Preparation of Intermediate 5R:

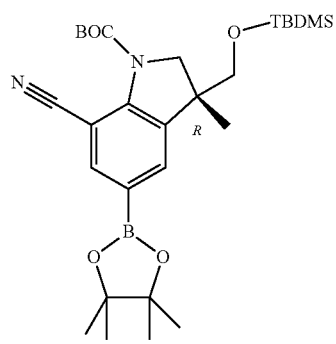

To a solution of intermediate 4R (20.00 g, 41.50 mmol) in 1,4-dioxane (200 mL), bis(pinacolato)diboron (13.20 g, 51.90 mmol) and potassium acetate (12.20 g, 124.60 mmol) were added. Then, [1,1'-bis(diphenylphosphino) ferrocene] palladium, (II) chloride complex with dichloromethane (1.70 g, 2.08 mmol) was added and stirred for 4 h at 85° C. under $N_2$. The mixture was cooled, partitioned between EtOAc (200 mL) and water (100 mL), and filtered through a pad of Celite®. The organic and aqueous layers were separated. The organic layer was washed successively with water (100 mL), brine (100 mL), dried over $Na_2SO_4$, and concentrated under vacuum. The residue was dissolved in a mixture of DCM/EtOAc (90:10, 200 mL), filtered through a plug of flash silica gel and washed with a mixture of DCM/EtOAc (90:10, 1 L). The filtrate was evaporated to give 25 g of crude intermediate 5R (brown oil) which was directly engaged in the next step.

Preparation of Intermediate 6:

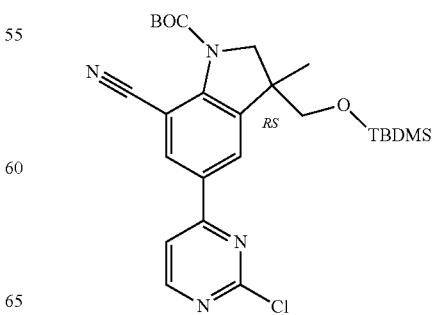

A solution of intermediate 5 (160.00 g, 302.70 mmol) in 1,4-dioxane (1.2 L) was treated with a solution of NaHCO$_3$ (76.30 g, 908.10 mmol) in water (400 mL). Then, 2,4-dichloropyrimidine (67.64 g, 545.06 mmol) and Pd(PPh$_3$)$_4$ (17.50 g, 15.13 mmol) were added under N$_2$. The reaction mixture was stirred at 80° C. under N$_2$. The mixture was cooled, partitioned between EtOAc (2 L) and water (800 mL), and the mixture was filtered through a pad of Celite®. The organic and aqueous layers were separated. The organic layer was washed successively with water (800 mL) and brine (500 mL), dried over Na$_2$SO$_4$ and concentrated under vacuum. The residue was purified by flash column chromatography on silica gel (SiO$_2$, mobile phase: petroleum ether/EtOAc, gradient from 100:0 to 10:1). The desired fractions were collected and the solvent was concentrated to dryness under vacuum to give 100 g of intermediate 6 (71% yield in 2 steps, yellow solid).

Preparation of Intermediate 6R and Intermediate 6S:

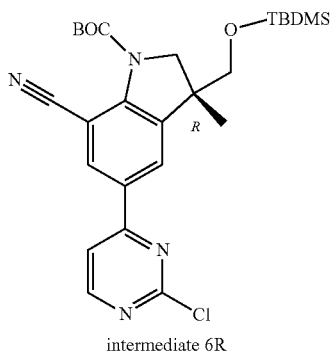

intermediate 6R

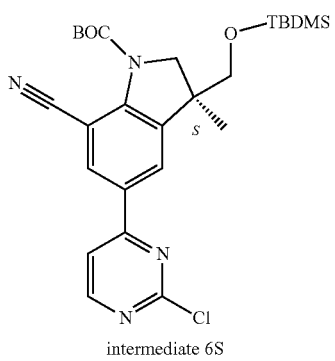

intermediate 6S

Intermediate 6 (52.00 g) was purified by chiral SFC (stationary phase: CHIRALPAK IC 5 μm 250×30 mm, mobile phase: 60% CO$_2$, 40% MeOH). The desired fractions were collected and the solvent was concentrated to dryness under vacuum to give 25 g of intermediate 6R containing small impurities (48% yield) and 25.1 g of intermediate 6S (48% yield).

Several combined batches of Intermediate 6R (50.10 g in total) were further purified by chiral SFC (stationary phase: CHIRALPAK IA 5 μm 250*20 mm, mobile phase: 87.5% CO$_2$, 12.5% MeOH). The pure fractions were mixed and the solvent was evaporated to afford 49.10 g of intermediate 6R.

Alternative Preparation of Intermediate 6R:

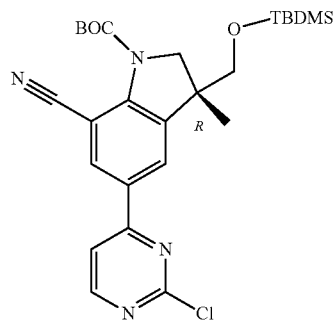

A solution of intermediate 5R (25.00 g, 41.90 mmol) in 1,4-dioxane (1.2 L) was treated with a solution of NaHCO$_3$ (10.50 g, 125.72 mmol) in water (80 mL). Then, 2,4-dichloropyrimidine (9.36 g, 62.86 mmol) and Pd(PPh$_3$)$_4$ (2.42 g, 2.09 mmol) were added under N$_2$. The reaction mixture was stirred at 80° C. under N$_2$. The mixture was cooled, partitioned between EtOAc (300 mL) and water (100 mL), and filtered through a pad of Celite®. The organic layer was washed with water (100 mL), brine (100 mL), dried over Na$_2$SO$_4$ and concentrated under vacuum. The resulting residue was combined with 3 other batches coming from reactions performed on 25 g of intermediate 5R. The residue was purified by flash column chromatography on silica gel (SiO$_2$, mobile phase: petroleum ether/EtOAc, gradient from 100:0 to 10:1). The desired fractions were collected and the solvent was concentrated to dryness under vacuum to give 63 g of intermediate 6R (70% yield over 2 steps, yellow solid).

Alternative Preparation of Intermediate 6R:

To a solution of intermediate 4R (50.0 g) in toluene (400 mL) was added bis(pinacolato)diboron (1.3 eq.), potassium acetate (3.0 eq.) and Pd(dppf)Cl$_2$ (0.05 eq.). The mixture was degassed 3 times with nitrogen and heated to 90° C. for 12-14 hours. Subsequently, the mixture was cooled to room temperature and filtered on a celite pad which was washed with toluene (150 mL). The filtrate was washed with water (250 mL) and was then filtered on a silica pad (10 g) to afford a toluene solution containing 49 g of intermediate 5R. To this solution was added 2,4-dichloropyrimidine (1.5 eq.), NaHCO$_3$ (3.0 eq.), water (25 mL) and Pd(PPh$_3$)$_4$ (0.05 eq.). After degassing three times with nitrogen, the mixture was stirred at 90° C. monitoring the conversion by HPLC. After complete conversion (24-48 hours), the mixture was cooled to room temperature, filtered on a celite pad and washed with water (250 mL). To the organic layer was added silica thiol scavenging resin (10 g) and the mixture was stirred at 90° C. for 3 hours, then cooled to room temperature and filtered. The solvent was switched completely to isopropanol by repeated distillation until about 100 mL of isopropanol solution remained. The solution was warmed to 50° C. and 250 mL of methanol were added. After stirring at 50° C. for 4 hours, the mixture was cooled to 0° C. in 4 h, held at the same temperature for 16 hours and finally filtered to obtain 26 g of intermediate 6R.

Preparation of Intermediate 6a:

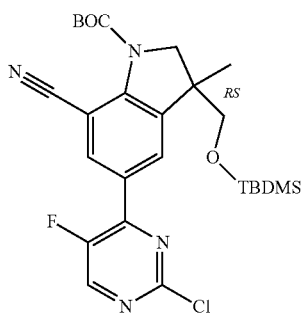

To a solution of intermediate 5 (3.89 g, 4.92 mmol), 5-fluoro-2,4-dichloropyrimidine (1.07 g, 6.40 mmol) and Cs$_2$CO$_3$ (4.81 g, 14.80 mmol) in 1,4-dioxane (25 mL) and distilled water (2.5 mL), Pd(PPh$_3$)$_4$ (0.28 g, 0.25 mmol) was added and the reaction mixture was heated overnight at 95° C. The mixture was poured into ice and extracted with EtOAc. The organic layer was washed with brine, dried over MgSO$_4$, filtered and the solvent was evaporated. The residue was purified by column chromatography on silica gel (240 g, 15-40 µm, mobile phase: heptane/EtOAc, gradient from 1:0 to 0:1). The pure fractions were mixed and the solvent was evaporated to give 1.92 g of intermediate 6a (73% yield).

The intermediates in the Table below were prepared by using an analogous starting from the respective starting materials.

| Intermediate number | Structure | Mass (mg) | Yield (%) |
|---|---|---|---|
| Intermediate 6aR | 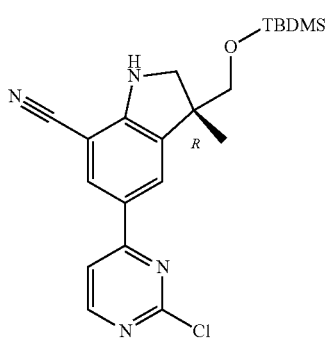<br>From intermediate 5R and 5-fluoro-2,4-dichloropyrimidine | 1820 | 83 |

Example A3

Preparation of Intermediate 7R:

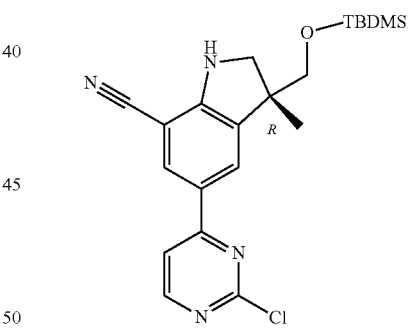

In a three neck round bottom flask, SiO$_2$ (35-70 µm) (200 g) was added to a solution of intermediate 6R (45.00 g, 87.36 mmol) in toluene (640 mL) at rt. The reaction mixture was reflux (bath temperature 125° C.) for 6 h under mechanical agitation. Then, SiO$_2$ (35-70 µm) was filtered off, washed successively with THF and EtOAc, and the filtrate was evaporated to dryness to give 37.2 g of crude intermediate 7R which was directly engaged in the next steps.

Preparation of Intermediate 392

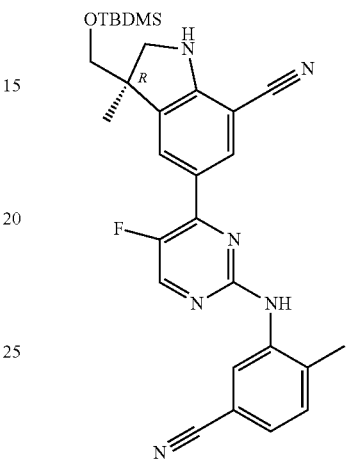

Intermediate 392 was prepared by using an analogous reaction protocol as the procedure described above to get intermediate 7R, but starting from intermediate 391 (310 mg; 98%).

Alternative Preparation of Intermediate 7R:

TFA (135 mL, 1.76 mol) was added dropwise at −10° C. (over 50 min) to a solution of intermediate 6R (20.00 g, 38.82 mmol) in DCM (550 mL). The reaction mixture was stirred below 0° C. for 15 min more, then poured in a mixture of crushed ice and a saturated aqueous solution of K$_2$CO$_3$. After extraction with DCM (twice), the organic layers were combined, washed with an aqueous solution of K$_2$CO$_3$, dried over MgSO$_4$ and evaporated to dryness. The residue (17.40 g) was purified by chromatography on silica gel (irregular SiOH, 80 g, mobile phase: NH$_4$OH/MeOH/DCM, gradient from 0% NH$_4$OH, 0% MeOH, 100% DCM to 0.2% NH$_4$OH, 2% MeOH, 98% DCM). The desired fractions were collected and the solvent was concentrated to dryness under vacuum to give 12.1 g of intermediate 7R (75% yield).

Preparation of Intermediate 7:

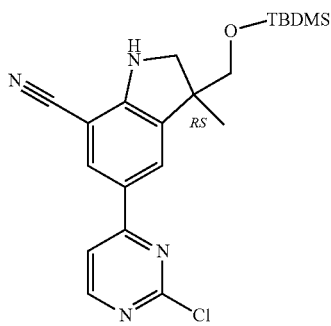

To a solution of intermediate 6 (1.50 g, 2.91 mmol) in DCM (30 mL), TFA (7 mL, 91.50 mmol) was added at 0-5° C. and stirred at 0-5° C. for 1 h, then rt for 1 h. The crude product was poured in a mixture of crushed ice and a saturated aqueous solution of NaHCO₃. After extraction with DCM (twice), the organic layers were combined, washed with a saturated solution of NaHCO₃, dried over MgSO₄ and concentrated under vacuum. The residue was purified by column chromatography on silica gel (Irregular SiOH, 40 μm, mobile phase: NH₄OH/MeOH/DCM, gradient from 0% NH₄OH, 0% MeOH, 100% DCM to 0.1% NH₄OH, 2% MeOH, 98% DCM). The desired fractions were collected and the solvent was concentrated to dryness under vacuum to give 524 mg of intermediate 7 (65% yield).

Example A4

Preparation of Intermediate 150:

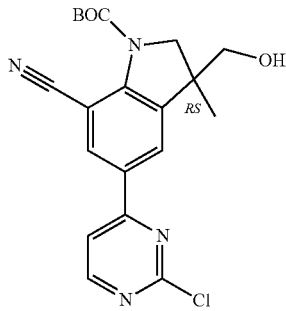 [SMILES: CC(C)(C)OC(=O)N1CC(C)(CO)c2cc(-c3ccnc(Cl)n3)cc(C#N)c21]

A solution of intermediate 6 (500.00 mg, 0.97 mmol) in THF (5.71 mL, 70.21 mmol) was treated with TBAF (1M in THF) (1.16 mL, 1.16 mmol) and stirred at rt for 12 h. The reaction mixture was poured in EtOAc. The organic layers were washed with water then brine, dried over MgSO₄ and evaporated in vacuo. The residue (483 mg) was purified by column chromatography on silica gel (Irregular SiOH, 40 μm, 40 g, mobile phase: DCM/MeOH/NH₄OH, gradient from 100% DCM to 98% DCM, 2% MeOH, 0.2% NH₄OH). The pure fractions were combined and the solvent was evaporated to give 358 mg of intermediate 150 (92% yield).

Example A5

Preparation of Intermediate 271:

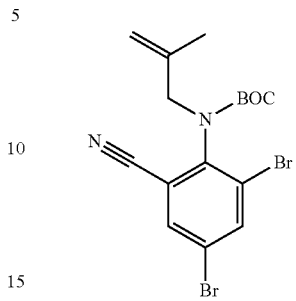

A solution of intermediate 2 (10.00 g, 26.59 mmol) and 2-methyl-2-propen-1-ol (4.50 mL, 53.69 mmol) in Me-THF (200 mL) was cooled with EtOH/ice bath under N₂ to an internal temperature of −5° C. Tri-n-butylphosphine (13.30 mL, 53.19 mmol) was added. Then a solution of 1,1'-(azodicarbonyl)piperidine (14.80 g, 58.62 mmol) in Me-THF (120 mL) was added dropwise over 25 min. The solution was stirred for 5 min more at this temperature then the cooling bath was removed and the solution stirred at rt for 18 h. The reaction mixture was poured onto a 10% aqueous solution of K₂CO₃ and extracted with DCM. The organic layer was decanted, dried over MgSO₄, filtered and evaporated to dryness. The residue (20 g) was taken up with heptane and the insoluble material was removed by filtration. The filtrate was concentrated to 20 mL and purified by column chromatography on silica gel (irregular SiOH, 80 g, mobile phase: heptane/EtOAc, gradient from 100:0 to 88:12). The pure fractions were collected and evaporated to dryness to give 10.80 g of intermediate 271 (94% yield).

Preparation of Intermediate 272 and Intermediate 272':

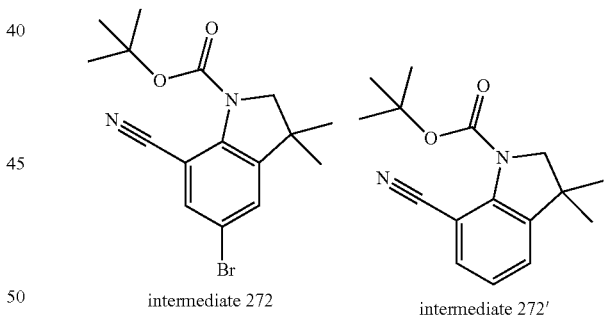

intermediate 272         intermediate 272'

A mixture of intermediate 271 (10.80 g, 25.11 mmol), sodium acetate (5.35 g, 65.28 mmol), sodium formate (4.44 g, 65.28 mmol) and tetraethylammonium chloride (5.20 g, 31.38 mmol) in DMF (100 mL) was de-gassed by sonication for 10 min under a stream of Ar. Pd(OAc)₂ (563.00 mg, 2.51 mmol) was added and the resulting orange suspension was then stirred at 85° C. (block temperature) for 4 h. The residue was diluted with EtOAc and water, then filtered through a plug of Celite®. The organic layer was decanted, washed successively with a saturated aqueous solution of NaHCO₃ and brine, dried over MgSO₄, filtered and evaporated to dryness. The residue (8.3 g, mixture of intermediates 272 and 272') was dissolved in CH₃CN (230 mL) and NBS (4.47 g, 25.11 mmol) was added. The reaction mixture was heated at 55° C. (block temp) for 18 h. The reaction mixture was evaporated to dryness and the residue was taken up with heptane/DCM. The precipitate was filtered off (1 g derivative) and the filtrate (10 g) was purified by column chromatography on silica gel (irregular SiOH, 120 g, injection in DCM, mobile phase: heptane/EtOAc, gradient from 100:0 to 80:20). The pure fractions were collected and evaporated to dryness to give 4 g of intermediate 272 (45% yield).

Preparation of Intermediate 273:

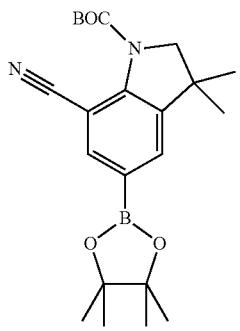 [SMILES: CC(C)(C)OC(=O)N1CC(C)(C)c2cc(B3OC(C)(C)C(C)(C)O3)cc(C#N)c21]

[1,1'-Bis(diphenylphosphino)ferrocene]dichloropalladium (II), complex with dichloromethane (243.00 mg, 0.30 mmol) was added to a solution of intermediate 272 (2.09 g, 5.95 mmol), bis(pinacolato)diboron (1.90 g, 7.44 mmol) and potassium acetate (1.75 g, 17.85 mmol) in 1,4-dioxane (45 mL) and the reaction mixture was heated for 18 h at 85° C. The reaction mixture was diluted with EtOAc and filtered through a pad of Celite®. The filtrate was washed with water, and the organic layer was decanted, dried over MgSO$_4$, filtered and evaporated to dryness. The residue was crystallized from DiPE and the precipitate was filtered and dried to give 1.85 g of intermediate 273 (78% yield).

Preparation of Intermediate 274:

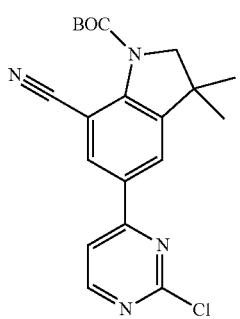 [SMILES: CC(C)(C)OC(=O)N1CC(C)(C)c2cc(-c3ccnc(Cl)n3)cc(C#N)c21]

A degassed suspension of intermediate 273 (1.12 g, 2.81 mmol), 2,4-dichloropyridine (502.00 mg, 3.37 mmol), Pd(PPh$_3$)$_4$ (162.00 mg, 0.14 mmol) and a solution of Na$_2$CO$_3$ 2M (4.20 mL, 8.14 mmol) in 1,4-dioxane (24 mL) was heated to 85° C. for 18 h. The reaction mixture was partitioned between DCM and saturated aqueous NaHCO$_3$. The organic layer was decanted, dried over MgSO$_4$, filtered and evaporated to dryness. The residue (2 g) was purified by column chromatography on silica gel (irregular SiOH, 40 g, mobile phase: heptane/EtOAc, gradient from 70:30 to 50:50). The pure fractions were collected and evaporated to dryness to give 933 mg of intermediate 274 (86% yield, 85% purity based on LC/MS).

Preparation of Intermediate 361:

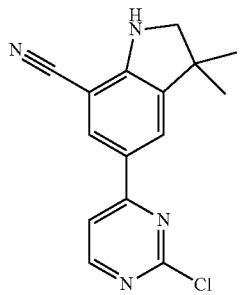 [SMILES: CC1(C)CNc2c(C#N)cc(-c3ccnc(Cl)n3)cc21]

TFA (6 mL) was added dropwise at 5° C. to a solution of intermediate 274 (3.00 g, 7.79 mmol) in DCM (60 mL) and the reaction mixture was stirred at 5° C. for 1 h. The reaction mixture was diluted with DCM and poured onto a mixture of ice and 10% aqueous K$_2$CO$_3$. The insoluble material was filtered, washed with water then Et$_2$O and dried to give 1.93 g of intermediate 361 (87% yield). M.P.=207° C. (K).

Example A6

Preparation of Intermediate 8R:

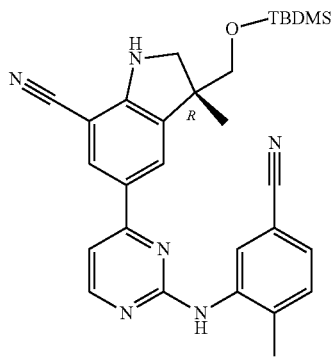

Method A:

In a sealed vessel, a solution of intermediate 7R (14.75 g, 35.54 mmol) in 1.4-dioxane (285 mL) was purged with N$_2$. 3-amino-4-methylbenzonitrile (7 g, 53.312 mmol) and Cs$_2$CO$_3$ (23.16 g, 71.083 mmol) were successively added and the suspension was degassed after each addition. Then, Pd(OAc)$_2$ (798.00 mg, 3.55 mmol) and BINAP (2.21 g, 3.55 mmol) were added. The reaction mixture was degassed with N$_2$ and stirred at 120° C. (pre-heated bath) for 3 h. The reaction mixture was cooled to rt, poured onto ice-water and extracted with EtOAc. The organic layer was decanted, washed with brine, dried over MgSO$_4$, filtered over a pad of Celite® and concentrated to vacuum. The residue (30 g) was purified by column chromatography on silica gel (irregular SiOH, 400 g, mobile phase: DCM/EtOAc, gradient from 100:0 to 85:15 (12×200 mL)). The desired fractions were collected and the solvent was concentrated to dryness under vacuum to give 14.3 g of intermediate 8R (79% yield contaminated by 7% of 3-amino-4-methylbenzonitrile as evaluated by $^1$HNMR). This solid was suspended in Et$_2$O/CH$_3$CN and the mixture was sonicated at rt for 15 min. The precipitate was filtered, washed with CH$_3$CN and dried to give 8.6 g of intermediate 8R (47% yield). The filtrate was evaporated and the residue was purified by column chromatography on silica gel (irregular SiOH, 80 g, mobile phase: DCM/EtOAc, gradient from 100:0 to 90:10). The fractions containing the product were collected and evaporated to dryness. The resulting solid was suspended in Et$_2$O/CH$_3$CN and the mixture was sonicated at rt for 15 min. The precipitate was filtered, washed with CH$_3$CN and dried to give additional 2.6 g of intermediate 8R (14% yield). The global yield of this reaction was 62% (11.2 g).

Method B:

SiO$_2$ 35-70 μm (25 g) was added to a solution of intermediate 9R (6.10 g, 10.00 mmol) in toluene (75 mL) at rt. The reaction mixture was refluxed (bath temperature 125° C.) for 6 h under vigorous agitation. Then, SiO$_2$ 35-70 μm was filtered off, washed successively with THF and EtOAc and the filtrate was evaporated to dryness. The residue was taken up with Et$_2$O and the precipitate was filtered and dried to give 4.34 g of intermediate 8R (85% yield).

The intermediates in the Table below were prepared by using an analogous method as described in Method A starting from the respective starting materials. The most relevant minor deviations from the initial method are indicated in the column 'Method'.

| Intermediate number | Structure | Mass (mg) | Yield (%) | Method |
|---|---|---|---|---|
| Intermediate 20 | 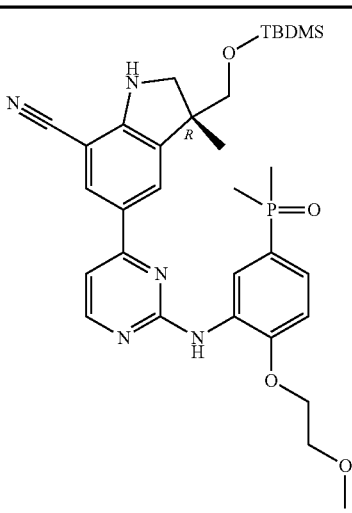 From intermediate 7R and intermediate 24 | 247 (82% of purity based on LC/MS) | 33 | A |
| Intermediate 21 | 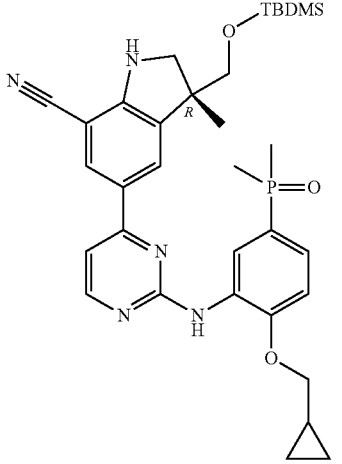 From intermediate 7R and intermediate 27 | 325 | 44 | A |

-continued

| Intermediate number | Structure | Mass (mg) | Yield (%) | Method |
|---|---|---|---|---|
| Intermediate 42 | From intermediate 7R and intermediate 41 | 618 orange oil | 32 | A |
| Intermediate 49 | From intermediate 7R and intermediate 48 | 292 (96% of purity based on LC/MS) 365 mg (79% of purity based on LC/MS) | 30 | A |
| Intermediate 52 | From intermediate 7R and intermediate 51 | 843 (80% of purity based on LC/MS) orange oil | 93 | A |

| Intermediate number | Structure | Mass (mg) | Yield (%) | Method |
|---|---|---|---|---|
| Intermediate 55 | From intermediate 7R and powder intermediate 54 | 1293 (94% of purity based on LC/MS) yellow powder | Quant. | A |
| Intermediate 57 | From intermediate 7R and intermediate 56 | 344 (98% of purity based on LC/MS) | 63 | A |
| Intermediate 60 | From intermediate 7 R and solid intermediate 59 | 1010 (73% of purity based on LC/MS) orange solid | — | A |

| Intermediate number | Structure | Mass (mg) | Yield (%) | Method |
|---|---|---|---|---|
| Intermediate 104 | 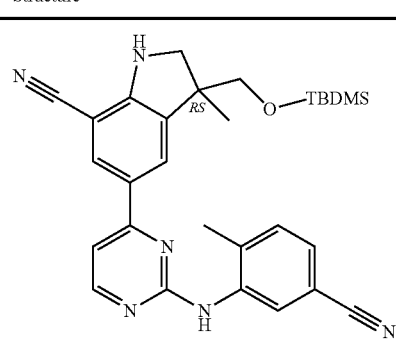<br>From intermediate 7 and 3-amino-4-methylbenzonitrile | 261 yellow solid | 47 | A with T = 95° C. |
| Intermediate 195 | 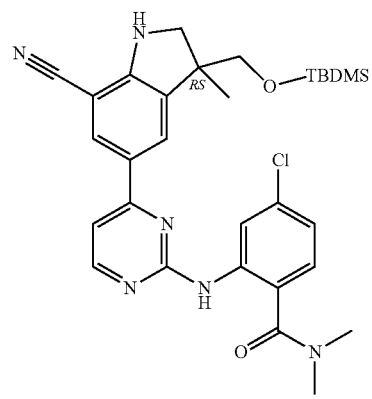<br>From intermediate 7 and 2-amino-4-chloro-N,N-dimethylbenzamide | 275 (94% of purity based on LC/MS) | 66 | A with T = 90° C. |
| Intermediate 199 | 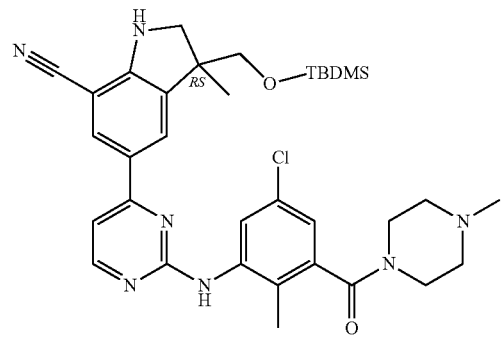<br>From intermediate 7 and intermediate 198 | 270 (80% of purity based on LC/MS) | 74 | A with T = 90° C. |

-continued

| Intermediate number | Structure | Mass (mg) | Yield (%) | Method |
|---|---|---|---|---|
| Intermediate 246 | From intermediate 7R and intermediate 245 | 423 | 65 | A |
| Intermediate 256 | From intermediate 7R and intermediate 255 | 1190 (94% of purity based on LC/MS) | 87 | A |
| Intermediate 394 | From intermediate 7R and intermediate 393 | 3100 | 55 | A |
| Intermediate 398 | From intermediate 7R and intermediate 397 | 220 | 52 | A With T = 80° C. |

-continued
| Intermediate number | Structure | Mass (mg) | Yield (%) | Method |
|---|---|---|---|---|
| Intermediate 404 | 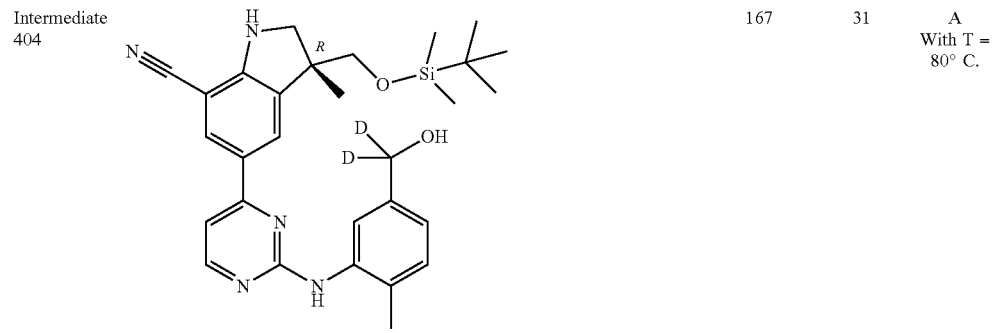<br>From intermediate 7R and intermediate 403 | 167 | 31 | A<br>With T = 80° C. |
| Intermediate 407 | 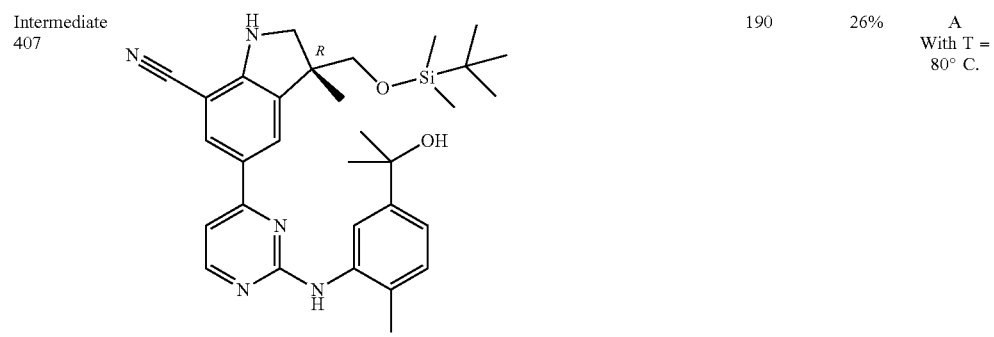<br>From intermediate 7R and intermediate 406 | 190 | 26% | A<br>With T = 80° C. |
| Intermediate 412 | 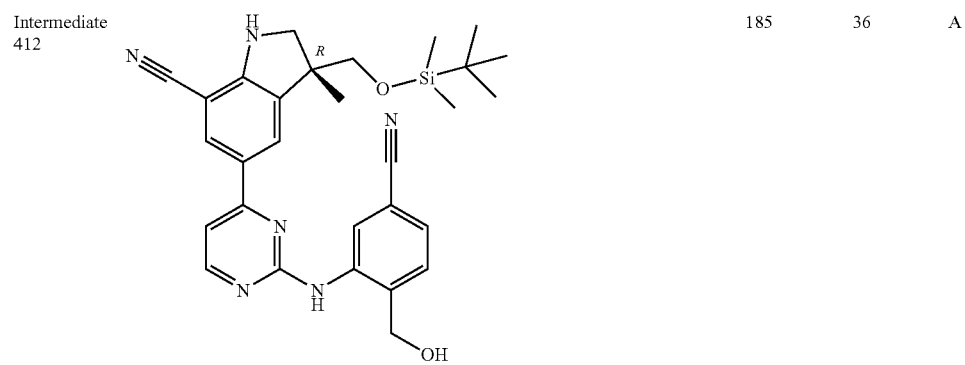<br>From intermediate 7R and 3-amino-4-(hydroxymethyl)benzonitrile | 185 | 36 | A |

| Intermediate number | Structure | Mass (mg) | Yield (%) | Method |
|---|---|---|---|---|
| Intermediate 433 | 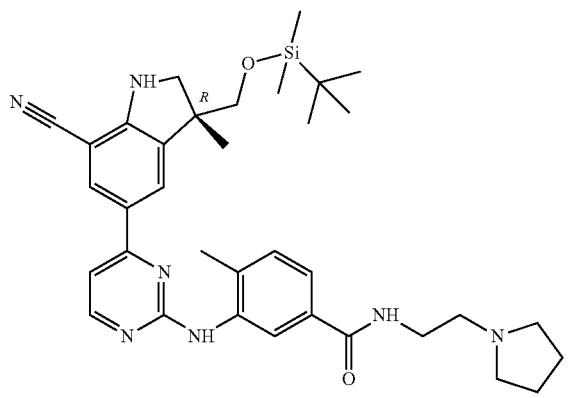<br>From intermediate 432 and intermediate 7R | 81 | 13 | A |
| Intermediate 435 | 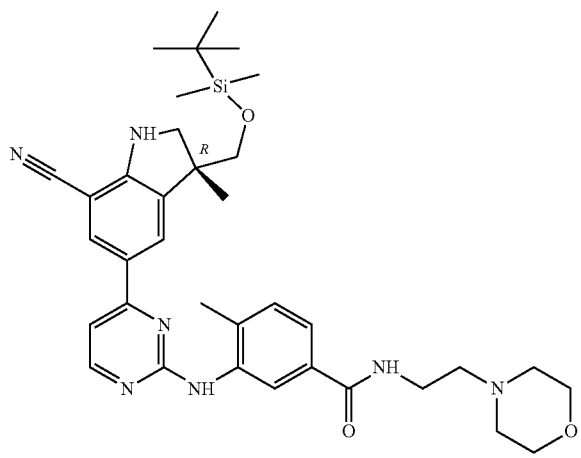<br>From intermediate 434 and intermediate 7R | 192 | 75 | A |
| Intermediate 437 | 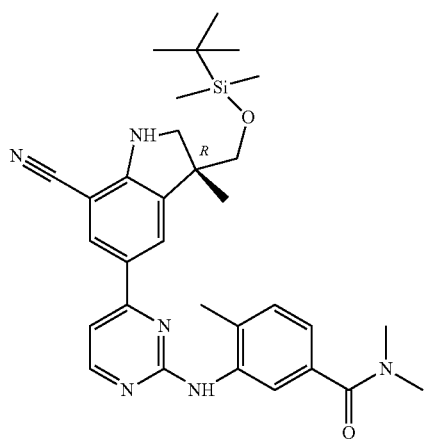<br>From intermediate 436 and intermediate 7R | 362 | 57 | A |

| Intermediate number | Structure | Mass (mg) | Yield (%) | Method |
|---|---|---|---|---|
| Intermediate 439 | 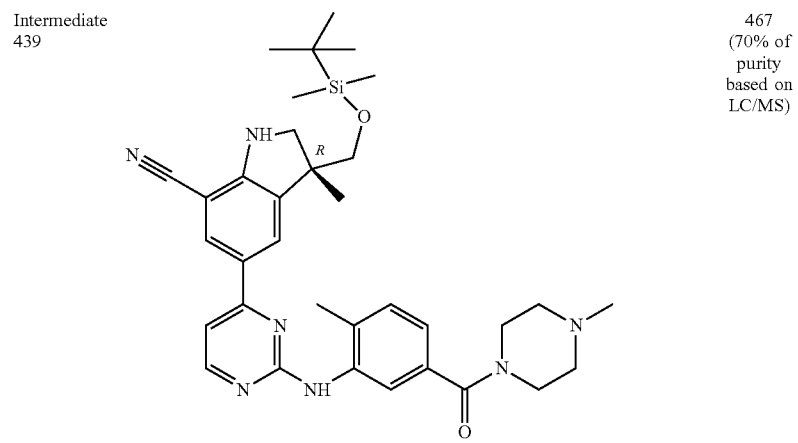<br>From intermediate 438 and intermediate 7R | 467 (70% of purity based on LC/MS) | 67 | A |
| Intermediate 440 | 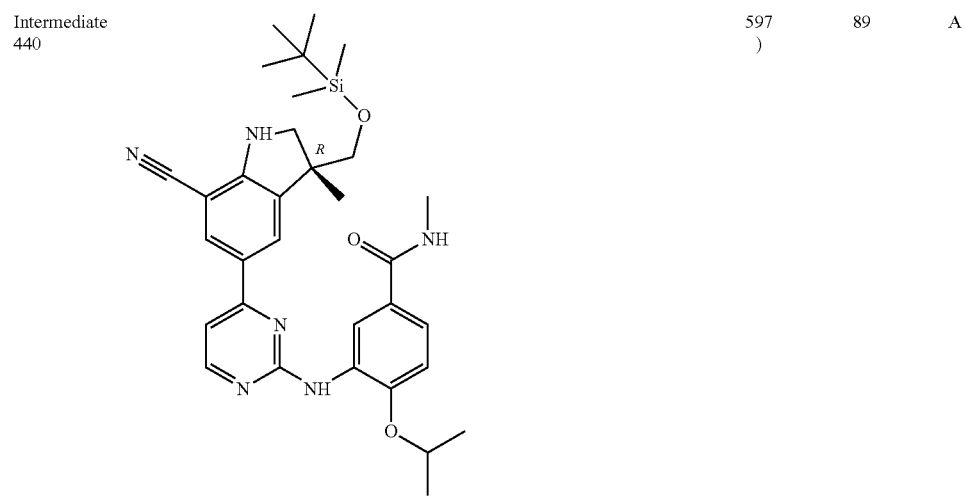<br>from 3-amino-4-isopropoxy-N-methylbenzamide and intermediate 7R | 597 | 89 | A |
| Intermediate 442 | 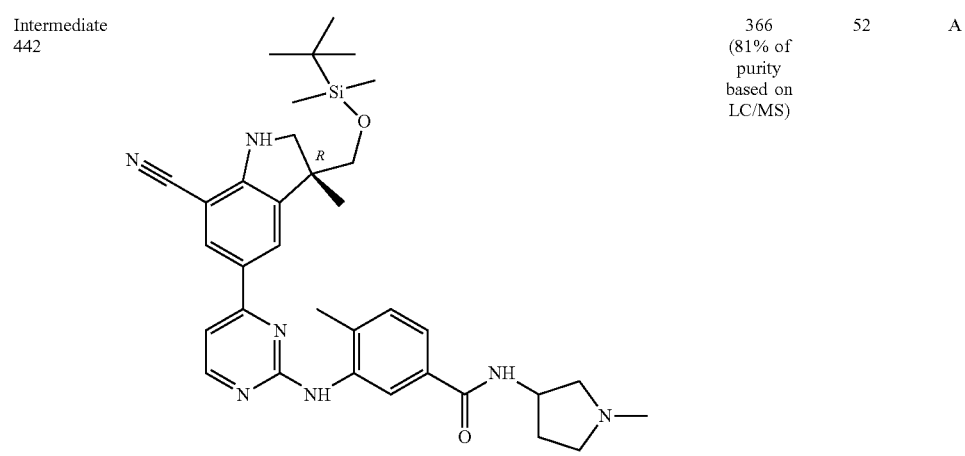<br>From intermediate 441 and intermediate 7R | 366 (81% of purity based on LC/MS) | 52 | A |

| Intermediate number | Structure | Mass (mg) | Yield (%) | Method |
|---|---|---|---|---|
| Intermediate 444 | 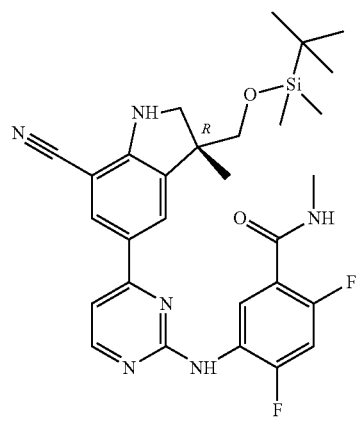<br>From intermediate 443 and intermediate 7R | 423 (100% of purity based on LC/MS) | 80 | A |
| Intermediate 448 | 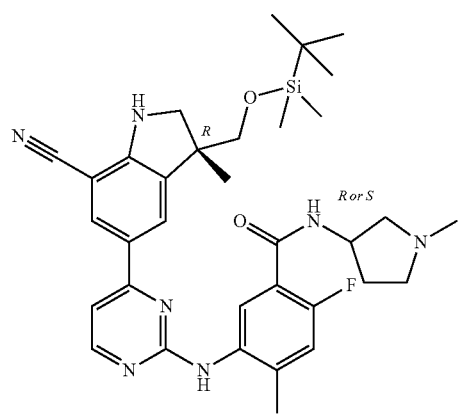<br>From intermediate 447 and intermediate 7R | 180 | 30 | A |
| Intermediate 449 | 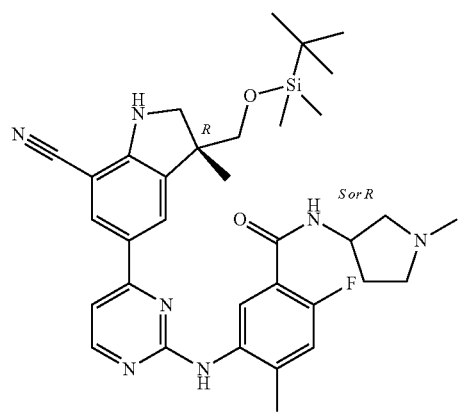<br>From intermediate 447 and intermediate 7R | 377 (100% of purity based on LC/MS) | 54 | A |

| Intermediate number | Structure | Mass (mg) | Yield (%) | Method |
|---|---|---|---|---|
| Intermediate 453 | 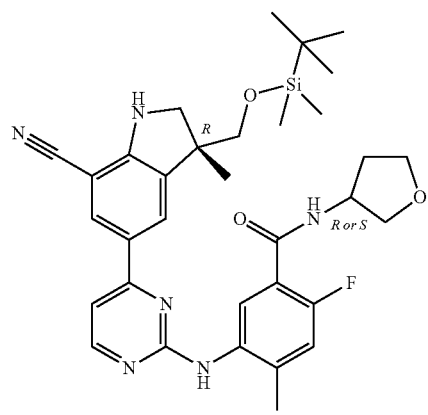<br>From intermediate 452 and intermediate 7R | 124 | 19 | A |
| Intermediate 454 | 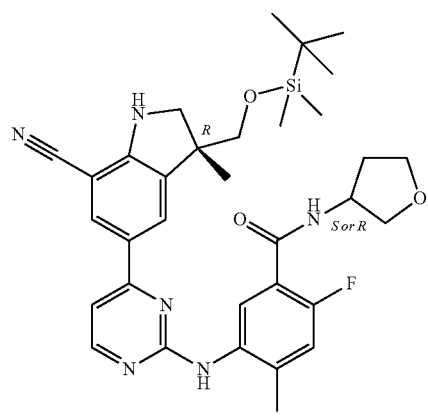<br>From intermediate 452 and intermediate 7R. | 315 | 47 | A |
| Intermediate 482 | 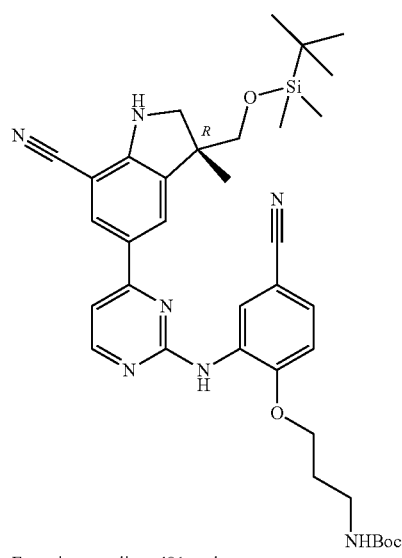<br>From intermediate 481 and intermediate 7R. | 690 (66% of purity based on LC/MS) | 86 | A |

-continued

| Intermediate number | Structure | Mass (mg) | Yield (%) | Method |
|---|---|---|---|---|
| Intermediate 483 | From intermediate 7R and methyl 5-amino-2-fluoro-4-methylbenzoate | 570 (79% of purity based on LC/MS) | 84 | A |
| Intermediate 486 | From intermediate 7R and intermediate 485 | 572 (83% of purity based on LC/MS) | 74 | A |
| Intermediate 491 | From intermediate 490 | 147 | 26 | A |

-continued

| Intermediate number | Structure | Mass (mg) | Yield (%) | Method |
|---|---|---|---|---|
| Intermediate 496 | From intermediate 7R and intermediate 495 | 165 | 19 | A |
| Intermediate 502 | From intermediate 7R and intermediate 499 | 568 | 80% | A (3 h 30@ 120° C.) |
| Intermediate 503 | From intermediate 7R and intermediate 500 | 88 | 29% Purity 82% (LCMS) | A (3 h 30@ 120° C.) |
| Intermediate 504 | From intermediate 7R and intermediate 500B | 442 | 65% | A (3 h 30@ 120° C.) |

| Intermediate number | Structure | Mass (mg) | Yield (%) | Method |
|---|---|---|---|---|
| Intermediate 511 | (structure) From intermediate 7R and intermediate 510 | 233 | 49% | A (3 h @ 120° C.) |
| Intermediate 514 | (structure) From intermediate 7R and intermediate 513 | 591 | 77% Purity 54% (LCMS) | A (5 h @ 120° C.) |
| Intermediate 518 | (structure) From intermediate 7R and rel-3-[cis-2,6-dimethyl-4-morpholinyl]methyl]-2-methyl-benzenamine | 142 | 86% Purity 70% (LCMS) | A (4 h @ 120° C.) |
| Intermediate 520 | (structure) From intermediate 7R and intermediate 519 | 221 | 61% | A (4 h @ 120° C.) |

-continued
| Intermediate number | Structure | Mass (mg) | Yield (%) | Method |
|---|---|---|---|---|
| Intermediate 521 | 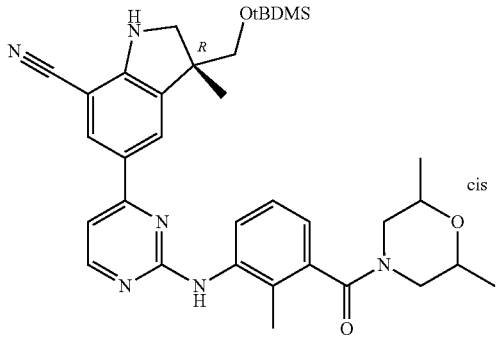<br>From intermediate 7R and intermediate 521b | 282 | 54% | A (4 h @ 120° C.) |
| Intermediate 522 | 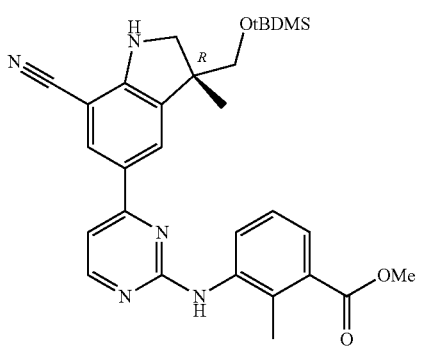<br>From intermediate 7R and methyl 3-amino-2-methylbenzoate | 1050 | 53% | A (3 h @ 120° C.) |
| Intermediate 528 | 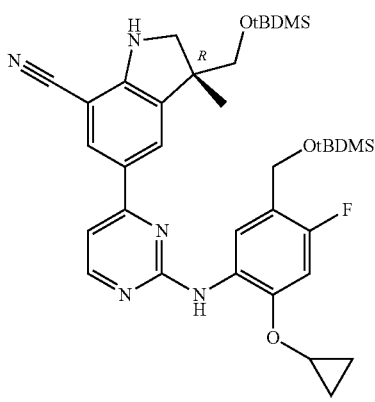<br>From intermediate 7R and intermediate 527 | 306 | 43% | A (4 h @ 120° C.) |

| Intermediate number | Structure | Mass (mg) | Yield (%) | Method |
|---|---|---|---|---|
| Intermediate 531 | 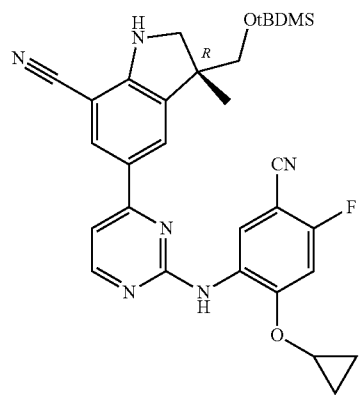<br>From intermediate 7R and intermediate 530 | 527 | 77% | A (4 h @ 120° C.) |
| Intermediate 581 | 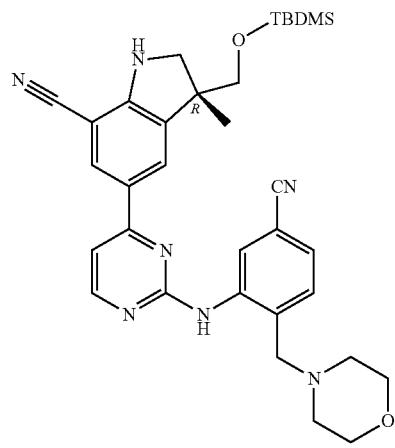<br>From intermediate 7R and intermediate 580 | 215 Pale brown oil | 65 | A |
| Intermediate 600 | 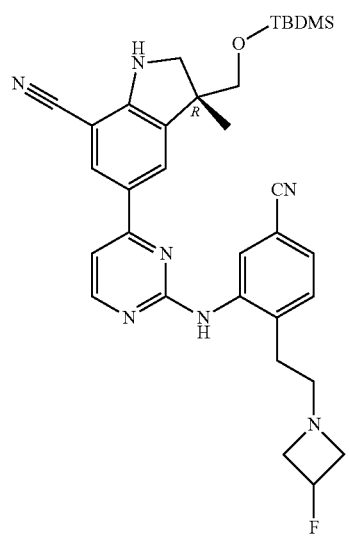<br>From intermediate 7R and intermediate 599 | 500 | Quant. | A |

-continued
| Intermediate number | Structure | Mass (mg) | Yield (%) | Method |
|---|---|---|---|---|
| Intermediate 619 | 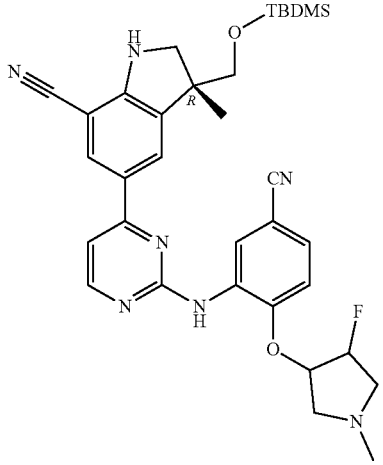<br>From intermediate 7R and intermediate 617 | 226 | 88 | A |
| Intermediate 622 | 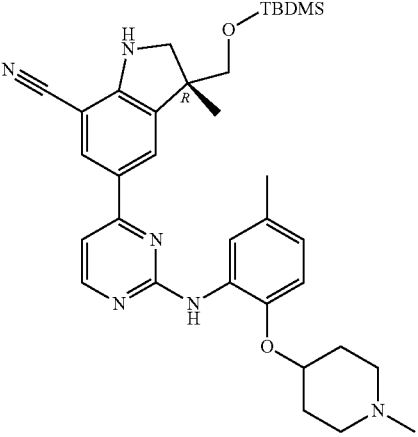<br>From intermediate 7R and intermediate 621 | 70<br>Yellow solid | 23 | A |
| Intermediate 637 | 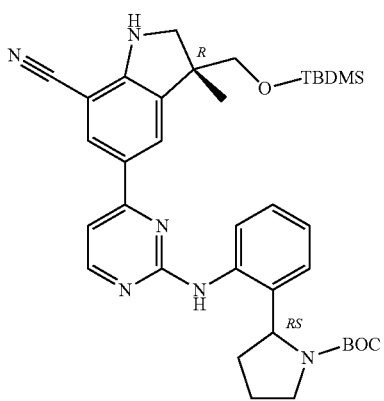<br>From intermediate 7R and intermediate 636 | 571 | 64 | A |

Preparation of Intermediate 423:

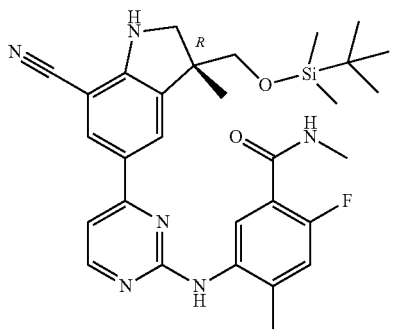

A mixture of intermediate 422 (8.68 g, 47.6 mmol), intermediate 7R (13.18 g, 31.8 mmol) and Cs$_2$CO$_3$ (20.7 g, 63.5 mmol) in 1,4-dioxane (260 mL) was purged with N$_2$. Pd(OAc)$_2$ (713 mg, 3.18 mmol) and BINAP (1.98 g, 3.18 mmol) were then added. The round bottom flask was sealed and the reaction mixture was purged with N$_2$ and was stirred at 120° C. for 3 hours. The resulting mixture was poured onto water and DCM. Then, filtered over Celite®, decanted and the organic layer was separated, dried over MgSO$_4$, filtered and evaporated. The residue (22.5 g) was purified by column chromatography over silica gel (Irregular SiOH, 40 μm, 120 g, mobile phase: heptane/EtOAc/MeOH: 60/35/5). The pure fractions were combined and the solvent was evaporated to give 10.66 g (60%) of intermediate 423 as a pale orange foam.

Preparation of Intermediate 430

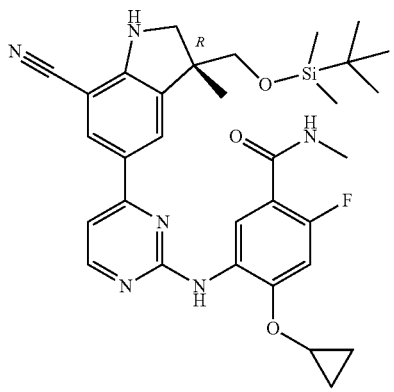

And Intermediate 431

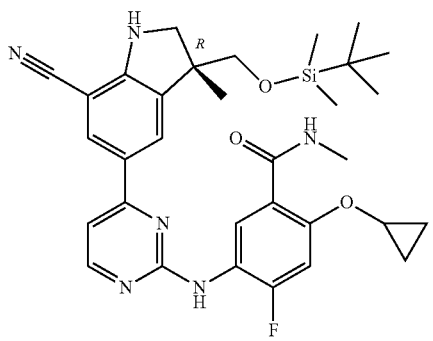

In a sealed tube, a mixture of intermediate 7R (936 mg; 2.25 mmol) in 1,4-dioxane (25 mL) was purged with N$_2$. A mixture of intermediates 428 and 429 (758 mg; 3.38 mmol) and cesium carbonate (1.47 g; 4.51 mmol) were successively added and the suspension was degassed after each addition. Then, Pd(OAc)$_2$ (51 mg; 0.226 mmol) and BINAP (140 mg; 0.226 mmol) were added. The flask was sealed, the reaction mixture was degassed with N$_2$ and stirred at 120° C. (pre-heated bath) for 4 hours.

The reaction mixture was cooled to room temperature, poured onto water and extracted with DCM. The organic layer was decanted, dried over MgSO$_4$, filtered over Celite® and evaporated to dryness. The residue was purified by chromatography over silica gel (irregular SiOH, 80 g; mobile phase: gradient from 20% EtOAc, 80% heptane to 40% EtOAc, 60% heptane). The pure fractions were collected and evaporated to dryness yielding 451 mg (33%) of intermediate 430 (33%) and 530 mg (39%) of intermediate 431.

Preparation of Intermediate 618:

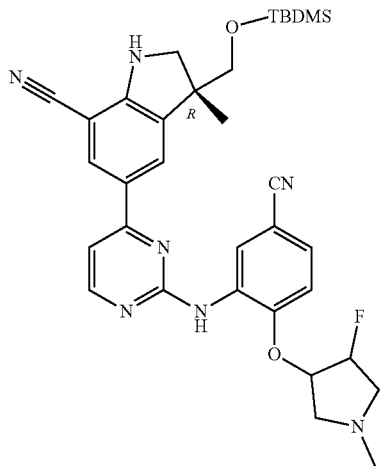

Trans A (RR or SS)

In a sealed vessel, a mixture of intermediate 7R (184 mg; 0.443 mmol) in dioxane (11 mL) was purged with N$_2$. Intermediate 616 (156 mg; 0.663 mmol) and cesium carbonate (289 mg; 0.886 mmol) were successively added and the suspension was degassed after each addition. Then Pd(OAc)2 (10 mg; 0.044 mmol) and BINAP (27 mg; 0.044 mmol) were added. The reaction mixture was degassed with N$_2$ and stirred at 120° C. (pre-heated bath) for 4 hours. The reaction mixture was cooled to room temperature, poured onto water and extracted with EtOAc. The organic layer was decanted, washed with water then brine, dried over MgSO$_4$, filtered and evaporated to dryness. The residue was purified by chromatography over silica gel (irregular SiOH, 50 g; mobile phase: gradient 0% MeOH, 100% DCM to 5% MeOH, 95% DCM). The fractions containing the product were collected and evaporated to dryness yielding 234 mg (86% yield, 87% purity evaluated by LCMS) of intermediate 618.

The intermediates in the Table below were prepared by using an analogous method as described in Method B starting from the respective starting materials. The most relevant minor deviations from the referenced method are indicated in the column 'Method'.

| Intermediate number | Structure | Mass (mg) | Yield (%) | Method |
|---|---|---|---|---|
| Intermediate 552 | (structure shown) From intermediate 551 | 197 yellow oil | 78 | B |
| Intermediate 556 | (structure shown) From a mixture of intermediate 555 and intermediate 556 | 50 orange oil | 60 | B |
| Intermediate 558 | (structure shown) From a mixture of intermediates 557 and intermediate 558 | 390 yellow oil | 94 | B |
| Intermediate 561 | (structure shown) From a mixture of intermediates 560 and intermediate 561 | 419 yellow oil | quant. | B |

-continued
| Intermediate number | Structure | Mass (mg) | Yield (%) | Method |
|---|---|---|---|---|
| Intermediate 563 | 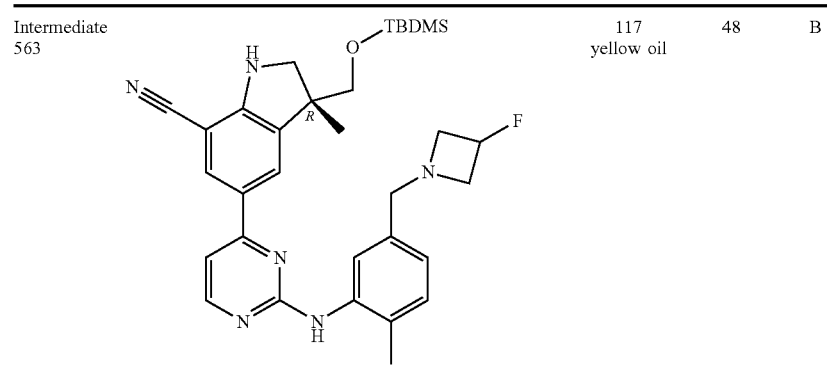<br>From a mixture of intermediate 562 and intermediate 563 | 117<br>yellow oil | 48 | B |
| Intermediate 577 | <br>From intermediate 576 | 363<br>Grey solid | 69 | B |
| Intermediate 593 | 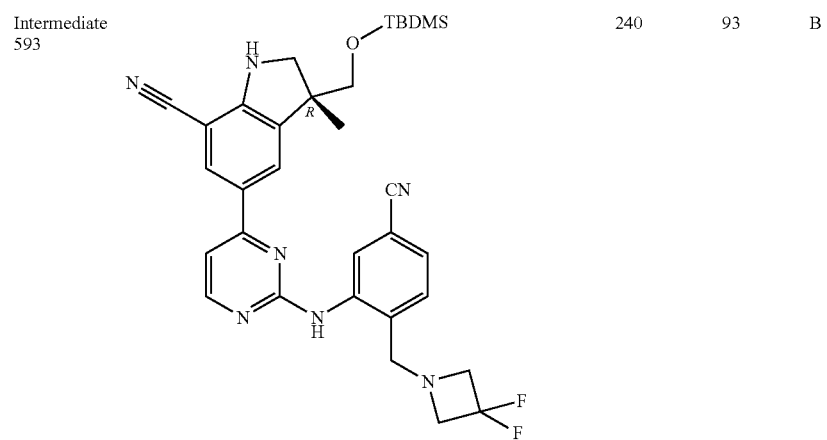<br>From intermediate 592 | 240 | 93 | B |

| Intermediate number | Structure | Mass (mg) | Yield (%) | Method |
|---|---|---|---|---|
| Intermediate 597 | 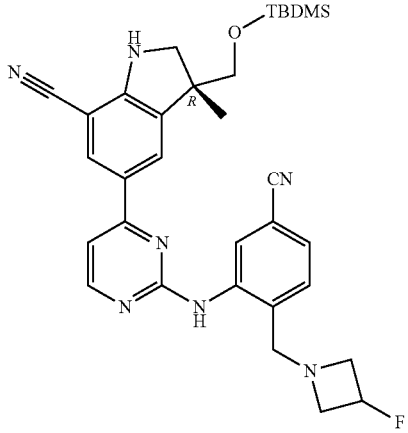 From intermediate 596 | 170 | 100 | B |
| Intermediate 606 | 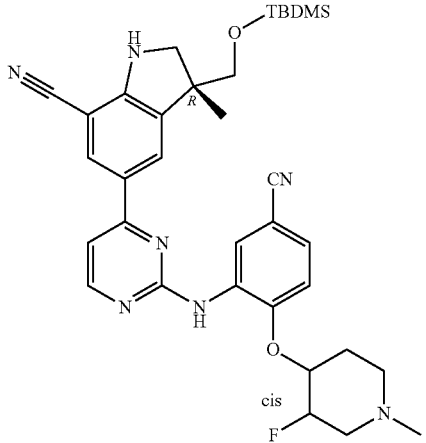 From intermediate 605 | 260 (75% purity evaluated by LCMS) | 97 | B |

| Intermediate number | Structure | Mass (mg) | Yield (%) | Method |
|---|---|---|---|---|
| Intermediate 612 | 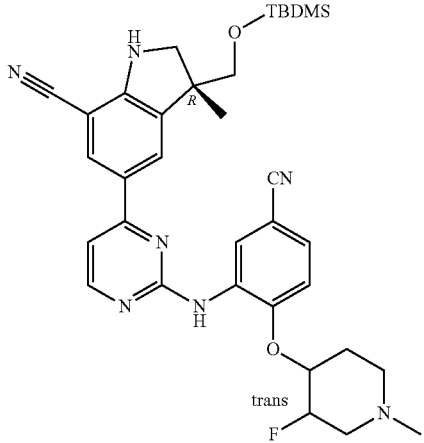 From intermediate 611 | 90 | 87 | B |
| Intermediate 641 | 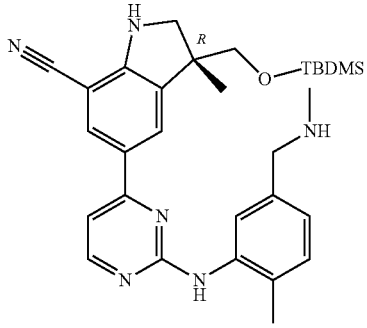 From intermediate 640 | 106 | 63 | B |

Example A7

Preparation of Intermediate 9R:

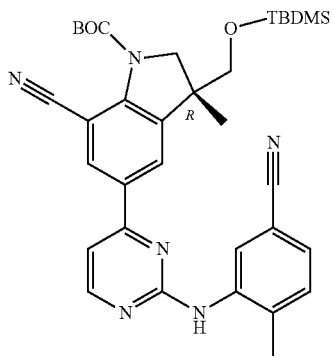

Method C:

In a Sealed vessel, a mixture of 6R (5.15 g, 10.00 mmol) in 1,4-dioxane (80 mL) was purged with $N_2$. 3-amino-4-methylbenzonitrile (2.00 g, 15.00 mmol) and $Cs_2CO_3$ (6.51 g, 20.00 mmol) were successively added and the suspension was degassed after each addition. Then Pd(OAc)$_2$ (224.45 mg, 1.00 mmol) and BINAP (622.53 mg, 1.00 mmol) were added. The reaction mixture was degassed with $N_2$ and stirred at 120° C. (pre-heated bath) for 3 h. The reaction mixture was cooled to rt, poured onto ice-water and extracted with EtOAc. The organic layer was decanted, washed with brine, dried over MgSO$_4$, filtered over a pad of Celite® and evaporated to dryness. The residue was purified by column chromatography on silica gel (irregular SiOH, 120 g, mobile phase: heptane/EtOAc, gradient from 85:15 to 70:30). The pure fractions were collected and evaporated to dryness to give 4.17 g of intermediate 9R (68% yield).

Method D:

NaH (60% dispersion in mineral oil) (0.90 g, 22.49 mmol) was added portionwise to a stirred solution of N-(5-cyano-2-methylphenyl)-formamide (2.40 g, 15.00 mmol) in DMF (100 mL) under a $N_2$ atmosphere at rt and stirred for 30 min. Then, intermediate 6R (5.15 g, 1.00 mmol) was added and the reaction mixture was stirred at rt for 18 h. The resulting crude product was poured into water and extracted with EtOAc. The organic layer was decanted, washed successively with water and brine, dried over MgSO$_4$, filtered and concentrated to dryness to give 7.8 g of crude intermediate 9R which was used without any further purification in the next step.

The intermediates in the Table below were prepared by using an analogous method as described in Method C starting from the respective starting materials. The most relevant minor deviations from the referenced method are indicated in the column 'Method'.

| Intermediate number | Structure | Mass (mg) | Yield (%) | Method |
|---|---|---|---|---|
| Mixture of Intermediate 11/ Intermediate 12 | 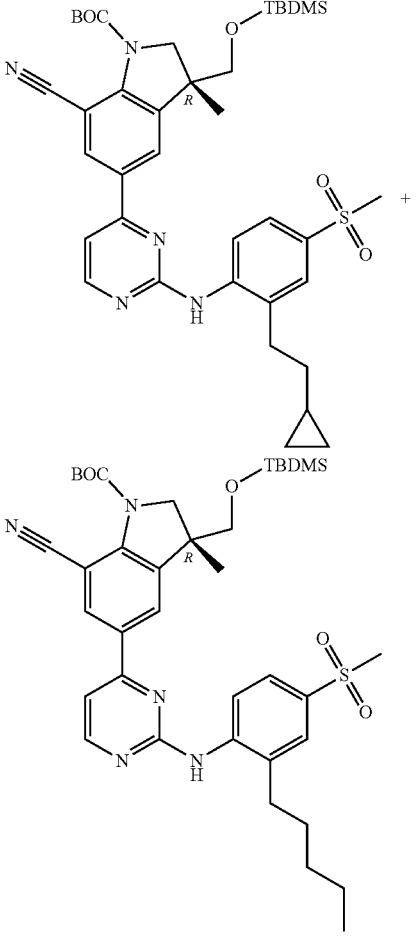<br>from intermediate 6R and a mixture of intermediates 16 and 17 | 1210 mixture of intermediate 11 and intermediate 12 (74:14 based on LC/MS) | — | C |
| Intermediate 18 | 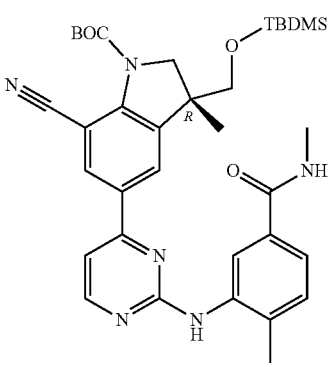<br>from intermediate 6R and 3-amino-N,4-dimethyl benzamide | 477 off-white foam | 76 | C |

-continued
| Intermediate number | Structure | Mass (mg) | Yield (%) | Method |
|---|---|---|---|---|
| Intermediate 29 | 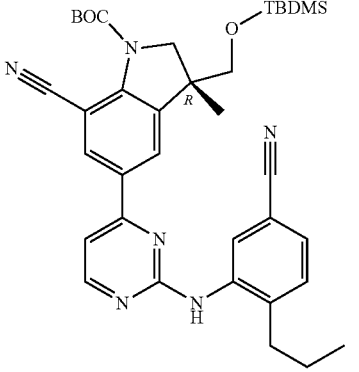 from intermediate 6R and intermediate 28 | 337 (92% of purity based on LC/MS) | 41 | C |
| Intermediate 33 and Intermediate 34 | 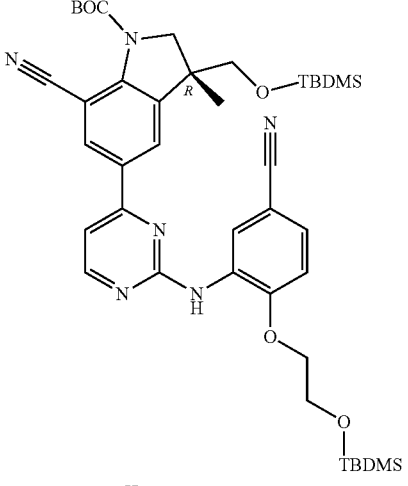 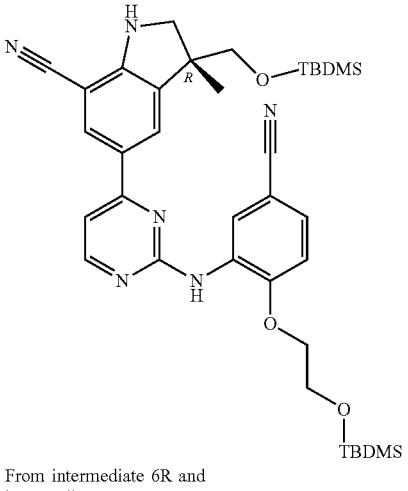 From intermediate 6R and intermediate 32 | 387 (intermediate 33) (89% of purity based on LC/MS) orange oil 474 (intermediate 34) (93% of purity based on LC/MS) orange oil | 32 39 | C |

-continued

| Intermediate number | Structure | Mass (mg) | Yield (%) | Method |
|---|---|---|---|---|
| Intermediate 38 | *(structure shown) From intermediate 6R and intermediate 37* | 778 | 60 | C |
| Intermediate 45 | *(structure shown) From intermediate 6R and intermediate 44* | 1090 (93% of purity based on LC/MS) beige solid | 89 | C |
| Intermediate 61 | *(structure shown) From intermediate 6R and intermediate 59* | 525 (93% of purity based on LC/MS) Light yellow powder | 83 | C |

-continued
| Intermediate number | Structure | Mass (mg) | Yield (%) | Method |
|---|---|---|---|---|
| Intermediate 63 | 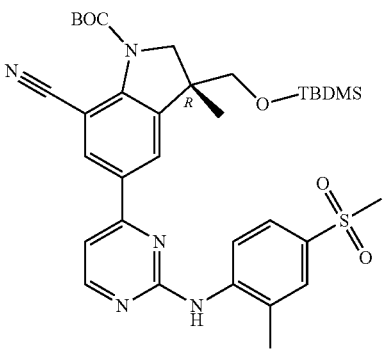<br>From intermediate 6R and methyl-4-(methylsulfonyl) aniline | 536 | 36 (46% purity based on LC/MS) | C |
| Mixture of Intermediate 68/ Intermediate 69 | 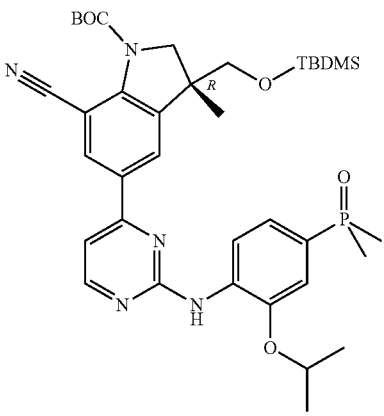<br>+<br>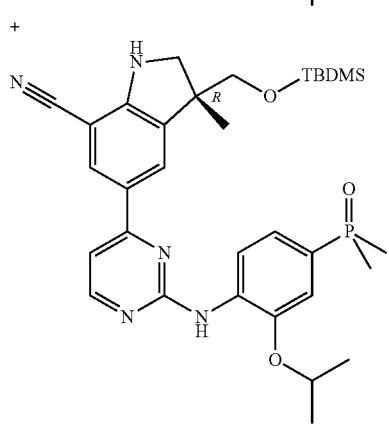<br>From intermediate 6R and intermediate 67 | 1210 (mixture of intermediates 68/69: 98.7/1.3) pale yellow foam | 93 | C with T = 80° C. |

-continued

| Intermediate number | Structure | Mass (mg) | Yield (%) | Method |
|---|---|---|---|---|
| Intermediate 74 | [Structure: BOC-protected indoline with CN, R-methyl, CH2-O-TBDMS, linked to pyrimidine-NH-phenyl with CN, tetrahydropyran, and O-CH2-cyclopropyl substituents]<br><br>From intermediate 6R and intermediate 73 | 2420<br>(73% of purity based on LC/MS)<br>brown foam | | C with T = 90° C. |
| Intermediate 77 | [Structure: BOC-protected indoline with CN, R-methyl, CH2-O-TBDMS, linked to pyrimidine-NH-phenyl with Cl, P(=O)(Me)2, and methyl substituents]<br><br>From intermediate 6R and intermediate 76 | 2500<br>(81% of purity based on LC/MS)<br>brown solid | | C |
| Intermediate 79 | [Structure: BOC-protected indoline with CN, R-methyl, CH2-O-TBDMS, linked to pyrimidine-NH-phenyl with CN and O-CH2-cyclopropyl substituents]<br><br>From intermediate 6R and intermediate 51 | 919<br>(96% of purity based on LC/MS)<br>orange powder | 86 | C |

| Intermediate number | Structure | Mass (mg) | Yield (%) | Method |
|---|---|---|---|---|
| Intermediate 85 | From intermediate 6 and intermediate 84 | 292 orange oil | — | C with T = 85° C. |
| Intermediate 89 | From intermediate 6 and intermediate 88 | 247 dark black foam | — | C with T = 95° C. |
| Intermediate 93 | From intermediate 6 and intermediate 92 | 698 | 68 (based on a purity of 70% by LC/MS) | C with T = 95° C. |

-continued
| Intermediate number | Structure | Mass (mg) | Yield (%) | Method |
|---|---|---|---|---|
| Intermediate 96 | 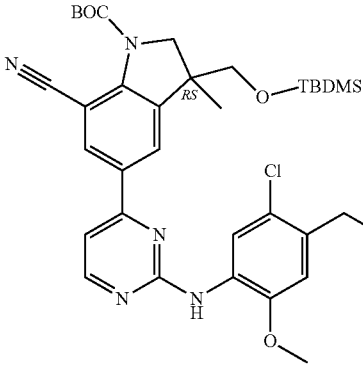<br>From intermediate 6 and intermediate 95 | 387<br>orange sticky oil | — | C |
| Intermediate 100 | 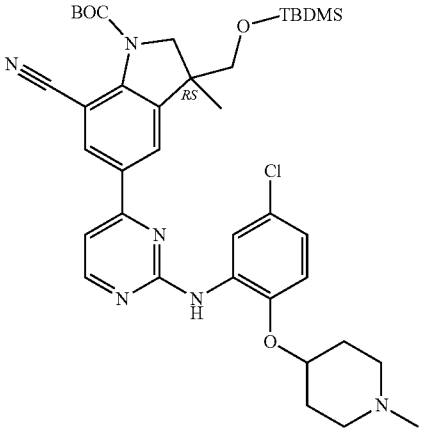<br>From intermediate 6 and intermediate 99 | 360 | — | C with T = 85° C. |
| Intermediate 102 | 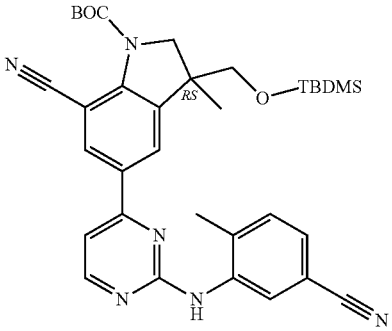<br>From intermediate 6 and 3-amino-4-methylbenzonitrile | 356<br>brown solid | — | C with T = 95° C. |

-continued

| Intermediate number | Structure | Mass (mg) | Yield (%) | Method |
|---|---|---|---|---|
| Intermediate 105 | From intermediate 6 and 5-chloro-2-methylaniline | 540 brown solid | — | C with T = 95° C. |
| Intermediate 110 | From intermediate 6 and intermediate 109 | 249 (62% of purity based on LC/MS) dark black foam | 98 | C with T = 95° C. |
| Intermediate 112 | From intermediate 6 and 2,5-dichloroaniline | 530 (80% of purity based on LC/MS) | Quant. | C with T = 95° C. |

| Intermediate number | Structure | Mass (mg) | Yield (%) | Method |
|---|---|---|---|---|
| Intermediate 114 | From intermediate 6 and 2-methoxy-5-(trifluoromethyl)aniline | 390 (55% of purity based on LC/MS) brown solid | — | C with T = 95° C. |
| Intermediate 116 | From intermediate 6 and 3-amino-4-methoxybenzonitrile | 365 brown oil | — | C with T = 95° C. |
| Intermediate 118 | From intermediate 6 and 3-amino-4-chlorobenzonitrile | 504 (70% of purity based on NMR) white solid | 82 | C with T = 95° C. |

-continued

| Intermediate number | Structure | Mass (mg) | Yield (%) | Method |
|---|---|---|---|---|
| Intermediate 120 | From intermediate 6 and 5-chloro-2-methoxyaniline | 960 (64% of purity based on LC/MS) brown solid | Quant. | C with T = 95° C. |
| Intermediate 124 | From intermediate 6 and intermediate 123 | 308 (86% of purity based on LC/MS) | 47 | C with T = 95° C. |
| Intermediate 128 | From intermediate 6 and intermediate 127 | 530 (68% of purity based on LC/MS) | 85 | C with T = 95° C. |

-continued

| Intermediate number | Structure | Mass (mg) | Yield (%) | Method |
|---|---|---|---|---|
| Intermediate 131 | (structure) From intermediate 6 and intermediate 130 | 530 M.P. (K) = 136° C. | 75 | C with T = 95° C. |
| Intermediate 135 | (structure) From intermediate 6 and intermediate 134 | 268 M.P. (K) = 133° C. | 37 | C with T = 95° C. |
| Intermediate 139 | (structure) From intermediate 6 and intermediate 138 | 308 | 45 | C with T = 95° C. |

| Intermediate number | Structure | Mass (mg) | Yield (%) | Method |
|---|---|---|---|---|
| Intermediate 143 (mixture of 4 unseparated diastereoisomers) | From intermediate 6 and intermediate 142 | 197 (87% of purity based on LC/MS) 200 (95% of purity based on LC/MS) | 25 27 | C with T = 95° C. |
| Intermediate 146 | From intermediate 6 and intermediate 145 | 370 | 64 | C with T = 95° C. |
| Intermediate 151 | From intermediate 150 and intermediate 149 | 139 | 38 (based on 74% of purity by LC/MS) | C with T = 95° C. |

-continued

| Intermediate number | Structure | Mass (mg) | Yield (%) | Method |
|---|---|---|---|---|
| Intermediate 157 | 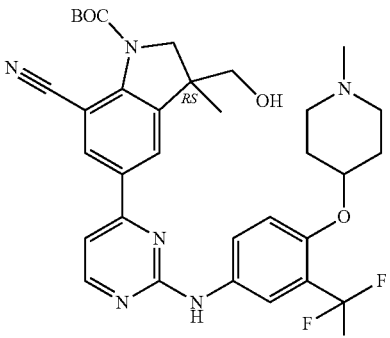<br>From intermediate 150 and intermediate 156 | 119<br>(98% of purity based on LC/MS) | 25 | C with T = 95° C. |
| Intermediate 161 | 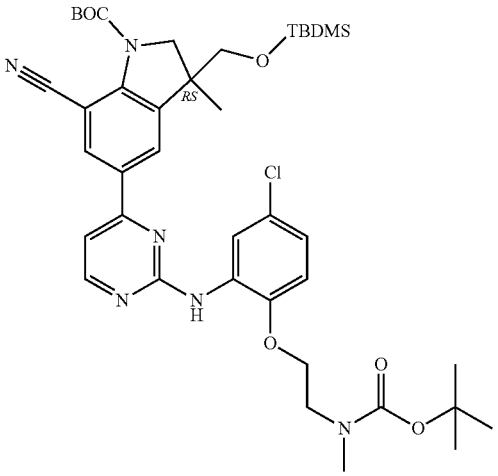<br>From intermediate 6 and intermediate 160 | 205<br>(95% of purity based on LC/MS)<br>white powder<br>80<br>(59% of purity based on LC/MS)<br>yellow oil | 34<br>13 | C |
| Intermediate 164 | 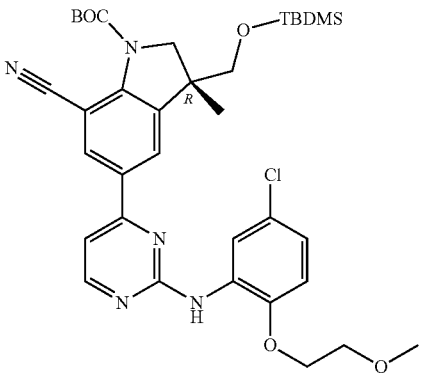<br>From intermediate 6R and intermediate 123 | 269<br>(71% of purity based on LC/MS) | 41 | C with T = 95° C. |

-continued
| Intermediate number | Structure | Mass (mg) | Yield (%) | Method |
|---|---|---|---|---|
| Intermediate 169 | 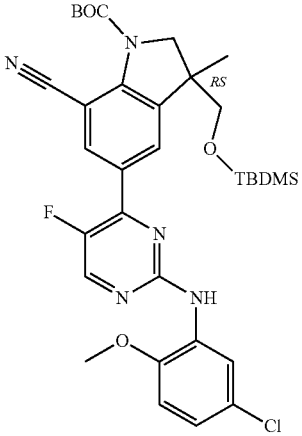<br>From intermediate 6a and 5-chloro-2-methoxyaniline | 411<br>(97% of purity based on LC/MS) | 96 | C |
| Intermediate 171 | 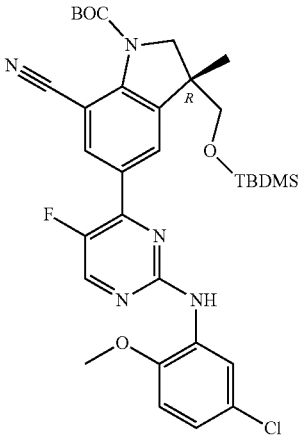<br>From intermediate 6aR and 5-chloro-2-methoxyaniline | 418<br>(91% of purity based on LC/MS) | 97 | C |
| Intermediate 196 | 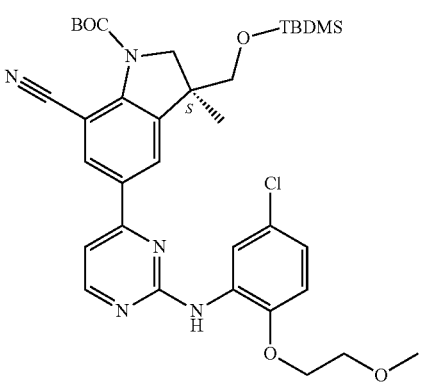<br>From intermediate 6S and intermediate 123 | 269 | 41 | C with T = 95° C. |

| Intermediate number | Structure | Mass (mg) | Yield (%) | Method |
|---|---|---|---|---|
| Intermediate 203 | 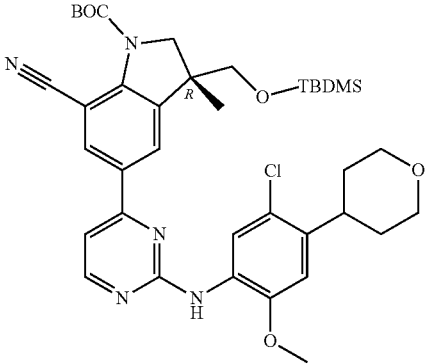<br>From intermediate 6R and intermediate 202 | 582 (59% of purity based on LC/MS) yellow solid | quant. | C with T = 95° C. |
| Intermediate 205 | 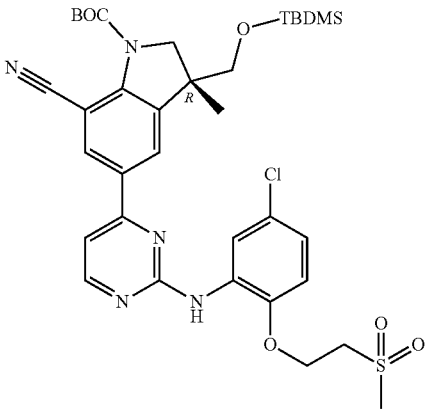<br>From intermediate 6R and 5-chloro-2-[2-methylsulfonyl] ethoxy]-benzamine | 190 | 27 | C |
| Intermediate 210 | 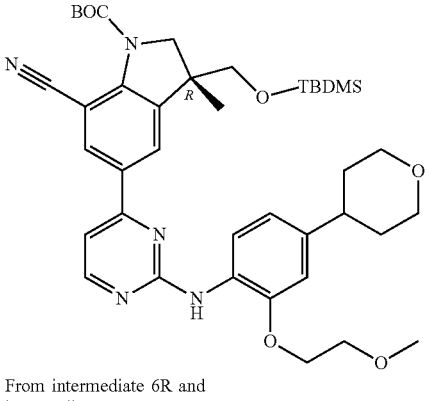<br>From intermediate 6R and intermediate 209 | 620 black foam | Quant. | C with T = 95° C. |

-continued

| Intermediate number | Structure | Mass (mg) | Yield (%) | Method |
|---|---|---|---|---|
| Intermediate 212 | 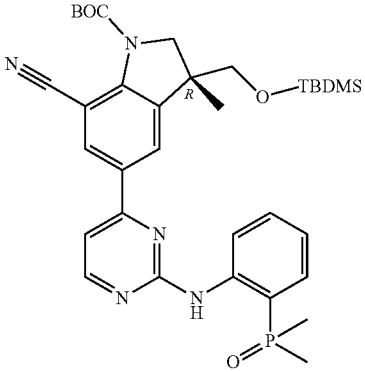<br>From intermediate 6R and 2-(aminophenyl)dimethylphosphine oxide | 740 (59% of purity based on LC/MS) brown foam | 99 | C with T = 95° C. |
| Intermediate 222 | 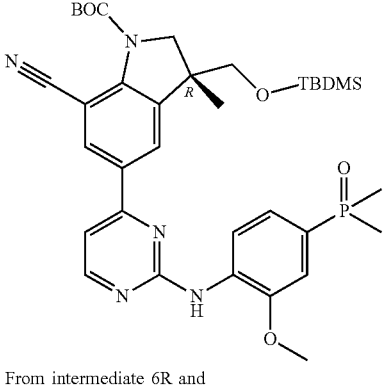<br>From intermediate 6R and intermediate 221 | 760 (66% purity evaluated by LC/MS) black foam | Quant. | C with T = 95° C. |
| Intermediate 228 | 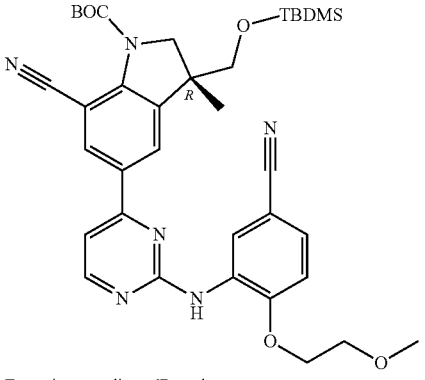<br>From intermediate 6R and intermediate 227 | 400 (97% purity evaluated by LC/MS) | 61 | C |

-continued
| Intermediate number | Structure | Mass (mg) | Yield (%) | Method |
|---|---|---|---|---|
| Intermediate 232 | 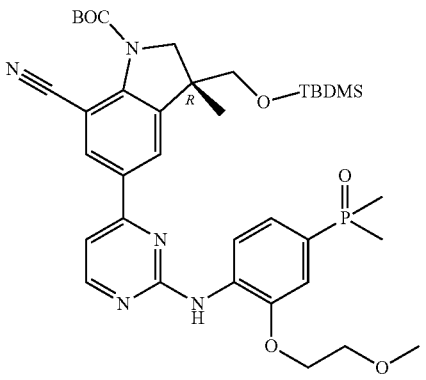<br>From intermediate 6R and intermediate 231 | 630 (85% purity evaluated by LC/MS) black foam | quant. | C with T = 90° C. |
| Intermediate 240 | 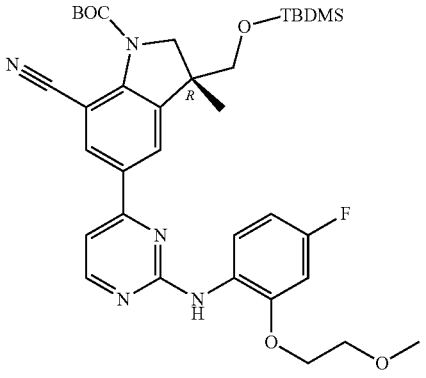<br>From intermediate 6R and intermediate 239 | 494 (93% purity evaluated by NMR) | 77 | C |
| Intermediate 242 | 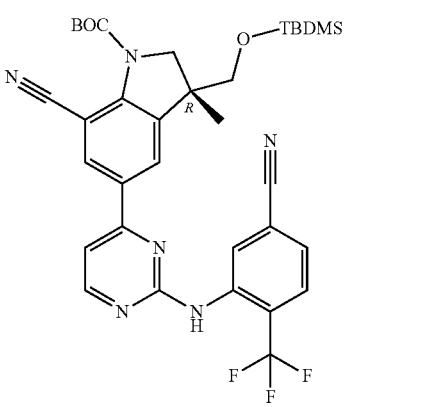<br>From intermediate 6R and 3-amino-4-(trifluoromethyl)benzonitrile | 613 | 95 | C |

-continued
| Intermediate number | Structure | Mass (mg) | Yield (%) | Method |
|---|---|---|---|---|
| Mixture of intermediate 247/intermediate 247' | 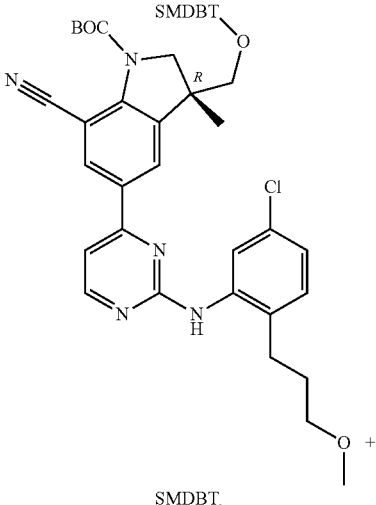<br>From intermediate 6R and intermediate 377/378 | 381 intermediate 247 (87% purity based on LC/MS) Intermediate 247' (11% purity based on LC/MS) | 48 | C |
| Intermediate 252 | 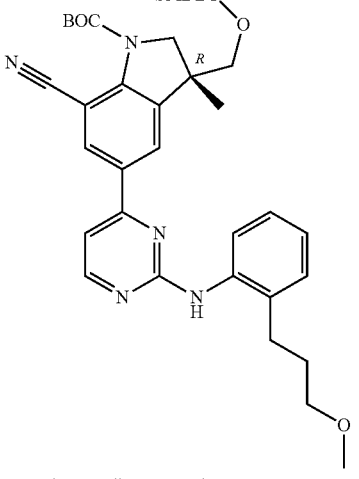<br>From intermediate 6R and intermediate 251 | 397 | 60 | C |

-continued
| Intermediate number | Structure | Mass (mg) | Yield (%) | Method |
|---|---|---|---|---|
| Intermediate 261 | 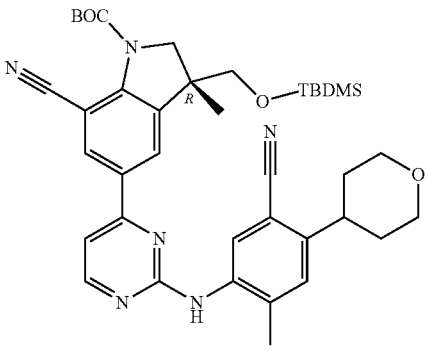 From intermediate 6R and intermediate 260 | 553 (84% purity evaluated by LC/MS) orange powder | 82 | C |
| Intermediate 265 | 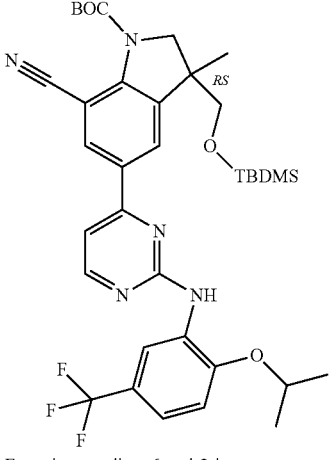 From intermediate 6 and 2-isopropoxy-5-(trifluoromethyl)aniline | 502 (57% purity evaluated by LC/MS) | 44 | C |
| Intermediate 269 | 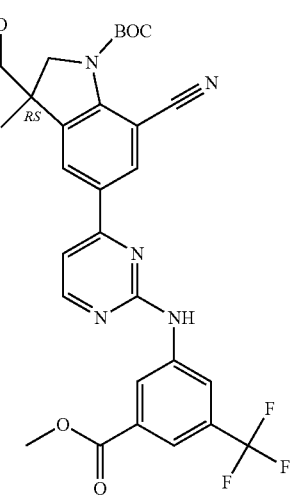 From intermediate 6 and intermediate 268 | 372 (78% purity evaluated by LC/MS) | 55 | C with T = 90° C. |

-continued
| Intermediate number | Structure | Mass (mg) | Yield (%) | Method |
|---|---|---|---|---|
| Intermediate 391 | 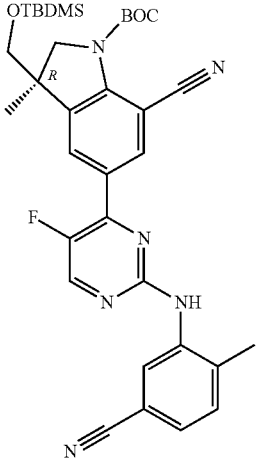<br>From intermediate 6aR and 3-amino-4-methylbenzonitrile | 375 | 90 | C |
| Intermediate 417 | 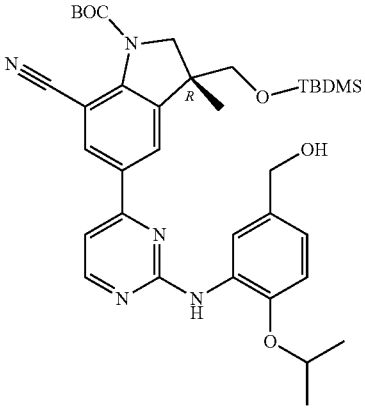<br>From intermediate 6R and intermediate 416 | 340 | 45 | C<br>With T = 80° C. |
| Intermediate 505 | 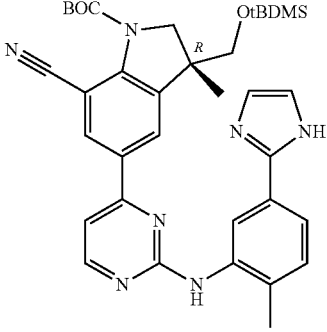<br>From intermediate 6R and intermediate 501 | 360 | 57%<br>Purity 84% (LCMS) | C<br>(o/n@95° C.) |

-continued

| Intermediate number | Structure | Mass (mg) | Yield (%) | Method |
|---|---|---|---|---|
| Intermediate 508 | From intermediate 6R and 2-methyl-5-(1-methyl-4-piperidinyl)-benzenamine | 100 | 17% | C (o/n @ 80° C.) |
| Intermediate 537 | From intermediate 6R and intermediate 536 | 488 | 16% Purity 49% (LCMS) | C (3 h @ 95° C) |
| Intermediate 551 | From intermediate 6R and 3-amino-4-methylbenzyl alcohol | 4690 yellow foam | 78 | C |

-continued
| Intermediate number | Structure | Mass (mg) | Yield (%) | Method |
|---|---|---|---|---|
| Intermediate 568 | 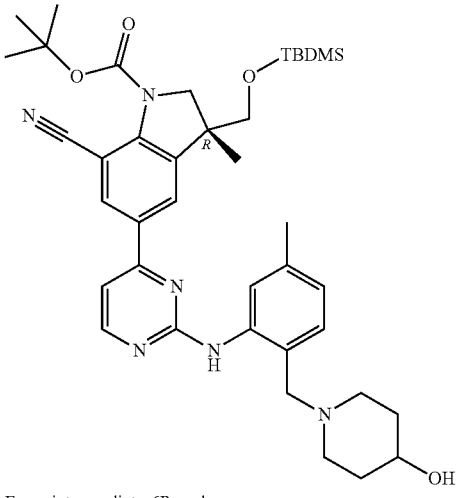<br>From intermediate 6R and intermediate 567 | 540 | 80 | C |
| Intermediate 572 | 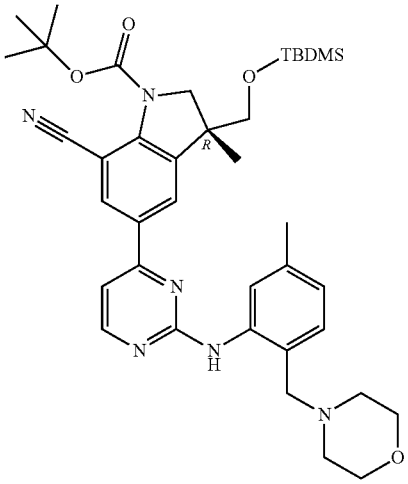<br>From intermediate 6R and intermediate 571 | 850 | 98 | C |
| Intermediate 576 | 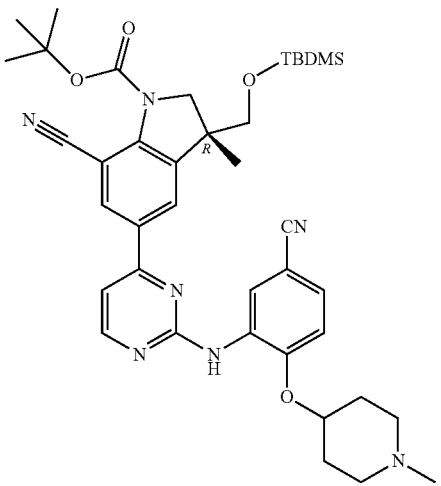<br>From intermediate 6R and intermediate 575 | 633<br>Pale brown oil | 82 | C |

| Intermediate number | Structure | Mass (mg) | Yield (%) | Method |
|---|---|---|---|---|
| Intermediate 584 | 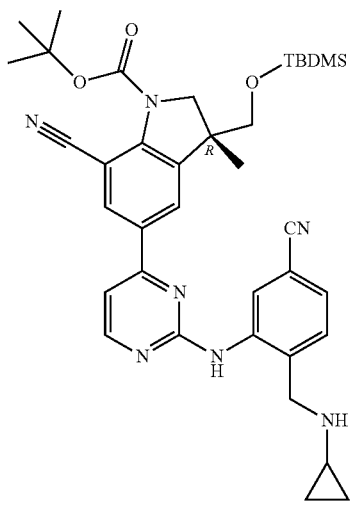<br>From intermediate 6R and intermediate 583 | 180 | 56 | C |
| Intermediate 588 | 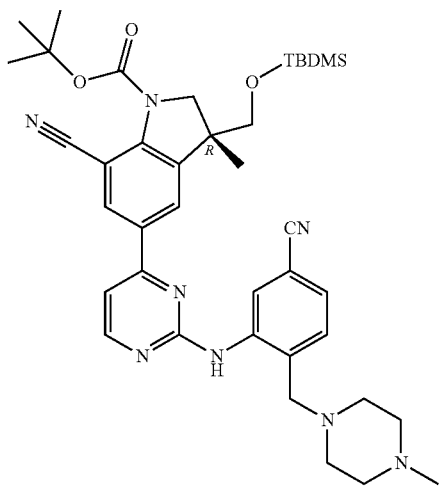<br>From intermediate 6R and intermediate 587 | 315<br>(85% purity evaluated by LCMS) | 77 | C |

-continued
| Intermediate number | Structure | Mass (mg) | Yield (%) | Method |
|---|---|---|---|---|
| Intermediate 592 | 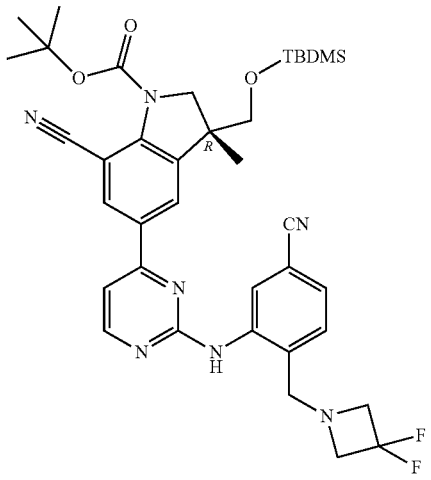 From intermediate 6R and intermediate 591 | 300 | 74 | C At 100° C. for 1 hour |
| Intermediate 596 | 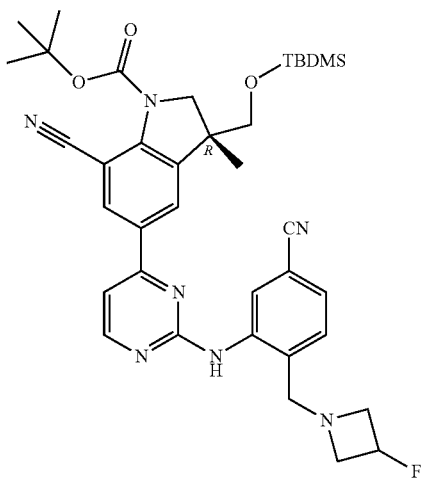 From intermediate 6R and intermediate 595 | 240 | 53 | C At 100° C. for 1 hour |
| Intermediate 605 | 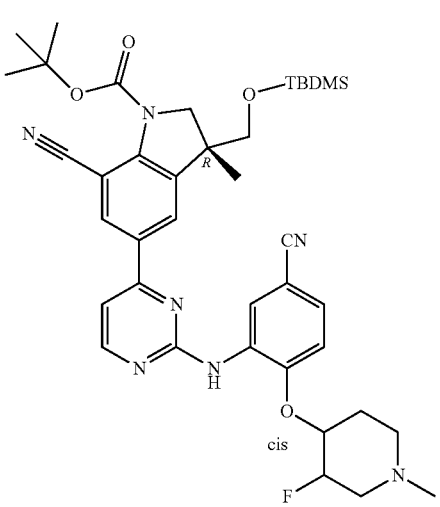 From intermediate 6R and intermediate 604 | 310 (85% purity evaluated by LCMS) | 73 | C |

-continued
| Intermediate number | Structure | Mass (mg) | Yield (%) | Method |
|---|---|---|---|---|
| Intermediate 611 | 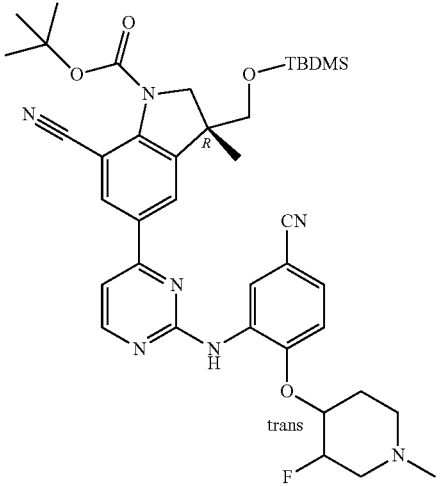<br>From intermediate 6R and intermediate 610 | 121<br>(55% purity evaluated by LCMS) | 70 | C<br>At 100° C. for 1 hour |
| Intermediate 627 | 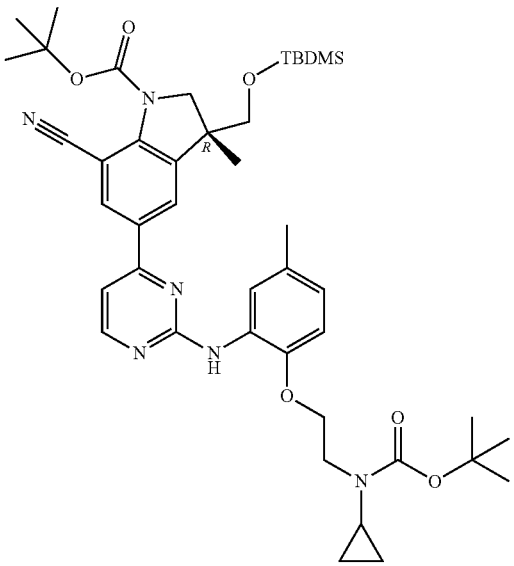<br>From intermediate 6R and intermediate 626 | 505 | 59 | C |
| Intermediate 633 | 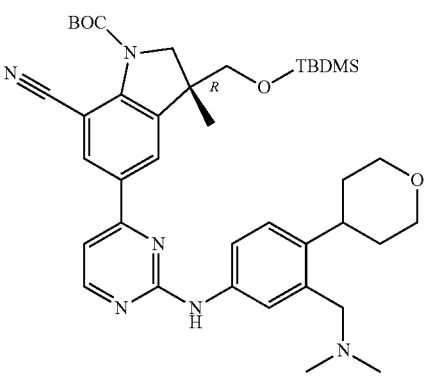<br>from intermediate 6R and intermediate 632 | 552 | 80 | C<br>@85° C. overnight |

Example A8

Preparation of Intermediate 154:

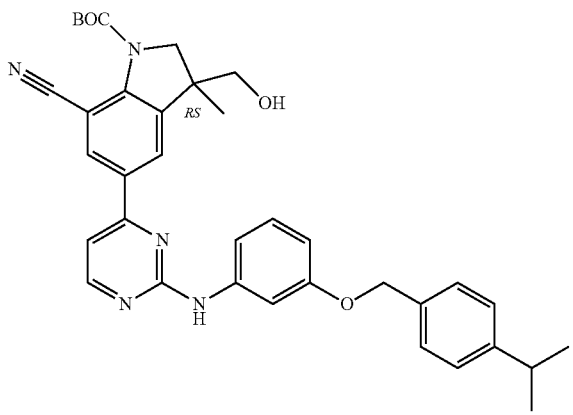 [SMILES: CC(C)c1ccc(COc2cccc(Nc3nccc(-c4cc(C#N)c5c(c4)C(C)(CO)CN5C(=O)OC(C)(C)C)n3)c2)cc1]

A mixture of intermediate 150 (300.00 mg, 0.75 mmol), intermediate 153 (198.67 mg, 0.82 mmol) and $Cs_2CO_3$ (609.59 mg, 1.87 mmol) in 1,4-dioxane (12.77 mL) was purged with $N_2$. A catalytic amount of $Pd(OAc)_2$ (13.44 mg, 59.87 μmol) and BINAP (37.28 mg, 59.87 μmol) were then added in the sealed tube. The reaction mixture was purged with $N_2$ and was stirred at 120° C. using one single mode microwave (Biotage Initiator EXP 60) with a power output ranging from 0 to 400 W for 30 min The resulting mixture was poured out onto water and DCM. Then, filtered over Celite®, decanted and the organic layer was separated, dried over $MgSO_4$, filtered and evaporated. The residue (948 mg) was purified by column chromatography on silica gel (Irregular SiOH, 40 μm, 40 g, mobile phase: heptane/EtOAc/MeOH/$NH_4OH$, gradient from 50% heptane, 50% EtOAc to 40% Heptane, 10% MeOH, 50% EtOAc, 1% $NH_4OH$). The pure fractions were combined and the solvent was evaporated to give 300 mg of intermediate 154 (66% yield).

The intermediates in the Table below were prepared by using an analogous method as the one used for the preparation of intermediate 154 starting from the respective starting materials.

| Intermediate number | Structure | Mass (mg) | Yield (%) |
|---|---|---|---|
| Intermediate 173 | 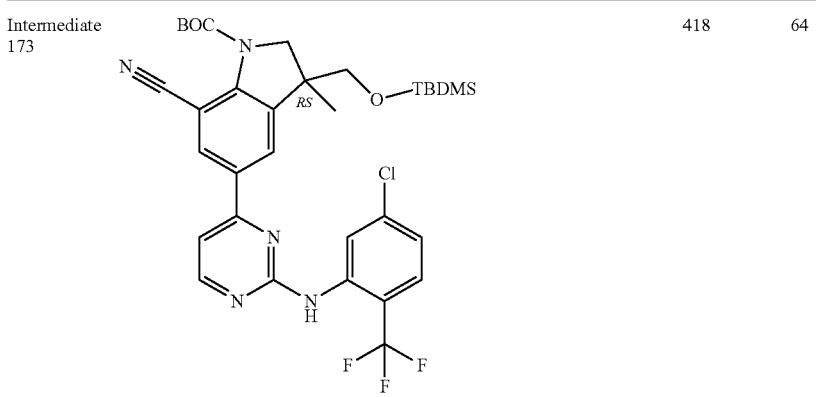 From intermediate 6 and 2-amino-4-chloro benzotrifluoride | 418 | 64 |
| Intermediate 179 | 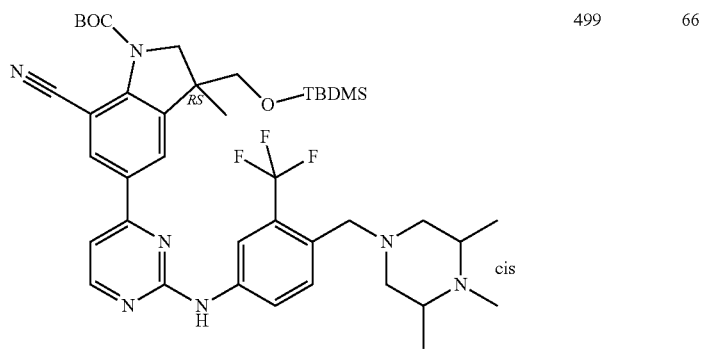 From intermediate 6 and intermediate 178 | 499 | 66 |

-continued
| Intermediate number | Structure | Mass (mg) | Yield (%) |
|---|---|---|---|
| Intermediate 181 | 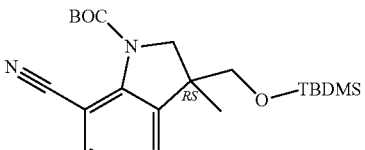 From intermediate 6 and 4-bromo-5-chloro-2-methylaniline | 180 | 27 |
| intermediate 183 | From intermediate 6 and 5-chloro-2-(trifluoromethoxy)aniline | 600 | 76 |
| intermediate 187 | From intermediate 6 and intermediate 186 | 600 (69% of purity based on LC/MS) | 89 |

-continued
| Intermediate number | Structure | Mass (mg) | Yield (%) |
|---|---|---|---|
| Intermediate 190 | 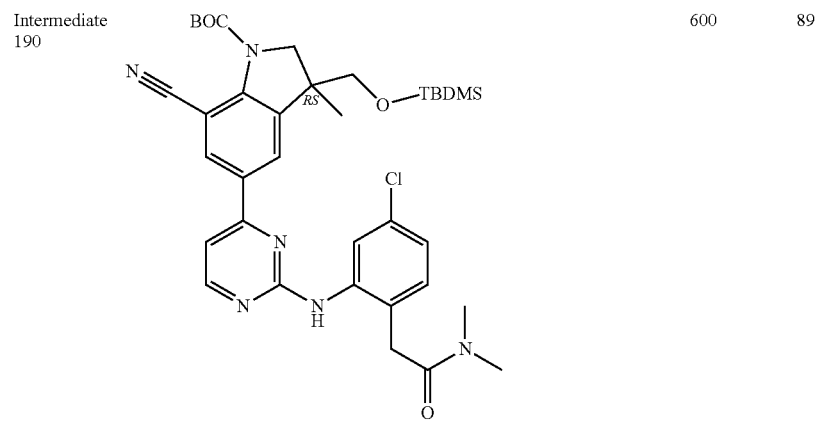<br>From intermediate 6 and intermediate 189 | 600 | 89 |
| Intermediate 193 | 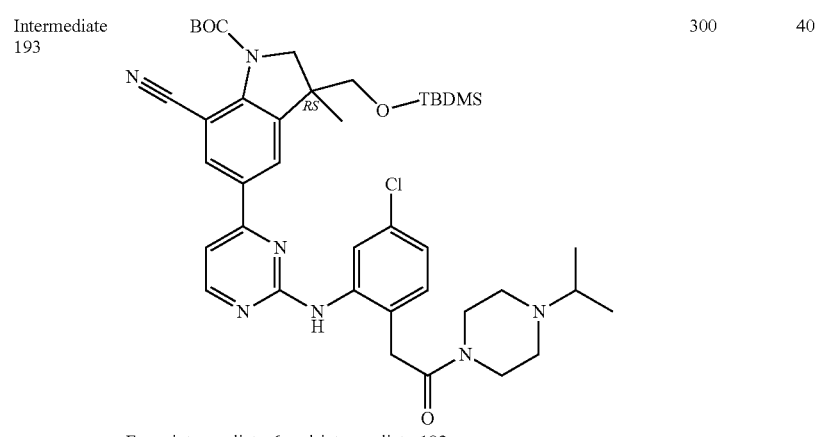<br>From intermediate 6 and intermediate 192 | 300 | 40 |
| Intermediate 218 | 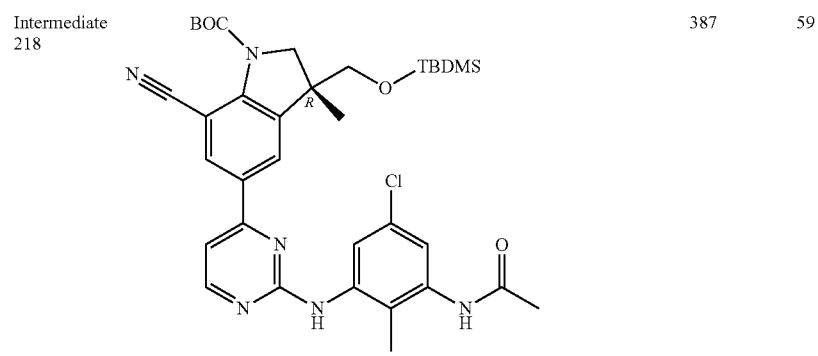<br>From intermediate 6R and intermediate 217 | 387 | 59 |

-continued
| Intermediate number | Structure | Mass (mg) | Yield (%) |
|---|---|---|---|
| Intermediate 224 | 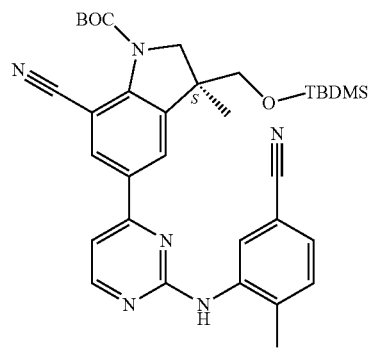 From intermediate 6S and 3-amino-4-methylbenzonitrile | 329 (82% purity evaluated by LC/MS) yellow powder | 55 |
| Intermediate 236 | 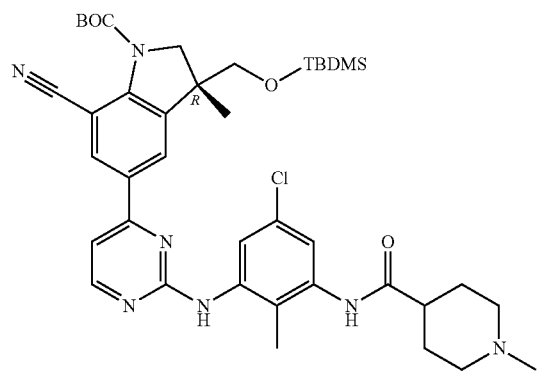 From intermediate 6R and intermediate 235 | 207 (92% purity evaluated by LC/MS) | 35 |
| Intermediate 411 | 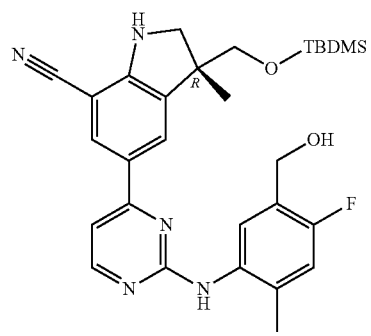 From intermediate 7R and intermediate 410 | 610 | 95 |

| Intermediate number | Structure | Mass (mg) | Yield (%) |
|---|---|---|---|
| Intermediate 458 | From intermediate 6R and intermediate 457 | 604 | 97 |
| Intermediate 463 | From intermediate 7R and intermediate 462 | 629 | 78 |
| Intermediate 468 | From intermediate 7R and intermediate 467 | 396 | 100 |

-continued
| Intermediate number | Structure | Mass (mg) | Yield (%) |
|---|---|---|---|
| Intermediate 471 | 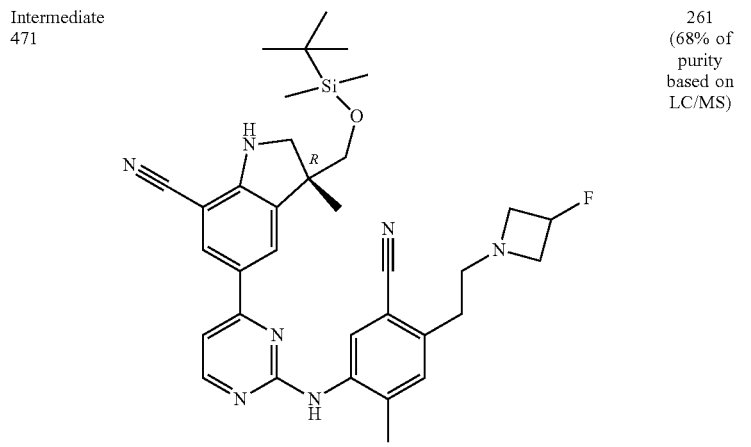From intermediate 7R and intermediate 470 | 261 (68% of purity based on LC/MS) | 68 |
| Intermediate 474 | 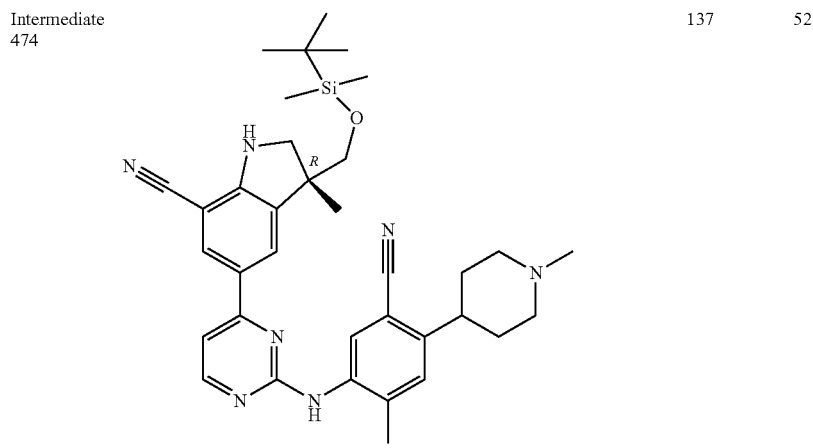From intermediate 473 and intermediate 7R. | 137 | 52 |
| Intermediate 479 | 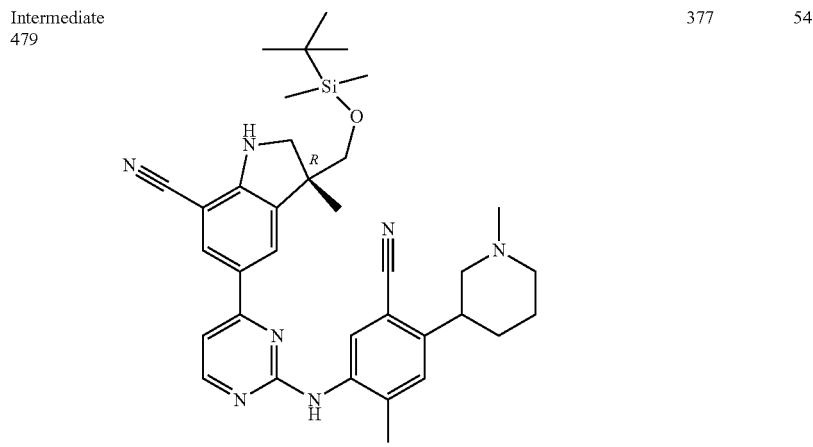From intermediate 478 and intermediate 7R. | 377 | 54 |

| Intermediate number | Structure | Mass (mg) | Yield (%) |
|---|---|---|---|
| Intermediate 644 | 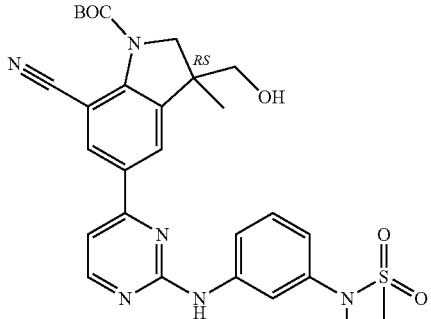<br>From intermediate 150 and intermediate 643 | 298 (85% of purity based on LC/MS) | 45 |

Example A9

Preparation of Intermediate 277.

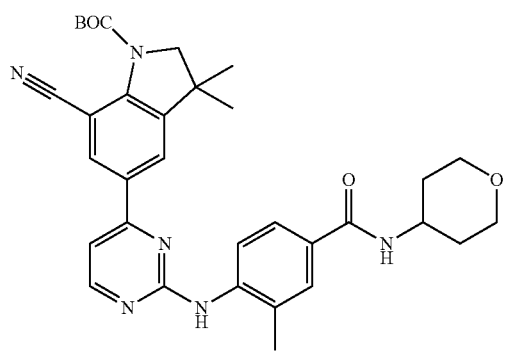 [SMILES: Cc1cc(C(=O)NC2CCOCC2)ccc1Nc1nccc(-c2cc(C#N)c3c(c2)C(C)(C)CN3C(=O)OC(C)(C)C)n1]

To a solution of intermediate 274 (0.10 g, 0.24 mmol), intermediate 276 (56.70 mg, 0.24 mmol), BINAP (14.90 mg, 0.024 mmol), $Cs_2CO_3$ (237.00 mg, 0.73 mmol) in 1,4-dioxane (3 mL) was added $Pd(OAc)_2$ (5.39 mg, 0.024 mmol) and the reaction mixture was heated for 30 min at 95° C. The reaction mixture was diluted with EtOAc, washed with water and brine. The organic layer was dried over $Na_2SO_4$, and concentrated in vacuo to give 227 mg of intermediate 277 (65% purity based on LC/MS, yellow oil) and used as it is in the next step.

The intermediates in the Table below were prepared by using an analogous method as the one used for the preparation of intermediate 277 starting from the respective starting materials.

| Intermediate number | Structure | Mass (mg) | Yield (%) |
|---|---|---|---|
| Intermediate 280 | 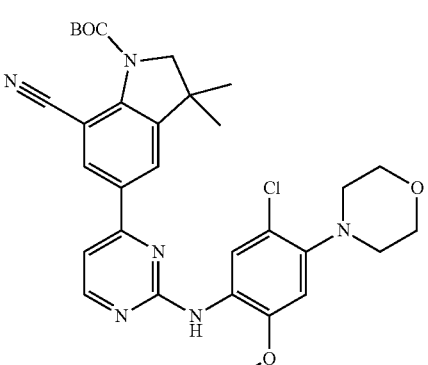<br>From intermediate 274 and intermediate 279 | 124 (69% based on LC/MS) | — |

-continued
| Intermediate number | Structure | Mass (mg) | Yield (%) |
|---|---|---|---|
| Intermediate 281 | 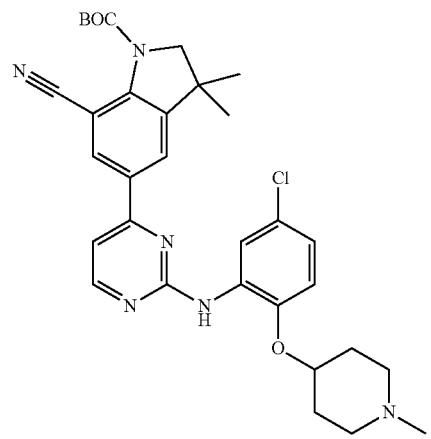<br>From intermediate 274 and intermediate 99 | 153<br>(90% based on LC/MS)<br>brown oil | — |
| Intermediate 282 | 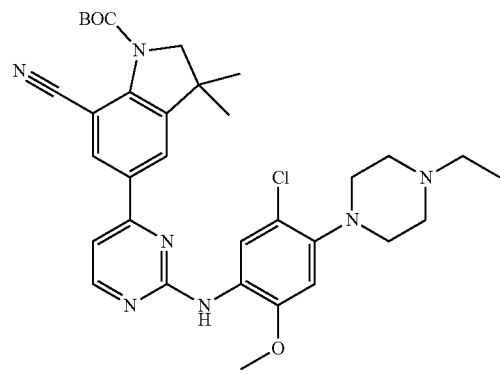<br>From intermediate 274 and intermediate 109 | 124<br>(95% based on LC/MS)<br>brown oil | Quant. |
| Intermediate 286 | 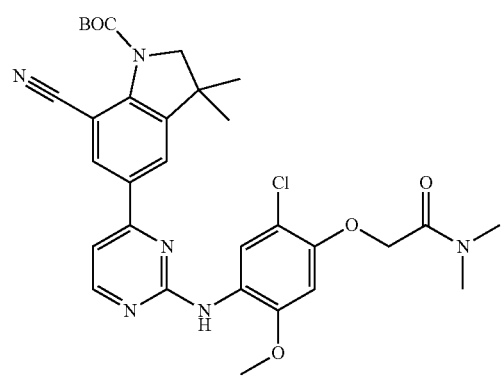<br>From intermediate 274 and intermediate 285 | 157<br>(90% based on LC/MS)<br>brown oil | Quant. |

-continued

| Intermediate number | Structure | Mass (mg) | Yield (%) |
|---|---|---|---|
| Intermediate 287 | From intermediate 274 and intermediate 88 | 126 (90% based on LC/MS) brown oil | Quant. |
| Intermediate 288 | From intermediate 274 and intermediate 95 | 107 (89% based on LC/MS) brown oil | Quant. |
| Intermediate 292 | From intermediate 274 and intermediate 291 | 152 (87% based on LC/MS) brown oil | Quant. |
| Intermediate 298 | From intermediate 274 and intermediate 297 | 101 (87% based on LC/MS) brown oil | Quant. |

-continued

| Intermediate number | Structure | Mass (mg) | Yield (%) |
|---|---|---|---|
| Intermediate 301 | From intermediate 274 and intermediate 300 | 199 (36% based on LC/MS) brown solid | — |
| Intermediate 304 | From intermediate 274 and intermediate 303 | 84 (93% based on LC/MS) brown oil | Quant. |
| Intermediate 306 | From intermediate 274 and intermediate 305 | 143 (20% based on LC/MS) brown solid | — |
| Intermediate 309 | From intermediate 274 and intermediate 308 | 152 (47% based on LC/MS) | — |

-continued

| Intermediate number | Structure | Mass (mg) | Yield (%) |
|---|---|---|---|
| Intermediate 312 | 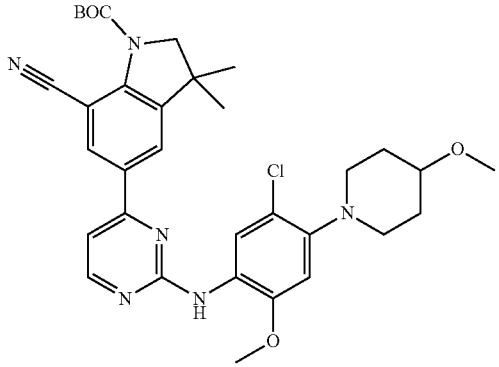<br>From intermediate 274 and intermediate 311 | 111<br>(85% based on LC/MS) | Quant. |
| Intermediate 315 | 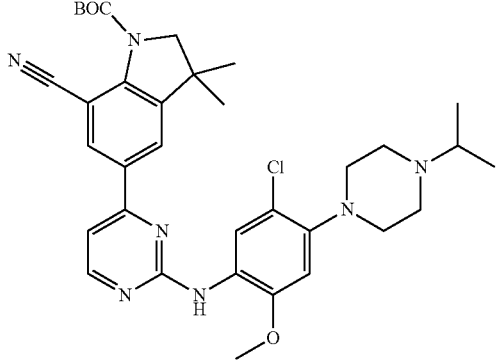<br>From intermediate 274 and intermediate 314 | 114<br>brown oil<br>(87% based on LC/MS) | Quant. |
| Intermediate 320 | 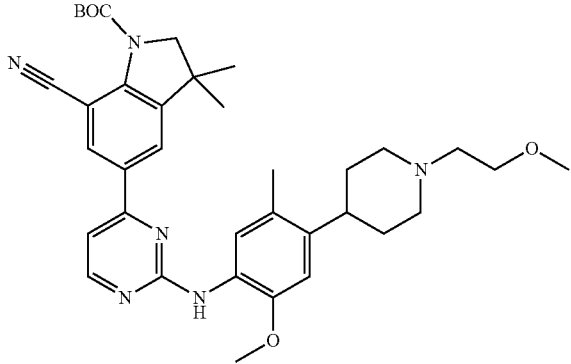<br>From intermediate 274 and intermediate 319 | 113<br>brown oil<br>(51% based on LC/MS) | Quant. |
| Intermediate 323 | 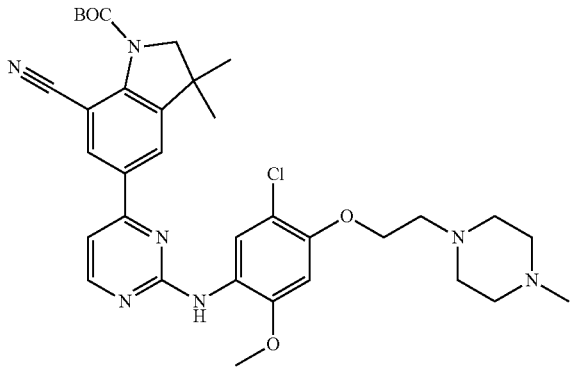<br>From intermediate 274 and intermediate 322 | 159<br>brown solid<br>(45% based on LC/MS) | — |

| Intermediate number | Structure | Mass (mg) | Yield (%) |
|---|---|---|---|
| Intermediate 327 | 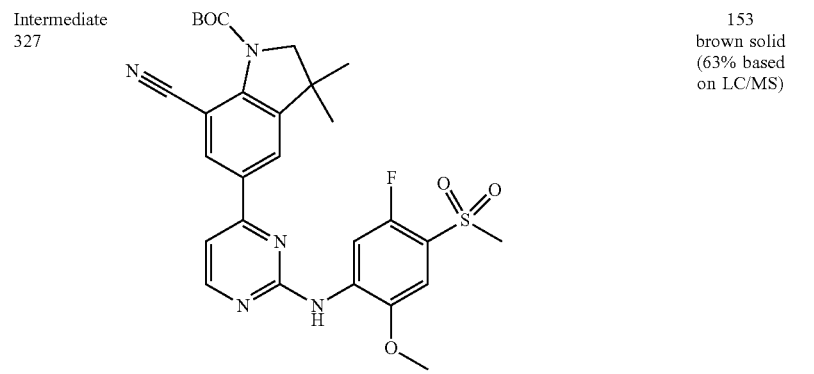<br>From intermediate 274 and intermediate 326 | 153<br>brown solid<br>(63% based on LC/MS) | — |
| Intermediate 330 | 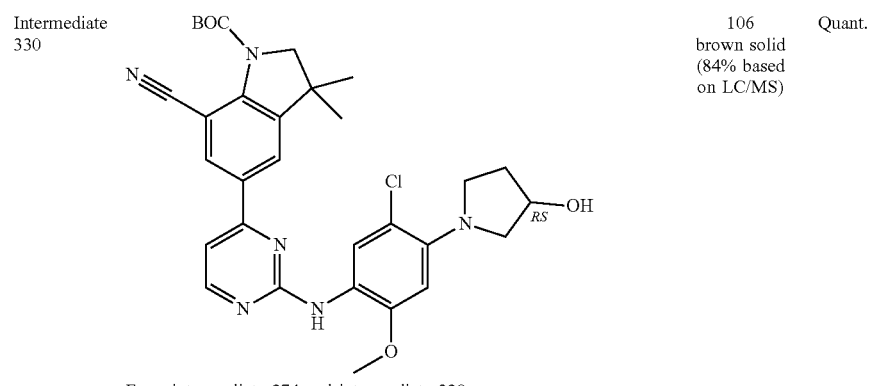<br>From intermediate 274 and intermediate 329 | 106<br>brown solid<br>(84% based on LC/MS) | Quant. |
| Intermediate 333 | 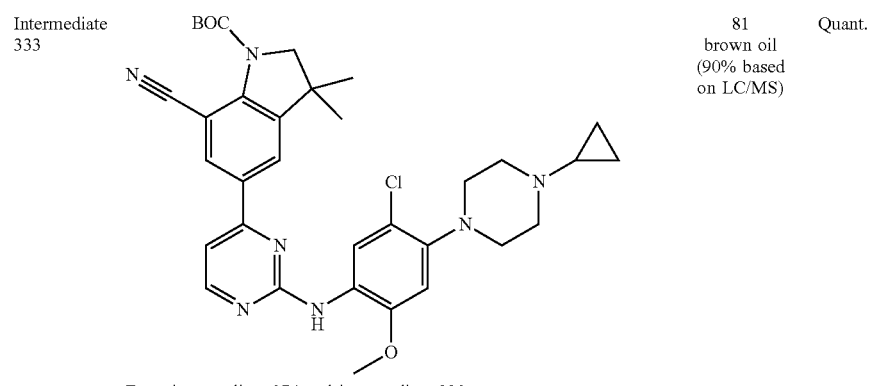<br>From intermediate 274 and intermediate 332 | 81<br>brown oil<br>(90% based on LC/MS) | Quant. |

| Intermediate number | Structure | Mass (mg) | Yield (%) |
|---|---|---|---|
| Intermediate 337 | 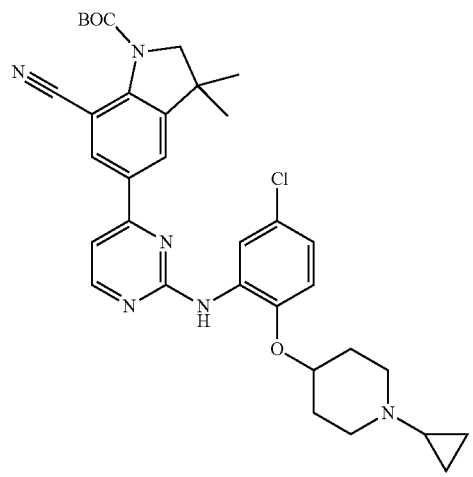 From intermediate 274 and intermediate 127 | 210 (80% based on LC/MS) | 75 |
| Intermediate 338 | 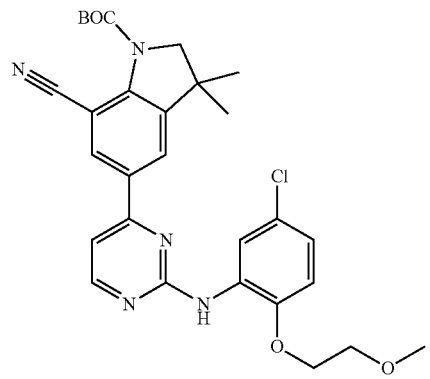 [SMILES: COCCOc1ccc(Cl)cc1Nc1nccc(-c2cc(C#N)c3c(c2)C(C)(C)CN3C(=O)OC(C)(C)C)n1] From intermediate 274 and intermediate 123 | 194 | 78 |
| Intermediate 339 | 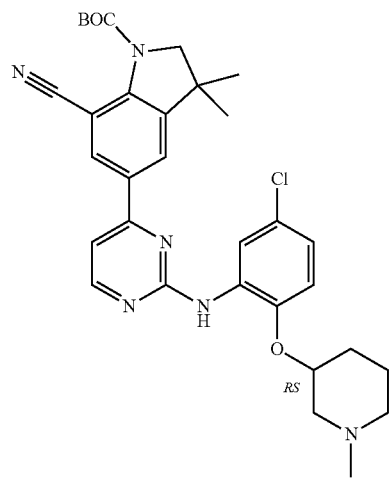 From intermediate 274 and intermediate 142 | 182 (90% based on LC/MS) | 70 |

| Intermediate number | Structure | Mass (mg) | Yield (%) |
|---|---|---|---|
| Intermediate 342 | 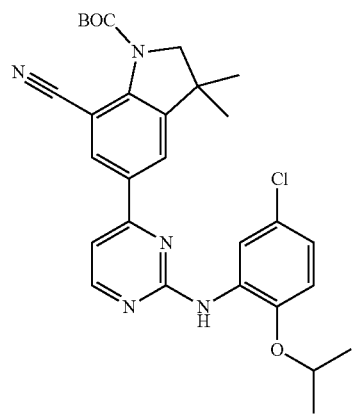<br>From intermediate 274 and intermediate 341 | 61<br>(66% based on LC/MS) | 25 |
| Intermediate 345 | 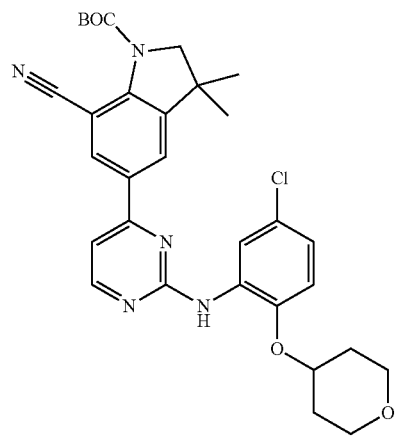<br>From intermediate 274 and intermediate 344 | 505<br>(80% based on LC/MS) | 59 |
| Intermediate 346 | 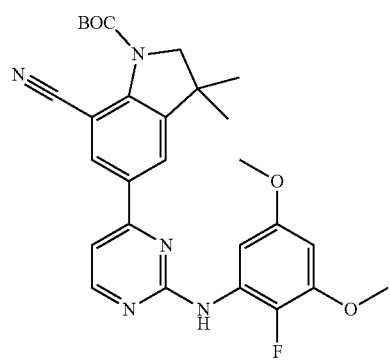<br>From intermediate 274 and 2-fluoro-3,5-dimethoxyaniline | 273<br>(91% based on LC/MS) | 81 |

| Intermediate number | Structure | Mass (mg) | Yield (%) |
|---|---|---|---|
| Intermediate 347 | 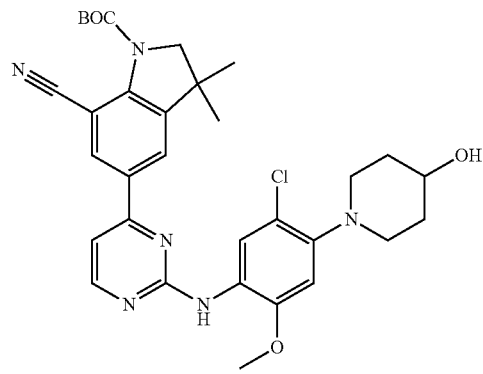<br>From intermediate 274 and intermediate 92 | 559 (61% based on LC/MS) | 62 |
| Intermediate 352 | 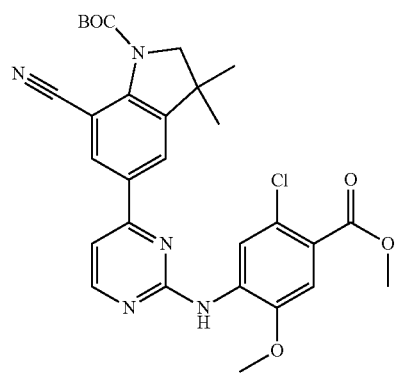 [SMILES: COC(=O)c1cc(OC)c(Nc2nccc(-c3cc(C#N)c4c(c3)C(C)(C)CN4C(=O)OC(C)(C)C)n2)cc1Cl]<br>From intermediate 274 and intermediate 351 | 1306 | 84 |
| Intermediate 353 | 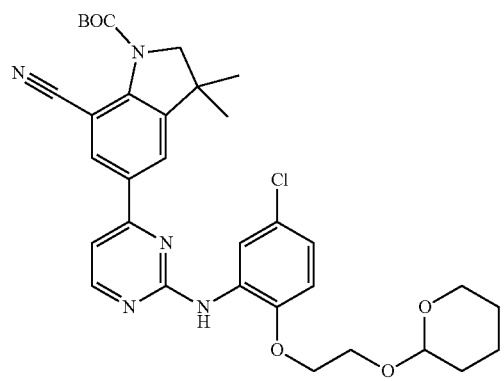<br>From intermediate 274 and intermediate 145 | 81 yellow powder (86% based on LC/MS) | 22 |

| Intermediate number | Structure | Mass (mg) | Yield (%) |
|---|---|---|---|
| Intermediate 356 | 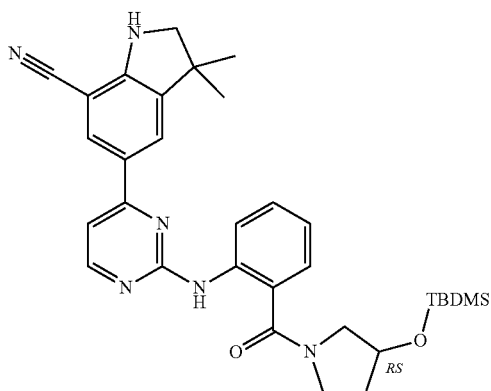<br>From intermediate 274 and intermediate 160 | 151<br>yellow oil<br>(89% based on LC/MS)<br>112<br>yellow oil<br>(58% based on LC/MS) | 27<br>13 |

Example A10

Preparation of Intermediate 362:

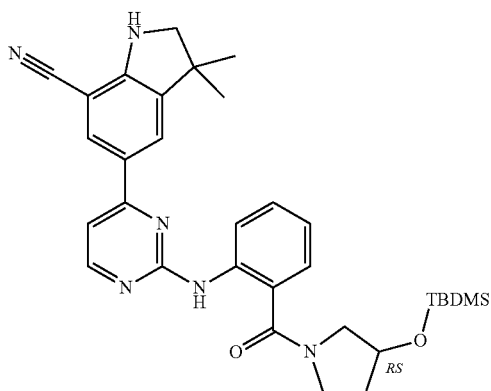

In a sealed tube, Pd(OAc)$_2$ (16.00 mg, 70.20 µmol) and BINAP (44.00 mg, 70.20 mmol) were added to a previously degassed solution of intermediate 361 (200.00 mg, 0.70 mmol), intermediate 360 (250.00 mg, 0.78 mmol) and Cs$_2$CO$_3$ (686.00 mg, 2.11 mmol) in 1,4-dioxane (10 mL) and the reaction mixture was heated at 120° C. using one single mode microwave (Biotage Initiator EXP 60) with a power output ranging from 0 to 400 W for 20 min. The reaction mixture was gathered with another batch (50.00 mg of intermediate 361) for the work up, diluted with EtOAc and poured onto water. The organic layer was decanted, washed with brine, dried over MgSO$_4$, filtered and evaporated to dryness. The residue was purified by column chromatography on silica gel (irregular SiOH, 24 g, mobile phase: heptane/EtOAc, gradient from 80:20 to 60:40). The pure fractions were collected and evaporated to dryness to give 168 mg of intermediate 362 (34% yield)

Example A11

Preparation of Intermediate 10R:

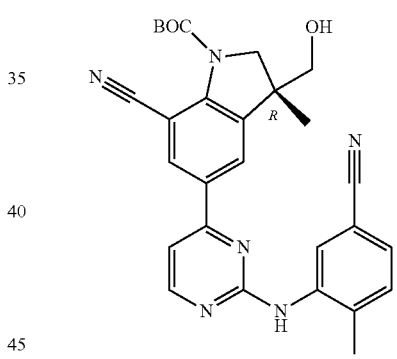

Method E

A mixture of intermediate 9R (5.30 g, 8.68 mmol) and TBAF (1M in THF, 17.3 mL, 17.35 mmol) in Me-THF (90 mL) was stirred at rt for 3 h. The reaction mixture was poured onto a 10% aqueous solution of K$_2$CO$_3$, diluted with EtOAc and then with a saturated solution of NaCl (to help the decantation). The organic layer was decanted, washed again with 10% aqueous solution of K$_2$CO$_3$ (+100 mL of a saturated solution of NaCl), then with a saturated solution of NaCl. The organic layer was dried over MgSO$_4$, filtered and concentrated under vacuum. The residue was taken up with CH$_3$CN and the precipitate was filtered and dried to give 2.72 g of intermediate 10R (63% yield).

The intermediates in the Table below were prepared by using an analogous method as described in Method E starting from the respective starting materials. The most relevant minor deviations from the referenced method are indicated in the column 'Method'.

| Intermediate number | Structure | Mass (mg) | Yield (%) | Method |
|---|---|---|---|---|
| Intermediate 30 | 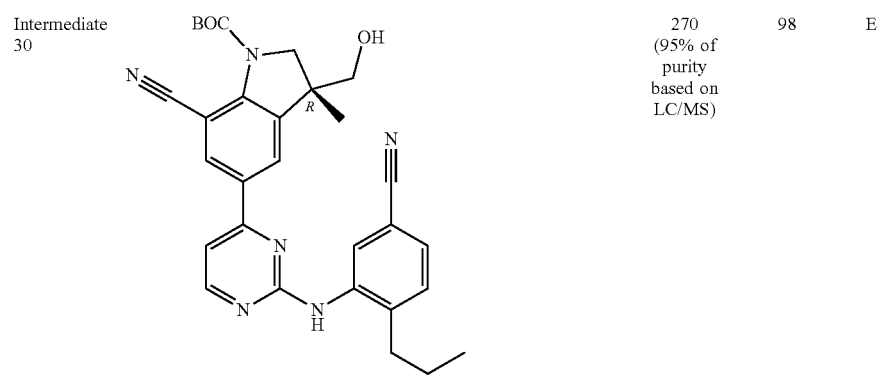<br>From intermediate 29 | 270 (95% of purity based on LC/MS) | 98 | E |
| Intermediate 35 | 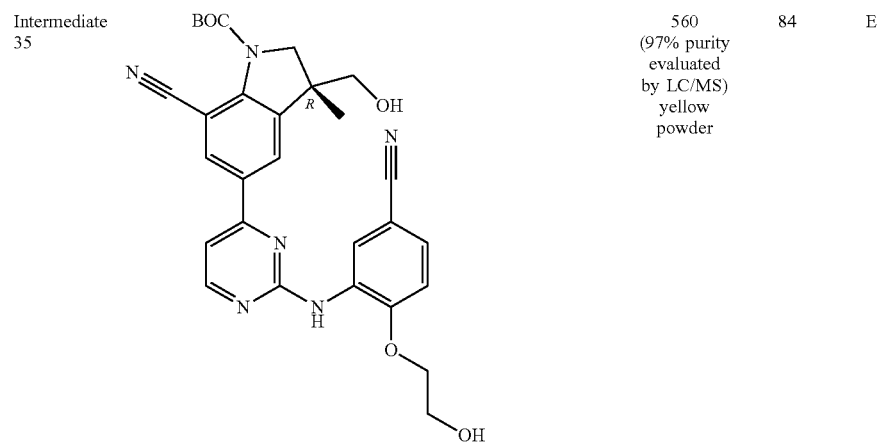<br>From intermediate 33 | 560 (97% purity evaluated by LC/MS) yellow powder | 84 | E |
| Intermediate 62 | 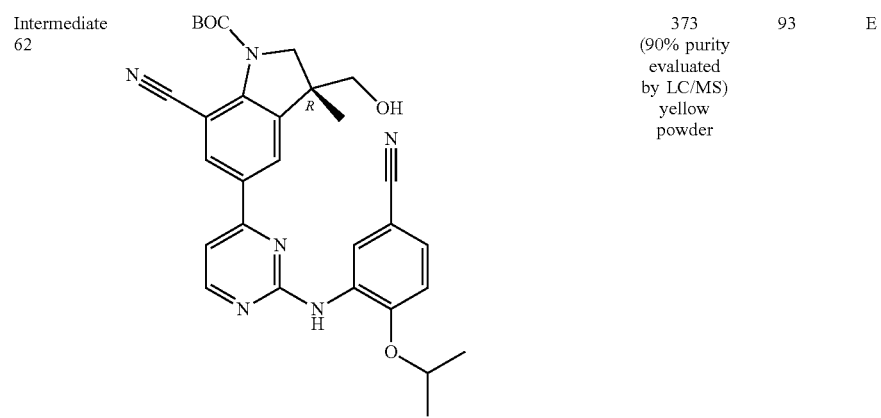<br>From intermediate 61 | 373 (90% purity evaluated by LC/MS) yellow powder | 93 | E |

-continued
| Intermediate number | Structure | Mass (mg) | Yield (%) | Method |
|---|---|---|---|---|
| Intermediate 64 | 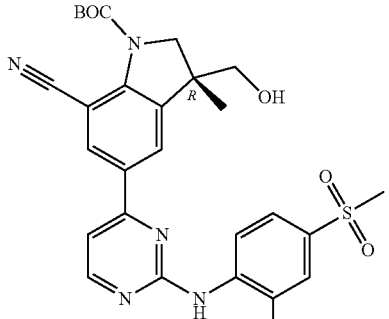<br>From intermediate 63 | 267 | Quant. | E with 1.4 equiv. of TBAF |
| Intermediate 70 | 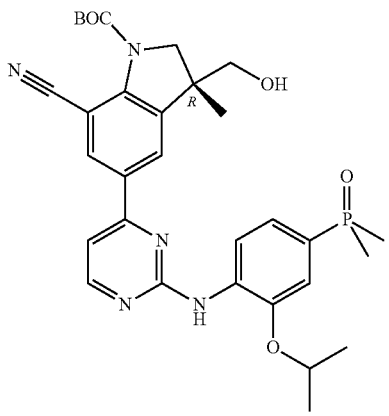<br>From Intermediate 68 | 893 off-white foam | 97 | E with 1 equiv. of TBAF |
| Intermediate 75 | 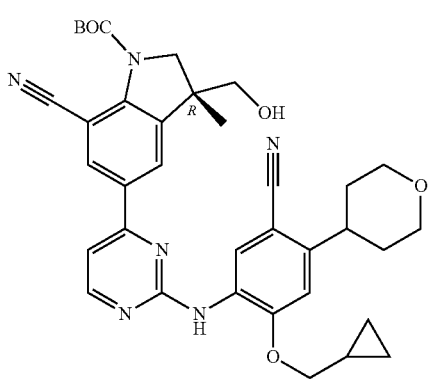<br>From Intermediate 74 | 887 | 60 | E with 1.7 equiv. of TBAF |
| Intermediate 78 | 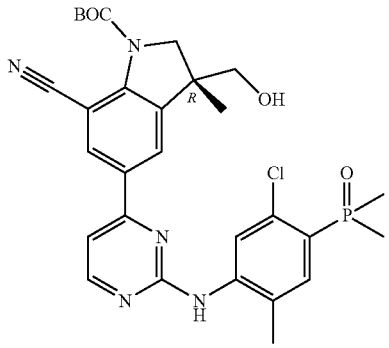<br>From Intermediate 77 | 952 (90% purity evaluated by LC/MS) white foam | 56 | E with 1 equiv. of TBAF |

| Intermediate number | Structure | Mass (mg) | Yield (%) | Method |
|---|---|---|---|---|
| Intermediate 80 | 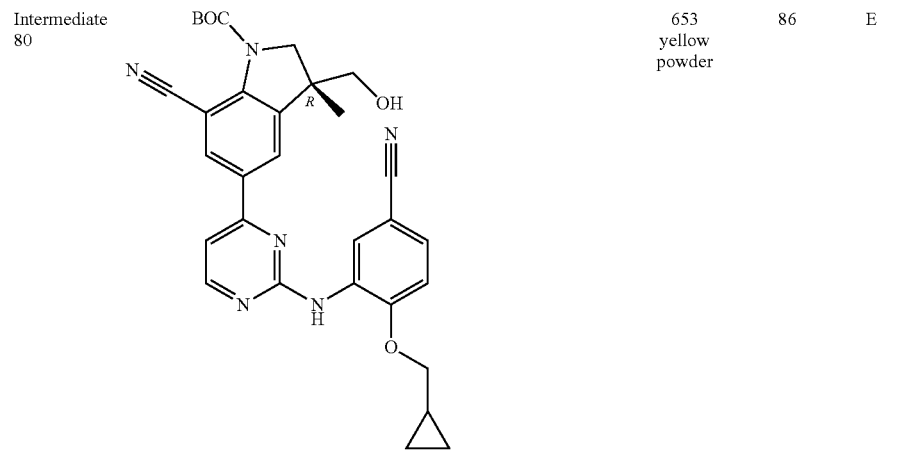<br>From Intermediate 79 | 653 yellow powder | 86 | E |
| Intermediate 90 | 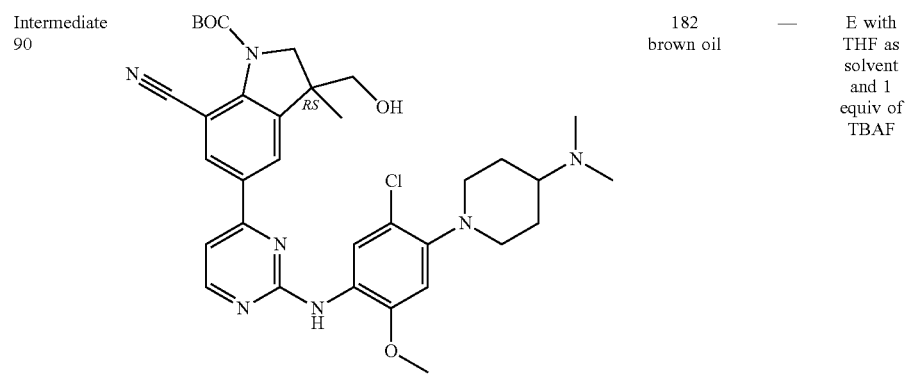<br>From intermediate 89 | 182 brown oil | — | E with THF as solvent and 1 equiv of TBAF |
| Intermediate 97 | 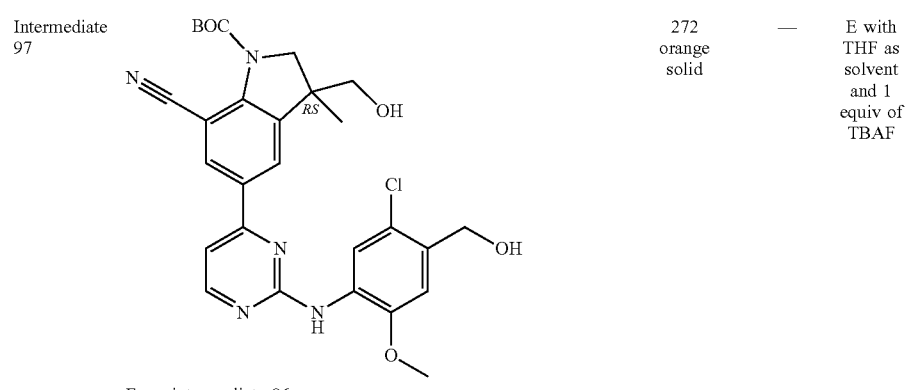<br>From intermediate 96 | 272 orange solid | — | E with THF as solvent and 1 equiv of TBAF |

-continued

| Intermediate number | Structure | Mass (mg) | Yield (%) | Method |
|---|---|---|---|---|
| Intermediate 101 | 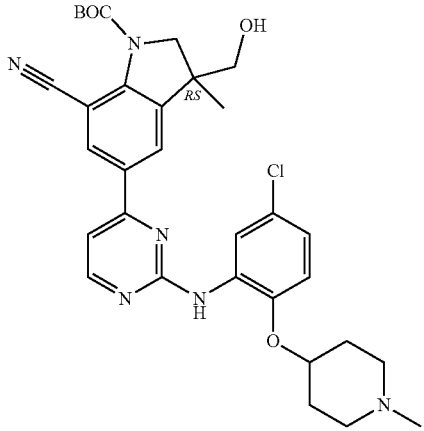<br>From intermediate 100 | 302<br>yellow oil | — | E with THF as solvent and 1 equiv of TBAF |
| Intermediate 103 | 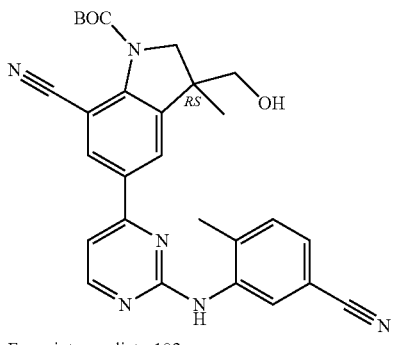<br>From intermediate 102 | 289 | — | E with THF as solvent and 1.1 equiv of TBAF |
| Intermediate 106 | 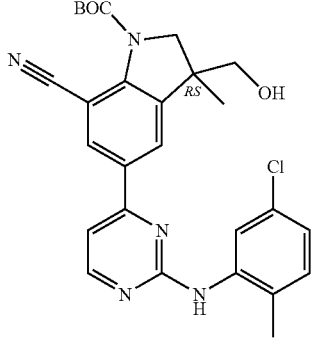<br>From intermediate 105 | 390<br>yellow solid | — | E with THF as solvent and 1.1 equiv of TBAF |
| Intermediate 111 | 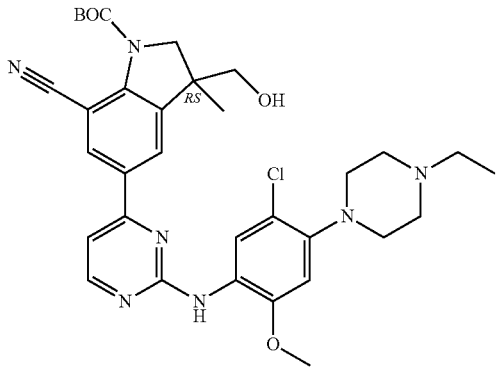<br>From intermediate 110 | 246<br>(68% purity evaluated by LC/MS)<br>dark oil | Quant. | E with THF as solvent and 1 equiv of TBAF |

-continued

| Intermediate number | Structure | Mass (mg) | Yield (%) | Method |
|---|---|---|---|---|
| Intermediate 113 | 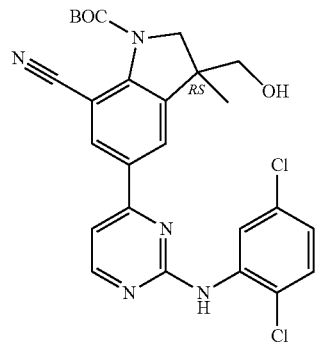<br>From intermediate 112 | 424<br>yellow solid | — | E with THF as solvent and 1.1 equiv of TBAF |
| Intermediate 115 | 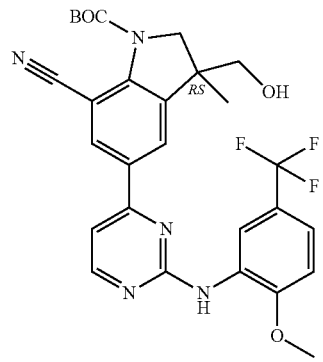<br>From intermediate 114 | 323<br>(77% purity evaluated by LC/MS) | Quant. | E with THF as solvent and 1.1 equiv of TBAF |
| Intermediate 117 | 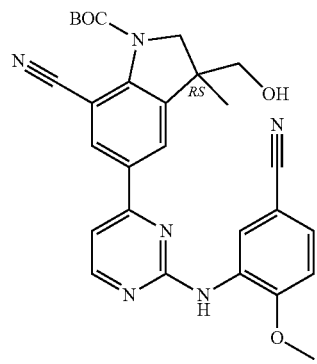<br>From intermediate 116 | 298<br>yellow solid | Quant. | E with THF as solvent and 1.2 equiv of TBAF |
| Intermediate 132 | 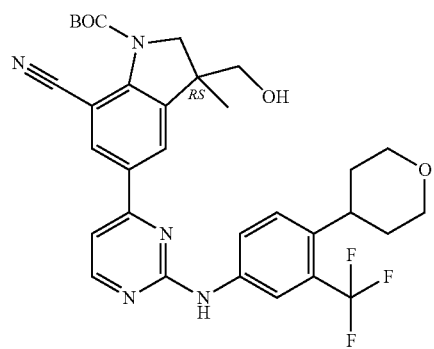<br>From intermediate 131 | 289<br>M.P. (K) = 203° C. | 59 | E with THF as solvent and 1.2 equiv of TBAF |

-continued
| Intermediate number | Structure | Mass (mg) | Yield (%) | Method |
|---|---|---|---|---|
| Intermediate 229 | 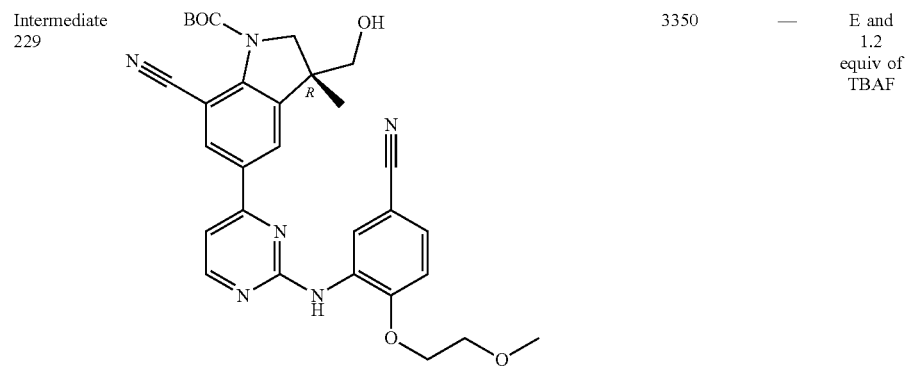<br>From intermediate 228 | 3350 | — | E and 1.2 equiv of TBAF |
| Intermediate 241 | 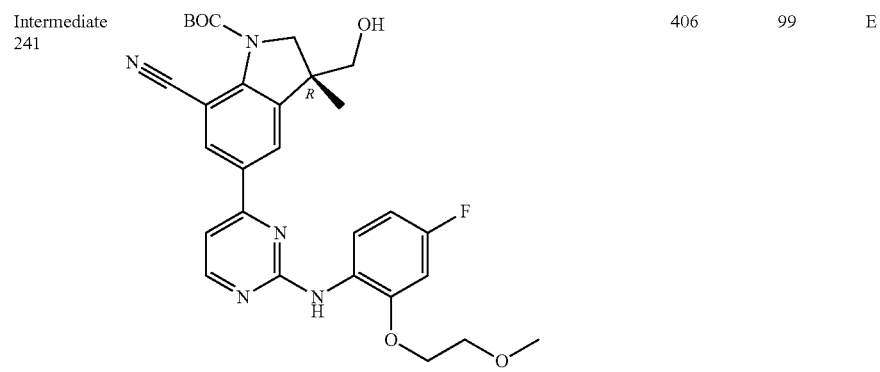<br>From intermediate 240 | 406 | 99 | E |
| Intermediate 243 | 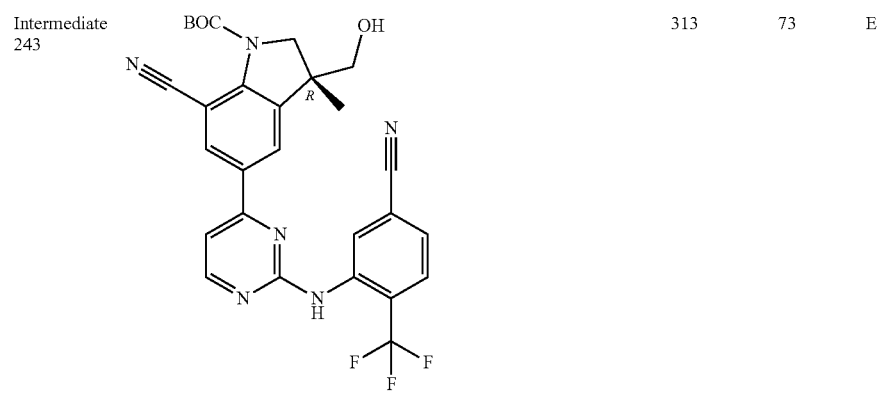<br>From intermediate 242 | 313 | 73 | E |

| Intermediate number | Structure | Mass (mg) | Yield (%) | Method |
|---|---|---|---|---|
| Intermediate 248 | 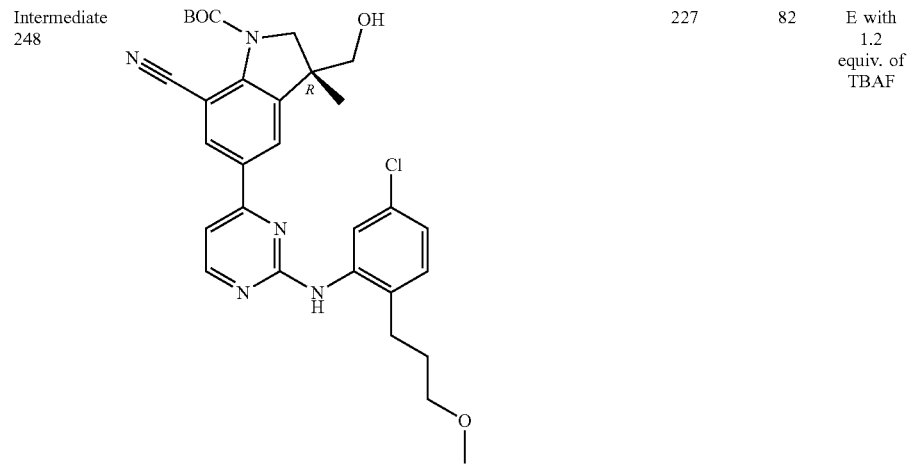 From intermediate 247 | 227 | 82 | E with 1.2 equiv. of TBAF |
| Intermediate 262 | 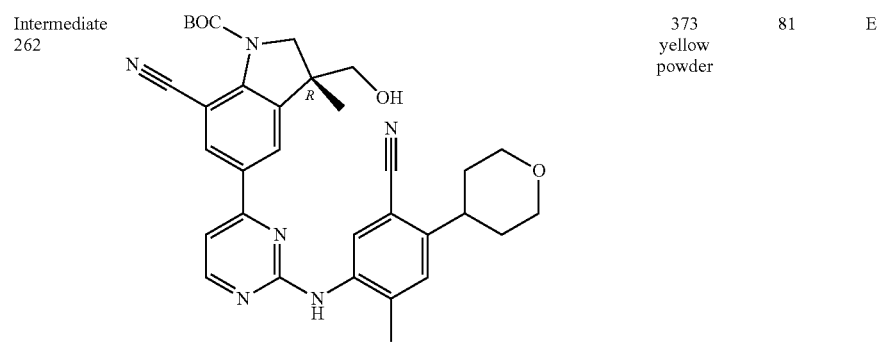 From intermediate 261 | 373 yellow powder | 81 | E |
| Intermediate 266 | 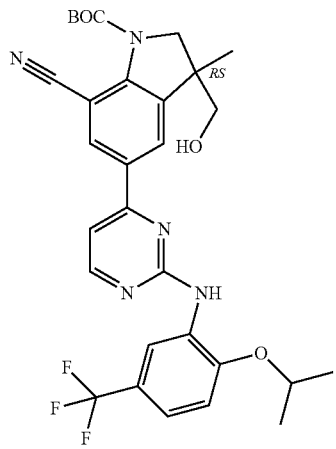 From intermediate 265 | 234 | 56 | E |

-continued
| Intermediate number | Structure | Mass (mg) | Yield (%) | Method |
|---|---|---|---|---|
| Intermediate 270 | 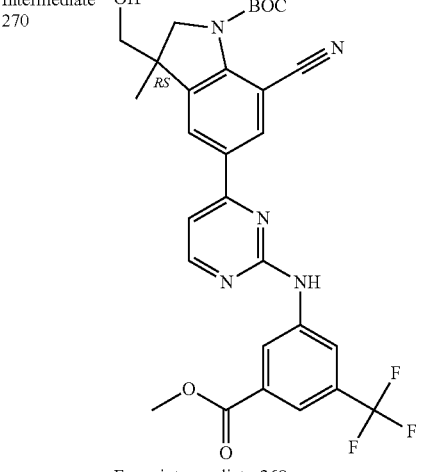<br>From intermediate 269 | 230 | 46 | E with THF and 1.9 equiv of TBAF |
| Intermediate 461 | 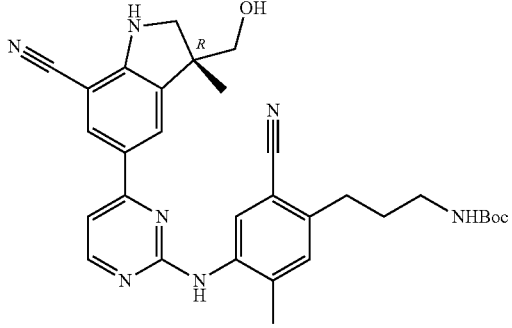<br>From intermediate 459 | 84 | 48 | E with 1.1 equiv of TBAF |
| Intermediate 464 | 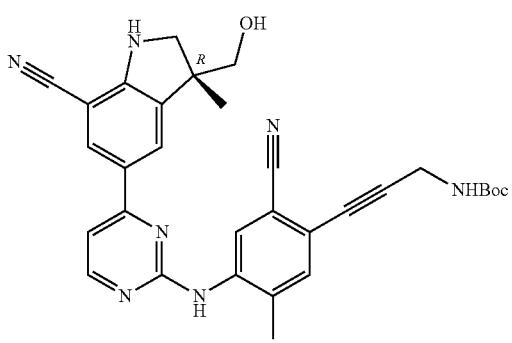<br>From intermediate 463 | 263 | 49 | E with 1.1 equiv of TBAF |

-continued

| Intermediate number | Structure | Mass (mg) | Yield (%) | Method |
|---|---|---|---|---|
| Intermediate 482bis | 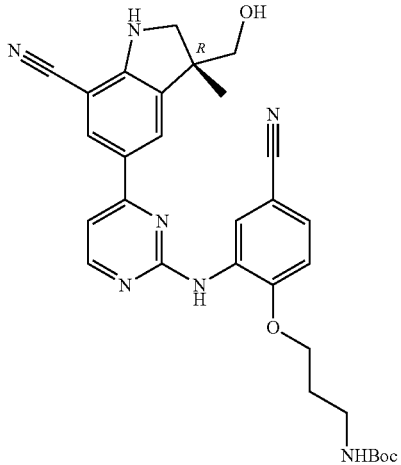<br>From intermediate 482 | 63 | 17 | with 0.5 equiv of TBAF |
| Intermediate 487 | 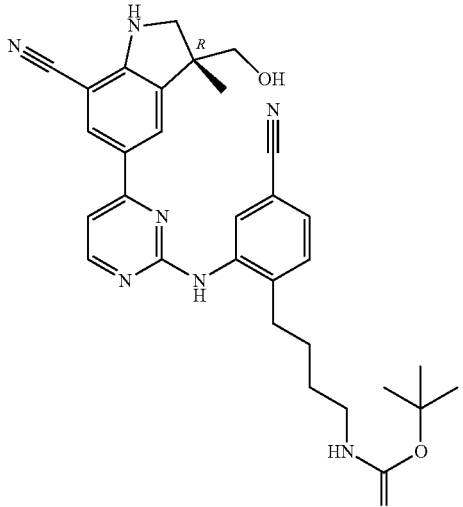<br>From intermediate 486 | 460 | 100 | |

Example A12

Preparation of Intermediate 225:

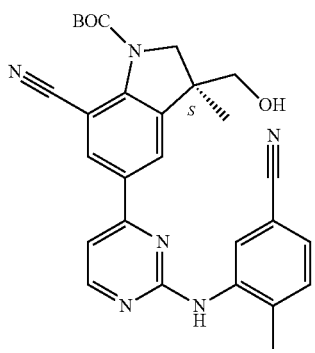

TBAF (on silica gel 1.5 mmol/g) (1.08 g, 1.62 mmol) was added to a solution of intermediate 224 (329.00 mg, 0.54 mmol) in Me-THF (13.5 mL) and the reaction mixture was stirred at rt for 18 h. The following day, the reaction was checked and it was finished. The reaction mixture was diluted with EtOAc, twice with water and NaCl. The layers were separated and the organic layer was dried over MgSO$_4$, filtered and the solvent was removed under reduced pressure. The residue (300 mg) was gathered with another batch (400 mg) for purification. Both crudes were purified by column chromatography on silica gel (irregular SiOH, 40 g, mobile phase DCM/MeOH, gradient from 100:0 to 96:4). The pure fractions were collected and evaporated to dryness to give 632 mg of intermediate 225 (light pink powder).

The intermediates in the Table below were prepared by using an analogous method starting as the one used for the preparation of intermediate 225 from the respective starting materials. The most relevant minor deviations to the referenced method are indicated as additional information in the column 'Mass (mg)'.

| Intermediate number | Structure | Mass (mg) | Yield (%) |
|---|---|---|---|
| Intermediate 39 | 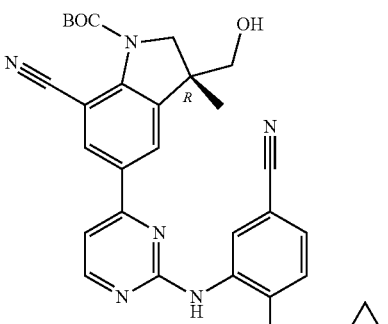<br>From intermediate 38 | 310 (94% purity evaluated by LC/MS) Procedure with 4 equiv. of TBAF | 48 |
| Intermediate 206 | From intermediate 205 | 91 Procedure with 6 equiv. of TBAF | 58 |
| Intermediate 229 | From intermediate 228 | 227 | 68 |

Example A13

Preparation of Intermediate 13 and Intermediate 14:

Method F

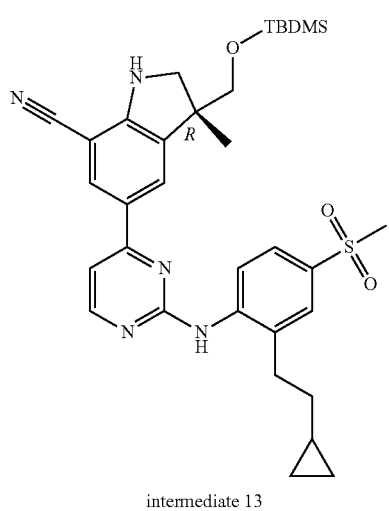

intermediate 13

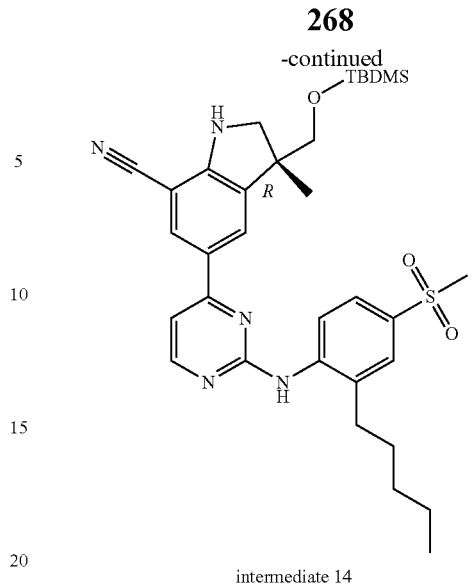

intermediate 14

To a solution of intermediate 11 and intermediate 12 (85/15) (1.11 g, 1.55 mmol) in DCM (35 mL), TFA (3.50 mL, 45.70 mmol) was added and stirred at rt for 30 min. The mixture was diluted with DCM and poured into an aqueous solution of NaHCO$_3$. The organic and aqueous layers were separated. The aqueous layer was extracted with DCM. The combined organic layers were dried over MgSO$_4$, filtered and evaporated under vacuum. The residue (960 mg) was purified by column chromatography on silica gel (irregular SiOH, 15-40 μm, 50 g, dry loading on Celite®, mobile phase: heptane/EtOAc/MeOH, gradient from 85% heptane, 15% EtOAc/MeOH (9:1) to 60% heptane, 40% EtOAc/MeOH (9:1)). The desired fractions were collected and the solvent was concentrated to dryness under vacuum to give 695 mg of a mixture of intermediate 13 and intermediate 14 (85/15) (73% yield).

The intermediates in the Table below were prepared by using an analogous method as described in Method F starting from the respective starting materials. The most relevant minor deviations from the referenced method are indicated in the column 'Method'.

| Intermediate number | Structure | Mass (mg) | Yield (%) | Method |
|---|---|---|---|---|
| Intermediate 19 | From intermediate 18 | 403 orange foam | — | F |

-continued

| Intermediate number | Structure | Mass (mg) | Yield (%) | Method |
|---|---|---|---|---|
| Intermediate 46 | 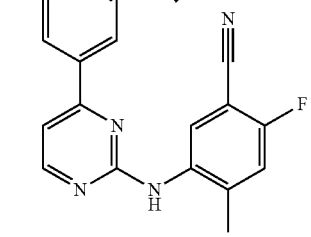<br>From intermediate 45 | 500<br>(67% purity evaluated by LC/MS)<br>pale yellow solid | 67 | F with DCM/TFA (6:1, v/v) |
| Intermediate 107 | 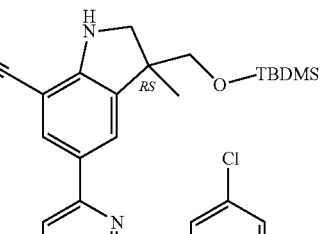<br>From intermediate 105 | 363<br>white solid | 51 | F with DCM/TFA (5:1, v/v) |
| Intermediate 119 | 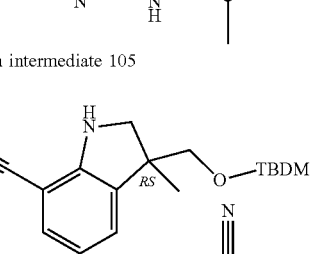<br>From intermediate 118 | 251<br>(83% purity evaluated by LC/MS)<br>yellow solid | 63 | F with DCM/TFA (7:1, v/v) |
| Intermediate 121 | 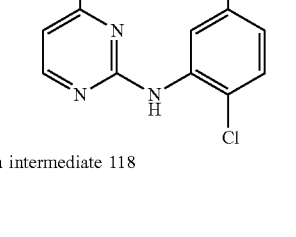<br>From intermediate 120 | 176<br>(34% purity evaluated by LC/MS)<br>white foam | 34 | F with DCM/TFA (4:1, v/v) |

| Intermediate number | Structure | Mass (mg) | Yield (%) | Method |
|---|---|---|---|---|
| Intermediate 136 | 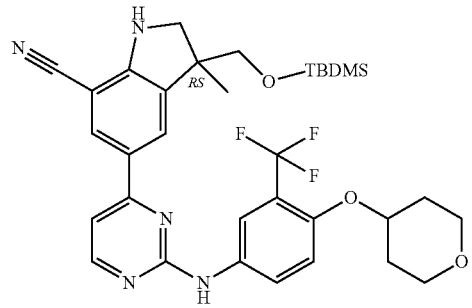<br>From intermediate 135 | 97<br>M.P. (K) = 224° C. | 66 | F with DCM/ TFA (4:1, v/v) |
| Intermediate 140 | 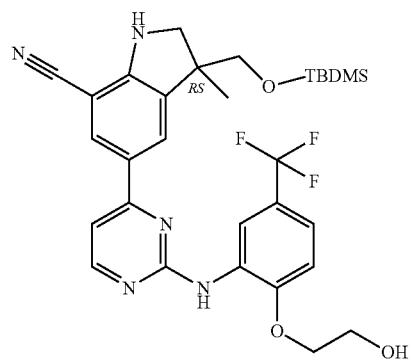<br>From intermediate 139 | 195 | 74 | F with DCM/ TFA (4:1, v/v) |
| Intermediate 170 | 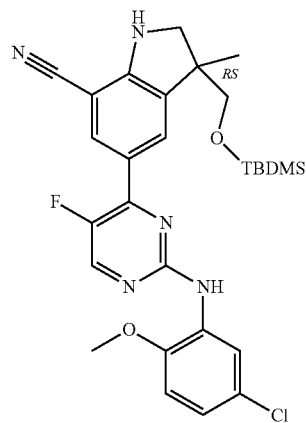<br>From intermediate 169 | 145<br>(96% purity evaluated by LC/MS) | 42 | F with T = 5° C. with DCM/ TFA (9:1, v/v) |

| Intermediate number | Structure | Mass (mg) | Yield (%) | Method |
|---|---|---|---|---|
| Intermediate 172 | (structure) From intermediate 171 | 133 | 38 | F with T = 5° C. with DCM/TFA (9:1, v/v) |
| Intermediate 174 | (structure) From intermediate 173 | 207 | 58 | F with T = 5° C. with DCM/TFA (4:1, v/v) |
| Intermediate 180 | (structure) CIS From intermediate 179 | 231 | — | F with T = 0-5° C. with DCM/TFA (4:1, v/v) |
| Intermediate 182 | (structure) From intermediate 181 | 104 (70% purity evaluated by LC/MS) | 67 | F with T = 0-5° C. with DCM/TFA (4:1, v/v) |

| Intermediate number | Structure | Mass (mg) | Yield (%) | Method |
|---|---|---|---|---|
| Intermediate 184 | 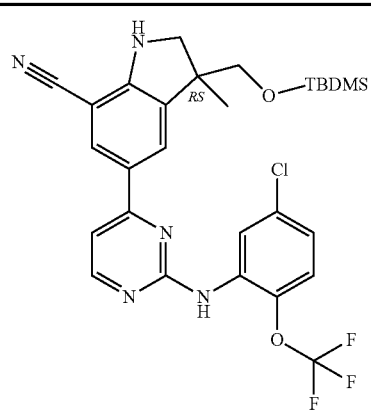<br>From intermediate 183 | 337 | 77 | F with T = 0-5° C. with DCM/ TFA (4:1, v/v) |
| Intermediate 188 | 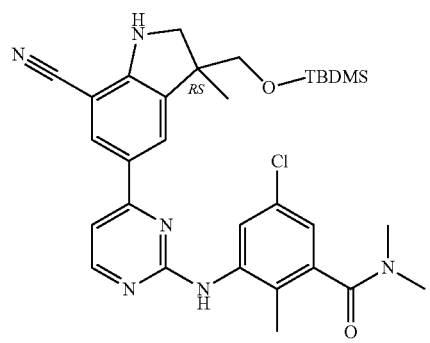<br>From intermediate 187 | 213 | 60 | F with T = 0-5° C. with DCM/ TFA (4:1, v/v) |
| Intermediate 191 | 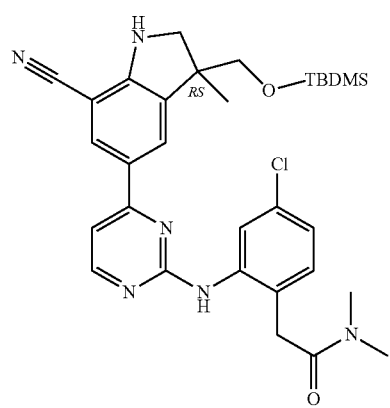<br>From intermediate 190 | 384 (65% purity evaluated by LC/MS) | 49 | F with T = 0-5° C. with DCM/ TFA (4:1, v/v) |

-continued

| Intermediate number | Structure | Mass (mg) | Yield (%) | Method |
|---|---|---|---|---|
| Intermediate 194 | From intermediate 193 | 252 (97% purity evaluated by LC/MS) | 96 | F with T = 0-5° C. with DCM/ TFA (4:1, v/v) |
| Intermediate 204 | From intermediate 203 | 168 white solid | 57 | F with DCM/ TFA (6:1, v/v) |
| Intermediate 211 | From intermediate 210 | 207 white foam | 48 | F with DCM/ TFA (7:1, v/v) |
| Intermediate 213 | From intermediate 212 | 240 orange solid | 65 | F with DCM/ TFA (4:1, v/v) |

| Intermediate number | Structure | Mass (mg) | Yield (%) | Method |
|---|---|---|---|---|
| Intermediate 219 | 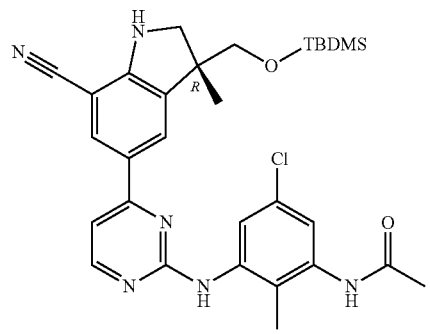<br>From intermediate 218 | 179 | 54 | F with T = 0° C. with DCM/ TFA (6:1, v/v) |
| Intermediate 223 | 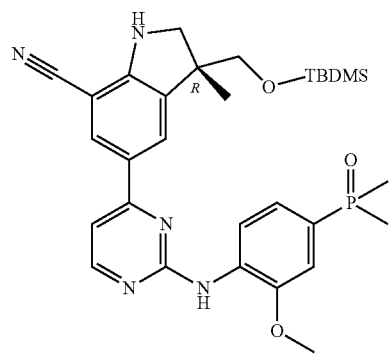<br>From intermediate 222 | 324 | 76 | F with DCM/ TFA (4:1, v/v) |
| Intermediate 233 | 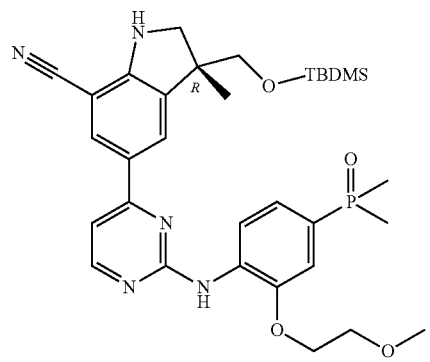<br>From intermediate 232 | 349 yellow solid | 76 | F with DCM/ TFA (7:1, v/v) |
| Intermediate 237 | 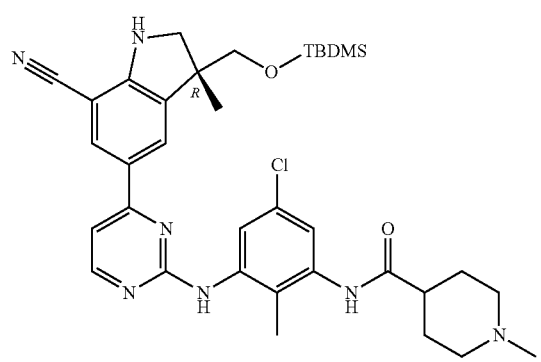<br>From intermediate 236 | 132 (81% purity evaluated by LC/MS) | 73 | F with T = 0° C. with DCM/ TFA (6:1, v/v) |

-continued

| Intermediate number | Structure | Mass (mg) | Yield (%) | Method |
|---|---|---|---|---|
| Intermediate 253 | (structure) From intermediate 252 | 221 | 65 | F with DCM/ TFA (17:1, v/v) |
| Intermediate 459 | (structure) From intermediate 458 | 213 | 44 | F With T = 5° C. DCM/ TFA (7:1, v/v) |
| Intermediate 460 | (structure) From intermediate 458 | 91 | 22 | F With T = 5° C. with DCM/ TFA (7:1, v/v) |

| Intermediate number | Structure | Mass (mg) | Yield (%) | Method |
|---|---|---|---|---|
| Intermediate 506 | From intermediate 505 | 370 | Quant. Purity 69% (LCMS) | F with DCM/TFA (4:1, v/v) |
| Intermediate 509 | From intermediate 508 | 85 | 83% Purity 81% (LCMS) | F with DCM/TFA (4:1, v/v) |
| Intermediate 538 | From intermediate 537 | 355 | 89% | F with DCM/TFA (5:1, v/v) |
| Intermediate 545 | From intermediate 544 | 1100 | 94% Purity 43% (LC/MS) | F with DCM/TFA (9:1, v/v) |

| Intermediate number | Structure | Mass (mg) | Yield (%) | Method |
|---|---|---|---|---|
| Intermediate 548 | 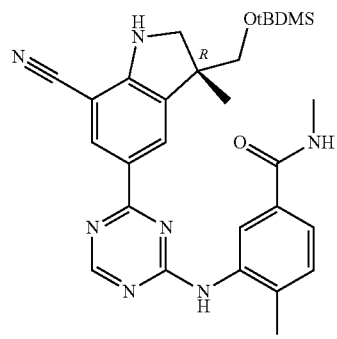<br>From intermediate 547 | 473 | 77%<br>Purity 77% (LCMS) | F with DCM/TFA (8:1, v/v) |
| Intermediate 569 | 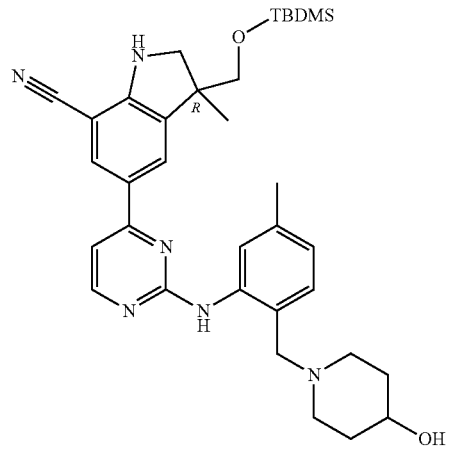<br>From intermediate 658 | 260 | 56 | F with T = 0° C. and DCM/TFA (4:1, v/v) |
| Intermediate 573 | 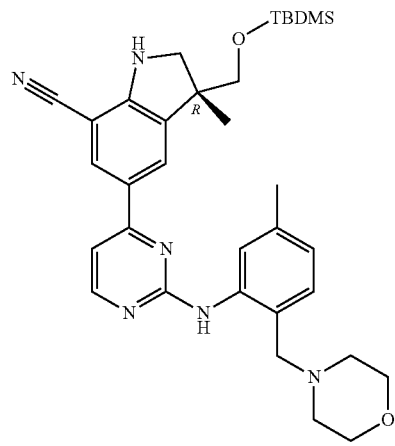<br>From intermediate 572 | 210 | 58 | F with T = 0° C. and DCM/TFA (4:1, v/v) |

| Intermediate number | Structure | Mass (mg) | Yield (%) | Method |
|---|---|---|---|---|
| Intermediate 585 | 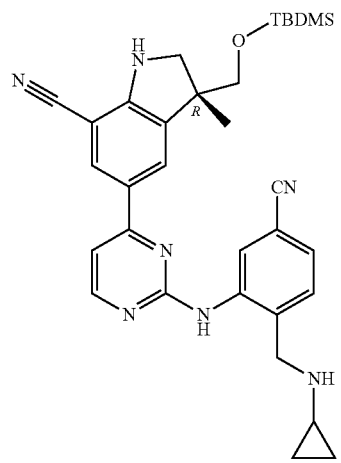<br>From intermediate 584 | 98 | 89 | F with T = 0° C. and DCM/ TFA (5:1, v/v) |
| Intermediate 589 | 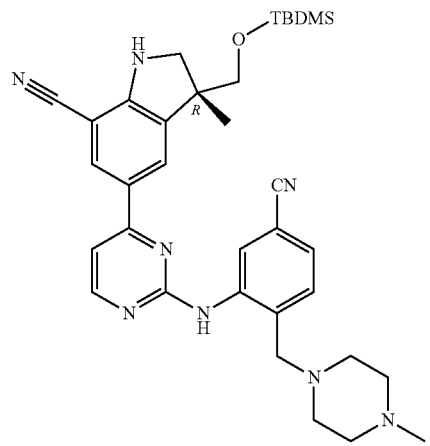<br>From intermediate 588 | 270 | 100 | F with T = 0° C. and DCM/ TFA (4:1, v/v) |
| Intermediate 634 | 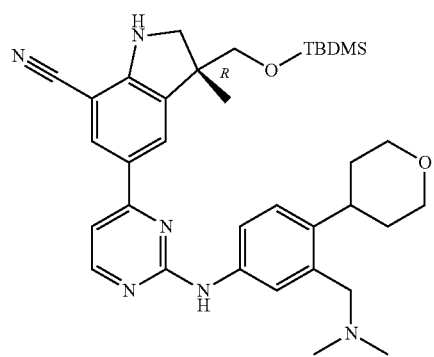<br>From intermediate 633 | 166 61% purity based on LC/MS | — | F with DCM/ TFA (18:1, v/v) during 15 hours |

Example A14

Preparation of Intermediate 354:

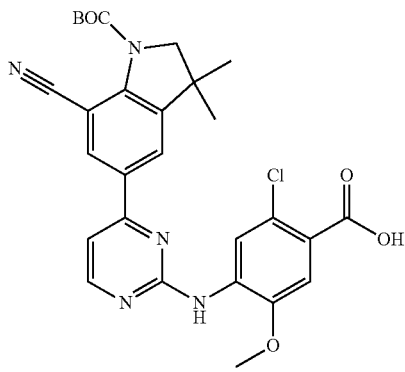 [SMILES: COc1cc(C(=O)O)c(Cl)cc1Nc1nccc(-c2cc(C#N)c3c(c2)C(C)(C)CN3C(=O)OC(C)(C)C)n1]

In a round bottom flask, intermediate 352 (0.10 g, 0.18 mmol) was diluted in a mixture of THF (1 mL) and water (1 mL). Then, LiOH (37.90 mg, 0.89 mmol) was added and the reaction mixture was stirred at 70° C. for 5 h 30 min. The reaction mixture was diluted with DCM and acidified with aqueous HCl 1M. The organic layer was separated quickly (to avoid any boc cleavage), dried over MgSO$_4$ and concentrated to afford 98 mg of intermediate 354 (quant. yield). Intermediate 354 was directly engaged in the next step without any further purification.

Preparation of Intermediate 355:

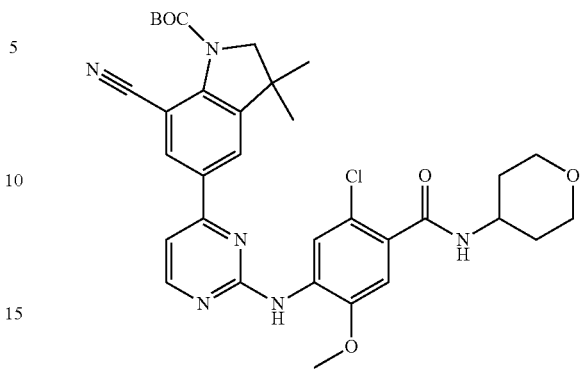

In a round bottom flask, intermediate 354 (98.00 mg, 0.18 mmol) and 4-aminotetrahydropyran (18.60 mg, 0.18 mmol) were diluted in DMF (2.5 mL) at rt. Then, HATU (135.00 mg, 0.36 mmol) and DIEA (92.10 µL, 0.53 mmol) were added and the reaction mixture was stirred at rt for 12 h. Then, the reaction mixture was partitioned between water and EtOAc, and the organic layer was washed with water, brine, dried over MgSO$_4$, filtered and concentrated. The residue was purified by column chromatography on silica gel (Irregular SiO$_2$, 24 g, mobile phase: DCM/MeOH, gradient from 100:0 to 95:5). The fraction containing the product were mixed and concentrated to afford 80 mg of intermediate 355 (71% yield).

The intermediates in the Table below were prepared by using an analogous method as the one used for the preparation of intermediate 355 starting from the respective starting materials.

| Intermediate number | Structure | Mass (mg) | Yield (%) |
|---|---|---|---|
| Intermediate 357 | ![structure] From intermediate 354 and 3-hydroxyazetidine hydrochloride | 160 (70% purity based on LC/MS) | 68 |

-continued

| Intermediate number | Structure | Mass (mg) | Yield (%) |
|---|---|---|---|
| Intermediate 364 | From intermediate 354 and 6-Boc-2,6-diazaspiro[3.5]nonane oxalate | 126 | 65 |
| Intermediate 365 | From intermediate 354 and tert-butyl 2,7-diazaspiro[3.5]nonane-7-carboxylate hydrochloride | 90 | 46 |
| Intermediate 366 | TRANS<br>From intermediate 354 and (1S,3S)-3-aminocyclopentanol | 120 (90% purity based on LC/MS) white solid | 62 |

-continued

| Intermediate number | Structure | Mass (mg) | Yield (%) |
|---|---|---|---|
| Intermediate 367 | 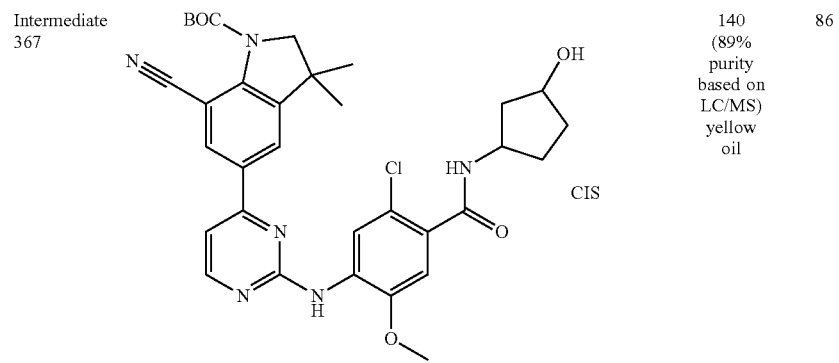<br>CIS<br>From intermediate 354 and cis-3-aminocylcopentanol | 140 (89% purity based on LC/MS) yellow oil | 86 |
| Intermediate 368 | 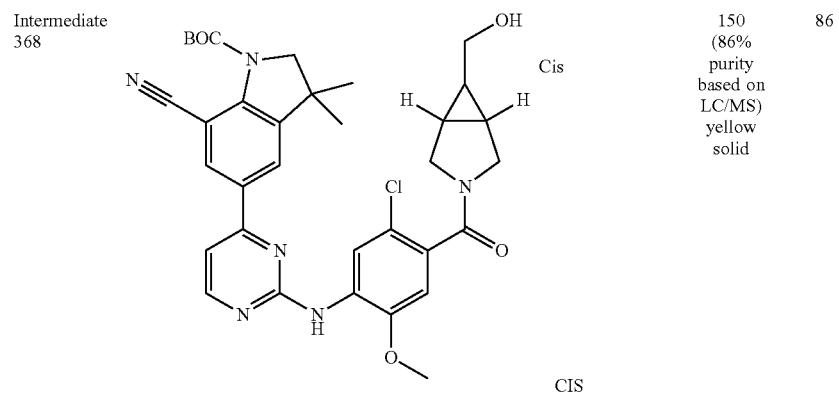<br>CIS<br>From intermediate 354 and 3-azabicyclo[3.1.0]hexane-6-methanol | 150 (86% purity based on LC/MS) yellow solid | 86 |
| Intermediate 369 | <br>From intermediate 354 and 3,3-difluorocyclobutanamine hydrochloride | 110 (97% purity based on LC/MS) | 61 |

| Intermediate number | Structure | Mass (mg) | Yield (%) |
|---|---|---|---|
| Intermediate 370 | 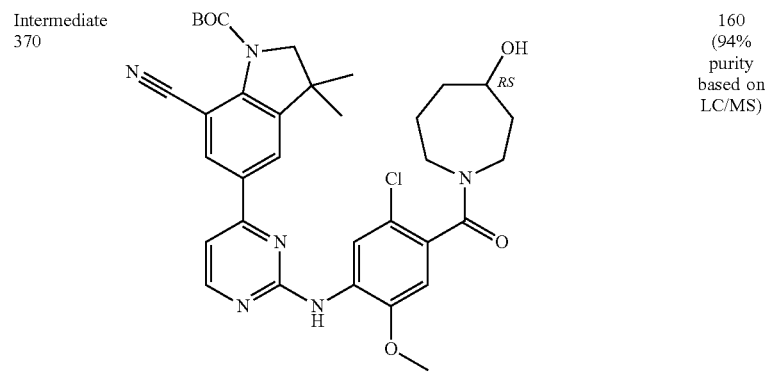<br>From intermediate 354 and 4-Hydroxyhexamethylenimine | 160 (94% purity based on LC/MS) | 92 |
| Intermediate 371 | 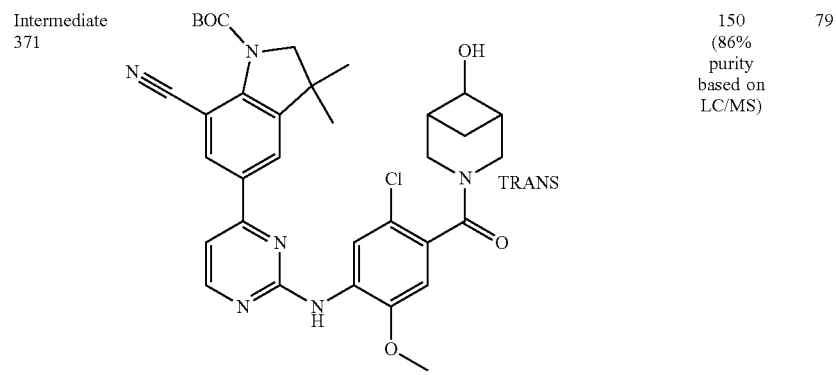<br>TRANS<br>From intermediate 354 and 3-Azabicyclo[3.1.1]heptan-6-ol hydrochloride | 150 (86% purity based on LC/MS) | 79 |
| Intermediate 372 | 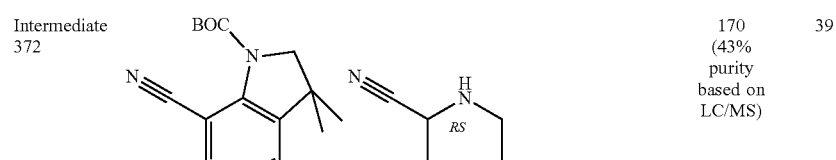<br>From intermediate 354 and 2-cyanopiperazine | 170 (43% purity based on LC/MS) | 39 |

-continued

| Intermediate number | Structure | Mass (mg) | Yield (%) |
|---|---|---|---|
| Intermediate 373 | CIS<br>From intermediate 354 and cis pyrrolo[3,4-b] pyrrole-5(1H)-carboxylic acid, hexahydro-, 1,1-dimethylethyl ester | 130 (86% purity based on LC/MS) | 68 |
| Intermediate 374 | From intermediate 354 and 2-azaspiro[3.3]heptan-6-ol | 200 (38% purity based on LC/MS) | 46 |
| Intermediate 375 (mixture of 4 unseparated diastereo-isomers) | From intermediate 354 and trans-3-amino-1-boc-4-hydroxypyrrolidine | 120 (96% purity based on LC/MS) yellow oil | 58 |

Example A15

Preparation of Intermediate 363:

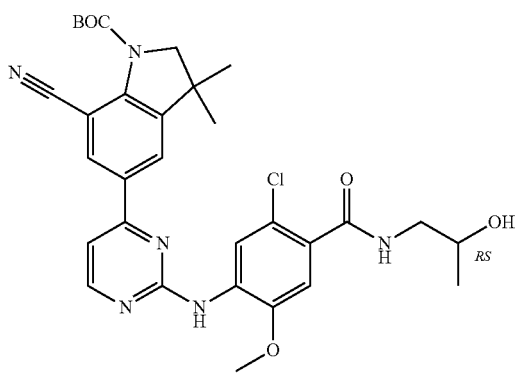 [SMILES: COc1cc(C(=O)NCC(C)O)c(Cl)cc1Nc1nccc(-c2cc(C#N)c3c(c2)C(C)(C)CN3C(=O)OC(C)(C)C)n1]

In a round bottom flask, intermediate 354 (0.10 g, 0.17 mmol) and amino-2-propanol (14.60 µL, 0.19 mmol) were mixed in DMF (2.33 mL). Then, EDC-HCl (53.1 mg, 0.34 mmol) and DIEA (147.00 µL, 0.85 mmol) were added and the reaction mixture was stirred for 3 h. As the conversion was very low, HATU (0.13 g, 0.34 mmol) and DIEA (2 equiv.) were added and the reaction mixture was stirred for 48 h. The reaction mixture was partitioned between water and EtOAc. The organic layer was washed one with water, then with brine, dried over MgSO$_4$, filtered and concentrated. The residue was purified by column chromatography on silica gel (irregular SiOH, 40 g, mobile phase DCM/MeOH, gradient from 100:0 to 96:4). The fractions containing the product were mixed and concentrated to afford 81 mg of intermediate 363 (78% yield).

Example A16

Preparation of Intermediate 15:

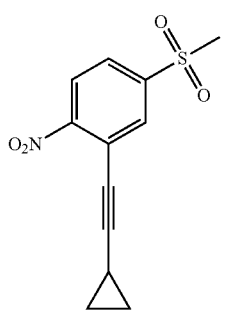 [SMILES: CS(=O)(=O)c1ccc([N+](=O)[O-])c(C#CC2CC2)c1]

In a Schlenck reactor, a mixture of 2-bromo-4-(methylsulfonyl)aniline (2.00 g, 8.00 mmol), ethynylcyclopropane (1.06 g, 16.00 mmol) and TEA (5.56 mL, 40.00 mmol) in dry DMF (40 mL) was purged with N$_2$. Then, Pd(PPh$_3$)$_2$Cl$_2$ (281.00 mg, 0.40 mmol) and CuI (152.00 mg, 0.80 mmol) were added. The mixture was purged with N$_2$ and stirred at 100° C. for 2 h. Then, additional ethynylcyclopropane (1.06 g, 16.00 mmol), Pd(PPh$_3$)$_2$Cl$_2$ (281 mg, 0.4 mmol) and CuI (152.00 mg, 0.80 mmol) were added. The mixture was purged with N$_2$ and stirred at 100° C. for 1 h. Then, additional ethynylcyclopropane (1.06 g, 16.00 mmol), Pd(PPh$_3$)$_2$Cl$_2$ (281 mg, 0.4 mmol) and CuI (152.00 mg, 0.80 mmol) were added. The mixture was purged with N$_2$ and stirred at 100° C. for 1 h. The resulting mixture was cooled down to rt and evaporated under vacuum. The residue (7 g) was purified by column chromatography on silica gel (irregular SiOH, 15-40 µm, 220 g, dry loading on Celite®, mobile phase: DCM/EtOAC, gradient from 100:0 to 98:2). The desired fractions were collected and the solvent was concentrated to dryness under vacuum to give 1.59 g of intermediate 15 (84% yield, containing 21% 2-bromo-4-(methylsulfonyl)aniline according to $^1$H NMR, orange solid).

Preparation of Intermediate 16 and Intermediate 17:

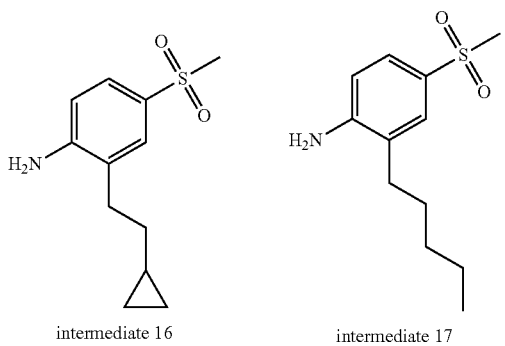 [SMILES: CS(=O)(=O)c1ccc(N)c(CCC2CC2)c1 ; CCCCCc1cc(S(C)(=O)=O)ccc1N]

intermediate 16        intermediate 17

In a sealed tube, a solution of intermediate 15 (930.00 mg, 3.95 mmol), ammonium formate (15.00 g, 237.14 mmol) and Pd/C (10 wt. %) (2.50 g, 2.37 mmol) in a mixture of iPrOH (32 mL) and Me-THF (16 mL) were added and stirred at 70° C. for 30 min.

The crude product was filtered through a pad of Celite® and the cake was washed with EtOAc and iPrOH. The filtrate was evaporated under vacuum and the residual oil was taken-up in DCM and washed with water. The organic layer was dried over MgSO$_4$, filtered off and concentrated under vacuum. The residue (880 mg) was purified by column chromatography on silica gel (irregular SiOH, 15-40 µm, 50 g, dry loading on Celite®, mobile phase: heptane/EtOAc/MeOH, gradient from 85% heptane, 13.5% EtOAc and 1.5% MeOH to 30% heptane, 63% EtOAc and 7% MeOH). The desired fractions were collected and the solvent was concentrated to dryness under vacuum to give 552 mg of a mixture of intermediate 16 and intermediate 17 (58% yield, pale yellow oil, 85/15 evaluating by $^1$H NMR).

Example A17

Preparation of Intermediate 22:

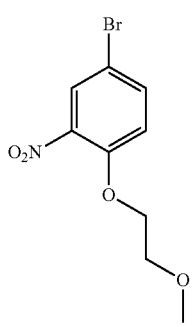

To a solution of 2-methoxyethanol (721.00 μL, 9.09 mmol) in THF (24 mL), LiHMDS (1.5 M in toluene, 6.06 mL, 9.09 mmol) was added dropwise at 5° C. After 30 min, 4-Fluoro-3-nitrobromobenzene (1.11 mL, 9.09 mmol) was quickly added and the reaction mixture was allowed to warm to rt and stirred overnight. The reaction mixture was quenched with water and diluted with EtOAc. The organic layer was decanted, washed with brine, dried over MgSO$_4$, filtered and concentrated under vacuum. The residue was purified by column chromatography on silica gel (SiO$_2$, 120 g, 15-40 μm, mobile phase: heptane/EtOAc, gradient from 100:0 to 0:100). The desired fractions were collected and the solvent was concentrated to dryness under vacuum to give 1.923 g of intermediate 22 (77% yield).

The intermediates in the Table below were prepared by using an analogous method as the one used for the preparation of intermediate 22 starting from the respective starting materials. The most relevant minor deviations to the referenced method are indicated as additional information in the column 'Mass (g)'.

| Intermediate number | Structure | Mass (g) | Yield (%) |
|---|---|---|---|
| Intermediate 25 | (structure) From 4-fluoro-3-nitrobromo benzene | 2.02 | 82 |
| Intermediate 50 | (structure) From 4-fluoro-3-nitro benzonitrile | 3.90 | 99 |
| Intermediate 71 | (structure) From 2-chloro-4-fluoro-5-nitrobenzonitrile | 2.35 brown solid Procedure with Me-THF | 93 |

-continued

| Intermediate number | Structure | Mass (g) | Yield (%) |
|---|---|---|---|
| Intermediate 226 | 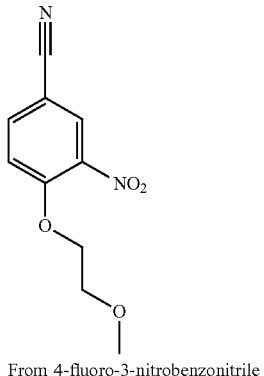<br>From 4-fluoro-3-nitrobenzonitrile | 1.28<br>Procedure with Me-THF | 96 |
| Intermediate 480 | 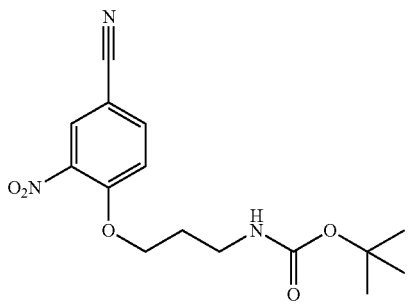 [SMILES: CC(C)(C)OC(=O)NCCCOc1ccc(C#N)cc1[N+](=O)[O-]]<br>From 3-(tert-butoxycarbonylamino)-1-propanol and 4-chloro-3-nitrobenzonitrile | 10.67<br>Procedure with LiHMDS 1N in THF | 40 |
| Intermediate 574 | 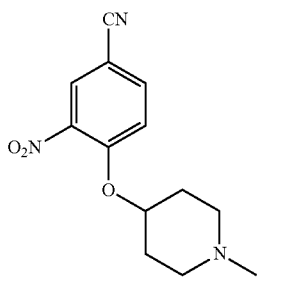<br>From 4-fluoro-3-nitrobenzonitrile and 4-hydroxy-1-methylpiperidine | 0.425<br>Procedure with Me-THF | 54 |
| Intermediate 601 | 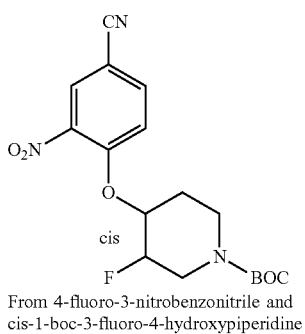<br>From 4-fluoro-3-nitrobenzonitrile and cis-1-boc-3-fluoro-4-hydroxypiperidine | 0.420<br>Procedure with LiHMDS (1M in THF) in Me-THF. | 92 |

-continued

| Intermediate number | Structure | Mass (g) | Yield (%) |
|---|---|---|---|
| Intermediate 607 | 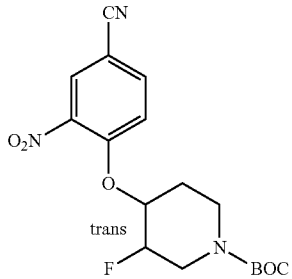 [SMILES: CC(C)(C)OC(=O)N1CCC(Oc2ccc(C#N)cc2[N+](=O)[O-])C(F)C1]<br>From 4-fluoro-3-nitrobenzonitrile and trans-1-boc-3-fluoro-4-hydroxypiperidine | 0.200<br>Procedure with LiHMDS (1M in THF) in Me-THF | 73 |
| Intermediate 620 | 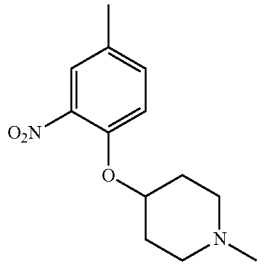<br>From 4-fluoro-3-nitrotoluene and 4-hydroxy-1-methylpiperidine | 0.273<br>Procedure in Me-THF | 34 |

Preparation of Intermediate 614 and Intermediate 615

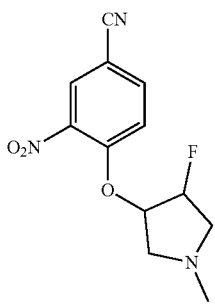

intermediate 614: Trans A (RR or SS)
intermediate 615: Trans B (SS or RR)

A solution of LiHMDS 1.5M in THF (5.6 mL; 8.42 mmol) was added dropwise at 5° C. to a solution of intermediate 614a (590 mg; 4.95 mmol) in Me-THF (18.4 mL). After 30 min, 4-fluoro-3-nitrobenzonitrile (823 mg; 4.95 mmol) was quickly added and the reaction mixture was allowed to warm to room temperature and stirred overnight. The reaction mixture was poured onto iced water, a 10% aqueous solution of $K_2CO_3$ and extracted with EtOAc. The organic layer was decanted, washed with brine, dried over $MgSO_4$, filtered and evaporated to dryness. The residue (1.16 g; yellow solid) was purified by chromatography over silica gel ($SiO_2$, 40 g, eluent: from 98% DCM, 2% MeOH, 0.2% $NH_4OH$ to 95% DCM, 5% MeOH, 0.5% $NH_4OH$). The fractions containing the products were collected and the solvent was evaporated to give 486 mg of yellow solid racemic trans product (37%).

The racemic trans product was purified by chiral SFC (Chiralpak AD-H 5 μm 250*30 mm, mobile phase: 95.7% $CO_2$, 4.3% MeOH (0.3% $iPrNH_2$)). The pure fractions were collected and the solvent was evaporated to give 177 mg (13%) of intermediate 614 (Trans A; RR or SS; eluted first) and 174 mg (13%) of intermediate 615 (Trans B; SS or RR; eluted second).

Preparation of Intermediate 614a:

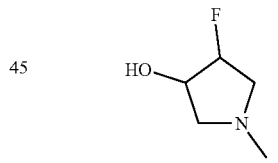

Trans mixture (RR and SS)

Formaldehyde (10.6 mL; 141.3 mmol) was added to a mixture of trans-4-fluoro-3-hydroxypyrrolidine hydrochloride (1 g; 7.06 mmol) and acetic acid (809 μL; 14.13 mmol) in methanol (55 mL) at rt. The reaction mixture was stirred at rt for 30 min, then sodium triacetoxyborohydride (3.74 g; 17.66 mmol) was added and the reaction mixture was stirred at rt for 3 h. The mixture was basified with a saturated aqueous $NaHCO_3$ solution at 5° C.

The mixture was diluted with diethylether and washed with saturated aqueous $NaHCO_3$ solution. Then, the aqueous layer was extracted with diethylether (3 times) but intermediate 614a was still in aqueous layer. Then, the aqueous layer was extracted with EtOAc (3 times) but intermediate 614a was still in aqueous layer. Then, the aqueous layer was extracted with DCM (3 times). The organic layers were combined, dried over $MgSO_4$, filtered and the solvent was evaporated at room temperature to give 1.09 g of intermediate 614a as a colourless volatile oil used without any further purification in the next step.

Example A18

Preparation of Intermediate 23:

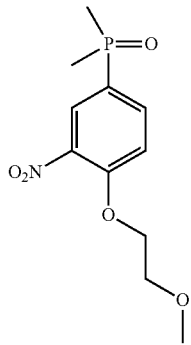

In a sealed tube, a solution of intermediate 22 (500.00 mg, 1.81 mmol), dimethylphosphine oxide (167.00 mg, 1.99 mmol) and K$_3$PO$_4$ (423.00 mg, 1.99 mmol) in dry DMF (7.5 mL) was purged with N$_2$. Then, Pd(OAc)$_2$ (40.70 mg, 0.18 mmol) and 4,5-bis(diphenylphosphino)-9,9-dimethylxanthene (105 mg, 0.18 mmol) were added. The mixture was purged with N$_2$ and stirred at 130° C. for 3 h. The reaction was performed twice on the same quantity of intermediate 22. The 2 batches were combined. The resulting mixture was filtered on a pad of Celite® and the cake was washed with EtOAc. The filtrate was evaporated under vacuum to give a brown oil. The residue was purified by column chromatography on silica gel (irregular SiOH, 15-40 μm, 80 g, dry loading on Celite®, mobile phase: DCM/MeOH, gradient from 99.5:0.5 to 95:5). The desired fractions were collected and the solvent was concentrated to dryness under vacuum to give 0.895 g of intermediate 23 (90% yield, orange oil).

The intermediates in the Table below were prepared by using an analogous method as the one used for the preparation of intermediate 23 starting from the respective starting materials. The most relevant minor deviations to the referenced method are indicated as additional information in the column 'Mass'.

| Intermediate number | Structure | Mass | Yield (%) |
|---|---|---|---|
| Intermediate 26 | From intermediate 25 | 569 mg | 58 |
| Intermediate 66 | From intermediate 65 | 765 mg orange gum | 74 |
| Intermediate 76 | From 4-bromo-5-chloro-2-methylaniline | 1 g white solid Procedure with reaction temperature = 150° C. | 51 |
| Intermediate 220 | From 4-bromo-2-methoxy-1-nitrobenzene | 334 mg brown solid Procedure with reaction temperature = 150° C. | 68 |
| Intermediate 230 | From intermediate 207 | 552 mg red solid Procedure with reaction temperature = 150° C. | 83 |

Preparation of Intermediate 24:

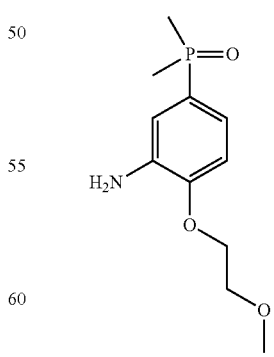

To a solution of intermediate 23 (877.00 mg, 3.21 mmol) in MeOH (23 mL), Raney nickel (19.00 mg, 0.32 mmol) was added under N$_2$. The mixture was stirred at rt under 1.5 bar of H$_2$ for 3 h. The mixture was filtered on a pad of Celite® and the cake was washed with EtOH. The filtrate was evaporated under vacuum to give 726 mg of intermediate 24 (93% yield).

The intermediates in the Table below were prepared by using an analogous starting as the one used for the preparation of intermediate 24 from the respective starting materials. The most relevant minor deviations to the referenced method are indicated as additional information in the column 'Mass'.

| Intermediate number | Structure | Mass | Yield (%) |
|---|---|---|---|
| Intermediate 27 | From intermediate 26 | 490 mg | 97 |
| Intermediate 134 | From intermediate 133 | 1.37 g Procedure with 3 bars pressure of H₂ | 94 |
| Intermediate 156 | From intermediate 155 | 2.1 g Procedure with 3 bars pressure of H₂ | 97 |
| Intermediate 268 | From intermediate 267 | 16.7 g Procedure with 3 bars pressure of H₂ | 100 |

Example A19

Preparation of Intermediate 28:

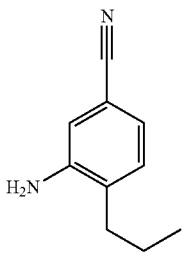

To a solution of 3-amino-4-iodobenzonitrile (0.50 g, 2.05 mmol) in THF (10 mL), a premixed degassed solution of Pd(t-Bu₃P)₂ (105 mg, 0.20 mmol) in a solution of n-propylzinc bromide in THF (0.5 M, 8.20 mL, 0.41 mmol) was added and stirred at rt for 2 h. The reaction mixture was poured onto a 10% aqueous solution of K₂CO₃ and EtOAc was added. The crude product was filtered through a pad of Celite® and the organic layer was decanted, washed with water, dried over MgSO₄, filtered and concentrated under vacuum. The residue was purified by column chromatography on silica gel (irregular SiOH, 24 g, mobile phase: heptane/EtOAc: gradient from 90% heptane, 10% EtOAc to 70% heptane, 30% EtOAc). The pure fractions were collected and evaporated to dryness to give 250 mg of intermediate 28 (76% yield).

The intermediates in the Table below were prepared by using an analogous method as the one used for the preparation of intermediate 28 starting from the respective starting materials.

| Intermediate number | Structure | Mass | Yield (%) |
|---|---|---|---|
| Intermediate 56 | From 3-amino-4-iodobenzonitrile | 212 mg | 59 |

Example A20

Preparation of Intermediate 31:

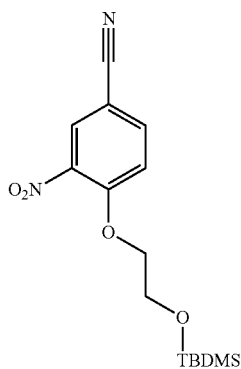

4-fluoro-3-nitrobenzonitrile (1.00 g, 6.02 mmol) and 2-(tert-butyldimethylsiloxy)ethanol (1.32 mL, 6.62 mmol) were dissolved in distilled THF (7 mL) (to give a 0.1-0.2 M solution) under Ar and cooled to 0° C. KHMDS (6.62 mL, 6.62 mmol) dissolved in distilled THF (5.3 mL) (to give 0.5 M solution) was added dropwise, resulting in a color change from colorless to dark. This solution was stirred from 0° C. to rt over 3 h and the reaction mixture was then diluted with DCM and washed once with saturated aqueous $NH_4Cl$. The aqueous layer was back-extracted once with DCM. The organic layers were combined, dried over $MgSO_4$, concentrated. The residue (1.5 g, black oil) was purified by column chromatography on silica gel (irregular SiOH, 80 g, mobile phase: heptane/EtOAc, gradient from 100% heptane, 0% EtOAc to 70% heptane, 30% EtOAc). The desired fractions were collected and evaporated to dryness to give 0.30 g of intermediate 31 (15% yield, orange powder). However, a purified again by column chromatography on silica gel (irregular SiOH, 80 g, deposit solid, mobile phase: heptane/EtOAc, gradient from 100:0 to 70:30). The desired fractions were collected and evaporated to dryness to give 0.659 g of intermediate 31 (34% yield, orange powder) with a global yield of 49%.

The intermediates in the Table below were prepared by using an analogous method as the one used for the preparation of intermediate 31 starting from the respective starting materials.

| Intermediate number | Structure | Mass (g) | Yield (%) |
|---|---|---|---|
| Intermediate 40 | 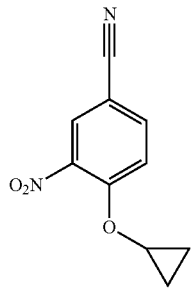 [SMILES: N#Cc1ccc(OC2CC2)c([N+](=O)[O-])c1] From 4-fluoro-3-nitrobenzonitrile | 1.354 yellow powder | 44 |
| Intermediate 47 | 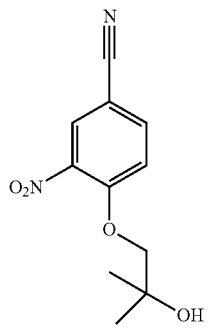 [SMILES: CC(C)(O)COc1ccc(C#N)cc1[N+](=O)[O-]] From 4-fluoro-3-nitrobenzonitrile | 1.636 yellow powder | 76 |

| Intermediate number | Structure | Mass (g) | Yield (%) |
|---|---|---|---|
| Intermediate 53 | 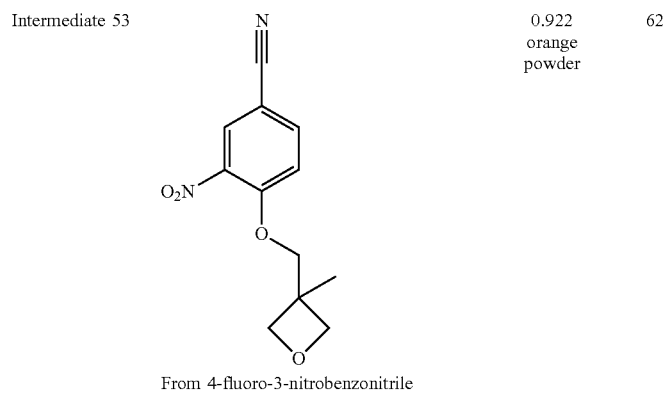 From 4-fluoro-3-nitrobenzonitrile | 0.922 orange powder | 62 |
| Intermediate 58 | 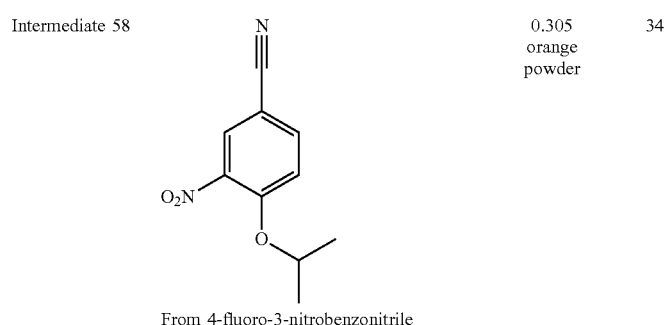 From 4-fluoro-3-nitrobenzonitrile | 0.305 orange powder | 34 |
| Intermediate 122 | 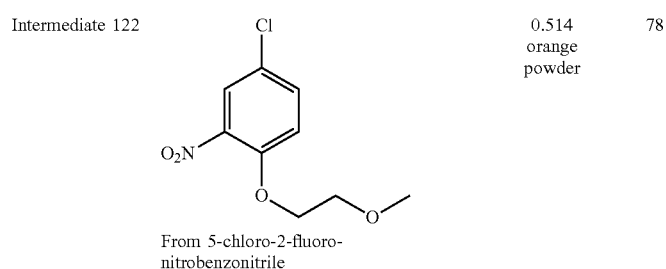 From 5-chloro-2-fluoro-nitrobenzonitrile | 0.514 orange powder | 78 |
| Intermediate 126 | 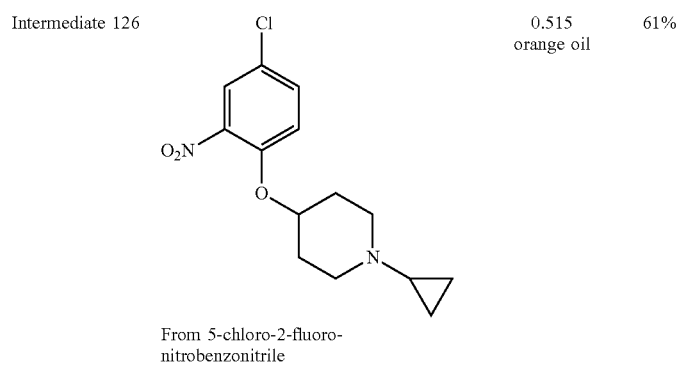 From 5-chloro-2-fluoro-nitrobenzonitrile | 0.515 orange oil | 61% |

-continued

| Intermediate number | Structure | Mass (g) | Yield (%) |
|---|---|---|---|
| Intermediate 141 | 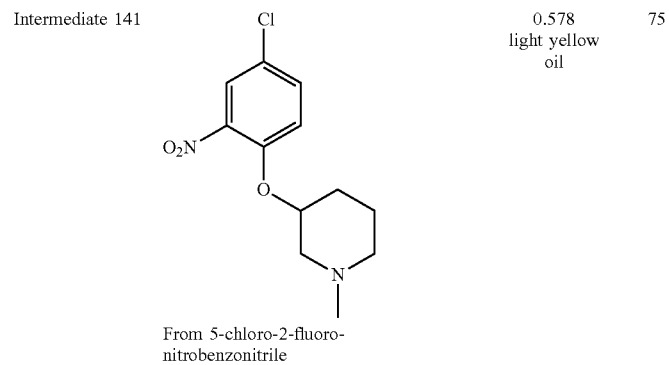<br>From 5-chloro-2-fluoro-nitrobenzonitrile | 0.578<br>light yellow oil | 75 |
| Intermediate 144 | 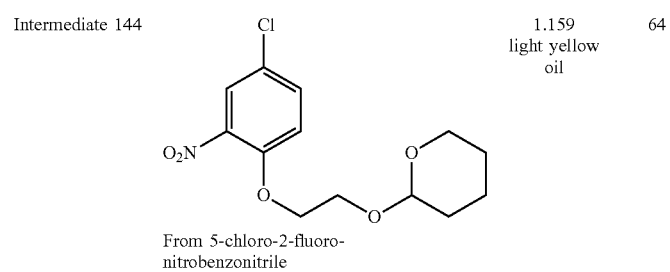<br>From 5-chloro-2-fluoro-nitrobenzonitrile | 1.159<br>light yellow oil | 64 |
| Intermediate 159 | 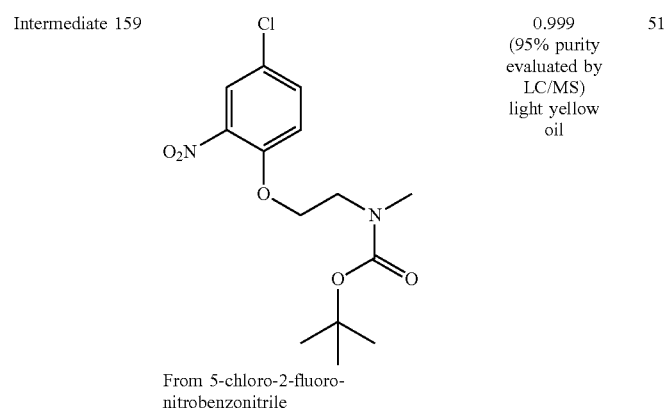<br>From 5-chloro-2-fluoro-nitrobenzonitrile | 0.999<br>(95% purity evaluated by LC/MS)<br>light yellow oil | 51 |
| Intermediate 340 | 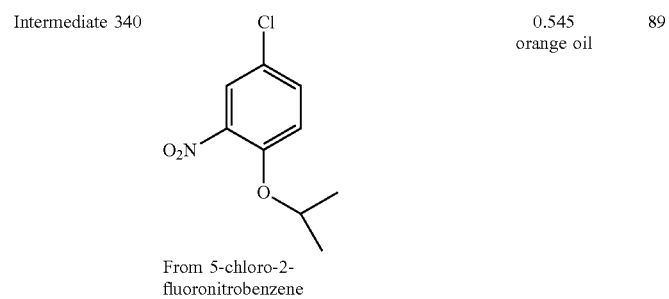<br>From 5-chloro-2-fluoronitrobenzene | 0.545<br>orange oil | 89 |

-continued

| Intermediate number | Structure | Mass (g) | Yield (%) |
|---|---|---|---|
| Intermediate 343 | 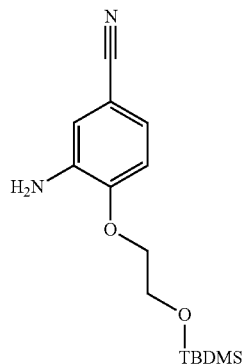 From 5-chloro-2-fluoronitro benzene | 0.653 colorless oil | 89 |

Preparation of Intermediate 32:

Iron powder (0.83 g, 14.87 mmol) was added to a solution of intermediate 31 (0.96 g, 2.97 mmol), NH$_4$Cl (0.64 g; 11.90 mmol) in EtOH (8.34 mL) and distilled water (4.19 mL). The reaction mixture was stirred at 75° C. for 3 h. The reaction mixture was filtered over a pad of Celite® and washed with DCM. A saturated solution of NaHCO$_3$ was added and the mixture was extracted with DCM. The organic layer was dried over MgSO$_4$, filtered and evaporated to dryness to give 701 mg of intermediate 32 (81% yield, brown oil).

Preparation of Intermediate 422:

A mixture of intermediate 421 (10.47 g; 49.35 mmol), iron powder (13.78 g; 246.72 mmol) and ammonium chloride (10.56 g; 197.38 mmol) in EtOH (350 mL) and water (118 mL) was heated at 80° C. for 1 hour. The reaction mixture was cooled down to room temperature, diluted with DCM, filtered over Celite® and basified with a 10% aqueous solution of K$_2$CO$_3$. The organic layer was decanted, dried over MgSO$_4$, filtered and the solvent was evaporated to give 8.68 g (97%) of intermediate 422 as an orange solid which was used without any further purification in the next step.

The intermediates in the Table below were prepared by using an analogous method starting from the respective starting materials as the one used for the preparation of intermediate 32. The most relevant minor deviations to the reference method are indicated as additional information in the column 'Mass (mg)'.

| Intermediate number | Structure | Mass (mg) | Yield (%) |
|---|---|---|---|
| Intermediate 41 | From intermediate 40 | 981 (90% purity evaluated by NMR) white powder | 84 |

-continued
| Intermediate number | Structure | Mass (mg) | Yield (%) |
|---|---|---|---|
| Intermediate 48 | 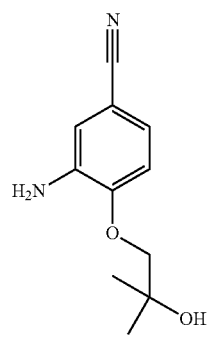<br>From intermediate 47 | 938<br>yellow powder | 66 |
| Intermediate 51 | 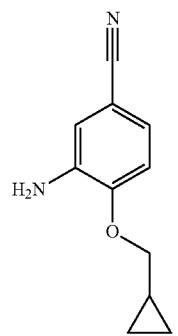<br>From intermediate 50 | 2440<br>(95% purity evaluated by LC/MS) | 65 |
| Intermediate 54 | 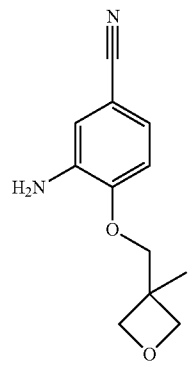 [SMILES: CC1(COc2ccc(C#N)cc2[N+](=O)[O-])COC1]<br>From intermediate 53 | 738<br>orange powder | 91 |
| Intermediate 59 | 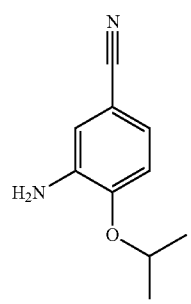<br>From intermediate 58 | 650<br>brown oil<br>Procedure with reaction temperature = 85° C. | 95 |

| Intermediate number | Structure | Mass (mg) | Yield (%) |
|---|---|---|---|
| Intermediate 88 | From intermediate 87 | 414 dark red solid | 86 |
| Intermediate 92 | From intermediate 91 | 997 | 68 |
| Intermediate 95 | From intermediate 94 | 351 pale yellow solid | 89 |
| Intermediate 99 | From intermediate 98 | 1280 off-white solid | 85 |
| Intermediate 109 | From intermediate 108 | 436 dark red solid | 95 |
| Intermediate 123 | From intermediate 122 | 580 yellow oil | — |

-continued

| Intermediate number | Structure | Mass (mg) | Yield (%) |
|---|---|---|---|
| Intermediate 127 | (structure: 4-chloro-2-amino-phenyl ether of 1-cyclopropylpiperidin-4-ol)<br>From intermediate 126 | 512<br>Procedure with reaction temperature = 85° C.<br>yellow oil | — |
| Intermediate 142 | (structure: 4-chloro-2-amino-phenyl ether of 1-methylpiperidin-3-ol, RS)<br>From intermediate 141 | 429<br>Procedure with reaction temperature = 85° C.<br>orange powder | 85 |
| Intermediate 145 | (structure: 4-chloro-2-amino-phenyl ether of 2-(tetrahydropyran-2-yloxy)ethanol)<br>From intermediate 144 | 650<br>Procedure with reaction temperature = 85° C.<br>yellow oil | 62 |
| Intermediate 160 | (structure: 4-chloro-2-amino-phenyl ether of N-Boc-N-methyl-2-aminoethanol)<br>From intermediate 159 | 771<br>Procedure with reaction temperature = 85° C.<br>yellow oil | 85 |
| Intermediate 186 | (structure: 3-amino-5-chloro-2-methyl-N,N-dimethylbenzamide)<br>From intermediate 185 | 315<br>(92% purity evaluated by LC/MS) | — |

-continued
| Intermediate number | Structure | Mass (mg) | Yield (%) |
|---|---|---|---|
| Intermediate 198 | 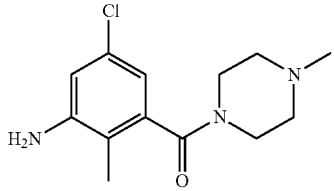<br>From intermediate 197 | 380<br>(96% purity evaluated by LC/MS) | 95 |
| Intermediate 227 | 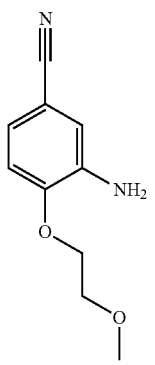<br>From intermediate 226 | 1.08<br>Procedure with reaction temperature = 100° C. | 97 |
| Intermediate 239 | 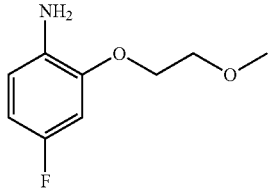<br>From intermediate 238 | 255 | 85 |
| Intermediate 245 | 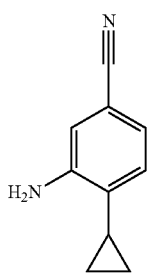<br>From intermediate 244 | 264 | 57 |
| Intermediate 251 | 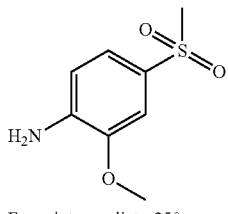<br>From intermediate 250 | 1360 | 96 |

| Intermediate number | Structure | Mass (mg) | Yield (%) |
|---|---|---|---|
| Intermediate 279 | 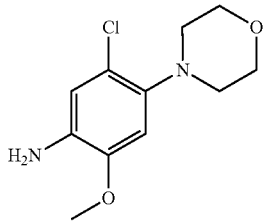<br>From intermediate 278 | 625<br>(83% based on LC/MS) | — |
| Intermediate 285 | 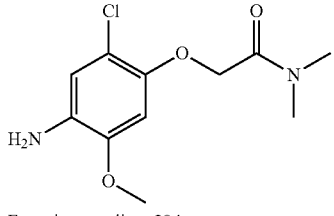<br>From intermediate 284 | 158<br>light brown solid | 28 |
| Intermediate 291 | 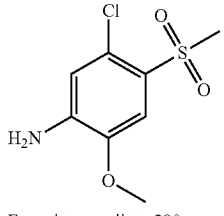<br>From intermediate 290 | 492<br>light brown solid | 64 |
| Intermediate 297 | 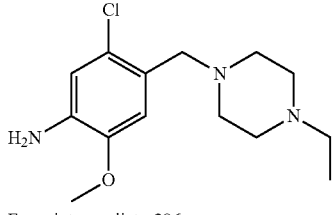<br>From intermediate 296 | 313<br>pale yellow foam | 82 |
| Intermediate 300 | 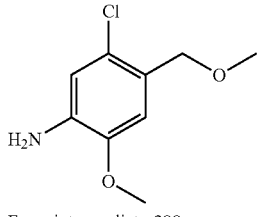<br>From intermediate 299 | 221<br>orange-brown syrup | 96 |
| Intermediate 303 | 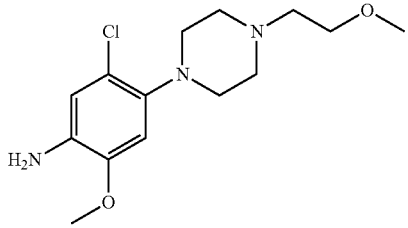<br>From intermediate 302 | 257<br>(58% purity evaluated by LC/MS)<br>brown oil | 97 |

-continued

| Intermediate number | Structure | Mass (mg) | Yield (%) |
|---|---|---|---|
| Intermediate 305 | Cl, H₂N, S(=O)(=O)CH₃ substituted benzene<br>From 4-chloro-1-methanesulfonyl-2-nitrobenzene | 450 (83% purity based on LC/MS) brown syrup | — |
| Intermediate 308 | Cl, 4-ethylpiperazinyl, H₂N, methyl substituted benzene<br>From intermediate 307 | 371 (40% purity based on LC/MS) brown solid | 84 |
| Intermediate 311 | Cl, 4-methoxypiperidinyl, H₂N, OMe substituted benzene<br>From intermediate 310 | 246 brown oil | 94 |
| Intermediate 314 | Cl, 4-isopropylpiperazinyl, H₂N, OMe substituted benzene<br>From intermediate 313 | 255 brown oil | 98 |
| Intermediate 322 | Cl, O-CH₂CH₂-(4-methylpiperazinyl), H₂N, OMe substituted benzene<br>From intermediate 321 | 143 (17% purity based on LC/MS) brown oil | 92 |
| Intermediate 329 | Cl, 3-hydroxypyrrolidinyl (RS), H₂N, OMe substituted benzene<br>From intermediate 328 | 217 brown oil | 93 |

-continued
| Intermediate number | Structure | Mass (mg) | Yield (%) |
|---|---|---|---|
| Intermediate 332 | 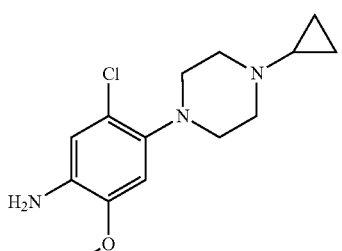<br>From intermediate 331 | 221<br>(90% purity based on LC/MS)<br>brown oil | 80 |
| Intermediate 341 | 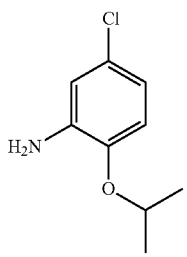<br>From intermediate 340 | 370<br>yellow oil | 79 |
| Intermediate 344 | 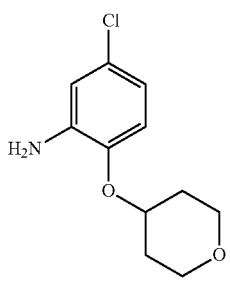 [SMILES: Nc1cc(Cl)ccc1OC1CCOCC1]<br>From intermediate 343 | 679 | — |
| Intermediate 351 | 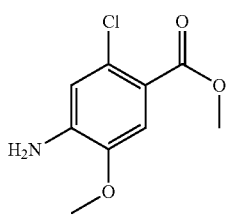<br>From intermediate 350 | 750 | Quant. |
| Intermediate 360 | 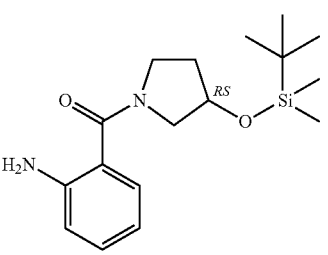 [SMILES: CC(C)(C)[Si](C)(C)OC1CCN(C(=O)c2ccccc2N)C1]<br>From intermediate 359 | 720 | 87 |

-continued
| Intermediate number | Structure | Mass (mg) | Yield (%) |
|---|---|---|---|
| Intermediate 410 | 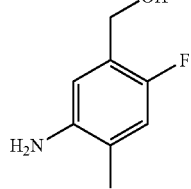 From intermediate 409 | 980 | 100 |
| Intermediate 447 | 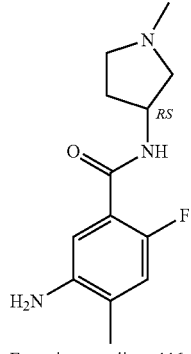 From intermediate 446 | 481 | 84 |
| Intermediate 452 | 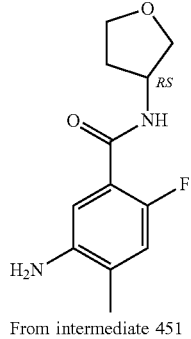 From intermediate 451 | 447 | 100 |
| Intermediate 462 | 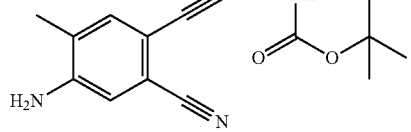 From intermediate 456 | 522 | 87 |
| Intermediate 467 | 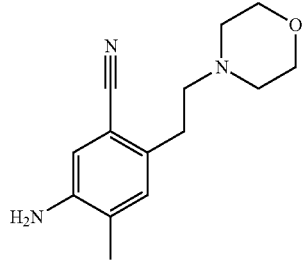 From intermediate 466 | 260 | 99 |

-continued
| Intermediate number | Structure | Mass (mg) | Yield (%) |
|---|---|---|---|
| Intermediate 470 | 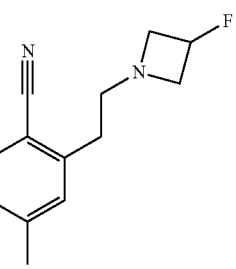<br>From intermediate 469 | 202 (74% of purity based on LC/MS) | 92 |
| Intermediate 490 | 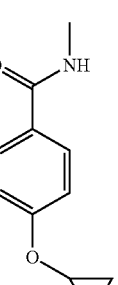<br>From intermediate 489 | 298 | 96 |
| Intermediate 567 | 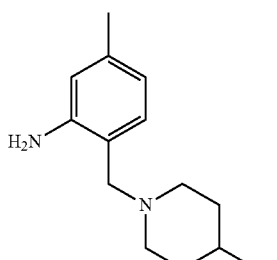<br>From intermediate 566 | 320 | 73 |
| Intermediate 571 | 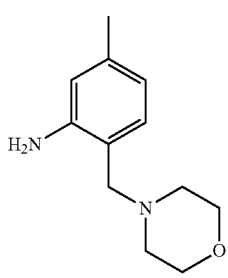<br>From intermediate 570 | 390 | 89 |
| Intermediate 575 | 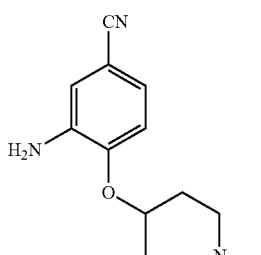<br>From intermediate 574 | 376 | 100 |

| Intermediate number | Structure | Mass (mg) | Yield (%) |
|---|---|---|---|
| Intermediate 580 | 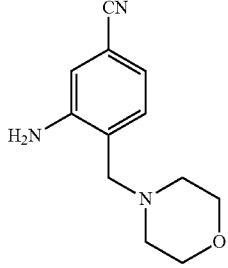 [SMILES: N#Cc1ccc(CN2CCOCC2)c(N)c1]<br>From intermediate 579 | 180<br>Yellow oil | 93 |
| Intermediate 587 | 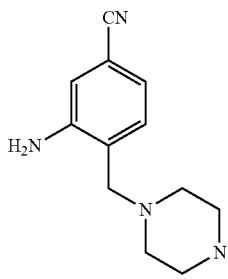<br>From intermediate 586 | 200 | 90 |
| Intermediate 591 | 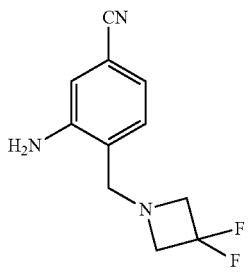<br>From intermediate 590 | 150 | 43 |
| Intermediate 595 | 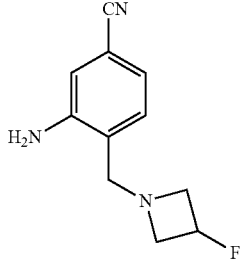<br>From intermediate 594 | 140 | 94 |
| Intermediate 599 | 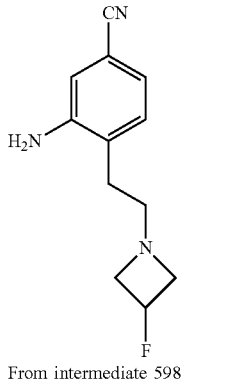<br>From intermediate 598 | 375 | 99 |

-continued
| Intermediate number | Structure | Mass (mg) | Yield (%) |
|---|---|---|---|
| Intermediate 604 | 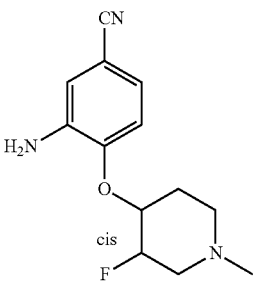 [SMILES: CN1CCC(Oc2ccc(C#N)cc2N)C(F)C1]From intermediate 603 | 160 | 72 |
| Intermediate 610 | 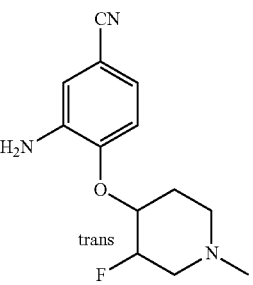 [SMILES: CN1CCC(Oc2ccc(C#N)cc2N)C(F)C1]From intermediate 609 | 64 | 72 |
| Intermediate 617 | 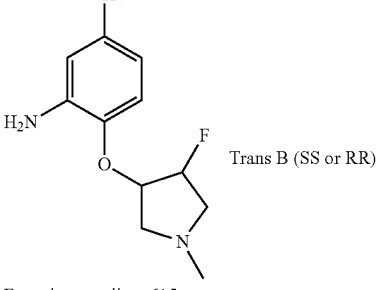Trans B (SS or RR)<br>From intermediate 615 | 148 | 96 |
| Intermediate 621 | 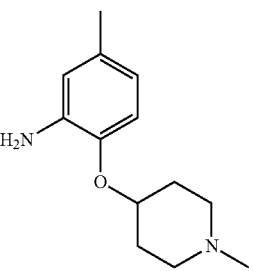 [SMILES: Cc1ccc(OC2CCN(C)CC2)c(N)c1]From intermediate 620 | 173 | 73 |
| Intermediate 521b | 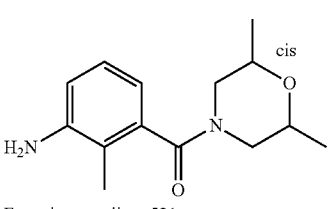From intermediate 521a | 836 | quantitative |

Preparation of Intermediate 397:

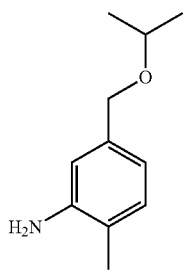

Intermediate 396 (2.1 g; 10 mmol) was dissolved in THF (40 mL), Methanol (20 mL) and water (20 mL). Iron (2.8 g; 50.18 mmol) and NH$_4$Cl (2.68 g; 50.18 mmol) were added. The mixture was refluxed for 2 hours. The mixture was extracted with ethyl acetate (50 mL*2). The organic phase was washed by water (20 mL), brine (20 mL), dried over Na$_2$SO$_4$, filtered, and evaporated in vacuum to give 1.75 g (97%) of intermediate 397 as a brown oil.

Preparation of Intermediate 481:

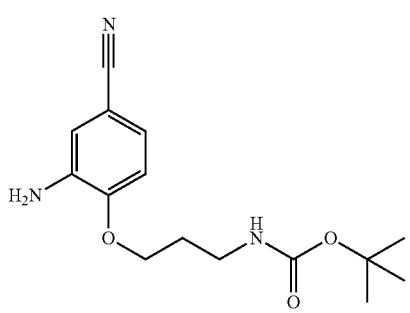

Intermediate 481 was prepared following an analogous method as the one used for the preparation of intermediate 397, starting from intermediate 480 (5.5 g; 99%).

Preparation of Intermediate 616.

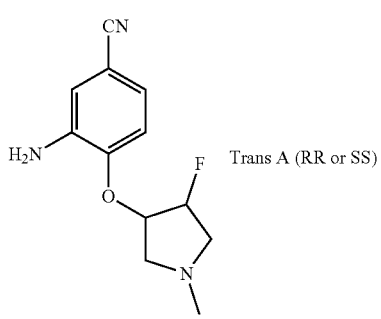 [SMILES: CN1CC(F)C(Oc2ccc(C#N)cc2N)C1]

Trans A (RR or SS)

A mixture of intermediate 614 (177 mg; 0.667 mmol), iron powder (186 mg; 3.337 mmol) and ammonium chloride (143 mg; 2.67 mmol) in ethanol (6 mL) and water (1 mL) was heated at 70° C. for 1 hour. The reaction mixture was cooled down to room temperature, diluted with DCM, filtered over Celite® and basified with a 10% aqueous solution of K$_2$CO$_3$. The organic layer was decanted, dried over MgSO$_4$, filtered and evaporated to dryness yielding 156 mg (99%) of intermediate 616.

Example A21

Preparation of Intermediate 36:

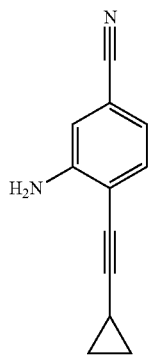

In a sealed tube, a solution of 3-amino-4-iodobenzonitrile (1.70 g, 6.97 mmol), cyclopropylacetylene (1.50 mL, 17.42 mmol) and TEA (3.00 mL, 20.90 mmol) in DMF (50 mL) was degassed (N$_2$ bubbling). Pd(PPh$_3$)$_2$Cl$_2$ (244.00 mg; 0.35 mmol) and CuI (267.00 mg; 1.39 mmol) were added and the reaction mixture was stirred at rt for 2 h.

The reaction mixture was poured onto water and extracted with Et$_2$O/EtOAc. The organic layer was decanted, washed with brine, dried over MgSO$_4$, filtered and evaporated to dryness. The residue was purified by column chromatography on silica gel (irregular SiOH, 40 g, mobile phase: heptane/EtOAc, gradient from 80% heptane, 20% EtOAc to 60% heptane, 40% EtOAc). The pure fractions were collected and evaporated to dryness to give 1.13 g of intermediate 36 (89% yield).

The intermediate in the Table below was prepared by using an analogous method as the one used for the preparation of intermediate 36 starting from the respective starting materials.

| Intermediate number | Structure | Mass (mg) | Yield (%) |
|---|---|---|---|
| Intermediate 254 | 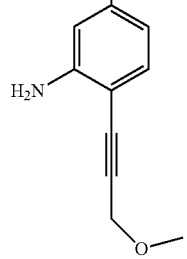 From 3-amino-4-iodobenzonitrile | 745 | 99 |

| Intermediate number | Structure | Mass (mg) | Yield (%) |
|---|---|---|---|
| Intermediate 484 | 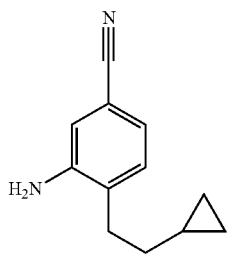 From 3-amino-4-iodobenzonitrile and tert-butyl but-3-yn-1-ylcarbamate | 7600 | 81 |

Preparation of Intermediate 37:

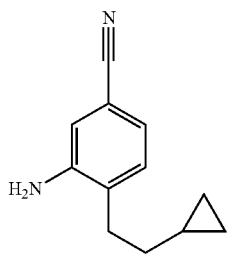

A suspension of activated charcoal (one spoon) and intermediate 36 (1.10 g, 6.04 mmol) in MeOH (30 mL) was stirred at room temperature all over the week end. The solids were removed by filtration over Celite® and the filtrate was evaporated to dryness. The residue was dissolved in MeOH (30 mL) and Pd/C (10 wt. %, 220 mg) was added. The suspension was hydrogenated under Atm pressure of $H_2$ at rt for 3 h. The catalyst was removed by filtration and the filtrate was evaporated to dryness. The residue was purified by column chromatography on silica gel (irregular SiOH, 40 g, mobile phase: heptane/EtOAc, gradient from 90% heptane, 10% EtOAc to 70% heptane, 30% EtOAc). The pure fractions were collected and evaporated to dryness to give 509 mg of intermediate 37 (45% yield).

The intermediate in the Table below was prepared by using an analogous method as the one used for the preparation of intermediate 37 starting from the respective starting materials.

| Intermediate number | Structure | Mass (mg) | Yield (%) |
|---|---|---|---|
| Intermediate 255 | From intermediate 254 | 577 | 91 |
| Intermediate 485 | From intermediate 484 | 6300 | 81 |

Example A22

Preparation of Intermediate 43:

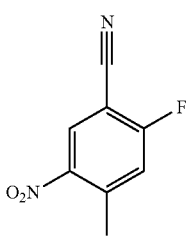

A solution of 2-fluoro-4-methylbenzonitrile (5.50 g, 40.70 mmol) in $H_2SO_4$ (45 mL) was cooled down at 0° C. $KNO_3$ (8.23 g, 81.40 mmol) was then added portionwise. After stirring at 0° C. for 2 h, the reaction mixture was poured into a stirred solution of $NaHCO_3$ (103.00 g, 1.22 mol) in 1 L of ice water. The heterogeneous mixture was filtered on a glass frit. The precipitate was washed twice with water and collected. The solid was dried in vacuo at 50° C. for 12 h to give 6.68 g of intermediate 43 (91% yield, white solid).

Preparation of Intermediate 44:

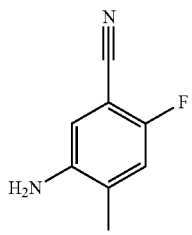

A solution of intermediate 43 (2.00 g, 11.10 mmol) in Me-THF (20 mL) and EtOH (20 mL) was hydrogenated at rt under 1 bar of $H_2$ in presence of a catalytic amount of Pd/C (10 wt. %, 591.00 mg, 0.55 mmol) for 2 h. The reaction mixture was filtered through a pad of Celite® and the filtrate was evaporated under vacuum. The residue was solubilized in Me-THF (20 mL) and EtOH (20 mL) was hydrogenated at rt under 1 bar of $H_2$ in presence of a catalytic amount of Pd/C (10 wt. %, 591.00 mg, 0.55 mmol) for 2 h. The reaction mixture was filtered through a pad of celite and the filtrate was evaporated under vacuum to give a black solid. The residue was purified by column chromatography on silica gel (irregular SiOH, 15-40 µm, 80 g, liquid loading, mobile phase: heptane/EtOAc, gradient: from heptane 80%, EtOAc 20% to heptane 60%, EtOAc 40%). The desired fraction were collected and evaporated to dryness to give 610 mg of intermediate 44 (37% yield, pale yellow solid).

Example A23

Preparation of Intermediate 65.

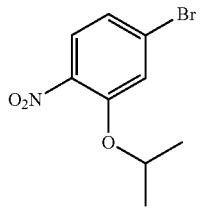

A mixture of 4-bromo-2-fluoro-1-nitrobenzene (3.00 g, 13.60 mmol) and $Cs_2CO_3$ (13.50 g, 41.40 mmol) in iPrOH (30 mL) was stirred and refluxed for 2 h. The mixture was cooled down to rt and filtered on a pad of Celite®. The cake was washed with iPrOH and the filtrate was evaporated in vacuo. The residue was taken-up in EtOAc and water. The layers were separated and the aqueous organic layer was washed with water, dried over $MgSO_4$, filtered off and evaporated in vacuo to give an orange liquid. The residue (3.6 g) was purified by column chromatography on silica gel (irregular SiOH, 15-40 µm, 120 g, dry loading on Celite®, mobile phase: heptane/DCM, gradient: from 80% heptane, 20% DCM to 50% heptane, 50% DCM). The desired fraction were collected and evaporated to dryness to give 3.12 g of intermediate 65 (88% yield, yellow liquid (which crystalized on standing)).

Preparation of Intermediate 67:

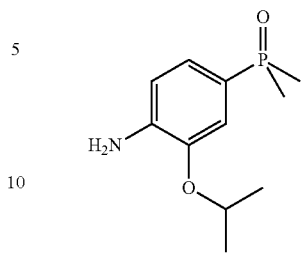

Pd/C (10 wt. %, 310.00 mg, 0.29 mmol) was added to a solution of intermediate 66 (750.00 mg, 2.92 mmol) in EtOH (30 ml) under $N_2$. The mixture was stirred at rt under $H_2$ atmosphere (P atm) for 3 h. The mixture was filtered on a pad of Celite® and the cake was washed with EtOH. The filtrate was evaporated in vacuo to give 630 mg of intermediate 67 (89% yield, dark green oil).

The intermediate in the Table below was prepared by using an analogous method as the one used for the preparation of intermediate 67 starting from the respective starting materials.

| Intermediate number | Structure | Mass (mg) | Yield (%) |
|---|---|---|---|
| Intermediate 326 | 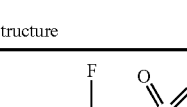 From intermediate 325 | 533 (94% purity based on LC/MS) | 96 |

Example A24

Preparation of Intermediate 72:

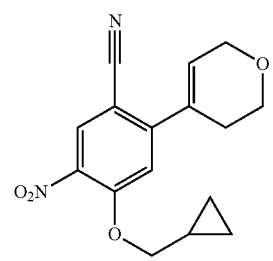 [SMILES: N#Cc1cc([N+](=O)[O-])c(OCC2CC2)cc1C1=CCOCC1]

A mixture of intermediate 71 (2.35 g, 9.30 mmol), 3,6-dihydro-2H-pyran-4-boronic acid pinacol ester (3.00 g, 14.30 mmol) and $K_2CO_3$ (1.64 g, 11.80 mmol) in a mixture of 1,4-dioxane (80 mL) and distilled water (15 mL) was purged with $N_2$. 1,1'-bis(di-tert-butylphosphino)ferrocene palladium dichloride (630.00 mg, 0.97 mmol) was added and the mixture was purged with $N_2$ and stirred at 90° C. for 18 h. The mixture was partitioned between with EtOAc/ water. The organic layer was washed with brine, dried over $MgSO_4$, evaporated and purified by column chromatography on silica gel (irregular SiOH 15-40 µm, 120 g, liquid injection (DCM), mobile phase: DCM/MeOH, gradient from 100:0 to 95:05 in 10 CV) to give 1.86 g of intermediate 72 (66% yield, brown solid).

The intermediates in the Table below were prepared by using an analogous method as the one used for the preparation of intermediate 72 starting from the respective starting materials. The most relevant minor deviations to the referenced method are indicated as additional information in the column 'Mass (mg)'.

| Intermediate number | Structure | Mass (mg) | Yield (%) |
|---|---|---|---|
| Intermediate 200 | From 4-chloro-3-iodoanisole | 660 (70% purity evaluated by LC/MS) light brown oil reaction temperature = 60° C. | 86 |
| Intermediate 208 | From intermediate 207 | 1130 pale brown solid reaction temperature = 60° C. | 99 |

Preparation of Intermediate 73:

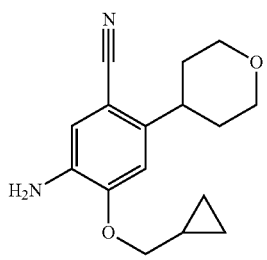

A mixture of intermediate 72 (0.80 g, 2.66 mmol) and Pd/C (10 wt. %, 140.00 mg, 0.13 mmol) in MeOH (25 mL) was stirred at rt under an atmosphere of H₂ for 2 h 15 min. The mixture was filtered over a pad of Celite® and rinsed with MeOH to give 525 mg of intermediate 73 (72% yield, white solid). Then, the Celite® was rinsed again with a mixture of DCM/MeOH (80:20) to give 200 mg of a mixture of intermediates 72 and 73.

The intermediate in the Table below was prepared by using an analogous method as the one used for the preparation of intermediate 73 starting from the respective starting materials.

| Intermediate number | Structure | Mass | Yield (%) |
|---|---|---|---|
| Intermediate 209 | From intermediate 208 | 1 g pale brown oil | 98 |

Example A25

Preparation of Intermediate 83:

To a solution of 3-methoxy-4-nitrobenzoic acid (0.50 g, 2.54 mmol), HATU (1.25 g, 3.30 mmol) and DIEA (1.32 mL, 7.61 mmol) in DCM (10 mL), 4-aminotetrahydropyran (0.26 g, 2.54 mmol) was added and the reaction mixture was stirred at rt for 2 h. The reaction mixture was diluted with DCM, washed with water, dried over Na₂SO₄ and concentrated in vacuo. The residue was triturated in a minimum amount of DCM, the solid formed was recovered by filtration and dried in vacuo to give intermediate 83 (72% yield, pale yellow solid).

The intermediate in the Table below was prepared by using an analogous method as the one used for the preparation of intermediate 83 starting from the respective starting materials.

| Intermediate number | Structure | Mass | Yield (%) |
|---|---|---|---|
| Intermediate 275 | From 3-methyl-4-nitrobenzoic acid | 2.12 g yellow solid | 81 |

Preparation of Intermediate 84:

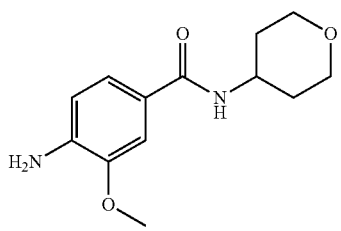 [SMILES: COc1cc(C(=O)NC2CCOCC2)ccc1[N+](=O)[O-]]

A suspension of intermediate 83 (0.51 g, 1.84 mmol), Pd/C (10 wt. %, 0.26 g) and ammonium formate (1.16 g, 18.37 mmol) in EtOH (50 mL) was stirred for 2 h at 80° C. The reaction mixture was filtered through a pad of Celite® and the solution was concentrated in vacuo. The residue was loaded onto an Isolute® SCX-2 cartridge (cation exchange chromatography) which was washed with MeOH and then the product was eluted with 2M ammonia in MeOH. The 2M ammonia in MeOH solution was concentrated in vacuo to give intermediate 84 (96% yield, white solid).

The intermediate in the Table below was prepared by using an analogous method as the one used for the preparation of intermediate 84 starting from the respective starting materials.

| Intermediate number | Structure | Mass | Yield (%) |
|---|---|---|---|
| Intermediate 276 | ![structure] From intermediate 275 | 1.97 g off-white solid | — |

Example A26

Preparation of Intermediate 86:

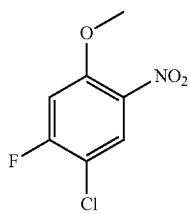

To a solution of 4-chloro-5-fluoro-2-nitrophenol (10.00 g, 52.21 mmol) in dry DMF (50 mL), K₂CO₃ was added (11.00, 79.60 mmol), followed by iodomethane (4.00 mL, 64.25 mmol) and the resulting suspension was stirred at rt for 2.5 days. The resulting dark orange suspension was concentrated in vacuo to remove the DMF solvent, and the residue partitioned between EtOAc (300 mL) and 1N HCl (100 mL). The resulting was separated and the organic layer washed successively with 1M NaOH (100 mL), water (100 mL) and brine (100 mL), dried over Na₂SO₄, filtered and evaporated to give 10.34 g of intermediate 86 (96% yield, dark orange solid).

Preparation of Intermediate 87:

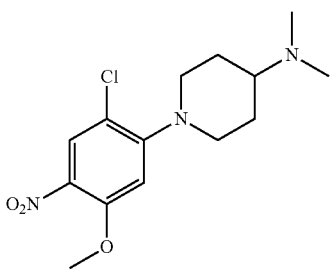

A suspension of intermediate 86 (0.35 g, 1.70 mmol), 4-(dimethylamino)piperidine (0.41 g, 1.87 mmol) and CsCO₃ (1.10 g, 3.41 mmol) in DMF (4 mL) was heated to 80° C. for 15 min. The reaction mixture was partitioned between EtOAc and a saturated solution of NaHCO₃. The organic layer was washed with brine, dried over Na₂SO₄ and concentrated in vacuo to give the 553 mg of intermediate 87 (quant. yield, yellow oil).

The intermediates in the Table below were prepared by using an analogous method as the one used for the preparation of intermediate 87 starting from the respective starting materials.

| Intermediate number | Structure | Mass (mg) | Yield (%) |
|---|---|---|---|
| Intermediate 91 | 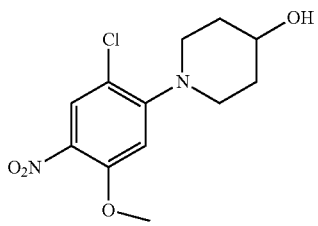 [SMILES: COc1cc(N2CCC(O)CC2)c(Cl)cc1[N+](=O)[O-]]<br>From intermediate 86 | 1630 | 78 |
| Intermediate 108 | 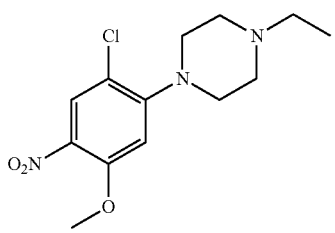 [SMILES: CCN1CCN(c2cc(OC)c([N+](=O)[O-])cc2Cl)CC1]<br>From intermediate 86 | 510<br>yellow oil | Quant. |
| Intermediate 302 | 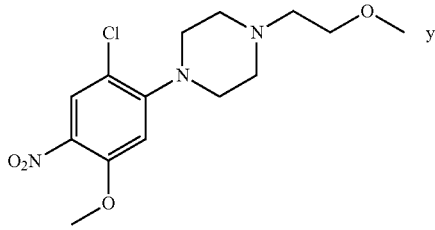<br>From intermediate 86 | 294<br>yellow oil | 92 |
| Intermediate 307 | 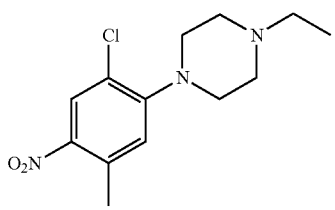<br>From 4-chloro-5-fluoro-2-nitrotoluene | 507<br>(46% purity evaluated by LC/MS)<br>orange-brown solid | 97 |
| Intermediate 310 | 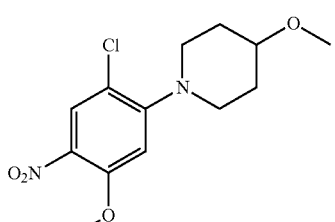<br>From intermediate 86 | 292<br>(46% purity evaluated by LC/MS)<br>yellow oil | Quant. |
| Intermediate 313 | 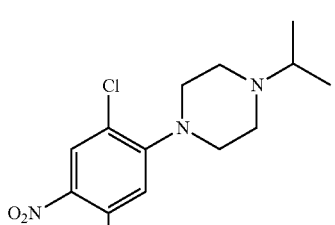<br>From intermediate 86 | 290<br>(52% purity evaluated by LC/MS)<br>yellow oil | 95 |

| Intermediate number | Structure | Mass (mg) | Yield (%) |
|---|---|---|---|
| Intermediate 328 | 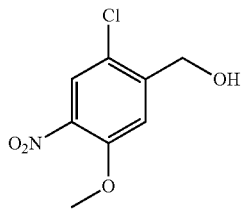 From intermediate 86 | 262 (47% purity evaluated by LC/MS) orange solid | 99 |
| Intermediate 331 | From intermediate 86 | 302 yellow oil | Quant. |

Example A27

Preparation of Intermediate 94:

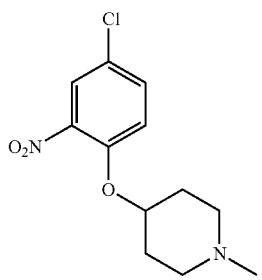 [SMILES: CN1CCC(Oc2ccc(Cl)cc2[N+](=O)[O-])CC1]

A suspension of 3-methoxy-4-nitrobenzoic acid (0.50 g, 2.73 mmol) and NCS (0.41 g, 3.00 mmol) in $CH_3CN$ (5 mL) was heated to 80° C. for 2 h. The reaction mixture was concentrated in vacuo and the residue was purified by column chromatography on silica gel (Si-PPC, 40 g, mobile phase cyclohexane/EtOAc, gradient from 100:0 to 20:80). The desired fraction were collected and evaporated to dryness to give 460 mg of intermediate 94 (77% yield, yellow solid).

Example A28

Preparation of Intermediate 98:

NaH (60% disp. in mineral oil) (0.41 g, 10.19 mmol) was added to a solution of N-methyl-4-piperidinol (1.08 g, 9.34 mmol) in DMF (9 mL) at 0° C. and the mixture was warmed to rt for 15 min. 5-chloro-2-fluoronitrobenzene (1.49 g, 8.49 mmol) was added and the mixture was stirred at rt for a further 2 h. The reaction mixture was partitioned between EtOAc and a saturated solution of $NaHCO_3$. The organic layer was washed with brine, and dried over $Na_2SO_4$ and concentrated in vacuo. The residue was purified by column chromatography on silica gel (Si-PPC, 40 g, mobile phase: DCM/2 M ammonia in MeOH, gradient from 100:0 to 90:10). The desired fraction were collected and evaporated to dryness to give 1.69 g of intermediate 94 (74% yield, yellow oil).

The intermediates in the Table below were prepared by using an analogous method as the one used for the preparation of intermediate 98 starting from the respective starting materials. The most relevant minor deviations to the referenced method are indicated as additional information in the column 'Structure'.

| Intermediate number | Structure | Mass | Yield (%) |
|---|---|---|---|
| Intermediate 133 | From 2-fluoro-5-nitrobenzotrifluoride | 1.63 g | 57 |

355
-continued

| Intermediate number | Structure | Mass | Yield (%) |
|---|---|---|---|
| Intermediate 137 | 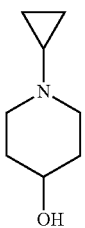 From 4-fluoro-3-nitrobenzotrifluoride | 451 mg | 47 |
| Intermediate 155 | 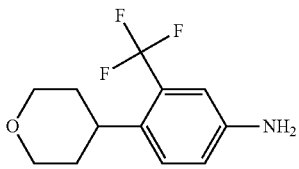 [SMILES: Nc1ccc(C2CCOCC2)c(C(F)(F)F)c1] From 2-fluoro-5-nitrobenzotrifluoride The reaction mixture was stirred at 100° C. overnight after addition of all reagents | 2.4 g | 81 |

Example A29

Preparation of Intermediate 125

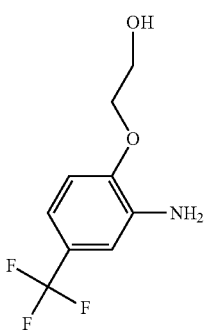 [SMILES: Nc1cc(C(F)(F)F)ccc1OCCO]

Sodium borohydride (0.54 g, 14.36 mmol) was added portion-wise to a solution of N-cyclopropyl-4-piperidinone (1.00 g, 7.18 mmol) in a mixture of DCM (33 mL) and MeOH (3.3 mL) at 0° C. under Ar. The mixture was stirred for 1 h and allowing to warm to rt. The pale yellow mixture was poured into 1M NaOH (20 mL). The layers were separated and the aqueous layer extracted with DCM (2×20 mL). The combined organic layers were passed through a phase separator and solvent evaporated under reduced pressure to obtain 1.25 g of intermediate 125 (yellow oil). The residue was used without further purification for the next step.

Example A30

Preparation of Intermediate 129:

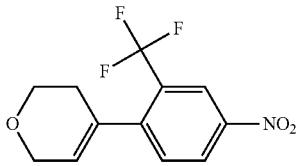

A solution of 2-bromo-5-nitrobenzotrifluoride (1.00 g, 3.704 mmol) and 3,6-dihydro-2H-pyran-4-boronic acid pinacol ester (1.01 g, 4.82 mmol) in a mixture of 1,4-dioxane (15.28 mL) and distilled water (2.59 mL) was treated with $K_2CO_3$ (2.36 g, 11.11 mmol) and purged with $N_2$. Dichloro [1,1'-bis(diphenylphosphino)ferrocene]palladium II, DCM adduct (303.20 mg, 370.36 μmol) was then added and the reaction mixture was purged again with $N_2$ and stirred at 120° C. using one single mode microwave (Biotage Initiator EXP 60) with a power output ranging from 0 to 400 W for 10 minutes [fixed hold time]. Then, water was added. The aqueous layer was extracted twice with DCM, dried over $MgSO_4$, filtered and evaporated. The residue was purified by column chromatography on silica gel (Irregular SiOH, 40 μm, mobile phase DCM, 100% DCM). The pure fractions were combined and the solvent was evaporated to give 900 mg of intermediate 129.

Preparation of Intermediate 130:

A solution of intermediate 129 (690.00 mg, 2.53 mmol) in MeOH (10.23 mL) was hydrogenated at 60° C. with Pd/C (10 wt. %, 71.64 mg, 67.30 μmol) as a catalyst under 8 bars pressure for 24 h. The catalyst was filtered off on a pad of Celite® and the filtrate was evaporated to give 609 mg of intermediate 130.

Example A31

Preparation of Intermediate 138:

A mixture of intermediate 137 (0.67 g, 2.65 mmol) was hydrogenated at rt in EtOAc (15.50 mL) and MeOH (15.60 mL) with Pd/C (10 wt. %, 0.12 g, 0.11 mmol) as a catalyst in a Parr® pressure vessel reactor under 4 bars of $H_2$. After 4 h, the catalyst was filtered off on a pad of Celite®. The solvent was evaporated until dryness to give 535 mg of intermediate 138 (91% yield). This product was used without further purification for the next step.

Example A32

Preparation of Intermediate 147:

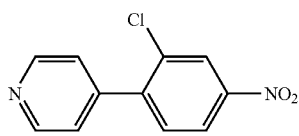

To a solution of 1-bromo-2-chloro-4-nitrobenzene (1.00 g, 4.42 mmol) and pyridine-4-boronic acid, pinacol ester (1.10 g, 5.36 mmol), $K_3PO_4$ (2.70 g, 12.72 mmol), dichloro[1,1'-bis(diphenylphosphino)ferrocene] palladium II, DCM adduct (0.350 g, 0.43 mmol) in a mixture of 1,4-dioxane (15.00 mL) and distilled water (2.50 mL) was purged again with $N_2$. The reaction mixture was stirred at 110° C. using one single mode microwave (Biotage Initiator EXP 60) with a power output ranging from 0 to 400 W for 10 min [fixed hold time]. This procedure was made with three batches of 1 g of 1-bromo-2-chloro-4-nitrobenzene. The three reactions were combined and water was added. The aqueous layer was extracted twice with DCM, dried over $MgSO_4$, filtered and evaporated to give. The residue (4.40 g) was purified by column chromatography on silica gel (Irregular SiOH, 40 µm, mobile phase: heptane/EtOAc, gradient from 60:40 to 50:50). The pure fractions were combined and the solvent was evaporated to afford 1.97 g of intermediate 147 (66% yield) used as it for the next step.

Preparation of Intermediate 148:

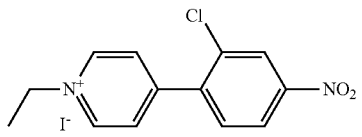 [SMILES: CC[n+]1ccc(-c2ccc([N+](=O)[O-])cc2Cl)cc1 ; [I-]]

Iodoethane (2.80 mL, 35.01 mmol) was added to a mixture of intermediate 147 (1.95 g, 8.31 mmol) in toluene (20 mL). This reaction was stirred in a sealed tube at reflux (115° C.) for 7 h. This reaction was cooled down to rt. Iodoethane (1.50 mL, 18.75 mmol) was added again and the mixture was stirred for further 5 h at reflux (120° C.). The solvent was concentrated to dryness to give 2.89 g of intermediate 148 (89% yield) used as it for the next step.

Preparation of Intermediate 149:

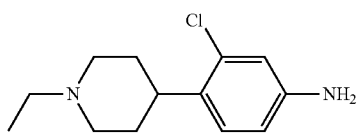 [SMILES: CCN1CCC(c2ccc(N)cc2Cl)CC1]

A mixture of intermediate 148 (1.00 g, 2.56 mmol) was hydrogenated at rt in EtOH (35 mL) with platinum (IV) oxide (300 mg, 1.30 mmol) as a catalyst at 3 bars. After overnight, the catalyst was filtered off on a pad of Celite® and the solvent was concentrated until dryness. This residue was purified by column chromatography on silica gel (Irregular SiOH, 40 µm, 40 g, mobile phase: $NH_4OH$/DCM/MeOH, gradient form: 0.5% $NH_4OH$, 95% DCM, 5% MeOH to 1% $NH_4OH$, 90% DCM, 10% MeOH). The pure fractions were collected and the solvent was concentrated until dryness to give 0.690 g of intermediate 149 (98% yield, purity=84% determined by LC/MS) used as it for the next step.

Example A33

Preparation of Intermediate 152:

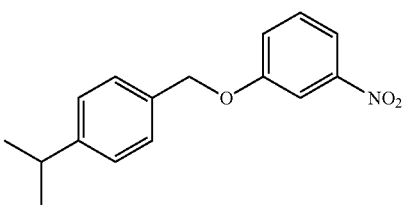 [SMILES: CC(C)c1ccc(COc2cccc([N+](=O)[O-])c2)cc1]

A mixture of 4-isopropylbenzyl bromide (4.18 g, 19.61 mmol), 3-nitrophenol (3.00 g, 21.57 mmol), $K_2CO_3$ (4.06 g, 29.41 mmol) in DMF was heated at 100° C. After completion, water and EtOAc were added. The organic layer was washed with water, decanted, dried over $MgSO_4$, filtered and evaporated to dryness. The residue was recrystallized with DiPE to give 2.87 g of intermediate 152 (54% yield). M. P.=88° C. (K).

Preparation of Intermediate 153.

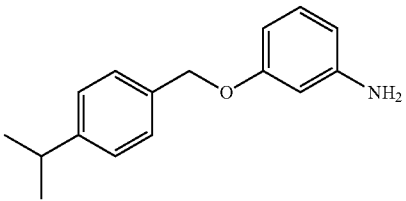 [SMILES: CC(C)c1ccc(COc2cccc(N)c2)cc1]

To a solution of intermediate 152 (2.80 g, 10.32 mmol) in a mixture of 1,4 dioxane (20 mL) and water (5 mL), Iron powder (5.80 g, 103.20 mmol) and iron(II) sulfate heptahydrate (6.30 g, 41.28 mmol) were added. The resulting solution was heated to reflux for overnight. The reaction mixture was filtered off on a pad of Celite® and washed with DCM. The organic layer was washed with water and $K_2CO_3$, dried over $MgSO_4$, filtered and evaporated to give 2.35 g of intermediate 153 (94% yield).

Example A34

Preparation of Intermediate 158:

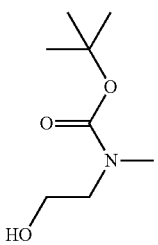

TEA (3.52 mL, 25.00 mmol) was added to a solution of Boc₂O (3.00 g, 13.77 mmol) and 2-(methylamino)ethanol (1.00 mL, 12.52 mmol) in DCM (80 ml) and stirred at rt overnight. The mixture was washed with brine, dried on MgSO₄, filtrated and concentrated to afford 2.40 g of intermediate 158 (colorless oil).

Example A36

Preparation of Intermediate 175.

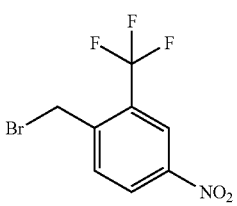 [SMILES: O=[N+]([O-])c1ccc(CBr)c(C(F)(F)F)c1]

To a suspension of 2-methyl-5-nitrobenzotrifluoride (14.00 g, 68.25 mmol) in AcOH (58.60 mL, 1.02 mol), NBS (12.75 g, 71.66 mmol) and benzoyl peroxide (1.65 g, 6.83 mmol) was added. The reaction mixture was heated at reflux overnight (120° C.). Upon cooling, the solvent was removed in vacuo, EtOAc and aqueous NaHCO₃ were added, and the layers were separated. The organic layer was dried over MgSO₄, filtered, and concentrated to afford 18 g of intermediate 175 (93% yield). It was used for the next step without further purification.

Preparation of Intermediate 176 (CIS):

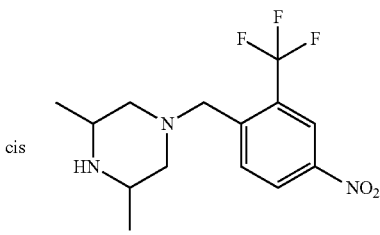 [SMILES: CC1CN(Cc2ccc([N+](=O)[O-])cc2C(F)(F)F)CC(C)N1]

Cis-2,6-dimethylpiperazine (1.00 g, 8.49 mmol) were added to a stirred solution of intermediate 175 (3.62 g, 12.74 mmol) and TEA (4.72 mL, 33.98 mmol) in DCM (10.88 mL) at rt for 48 h. The reaction mixture was washed with a solution of 10% K₂CO₃. The organic layer was dried over MgSO₄, filtered and evaporated. The residue was purified by column chromatography on silica gel (irregular SiOH, 15-40 μm, 80 g, mobile phase: DCM/MeOH/NH₄OH, gradient from DCM: 100% to DCM: 98%, MeOH: 2%, NH₄OH: 0.1%) to give 1.82 g of intermediate 176 (68% yield).

Preparation of Intermediate 177 (CIS):

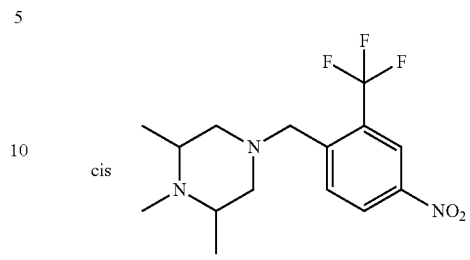

Sodium cyanoborohydride (403.89 mg, 6.43 mmol) was added to a stirred a solution of intermediate 176 (1.70 g, 5.36 mmol) and formaldehyde (37 wt. % in water) (481.96 μL, 6.43 mmol) in a mixture of MeOH (6.39 mL, 157.64 mmol) and AcOH (756.69 μL, 13.22 mmol) at rt under N₂ and stirred at rt for 2 h. Then, the reaction mixture was poured out onto water, made basic with K₂CO₃ powder, extracted with DCM, dried over MgSO₄, filtered and evaporated to give intermediate 177 (96% yield). It was used for the next step without purification.

Preparation of Intermediate 178: (CIS)

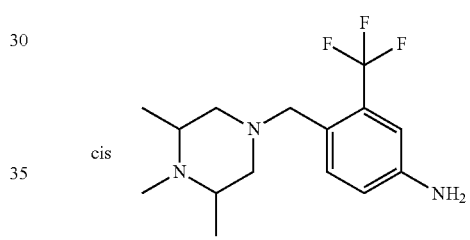

Intermediate 177 (500.00 mg, 1.51 mmol) in MeOH (12.41 mL) was hydrogenated with RaNi (329.95 mg, 5.62 mmol) as a catalyst at rt under 3 bars pressure for 12 h. The catalyst was filtered off on a pad of Celite® and the filtrate was evaporated to give 489 mg of intermediate 178.

Example A37

Preparation of Intermediate 185:

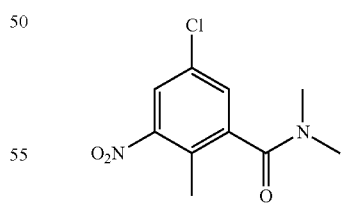

Under N₂ at rt, a solution of dimethylamine in THF (2.0 M, 1.18 mL, 2.37 mmol) was added to a solution of 5-chloro-2-methyl-3-nitrobenzoic acid (340.00 mg, 1.58 mmol), HBTU (598.09 mg, 1.58 mmol) and DIPEA (679.42 μL, 3.94 mmol) in DMF (9.77 mL, 126.16 mmol). The solution was stirred at rt for 6 h. The solution was poured out into cooled water, and extracted with EtOAc. The organic layer was dried over MgSO₄, filtered and evaporated to dryness. The residue (2.07 g) was purified by colonne chromatography on silica gel (SiO$_2$, 40 g, mobile phase: DCM/MeOH/NH$_4$OH, gradient form 100% DCM to 97% DCM, 3% MeOH, 0.3% NH$_4$OH). The pure fractions were collected and the solvent was evaporated until dryness to give 315 mg of intermediate 185 (82% yield).

The intermediates in the Table below were prepared by using an analogous method as the one used for the preparation of intermediate 185 starting from the respective starting materials.

| Intermediate number | Structure | Mass | Yield (%) |
|---|---|---|---|
| Intermediate 189 | ![structure] From (2-amino-4-chlorophenyl) acetic acid | 530 mg | 66 |
| Intermediate 192 | ![structure] From (2-amino-4-chlorophenyl) acetic acid | 950 mg | 85 |
| Intermediate 197 | ![structure] 5-chloro-2-methyl-3-nitrobenzoic acid | 444 mg | 80 |

Example A38

Preparation of Intermediate 201:

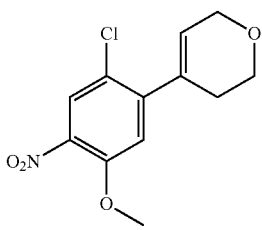 [SMILES: COc1cc(C2=CCOCC2)c(Cl)cc1[N+](=O)[O-]]

A mixture of intermediate 200 (68.00 mg, 0.21 mmol) and sodium nitrate (18.00 mg; 0.21 mmol) in TFA (0.70 mL) was stirred at rt for 6 h. The mixture was poured in a mixture of ice and aqueous NaHCO$_3$, extracted with EtOAc, washed with brine, dried over MgSO$_4$ and evaporated. The residue (60 g, black oil) was purified by column chromatography on silica gel (irregular SiOH, 15-40 µm, 12 g, liquid injection (DCM), mobile phase: DCM/MeOH, gradient from: 100:0 to 95:05 in 10 CV) to give 40 mg of a residue as a light yellow oil 2 containing intermediate 201 (66% purity). Further purification by achiral SFC (Stationary phase: CYANO 6 µm 150×21.2 mm, mobile phase: 95% CO$_2$, 5% MeOH) was achieved to give 17 mg of intermediate 201 (30% yield, white solid).

Preparation of Intermediate 202:

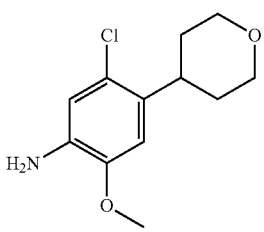

A mixture of intermediate 201 (650.00 mg, 2.41 mmol) and platinum (IV) oxide (130.00 mg, 0.57 mmol) in a mixture of MeOH (20 mL) and THF (5 mL) was stirred at rt under an atmosphere of H$_2$ for 20 min (purged with H$_2$, 3 times (total time reaction: 1 h)). The mixture was filtered over a pad of Celite®. The organic layer was evaporated and purified by column chromatography on silica gel (irregular SiOH, 15-40 µm, 80 g, liquid injection (DCM), mobile phase: heptane/EtOAc, gradient from 100:0 to 0:100 in 10 CV). The pure fractions were collected and the solvent was evaporated until dryness to give 174 mg of intermediate 202 (30% yield, white solid).

Example A39

Preparation of Intermediate 207:

NaH (60% dispersion in mineral oil) (182.00 mg, 4.55 mmol) was added slowly at 0° C. to 2-methoxyethanol (0.36 mL, 4.55 mmol) in THF (20 mL). The mixture was stirred under N$_2$ at 0° C. for 30 min. 4-bromo-2-fluoronitrobenzene (1.00 g, 4.55 mmol) was added and the mixture was stirred and heated slowly to rt for 5 h. The mixture was neutralized with HCl 1N (pH=7) then extracted with a mixture of EtOAc/NaHCO$_3$. The organic layer was washed with brine, dried over MgSO$_4$, evaporated and purified by column chromatography on silica gel (irregular SiOH, 15-40 µm, 80 g, liquid injection (DCM), mobile phase; heptane/EtOAc, gradient from 100:0 to 50:50 in 10 CV) to give 1.13 g of intermediate 207 (90% yield, white solid).

Example A40

Preparation of Intermediate 214:

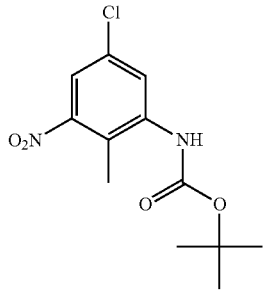

5-chloro-2-methyl-3-nitrobenzoic acid (3.00 g, 13.91 mmol), diphenylphosphoryl azide (4.49 mL, 20.87 mmol) and TEA (2.71 mL, 19.48 mmol) in a mixture of Me-THF (3.75 mL, 37.44 mmol) and 2-methyl-2-propanol (3.91 mL, 41.74 mmol) were refluxed at 3 h. The mixture was poured into NH₄Cl and the organic layer was extracted twice with EtOAc, dried over MgSO₄ and the solvent was evaporated until dryness. The residue (5.08 g) was taken up into EtOAc and a precipitate was appeared and was filtered (impurities). The filtrate was evaporated until dryness. The residue (4.77 g) was taken up in CH₃CN, and a precipitate was appeared and was filtered. The filtrate was evaporated until dryness and purified by column chromatography on silica gel (Irregular SiOH and Si 60 15-40 µm, 40 µm, 80 g, solid deposit, mobile phase: Heptane/EtOAc, 80:20). The pure fractions were combined and the solvent was evaporated to give 3.42 g of intermediate 214 (86% yield).

Preparation of Intermediate 215:

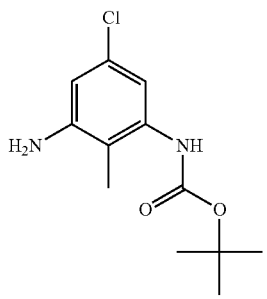 [SMILES: Cc1c(NC(=O)OC(C)(C)C)cc(Cl)cc1[N+](=O)[O-]]

To a stirred solution of intermediate 214 (200.00 mg, 0.70 mmol) in AcOH (8 mL), iron (389.56 mg, 6.98 mmol) was added and stirred at 70° C. for 2 h. The crude mixture was diluted with EtOAc, filtered over Celite®, and the cake was washed with EtOAc. Water was added to the filtrate then K₂CO₃ powder until basic pH. The organic layer was washed with brine, dried over MgSO₄, filtered and evaporated. The residue (180 mg) was purified by column chromatography on silica gel (Irregular SiOH, 40 µm, 24 g, mobile phase: heptane/EtOAc, 60:40).

The pure fractions were combined and the solvent was evaporated to give 95 mg of intermediate 215 (53% yield).

Preparation of Intermediate 216:

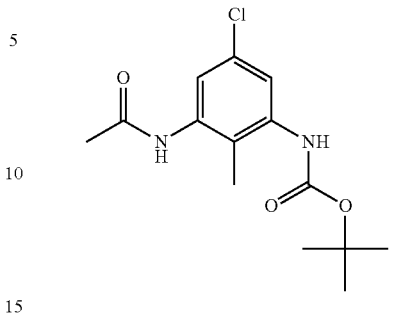

Intermediate 215 (1.00 g, 3.89 mmol), acetyl chloride (0.35 mL, 4.87 mmol) and TEA (3.25 mL, 23.37 mmol) in DCM (50 mL) were added at 0° C. stirred at rt overnight. The mixture was poured into NH₄Cl and the organic layer was extracted with DCM, washed with NaCl, and dried. The precipitate was filtered to give 483 mg of intermediate 216 (42% yield). The filtrate was evaporated until dryness and the residue (750 mg) was purified by column chromatography on silica gel (Irregular SiOH, 40 g, mobile phase: DCM/MeOH, gradient from 100:0 to 98:2). The pure fractions were combined and the solvent was evaporated to give 236 mg of intermediate 216 (20% yield). The two batches was gathered to give 719 mg of intermediate 216 (62% yield).

Preparation of Intermediate 217:

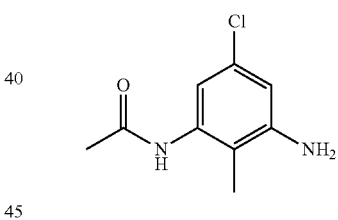

At 0° C., a solution of HCl 4M in dioxane (2.76 mL, 11.04 mmol) was added to a stirred solution of intermediate 216 (660.00 mg, 2.21 mmol) in CH₃CN (49.5 mL). The mixture was stirred at 0° C. for 30 min and at rt for 1 h. The mixture was poured into cooled water and basified with NH₄OH. The organic layer was extracted twice with EtOAc, washed with brine, dried over MgSO₄, filtered and evaporated until dryness. The residue was taken up in DCM, washed with brine, evaporated and purified by column chromatography on silica gel (Irregular SiOH, 24 g, solid deposit, mobile phase: heptane/MeOH/EtOAc/NH₄OH, 60:38:2:0.1). The pure fraction were combined and the solvent was evaporated to give 210 mg of intermediate 217 (48% yield).

The intermediate in the Table below was prepared by using an analogous method as the one used for the preparation of intermediate 217 starting from the respective starting materials.

| Intermediate number | Structure | Mass | Yield (%) |
|---|---|---|---|
| Intermediate 235 | 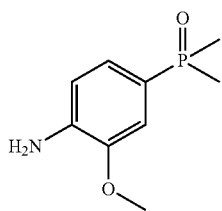  From intermediate 234 | 251 mg | Quant. |

Example A41

Preparation of Intermediate 221

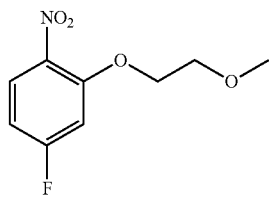

A mixture of intermediate 220 (334.00 mg, 1.46 mmol), zinc (953.00 mg, 14.60 mmol) and AcOH (0.83 mL, 14.60 mmol) in MeOH (8 mL) was stirred at rt for 2 h. The mixture was filtered on a pad of Celite® then an extraction was performed with EtOAc and HCl 1N. The aqueous layer was basified with NaOH 1N and extracted with EtOAc (10 times). The organic layers were washed with brine, dried with MgSO$_4$ and evaporated to give 226 mg of intermediate 221 (78% yield, brown oil).

The intermediate in the Table below was prepared by using an analogous method starting from the respective starting materials

| Intermediate number | Structure | Mass | Yield (%) |
|---|---|---|---|
| Intermediate 231 | From intermediate 230 | 496 mg pale brown oil | 97 |

Example A42

Preparation of Intermediate 234:

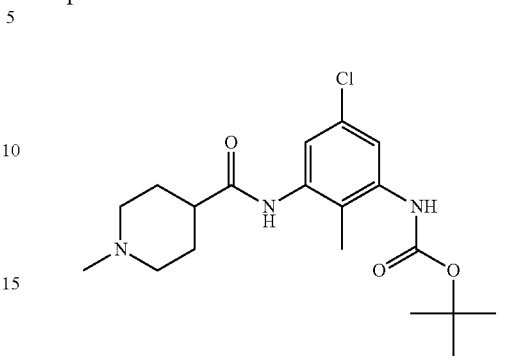

A solution of HATU (2.02 g, 5.32 mmol), DIPEA (1.85 mL, 10.63 mmol) and ethyl 1-methyl-4-piperidine carboxylate, HCl salt (827.80 mg, 4.61 mmol) in Me-THF (9.10 mL, 90.86 mmol) were stirred at 70° C. for 2 h. Then, intermediate 215 (910.00 mg, 3.54 mmol) was added and the mixture was stirred at 70° C. overnight. The mixture was poured out onto water and the organic layer was extracted twice with DCM, dried over MgSO$_4$, filtered and evaporated until dryness. The residue (776 mg) was taken up in MeOH and DCM, triturated and filtered. The precipitate was dried until dryness to give 315 mg of intermediate 234 (23% yield).

Example A43

Preparation of Intermediate 238:

DIAD (3.00 mL, 15.28 mmol) was added dropwise at 5° C. to a mixture of 5-fluoro-2-nitrophenol (1.60 g, 10.18 mmol), 2-methoxyethanol (807.00 µL, 10.18 mmol) and PPh$_3$ (1.4 mmol/g on polystyrene) (10.90 g, 15.28 mmol) in THF (30 mL). The mixture was stirred at rt for 2 h. Water was added and the reaction mixture was extracted with DCM. The organic layer was decanted, dried over MgSO$_4$, filtered and evaporated to dryness. The residue was purified by column chromatography on silica gel (irregular SiOH, 40 g, mobile phase: heptane/EtOAc, gradient from 80:20 to 60:40). The fractions were collected and evaporated to dryness to give 954 mg of intermediate 238 (43% yield).

Example A44

Preparation of Intermediate 244:

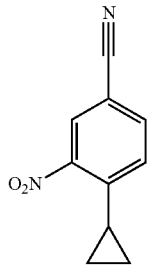

Di(1-adamantyl)-N-butylphosphine (157.00 mg, 0.44 mmol) and Pd(OAc)$_2$ (98.00 mg, 0.44 mmol) were added to a degassed N$_2$ solution of 4-chloro-3-nitrobenzonitrile (800.00 mg, 4.38 mmol), potassiumcyclopropyltrifluoroborate (972.00 mg, 6.57 mmol) and CsCO$_3$ (2.85 g, 8.76 mmol) in a mixture of 1,4-dioxane (18 mL) and distilled water (4 mL). The reaction mixture was stirred and heated at 100° C. for 18 h. Then, it was cooled to rt, diluted with DCM and poured onto water. The organic layer was decanted, dried over MgSO$^4$, filtered over Celite® and evaporated to dryness. The residue was purified by column chromatography on silica gel (irregular SiOH, 24 g, mobile phase: DCM/MeOH, gradient from 100:0 to 98:2). The pure fractions were collected and evaporated to dryness to give 546 mg of intermediate 244 (66% yield).

Example A45

Preparation of Intermediate 249:

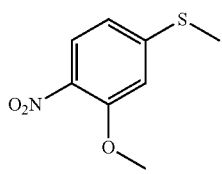

To a solution of 4-fluoro-2-methoxy-1-nitrobenzene (2.00 g, 11.70 mmol) in MeOH (38 mL), a solution of sodium thiomethoxide (1.50 g, 21.00 mmol) was added dropwise in distilled water (6.5 ml) and MeOH (38 mL) and the resulting mixture was stirred at reflux under N$_2$ overnight. The mixture was cooled to rt and concentrated in vacuo. The residue was triturated in a mixture of DCM and MeOH (1:1) and the solid was filtered off. The filtrate was purified by column chromatography on silica gel (15-40 μm, 240 g, mobile phase: heptane/EtOAc, gradient from 100:0 to 50:50). The pure fractions were mixed and the solvent was evaporated to give 2.11 g of intermediate 249 (91% yield).

The intermediates in the Table below were prepared by using an analogous method as the one used for the preparation of intermediate 249 starting from the respective starting materials. The most relevant minor deviations to the referenced method are indicated as additional information in the column 'Mass (mg)'.

| Intermediate number | Structure | Mass (mg) | Yield (%) |
|---|---|---|---|
| Intermediate 289 | 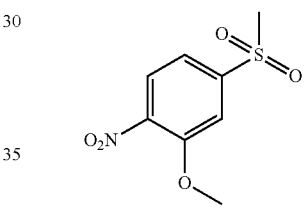 From intermediate 86 | 1194 (Procedure with EtOH and distilled water) yellow solid | Quant. |
| Intermediate 324 | ![F-substituted structure] From 3,4-difluoro-6-nitroanisole | 195 (Procedure with EtOH and distilled water) | 8 |

Preparation of Intermediate 250:

A solution of intermediate 249 (2.11 g, 10.60 mmol) in DCM (106 ml) under an Ar atmosphere was treated with mCPBA (5.49 g, 31.80 mmol) and stirred at rt for 24 h. The mixture was filtered off. The filtrate was concentrated and purified by column chromatography on silica gel (SiO2, dry loading, mobile phase: heptane/EtOAc, gradient from 1:0 to 0:1). The pure fractions were combined and concentrated to dryness to afford 1.65 g of intermediate 250 (67% yield, pale yellow crystalline solid).

The intermediates in the Table below were prepared by using an analogous method as the one used for the preparation of intermediate 250 starting from the respective starting materials.

| Intermediate number | Structure | Mass (mg) | Yield (%) |
|---|---|---|---|
| Intermediate 290 | From intermediate 289 | 864 pale yellow crystaline solid | 65 |

| Intermediate number | Structure | Mass (mg) | Yield (%) |
|---|---|---|---|
| Intermediate 325 | 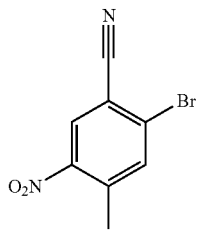　From intermediate 324 | 629 white solid | 62 |

Example A46

Preparation of Intermediate 257:

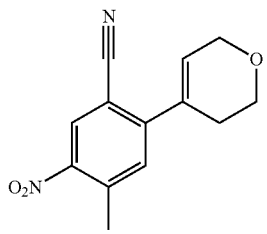 [SMILES: Cc1cc(C2=CCOCC2)c(C#N)cc1[N+](=O)[O-]]

To a solution of 2-bromo-4-methylbenzonitrile (2.00 g, 10.20 mmol) in H₂SO₄ (7 mL) at 0° C., a solution of KNO₃ in H₂SO₄ (5 mL) was added (1.03 g, 10.20 mmol). After stirring at 0° C. for 1.5 h, the reaction mixture was poured into 500 mL of ice water. The precipitate was collected by filtration and washed with copious amounts of water. The precipitate was dried to provide 2.01 g of intermediate 257 (82% yield, white powder).

Preparation of Intermediate 258:

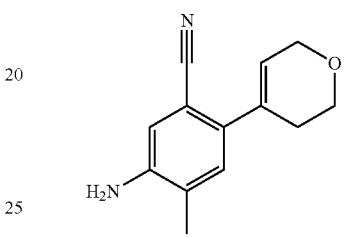

In a sealed tube, a solution of intermediate 257 (1.00 g, 4.15 mmol), 3,6-dihydro-2H-pyran-4-boronic acid pinacol ester (1.05 g, 4.98 mmol) and K₃PO₄ (1.76 g, 8.30 mmol) in a mixture of 1,4-dioxane (29 mL) and distilled water (3.86 mL) was degassed under N2. [1,1'-bis(diphenylphosphino)ferrocene]dichloropalladium(II), complex with dichloromethane (340.00 mg, 0.41 mmol) was added and the reaction mixture was degassed again under N2 and heated at 80° C. for 5 h. The reaction mixture was cooled to rt, poured onto water and extracted with DCM. The organic layer was decanted, dried over MgSO₄, filtered and evaporated to dryness. The residue (2 g, black oil) was purified by column chromatography on silica gel (irregular SiOH, 80 g, mobile phase: heptane/EtOAc, gradient from 100:0 to 75:25). The pure fractions were collected and evaporated to dryness to give 0.787 g of intermediate 258 (78% yield, white powder).

Preparation of Intermediate 259:

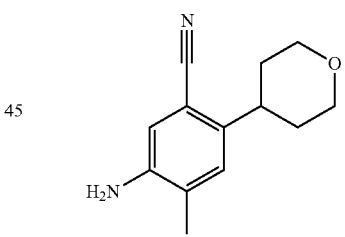

A mixture of intermediate 258 (0.79 g, 3.22 mmol) and Pd/C (10 wt. %, 72.00 mg, 0.067 mmol) in EtOAc (10 mL) was stirred at rt under an atmosphere of H₂ overnight. The mixture was filtered over a pad of Celite® and evaporated to dryness to give intermediate 259 (white solid). This residue was used as such in the next reaction step.

Preparation of Intermediate 260:

A mixture of intermediate 259 (0.70 g, 3.27 mmol) and Pd/C (10 wt. %, 174.00 mg, 0.16 mmol) in EtOH (11.5 mL) was stirred at rt under an atmosphere of H₂ overnight. The mixture was filtered over a pad of Celite®. The organic layer was evaporated to give 512 mg of intermediate 260 (72% yield, 90% purity based on LC/MS, white solid).

The intermediates in the Table below were prepared by using an analogous method as the one used for the preparation of intermediate 259 starting from the respective starting materials. The most relevant minor deviations from the original procedure are indicated in the column "Mass"

| Intermediate number | Structure | Mass (mg) | Yield (%) |
|---|---|---|---|
| Intermediate 583 | 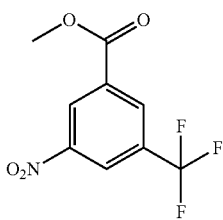 [SMILES: COC(=O)c1cc([N+](=O)[O-])cc(C(F)(F)F)c1]<br>From intermediate 582 | 225 | 93 |
| Intermediate 626 | 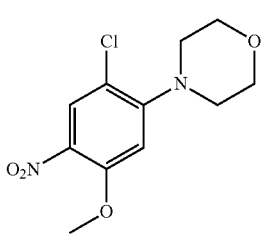 [SMILES: COc1cc(N2CCOCC2)c(Cl)cc1[N+](=O)[O-]]<br>From intermediate 625 | 500<br>Procedure with EtOAc as solvent | 78 |

Example A47

Preparation of Intermediate 267:

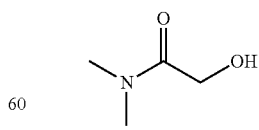

AcCl (19.5 mL) was added dropwise to a solution of 3-nitro-5-(trifluoromethyl)benzoic acid (19.50 g, 83.00 mmol) in MeOH (195 mL) at rt and stirred 18 h. The resulting mixture was concentrated under vacuum, washed with a solution of 10% of $K_2CO_3$, extracted twice with DCM, dried over $MgSO_4$, filtrated and concentrated under vacuum to give 19 g of intermediate 267 (92% yield).

Example A48

Preparation of Intermediate 278:

A mixture of 1-bromo-2-chloro-5-methoxy-4-nitrobenzene (1.00 g, 3.75 mmol), morpholine (395.00 μL, 4.12 mmol), $K_2CO_3$ (1.04 g, 7.51 mmol) in DMF (10 mL) was stirred and heated at 80° C. for 18 h. Further morpholine (35.00 μL, 0.40 mmol) was added and the reaction mixture was stirred and heated at 80° C. for a further 23 h. The reaction mixture was added to ice/water and stirred to give a yellow precipitate. It was filtered off, washed with water and $EtO_2$, dried over $MgSO_4$ and concentrated in vacuo to give a yellow solid. The filtrate was further extracted with EtOAc (twice) and the combined organics were washed successively with water, and saturated brine, dried over anhydrous $Na_2SO_4$. Solvent was removed in vacuo to give a brown solid (100 mg) which was combined with the precipitate and purified by column chromatography on silica gel (80 g silica cartridge, mobile phase: cyclohexane/EtOAc containing 0-40% EtOAc) to give 703 mg of intermediate 278 (69% yield, yellow solid).

Example A49

Preparation of Intermediate 283.

Ethyl glycolate (0.91 mL, 9.61 mmol) was dissolved in dimethylamine (40% in water) (10 mL) and the resulting mixture was stirred at rt for 18 h. The reaction was evaporated under reduced pressure. The residue was taken up in EtOH and evaporated under reduced pressure (twice) to give a colorless oil. The residue (950 mg) was purified by column chromatography on silica gel (SiO$_2$, 25 g, mobile phase DCM/MeOH, gradient from 100:0 to 95:5). The fractions containing the product were combined and evaporated under reduced pressure to give 576 mg of intermediate 283 (58% yield, colorless oil).

Preparation of Intermediate 284:

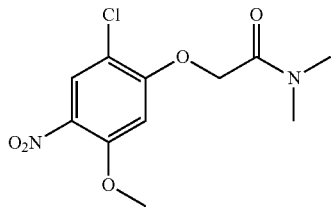

To a solution of intermediate 283 (376.00 mg, 3.65 mmol) in THF (20 mL), NaH (60% dispersed in mineral oil) (145.92 mg, 3.65 mmol) was added portionwise and the resulting mixture was stirred at rt under N$_2$ for 30 min. Intermediate 86 (0.50 g, 2.43 mmol) was added and the resulting mixture was stirred for 1 h. The reaction was quenched with 1M aqueous NH$_4$Cl and extracted with thrice with EtOAc. The organic layer were separated, combined, dried over Na$_2$SO$_4$ and evaporated under reduced pressure. The residue was purified by column chromatography on silica gel (SiO$_2$, 40 g, mobile phase: DCM/MeOH, gradient from 100:0 to 95:5). The fractions containing the product were combined and evaporated under reduced pressure to give 619 mg of intermediate 284 (88% yield, off-white solid).

The intermediate in the Table below was prepared by using an analogous method as the one used for the preparation of intermediate 284 starting from the respective starting materials.

| Intermediate number | Structure | Mass (mg) | Yield (%) |
|---|---|---|---|
| Intermediate 321 | 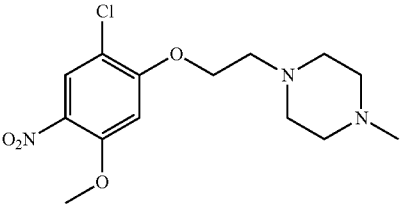<br>From intermediate 86 and 1-(2-hydroxyethyl)-4-methyl piperazine | 344<br>(43% purity based on LC/MS)<br>yellow solid | 72 |

Example A50

Preparation of Intermediate 294:

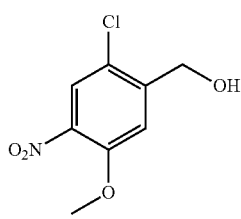

A suspension of 3-methoxy-4-nitro-phenyl-methanol (1.00 g, 5.46 mmol) and NCS (1.14 g, 8.54 mmol) in CH$_3$CN (10 mL) was heated to 80° C. for 2 h. The reaction mixture was concentrated in vacuo and the residue was purified by column chromatography on silica gel (SiO$_2$, mobile phase: cyclohexane/EtOAc, gradient from 1:0 to 1:1). The desired fractions were collected to afford the 1.093 g of intermediate 294 (89% yield, yellow solid).

Preparation of Intermediate 295:

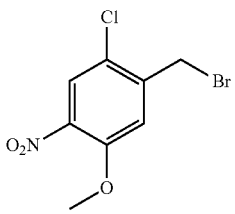

A stirred mixture of intermediate 294 (0.60 g, 2.76 mmol), CBr$_4$ (1.19 g, 3.59 mmol), PPh$_3$ (0.94 g, 3.59 mmol) and THF (5.5 ml) under N$_2$ atmosphere at 0° C. was warmed to rt and stirred for 30 min. The mixture was diluted with water and extracted with DCM. The organic phase was dried over MgSO$_4$, filtered and the filtrate concentrated in vacuo. The residue was purified by column chromatography on silica gel (SiO$_2$, mobile phase: cyclohexane/EtOAc, gradient from 1:0 to 0:1). The desired fractions were collected to afford 714 mg of intermediate 295 (95% yield, off-white solid).

Preparation of Intermediate 296:

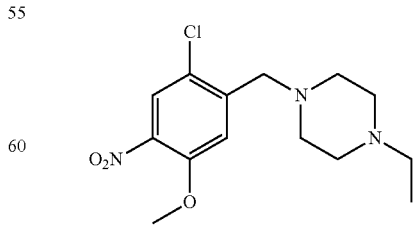

A stirred mixture of intermediate 295 (0.41 g, 1.45 mmol), 1-ethylpiperazine (0.41 ml, 3.20 mmol), K$_2$CO$_3$ (0.44 g, 3.20 mmol) and DMF (6 ml) was heated at 80° C. for 30 min. The mixture was cooled to rt and partitioned between

Example A51

Preparation of Intermediate 299:

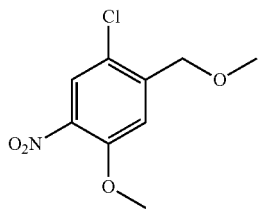

To a stirred suspension of intermediate 294 (100.00 mg, 0.46 mmol) and Cs$_2$CO$_3$ (0.450 g, 1.38 mmol) in a mixture of THF (0.5 mL) and DMF (0.5 mL) under an Ar atmosphere, was added iodomethane (286 µL, 4.60 mmol). The reaction mixture was stirred at rt for 18 h. The reaction mixture was partitioned between EtOAc and water. The aqueous layer was extracted with EtOAc. The combined organic extracts were washed with saturated brine, dried over Na$_2$SO$_4$, and concentrated under vacuum. The residue was purified by column chromatography on silica gel (SiO$_2$, 12 g silica cartridge, mobile phase: cyclohexane/EtOAc, gradient from 100:0 to 70:30). The desired fractions were collected to give 39 mg of intermediate 299 (36% yield, very pale yellow solid).

Example A52

Preparation of Intermediate 316:

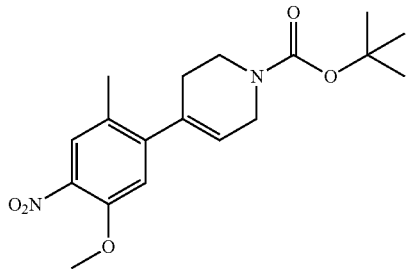 [SMILES: COc1cc(C2=CCN(C(=O)OC(C)(C)C)CC2)c(C)cc1[N+](=O)[O-]]

A solution of 5-bromo-4-methyl-2-nitroanisole (60.00 mg, 0.24 mmol) and N-Boc 1,2,5,6-tetrahydropyridine-4-boronic acid pinacol ester (202.00 mg, 0.65 mmol) in 1,4-dioxane (5 mL) was degassed by bubbling Ar through the stirred solution in a 10 mL screw-top reaction vial for 10 min. Freshly prepared 2M aqueous sodium carbonate (0.50 ml, 1.0 mmol), degassed by bubbling N$_2$ through the stirred solution for 15 min, was added, followed by the catalyst [1,1'-bis(diphenylphosphino)ferrocene]dichloropalladium (II), complex with dichloromethane (20.00 mg, 0.027 mmol). The reaction vial was sealed under Ar and the mixture heated to 100° C. (block temperature) for 16 h. The mixture was cooled to rt and diluted with EtOAc (50 mL) and water (25 mL). The aqueous layer was separated and further extracted with EtOAc (25 mL). The combined organic layers were washed with water (25 mL), brine (10 mL), dried over Na$_2$SO$_4$, filtered through a plug of Celite® and evaporated to give a red gum. This residue was purified by column chromatography on silica gel (SiO$_2$, 4 g, 50 µm cartridge, mobile phase: cyclohexane/EtOAc, 1CV 100% cyclohexane, then linear gradient from 1:0 to 0:1). The desired fractions were combined and evaporated to give 94 mg of intermediate 316 (quant. yield, red glass).

Preparation of Intermediate 317:

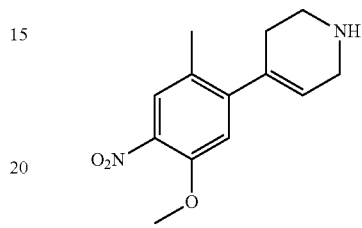

A solution of intermediate 316 (850.00 mg, 2.40 mmol) and TFA (1.90 mL, 24.80 mmol) in DCM (20 mL) was stirred at rt for 6 h. The reaction mixture was directly purified by cation exchange chromatography (50 g Isolute SCX-2 cartridge, mobile phase: DCM/MeOH, gradient from 1:0 (200 mL), 1:1 (100 mL) to 0:1 (50 mL). The receiver flask was exchanged and the product released from the cartridge with a solution of 2M ammonia in MeOH (150 mL). The resulting red product solution was evaporated to dryness to give 566 mg of intermediate 317 (93% yield, red coloured glass).

Preparation of Intermediate 318:

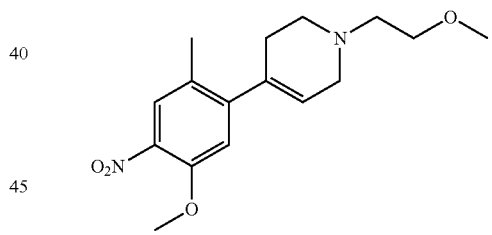

A solution of intermediate 317 (566.00 mg, 2.28 mmol), 2-bromo-1-methoxyethane (520.00 µL, 2.77 mmol) and DIEA (1.20 mL, 7.01 mmol) in DMF (20 mL) was stirred at rt for 18 h. The reaction was not complete, also 260 µL (2.77 mmol) of 2-bromo-1-methoxyethane was added portionwise again and stirring continued for a further 7 h. Then the mixture was stood at rt over the weekend. The reaction mixture was then diluted with DCM (20 mL) and directly purified by cation exchange chromatography (50 g Isolute SCX-2 cartridge, mobile phase: DCM/MeOH, gradient from 1:0 (100 mL), 1:1 (100 mL) to 0:1 (50 mL). The receiver flask was exchanged and the cartridge eluted with a solution of 2M ammonia in MeOH to release the product as a red solution. The solvents were evaporated and the crude product purified by column chromatography on silica gel (SiO$_2$, 12 g, 15 µm SiO2 cartridge, mobile phase: DCM/MeOH, gradient from 100:0 to 95:5). Relevant fractions were combined and evaporated to give 461 mg of intermediate 318 (66% yield, pale yellow gum).

(the residue text at top of page 375:)
water and EtOAc. The organic phase was dried over Na$_2$SO$_4$, filtered and the filtrate concentrated in vacuo.

The residue was purified by column chromatography on silica gel (SiO2, mobile phase: pentane and EtOAc (1:1 to 0:1) followed by DCM and MeOH (1:0 to 9:1)). The desired fractions were collected to afford 421 mg of intermediate 296 (92% yield, yellow oil).

Preparation of Intermediate 319:

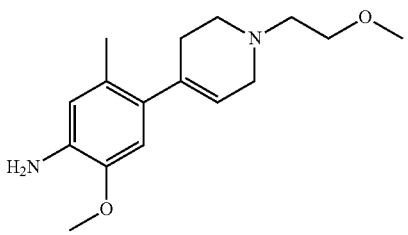 [SMILES: COCCN1CC=C(c2cc(OC)c([N+](=O)[O-])cc2C)CC1]

A suspension of intermediate 318 (461.00 mg, 1.51 mmol), and Pd/C (10 wt. %, 100 mg) in DCM (15 ml) and MeOH (5 mL) was stirred at rt under an $H_2$ atmosphere for 1 h. The reaction mixture was filtered through a pad of Celite® and concentrated in vacuo. The residue was re-suspended in DCM (15 mL) and MeOH (5 mL) with Pd/C (10 wt. %, (100 mg) and stirred under an $H_2$ atmosphere for a further 72 h. The reaction mixture was filtered through a pad of Celite® and concentrated in vacuo to give 420 mg of intermediate 319 (quant. yield, yellow oil).

Example A53

Preparation of Intermediate 334:

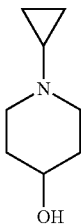

$NaBH_4$ (0.54 g, 14.36 mmol) was added portionwise to a solution of N-cyclopropyl-4-piperidine (1.00 g, 7.18 mmol) in a mixture of DCM (33 mL) and MeOH (3.3 mL) at 0° C. under Ar. The mixture was stirred for 1 h and allowing to warm to rt. The, the pale yellow mixture was poured into 1M NaOH (20 mL) and the phases were separated. The aqueous phase was extracted with dichloromethane (2×20 mL). The combined organic layers were passed through a phase separator and solvent evaporated under reduced pressure to obtain 1.25 g of intermediate 334 (yellow oil). The residue was used as it for the next step.

Example A54

Preparation of Intermediate 348:

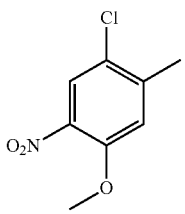

NaH (60% dispersed in mineral oil) (1.28 g, 31.99 mmol) was added portionwise to a solution of 4-chloro-3-methyl-6-nitrophenol (5.00 g, 26.66 mmol) in DMF (60 mL) at 0° C. and the mixture was stirred for 15 min at this temperature. Iodomethane (1.83 mL, 29.33 mmol) was added and the mixture was warmed to rt and stirred for 24 h. The reaction mixture was partitioned between EtOAc and water. The organic layer was washed with brine, dried over $Na_2SO_4$ and concentrated in vacuo. The residue was purified by column chromatography on silica gel (Si-PPC, 80 g, mobile phase: cyclohexane/EtOAc, gradient from 1:0 to 4:1). The desired fraction were collected and concentrated under vacuum to give 4.09 g of intermediate 348 (76% yield, pale yellow solid).

Preparation of Intermediate 349:

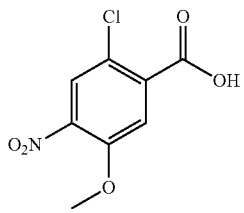

A suspension of intermediate 348 (4.00 g, 19.80 mmol) and $KMnO_4$ (6.27 g, 39.70 mmol) in distilled water (400 mL) was heated at reflux for 24 h. A second portion of $KMnO_4$ (6.27 g, 39.70 mmol) was added and heating was continued for a further 24 h. Then, the reaction mixture was cooled down to 0° C. and acidified to pH 2 with conc. HCl. The aqueous layer was extracted several times with EtOAc. The organic layer was dried over $MgSO_4$ and concentrated under vacuum. The residue was taken up with DCM and the precipitate was filtered to afford 1.81 g of intermediate 349 (23% yield based on a purity of 60% evaluated by $^1H$ NMR). Intermediate 349 was directly engaged in the next step without any further purification.

Preparation of Intermediate 350:

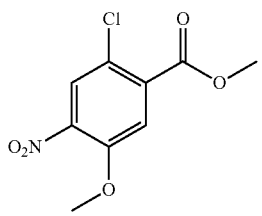 [SMILES: COC(=O)c1cc(OC)c([N+](=O)[O-])cc1Cl]

Intermediate 349 (1.81 g, 4.69 mmol) was dissolved in MeOH (90 mL). Then, conc. $H_2SO_4$ (1.81 mL) was added and the resulting mixture was heated under reflux for 18 h. Then, the reaction mixture was cooled down to rt, mixed with another batch (from 498 mg of intermediate 349) and partitioned between water and EtOAc. The organic layer was separated, dried over $MgSO_4$, filtered and concentrated. The residue was purified by column chromatography on silica gel (irregular $SiO_2$, 80 g, mobile phase: heptane/EtOAc, 80:20). The fractions containing the products were mixed and the solvent was concentrated to afford 830 mg of intermediate 350 (77% yield).

Example A55

Preparation of Intermediate 358:

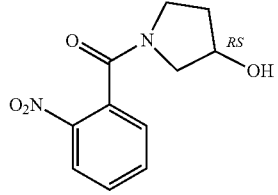 [SMILES: O=C(c1ccccc1[N+](=O)[O-])N1CCC(O)C1]

A mixture of 2-nitrobenzoic acid (1.00 g, 5.98 mmol), 3-pyrrolidinol (727.00 µL, 8.97 mmol), HATU (3.40 g, 8.97 mmol) and TEA (2.50 mL, 17.95 mmol) in a mixture of DCM/THF (40 mL, 1:1, v/v) was stirred at rt for 2 h. The reaction mixture was diluted with DCM and poured onto a 10% aqueous solution of $K_2CO_3$. The organic layer was decanted, dried over $MgSO_4$, filtered and evaporated to dryness. The residue (2.6 g) was purified by column chromatography on silica gel (irregular SiOH, 24 g, mobile phase: $NH_4OH$/MeOH/DCM, gradient from 0% $NH_4OH$, 0% MeOH, 100% DCM to 1% $NH_4OH$, 10% MeOH, 90% DCM). The pure fractions were collected and evaporated to dryness to give 2 g of intermediate 358 used as it is for the next step.

Preparation of Intermediate 359.

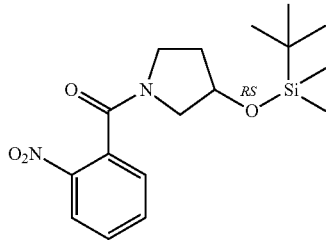 [SMILES: CC(C)(C)[Si](C)(C)OC1CCN(C(=O)c2ccccc2[N+](=O)[O-])C1]

A solution of TBDMS-Cl (1.08 g, 7.18 mmol) in DCM (5 mL) was added to a mixture of intermediate 358 (1.41 g, 5.98 mmol) and imidazole (1.22 g, 17.95 mmol) in Me-THF (25 mL) and the reaction mixture was stirred overnight at rt. The reaction mixture was diluted with DCM and poured onto water. The organic layer was decanted, dried over $MgSO_4$, filtered and evaporated to dryness. The residue was purified by column chromatography on silica gel (irregular SiOH, 40 g, mobile phase: DCM/MeOH, gradient from 100:0 to 97:3). The pure fractions were collected and evaporated to dryness to give 921 mg of intermediate 359 (44% yield). Intermediate 359 was used as it is for the next step.

Example A56

Preparation of Intermediate 37

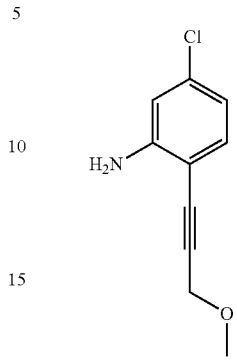

In a round bottom flask, 5-chloro-2-iodoaniline (2.00 g, 7.89 mmol), methyl propargyl ether (1.00 mL, 11.84 mmol) and TEA (1.92 mL, 13.41 mmol) were diluted in DMF. The mixture was degassed ($N_2$ bubbling) and $Pd(PPh_3)_2Cl_2$ (0.28 g, 0.39 mmol) and CuI (0.30 g, 1.58 mmol) were added. The reaction mixture was stirred at rt for 4 h. The reaction mixture was partitioned between water and EtOAc. The organic layer was washed with brine, dried over $MgSO_4$, filtered and concentrated. The crude was purified by column chromatography on silica gel (irregular $SiO_2$, 40 g, mobile phase: heptane/EtOAc, gradient from 90:10 to 80:20). The product fractions were concentrated to afford 1.013 g of intermediate 376 (70% yield, orange liquid which solidify upon standing).

Preparation of Intermediate 377 and intermediate 378:

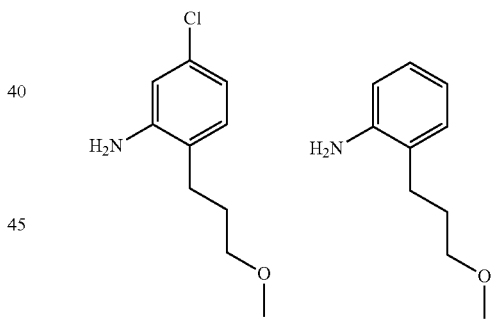

Intermediate 377          Intermediate 378

In a round bottom flask, intermediate 376 (1.01 g, 5.58 mmol) was diluted in MeOH (50.8 mL). Then the solution was degassed with $N_2$ and Pd/C (10 wt. %, 0.50 g, 4.74 mmol) was added. The reaction mixture was then hydrogenated at 1 bar for 4 h. The reaction mixture was filtered over a pad of Celite® and the filtrate was concentrated. Then, the residue was diluted in MeOH (50 mL) and degassed with $N_2$. Pd/C (10 wt. %, 0.50 g, 4.74 mmol) was added and the reaction mixture was then hydrogenated at 1 bar for 4 h. The reaction mixture was filtered over a pad of Celite® and the filtrate was concentrated. The residue was purified by column chromatography on silica gel (irregular SiOH, 80 g, mobile phase: heptane/EtOAc, gradient from 95:5 to 80:20). The fractions containing the product were mixed and concentrated to afford 336 mg of a mixture of intermediates 377 and 378 (21% yield, purity 70:30 based on NMR).

Example A57

Preparation of Intermediate 380:

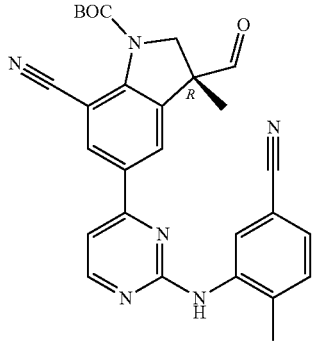

DCM (30 mL) was cooled to −78° C. and oxalyl chloride (4.53 mL, 9.06 mmol) was added followed by dodecylmethyl sulfoxide (2.11 g, 9.06 mmol). After 30 min, a suspension of intermediate 10R (3.00 g, 6.04 mmol) in DCM (30 mL) was added dropwise. The reaction mixture was stirred for 30 min at −78° C., then DIPEA (5.21 mL, 30.21 mmol) was added. The stirring was continued for 3 h at −78° C. and the reaction mixture was allowed to warm to rt and stirred for overnight. A diluted solution of NH₄Cl was added and the aqueous layer was extracted twice with DCM. The combined layers were dried over MgSO₄, filtered and evaporated to dryness. The residue was crystallized from Et₂O and the precipitate was filtered, washed with DiPE and dried to give 2.62 g of intermediate 380 (87% yield).

Preparation of Intermediate 381:

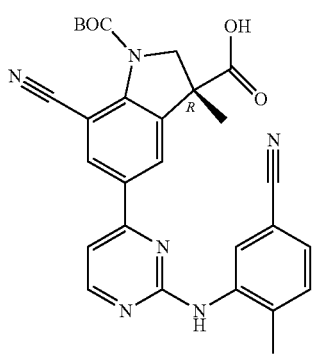

Intermediate 380 (600.00 mg, 1.21 mmol) was dissolved in a mixture of tert-butyl alcohol (44 mL) and 2-methyl-2-butene (22 mL). Then, distilled water (44 mL) was added, followed by sodium dihydrogenophosphate (2.18 g, 18.20 mmol) and NaO₂Cl (2.19 g, 24.26 mmol). The suspension was stirred vigorously at rt overnight. The mixture was poured into NH₄Cl and extracted with EtOAc. The organic layer was dried over MgSO₄, filtered and the solvent was evaporated to give 619 mg of intermediate 381 (100% yield).

Preparation of Intermediate 382:

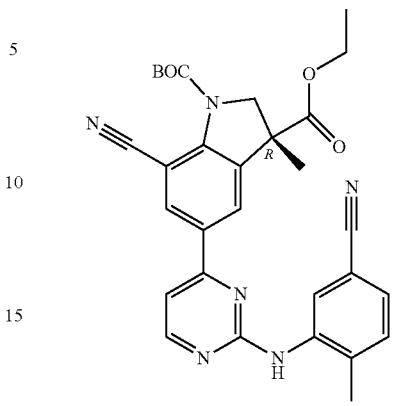

A mixture of EtOH (0.28 mL, 4.85 mmol), intermediate 381 (0.62 g, 1.21 mmol), HATU (0.51 mg, 1.33 mmol), DIPEA (0.52 mL, 3.03 mmol) and DMAP (14.80 mg, 0.12 mmol) in DMF (14.4 mL) was stirred at rt for 24 h. The solution was poured onto water and extracted with EtOAc. The organic layer was washed successively with water and brine, dried over MgSO₄, filtered and evaporated to dryness. The residue was purified by column chromatography on silica gel (15-40 μm, 40 g, mobile phase: DCM/MeOH, gradient from 100:0 to 98:2). The pure fractions were combined and evaporated to dryness to give 239 mg of intermediate 382 (37% yield, 98% purity based on LC/MS).

Preparation of Intermediate 383.

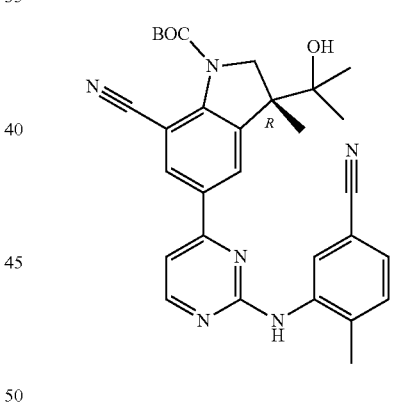

In a round bottom flask, intermediate 382 (0.18 g, 0.34 mmol) was diluted in THF (33 mL). Then, the solution was cooled to 0° C. and methylmagnesium bromide (0.42 mL, 1.36 mmol) was added dropwise. The solution was stirred allowing the temperature to raise rt. Additional methylmagnesium bromide (0.42 mL, 1.36 mmol) was added at rt and the reaction mixture was stirred for an additional 2 h. The mixture was poured into a saturated aqueous solution of NH₄Cl and extracted with EtOAc. The organic layer was washed with brine, dried over MgSO₄, filtered and the solvent was evaporated. The residue was purified by column chromatography on silica gel (15-40 μm, 24 g, mobile phase: DCM/MeOH, gradient from 100:0 to 95:5). The pure fractions were mixed and the solvent was evaporated to give 178 mg of intermediate 383 (100% yield, 90% purity based on LC/MS).

Example A58

Preparation of Intermediate 384:

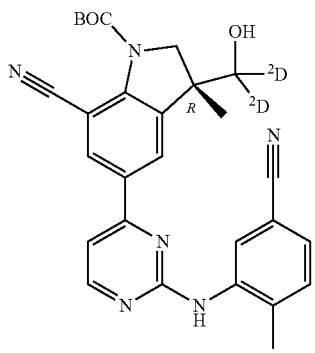

In a round bottom flask, intermediate 382 (164.00 mg, 0.30 mmol) was dissolved in THF (5.2 mL). Then, the reaction mixture was cooled down to 0° C. and lithium aluminium deuteride (34.72 mg, 0.61 mmol) was added. The mixture was stirred for 1 h at 0° C. The reaction mixture was quenched with 10% aqueous NaHCO$_3$ and mixed with another batch (from 87 mg of intermediate 382). Then, the mixture was diluted with EtOAc. The organic layer was washed with brine, dried over MgSO$_4$, filtered and the solvent was evaporated. The residue was purified by column chromatography on silica gel (irregular SiOH, 24 g, mobile phase: DCM/MeOH, gradient from 99:1 to 95:5). The fractions containing the product were mixed and concentrated to afford intermediate 384 (168 mg; 72% based on these two batches).

Example A59

Preparation of Intermediate 385:

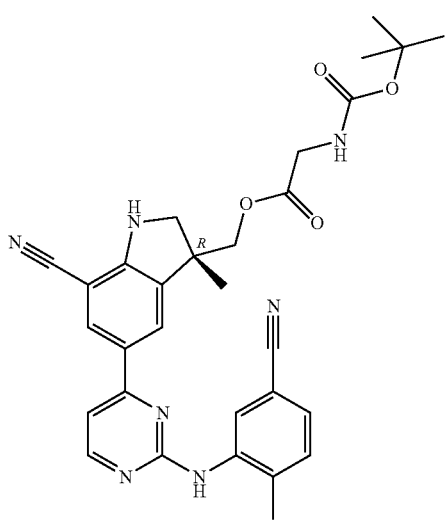

A mixture of compound 1 (4 g; 10.1 mmol), Boc-Glycine (4.4 g; 25.22 mmol), HATU (9.6 g; 25.22 mmol), DIPEA (8.7 mL; 50.45 mmol) and DMAP (67 mg; 0.546 mmol) in DMF (120 mL) was stirred at room temperature for 18 hours. The solution was poured onto ice water. Then, the precipitate was filtered and washed with water. The solid was dissolved in EtOAc. The organic layer was washed with H$_2$O, then brine, dried over MgSO$_4$, filtered and evaporated to dryness. The residue was purified by chromatography over silica gel (irregular SiOH, 120 g; mobile phase: 65% Heptane, 5% MeOH (+10% NH$_4$OH), 35% AcOEt). The pure fractions were collected and evaporated to dryness yielding 3.57 g (64%) of intermediate 385.

Preparation of Intermediate 386

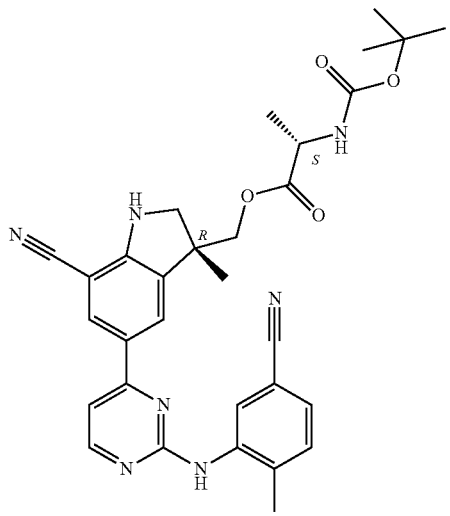

A mixture of compound 1 (2.1 g; 5.30 mmol), Boc-L-Alanine (2.5 g; 13.24 mmol), HATU (5 g; 13.24 mmol), DIPEA (4.5 mL; 26.48 mmol) and DMAP (35 mg; 0.29 mmol) in DMF (63 mL) was stirred at room temperature for 18 hours. The solution was poured onto water and extracted with EtOAc. The organic layer was washed with H$_2$O, then brine, dried over MgSO$_4$, filtered and evaporated to dryness. The residue was purified by chromatography over silica gel (irregular SiOH, 150 g; mobile phase: 65% Heptane, 5% MeOH (+10% NH$_4$OH), 35% AcOEt). The pure fractions were collected and evaporated to dryness yielding 2.73 g (91%) of intermediate 386.

The intermediates in the Table below were prepared by using an analogous method as reported for the preparation of intermediates 385 and 386, starting from the respective starting materials.

| Intermediate number | Structure | Mass (mg) | Yield (%) |
|---|---|---|---|
| Intermediate 387 | 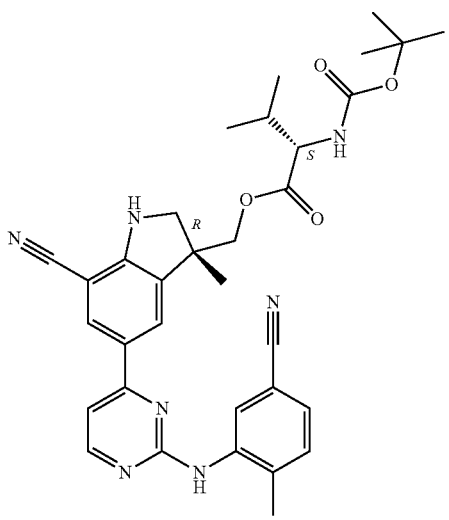<br>From compound 1 and Boc-L-Valine | 438 | 58 |
| Intermediate 388 | 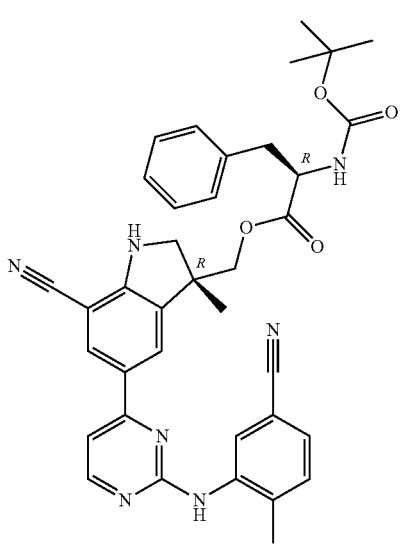<br>From compound 1 and Boc-D-Phenylalanine | 800 | 98 |
| Intermediate 389 | 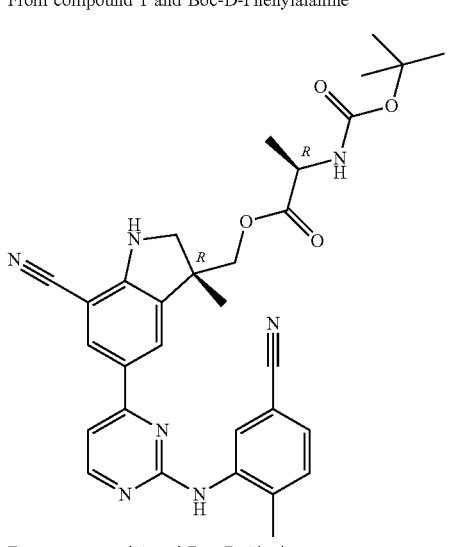<br>From compound 1 and Boc-D-Alanine | 288 | Quantitive |

| Intermediate number | Structure | Mass (mg) | Yield (%) |
|---|---|---|---|
| Intermediate 390 | 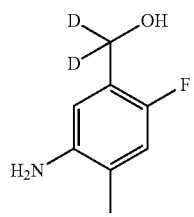 From compound 1 and 3-tert-butoxypropanoic acid | 364 | 54 |

Example A60

Preparation of Intermediate 393:

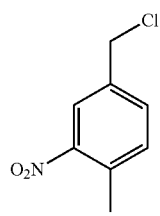

Lithium aluminium deuteride (263 mg; 6.27 mmol) was added portionwise at 5° C. to a solution of methyl-5-amino-2-fluoro-4-methylbenzoate (383 mg; 2.09 mmol) in THF (20 mL) and the reaction mixture was stirred at room temperature for 5 h. The reaction mixture was quenched carefully by adding EtOAc and poured onto ice water. Then, more EtOAc was added and the organic layer was decanted, washed with brine, dried over MgSO$_4$, filtered and the solvent was evaporated to give 337 mg (quant.) of a brown solid which was used without purification in the next step.

Example A61

Preparation of Intermediate 395:

A mixture of 4-Methyl-3-nitrobenzyl alcohol (2.5 g; 14.95 mmol) and thionyle chloride (10 mL) in DCM (40 mL) was stirred at 80° C. overnight. The mixture was evaporated in vacuum.

The crude compound (3 g) was purified by silica gel column chromatography (eluent: Petrol ether/Ethyl acetate: 10/1). The fractions containing the product were evaporated in vacuum to give 2.7 g (97%) of intermediate 395 as a yellow solid.

Preparation of Intermediate 396:

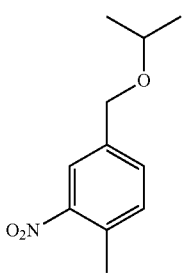

A mixture of intermediate 395 (2.7 g; 14.55 mmol) and sodium isopropoxide (8.63 g; 105.14 mmol) in isopropanol was stirred at 100° C. overnight. Water (100 mL) was added, and the aqueous layer was extracted with ethyl acetate (150 mL*2). The organic layer was washed by brine (100 mL), dried over Na$_2$SO$_4$, filtered, and evaporated in vacuum.

The crude compound (3 g) was purified by column chromatography over silica gel (eluent: Petrol ether/Ethyl acetate:10/1). The fractions containing the product were evaporated in vacuum to give 2.1 g (69%) of intermediate 396 as clear oil.

Example A62

Preparation of Intermediate 399:

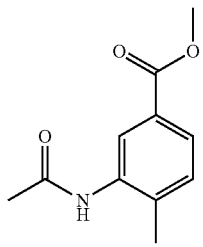

To a solution of Methyl 3-amino-4-methylbenzoate (5 g; 30.27 mmol) and triethylamine (4.59 g; 45.4 mmol) in DCM (50 mL) was added dropwise acetyl chloride (3.09 g; 39.35 mmol) at 0° C. The reaction mixture was stirred at room temperature overnight. An aqueous saturated solution of $NaHCO_3$ (100 mL) was added. The mixture was filtered and the filter cake was washed by water (30 mL*2) and petroleum ether (30 mL*2). The cake was dried in vacuum to give 5.6 g (88%) of intermediate 399 as a white solid.

Preparation of Intermediate 400

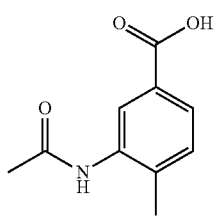

To a solution of intermediate 399 (3.4 g; 16.24 mmol) in a 1/2 mixture of THF/water (30 mL) was added sodium hydroxide (3.25 g; 81.2 mmol) at room temperature. The mixture was stirred at room temperature for 24 hours and poured into a mixture of water (30 mL) and ethyl acetate (30 mL). The aqueous layer was separated and acidified by HCl (12M) until pH=2. The precipitated solid was filtered and dried to afford 2.7 g (86%) of intermediate 400 as white solid.

Preparation of Intermediate 401:

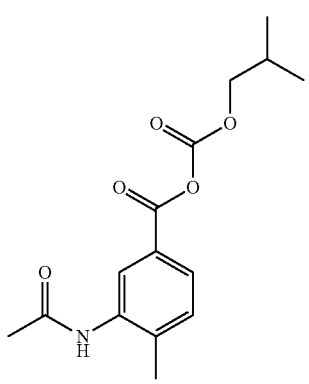 [SMILES: CC(=O)Nc1cc(C(=O)OC(=O)OCC(C)C)ccc1C]

To a solution of intermediate 400 (2.7 g; 13.97 mmol) in THF (20 mL) was added dropwise isobutyl chloroformate (2.3 g; 16.8 mmol) at 0° C. Then, DIPEA (5.42 g; 41.93 mmol) was added at 0° C. and the mixture was stirred at 0° C. for 2 hours. The mixture was diluted with ethyl acetate (30 mL) and the organic layer was washed with water (15 mL*3). The organic layer was dried ($MgSO_4$), filtered and concentrated to afford 3.87 g (94%) of intermediate 401 as a light yellow solid.

Preparation of Intermediate 402:

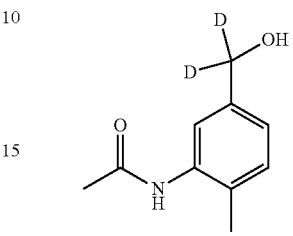

To a solution of intermediate 401 (2 g; 6.82 mmol) in deuterated methanol (50 mL) was added, slowly at 0° C., sodium borodeuteride (1.43 g; 34.1 mmol). The mixture was stirred at room temperature for 30 min. The mixture was concentrated and the residue was purified by column chromatography on silica gel (eluent: petrol/ethyl acetate: from 100:0 to 0:100. The fractions containing the product were collected and the solvent was evaporated to afford 988 mg (80%) of intermediate 402 as a white solid.

Preparation of Intermediate 403:

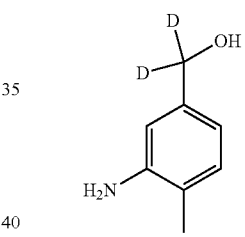

The mixture of intermediate 402 (980 mg; 5.41 mmol) and sodium hydroxide (18.2 g; 324.45 mmol) in a 4/1 mixture of methanol/water (20 mL) was stirred at 90° C. for 48 hours. The mixture was concentrated, diluted with water (20 mL) and extracted with ethyl acetate (15 mL*3). The organic layer was dried ($MgSO_4$), filtered and concentrated to afford 650 mg (86%) of intermediate 403 as a light yellow solid.

Example A63

Preparation of Intermediate 405.

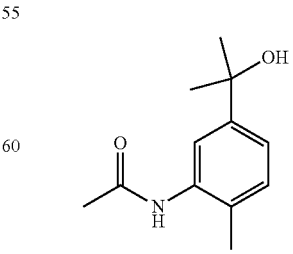

To a solution of intermediate 399 (1 g; 4.82 mmol) in THF (30 mL) was added, dropwise at −78° C. under $N_2$, methylmagnesium bromide (3M in Et₂O; 8.04 mL; 24.13 mmol). The reaction mixture was stirred at room temperature overnight. A saturated solution of NH₄Cl (60 mL) was added and, the reaction mixture was extracted with ethyl acetate (50 mL*3). The organic layer was washed by brine (50 mL), dried over Na₂SO₄, filtered, and evaporated in vacuum to give the crude compound.

The crude compound (0.9 g) was purified by column chromatography over silica gel (eluent: Petroleum ether/Ethyl acetate:1/3). The fractions containing the product were evaporated in vacuum to give 700 mg (70%) of intermediate 405 as white solid.

Preparation of Intermediate 406:

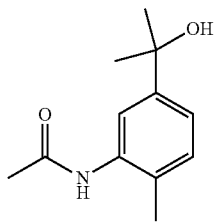

Intermediate 406 was prepared following a similar procedure than the one used for the preparation of intermediate 403, starting from intermediate 405 (490 mg; 89%; yellow solid).

Example A64

Preparation of Intermediate 408:

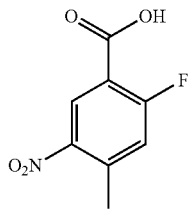

To a solution of 2-fluoro-4-methylbenzoic acid (1 g; 6.5 mmol) in sulfuric acid (15 mL) was added, dropwise over 3 minutes at 0° C., a mixture of freshly prepared C (0.415 mL) and B (0.44 mL: 10.5 mmol). The mixture was stirred at 0° C. for 3 hrs and added cautiously to 66 ml of ice/ice water. The resulting mixture was stirred for 1 hour. The obtained precipitate was filtered and dried under vacuum at 50° C. to give 1.26 g (98%) of intermediate 408 as a white solid.

Preparation of Intermediate 409:

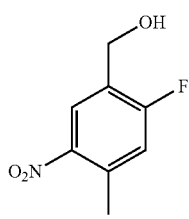

Intermediate 408 (1.26 g; 6.32 mmol) was dissolved in THF (15.7 mL). Borane-THF complex (1M; 19 mL; 19 mmol) was added dropwise at 0° C. The mixture was stirred overnight at 50° C. The mixture was quenched with 60 mL of a saturated aqueous NaHCO₃ and extracted with ethyl acetate (80 mL*3). The organic layer was washed with brine (100 mL), dried over MgSO₄ and filtered. The solvent was removed under vacuum to give 1.17 g (100%) of intermediate 409 as yellow solid.

Example A65

Preparation of Intermediate 413

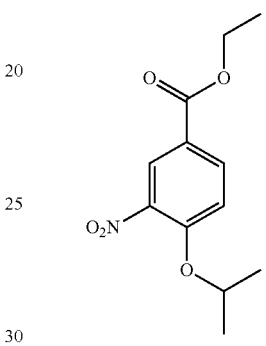

and Intermediate 414

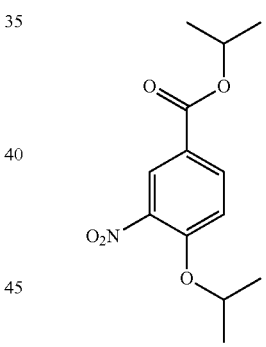

Sodium bis(trimethylsilyl)amide (28.15 mL; 28.15 mmol) was added dropwise to a solution of isopropanol (2.15 mL; 28.15 mmol) and THF (150 mL) at 0° C. and the reaction was stirred for 10 minutes. The resulting solution was added to a solution of ethyl-4-fluoro-3-nitrobenzoate (4 g; 18.76 mmol) in THF (50 mL) at 0° C. and the reaction mixture stirred overnight. Water (80 mL) was added and the mixture was extracted with ethyl acetate (100 mL*3), dried over sodium sulfate, filtered and evaporated to give a yellow solid.

The residue was purified by flash column chromatography over silica gel (eluent: petroleum ether/ethyl acetate from 100/0 to 60/40). The fractions containing the product were collected and the solvent was concentrated to dryness under vacuum to give 3.2 g of an undetermined mixture of intermediates 413 and 414 as yellow solid.

Preparation of Intermediate 415

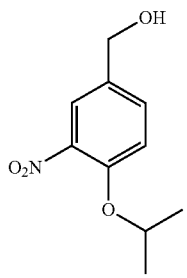

Lithium aluminium hydride (0.7 g; 18.44 mmol) was added to a solution of intermediates 413 and 414 (3.2 g) in THF (60 mL) at 0° C. The mixture was stirred overnight at rt. At 0° C., water (0.49 ml) was added followed by a 10% aqueous solution NaOH (0.49 ml) and additional water (1.47 ml). The mixture was dried over MgSO$_4$, filtered and the filtrate was concentrated under vacuum. The residue was purified by flash column chromatography over silica gel (eluent: petroleum ether/ethyl acetate from 100/0 to 60/40). The fractions containing the product were collected and the solvent was concentrated to dryness under vacuum to give 420 mg (32%) of intermediate 415 as a yellow oil.

Preparation of Intermediate 416

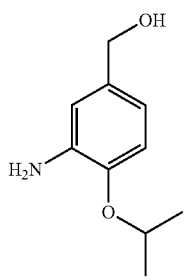

A mixture of intermediate 415 (500 mg; 2.37 mmol) in methanol (10 mL) was hydrogenated at rt (15 Psi) with platinum on activated charcoal as a catalyst. After uptake of H$_2$ (3 equiv), the mixture was stirred overnight at rt. The catalyst was filtered off and the filtrate was evaporated to give 400 mg (93%) of intermediate 416 as a brown oil.

Preparation of Intermediate 418:

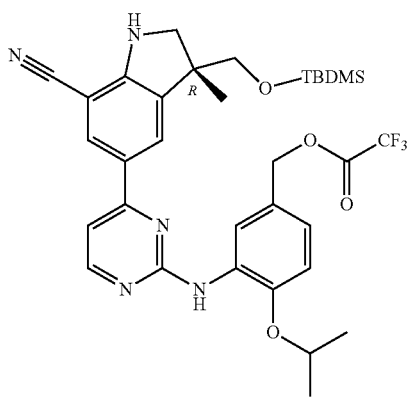

To a solution of intermediate 417 (340 mg; 0.41 mmol) in DCM was added trifluoroacetic acid (0.8 mL; 10.45 mmol). The mixture was stirred for 2 h at rt, then poured onto water (15 mL) and the pH was adjusted to 10 with a saturated aqueous Na$_2$CO$_3$. The mixture was extracted with DCM (30 mL*3), dried over MgSO$_4$, filtered and evaporated to give 420 mg (59%) of intermediate 418 as yellow solid.

Preparation of Intermediate 419:

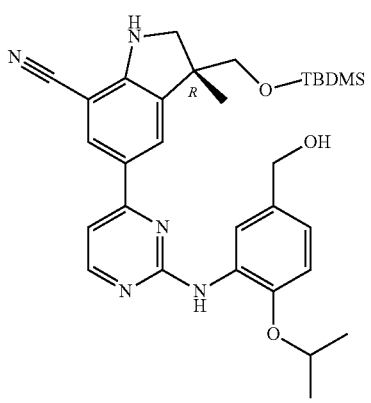

A mixture of intermediate 418 (400 mg; 0.36 mmol) and potassium carbonate (178.5 mg; 1.29 mmol) in methanol (5 mL) was stirred for 30 mn at 80° C. The suspension was filtered through a pad of Celite which was washed with EtOAc (10 mL*3). The combined filtrates were concentrated to dryness to give 320 mg (95%) of intermediate 419 as a yellow oil.

Example A66

Preparation of Intermediate 420:

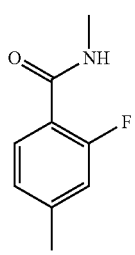

This reaction was made twice on 5 g of 2-fluoro-4-methylbenzoic acid. A mixture of 2-fluoro-4-methylbenzoic acid (5 g; 32.4 mmol), HATU (13.6 g; 35.7 mmol), and DIPEA (12.3 mL; 71.4 mmol) was stirred in DCM (129 mL) for 30 min and methylamine (17.8 mL g; 35.7 mmol) was added. The mixture was stirred at rt for 5 h. The mixture was evaporated. The residue was purified by chromatography over silica gel (15-40 μm, 120 g, eluent: heptane/EtOAc: 80/20 to 10/90). The pure fractions were mixed and the solvent was evaporated to give 9.07 g (84%) of intermediate 420.

The intermediates in the Table below were prepared by using an analogous method as reported for the preparation of intermediates 420, starting from the respective starting materials. The most relevant minor deviations from the existing procedure are indicated in the column "Mass"

| Intermediate number | Structure | Mass (mg) | Yield (%) |
|---|---|---|---|
| Intermediate 432 | from 3-amino-4-methylbenzoic acid and 1-(2-aminoethyl)pyrrolidine | 288 | 36 |
| Intermediate 434 | From 3-amino-4-methylbenzoic acid and 2-(4-morpholino)ethylamine | 126 | 12 |
| Intermediate 436 | From 3-amino-4-methylbenzoic acid and dimethylamine | 700 | 100 |
| Intermediate 438 | From 3-amino-4-methylbenzoic acid and 2-(4-morpholino)ethylamine. | 1530 | 100 |
| Intermediate 441 | From 3-amino-4-methylbenzoic acid and 1-methylpyrrolidin-3-amine | 441 Procedure with 2.5 eq. of COMU instead of 1.1 eq. of HATU | 53 |
| Intermediate 443 | From 2-fluoro-4-methylbenzoic acid and methylamine | 356 | 66 |
| Intermediate 445 | From 2-fluoro-4-methylbenzoic acid and 1-methylpyrrolidin-3-amine | 773 | 100 |

| Intermediate number | Structure | Mass (mg) | Yield (%) |
|---|---|---|---|
| Intermediate 450 | 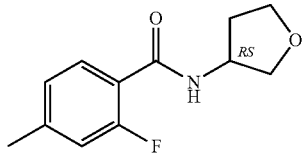 [SMILES: Cc1ccc(C(=O)NC2CCOC2)c(F)c1]<br>From 2-fluoro-4-methylbenzoic acid and 3-aminotetrahydrofuran hydrochloride | 554 | 77 |
| Intermediate 495 | 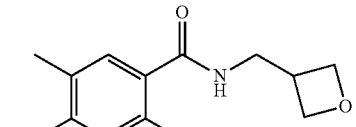<br>From oxetan-3-ylmethanamine and intermediate 494 | 900 | 76 |
| Intermediate 521a | 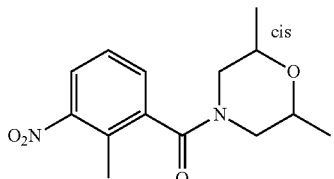<br>From 2-methyl-3-nitrobenzoic acid and cis-2,6-dimethylmorpholine | 1500 | 98 |

Preparation of Intermediate 421:

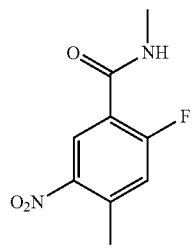

A mixture of fuming nitric acid (3.3 mL; 79.28 mmol) in sulfuric acid (4 mL) was added dropwise at 5° C. over 3 minutes (ice bath) to a solution of intermediate 420 (9 g; 53.83 mmol) in sulfuric acid (120 mL) [no exothermicity]. The reaction mixture was stirred at 5° C. for 3 hours and quenched precautionously with ice/ice-water (500 mL) at 0-5° C. The mixture was vigorously stirred for 1 h. The precipitate was filtered, washed with ice-water (3×300 mL) and dried. The obtained solid was solubilized with DCM and the organic layer was dried over MgSO$_4$, filtered and the solvent was evaporated to give 10.47 g (92%) of intermediate 421 as a white solid.

Example A67

Preparation of Intermediate 424

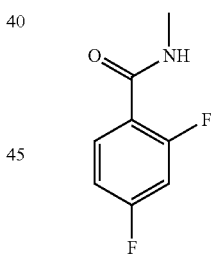

A mixture of 2,4-difluorobenzoic acid (2 g; 12.65 mmol), HATU (5.3 g; 13.915 mmol), and DIPEA (4.8 mL; 27.83 mmol) in DCM (50 mL) was stirred for 30 min and 2N methylamine in THF (7 mL; 13.915 mmol) was added. The reaction mixture was stirred at room temperature for 18 hours, poured onto water and extracted with DCM. The organic layer was decanted, filtered through Chromabond® and evaporated to dryness. The residue was purified by chromatography over silica gel (irregular SiOH, 40 g; gradient: 20% EtOAc, 80% heptane to 40% EtOAc, 60% heptane). The pure fractions were collected and evaporated to dryness yielding 1.68 g (77%) of intermediate 424.

Preparation of Intermediate 425:

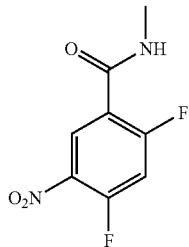

A mixture of fuming nitric acid (0.6 mL; 14.456 mmol) in concentrated sulphuric acid (1 mL) was added dropwise at 5° C. to a solution of intermediate 424 (1.68 g; 9.816 mmol) in concentrated sulphuric acid (21 mL). The reaction mixture was stirred at 5° C. for 4 hours and poured onto ice water. The suspension was stirred at room temperature for 30 min and the precipitate was filtered, washed with water and dried yielding 1.38 g (65%) of intermediate 425.

The intermediates in the Table below were prepared by using an analogous method as reported for the preparation of intermediates 425, starting from the respective starting materials.

| Intermediate number | Structure | Mass (mg) | Yield (%) |
|---|---|---|---|
| Intermediate 446 | 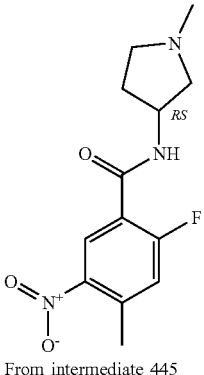<br>From intermediate 445 | 638 | 70 |
| Intermediate 451 | 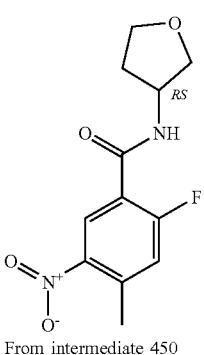<br>From intermediate 450 | 426 | 65 |
| Intermediate 489 | 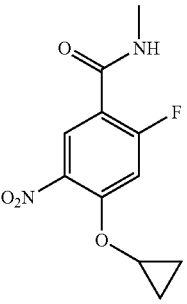 [SMILES: CNC(=O)c1cc([N+](=O)[O-])c(OC2CC2)cc1F]<br>From intermediate 488 | 354 | 53 |

Preparation of Intermediate 426

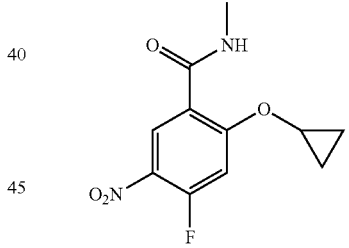

And Intermediate 427

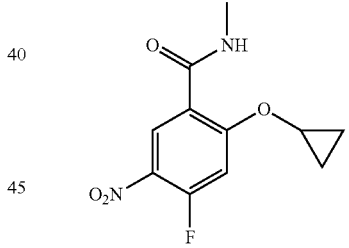

A mixture of intermediate 425 (1.15 g; 5.32 mmol), cyclopropanol (337 µL; 5.32 mmol) and cesium carbonate (3.5 g; 10.64 mmol) in 1,4-dioxane (15 mL) was heated at 80° C. for 1 hour. The reaction mixture was cooled to room temperature, and diluted with DCM. The organic layer was washed with water, filtered through Chromabond® and evaporated to dryness. The residue was purified by chromatography over silica gel (irregular SiOH, 50 g; mobile phase: gradient from 20% EtOAc, 80% heptane to 40% EtOAc, 60% heptane). The fractions containing the products were collected and evaporated to dryness yielding 860 mg (63%) of a mixture of intermediates 426 and 427 directly used in the next step without any further purification.

Preparation of Intermediate 428

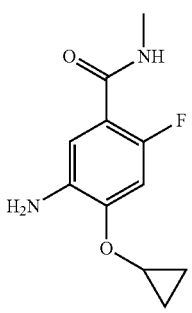

And Intermediate 42C

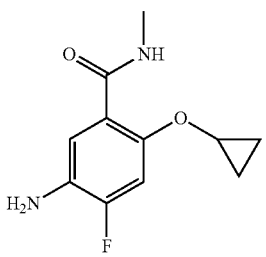 [SMILES: CNC(=O)c1cc([N+](=O)[O-])c(F)cc1OC1CC1]

A mixture of intermediate 426 and 427 (860 mg; 3.38 mmol), iron powder (945 mg; 16.91 mmol) and ammonium chloride (724 mg; 13.53 mmol) in ethanol (22 mL) and water (5.6 mL) was heated at 70° C. for 1 hour. The reaction mixture was cooled down to room temperature, diluted with DCM, filtered over Celite® and basified with a 10% aqueous solution of $K_2CO_3$. The organic layer was decanted, dried over $MgSO_4$, filtered and evaporated to dryness yielding 791 mg of a mixture of intermediates 428 and 429 directly engaged in the next step.

Example A68

Preparation of Intermediate 455:

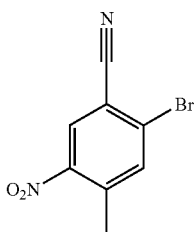

To a solution of 2-bromo-4-methylbenzonitrile (4.0 g; 20.40 mmol) in sulfuric acid (6 mL) at 0° C. was added potassium nitrate (2.063 g; 20.40 mmol) in sulfuric acid (18 mL). After stirring at 0° C. for 1.5 hour, the reaction mixture was poured into 500 mL of ice water. The precipitate was collected by filtration and washed with copious amounts of water. The precipate was dried to give 4.5 g (91%) of intermediate 455.

Preparation of Intermediate 456:

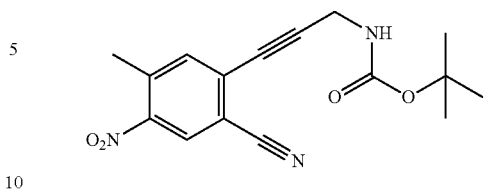

A mixture of intermediate 455 (500 mg; 2.07 mmol), N-boc-propargylamine (483 mg; 3.11 mmol), tri-tert-butylphosphine (0.0287 mL; 0.122 mmol), diisopropylamine (0.33 mL; 2.41 mmol), copper (I) iodide (4.7 mg; 0.024 mmol) and dichlorobis(triphenylphosphine)palladium (57 mg; 0.081 mmol) in 1,4-dioxane (8.8 mL) was purged with $N_2$ three times and was heated at 45° C. for 1 h. The mixture was poured into ice and extracted with EtOAc. The organic layer was washed with brine, dried over $MgSO_4$, filtered and the solvent was evaporated. The residue was purified by chromatography over silica gel (80 g; 15-40 μm, eluent: heptane/EtOAc: 100/0 to 0/100). The pure fractions were mixed and the solvent was evaporated to give 0.594 g (91%) of intermediate 456.

Preparation of Intermediate 457:

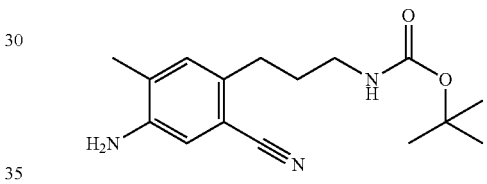

A mixture of intermediate 456 (555 mg; 1.76 mmol) and Pd (10%) on activated charcoal (187 mg) in EtOAc (11 mL) was hydrogenated at rt under 1 bar of $H_2$ overnight. The mixture was filtered over celite and the filtrate was evaporated until dryness to give 0.352 g (69%) of intermediate 457.

Example A69

Preparation of Intermediate 465:

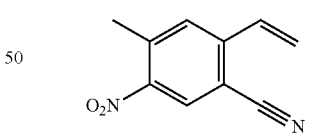

A mixture of intermediate 455 (0.5 g; 2.074 mmol), 2-vinyl-4,4,5,5-tetramethyl-1,3,2-dioxaborolane (0.528 mL; 3.11 mmol) and tetrakis(triphenylphosphine)palladium(0) (120 mg; 0.104 mmol) in 2N $Na_2CO_3$ (1.82 mL; 3.63 mmol) and 1,4-dioxane (5.2 mL) was degassed and then heated at 100° C. overnight. The mixture was poured into ice and extracted with EtOAc. The organic layer was washed with brine, dried over $MgSO_4$, filtered and the solvent was evaporated. The residue was purified by chromatography over silica gel (80 g, 15-40 μm, eluent: heptane/EtOAc: 100/0 to 0/100). The pure fractions were mixed and the solvent was evaporated to give 0.181 g (46%) of intermediate 465.

Preparation of Intermediate 466:

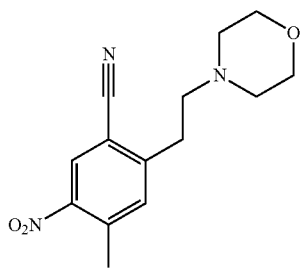

A mixture of intermediate 465 (250 mg; 1.33 mmol) and morpholine (821 mg; 6.64 mmol) in MeOH (4.7 mL) was stirred at 60° C. for 1 h in a sealed tube. The mixture was poured into ice and extracted with DCM. The organic layer was washed with brine, dried over MgSO$_4$, filtered and the solvent was evaporated. The residue was purified by chromatography over silica gel (15-40 µm, 24 g, eluent: DCM/MeOH: 100/0 to 95/5). the pure fractions were mixed and the solvent was evaporated to give 0.329 g (90%) of intermediate 466.

Preparation of Intermediate 469:

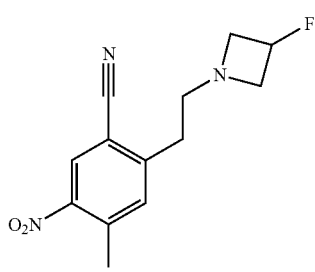 [SMILES: Cc1cc(CCN2CC(F)C2)c(C#N)cc1[N+](=O)[O-]]

Intermediate 469 was prepared using an analogous method as the one used for the preparation of intermediate 466, starting from intermediate 465 and 3-fluoroazetidine hydrochloride (247 mg; 67%).

Example A70

Preparation of Intermediate 472:

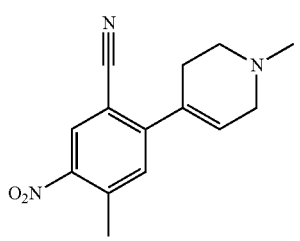 [SMILES: Cc1cc(C2=CCN(C)CC2)c(C#N)cc1[N+](=O)[O-]]

A mixture of intermediate 455 (500 mg; 2.07 mmol), 1-methyl-1,2,3,6-tetrahydropyridine-4-boronic acid pinacol ester (509 mg; 2.28 mmol) and potassium phosphate (881 mg; 41.5 mmol) in 1,4-dioxane (7 mL) and water (4 mL) was degassed with N$_2$. 1,1'-Bis (diphenylphosphino) ferrocene-palladium(ii) dichloride dichloromethane (17 mg; 0.0207 mmol) was added and the reaction mixture was heated at 120° C. for 15 min using one single mode microwave (Biotage Initiator EXP 60) with a power output ranging from 0 to 400 W. The mixture was poured onto water and extracted with DCM. The organic layer was washed with brine, dried over MgSO$_4$, filtered and evaporated to dryness. The residue was purified by chromatography over silica gel (irregular SiOH, 80 g; mobile phase: DCM/MeOH: 100/0 to 95/5). The fractions containing the product were collected and evaporated to dryness to give 0.515 g (96%) of intermediate 472.

Preparation of Intermediate 475:

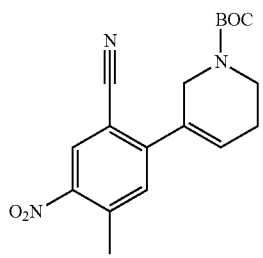 [SMILES: Cc1cc(C2=CCCN(C(=O)OC(C)(C)C)C2)c(C#N)cc1[N+](=O)[O-]]

Intermediate 475 was synthesized by using the same method than the one used for the preparation of intermediate 472 starting from intermediate 455 and tert-butyl 3-(4,4,5,5-tetramethyl-1,3,2-dioxaborolan-2-yl)-5,6-dihydropyridine-1 (2H)-carboxylate (1.45 g; 93%).

Preparation of Intermediate 473.

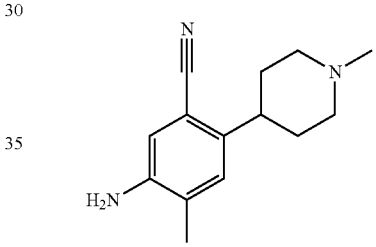

A solution of intermediate 472 (0.478 mg; 1.86 mmol) in MeOH (21.9 mL) was hydrogenated under 2 bars of H$_2$ at rt in presence of 10% palladium on activated charcoal (54.8 mg) overnight. The mixture was filtered off over celite and the filtrate was evaporated. The residue was purified by chromatography over silica gel (40 g, 15-40 µm, eluent: DCM/MeOH: 100/0 to 90/10). The fractions containing the product were mixed and the solvent was evaporated to give 0.155 g (36%) of intermediate 473.

Example A71

Preparation of Intermediate 476:

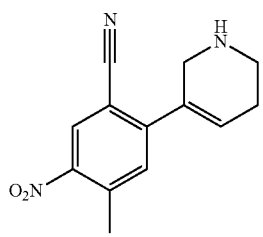 [SMILES: Cc1cc(C2=CCCNC2)c(C#N)cc1[N+](=O)[O-]]

TFA (4.4 mL; 58 mmol) was added to a solution of intermediate 475 (1.45 g; 4.22 mmol) in DCM (22 ml) and the mixture stirred for 30 mins, then poured into ice, basified with K₂CO₃ and extracted with DCM. The organic layer was washed with brine, dried over MgSO₄, filtered and the solvent was evaporated yielding 0.89 g (87%) of intermediate 476.

Preparation of Intermediate 477:

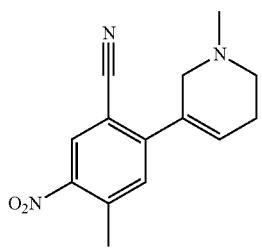 [SMILES: Cc1cc(C2=CCCN(C)C2)c(C#N)cc1[N+](=O)[O-]]

Formaldehyde (0.54 mL; 7.24 mmol) was added to a solution of intermediate 476 (0.873 g; 3.59 mmol) and sodium acetate (0.295 g; 3.6 mmol) in MeOH (30 ml) and DCM (15 ml) and the mixture stirred at room temperature for 5 minutes. Sodium triacetoxyborohydride (1.53 g; 7.19 mmol) was then added and the mixture was stirred for 1 h. The mixture was poured into ice, basified with K₂CO₃ and extracted with DCM. The organic layer was washed with brine, dried over MgSO₄, filtered and the solvent was evaporated. The residue was purified by chromatography over silica gel (15-40 µm, 80 g, eluent: DCM/MeOH: 100/0 to 90/10). The pure fractions were mixed and the solvent was evaporated to give 1.15 g (99%) of intermediate 477.

Preparation of Intermediate 478:

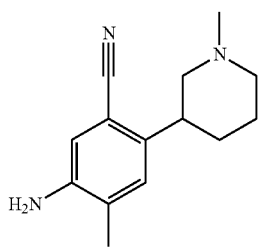 [SMILES: Cc1cc(C2CCCN(C)C2)c(C#N)cc1N]

Intermediate 478 was synthesized by using analogous method than the one used for the preparation of intermediate 473 starting from intermediate 477 (1.04 g; 84% of purity based on LC/MS).

Example A72

Preparation of Intermediate 488:

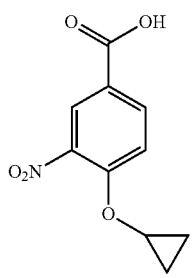

A mixture of intermediate 40 (575 mg; 2.816 mmol) in concentrated HCl (11 mL) was heated at 100° C. for 5 hours. The reaction mixture was cooled to room temperature, poured onto iced water and extracted with Et₂O. The organic layer was decanted, dried over MgSO₄, filtered and evaporated to dryness yielding 632 mg of intermediate 488.

Example A73

Preparation of Intermediate 492:

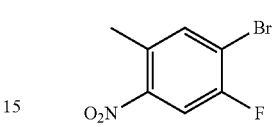

A solution of potassium nitrate (2.46 g; 0.024 mol) in concentrated sulfuric acid (36 ml) was added dropwise at a temperature below 5° C. to a solution of 3-bromo-4-fluoro-toluene (2.52 mL; 0.02 mol) in concentrated sulfuric acid (4 ml). The mixture was stirred at 5° C. for 2 hours, then, poured onto ice water. The obtained precipitate was filtered and dried yielding 3.94 g (84%) of intermediate 492.

Preparation of Intermediate 493:

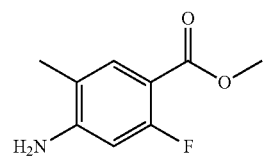

Into an autoclave (300 mL) purged with N₂ was added intermediate 492 (2.93 g; 12.5 mmol) in MeOH (117 mL). Triethylamine (3.58 mL; 25 mmol) was added then 1,1'-bis (diphenylphosphino)ferrocene]palladium(II) dichloride (0.615 g; 0.751 mmol). The autoclave was purged and the mixture was stirred overnight under 30 bars of carbon monoxyde at 90° C. The mixture was evaporated. The residue was purified by chromatography over silica gel (15-40 µm, 90 g, eluent: heptane/EtOAc: 100/0 to 0/100). The pure fractions were mixed and the solvent was evaporated to give 1.22 g (28%) of intermediate 493.

Preparation of Intermediate 494:

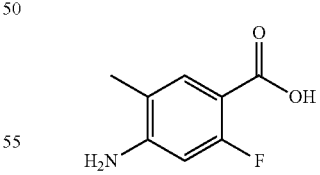

A solution of lithium hydroxide (0.9 g; 21.4 mmol) in water (4.4 mL) was added to a solution of intermediate 494 (0.982 g; 5.36 mmol) in THF (47 mL). The reaction mixture was refluxed overnight. The mixture was poured into ice, acidified with aqueous 3N HCl and extracted with EtOAc. The organic layer was washed with brine, dried over MgSO₄, filtered and the solvent was evaporated yielding 907 mg of intermediate 494 directly engaged in the next step.

Example A74

Preparation of Intermediate 497:

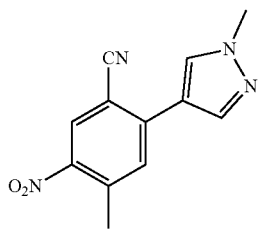 [SMILES: Cc1cc(-c2cnn(C)c2)c(C#N)cc1[N+](=O)[O-]]

In a sealed tube, a solution of 2-bromo-4-methyl-5-nitrobenzonitrile (1.0 g; 4.15 mmol), 1-methyl-4-(4,4,5,5-tetramethyl-1,3,2-dioxaborolan-2-yl)-1H-pyrazole (1.29 g; 6.22 mmol) and $K_3PO_4$ (2.64 g; 12.44 mmol) in 1,4-dioxane (30.8 mL) and distilled water (9.7 mL) was purged with $N_2$. $PdCl_2dppf$ (340 mg; 415 µmol) was added, the reaction mixture was purged again with $N_2$ and heated at 80° C. for 18 h. The reaction mixture was poured into an aqueous solution of $K_2CO_3$ and extracted with EtAOc. The organic layer was dried over $MgSO_4$, filtered and evaporated until dryness. The residue was purified by chromatography over silica gel (irregular SiOH, 40 g; mobile phase: gradient from 0% EtOAc, 100% heptane to 40% EtOAc, 60% heptane). The fractions were collected and evaporated to dryness yielding 800 mg (80%) of intermediate 497.

The compounds in the table below were prepared using analogous method as described for intermediate 497 starting from the respective starting materials.

| Intermediate number | Structure | Quantity | Yield |
|---|---|---|---|
| Intermediate 498 | From 5-bromo-1-methyl-1H-imidazole and 4,4,5,5-tetramethyl-2-(4-methyl-3-nitrophenyl)-1,3,2-Dioxaborolane | 170 mg | 52% |

Intermediate 499:

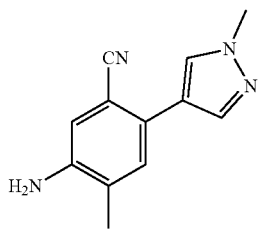

A mixture of intermediate 497 (800 mg; 3.30 mmol) and Pd/C (10% wt; 176 mg) in MeOH (8.3 mL) was stirred at room temperature under 1 atm. of $H_2$ overnight. The reaction mixture was filtered over Celite® and the filtrate was evaporated to dryness yielding 700 mg of intermediate 499.

The compounds in the table below were prepared using analogous method as described for the preparation of intermediate 499, starting from the respective starting materials.

| Intermediate number | Structure | Quantity | Yield |
|---|---|---|---|
| Intermediate 500 | From intermediate 498 | 147 mg | 100% |
| Intermediate 500B | From intermediate 500A | 700 mg | 93% |
| Intermediate 501 | From 2-(4-methyl-3-nitrophenyl)-1H-imidazole | 1.4 g | 87% |

Example A75

Intermediate 500A:

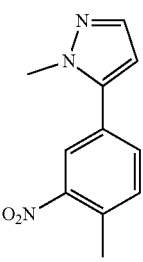 [SMILES: Cc1ccc(-c2ccnn2C)cc1[N+](=O)[O-]]

A mixture of 2-nitro-4-bromo toluene (1 g; 4.629 mmol), 1-Methyl-/H-pyrazole-5-boronic acid (874 mg; 6.94 mmol), $K_2CO_3$ (1.024 g; 7.406 mmol), $PdCl_2dppf$ (339 mg; 0.463 mmol) in DMF (19 mL) was stirred at 85° C. for 18 h. The reaction mixture was evaporated. The residue was dissolved with EtOAc. The organic layer was washed with water then brine, dried over $MgSO_4$, filtered and evaporated to dryness.

The residue was purified by chromatography over silica gel (mobile phase: gradient from 0% EtOAc, 100% heptane to 30% EtOAc, 70% heptane). The fractions were collected and evaporated to dryness yielding 870 mg (87%) of intermediate 500A.

Example A76

Intermediate 510:

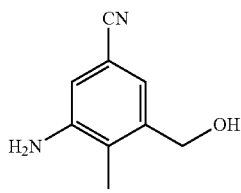

A solution of lithium aluminium hydride 1M in THF (1.5 mL; 1.56 mmol) was added drop wise at 0° C. to a solution of 3-amino-5-cyano-2-methyl-benzoic acid methyl ester (297 mg; 1.56 mmol) in THF (10 mL) and the reaction mixture was stirred at room temperature for 3 hours. The reaction mixture was poured onto iced water and extracted with EtOAc. The organic layer was decanted, washed with brine, dried over $MgSO_4$, filtered and evaporated to dryness yielding 216 mg (85%) of intermediate 510.

Intermediate 512:

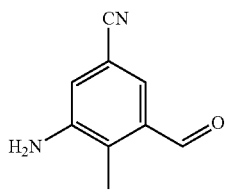

A mixture of intermediate 510 (341 mg; 2.10 mmol) and manganese dioxide (913 mg; 10.51 mmol) in 1,4-dioxane (20 mL) was heated at 100° C. for 6 hours. The reaction mixture was cooled to room temperature, diluted with DCM, filtered through a pad of Celite® and evaporated to dryness yielding 300 mg (89%) of intermediate 512 which was directly engaged in the next step.

The compounds in the table below were prepared using analogous method as described for the preparation of intermediate 512 starting from the respective starting materials.

The most relevant minor deviations from the original method are indicated in the column "Quantity"

| Intermediate number | Structure | Quantity | Yield |
|---|---|---|---|
| Intermediate 515 | 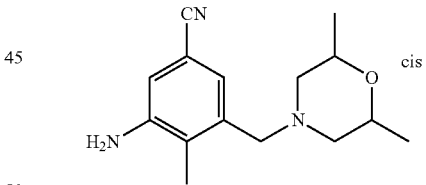<br>From intermediate 511 | 120 mg<br>Prodedure modification:<br>18 h @ 100° C. | 42% |

Preparation of Intermediate 513:

A mixture of intermediate 512 (551 mg; 3.44 mmol), cis-2,6-dimethylmorpholine (847 µL; 6.88 mmol) and AcOH (387 µL; 6.76 mmol) in DCM (20 mL) was stirred at room temperature for 1 hour. Then sodium triacetoxyborohydride (1.45 g; 6.88 mmol) was added. The reaction mixture was stirred at room temperature over the weekend. The reaction mixture was poured onto a 10% aqueous solution of $K_2CO_3$ and extracted with DCM. The organic layer was decanted, filtered through Chromabond® and evaporated to dryness. The residue was purified by chromatography (irregular SiOH, 24 g; mobile phase: gradient from 20% EtOAc, 80% heptane to 40% EtOAc, 60% heptane). The pure fractions were collected and evaporated to dryness yielding 632 mg (52%, purity 73% based on LC/MS) of intermediate 513 which was directly engaged in the next step.

The compounds in the table below were prepared using analogous method as described for the preparation of intermediate 513, starting from the respective starting materials.

| Intermediate number | Structure | Quantity | Yield |
|---|---|---|---|
| Intermediate 516 | 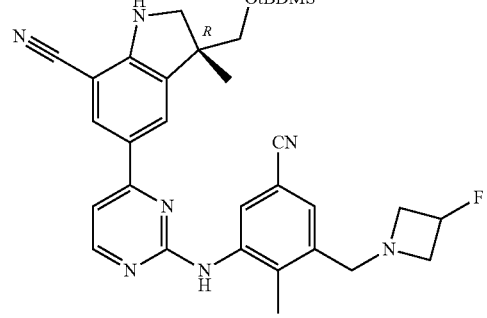<br>From intermediate 515 and 3-fluoroazetidine hydrochloride | 100 mg | 55% |
| Intermediate 517 | 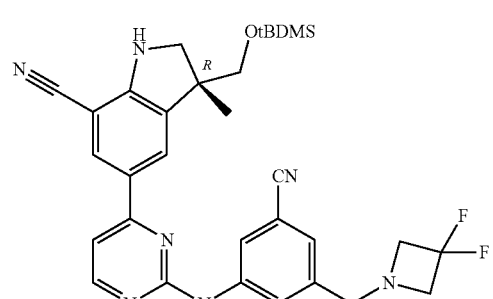<br>From intermediate 515 and 3,3-difluoroazetidine | 106 mg | 31% Purity 81% (LCMS) |

Example A77

Preparation of Intermediate 519:

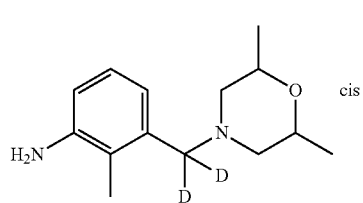 [SMILES: [2H]C([2H])(c1cccc(N)c1C)N1CC(C)OC(C)C1]

Lithium aluminium deuteride (203 mg; 4.832 mmol) was added portion wise at 5° C. to a solution of intermediate 521b (400 mg; 1.61 mmol) in THF (16 mL) and the reaction mixture was stirred at room temperature for 3 days. The reaction mixture was quenched carefully by adding EtOAc and poured onto ice water and more EtOAc was added. The organic layer was decanted, washed with brine, dried over MgSO$_4$, filtered and evaporated to dryness. The residue was purified by chromatography over silica gel (irregular SiOH, 12 g; mobile phase: gradient from 0% MeOH, 100% DCM to 5% MeOH, 95% DCM). The pure fractions were collected and evaporated to dryness yielding 286 mg (75%) of intermediate 519.

Example A78

Preparation of Intermediate 523:

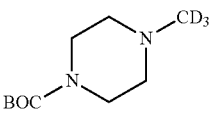

A mixture of 1-Boc-piperazine (5 g; 26.845 mmol), iodomethane-D3 (1.7 mL; 26.845 mmol) and potassium carbonate (11 g; 80.54 mmol) in ACN (200 mL) was heated to 85° C. for 18 h. The suspension was filtered and the insoluble material was washed with EtOAc. The combined filtrates were evaporated to dryness. The residue was taken up with DCM and the insoluble material was filtered. The filtrate was concentrated and purified by chromatography over silica gel (irregular SiOH, 40 g; mobile phase: gradient from 5% MeOH, 95% DCM to 10% MeOH, 90% DCM). The pure fractions were collected and evaporated to dryness yielding 3.25 g (59%) of intermediate 523.

Preparation of Intermediate 524.

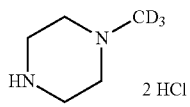

A solution of HCl 4N in 1,4-dioxane (11 mL; 44.27 mmol) was added to a solution of intermediate 523 (3 g; 14.757 mmol) in ACN (70 mL) and the reaction mixture was stirred for 18 hours. The precipitate was filtered, washed with ACN, then Et$_2$O and dried yielding 2.54 g (98%) of intermediate 524.

Example A79

Preparation of Intermediate 525:

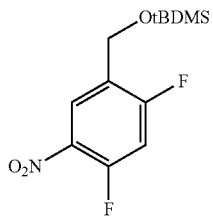

A solution of chloro tert-butyldimethyl silane (391 mg; 2.59 mmol) in DCM (1.7 mL) was added drop wise at 5° C. to a solution of 2,4-difluoro-5-nitro-benzenemethanol (490 mg; 2.59 mmol) and Et$_3$N (720 µL; 5.18 mmol) in DCM (3 mL) and the reaction mixture was stirred at room temperature overnight.

Alternatively, the same reaction was perform using the same conditions starting from of 2,4-difluoro-5-nitro-benzenemethanol (500 mg; 2.644 mmol) and trifluoromethanesulfonic acid tert-butyldimethylsilyl ester (0.607 mL; 2.64 mmol) The two reaction mixtures were combined for the work-up:

DCM was added and the suspension was poured onto a saturated aqueous solution of NH$_4$Cl. The organic layer was decanted, washed with water then with a 10% aqueous solution of K$_2$CO$_3$, dried over MgSO$_4$, filtered and evaporated to dryness. The residue was purified by chromatography over silica gel (irregular SiOH, 40 g; mobile phase: gradient from 10% EtOAc, 90% heptane to 30% EtOAc, 70% heptane). The pure fractions were collected and evaporated to dryness yielding 858 mg of intermediate 525 (quantitative).

Preparation of Intermediate 526:

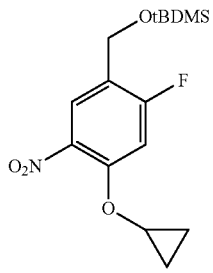

A mixture of intermediate 525 (858 mg; 2.83 mmol), cyclopropanol (717 µL; 11.3 mmol) and cesium carbonate (1.84 g; 5.66 mmol) in 1,4-dioxane (9.5 mL) was heated at 100° C. for 2 h. The reaction mixture was heated at 100° C. overnight, cooled to room temperature and diluted with DCM. Water was added and the reaction mixture was extracted with DCM (three times). The combined organic layers were washed with water, dried over MgSO$_4$, filtered and evaporated to dryness. The residue was purified by chromatography over silica gel (irregular SiOH, 40 g; mobile phase: gradient from 10% EtOAc, 90% heptane to 20% EtOAc, 80% heptane). The pure fractions were collected and evaporated to dryness yielding 581 mg (60%) of intermediate 526.

The intermediate in the table below was prepared using analogous method as described for the preparation of intermediate 526 starting from the respective starting material. The most relevant minor deviation from the original procedure is indicated in the column "yield"

| Intermediate number | Structure | Quantity | Yield |
|---|---|---|---|
| Intermediate 529 | 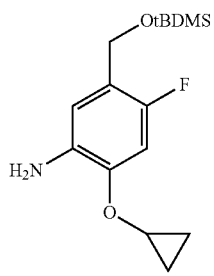<br>From 2,4-difluoro-5-nitrobenzonitrile | 790 mg | 65%<br>Procedure modification:<br>1 h @ 80° C. |

Preparation of Intermediate 527:

A mixture of intermediate 526 (527 mg; 1.543 mmol), iron powder (431 mg; 7.717 mmol) and NH$_4$Cl (330 mg; 6.174 mmol) in EtOH (10 mL) and distilled water (2.5 mL) was heated at 70° C. for 1 hour. The reaction mixture was cooled down to room temperature, diluted with DCM, filtered over Celite® and basified with a 10% aqueous solution of K$_2$CO$_3$. The organic layer was decanted, dried over MgSO$_4$, filtered and evaporated to dryness yielding 485 mg (quantitative) of intermediate 527 directly engaged in the next step without any further purification.

The intermediate in the table below was prepared using analogous method as described for the preparation of intermediate 527 starting from the respective starting material.

| Intermediate number | Structure | Quantity | Yield |
|---|---|---|---|
| Intermediate 530 | 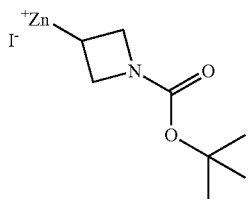 From intermediate 529 | 670 mg | 98% |

Example A80

Preparation of Intermediate 532:

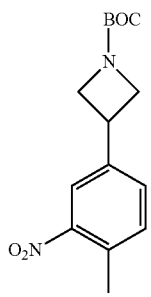

In a dried flask, zinc (4.05 g; 62 mmol) was suspended in dried dimethylacetamide (200 mL) under N₂. The suspension was warmed to 65° C., and then dibromoethane (0.45 g; 2.39 mmol) and chlorotrimethylsilane (0.207 g; 1.91 mmol) were added, and then stirred at 65° C. for 0.5 hour. 1-tert-Butoxycarbonyl-3-iodoazetidine (13.5 g; 47.68 mmol) in dimethylacetamide (100 mL) was added dropwise at 65° C. and the reaction mixture was stirred at room temperature for 1 hour. The crude product was directly used without work-up and purification for the next reaction step.

Preparation of Intermediate 533:

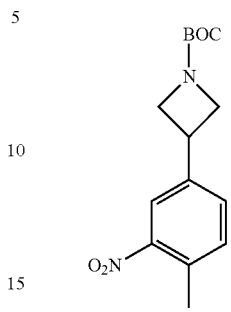

A mixture of 4-bromo-1-methyl-2-nitrobenzene (6.06 g; 28.08 mmol), intermediate 532 (16.62 g; 47.68 mmol), Pd(dppf)Cl₂.DCM (703 mg; 0.86 mmol) and copper (I) iodide (323.7 mg; 1.7 mmol) in dimethylacetamide (300 mL) was stirred at 90° C. overnight under N₂. Water (900 mL) was added and the reaction mixture was extracted with ethyl acetate (600 mL*2). The organic layers were combined, washed with water, brine, dried over Na₂SO₄, filtered, and evaporated in vacuum. The crude intermediate (8 g) was purified by column chromatography over silica gel (eluent: Petrol ether/Ethyl acetate=3/1). The fractions containing the product were mixed and evaporated in vacuum to give 5 g of intermediate 533 (61%) as a yellow oil.

Preparation of Intermediate 534:

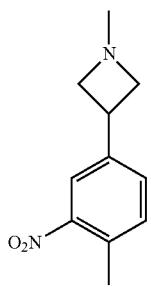

A solution of intermediate 533 (5 g; 17.1 mmol) and HCl 4M in dioxane (50 mL; 200 mmol) in dioxane (20 mL) was stirred at room temperature overnight. The mixture was evaporated in vacuum to give 3.91 g of crude intermediate 534 which was directly engaged in the next reaction step without any further purification.

Preparation of Intermediate 535:

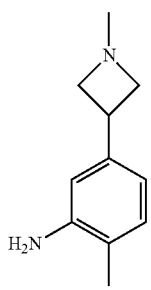

A mixture of intermediate 534 (3.9 g; 17.10 mmol), paraformaldehyde (3 g; 102.62 mmol) and sodium acetate (1.4 g; 17.10 mmol) in MeOH (150 mL) was stirred at room temperature for 2 hours. Sodium triacetoxyborohydride (21.7 g; 102.62 mmol) was added and the reaction mixture was stirred at room temperature overnight. The reaction mixture was slowly basified with a saturated aqueous solution of NaHCO₃ (400 mL) and extracted with DCM (2×300 mL). The organic layer was washed by brine, dried over Na₂SO₄, filtered, and evaporated to dryness. The residue was purified by chromatography over silica gel (mobile phase: petrol ether/EtOAc (1/2)). The desired fractions were evaporated to dryness yielding 1.58 g (45%) of intermediate 535.

Preparation of Intermediate 536:

Intermediate 535 (1.58 g; 7.66 mmol) was dissolved in THF (20 mL), MeOH (10 mL) and distilled water (10 mL). Iron powder (2.1 g; 38.35 mmol) and $NH_4Cl$ (2 g; 38.30 mmol) were added. The reaction mixture was refluxed overnight, filtered through Celite® and the filter cake was washed with 80 mL of a mixture EtOAc/MeOH (8/1). The filtrate was evaporated to dryness. The residue was purified by chromatography over silica gel (mobile phase: EtOAc/MeOH (5/1)). The desired fractions were evaporated to dryness yielding 880 mg (65%) of intermediate 536.

Example A81

Alternative Preparation of Intermediate 380:

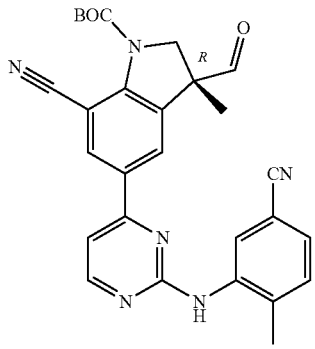

DCM (5 mL) was cooled to −78° C. and oxalyl chloride (3 mL; 6.04 mmol) was added followed by DMSO (865 μL; 12.1 mmol). After 30 min, a suspension of intermediate 10R (2 g; 4.03 mmol) in DCM (15 mL) was added drop wise. The reaction mixture was stirred for 30 min at −78° C., then DIPEA (4.1 mL; 24.17 mmol) was added. The stirring was continued for 3 hours at −78° C. and the reaction mixture was allowed to warm to room temperature and stirred for 30 min. A diluted aqueous solution of $NH_4Cl$ was added and the aqueous layer was extracted with DCM (twice). The combined layers were dried over $MgSO_4$, filtered and evaporated to dryness. The residue was crystallized from $Et_2O$ and the precipitate was filtered, washed with DiPE and dried yielding 2 g of intermediate 380.

Preparation of Intermediate 540:

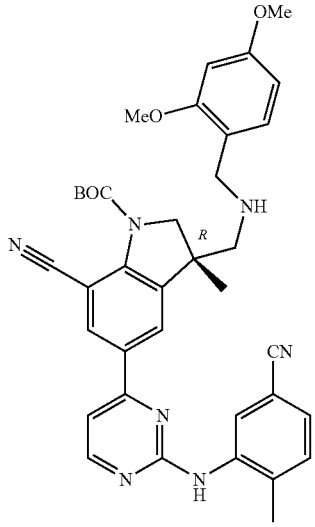

A solution of intermediate 380 (2 g; 4.044 mmol), 2,4-dimethoxybenzylamine (3.6 mL; 24.26 mmol) and AcOH (1.4 mL; 24.26 mmol) in DCE (100 mL) was stirred for 3 hours and $NaBH(OAc)_3$ (8.5 g; 40.44 mmol) was added. The reaction mixture was stirred at room temperature overnight. A saturated aqueous solution of $NaHCO_3$ was added and the aqueous layer was extracted with DCM. The organic layer was dried over $MgSO_4$, filtered and evaporated to dryness. The residue was purified by chromatography over silica gel (irregular SiOH, 80 g; mobile phase: gradient from 40% EtOAc, 60% heptane to 2% MeOH, 60% EtOAc, 40% heptane). The fractions containing the product were collected and evaporated to dryness yielding 1 g (38%) of intermediate 540 and 855 mg of intermediate 380.

Preparation of Intermediate 541:

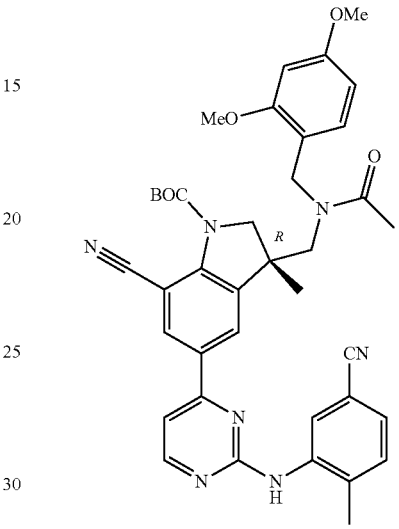

A mixture of intermediate 540 (500 mg; 0.77 mmol), acetyl chloride (66 μL; 0.93 mmol) and $Et_3N$ (215 μL; 1.55 mmol) in THF (10 mL) was stirred at room temperature for 18 hours. The reaction mixture was poured onto a 10% aqueous solution of $K_2CO_3$ and extracted with DCM. The organic layer was decanted, dried over $MgSO_4$, filtered and evaporated to dryness. The residue was purified by chromatography over silica gel (irregular SiOH, 24 g; mobile phase: gradient from 0% MeOH, 100% DCM to 6% MeOH, 94% DCM). The fractions containing the product were collected and evaporated to dryness yielding 540 mg (quantitative) of intermediate 541.

Preparation of Intermediate 542:

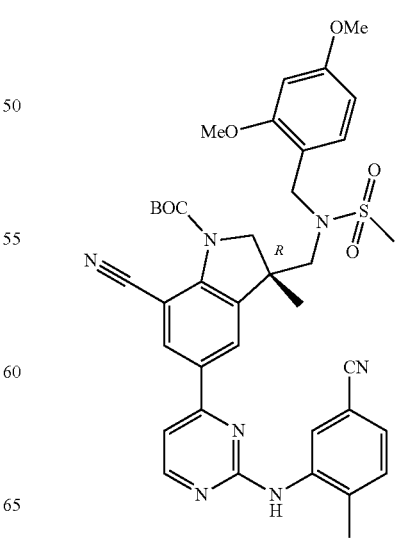

A mixture of intermediate 540 (415 mg; 0.64 mmol), methanesulfonyl chloride (74 µL; 0.96 mmol) and Et₃N (223 µL; 1.61 mmol) in THF (8 mL) was stirred at room temperature for 18 hours. The reaction mixture was poured onto a 10% aqueous solution of K₂CO₃ and extracted with DCM. The organic layer was decanted, dried over MgSO₄, filtered and evaporated to dryness. The residue was purified by chromatography over silica gel (irregular SiOH, 40 g; mobile phase: 0.1% NH₄OH, 99.5% DCM, 0.5% MeOH). The fractions containing the product were collected and evaporated to dryness yielding 318 mg (68%) of intermediate 542.

Example A82

Preparation of Intermediate 543:

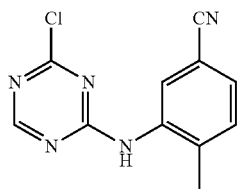 [SMILES: Cc1ccc(C#N)cc1Nc1ncnc(Cl)n1]

DIPEA (1 mL; 5.8 mmol) was added to a solution of 3-amino-4-methylbenzonitrile (661 mg; 5 mmol) and 2,4-dichloro-1,3,5-triazine (750 mg; 5 mmol) in ACN (30 mL). The reaction mixture was stirred overnight at room temperature. The solvent was removed by evaporation and the residue was partioned between water and EtOAc. The organic layer was decanted, washed with water, then brine, dried over MgSO₄, filtered and evaporated to dryness. The residue was purified by chromatography over silica gel (irregular SiOH; mobile phase: gradient from 0% EtOAc, 100% petroleum ether to 50% EtOAc, 50% petroleum ether). The fractions containing the product were collected and evaporated to dryness yielding 700 mg (57%) of intermediate 543.

The intermediate in the table below was prepared using analogous method as described for the preparation of intermediate 243, starting from the respective starting materials. The most relevant minor deviation from the original method is indicated in the column "Quantity"

| Intermediate number | Structure | Quantity | Yield |
|---|---|---|---|
| Intermediate 546 | ![structure] From 3-amino-N,4-dimethylbenzamide and 2,4-dichloro-1,3,5-triazine | 740 mg Procedure with acetone as solvent in place of ACN | 40% |

Preparation of Intermediate 544:

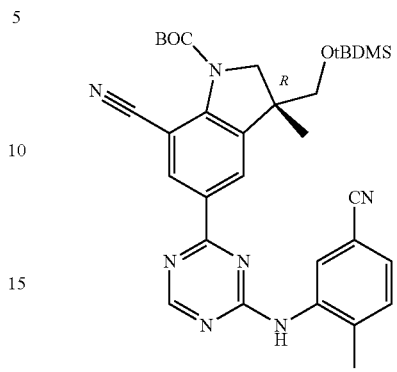

A solution of intermediate 5R (1.58 g; 3 mmol), intermediate 243 (663 mg; 2.7 mmol) and aqueous 2M NaHCO₃ (6 mL; 12 mmol) in 1,4-dioxane (24 mL) was purged with N₂. PdCl₂dppf (219 mg; 0.3 mmol) was added, the reaction mixture was purged again with N₂ and heated at 80° C. for 10 h. The reaction mixture was poured into water and extracted with EtOAc. The organic layer was dried over MgSO₄, filtered and evaporated until dryness. The residue was purified by chromatography over silica gel (irregular SiOH; mobile phase: gradient from 0% EtOAc, 100% petroleum ether to 50% EtOAc, 50% petroleum ether). The fractions were collected and evaporated to dryness yielding 600 mg (32%) of intermediate 544.

The intermediate in the table below was prepared using analogous method as described for the preparation of intermediate 544, starting from the respective starting materials.

| Intermediate number | Structure | Quantity | Yield |
|---|---|---|---|
| Intermediate 547 | ![structure] From intermediate 5R and intermediate 546 | 560 mg | 46% |

Example A83

Preparation of Intermediate 549:

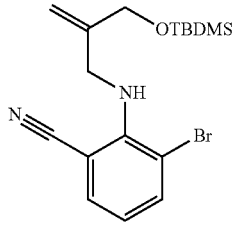 [SMILES: C=C(CNc1c(Br)cccc1C#N)CO[Si](C)(C)C(C)(C)C]

To a solution of 2-Amino-3-bromobenzonitrile (30.0 g) in THF (240 mL) was added sodium tert-butoxide (1.1 eq.) and the mixture was stirred at −5 to 5° C. for 1 hour. A solution of intermediate 3a in THF (85.0 g) was then added dropwise and the mixture was stirred for 2-4 hours monitoring the conversion by High Performance Liquid Chromatography (HPLC). Water (210 mL) was then added dropwise and the mixture was concentrated to remove most of THF. Heptane (300 mL) was then added and the mixture was stirred for 30 min. After phase separation, the organic layer was washed with water (210 mL), concentrated to 2-3 volumes and filtered through a pad of silica gel (60 g), washing the pad with heptane (300 mL), affording 63.3 g of intermediate 549.

Preparation of Intermediate 550:

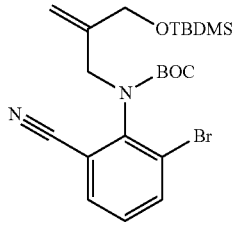 [SMILES: C=C(CO[Si](C)(C)C(C)(C)C)CN(C(=O)OC(C)(C)C)c1c(Br)cccc1C#N]

To a solution of intermediate 549 (50.0 g) in dry THF (500 mL) was added dimethylaminopyridine (0.5 eq.) and the temperature was adjusted to 65-70° C. Di-tert-butyldicarbonate (2.2 eq.) was then added and the mixture was stirred for 2 hours monitoring the conversion by HPLC. Water (350 mL) was added and the mixture was concentrated to 350-400 mL. Heptane (500 mL) was added and the pH was adjusted by addition of 20% aqueous AcOH to 4-6. The layers were separated and water (350 mL) was added. After pH adjustment to 7-8 with aqueous 8% NaHCO₃, the layers were separated and the organic layer was washed with water (350 mL) and concentrated to afford 64 g (quantitative) of intermediate 550.

Example A84

Preparation of Intermediate 553

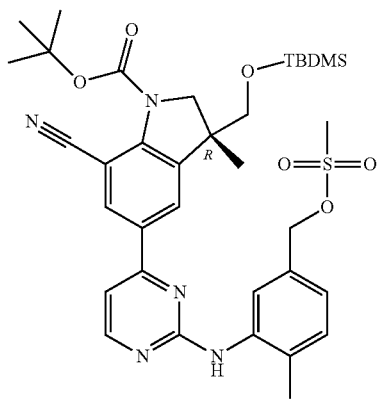

And Intermediate 554

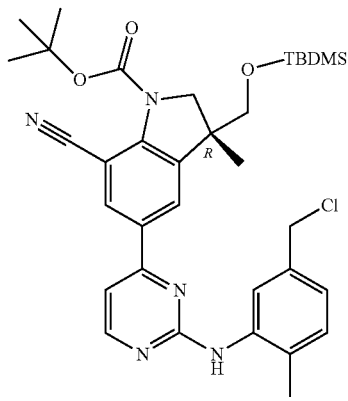

Methanesulfonyl chloride (377 µL; 4.87 mmol) was added dropwise to a solution of intermediate 8 (1.5 g; 2.44 mmol) and Et₃N (848 µL; 6.09 mmol) in DCM (24 mL) at 5° C. under N₂ flow. The reaction mixture was stirred at 5° C. for 1 h, and then 2 h at room temperature. The reaction mixture was poured out into ice water and DCM was added. The organic layer was filtered through CHROMABOND® and the solvent was evaporated (30° C.) to give 1.86 g of orange foam intermediate 553 and intermediate 554. The crude product was used without further purification in the next reaction step.

Preparation of Intermediate 555

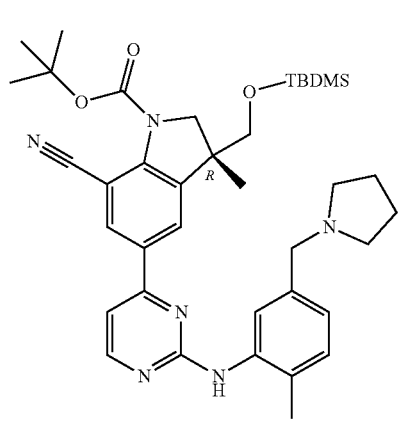

And Intermediate 556

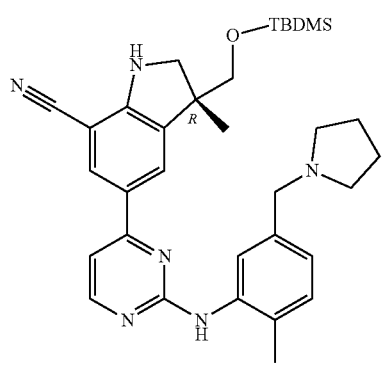

In a sealed tube, a mixture of intermediate 553 and intermediate 554 (269 mg; 0.39 mmol), pyrrolidine (0.32 mL; 3.88 mmol) in ACN (2 mL) was heated at 140° C. using one single mode microwave (Anton Parr®) with a power output ranging from 0 to 400 W for 1 h. The mixture was poured into water and EtOAc. The organic layer was washed with water, brine, dried over MgSO$_4$, filtered and evaporated to dryness. The residue (160 mg, yellow oil) was purified by chromatography over silica gel (irregular bare silica 40 g, mobile phase: 0.4% NH$_4$OH, 96% DCM, 4% MeOH). The fractions containing the products were collected and the solvent was evaporated to give 59 mg of intermediate 555 (23%) and 39 mg of mixture of intermediate 555 and intermediate 556. The two fractions were combined for the next reaction step.

Preparation of Intermediate 560

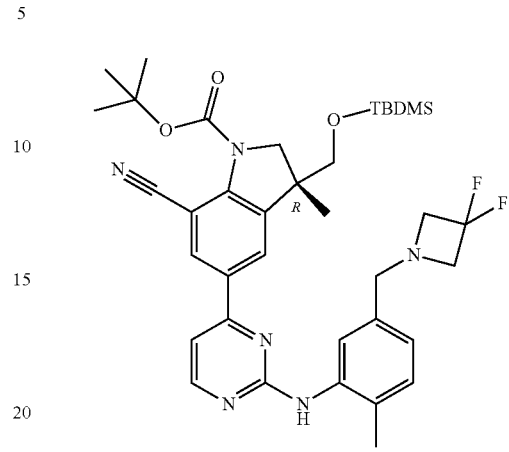

And Intermediate 561

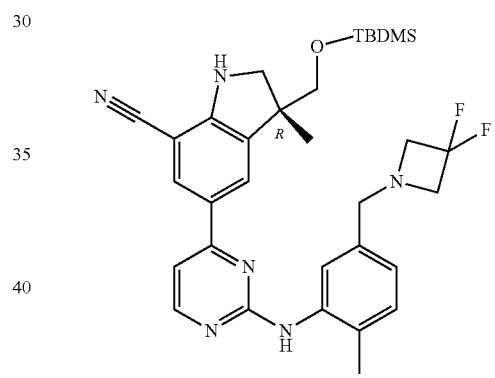

In a sealed tube, a mixture of intermediate 553 and intermediate 554 (850 mg; 1.23 mmol), 3,3-difluoroazetidine hydrochloride (476 mg; 3.68 mmol) and DIPEA (844 μL; 4.9 mmol) in ACN (10 mL) was heated at 140° C. using one single mode microwave (Anton Parr) with a power output ranging from 0 to 400 W for 1 h fixed hold time. The mixture was poured into water and EtOAc. The organic layer was washed with brine, dried over MgSO$_4$, filtered and evaporated to dryness. The residue (1.05 g; orange oil) was purified by chromatography over silica gel (irregular bare silica 40 g; mobile phase: 99% DCM, 1% MeOH). The fractions containing the products were collected and the solvent was evaporated to give 555 mg of mixture of intermediate 560 and intermediate 561.

Preparation of Intermediate 562

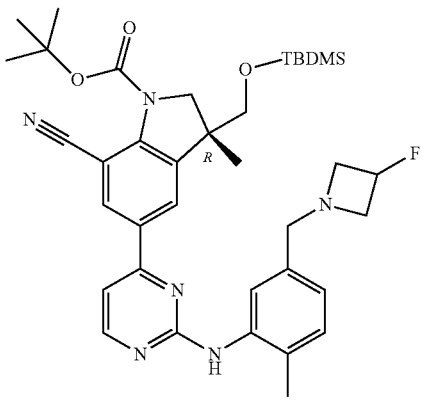

And Intermediate 563

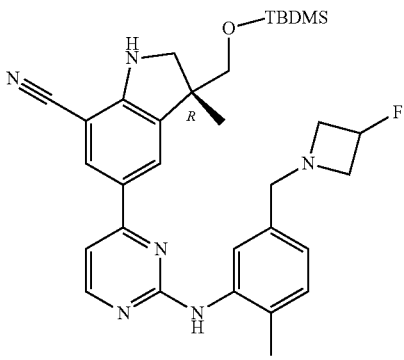

Intermediate 562 and intermediate 563 were prepared according to an analogous procedure as described for the synthesis of a mixture of intermediate 560 and intermediate 561, using a mixture of intermediate 553 and intermediate 554 and 3-fluoroazetidine hydrochloride as starting materials (289 mg; yellow oil mixture of intermediate 562 and intermediate 563).

Preparation of Intermediate 557

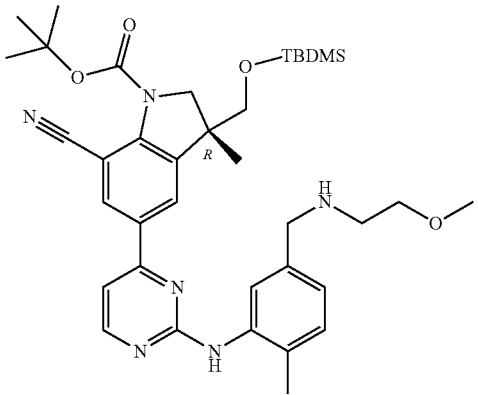

And Intermediate 558

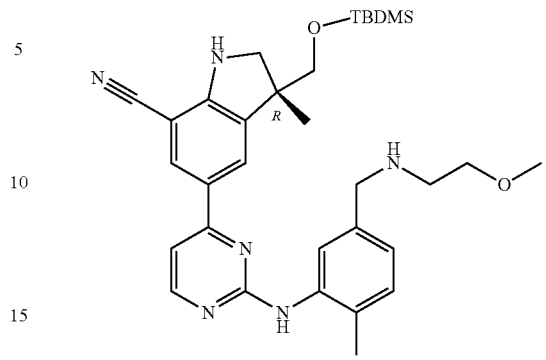

Intermediate 557 and intermediate 558 were prepared according to an analogous procedure as described for the synthesis of a mixture of intermediate 555 and intermediate 556, using a mixture of intermediate 553 and intermediate 554 and 2-methoxyethylamine as starting materials (485 mg).

Preparation of Intermediate 559

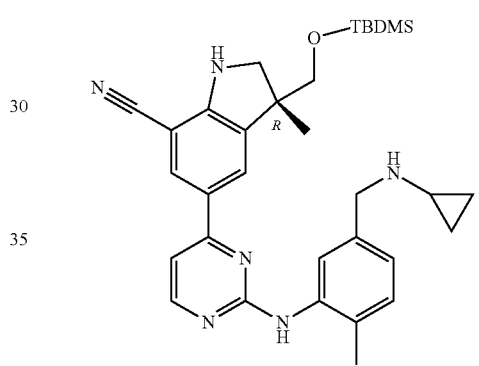

And Intermediate 559Bis

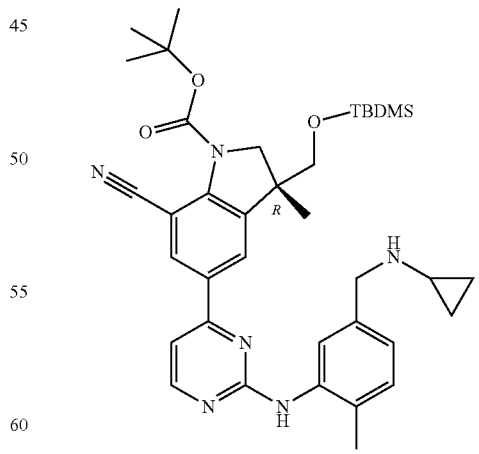

Intermediate 559 (145 mg; 10%) and intermediate 559bis (168 mg; 10%) was prepared according to an analogous procedure as described for the synthesis of a mixture of intermediate 555 and intermediate 556, using a mixture of intermediate 553 and intermediate 554 and cyclopropylamine as starting materials. The time of the reaction was reduced to 5 min due to overpressure.

Example A85

Preparation of Intermediate 564:

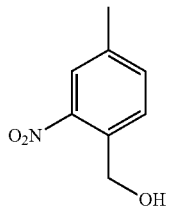

Borane dimethyl sulfide complex (9.9 mL; 19.87 mmol) was added dropwise to a solution of 4-methyl-2-nitrobenzoic acid (3 g; 16.56 mmol) in THF (18 mL) and the mixture was stirred at 80° C. overnight. The mixture was cooled down to rt and a 3M aqueous solution of HCl was added dropwise into the reaction system until effervescence was no longer observed. The mixture was extracted with EtOAc. The organic layer was washed with a saturated aqueous solution of $Na_2CO_3$ and brine, dried over $MgSO_4$, filtered and removed under reduced pressure to give 2.46 g (89%) of intermediate 24.

Preparation of Intermediate 565:

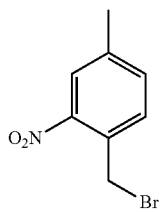

Phosphorus tribromide was added to a solution of intermediate 564 (2.46 g; 14.70 mmol) in diethylether (150 mL). The reaction was stirred at rt overnight. Then, a saturated aqueous solution of $NaHCO_3$ was added dropwise to the reaction mixture until neutral pH was obtained. The mixture was extracted with diethyl ether and the organic layer was washed with brine. The resulting organic layer was dried over $MgSO_4$, filtered and concentrated in vacuo to give 2.39 g (71%) of intermediate 656.

Preparation of Intermediate 567:

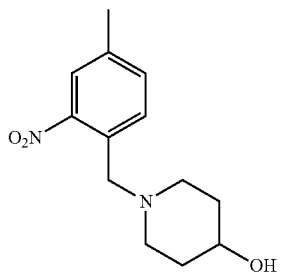 [SMILES: Cc1ccc(CN2CCC(O)CC2)c([N+](=O)[O-])c1]

A mixture of intermediate 566 (1.17 g; 5.09 mmol), 4-hydroxypiperidine (1.03 g; 10.17 mmol) and $Et_3N$ (2.13 mL; 15.26 mmol) in ACN (25 mL) was stirred at reflux 1 h and then, stirred at rt overnight. The reaction mixture was diluted with EtOAc and washed with water and brine. The organic layer was removed under reduced pressure to yield 1 g (78%) of intermediate 567 that was used in the next reaction step without further purification.

Preparation of Intermediate 570:

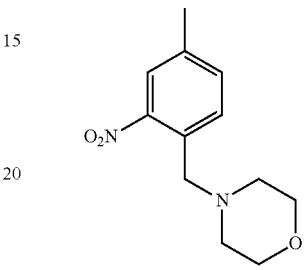

Tetrahydro-1,4-oxazine (574 µL; 6.52 mmol) was added to intermediate 565 (500 mg; 2.17 mmol) in ACN (10 mL) and the solution was heated at 80° C. for 1 h. The mixture was diluted with EtOAc and washed with aqueous $NaHCO_3$ and brine. The organic layer was dried over $MgSO_4$, filtered and removed under reduced pressure to give 500 mg (97%) of intermediate 570.

Example A86

Preparation of Intermediate 578:

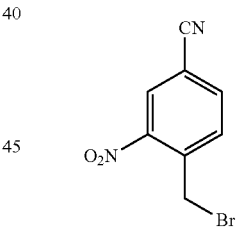

A mixture of 3-nitro-p-tolunitrile (1.2 g; 7.40 mmol), N-bromosuccinimide (2.6 g; 14.80 mmol) and benzoyl peroxide (182 mg; 0.75 mmol) in acetic acid (15 mL) in a sealed tube was heated at 140° C. using one single mode microwave (Biotage Initiator EXP 60®) with a power output ranging from 0 to 400 W for 40 min. The mixture was poured into ice-water, $K_2CO_3$ solid and EtOAc were added. The mixture was extracted with EtOAc (3×). The organic layer was dried over $MgSO_4$, filtered and the solvent was evaporated. The residue was taken up with toluene and the solvent was evaporated to give 1.47 g of brown oil of a mixture of intermediate 578 and 3-nitro-p-tolunitrile which was used in the next reaction step without any further purification.

Preparation of Intermediate 579:

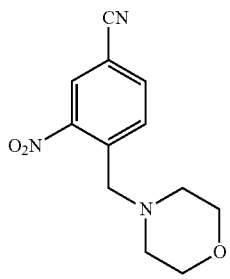

Et$_3$N (1.71 mL; 12.20 mmol) was added to a solution of a mixture intermediate 578 and 3-nitro-p-tolunitrile (1.47 g; 6.10 mmol) and morpholine (0.8 mL; 9.15 mmol) in DCM (20 mL). The reaction was stirred at rt overnight. Water and DCM were added. The mixture was extracted with DCM (3×). The organic layer was dried over MgSO$_4$, filtered and the solvent was evaporated to dryness. The residue (3.07 g) was taken up with DCM and the mixture was filtered off. The cake was washed with DCM (twice) and the filtrate was evaporated to dryness. The residue (1.33 g; brown oil) was purified by chromatography over silica gel (SiO2; 40 g, eluent: from 90% heptane, 10% EtOAc to 80% heptane, 20% EtOAc). The fractions containing the product were collected and the solvent was evaporated to give 226 mg (15%) intermediate 579 as a yellow oil.

Preparation of Intermediate 582.

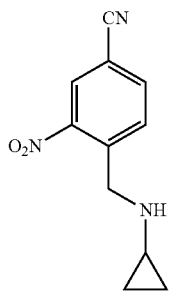 [SMILES: N#Cc1ccc(CNC2CC2)c([N+](=O)[O-])c1]

Cyclopropylamine (367 µL; 5.29 mmol) was added to a mixture of intermediate 578 (500 mg; 1.76 mmol) in ACN (6 mL). The reaction mixture was stirred at room temperature for 1 h. The crude was diluted with EtOAc and washed with NaHCO$_3$ and brine. The organic layer was dried over MgSO$_4$ and removed under reduced pressure to give a crude that was purified by flash chromatography eluting with DCM-MeOH to give 350 mg (91%) of intermediate 582.

Preparation of Intermediate 586:

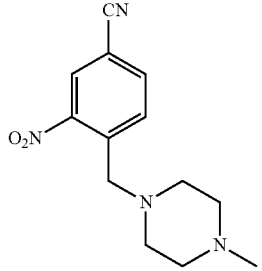 [SMILES: CN1CCN(Cc2ccc(C#N)cc2[N+](=O)[O-])CC1]

Intermediate 578 (400 mg; 1.66 mmol) was added to a mixture of N-methylpiperazine (502 µL; 3.32 mmol) and Et$_3$N (694 µL; 4.98 mmol) in ACN (5 mL). The reaction mixture stirred at room temperature overnight. The solvent was removed and the crude was dissolved in EtOAc and quenched with water. The organic layer was dried, filtered and concentrated. The crude was purified by flash chromatography use heptane and DCM. The pure fractions were collected and the solvent was evaporated to give 250 mg (58%) of intermediate 586.

The compounds in the Table below were prepared by using an analogous method as the one used for the preparation of, starting from the respective starting materials.

| Intermediate number | Structure | Mass (mg) | Yield (%) |
|---|---|---|---|
| Intermediate 590 | 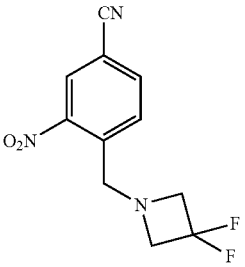 [SMILES: N#Cc1ccc(CN2CC(F)(F)C2)c([N+](=O)[O-])c1]<br>From intermediate 578 and 3,3-difluoroazetidine hydrochloride | 320 | 61 |
| Intermediate 594 | 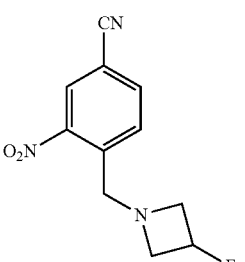<br>From intermediate 578 and 3-fluoroazetidine hydrochloride | 125 (92% purity evaluated by LCMS) | 64 |

Example A87

Preparation of Intermediate 598:

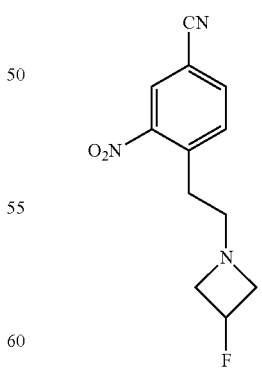

In a sealed tube, a mixture of 4-ethenyl-3-nitro-benzonitrile (353 mg; 2.03 mmol), 3-fluoroazetidine hydrochloride (678 mg; 6.08 mmol) and Et$_3$N (1.1 mL; 8.11 mmol) in MeOH (9 mL) was refluxed for 1 h. The reaction mixture was poured onto water and extracted with DCM. The organic layer was decanted, dried over MgSO$_4$, filtered and evaporated to dryness. The residue (519 mg) was purified by chromatography over silica gel (irregular SiOH, 24 g; mobile phase: gradient from 0.2% NH$_4$OH, 2% MeOH, 98% DCM to 0.5% NH$_4$OH, 5% MeOH, 95% DCM). The fractions containing the product were collected and evaporated to give 431 mg (85%) of intermediate 598.

Example A88

Preparation of Intermediate 602:

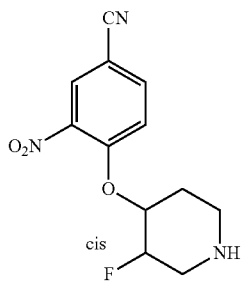 [SMILES: N#Cc1ccc(OC2CCNCC2F)c([N+](=O)[O-])c1]

In a round bottom flask containing intermediate 601 (440 mg; 1.20 mmol) and 1,4-dioxane (7 mL) was added 4M solution of HCl in dioxane (7.5 mL; 30.11 mmol) and the reaction mixture was stirring to room temperature overnight. The crude was concentrated and was quenched with a saturated solution of NaHCO$_3$ and extracted with DCM. The organic layer was dried over anhydrous sodium sulfate and concentrated under vacuum to give 300 mg of intermediate 602 (94%).

The compound in the table below was prepared by using an analogous method as the one used for the preparation of intermediate 602, starting from the respective starting materials.

| Intermediate number | Structure | Mass (mg) | Yield (%) |
|---|---|---|---|
| Intermediate 608 | 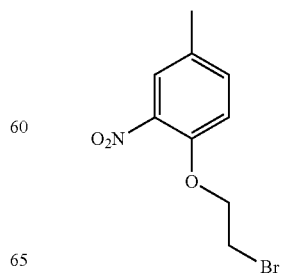 From intermediate 607 | 130 | 90 |

Preparation of Intermediate 603:

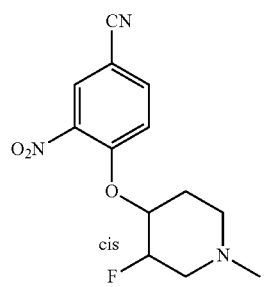 [SMILES: CN1CCC(Oc2ccc(C#N)cc2[N+](=O)[O-])C(F)C1]

To a solution of intermediate 602 (300 mg; 1.13 mmol) in MeOH (mL) was added formaldehyde (184 µL; 2.26 mmol) and then formic acid (427 µL; 0.01 mmol). The reaction mixture was stirred at room temperature 1 h. Then, sodium triacetoxyborohydride (300 mg; 1.41 mmol) was added and the stirring was continued for 1 h. Then, the reaction mixture was carefully quenched by addition of saturated solution of NaHCO$_3$ and extracted with EtOAc. The organic layer was evaporated to dryness and loaded into a silica gel column (ethyl acetate 100%). The pure fractions were collected and the solvent was evaporated to give 250 mg (79%) of intermediate 603.

The compound in the table below was prepared by using an analogous method as the one used for the preparation of intermediate 603 starting from the respective starting materials.

| Intermediate number | Structure | Mass (mg) | Yield (%) |
|---|---|---|---|
| Intermediate 609 | From intermediate 608 | 99 | 72 |

Example A89

Preparation of Intermediate 623:

4-Methyl-2-nitrophenol (1 g; 6.53 mmol) was dissolved in ACN (50 mL), producing a clear, bright yellow solution. K$_2$CO$_3$ (4.5 g; 32.65 mmol) was added, and the reaction was stirred until the color darkened to a deep red. 1,2-dibromoethane (2.8 mL; 32.65 mmol) was added and the reaction was refluxed 80° C. overnight. The reaction mixture was filtered and the filtrate was evaporated. The crude (yellow oil) was purified on a silica gel column, eluting with 5% EtOAc/heptane to give 1.37 g (80%) of intermediate 623.

Preparation of Intermediate 624:

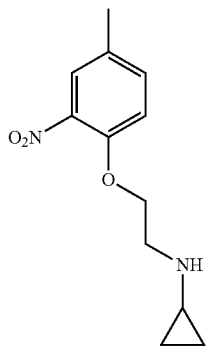

Intermediate 624 was prepared following a similar protocols than the one used for the preparation of intermediate 570 starting from intermediate 623 and cyclopropylamine (600 mg; 48%).

Preparation of Intermediate 625:

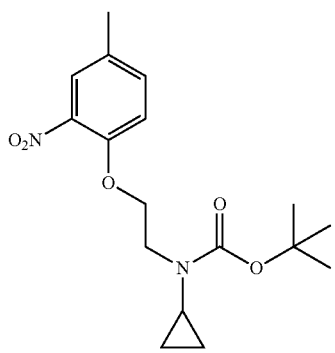 [SMILES: Cc1ccc(OCCN(C(=O)OC(C)(C)C)C2CC2)c([N+](=O)[O-])c1]

A solution of intermediate 624 (550 mg; 2.33 mmol) in DCM (10 mL) at 0° C. was added Boc$_2$O (559 mg; 2.56 mmol). The mixture was stirred at rt for 2 h. The crude was diluted with DCM and washed with water, dried over MgSO$_4$ and removed under reduced pressure to give a crude that was purified by flash chromatography eluting with DCM-MeOH. The fractions containing the product were collected and the solvent was evaporated to give 704 mg (90%) of intermediate 625.

Example A90

Preparation of Intermediate 628:

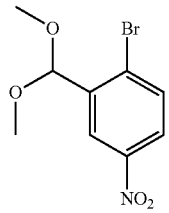

In a round bottom flask, 2-bromo-5-nitrobenzene carbaldehyde (29.17 g, 0.127 mol), trimethyl orthoformate (21 mL, 0.192 mol), p-toluenesulfonic acid monohydrate (2.4 g, 12.6 mmol) were mixed in MeOH (600 mL). Then, the reaction mixture was refluxed for 8 hours. The reaction was cooled down and the solvent was removed. The residue was taken up with water, K$_2$CO$_3$ and DCM. The organic layer was separated, dried over MgSO$_4$, filtered and evaporated until dryness to give 34 g (97%) of intermediate 628.

Preparation of Intermediate 629:

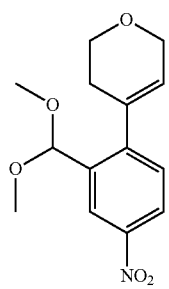 [SMILES: COC(OC)c1cc([N+](=O)[O-])ccc1C1=CCOCC1]

A mixture of intermediate 628 (15 g; 54.33 mmol), 1,2,3,6-Tetrahydropyran-4-boronic acid pinacol ester (13.8 g; 65.7 mmol), potassium phosphate (34.8 g; 0.164 mol), PdCl$_2$dppf.DCM (4.5 g; 5.5 mmol) in dioxane (210 mL) and water (60 mL) was degassed with N$_2$ in a sealed tube and heated at 80° C. for 16 hours. The mixture was poured into a mixture of water and K$_2$CO$_3$ and extracted with EtOAc. The organic layer was dried over MgSO$_4$, filtered and evaporated until dryness. The residue (25.5 g) was purified by silica gel chromatography (330 g of SiOH 35-40 μm, gradient from 90% heptane 10% EtOAc to 60% heptane 40% EtOAc). The fractions were collected and evaporated until dryness to give 12.21 g (80%) of intermediate 629.

Preparation of Intermediate 630:

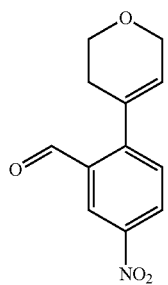 [SMILES: O=Cc1cc([N+](=O)[O-])ccc1C1=CCOCC1]

HCl (3M in water; 58.28 mL; 0.175 mol) was added to a solution of intermediate 630 (12.21 g; 43.72 mmol) in 1,4-dioxane (233 mL) at room temperature. The mixture was stirred for 2 hours. Water then EtOAc was added. The organic layer was separated, dried over MgSO$_4$, filtered and evaporated until dryness to afford 8.97 g (88%) of intermediate 630.

Preparation of Intermediate 631:

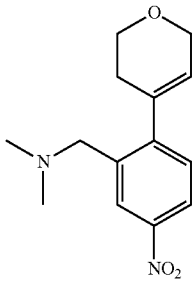 [SMILES: CN(C)Cc1cc([N+](=O)[O-])ccc1C1=CCOCC1]

A solution of intermediate 630 (8.97 g; 38.5 mmol), dimethylamine (9.7 mL; 76.6 mmol) in ACN (240 mL) was stirred for 30 min. Then, sodium triacetoxyborohydride (16.3 g; 76.9 mmol) was added and stirred at room temperature for 15 hours. Water was added and the reaction mixture was basified with K$_2$CO$_3$ and extracted with EtOAc. The organic layer was dried over MgSO$_4$, filtered and evaporated until dryness. A purification of the residue (8.24 g) was performed by silica gel chromatography (Stationary phase: irregular SiOH 15-40 µm 120 g, Mobile phase: gradient from DCM 100% to DCM 95%, MeOH 5%, 0.1% NH$_4$OH). The desired fractions were collected and solvent evaporated until dryness to give 2.15 g of intermediate 631 and 4.22 g of an impure fraction which was purified by silica gel chromatography (Stationary phase: irregular SiOH 15-40 µm 80 g, Mobile phase: gradient from DCM 100% to DCM 95%, MeOH 5%, 0.1% NH$_4$OH). The desired fractions were collected and solvent evaporated until dryness to give additional 2.65 g of intermediate 631. Global yield: 47%

Preparation of Intermediate 632:

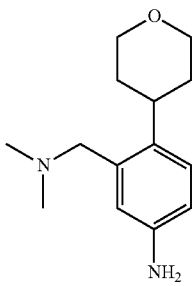 [SMILES: CN(C)Cc1cc(N)ccc1C1CCOCC1]

A mixture of intermediate 632 (2.15 g; 8.2 mmol), Pd/C 10% (0.43 g) in MeOH (50 mL) was hydrogenated with 3 bars of H$_2$ at room temperature for 15 hours. The mixture was filtered through a Celite® pad and the filtrate was evaporated until dryness to give 1.76 g (92%) of intermediate 632.

Example A91

Preparation of Intermediate 635:

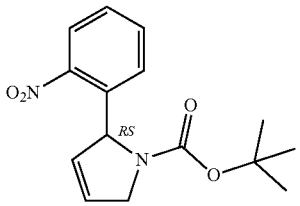 [SMILES: CC(C)(C)OC(=O)N1CC=CC1c1ccccc1[N+](=O)[O-]]

In a sealed glassware, a mixture of 1-bromo-2-nitrobenzene (800 mg; 3.96 mmol), N-Boc-2,3-dihydro-1H-pyrrole (938 mg; 5.54 mmol) and potassium carbonate (1.6 g; 11.88 mmol) in DMF dry (30 mL) was bubbled with nitrogen (10 minutes). Then, triphenylphosphine (207 mg; 0.792 mmol) and Pd(OAc)$_2$ (89 mg; 0.396 mmol) were added. The reaction mixture was heated to 100° C. overnight, cooled to room temperature, poured onto water and extracted with EtOAc. The mixture was filtered through a pad of Celite® and the organic layer was decanted, washed with brine, dried over MgSO$_4$, filtered and evaporated to dryness. The residue was purified by chromatography over silica gel (irregular SiOH, 40 g; mobile phase: gradient from 20% EtOAc, 80% heptane to 40% EtOAc, 60% heptane). The fractions containing the product were collected and evaporated to dryness yielding 482 mg (42%) of intermediate 635.

Preparation of Intermediate 636:

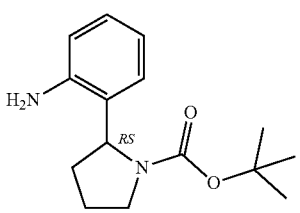 [SMILES: CC(C)(C)OC(=O)N1CCCC1c1ccccc1N]

A mixture of intermediate 635 (482 mg; 1.66 mmol) and Adam's catalyst (Platinum(IV) oxide) (75 mg; 0.332 mmol) in EtOH (40 mL) were hydrogenated under 2 bars of H$_2$ for 2 h. The catalyst was removed by filtration over Celite® and the filtrate was evaporated to dryness yielding 437 mg of intermediate 636.

Example A92

Preparation of Intermediate 638

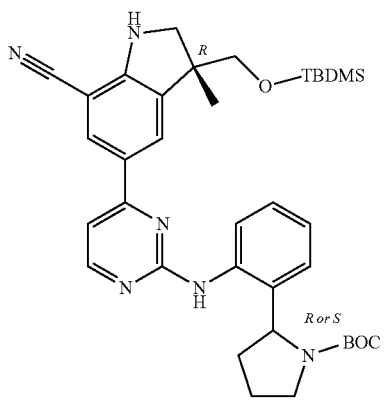

And Intermediate 639

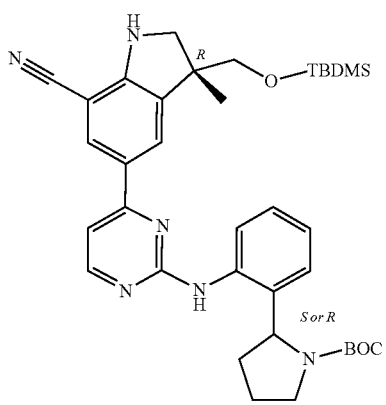

Intermediates 638 and 639 were obtained via a SFC separation performed on intermediate 637 (CHIRALPAK AD-H 5 μm 250×20 mm; mobile phase: 80% CO$_2$, 20% iPrOH). The pure fractions were collected and evaporated to dryness yielding 169 mg of intermediate 638 and 177 mg of intermediate 639

Example A93

Preparation of Intermediate 640

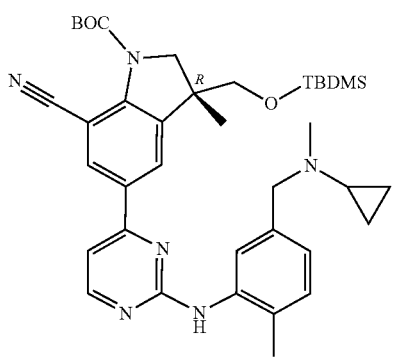

Sodium triacetoxyborohydride (133 mg; 0.63 mmol) was added to a mixture of intermediate 559bis (164 mg; 0.25 mmol), formaldehyde (375 μL; 5.01 mmol), acetic acid (28.7 μL; 0.50 mmol) in MeOH (2 mL) at rt. The reaction mixture was stirred at rt under N$_2$ overnight. The mixture was basified with a saturated aqueous solution of NaHCO$_3$ and the solvent was evaporated. The mixture was diluted with EtOAc and washed with a saturated aqueous solution of NaHCO$_3$. The aqueous layer was extracted with EtOAc (2×). The organics layers were combined and washed with water, brine, dried over MgSO$_4$, filtered and the solvent was evaporated.

The residue (209 mg) was purified by chromatography over silica gel (SiO$_2$, 4 g; eluent: from 99% DCM, 1% MeOH, 0.1% NH$_4$OH to 99% DCM, 1% MeOH, 0.1% NH$_4$OH). The fractions containing the product were collected and the solvent was evaporated to afford 106 mg (63%) of intermediate 640 as a yellow oil.

Example A94

Preparation of Intermediate 642:

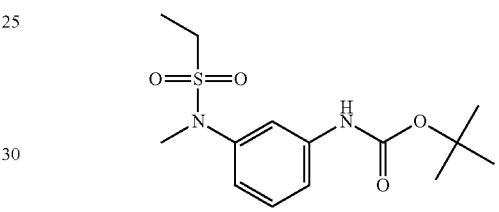

Ethanesulfonyl chloride (1.28 mL; 13.5 mmol) was added into a solution of tert-butyl-(3-(methylamino)phenyl)carbamate (2 g, 9 mmol), triethylamine (3.79 mL, 26.99 mmol) in ACN (100 mL) at room temperature. The solution was stirred at room temperature for 4 h00. Water was added and the reaction mixture was extracted with DCM. The organic layer was separated and dried over MgSO$_4$, filtered and the solvent was evaporated.

The residue (3.2 g) was purified by silica gel chromatography (Irregular SiOH, 40 μm, 80 g, Mobile phase: gradient from 90%: DCM, 10% Heptane to 97% DCM, 3% MeOH, 0.3% NH$_4$OH. The fractions were combined and the solvent was evaporated to give 2.55 g of an impure fraction which was repurified by silica gel chromatography (Irregular SiOH, 40 μm, 80 g, Mobile phase: gradient from 70%: DCM, 30% Heptane to 97% DCM, 3% MeOH, 0.3% NH$_4$OH. The fractions were combined and the solvent was evaporated to give 1.24 g (39%, 88% of purity based on LC/MS) of intermediate 642 (39% pure at 88%).

Preparation of Intermediate 643:

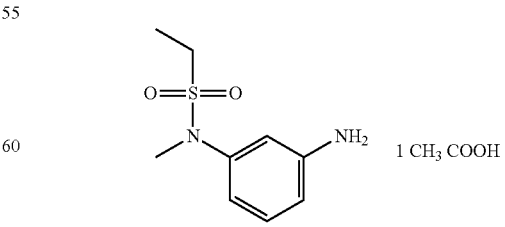

A solution of intermediate 642 (1.24 g, 3.47 mmol) in TFA (2.66 mL, 34.71 mmol) and DCM (22.1 mL) was stirred at rt for 12 h. The solvent was evaporated.

439

The residue was purified by silica gel chromatography (irregular SiOH, 15-40 μm, 40 g, mobile phase: from DCM: 100% to DCM: 97%, MeOH: 3%, NH₄OH: 0.3%) to give 1.17 g of intermediate 643.

B. Preparation of the Final Compounds

Example B1

Preparation of Compound 1

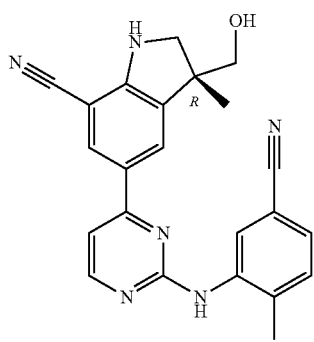

A mixture of intermediate 8R (36.00 g, 71.08 mmol) and TBAF (1M in THF, 142.15 mL, 142.15 mmol) in Me-THF (0.7 L) was stirred at rt for 3 h 30 min. The reaction mixture was poured onto a 10% aqueous solution of K₂CO₃ (700 mL), diluted with EtOAc (700 mL). Then, 100 mL of a saturated solution of NaCl was added (to help the decantation). The organic layer was decanted, washed again with 300 mL of a 10% aqueous solution of K₂CO₃ (+100 mL of a saturated solution of NaCl), then with a saturated solution of NaCl (200 mL). The organic layer was dried over MgSO₄, filtered and concentrated under vacuum. The residue was taken up 3 times with 300 mL of EtOH and evaporated to dryness. The residue was taken up with CH₃CN and stirred at 50° C. Then, the precipitate was filtered and dried (50° C. under vacuum for 5 h) to give 27 g of compound 1 (96% yield). Then, different batches of compound 1 coming from different reactions (batch 1: 36.8 g, batch 2: 27 g, batch 3: 5.7 g, batch 4: 7.45 g and batch 5: 6.7 g) were mixed together in CH₃N (250 mL) and the suspension was stirred for 15 min. The precipitate was filtered and dried at 50° C. overnight to give 81.1 g of compound 1 (97.1% yield). M.P.: 222° C. (DSC).

Preparation of Compound 4:

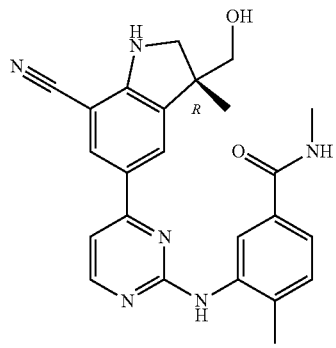

A solution of intermediate 19 (403.00 mg, 0.74 mmol) in Me-THF (8.9 mL) was treated with TBAF (1M in THF) (0.82 mL, 0.82 mmol) and stirred at rt for 17 h. Celite® was added and the crude mixture was evaporated in vacuo to give a dry load which was purified by column chromatography on silica gel (irregular SiOH 15-40 μm, 40 g, mobile phase: DCM/(MeOH containing 5% aq. NH₃), gradient from 98:2 to 85:15). The fractions containing the product were combined and evaporated to dryness to give a solid. This solid was recrystallized from EtOH. After cooling down to rt, the mixture was filtered on a glass frit. The solid was washed with Et₂O, collected and dried in vacuo to afford 191 mg of compound 4 (60% yield over 2 steps, pale yellow solid). M.P.=193° C. (DSC).

Preparation of Compound 68:

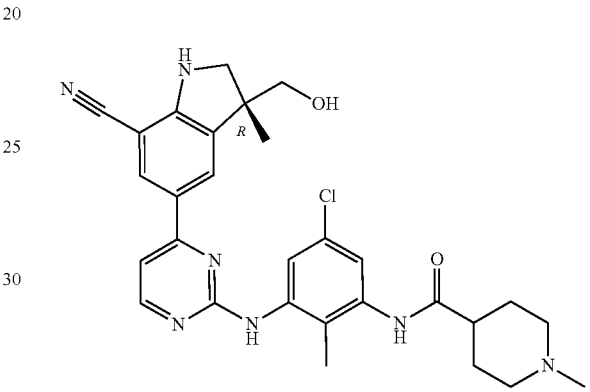

A mixture of intermediate 237 (132.00 mg, 0.20 mmol) and TBAF (1M in THF) (0.30 mL, 1 M, 0.30 mmol) in Me-THF (1.60 mL) was stirred at rt for 24 h. The mixture was poured out onto water and the organic layer was extracted with EtOAc, dried over MgSO₄, filtered and evaporated until dryness (batch 1, 52 mg). The aqueous phase was extracted again with DCM and MeOH. The organic layer was dried over MgSO₄, filtered and evaporated to dryness (batch 2, 770 mg). An insoluble product in the aqueous layer was filtered over Celite®. The celite was washed successively with DCM and MeOH. This organic layer was dried over MgSO₄, filtered and evaporated to dryness (batch 3, 300 mg). The batches were combined and purified by column chromatography on silica gel (Irregular SiOH, solid deposits, mobile phase: DCM/MeOH, gradient from 100:0 to 90:10). The pure fractions were collected and the solvent was evaporated. The residue (84 mg) was taken up in EtOH, triturated, filtered and dried to give 31 mg of compound 68 (28% yield).

The compounds in the Table below were prepared by using an analogous method as the one reported for the preparation of compound 1, starting from the respective starting materials. The most relevant minor deviations to the reference method are indicated as additional information in the column 'Mass (mg)'.

| Compound number | Structure | Mass (mg) | Yield (%) |
|---|---|---|---|
| Compound 2 | 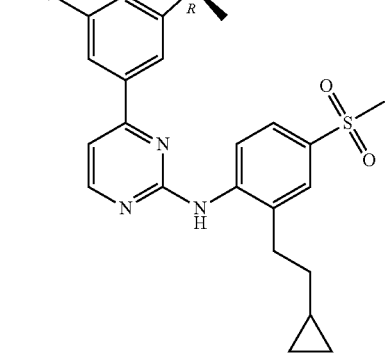 From a mixture of intermediate 13 and intermediate 14 | 310 pale yellow foam Procedure with 1 equiv of TBAF | 55 |
| Compound 3 | 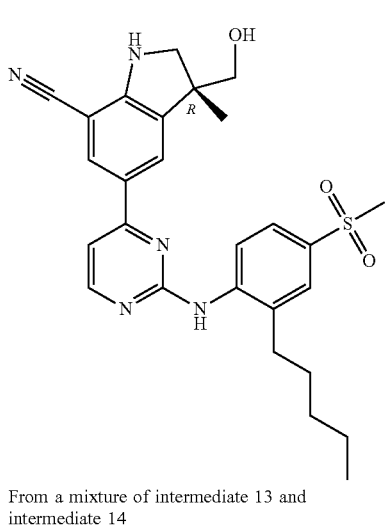 From a mixture of intermediate 13 and intermediate 14 | 52 yellow fluffy solid Procedure with 1 equiv of TBAF | 9 |
| Compound 5 | 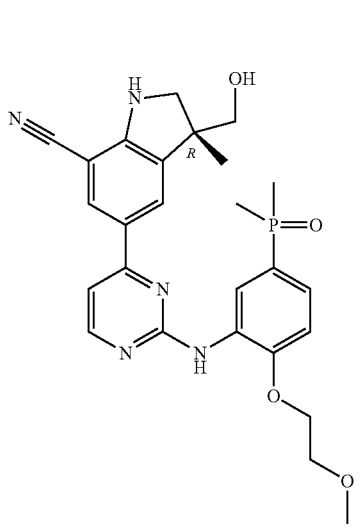 From intermediate 20 | 79 Procedure with 1 equiv of TBAF | 39 |

-continued

| Compound number | Structure | Mass (mg) | Yield (%) |
|---|---|---|---|
| Compound 6 | From intermediate 21 | 173 Procedure with 1 equiv of TBAF | 65 |
| Compound 10 | From intermediate 42 | 37 white powder | 8 |
| Compound 11 | From intermediate 46 | 228 off-white solid Procedure with 1 equiv of TBAF | 87 |

| Compound number | Structure | Mass (mg) | Yield (%) |
|---|---|---|---|
| Compound 12 | 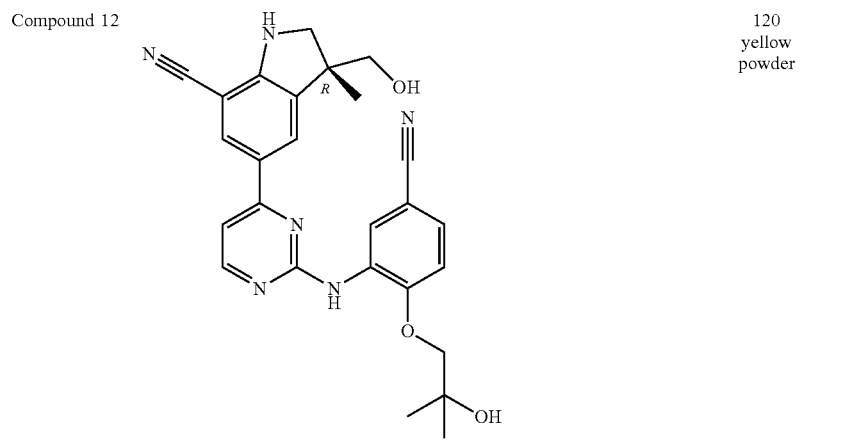<br>From intermediate 49 | 120<br>yellow<br>powder | 41 |
| Compound 13 | 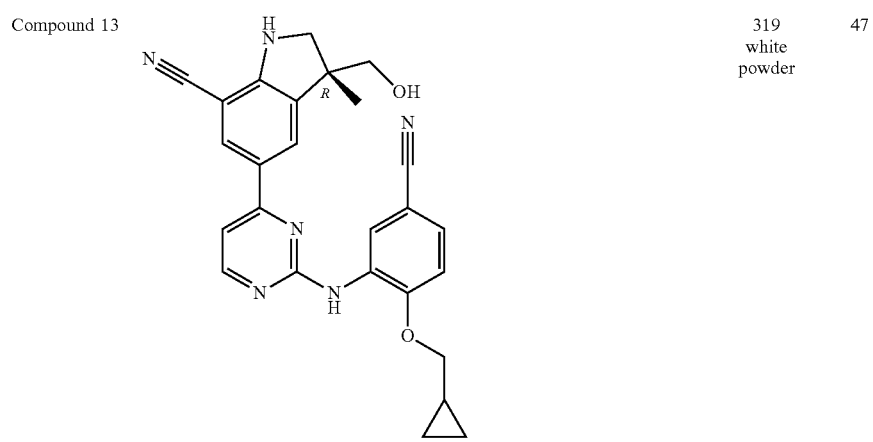<br>From intermediate 52 | 319<br>white<br>powder | 47 |
| Compound 14 | 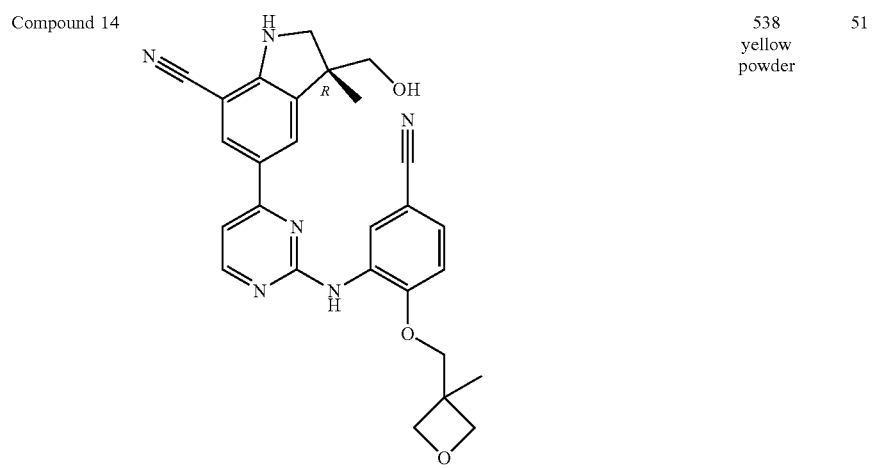<br>From intermediate 55 | 538<br>yellow<br>powder | 51 |

-continued
| Compound number | Structure | Mass (mg) | Yield (%) |
|---|---|---|---|
| Compound 16 | 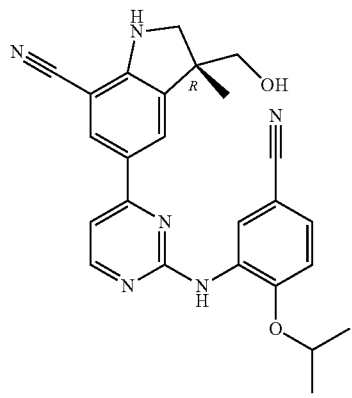<br>From intermediate 60 | 426 yellow powder | 53 |
| Compound 26 | 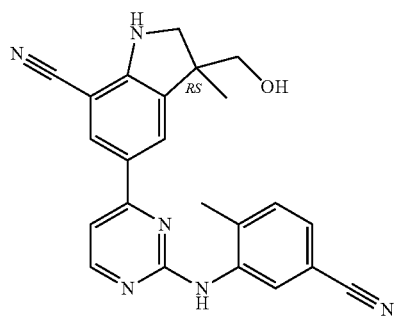<br>From intermediate 104 | 121 yellow solid Procedure with 1 equiv of TBAF | 60 |
| Compound 27 | 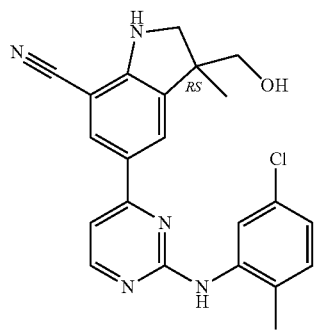<br>From intermediate 107 | 276 white solid Procedure with 1 equiv of TBAF | 97 |
| Compound 32 | 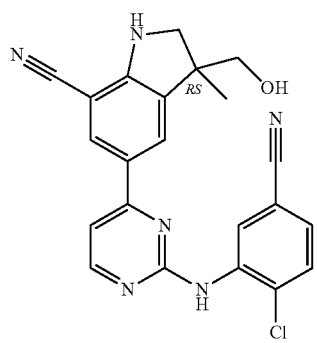<br>From intermediate 119 | 68 white solid Procedure with 1 equiv of TBAF | 35 |

-continued

| Compound number | Structure | Mass (mg) | Yield (%) |
|---|---|---|---|
| Compound 33 | From intermediate 121 | 49 yellow solid Procedure with 1 equiv of TBAF | 35 |
| Compound 37 | From intermediate 136 | 44 Procedure with 1 equiv of TBAF | 59 |
| Compound 38 | From intermediate 140 | 102 Procedure with 1 equiv of TBAF | 65 |
| Compound 47 | From intermediate 170 | 70 Procedure with 1 equiv of TBAF | 61 |

-continued

| Compound number | Structure | Mass (mg) | Yield (%) |
|---|---|---|---|
| Compound 48 | From intermediate 172 | 62 Procedure with 1 equiv of TBAF | 59 |
| Compound 49 | From intermediate 174 | 69 Procedure with 1 equiv of TBAF | 42 |
| Compound 50 | CIS From intermediate 180 | 94 Procedure with 1 equiv of TBAF | 49 |
| Compound 51 | From intermediate 182 | 47 Procedure with 1 equiv of TBAF | 80 |

-continued
| Compound number | Structure | Mass (mg) | Yield (%) |
|---|---|---|---|
| Compound 52 | 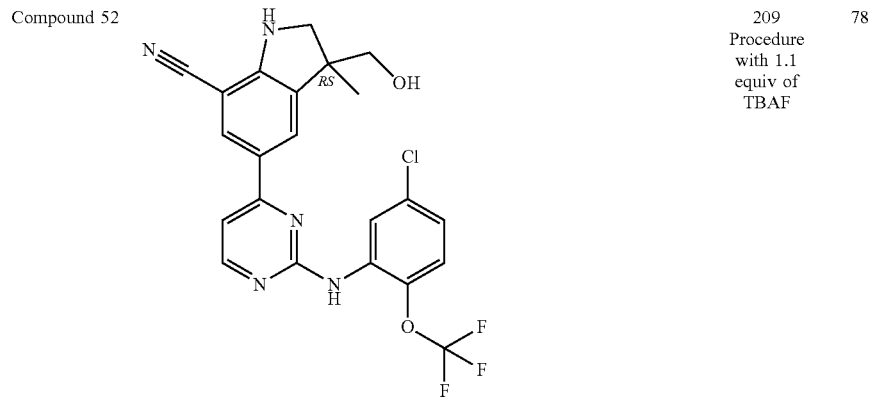<br>From intermediate 184 | 209<br>Procedure with 1.1 equiv of TBAF | 78 |
| Compound 53 | 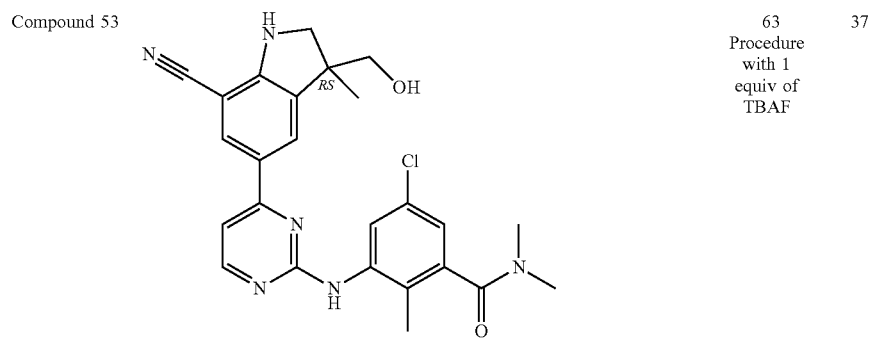<br>From intermediate 188 | 63<br>Procedure with 1 equiv of TBAF | 37 |
| Compound 54 | 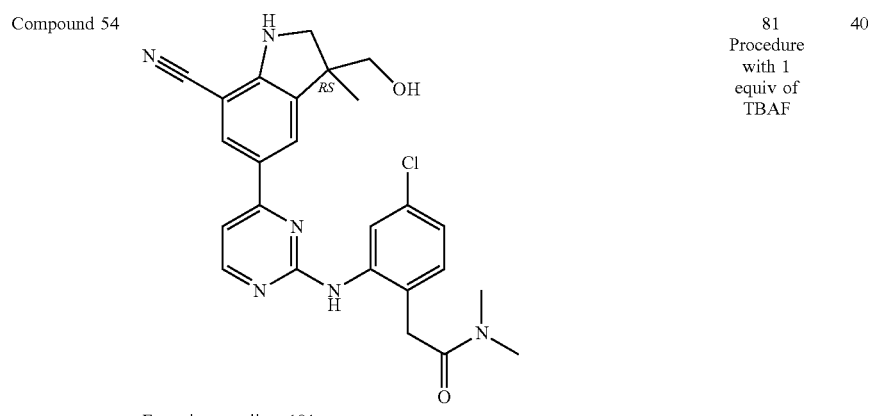<br>From intermediate 191 | 81<br>Procedure with 1 equiv of TBAF | 40 |

-continued

| Compound number | Structure | Mass (mg) | Yield (%) |
|---|---|---|---|
| Compound 55 | From intermediate 194 | 103 Procedure with 1 equiv of TBAF | 49 |
| Compound 56 | From intermediate 195 | 68 Procedure with 1 equiv of TBAF | 31 |
| Compound 58 | From intermediate 199 | 121 Procedure with 1 equiv of TBAF | 54 |
| Compound 59 | From intermediate 204 | 115 Procedure with 1.3 equiv of TBAF | 84 |

-continued

| Compound number | Structure | Mass (mg) | Yield (%) |
|---|---|---|---|
| Compound 61 | 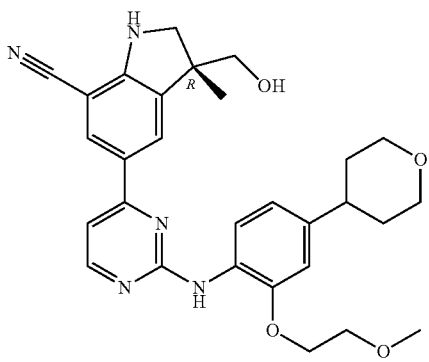<br>From intermediate 211 | 164<br>off-white<br>solid<br>Procedure<br>with 1.5<br>equiv of<br>TBAF | 97 |
| Compound 62 | 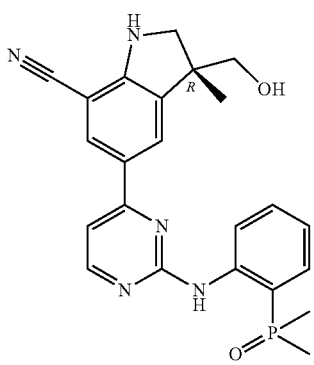<br>From intermediate 213 | 175<br>yellow<br>solid<br>Procedure<br>with 1.6<br>equiv of<br>TBAF | 92 |
| Compound 63 | 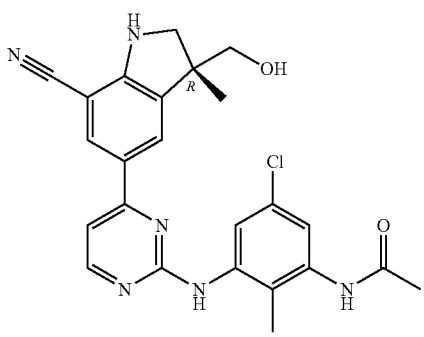<br>From intermediate 219 | 70<br>Procedure<br>with 1.5<br>equiv of<br>TBAF | 49 |
| Compound 64 | 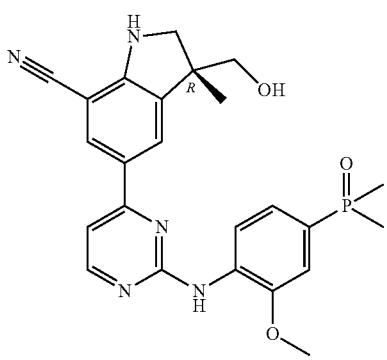<br>From intermediate 223 | 105<br>white solid<br>Procedure<br>with 1.8<br>equiv of<br>TBAF | 40 |

-continued

| Compound number | Structure | Mass (mg) | Yield (%) |
|---|---|---|---|
| Compound 67 | From intermediate 233 | 184 white solid Procedure with 1.8 equiv of TBAF | 65 |
| Compound 147 | From intermediate 392 | 310 White morphous solid Procedure with 4 equiv of TBAF and solvent | 98 |
| Compound 148 | From intermediate 394 | 1987 | 81 |
| Compound 149 | From intermediate 398 | 45 Procedure with 1.2 equiv of TBAF and THF as solvent | 25 |

-continued

| Compound number | Structure | Mass (mg) | Yield (%) |
|---|---|---|---|
| Compound 150 | From intermediate 404 | 108 Procedure with 1.2 equiv of TBAF and THF as solvent | 80 |
| Compound 151 | From intermediate 407 | 24 Procedure with 1.2 equiv of TBAF and THF as solvent | 32 |
| Compound 152 | From intermediate 411 | 234 Procedure with 1.1 equiv of TBAF | 49 |
| Compound 153 | From intermediate 412 | 74 | 51 |

-continued
| Compound number | Structure | Mass (mg) | Yield (%) |
|---|---|---|---|
| Compound 154 | 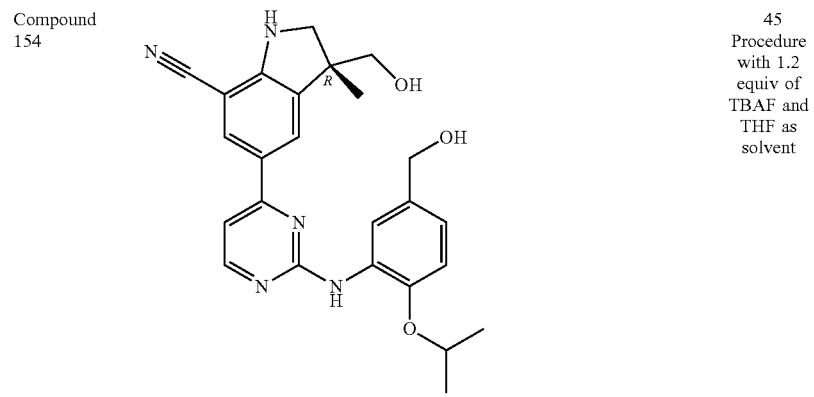<br>From intermediate 419 | 45<br>Procedure with 1.2 equiv of TBAF and THF as solvent | 26 |
| Compound 157 | 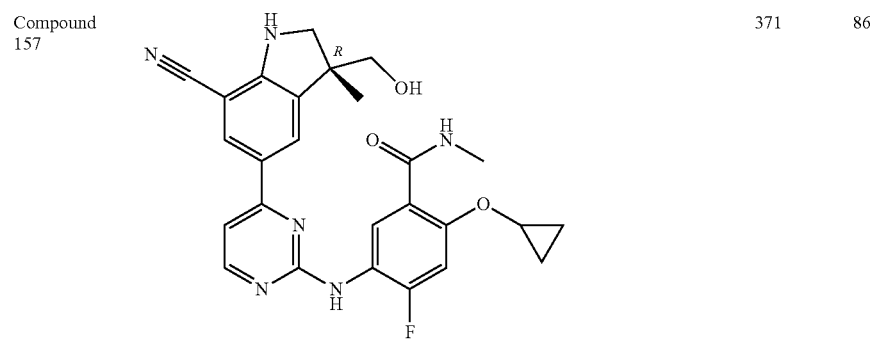<br>From intermediate 431 | 371 | 86 |
| Compound 158 | 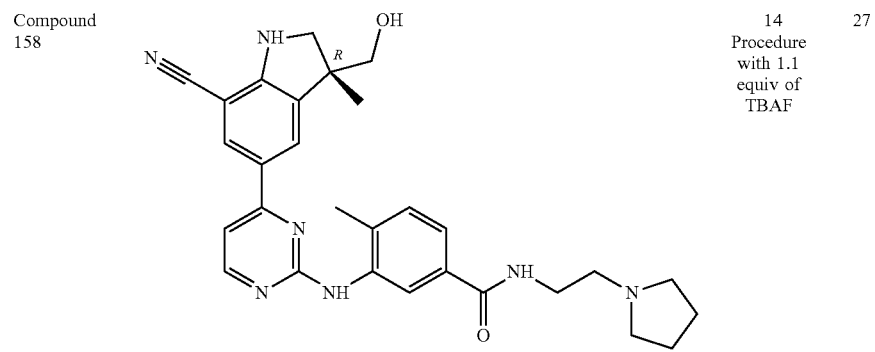<br>From intermediate 433 | 14<br>Procedure with 1.1 equiv of TBAF | 27 |
| Compound 159 | 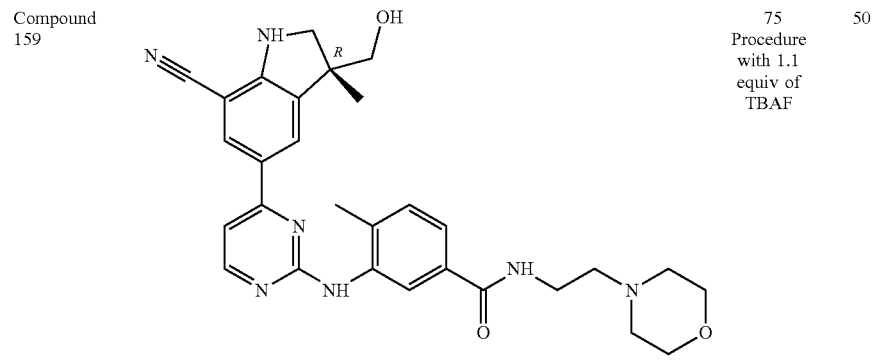<br>From intermediate 435 | 75<br>Procedure with 1.1 equiv of TBAF | 50 |

-continued
| Compound number | Structure | Mass (mg) | Yield (%) |
|---|---|---|---|
| Compound 160 | 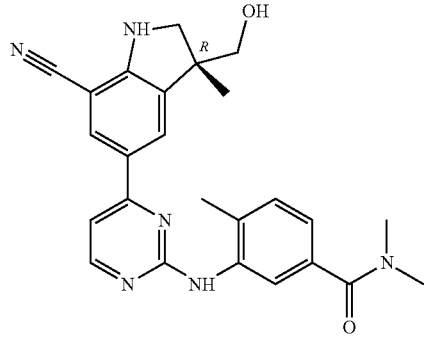<br>From intermediate 437 | 205 Procedure with 1.1 equiv of TBAF | 73 |
| Compound 161 | 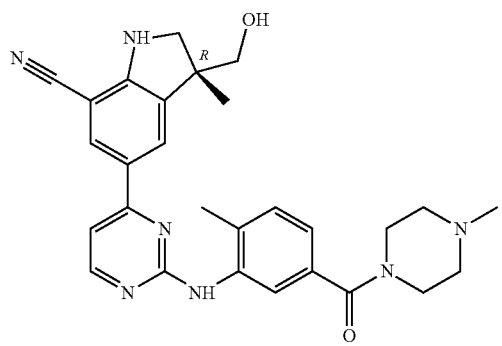<br>From intermediate 439 | 236 Procedure with 1.1 equiv of TBAF | 66 |
| Compound 162 | 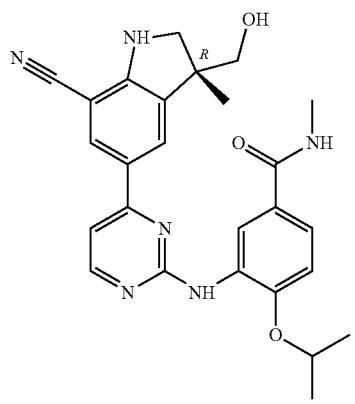<br>From intermediate 440 | 302 | 63 |
| Compound 163 | 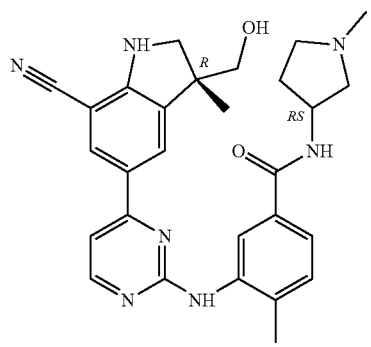<br>From intermediate 442 | 148 | 50 |

-continued

| Compound number | Structure | Mass (mg) | Yield (%) |
|---|---|---|---|
| Compound 165 | From intermediate 444 | 233 | 69 |
| Compound 166 | From intermediate 448 | 100 | 68 |
| Compound 167 | From intermediate 449 | 103 | 72 |
| Compound 168 | From intermediate 453 | 72 | 71 |

-continued

| Compound number | Structure | Mass (mg) | Yield (%) |
|---|---|---|---|
| Compound 169 | From intermediate 454 | 215 | 84 |
| Compound 170 | 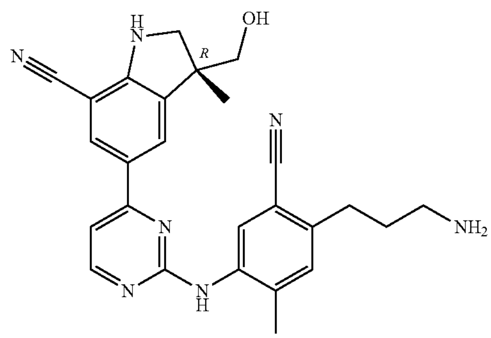 | 41 Procedure with 1.1 equiv of TBAF | 56 |
| Compound 173 | From intermediate 468 | 143 Procedure with 1.1 equiv of TBAF | 44 |
| Compound 174 | From intermediate 471 | 90 Procedure with 1.1 equiv of TBAF | 42 |

| Compound number | Structure | Mass (mg) | Yield (%) |
|---|---|---|---|
| Compound 175 | From intermediate 474 | 51 Procedure with 1.1 equiv of TBAF | 46 |
| Compound 177 | From intermediate 479 | 180 Procedure with 1.1 equiv of TBAF | 61 |
| Compound 186 | From intermediate 491 | 87 | 74 |
| Compound 187 | From intermediate 496 | 89 | 66 |

-continued
| Compound number | Structure | Mass (mg) | Yield (%) |
|---|---|---|---|
| Compound 188 | 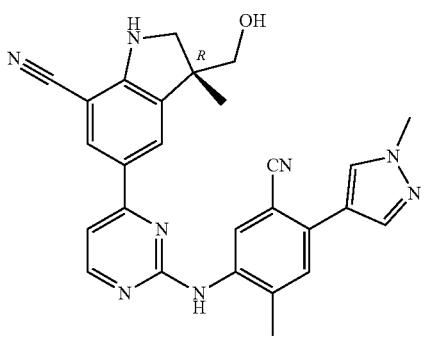<br>From intermediate 502 | 177 | 39 |
| Compound 189 | 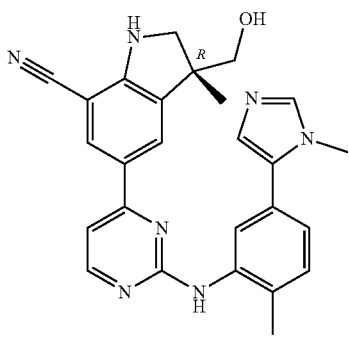<br>From intermediate 503 | 29 | 41 |
| Compound 190 | 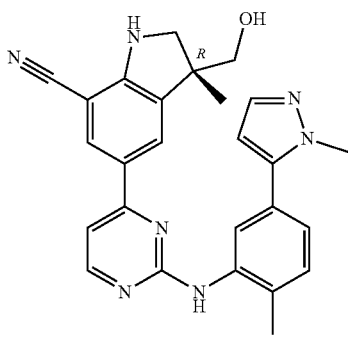<br>From intermediate 504 | 300 | 85 |
| Compound 191 | 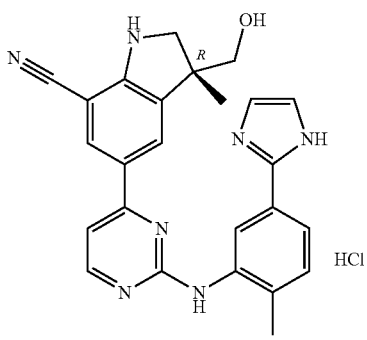<br>From intermediate 506 | 152<br>Procedure with 1 equiv. of TBAF and THF as solvent | 68 |

-continued
| Compound number | Structure | Mass (mg) | Yield (%) |
|---|---|---|---|
| Compound 192 | 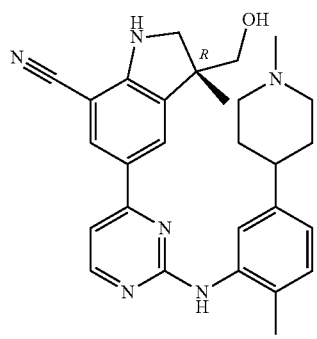<br>From intermediate 509 | 25<br>Procedure with 1 equiv. of TBAF and THF as solvent | 37 |
| Compound 193 | 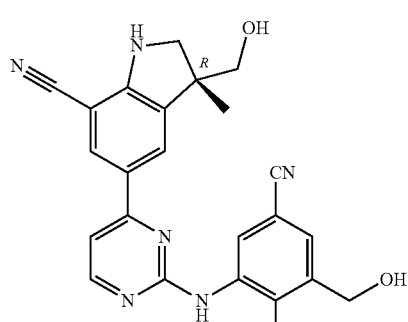<br>From intermediate 511 | 52 | 28 |
| Compound 194 | 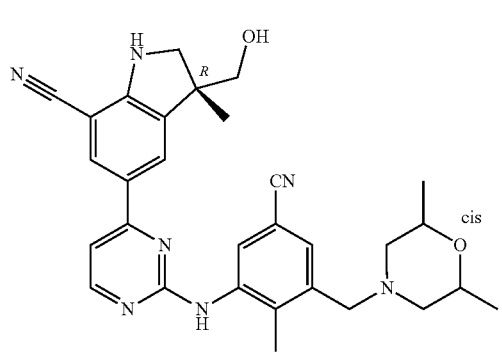<br>From intermediate 514 | 163 | 33 |
| Compound 195 | 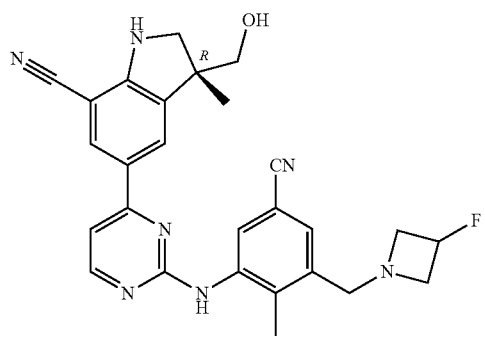<br>From intermediate 516 | 62 | 76 |

| Compound number | Structure | Mass (mg) | Yield (%) |
|---|---|---|---|
| Compound 196 | 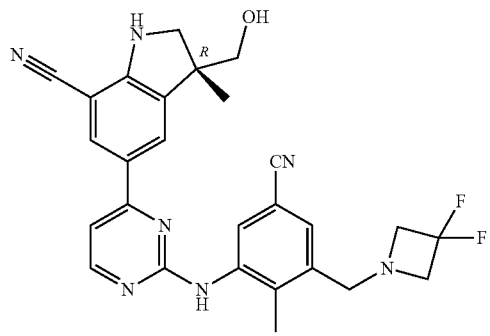<br>From intermediate 517 | 45 | 52 |
| Compound 197 | 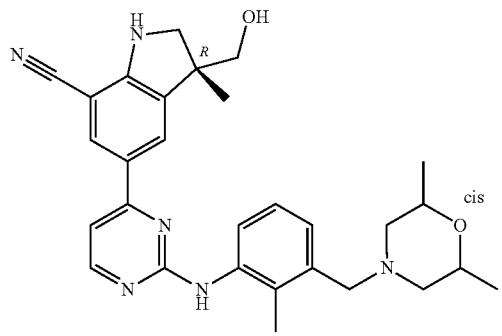<br>From intermediate 518 | 51 | 43 |
| Compound 198 | 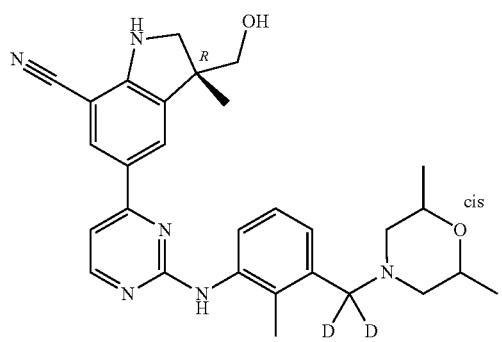<br>From intermediate 520 | 127 | 71 |
| Compound 199 | 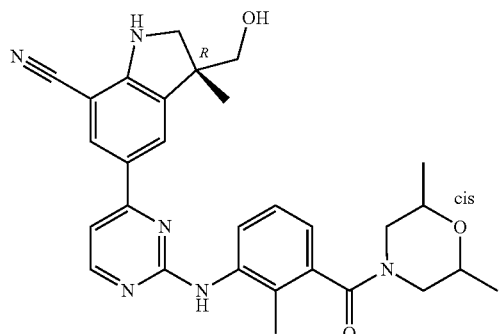<br>From intermediate 521 | 65 | 28 |

-continued

| Compound number | Structure | Mass (mg) | Yield (%) |
|---|---|---|---|
| Compound 208 | From intermediate 528 | 168 Procedure with 5 equiv. of TBAF | 86 |
| Compound 209 | From intermediate 531 | 267 | 63 |
| Compound 210 | From intermediate 538 (2 HCl) | 57 Procedure with 3 equiv. of TBAF and THF as solvent | 38 |
| Compound 213 | From intermediate 545 | 170 Procedure with 4 equiv. of TBAF and THF as solvent | 45 |

-continued

| Compound number | Structure | Mass (mg) | Yield (%) |
|---|---|---|---|
| Compound 214 | From intermediate 548 | 150 Procedure with THF as solvent | 51 |
| Compound 215 | From intermediate 552 | 129 Off-white solid | 48 |
| Compound 216 | From intermediate 556 | 34 Yellow foam | 85 |
| Compound 217 | From intermediate 558 | 236 White solid | 76 |

-continued

| Compound number | Structure | Mass (mg) | Yield (%) |
|---|---|---|---|
| Compound 218 | From intermediate 559 | 25<br>Yellow solid | 22 |
| Compound 219 | From intermediate 561 | 262<br>Pale yellow solid | 78 |
| Compound 220 | From intermediate 563 | 38<br>Off-white solid | 44 |
| Compound 223 | From intermediate 577 | 243<br>Pale yellow solid<br>Procedure with 3 equiv. of TBAF | 82 |

| Compound number | Structure | Mass (mg) | Yield (%) |
|---|---|---|---|
| Compound 224 | 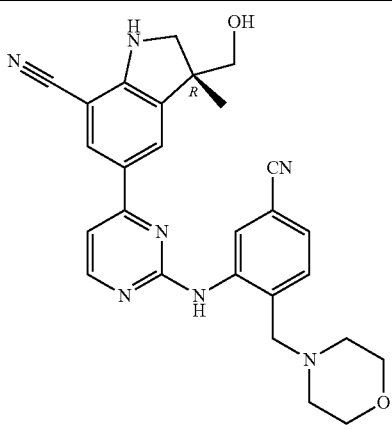<br>From intermediate 581 | 129<br>Orange solid | 74 |
| Compound 229 | 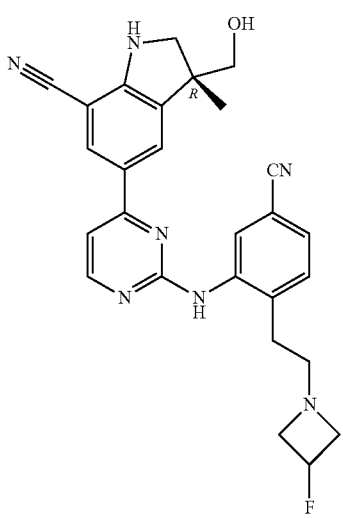<br>From intermediate 600 | 270 | 67 |
| Compound 233 | 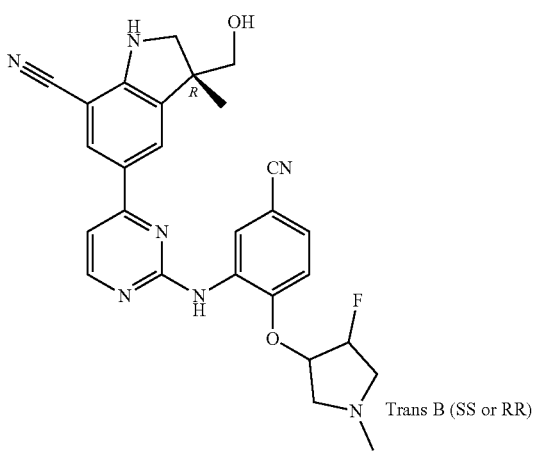<br>From intermediate 619 | 123 | 78 |

| Compound number | Structure | Mass (mg) | Yield (%) |
|---|---|---|---|
| Compound 234 | From intermediate 622 | 38 Off-white solid Procedure with 3 equiv. of TBAF | 67 |
| Compound 236 | From intermediate 634 | 147 | — |
| Compound 239 | From intermediate 641 | 8 | 21 |

Preparation of Compound 155.

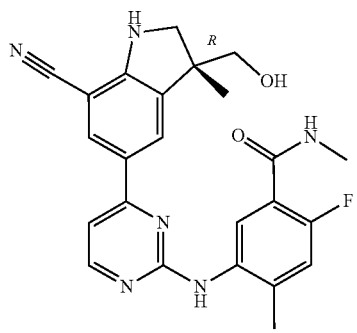

A solution of intermediate 423 (10.66 g, 19 mmol) in Me-THF (210 mL) was treated with TBAF (1M in THF) (38 mL, 38 mmol) and stirred at rt for 3 h. The reaction mixture was poured onto a 10% aqueous solution of $K_2CO_3$ and concentrated.

DCM/MeOH (9/1) was added and the mixture was washed with 10% aqueous $K_2CO_3$ (3×400 mL), water (2×200 mL) and with brine (2×400 mL). The organic layer was dried over $MgSO_4$, filtered and the solvent was evaporated. The residue was dissolved under reflux in $CH_3CN$ (800 mL+200 mL). The solution was allowed to cool to room temperature overnight. Then, the precipitate was filtered and dried to give 6.37 g of compound 155 (75%) as an off-white solid. M.P.: 218° C. (DSC).

Preparation of Compound 156:

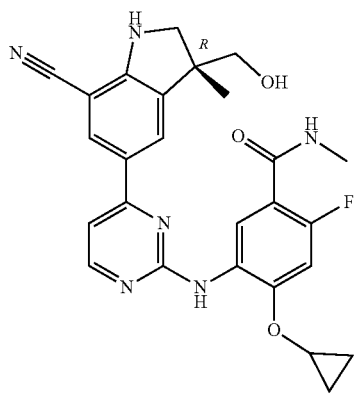

TBAF (1M in THF) (1.5 mL; 1.5 mmol) was added dropwise to a solution of intermediate 430 (451 mg; 0.748 mmol) in Me-THF (15 mL) and the reaction mixture was stirred at room temperature for 3 hours. The reaction mixture was poured onto a 10% aqueous solution of $K_2CO_3$ and extracted with EtOAc. The organic layer was washed with 10% aqueous $K_2CO_3$ (2×30 mL), water (30 mL) and brine (30 mL), dried over $MgSO_4$, filtered and evaporated to dryness. The residue was crystallized from ACN. The precipitate was filtered, washed with $Et_2O$ and dried yielding 295 mg (81%) of compound 156. M.P.: 206° C. (DSC)

Preparation of Compound 232:

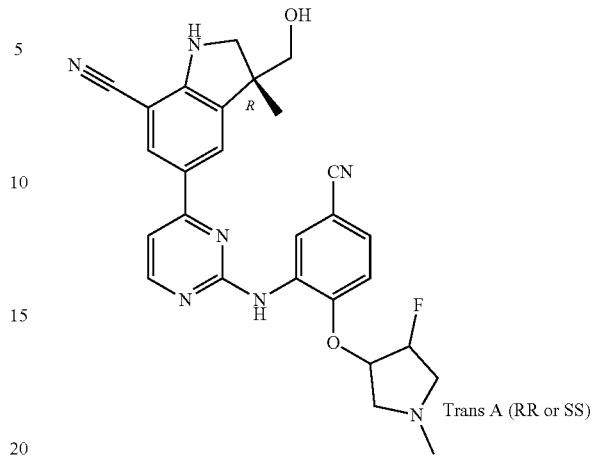

TBAF (1M in THF; 0.65 mL; 0.65 mmol) was added dropwise to a solution of intermediate 618 (234 mg; 0.328 mmol) in Me-THF (10 mL) and the reaction mixture was stirred at room temperature for 3 hours. The reaction mixture was poured onto a 10% aqueous solution of $K_2CO_3$ and extracted with EtOAc. The organic layer was washed with 10% aqueous $K_2CO_3$ (2×30 mL), water (30 mL) and brine (30 mL), dried over $MgSO_4$, filtered and evaporated to dryness. The residue was crystallized from ACN and the precipitate was filtered, washed with $Et_2O$ and dried yielding 133 mg of an intermediate compound which was suspended in MeOH at 50° C. and stirred for 30 min. The precipitate was filtered and dried yielding 77 mg (47%) of compound 232. M.P.: 167° C. (DSC)

Preparation of Compound 221:

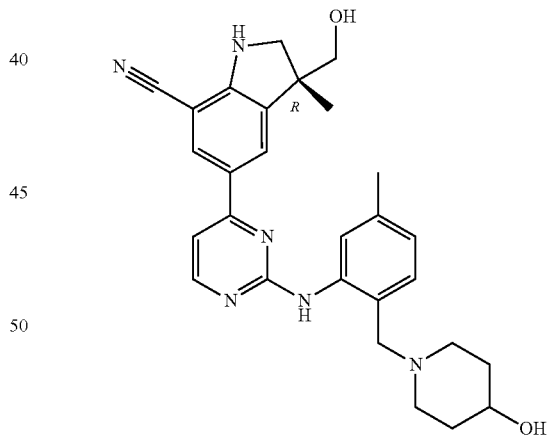

Tetrabutylammonium fluoride trihydrate (164.4 mg; 0.52 mmol) was added to a mixture of intermediate 569 (260 mg; 0.43 mmol) in Me-THF (2 mL) and stirred overnight. The reaction mixture was quenched by addition of saturated aqueous $NaHCO_3$ and extracted with DCM. The organic layer was dried, filtered and concentrated under reduced pressure. The crude was purified with by silica gel chromatography heptane and ethyl acetate as eluent starting with heptane and increasing the proportion of EtOAc. The fractions containing the product were mixed and concentrated affording 170 mg (81%) of compound 221. MP=181° C. (MP50).

The compounds in the Table below were prepared by using an analogous method as the one reported for the preparation of compound 221, starting from the respective starting materials. The most relevant minor deviations to the reference method are indicated as additional information in the column 'Mass (mg)'.

| Compound number | Structure | Mass (mg) | Yield (%) |
|---|---|---|---|
| Compound 222 | 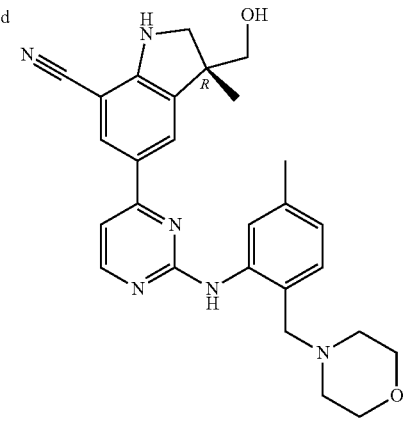<br>From intermediate 573 | 110 | 65 |
| Compound 225 | 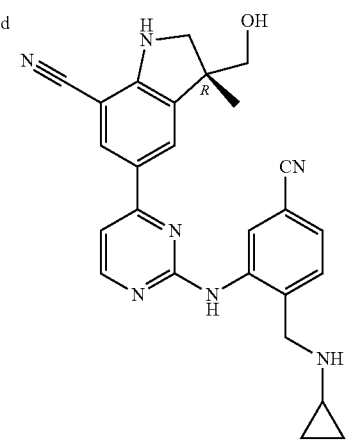<br>From intermediate 585 | 42 | 55 |
| Compound 226 | 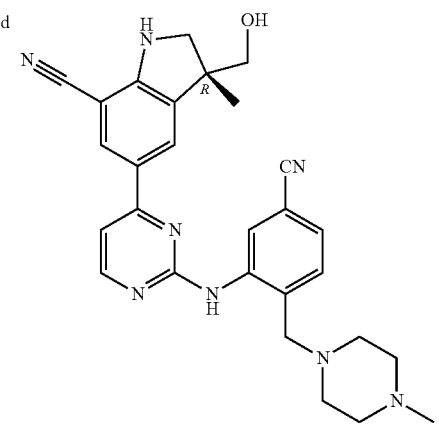<br>From intermediate 589 | 120 | 31 |

-continued
| Compound number | Structure | Mass (mg) | Yield (%) |
|---|---|---|---|
| Compound 227 | 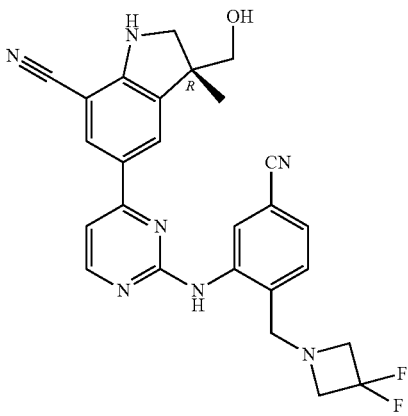<br>From intermediate 593 | 140 | 72 |
| Compound 228 | 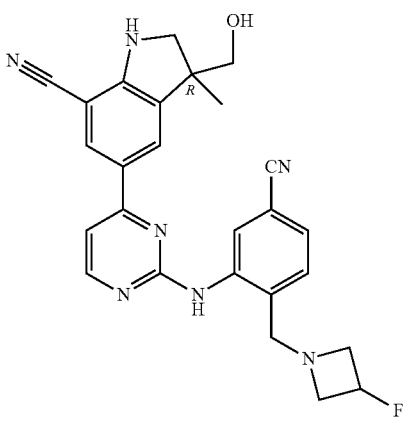<br>From intermediate 597 | 110 | 83 |
| Compound 230 | 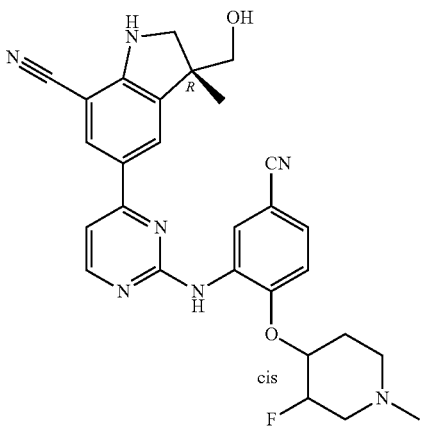<br>From intermediate 606 | 130 | 61 |

| Compound number | Structure | Mass (mg) | Yield (%) |
|---|---|---|---|
| Compound 231 | 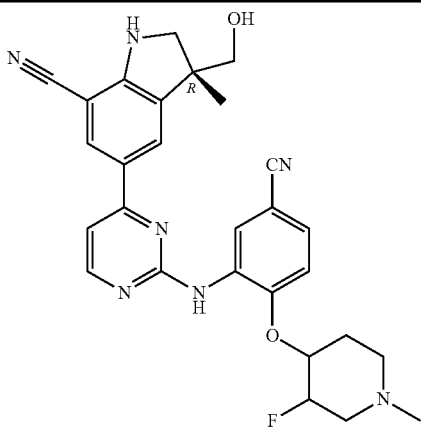<br>trans<br>From intermediate 612 | 38 | 52 |

Example B2

Alternative Preparation a of Compound 1

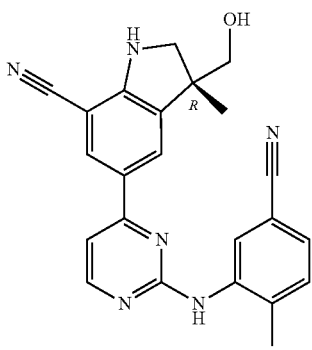

To a solution of intermediate 7R (231 g, 0.556 mol) in 1,4-dioxane (2.3 L), p-toluenesulfonic acid monohydrate (179 g, 0.95 mol) and 3-amino-4-methylbenzonitrile (110 g, 0.83 mol) were added, purged three times with $N_2$ and stirred at 95° C. for 12 h. Then, the reaction mixture was cooled down to 20° C., and a solution of $NaHCO_3$ was added to neutralize the mixture. The precipitated solid formed was filtrated and combined with another precipitate coming from a reaction performed on 179 g of intermediate 7R. The resulting solid was dissolved in Me-THF (5 L), washed with water three times (3×5 L). A silanethiol resin [from Shanghai Meryer CO., LTD] (60 g) was added to the mixture and reflux for 1.5 h. Then, the resulting mixture was filtered through a pad of Celite® and concentrated under vacuum. The residue was suspended in EtOH (5 L) overnight, filtered and dissolved in THF (3 L). Methyl tert-butylether (6 L) was added to THF and the solid was precipitated, filtered and dried to afford 243 g of compound 1.

Alternative Preparation B of Compound 1:

A solution of intermediate 6R (10.0 g) and p-toluenesulfonic acid (3.0 eq) in dioxane (100 mL) was azeotropically dried until the content of water was <0.1% (determined by KF titration). 3-Amino-4-methylbenzonitrile (1.3 eq.) was then added and the mixture was azeotropically dried until the content of water was <0.3% (determined by KF titration) and the volume was approximately 50 mL. The mixture was then heated to 90° C. for 24 hours monitoring the conversion by HPLC. After complete conversion, the mixture was cooled to room temperature and water (50 mL) was added. After 1 hour of stirring, the layers were separated. The organic layer was concentrated to approximately 50 mL and methyl tert-butylether (100 mL) was added over 2 hours at 50° C. The mixture was cooled to 10° C. over 4 hours, and then filtered affording after drying 5 g (purity 98% evaluated by HPLC) of compound 1.

Recrystallization of Compound 1:

To a solution of compound 1 (270 g) in THF (1350 mL) at room temperature, methyl tert-butylether (2160 mL) was slowly added. The mixture was filtered and the product was dried under vacuum at 50° C., to obtain 210 g (99.4% of purity evaluated by HPLC) of compound 1 as a yellow solid.

Alternative Preparation of Compound 148:

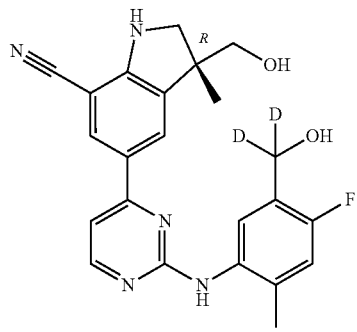

Compound 148 was also prepared following a similar procedure than the alternative preparation A of compound 1 starting from intermediate 7R and intermediate 393 (151 mg; 24%)

Alternative Preparation of Compound 152:

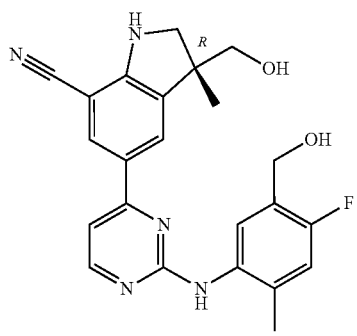

Compound 152 was also prepared following a similar procedure than the alternative preparation A of compound 1 starting from intermediate 7R and intermediate 410.

Preparation of Compound 200:

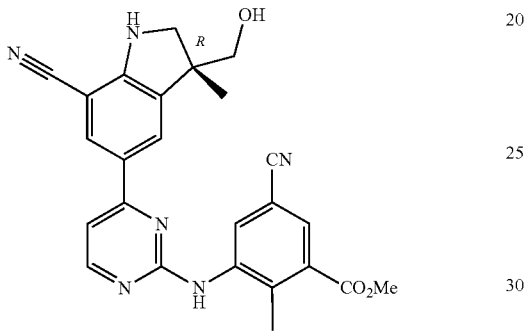

A mixture of intermediate 7R (415 mg; 1 mmol), 3-amino-5-cyano-2-methyl-benzoic acid methyl ester (285 mg; 1.5 mmol) and p-toluenesulfonic acid monohydrate (323 mg; 1.7 mmol) in 1,4-dioxane (5 mL) was heated at 95° C. overnight. The reaction mixture was poured onto a 10% aqueous solution of $K_2CO_3$ and extracted with a mixture of DCM/MeOH. The organic layer was decanted, dried over $MgSO_4$, filtered and evaporated to dryness. The residue was taken up with ACN and the precipitate was filtered and dried yielding 216 mg (47%) of compound 200. M.P.: 260° C. (Kofler)

Example B3

Preparation of Compound 15:

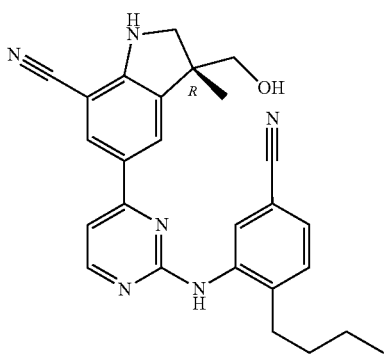

TBAF (1.5 mmol/g on silica) (1.60 g, 2.46 mmol) was added at rt to a solution of intermediate 57 (340.00 mg, 0.61 mmol) in Me-THF (15 mL) and the reaction mixture was stirred at rt for 18 h. The reaction was not complete. Also, a solution of TBAF (1M in THF) (1.00 mL, 1.00 mmol) was added and the reaction mixture was stirred at rt for 1 h. The reaction mixture was diluted with EtOAc, filtered through paper and poured onto a 10% aqueous solution of $K_2CO_3$. The organic layer was decanted, washed with water, then brine, dried over $MgSO_4$, filtered and evaporated to dryness. The residue was purified by column chromatography on silica gel (irregular SiOH, 40 g, mobile phase $NH_4OH$/MeOH/EtOAc/heptane, 0.5% $NH_4OH$, 10% MeOH, 50% EtOAc, 40% heptane). The pure fractions were collected and evaporated to dryness. The residue was taken up with $Et_2O$ and the precipitate was filtered and dried to give 134 mg of compound 15 (50% yield). M.P. (gum)=110° C. (K).

Preparation of Compound 73

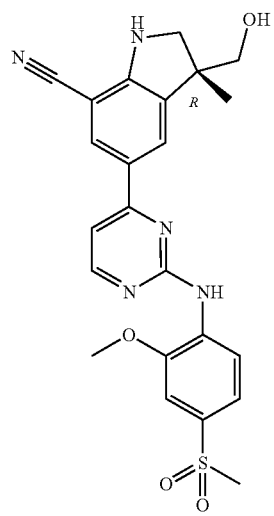

In a round bottom flask, intermediate 253 (221.00 mg, 0.38 mmol) was diluted in Me-THF (10.3 mL). Then, the solution was cooled to 0° C. and TBAF (on silica gel 1.5 mmol/g, 1.52 mL, 2.29 mmol) was added. The reaction mixture was stirred for 3 h allowing the temperature to reach rt and then partitioned between a saturated solution of $NaHCO_3$ and DCM. The layers were separated. The aqueous layer was extracted again with DCM. The organic layers were mixed, dried over $MgSO_4$, filtered and concentrated. The residue (225 mg) was purified by column chromatography on silica gel (irregular SiOH, 40 g, mobile phase: $NH_4OH$/DCM/MeOH, gradient from 0.2% $NH_4OH$, 2% MeOH, 98% DCM to 1% $NH_4OH$, 10% MeOH, 90% DCM). The pure fractions were collected, evaporated to dryness. The residue (79 mg, 44%) was crystallized from $Et_2O$. The precipitate was filtered and dried to give 54 mg of compound 73 (30% yield). M.P.=201° C. (DSC).

Preparation of Compound 74:

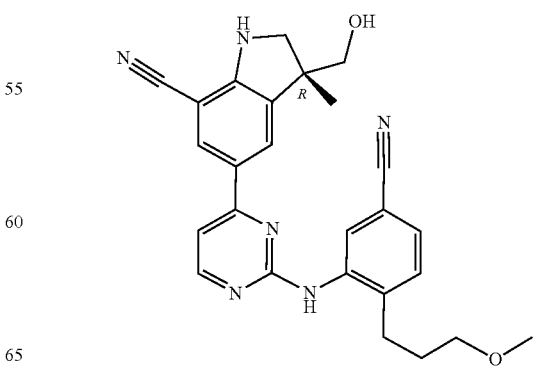

TBAF (on silica gel 1.5 mmol/g) (3.70 g, 5.57 mmol) was added to a solution of intermediate 256 (1.20 g, 1.39 mmol) in Me-THF (35 mL) and the reaction mixture was stirred at rt for 18 h. TBAF (1M in THF) (2.80 mL, 2.78 mmol) was added and the reaction mixture was stirred at rt for 2 additional hours. The reaction mixture was diluted with DCM, filtered through paper and poured onto a 10% aqueous solution of $K_2CO_3$. The organic layer was decanted, washed with water, dried over $MgSO_4$, filtered and evaporated to dryness. The residue was purified by column chromatography on silica gel (irregular SiOH, 40 g, mobile phase DCM/MeOH/$NH_4OH$, gradient from 0.3% $NH_4OH$, 3% MeOH, 97% DCM to 1% $NH_4OH$, 10% MeOH, 90% DCM). The fractions containing the product were collected and evaporated to dryness and the residue was purified a second time by column chromatography on silica gel (irregular SiOH, 40 g, mobile phase DCM/MeOH/$NH_4OH$ with 0.5% $NH_4OH$, 5% MeOH, 95% DCM). The pure fractions were collected and evaporated to dryness. The residue (520 mg, 54%) was crystallized from $CH_3CN/Et_2O$ and the precipitate was filtered and dried to give 443 mg of compound 74 (46% yield). M.P.=124° C. (K).

The compound in the Table below was prepared by using an analogous method starting from the respective starting materials. The most relevant minor deviations to the referenced method are indicated as additional information in the column 'Mass (mg)'.

TFA (1.50 mL, 19.60 mmol) was added dropwise to a solution of intermediate 30 (270.00 mg, 0.51 mmol) in DCM (stab. with amylene 10 mL) at 5° C. and the reaction mixture was stirred for 1 h at this temperature. The reaction mixture was quenched with a 10% aqueous solution of $K_2CO_3$ and extracted with DCM. The organic layer was decanted, dried over $MgSO_4$, filtered and evaporated to dryness. The residue was crystallized from $CH_3CN$ and the precipitate was filtered and dried to give 165 mg of compound 7 (75% yield). M.P.: 215° C. (DSC).

Alternative Preparation of Compound 1:

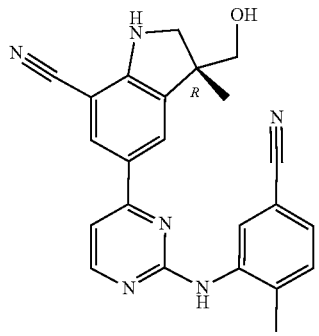

| Compound number | Structure | Mass (mg) | Yield (%) |
|---|---|---|---|
| Compound 71 | 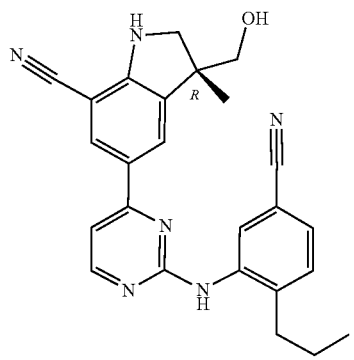<br>From intermediate 246 | 160<br>Procedure with 3 equiv. of TBAF (1.5 mmol/g on silica) | 48 |

Example B4

Preparation of Compound 7:

TFA (3.93 mL, 51.35 mmol) was added at 5° C. to a solution of intermediate 10R (1.16 g, 2.33 mmol) in DCM (25.4 mL). The reaction mixture was stirred for 30 min. The reaction mixture was diluted with DCM and poured onto a 10% aqueous solution of $K_2CO_3$, dried over $MgSO_4$, filtered and evaporated to dryness. The residue (1200 mg, yellow solid) was purified by column chromatography on silica gel (irregular SiOH, deposit solid, 30 g, mobile phase: $NH_4OH$/DCM/MeOH, gradient from 100% DCM to 95% DCM 5% MeOH, 0.5% $NH_4OH$). The fractions containing the products were collected and evaporated to dryness to give three batches (batch 1: 167 mg, batch 2: 568 mg and batch 3: 253 mg as yellow powder). The batches 2 and 3 were gathered and purified via chiral SFC (Stationary phase: CHIRALPAK IC 5 μm 250×30 mm, mobile phase: 60% $CO_2$, 36% EtOH, 4% DCM). The fractions containing the product were combined and evaporated to dryness. The residue (388 mg) was combined with two other batches of compound 1 (517 mg and 200 mg) and taken up with $CH_3CN$ to provide 1.165 g of compound 1 (light yellow powder).

Preparation of Compound 66:

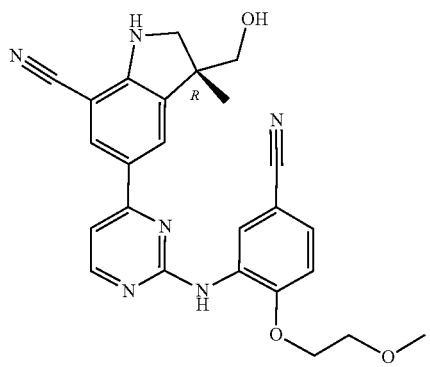

TFA (0.47 mL, 6.12 mmol) was added at 5° C. to a solution of intermediate 229 (227.00 mg, 0.41 mmol) in DCM (10 mL, stabilized with amylene). The reaction mixture was stirred at 0° C. for 1 h, diluted with DCM and poured onto a 10% aqueous solution of $K_2CO_3$. The organic layer was decanted, washed with water, dried over $MgSO_4$, filtered and evaporated to dryness. The residue was suspended in EtOH and the mixture was heated at 50° C. for 2 h. The precipitate was filtered and dried to give 114 mg of compound 66 (61% yield). M.P.=165° C. (K).

The compounds in the Table below were prepared by using an analogous method as the ones reported for the preparation of compounds 7, 1 or 66 starting from the respective starting materials. The most relevant minor deviations to the referenced method are indicated as additional information in the column 'Mass (mg)'.

| Compound number | Structure | Mass (mg) | Yield (%) |
| --- | --- | --- | --- |
| Compound 8 | From intermediate 35 | 32 yellow powder Procedure with DCM/TFA (10:1, v/v) | 7 |
| Compound 9 | From intermediate 39 | 160 | 63 |

-continued

| Compound number | Structure | Mass (mg) | Yield (%) |
|---|---|---|---|
| Compound 13 | From intermediate 80 | 188 yellow powder | 35 |
| Compound 16 | From intermediate 62 | 79 light yellow powder | 24 |
| Compound 17 | From intermediate 64 | 57 Procedure with DCM/TFA (5:1, v/v) | 27 |

-continued

| Compound number | Structure | Mass (mg) | Yield (%) |
|---|---|---|---|
| Compound 18 | From intermediate 70 | 583 off-white solid Procedure with DCM/TFA (10:1, v/v) | 79 |
| Compound 19 | From intermediate 75 | 339 white solid Procedure with DCM/TFA (10:1, v/v) | 45 |
| Compound 20 | From intermediate 78 | 440 white solid Procedure with DCM/TFA (10:1, v/v) | 58 |
| Compound 22 | From intermediate 90 | 30 (98% purity based on LC/MS) off-white solid with DCM/TFA (1:1, v/v) | 20 |

-continued

| Compound number | Structure | Mass (mg) | Yield (%) |
|---|---|---|---|
| Compound 24 | From intermediate 97 | 17 off-white solid Procedure with DCM/TFA (1:1, v/v) | 9 |
| Compound 25 | From intermediate 101 | 139 pale yellow solid Procedure with DCM/TFA (1:1, v/v) | 55 |
| Compound 26 | From intermediate 103 | 52 white solid Procedure with DCM/TFA (5:2, v/v) | 23 |
| Compound 27 | From intermediate 106 | 38 white solid Procedure with DCM/TFA (5:2, v/v) | 16 |

-continued

| Compound number | Structure | Mass (mg) | Yield (%) |
|---|---|---|---|
| Compound 28 | 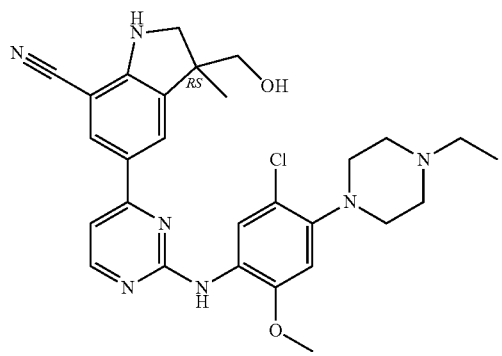<br>From intermediate 111 | 32<br>off-white solid<br>Procedure with DCM/TFA (1:1, v/v) | 23 |
| Compound 29 | 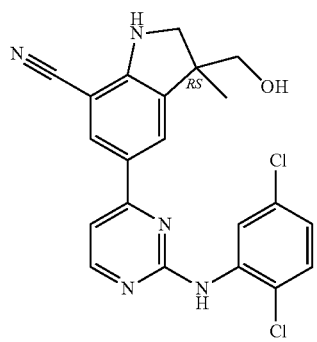<br>From intermediate 113 | 60<br>white solid<br>Procedure with DCM/TFA (5:2, v/v) | 24 |
| Compound 30 | 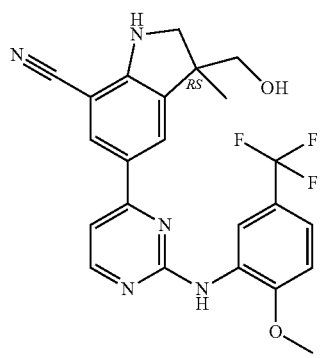<br>From intermediate 115 | 116<br>beige solid<br>Procedure with DCM/TFA (5:2, v/v) | 44 |
| Compound 31 | 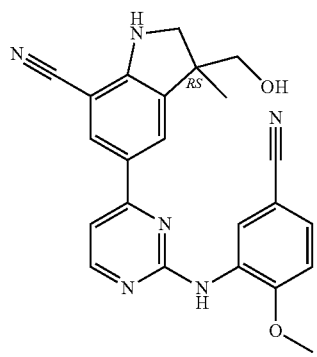<br>From intermediate 117 | 40<br>orange solid<br>Procedure with DCM/TFA (5:2, v/v) | 17 |

-continued

| Compound number | Structure | Mass (mg) | Yield (%) |
|---|---|---|---|
| Compound 36 | From intermediate 132 | 71 Procedure with DCM/TFA (4:1, V/V) | 29 |
| Compound 41 | From intermediate 151 | 30 Procedure with DCM/TFA (4:1, v/v) | 36 |
| Compound 42 | From intermediate 154 | 55 Procedure with DCM/TFA (4:1, v/v) | 22 |
| Compound 43 | From intermediate 157 | 35 Procedure with DCM/TFA (4:1, v/v) | 35 |

-continued

| Compound number | Structure | Mass (mg) | Yield (%) |
|---|---|---|---|
| Compound 60 | From intermediate 206 | 15<br>Procedure with DCM/TFA (12:1, v/v) | 20 |
| Compound 65 | From intermediate 225 | 142<br>yellow powder<br>Procedure with DCM/TFA (6:1, v/v) | 28 |
| Compound 69 | From intermediate 241 | 75<br>Procedure with DCM/TFA (6:1, v/v) | 24 |
| Compound 70 | From intermediate 243 | 117<br>Procedure with DCM/TFA (8:1, v/v) | 46 |

-continued
| Compound number | Structure | Mass (mg) | Yield (%) |
|---|---|---|---|
| Compound 72 | 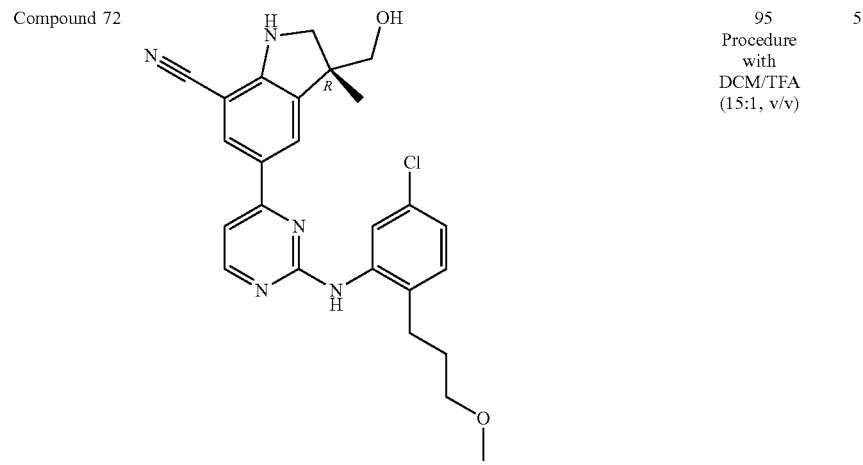<br>From intermediate 248 | 95<br>Procedure with DCM/TFA (15:1, v/v) | 51 |
| Compound 75 | 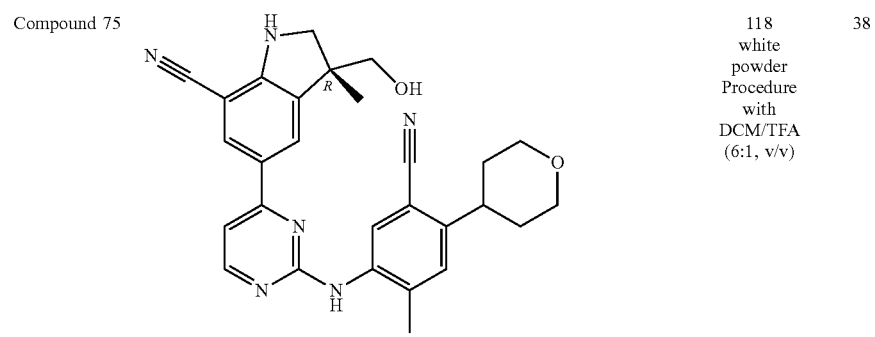<br>From intermediate 262 | 118<br>white powder<br>Procedure with DCM/TFA (6:1, v/v) | 38 |
| Compound 76 | <br>From intermediate 266 | 65<br>Procedure with DCM/TFA (4:1, v/v) | 34 |

-continued

| Compound number | Structure | Mass (mg) | Yield (%) |
|---|---|---|---|
| Compound 77 | From intermediate 270 | 65 Procedure with DCM/TFA (5:1, v/v) | 34 |
| Compound 211 | From intermediate 541 | 113 Procedure with DCM/TFA (7.5:1, v/v) at room temperature | 33% |
| Compound 212 | From intermediate 542 | 88 Procedure with DCM/TFA (7.5:1, v/v) at room temperature | 43% |

| Compound number | Structure | Mass (mg) | Yield (%) |
|---|---|---|---|
| Compound 236 | From intermediate 633 | 198 with DCM/TFA (18:1, v/v) during 15 hours) | 51 |
| Compound 240 | Form intermediate 644 | 85 with DCM/TFA (4:1, v/v) | 40 |

Example B5

Preparation of Compound 21:

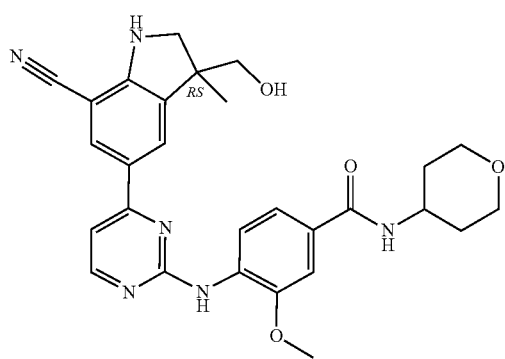

To a solution of intermediate 85 (0.28 g, 0.29 mmol) in DCM (3 mL), TFA (3 mL) was added and the reaction mixture was stirred at rt for 2 h. The solution was concentrated in vacuo and neat TFA (3 mL) was added, the reaction mixture was stirred for a further 4 h. The reaction mixture was stirred for a further 1 h and the solution was concentrated in vacuo. The residue was treated with $K_2CO_3$ (0.24 g, 1.75 mmol) in DMF (2 mL) for 2 h at 50° C. The reaction mixture was partitioned between EtOAc and water, and the organic layer was dried over $Na_2SO_4$ and concentrated in vacuo. The residue was purified by mass triggered auto purification system.

Example B6

Preparation of Compound 23:

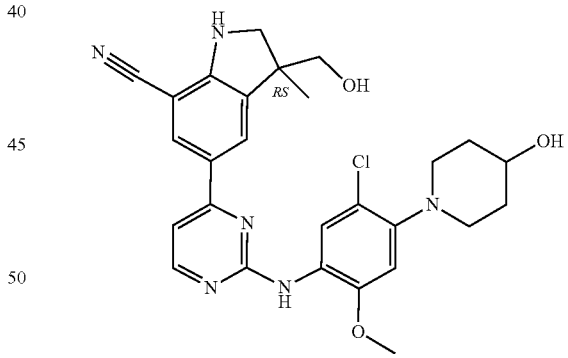

HCl (3M in $H_2O$) (2.18 mL, 6.55 mmol) was added to a solution of intermediate 93 (698.00 mg, 0.65 mmol) in MeOH (10 mL) and the reaction mixture was stirred 6 h at reflux. The reaction mixture was cooled down to rt, diluted with DCM and carefully neutralized with a saturated solution of $NaHCO_3$. Then, few mL of MeOH were added to solubilize the precipitate. The reaction mixture was separated and the aqueous layer was extracted with DCM/MeOH (9/1). The organic layers were combined, dried over $MgSO_4$, filtered and concentrated. The residue (620 mg) was taken up with DCM/MeOH (9/1). The precipitate was filtered and taken up again with 15 mL DCM/MeOH (9/1). The resulting slurry suspension was stirred 30 min at rt. The precipitate was filtered, washed with Et$_2$O and dried. The resulting residue (226 mg) was purified by column chromatography on silica (irregular SiOH, solid deposit, 40 g, mobile phase: DCM/MeOH, gradient from 98:2 to 94:6). The fractions containing the product were concentrated to give two batches of compound 23: batch A (131 mg, 38% yield) and batch B (23 mg, 6% yield). The batch A, containing some solvents, was solubilized in DCM/MeOH, concentrated and taken up with CH$_3$CN. The precipitate was filtered to afford after drying a batch C of compound 23 (112 mg) but still containing some solvent. Finally, the batch C was dissolved in DCM/EtOH, concentrated and taken up with CH$_3$CN. The precipitate was filtered and dried to afford additional 93 mg of compound 23 (27% yield). M.P.: >260° C. (K).

The global yield was 33%.

Preparation of Compound 45:

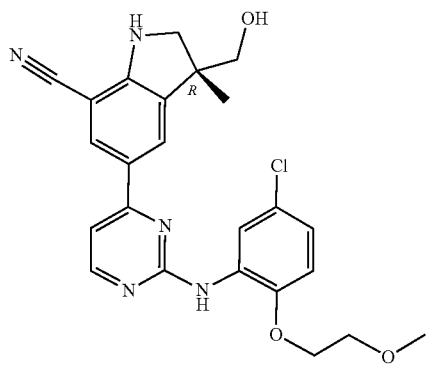

HCl (3M in H$_2$O) (1.32 mL, 3.95 mmol) was added to a solution of intermediate 164 (269.00 mg, 0.40 mmol) in MeOH (6.0 mL) and the reaction mixture was stirred 10 h at reflux. The reaction mixture was cooled to rt, poured onto a 10% aqueous solution of K$_2$CO$_3$ and extracted with DCM. The organic layer was decanted, dried over MgSO$_4$, filtered and evaporated to dryness to provide an orange powder. The residue (220 mg) was purified by column chromatography on silica gel (Irregular SiOH, 25 g, solid deposit, mobile phase NH$_4$OH/DCM/MeOH, gradient from 0% NH$_4$OH, 0% MeOH, 100% DCM to 1% NH$_4$OH, 10% MeOH, 90% DCM). The fractions containing the product were collected and evaporated to dryness to give 69 mg of a yellow solid. This solid was taken up in Et$_2$O to provide 62 mg of compound 45 (34% yield, white powder).

M.P.=169° C. (K).

The compounds in the Table below were prepared by using an analogous method as the ones reported for the preparation of compounds 23 or 45, starting from the respective starting materials.

| Compound number | Structure | Mass (mg) | Yield (%) |
|---|---|---|---|
| Compound 23 | *structure shown; From intermediate 93* | 93 | 27 |
| Compound 34 | *structure shown; From intermediate 124* | 96 white powder | 47 |

-continued
| Compound number | Structure | Mass (mg) | Yield (%) |
|---|---|---|---|
| Compound 35 | 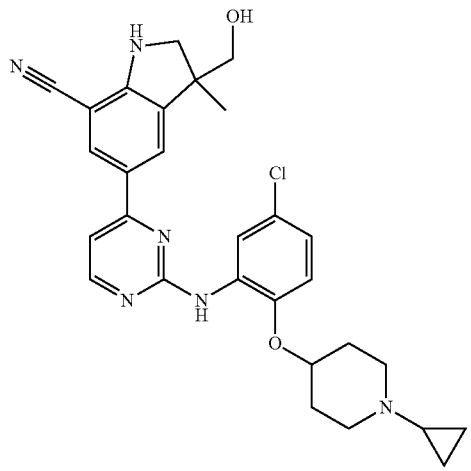 [SMILES: CC1(CO)CNc2c(C#N)cc(-c3ccnc(Nc4cc(Cl)ccc4OC4CCN(C5CC5)CC4)n3)cc21]<br>From intermediate 128 | 105 white powder | 28 |
| Compound 39 (mixture of 4 unseparated diastereoisomers) | 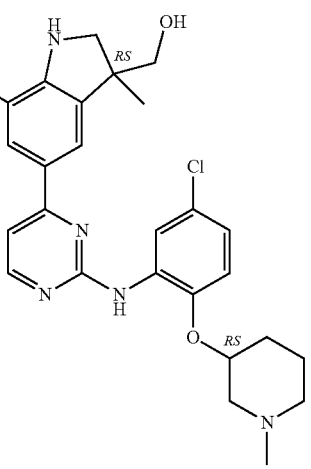<br>From intermediate 143 | 77 white powder | 61 |
| Compound 40 | 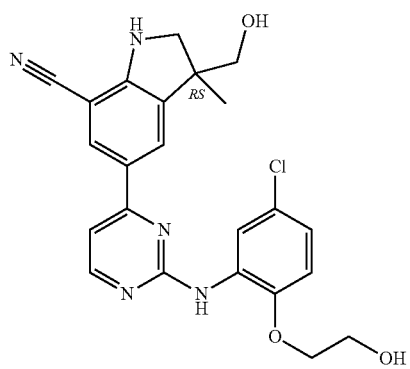 [SMILES: CC1(CO)CNc2c(C#N)cc(-c3ccnc(Nc4cc(Cl)ccc4OCCO)n3)cc21]<br>From intermediate 146 | 83 yellow powder | 37 |

-continued
| Compound number | Structure | Mass (mg) | Yield (%) |
|---|---|---|---|
| Compound 44 | 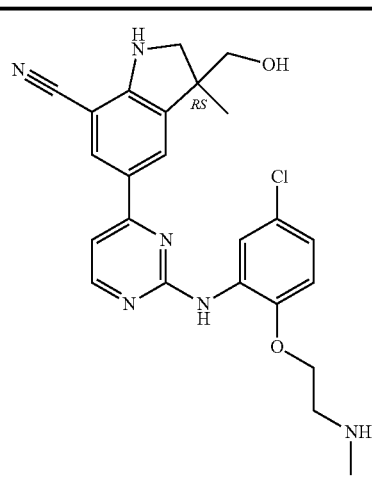<br>From intermediate 161 | 37 white powder | 31 |
| Compound 57 | 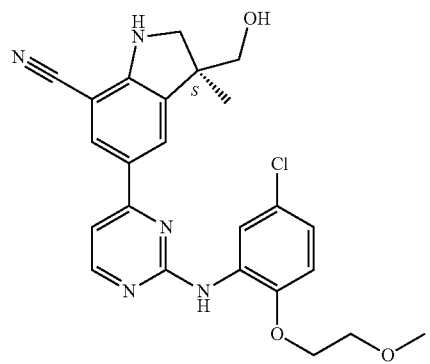<br>From intermediate 196 | 39 | 21 |

Preparation of Compound 170:

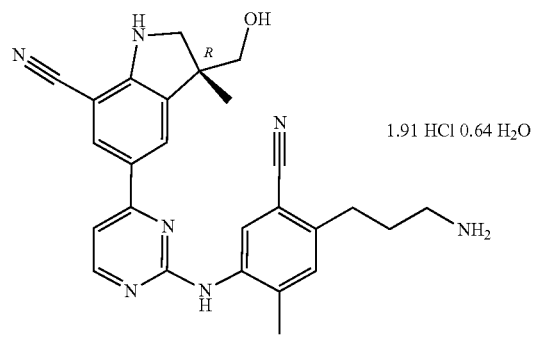

1.91 HCl 0.64 H₂O

4 N HCl in 1,4-dioxane (0.19 mL; 0.759 mmol) was added at room temperature to a solution of intermediate 461 (84 mg; 0.152 mmol) in acetonitrile (2.4 mL) and the reaction mixture was stirred for 3 hours. The precipitate was filtered, washed with acetonitrile and dried at 50° C. under vacuo to give 0.068 g (82%) of compound 170. MP=207° C. (kofler).

Preparation of Compound 171:

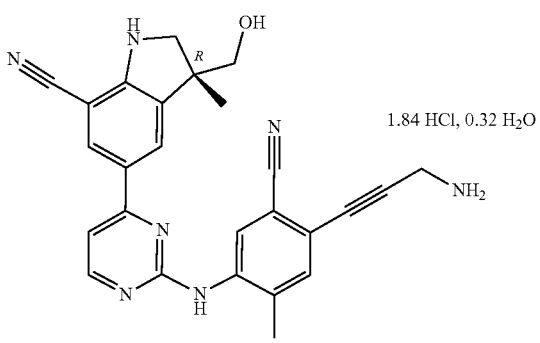

1.84 HCl, 0.32 H₂O

Compound 171 was synthesized by using an analogous method than the one used for the preparation of compound 170, starting from intermediate 464 (235 mg; 99%; MP=249° C., kofler).

Preparation of Compound 180:

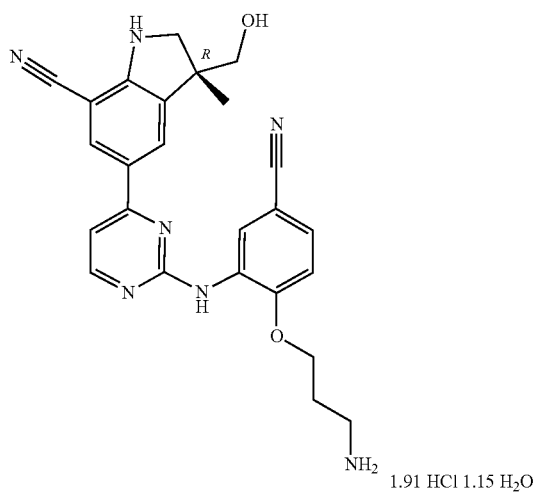

1.91 HCl 1.15 H₂O

Compound 180 was synthesized by using an analogous method than the one used for the preparation of compound 170, starting from intermediate 482bis (162 mg; 81%; MP=gum at 194° C., kofler).

Preparation of Compound 184:

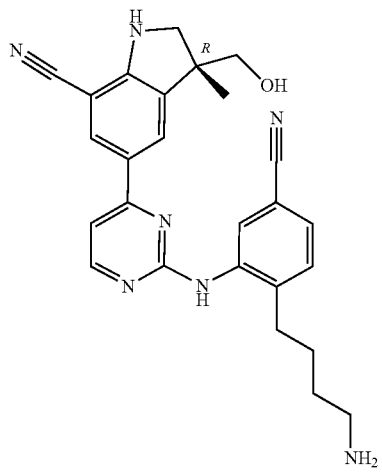

Compound 184 was synthesized by using an analogous method (using HCl 3N in cyclopentylmethyl ether) than the one used for the preparation of compound 170, starting from intermediate 487 (223 mg; 60%; MP=gum at 134° C., kofler).

Preparation of Compound 235:

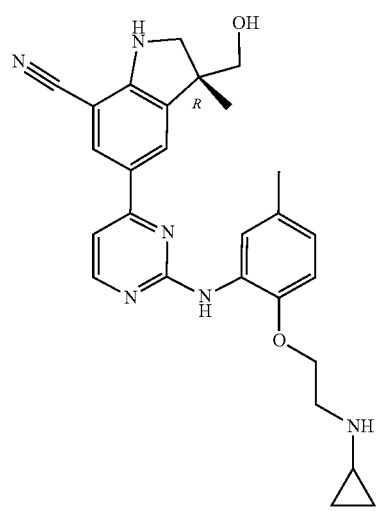

In a round bottom flask containing intermediate 627 (500 mg; 0.64 mmol) and 1.4-dioxane (20 mL) was added HCl 4M/dioxane (3.5 mL; 14.01 mmol) and the reaction mixture was stirred at room temperature overnight. The crude was concentrated and was quenched with a saturated solution of NaHCO₃ and extracted with DCM (2×50 mL). The organic layer was dried over anhydrous sodium sulfate and concentrated under vacuum to give a crude that was purified by flash chromatography eluting with DCM (75%):MeOH (25%). The fractions containing the product were collected and the solvent was evaporated to give 95 mg (32%) of compound 235.

Preparation of Compound 237:

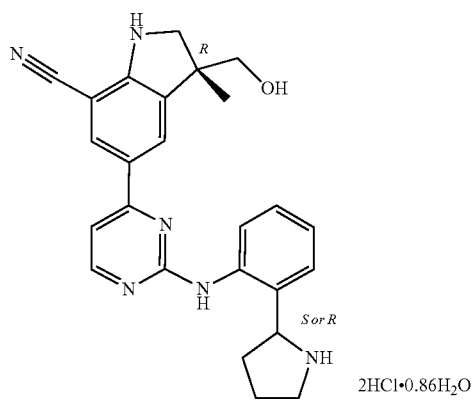

2HCl·0.86H₂O

Compound 237 was synthesized by using an analogous method (using DCM as solvent) than the one used for the preparation of compound 235 starting from intermediate 639 (123 mg; 86%).

Preparation of Compound 238:

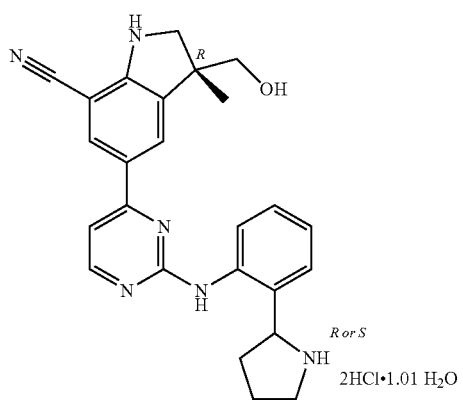

2HCl·1.01 H₂O

Compound 238 was synthesized by using an analogous method (using DCM as solvent) than the one used for the preparation of compound 235 starting from intermediate 638 (116 mg; 88%).

Example B7

Preparation of Compound 78:

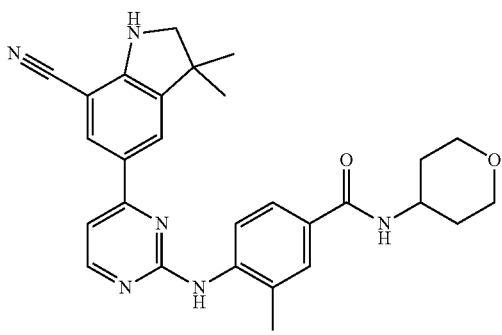 [SMILES: Cc1cc(C(=O)NC2CCOCC2)ccc1Nc1nccc(-c2cc(C#N)c3c(c2)C(C)(C)CN3)n1]

To a solution of intermediate 277 (227.00 mg, 0.242 mmol) in DCM (3 mL), TFA (3 mL) was added and stirred at rt for 2 h. The solution was concentrated in vacuo to give an orange oil. The residue was purified by reverse phase semi-preparative HPLC (C18 column, Mobile phase: H₂O+ 0.1% HCO₂H/CH₃CN, gradient 30% to 80% in CH₃CN). The desired fractions were combined and freeze-dried to give 32 mg of compound 78 (26%, yellow solid).

Preparation of Compound 110:

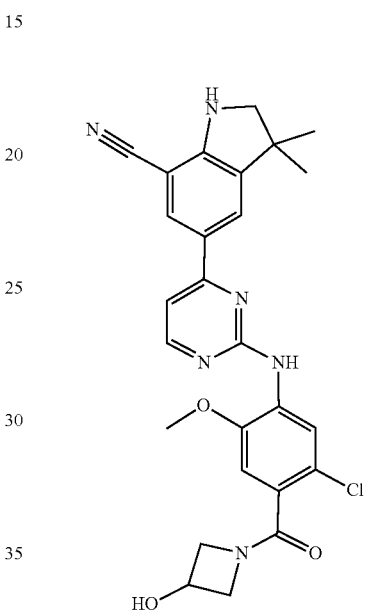

Intermediate 357 (500 mg, 0.83 mmol) was stirred in DCM (37.5 mL). To this solution, TFA (12.5 ml) was added at 0° C. and stirred at rt for 1 h. To the resulting reaction mixture, NaHCO₃ was added until pH=8. Some solids precipitated and were filtered to give the crude product. The residue was purified by preparative high-performance liquid chromatography (Waters Xbridge Prep OBD C18 100×19 mm×5 μm, mobile phase: CH₃CN/H₂O (10 mM NH₄HCO₃) from 30% to 60% of CH₃CN in 12 min, then 100% of CH₃CN in 2 min, flow rate=25 mL/min). The pure fractions were collected and the solvent was evaporated under vacuum. The aqueous layer was lyophilized to give 102 mg of compound 110 (24% yield, white solid).

The compounds in the Table below were prepared by using an analogous method as the ones reported for the synthesis of compounds 78 or 110 starting from the respective starting materials. The most relevant minor deviations to the referenced method are indicated as additional information in the column 'Mass (mg)'.

| Compound number | Structure | Mass (mg) | Yield (%) |
|---|---|---|---|
| Compound 79 | From intermediate 280 | 15 Procedure with DCM/TFA (5:2, v/v) white solid | 15 |
| Compound 80 | From intermediate 281 | 65 off-white solid Procedure with DCM/TFA (2:1, v/v) | 51 |
| Compound 81 | From intermediate 282 | 57 off-white solid Procedure with DCM/TFA (2:1, v/v) | 50 |
| Compound 82 | From intermediate 286 | 40 off-white solid | 30 |

-continued

| Compound number | Structure | Mass (mg) | Yield (%) |
|---|---|---|---|
| Compound 83 | From intermediate 287 | 12<br>Procedure with DCM/TFA (2:1, v/v)<br>off-white solid | 12 |
| Compound 84 | From intermediate 288 | 31<br>Procedure with DCM/TFA (2:1, v/v)<br>white solid | 36 |
| Compound 85 | From intermediate 282 | 35<br>off-white solid | 28 |
| Compound 87 | From intermediate 298 | 33<br>off-white solid | 39 |

-continued
| Compound number | Structure | Mass (mg) | Yield (%) |
|---|---|---|---|
| Compound 88 | 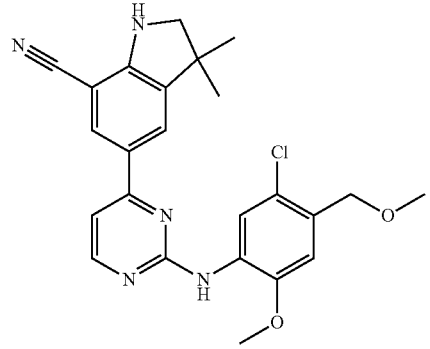 [SMILES: COCc1cc(OC)c(Nc2nccc(-c3cc(C#N)c4c(c3)C(C)(C)CN4)n2)cc1Cl]<br>From intermediate 301 | 8<br>Procedure with DCM/TFA (2:1, v/v) | 10 |
| Compound 89 | 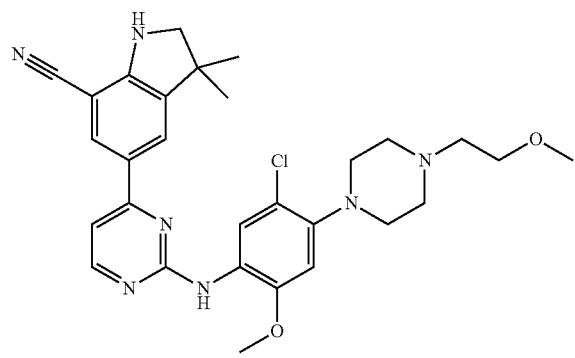 [SMILES: COCCN1CCN(c2cc(OC)c(Nc3nccc(-c4cc(C#N)c5c(c4)C(C)(C)CN5)n3)cc2Cl)CC1]<br>From intermediate 304 | 38 | 53 |
| Compound 90 | 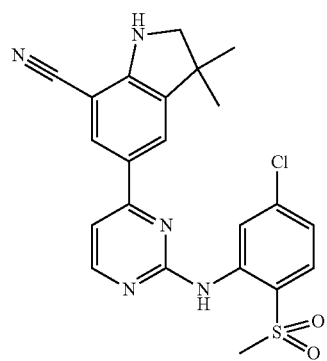 [SMILES: CC1(C)CNc2c(C#N)cc(-c3ccnc(Nc4cc(Cl)ccc4S(C)(=O)=O)n3)cc21]<br>From intermediate 306 | 9.2<br>off-white solid | 11 |
| Compound 91 | 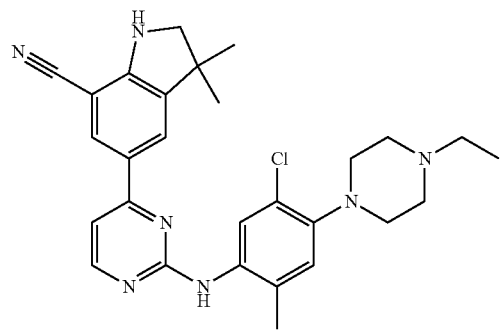 [SMILES: CCN1CCN(c2cc(C)c(Nc3nccc(-c4cc(C#N)c5c(c4)C(C)(C)CN5)n3)cc2Cl)CC1]<br>From intermediate 310 | 22<br>Procedure with DCM/TFA (2:1, v/v) | 24 |

-continued
| Compound number | Structure | Mass (mg) | Yield (%) |
|---|---|---|---|
| Compound 92 | 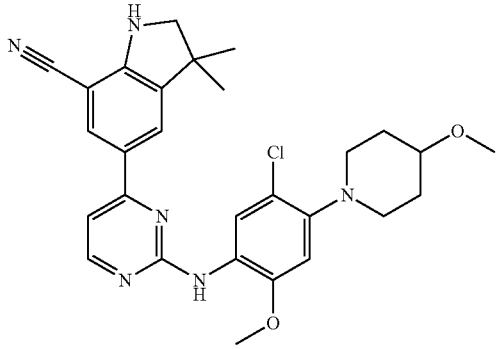 [SMILES: COc1cc(N2CCC(OC)CC2)c(Cl)cc1Nc1nccc(-c2cc(C#N)c3c(c2)C(C)(C)CN3)n1]<br>From intermediate 312 | 51<br>pale yellow solid | 54 |
| Compound 93 | 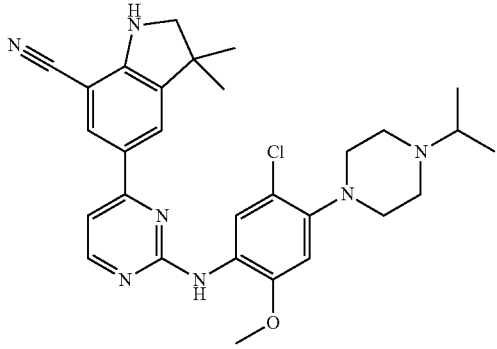 [SMILES: COc1cc(N2CCN(C(C)C)CC2)c(Cl)cc1Nc1nccc(-c2cc(C#N)c3c(c2)C(C)(C)CN3)n1]<br>From intermediate 315 | 56<br>pale yellow solid | 58 |
| Compound 94 | 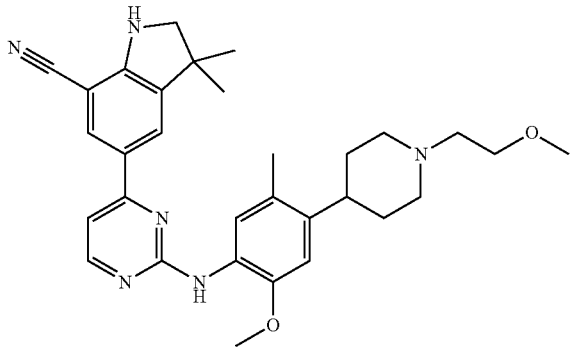 [SMILES: COCCN1CCC(c2cc(OC)c(Nc3nccc(-c4cc(C#N)c5c(c4)C(C)(C)CN5)n3)cc2C)CC1]<br>From intermediate 320 | 26<br>pale yellow solid | 27 |
| Compound 95 | 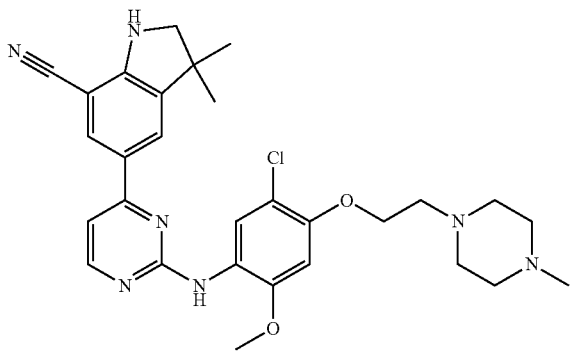 [SMILES: COc1cc(OCCN2CCN(C)CC2)c(Cl)cc1Nc1nccc(-c2cc(C#N)c3c(c2)C(C)(C)CN3)n1]<br>From intermediate 323 | 5<br>yellow solid<br>Procedure with DCM/TFA (2:1, v/v) | 5 |

-continued
| Compound number | Structure | Mass (mg) | Yield (%) |
|---|---|---|---|
| Compound 96 | 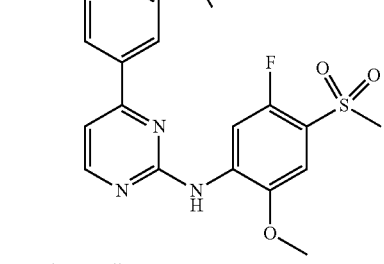<br>From intermediate 327 | 27<br>tan solid<br>Procedure with DCM/TFA (2:1, v/v) | 32 |
| Compound 97 | 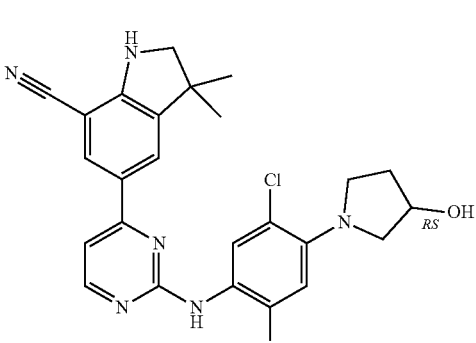<br>From intermediate 330 | 42<br>pale yellow solid | 47 |
| Compound 98 | 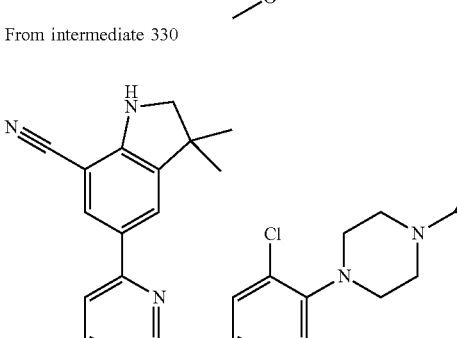<br>From intermediate 333 | 38<br>pale yellow solid | 55 |
| Compound 104 | 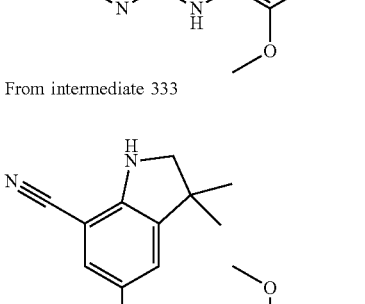<br>From intermediate 346 | 63<br>Procedure with DCM/TFA (10:3, v/v) | 29 |

-continued

| Compound number | Structure | Mass (mg) | Yield (%) |
|---|---|---|---|
| Compound 105 | From intermediate 347 | 113 Procedure with DCM/TFA (9:1, v/v) | 24 |
| Compound 106 | From intermediate 352 | 27 Procedure with DCM/TFA (10:1, v/v) | 33 |
| Compound 108 | From intermediate 355 | 10 Procedure with DCM/TFA (10:1, v/v) | 15 |
| Compound 112 | From intermediate 363 | 16 Procedure with DCM/TFA (10:1, v/v) | 23 |

-continued

| Compound number | Structure | Mass (mg) | Yield (%) |
|---|---|---|---|
| Compound 113 | From intermediate 364 | 16 Procedure with DCM/TFA (5:1, v/v) | 17 |
| Compound 114 | From intermediate 365 | 10 Procedure with DCM/TFA (11:1, v/v) | 15 |
| Compound 115 | TRANS; From intermediate 366 | 36.5 Procedure with DCM/TFA (5:1, v/v) white solid | 40 |
| Compound 116 | CIS; From intermediate 367 | 6.8 Procedure with DCM/TFA (3:1, v/v) yellow solid | 6 |

-continued

| Compound number | Structure | Mass (mg) | Yield (%) |
|---|---|---|---|
| Compound 117 | CIS; From intermediate 368 | 45 white solid | 53 |
| Compound 118 | From intermediate 369 | 42 white solid Procedure with DCM/TFA (3:1, v/v) | 45 |
| Compound 119 | From intermediate 370 | 60 white solid | 44 |
| Compound 120 | TRANS From intermediate 371 | 50 white solid | 85 |

-continued

| Compound number | Structure | Mass (mg) | Yield (%) |
|---|---|---|---|
| Compound 121 | From intermediate 372 | 20 | 39 |
| Compound 122 | CIS; From intermediate 373 | 56 white solid | 58 |
| Compound 123 | From intermediate 374 | 16 white solid | 19 |
| Compound 124 (mixture of 4 unseparated diastereoisomers) | From intermediate 375 | 40 white solid | 54 |

Example B8

Preparation of Compound 80

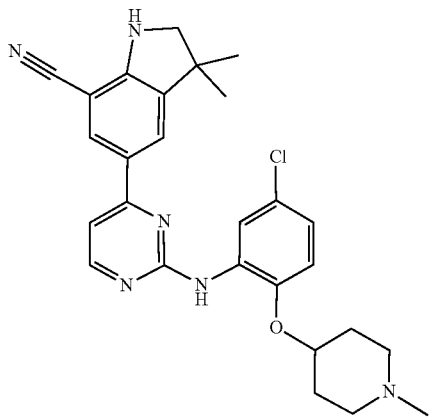 [SMILES: CN1CCC(Oc2ccc(Cl)cc2Nc2nccc(-c3cc(C#N)c4c(c3)C(C)(C)CN4)n2)CC1]

HCl (3M in H₂O) (1.72 mL, 5.16 mmol) was added to a solution of intermediate 281 (304.00 mg, 0.52 mmol) in EtOAc (19.3 mL) and the reaction mixture was stirred 2 h at rt. The reaction was checked by LC/MS after 2 h but no conversion was observed. Also, the reaction was heated at 45° C. overnight. In order to speed the conversion, the temperature was elevated until 65° C. for one more day. After completion of the reaction, the resulting mixture was cooled to rt, poured onto a 10% aqueous solution of K₂CO₃ and extracted with DCM. The organic layer was decanted, dried over MgSO₄, filtered and evaporated to dryness. The residue (183 mg, yellow oil) was purified by column chromatography on silica gel (irregular SiOH, 24 g, mobile phase: NH₄OH/MeOH/DCM, gradient from 0% NH₄OH, 0% MeOH, 100% DCM to 1.5% NH₄OH, 15% MeOH, 85% DCM). The fractions containing the product were evaporated. The residue (103 mg, yellow oil) was purified by reverse phase semi-preparative HPLC (Stationary phase: X-Bridge-C18, 5 μm 30×150 mm, mobile phase: gradient from 40% NH₄HCO₃ 0.5%, 60% MeOH to 0% NH₄HCO₃ 0.5%, 100% MeOH). The fractions containing the product were concentrated to give a colorless oil. The residue (60 mg) was precipitated with Et2O to give 54 mg of compound 78 (21% yield, white powder). M. P=192° C. (K).

The compounds in the Table below were prepared by using an analogous method as the one reported for the preparation of compound 80 starting from the respective starting materials. The most relevant minor deviations to the referenced method are indicated as additional information in the column 'Mass (mg)'.

| Compound number | Structure | Mass (mg) | Yield (%) |
|---|---|---|---|
| compound 99 | From intermediate 337 | 63 white powder Procedure with MeOH as solvent | 36 |
| Compound 100 | From intermediate 338 | 18 white powder Procedure with MeOH as solvent | 11 |

-continued

| Compound number | Structure | Mass (mg) | Yield (%) |
|---|---|---|---|
| Compound 101 | 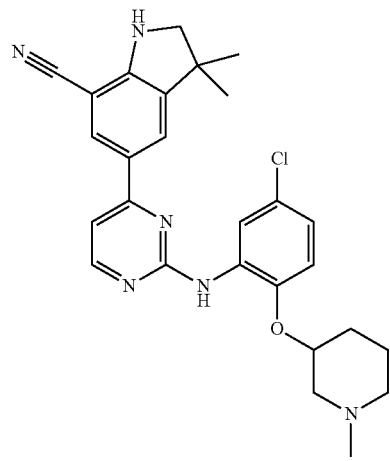 [SMILES: CN1CCCC(Oc2ccc(Cl)cc2Nc2nccc(-c3cc(C#N)c4c(c3)C(C)(C)CN4)n2)C1]<br>From intermediate 339 | 40<br>white powder<br>Procedure with MeOH as solvent | 26 |
| Compound 102 | 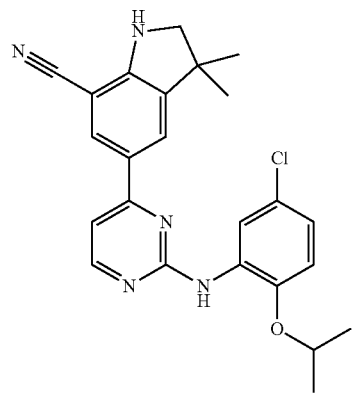<br>From intermediate 342 | 80<br>(100% purity based on LC/MS)<br>Procedure with EtOAc as solvent<br>white powder<br>22<br>Procedure with MeOH as solvent<br>(100% purity based on LC/MS)<br>white powder | 23<br><br><br><br><br><br>44 |
| Compound 103 | 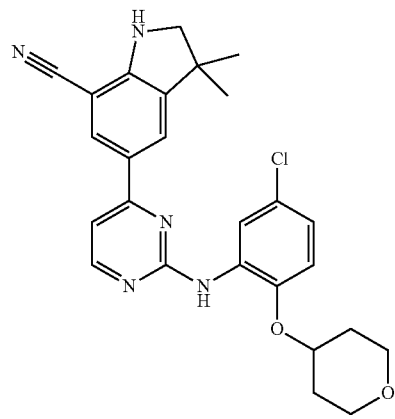 [SMILES: CC1(C)CNc2c(C#N)cc(-c3ccnc(Nc4cc(Cl)ccc4OC4CCOCC4)n3)cc21]<br>From intermediate 345 | 83<br>yellow powder | 20 |

| Compound number | Structure | Mass (mg) | Yield (%) |
|---|---|---|---|
| Compound 107 | From intermediate 353 | 15 white powder Procedure with MeOH as solvent | 26 |
| Compound 109 | From intermediate 356 | 48 yellow powder Procedure with MeOH as solvent | 63 |

Example B9

Preparation of Compound 110:

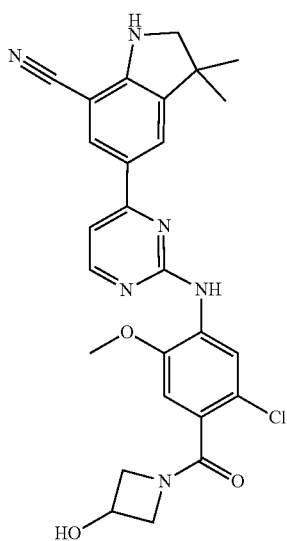 [SMILES: COc1cc(C(=O)N2CC(O)C2)c(Cl)cc1Nc1nccc(-c2cc(C#N)c3c(c2)C(C)(C)CN3)n1]

A mixture of intermediate 357 (160.00 mg, 0.26 mmol) in HCl/Dioxane (4M) was stirred at rt for 3 h. The mixture was evaporated under vacuo and purified by high-performance liquid chromatography (Column: Waters Xbridge Prep OBD C18 150×30, 5 nm, mobile phase: water (0.05% ammonia hydroxide v/v)/CH$_3$CN, gradient from 33% to 63% of CH$_3$CN in 10 min, then 100% of CH$_3$CN in 3 min with a flow rate of 25 mL/min). The desired fractions were collected, and the solvent was concentrated in vacuum to give 38 mg of compound 110 (28% yield).

Example B10

Preparation of Compound 111:

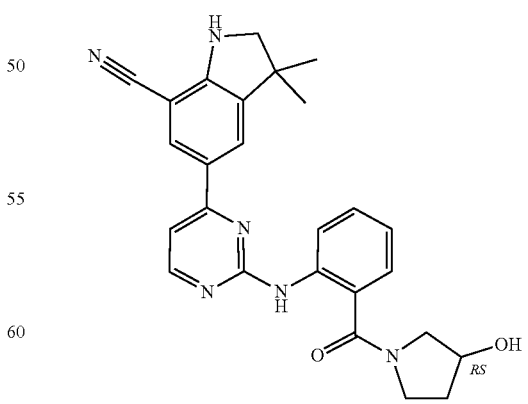

TBAF (1M in THF) (0.59 mL, 0.59 mmol) was added to a solution of intermediate 362 (168.00 mg, 0.29 mmol) in Me-THF (5 mL) and the reaction mixture was stirred at rt for 4 h. The reaction mixture was diluted with EtOAc and Example B11

Preparation of Compound 135:

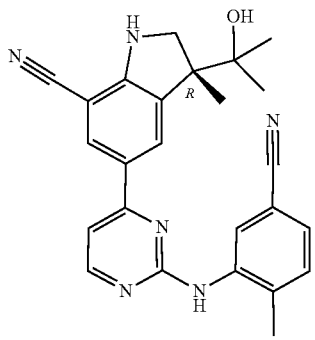

TFA (0.88 mL, 11.50 mmol) was added dropwise to a solution of intermediate 383 (178.00 mg, 0.34 mmol) in DCM (stabilized with amylene) (6 mL) at 5° C. and the reaction mixture was stirred for 30 min at this temperature. The reaction mixture was quenched with a 10% aqueous solution of $K_2CO_3$ and extracted with DCM. The organic layer was decanted, dried over $MgSO_4$, filtered and evaporated to dryness. The residue was purified by column chromatography on silica gel (irregular SiOH, 24 g, mobile phase: DCM/MeOH, gradient from 97:3 to 95:5). The pure fractions were collected and evaporated to dryness. The residue (98 mg) was purified by chromatography over silica gel by achiral SFC (Stationary phase: 2-ethylpyridine 6 μm 150×21.2 mm, mobile phase: 75% $CO_2$, 25% MeOH (0.3% $iPrNH_2$)). The pure fractions were mixed and the solvent was evaporated. The residue (52 mg) was crystallized from $Et_2O$, filtered and dried to give 25 mg of compound 135 (17% yield).

Preparation of Compound 136:

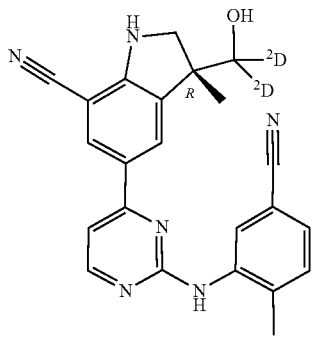

TFA (0.77 mL, 10.02 mmol) was added dropwise to a solution of intermediate 384 (147.00 mg, 0.29 mmol) in DCM (stabilized with amylene) (5 mL) at 5° C. and the reaction mixture was stirred for 1 h at this temperature. The reaction mixture was quenched with a 10% aqueous solution of $K_2CO_3$ and extracted with DCM. The organic layer was decanted, dried over $MgSO_4$, filtered and evaporated to dryness. The residue was purified by column chromatography on silica gel (irregular SiOH, 24 g, mobile phase: DCM/MeOH, gradient from 97:3 to 95:5). The pure fractions were collected and evaporated to dryness. The residue (44 mg) was purified by reverse phase (stationary phase: YMC-actus Triart-C18, 10 μm, 30×150 mm, mobile phase: gradient from 60% $NH_4HCO_3$ 0.2%, 40% MeOH to 0% $NH_4HCO_3$ 0.2%, 100% MeOH). The mixture was taken up by $CH_3CN$, filtered and dried to give 24 mg of compound 136 (20% yield).

Example B12

Preparation of Compound 137:

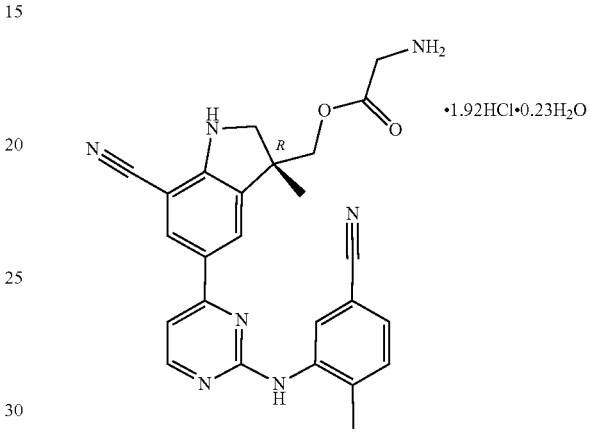

HCl (4M in dioxane) (8 mL; 32.24 mmol) was added at room temperature to a solution of intermediate 385 (3.57 g; 6.45 mmol) in ACN (95 mL) and the reaction mixture was stirred for 3 hours. The suspension was sonicated for 15 min and, then, the precipitate was filtered, washed with ACN and dried at 50° C. under vacuo yielding 2.92 g (86%) of compound 137, M.P.: 290° C. (DSC).

Preparation of Compound 13a.

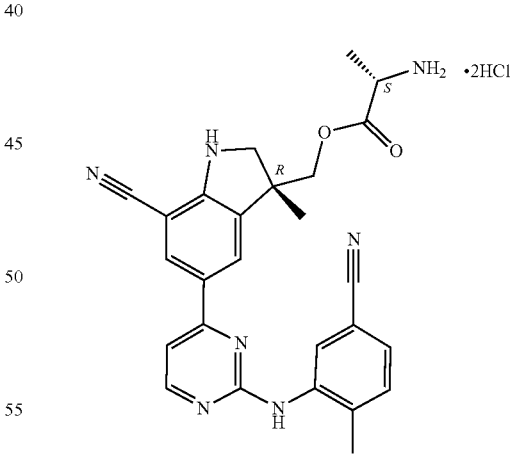

HCl (4M in dioxane) (35.2 mL; 140.93 mmol) was added at room temperature to a solution of intermediate 386 (16 g; 28.19 mmol) in ACN (400 mL) and the reaction mixture was stirred for 3 hours. Then, the suspension was sonicated for 30 minutes. The precipitate was filtered, washed with ACN and dried yielding 14.21 g (93%) of compound 138.

The compounds in the Table below were prepared by using an analogous method as reported for the preparation compounds 137 and 138, starting from the respective starting materials.

| Intermediate number | Structure | Mass (mg) | Yield (%) |
|---|---|---|---|
| Compound 139 | 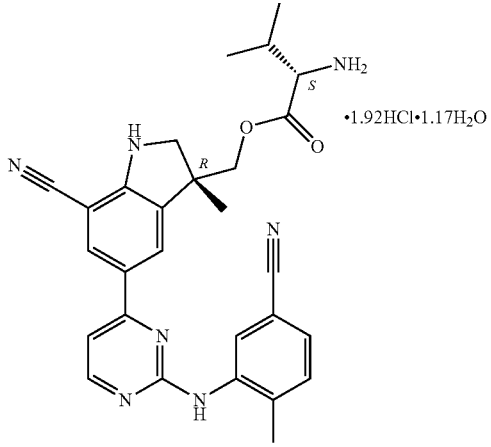 From intermediate 387 | 230 | 54 |
| Compound 140 | 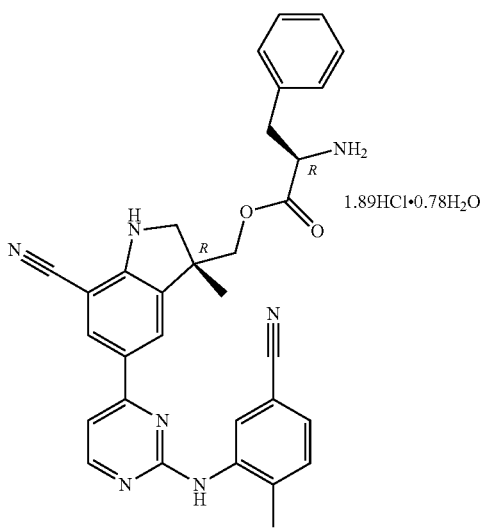 From intermediate 388 | 563 | 72 |
| Compound 141 | 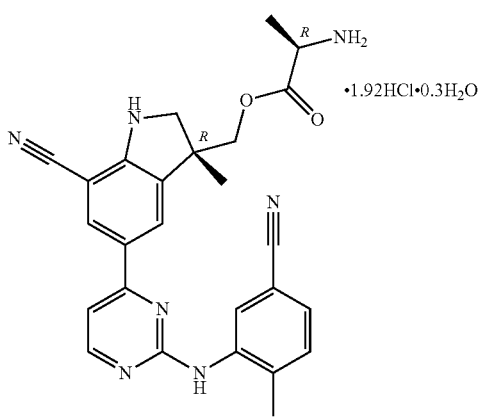 From intermediate 389 | 241 | 88 |

-continued

| Intermediate number | Structure | Mass (mg) | Yield (%) |
|---|---|---|---|
| Compound 142a | From intermediate 390 | 80 | 24 |
| Compound 142b | •0.93HCl•0.11H₂O  From intermediate 390 | 200 | 47 |

Example B13

Preparation of Compound 182:

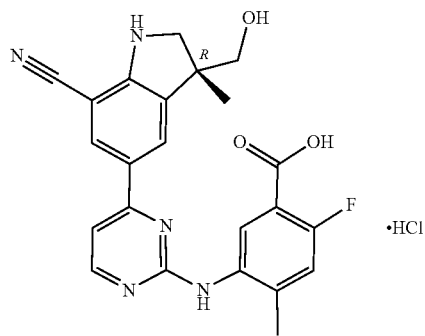

A solution of lithium hydroxide (213 mg; 5.074 mmol) in water (5 mL) was added to a solution of intermediate 483 (570 mg; 1.015 mmol) in THF (25 mL) and the reaction mixture was stirred for 18 hours. A solution of lithium hydroxide (213 mg; 5.074 mmol) in water (2 mL) was added again and the reaction mixture was stirred at room temperature for 24 hours more. The reaction mixture was heated at 60° C. for 4 hours. The reaction mixture was acidified with 3N aqueous HCl, diluted with ACN and concentrated. The residue was crystallized from water. The precipitate was filtered and dried to give 402 mg (84%) of compound 182.

Preparation of Compound 202:

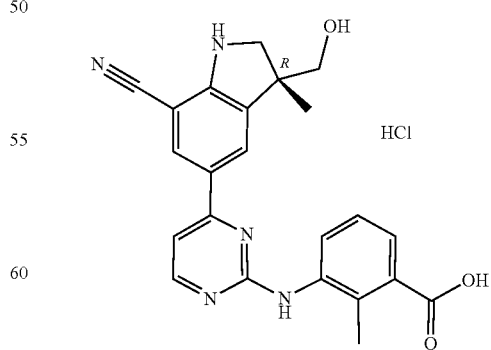

Compound 202 was prepared following an analogous method than the one used for the preparation of compound 182 starting from intermediate 522 (491 mg; 84%).

C. CONVERSION OF THE FINAL COMPOUNDS

Example C1

Preparation of Compound 125:

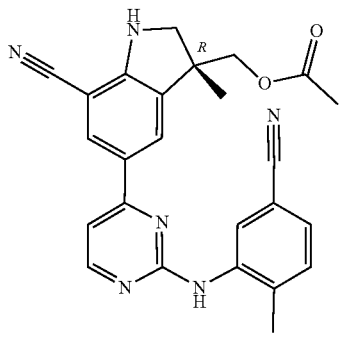

DIPEA (2.16 mL, 12.51 mmol) was added dropwise at 5° C. to a mixture of compound 1 (992.00 mg, 2.50 mmol), acetic acid (0.28 mL, 5.00 mmol) and HATU (3.80 g, 10.01 mmol) in a mixture of THF (4.07 mL) and DMF (3.88 mL). The mixture was stirred at rt overnight. Then, water was added and the reaction mixture was extracted with DCM. The organic layer was decanted, dried over MgSO$_4$, filtered and evaporated to dryness. The residue (2 g, yellow oil) was purified by column chromatography on silica gel (irregular SiOH, 120 g, mobile phase: DCM/MeOH, gradient from 100:0 to 98:2). The fractions containing the product were collected and evaporated to dryness to give 566 mg of a first batch of compound 125 (58% purity based on LC/MS, yellow oil). The others fractions were collected and evaporated to dryness to give a second batch of compound 125 (800 mg, yellow oil). This batch was purified again by column chromatography on silica gel (irregular SiOH, 40 g, mobile phase: DCM, 100%). The fractions containing the products were gathered and evaporated. The residue (563 mg, yellow powder) was taken up with CH$_3$CN to provide 393 mg of compound 125 (36% yield, yellow powder). M.P=213° C. (K).

The compounds in the Table below were prepared by using an analogous method as the one reported for the compound 125 starting from the respective starting materials. The most relevant minor deviations to the referenced method are indicated as additional information in the column 'Mass (mg)'.

| Compound number | Structure | Mass (mg) | Yield (%) |
|---|---|---|---|
| Compound 126 | From compound 1 | 30 white powder | 6 |
| Compound 127 | From compound 66 | 55 white powder | 18 |
| Compound 128 | From compound 13 | 40 white powder | 32 |

Example C2

Preparation of Compound 129:

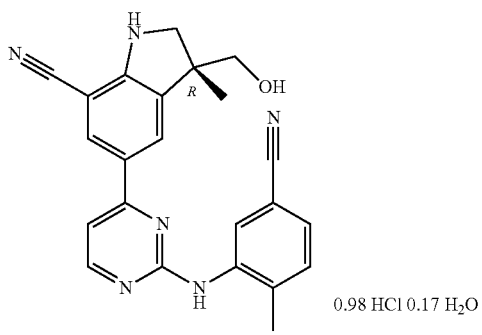

0.98 HCl 0.17 H₂O

HCl (4M in dioxane) (126.00 μL, 0.50 mmol) was added dropwise at 5° C. to a suspension of compound 1 (200.00 mg, 0.50 mmol) in CH₃CN (20 mL). The reaction mixture was allowed to warm to rt and stirred overnight. The precipitate was filtered, washed with CH₃CN and dried at 50° C. under vacuum all over the week end to give 204 mg of compound 129 (93% yield). M.P.=190° C. (K).

Example C3

Preparation of Compound 130

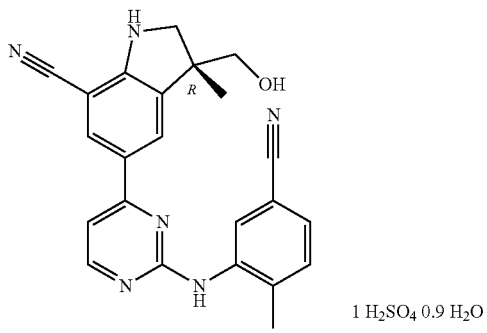

1 H₂SO₄ 0.9 H₂O

Aqueous H₂SO₄ (3M) (168.00 μL, 0.50 mmol) was added dropwise at 5° C. to a suspension of compound 1 (200.00 mg, 0.50 mmol) in CH₃CN (20 mL). The reaction mixture was allowed to warm to rt and stirred overnight. The precipitate was filtered, washed with CH₃CN and dried at 50° C. under vacuum all over the week end to give 214 mg of compound 130 (83% yield). M.P.=264° C. (K).

Example C4

Preparation of Compound 131:

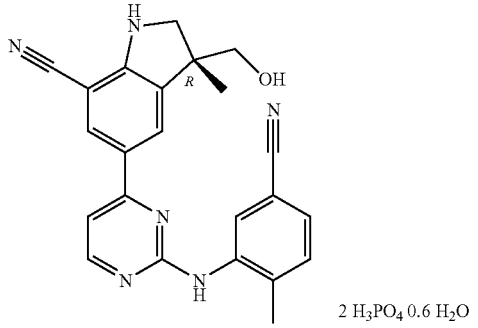

2 H₃PO₄ 0.6 H₂O

Phosphoric acid (3M) (168.00 μL, 0.50 mmol) was added dropwise at 5° C. to a suspension of compound 1 (200.00 mg, 0.50 mmol) in CH₃CN (20 mL). The reaction mixture was allowed to warm to rt and stirred overnight. The precipitate was filtered, washed with CH₃CN and dried at 50° C. under vacuum all over the week end to give 228 mg of compound 131 (75% yield). M.P.=174° C. (K).

Example C5

Preparation of Compound 132:

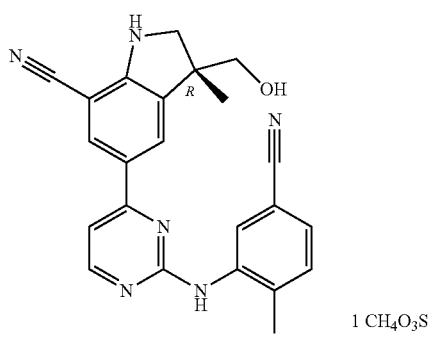

1 CH₄O₃S

Methanesulfonic acid (33.00 μL, 0.50 mmol) was added dropwise to a suspension of compound 1 (200.00 mg, 0.50 mmol) in CH₃CN (20 mL). The reaction mixture was stirred overnight. The precipitate was filtered, washed with Et₂O and dried at 50° C. under vacuum to give 115 mg of compound 132 (46% yield). M.P.=234° C. (K).

Example C6

Preparation of Compound 133:

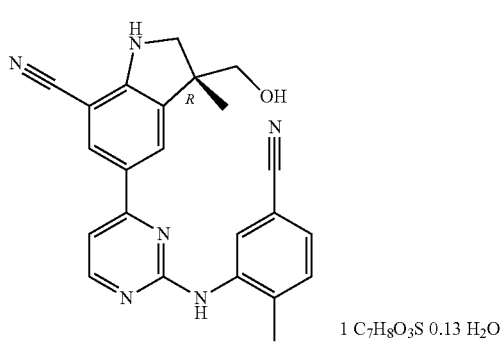

1 C₇H₈O₃S 0.13 H₂O

A solution of p-toluenesulfonic acid, monohydrate (96.00 mg, 0.50 mmol) in water (0.5 mL) was added dropwise to a suspension of compound 1 (200.00 mg, 0.50 mmol) in CH₃CN (20 mL). The reaction mixture was stirred overnight. The precipitate was filtered, washed with Et₂O and dried at 50° C. under vacuum to give 229 mg of compound 133 (79% yield). M.P.=262° C. (K).

Example C7

Preparation of Compound 134:

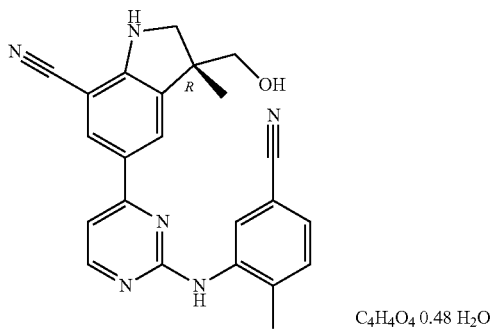

C₄H₄O₄ 0.48 H₂O

A solution of maleic acid (58.56 mg, 0.50 mmol) in CH₃CN (0.50 mL) and water (0.50 mL) was added dropwise to a suspension of compound 1 (200.00 mg, 0.50 mmol) in CH₃CN (20 mL). The reaction mixture was allowed to warm to rt and stirred overnight. The precipitate was filtered, washed with Et₂O and dried at 50° C. under vacuum to give 169 mg of compound 134 (65% yield). M.P.=190° C. (K).

Example C8

Preparation of Compound 143:

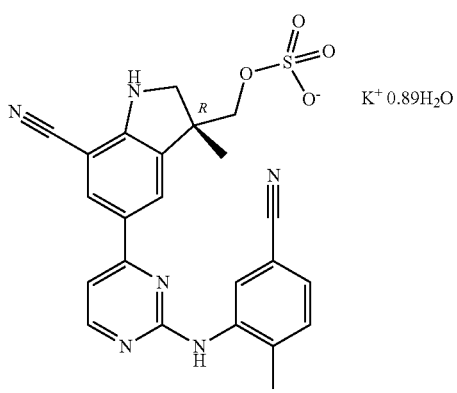

K⁺ 0.89H₂O

Compound 1 (200 mg; 0.504 mmol) was added to a suspension of pyridine sulfure trioxide (48-50%) (163 mg; 0.504 mmol) in THF (2 mL) and the reaction mixture was stirred at room temperature for 3 hours. A solution of potassium hydroxide (28 mg; 0.504 mmol) in water (0.5 mL) was added and the resulting solution was cooled to 5° C. before acetone was added. The product precipitated under standing. Then, it was filtered and washed with acetone yielding 250 mg of Fraction A (>100%).
Fraction A was taken up with toluene, then EtOH and the solvent was evaporated to dryness. The precipitate was taken up with ACN, filtered and dried yielding 233 mg of Fraction B (97%).
Fraction B was suspended in water and stirred for 15 minutes, then filtered and dried yielding 159 mg (59%) of compound 143, M.P.: >270° C. (Kofler).

Preparation of Compound 144:

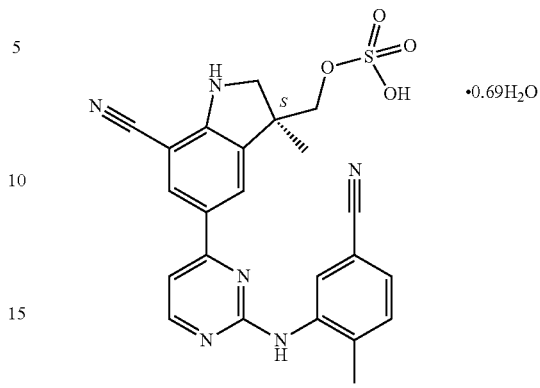

·0.69H₂O

Compound 65 (200 mg; 0.504 mmol) was added to a suspension of pyridine sulfure trioxide (164 mg; 0.504 mmol) in THF (2 mL) and the reaction mixture was stirred at room temperature for 3 hours. A solution of potassium hydroxide (28 mg; 0.504 mmol) in wt are (0.5 mL) was added and the solution was cooled to 5° C. before acetone was added. The product precipitated under standing. Then, it was filtered and washed with acetone yielding 249 mg of Fraction A (>100%).
Fraction A was washed with water then acetone and dried yielding 127 mg (51%) of compound 144.

Example C9

Preparation of Compound 145

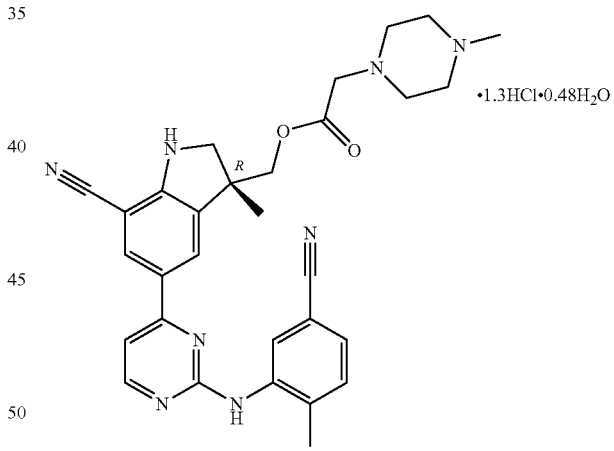

·1.3HCl·0.48H₂O

A mixture of compound 1 (250 mg; 0.63 mmol), 4-methyl-1-piperazineacetic acid (249 mg; 1.58 mmol), HATU (599 mg; 1.58 mmol), DIPEA (543 µL; 3.15 mmol) and DMAP (4 mg; 0.034 mmol) in DMF (7.5 mL) was stirred at room temperature for 18 hours. The solution was poured onto water and extracted with EtOAc. The organic layer was washed with H₂O, then brine, dried over MgSO4, filtered and evaporated to dryness. The residue was purified by chromatography over silica gel (irregular SiOH, 24 g; mobile phase: 0.2% NH₄OH, 2% MeOH, 98% DCM to 0.5% NH₄OH, 5% MeOH, 95% DCM). The pure fractions were collected and evaporated to dryness yielding 395 mg of an intermediate fraction which was dissolved in ACN (15 mL). The solution was cooled to 5° C. and HCl (4M indioxane) (473 µL; 1.89 mmol) was added. The suspension was stirred for 3 hours and the precipitate was filtered and dried yielding 203 mg (54%) compound 145, M.P.: gum at 216° C. (Kofler).

Preparation of Compound 146:

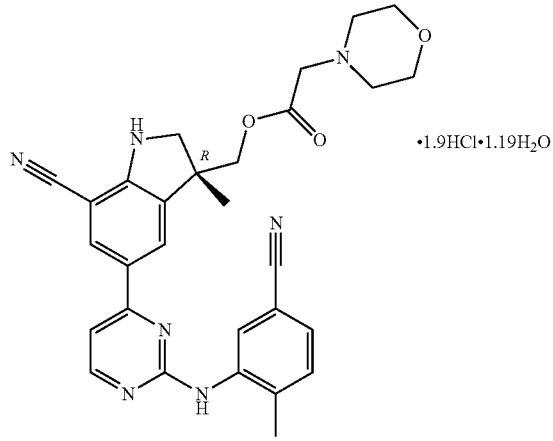

Compound 146 was prepared following a similar procedure than the one used for the preparation of compound 145 starting from compound 1 and 4-methyl-1-morpholine acetic acid. 86 mg (22%) of compound 146 were obtained, gum at 186° C. (Kofler).

Example C10

Preparation of Compound 164:

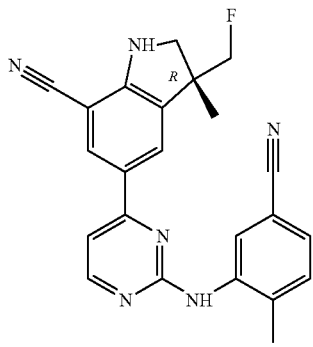

Diethylaminosulfur trifluoride (0.247 mL; 2.02 mmol) was added to a solution of compound 1 (200 mg; 0.504 mmol) in THF (7 mL) at −78° C. After 2 hours, diethylaminosulfur trifluoride (0.247 mL; 2.02 mmol) was added again and the mixture was stirred at rt for 20 hours. The mixture was poured into ice. The obtained precipitate was filtered off. The mother layer were basified by potassium carbonate and extracted with EtOAc. The organic layer was washed with brine, dried over MgSO$_4$, filtered and the solvent was evaporated. The residue was purified by chromatography over silica gel (50 g, 15-40 μm, solid deposit, eluent: DCM/MeOH: 100/0 to 95/5). The pure fractions were mixed and the solvent was evaporated. The resulting residue (0.05 g) was purified via achiral SFC (stationary phase: diethylaminopropyl 5 μm 150×21.2 mm, mobile phase: 85% CO$_2$, 15% MeOH). The pure fractions were mixed and the solvent was evaporated to give 0.02 g (10%) of compound 164. M.P.=194° C. (Kofler).

Example C11

Preparation of Compound 172:

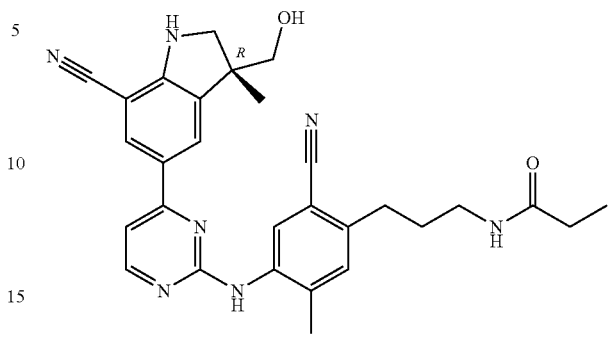

A mixture of compound 170 (39 mg; 0.086 mmol), propanoic acid (0.095 mL; 0.0946 mmol), HATU (36 mg; 0.0946 mmol) and DIPEA (0.0445 mL; 0.258 mmol) in DCM (0.8 mL) was stirred at room temperature for 18 hours. The solution was poured onto water and extracted with DCM. The organic layer was washed with brine, dried over MgSO$_4$, filtered and evaporated to dryness. The residue was purified by chromatography over silica gel (irregular SiOH, 4 g; mobile phase: DCM/MeOH: 100/0 to 95/5). The pure fractions were collected and evaporated to dryness to give 20 mg (46%) of compound 172. MP=193° C. (Kofler).

Preparation of Compound 176:

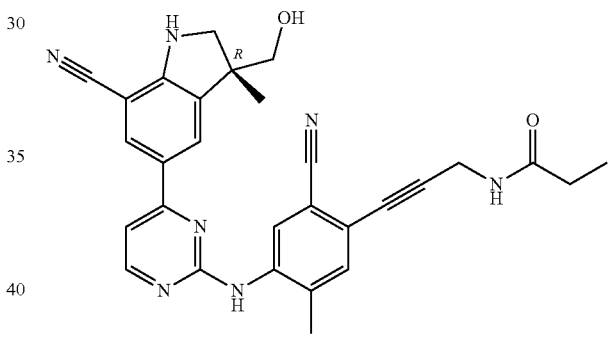

Compound 176 was synthesized by using an analogous method than the one used for the preparation of compound 172 above, starting from compound 171 (21 mg; 20%).

Preparation of Compound 18

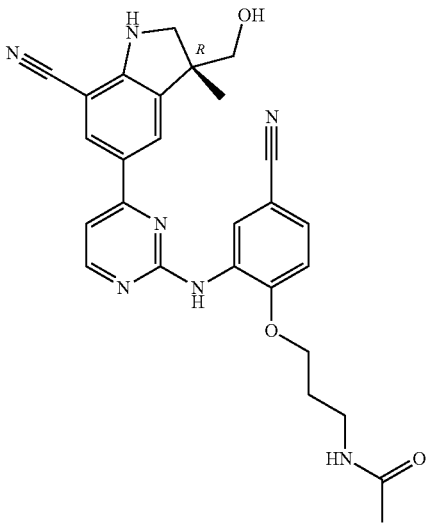

Compound 181 was synthesized by using an analogous method as the one used for the preparation of compound 172, starting from compound 180 (4 mg; 18%).

Preparation of Compound 183:

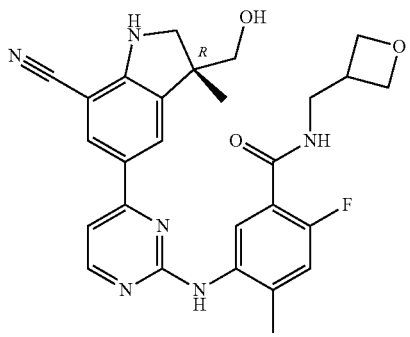

Compound 183 was synthesized by using an analogous method (solvent: DCM/THF/DMF: 50/50/5) as the one used for the preparation of compound 172, starting from compound 182 (280 mg; 65%; MP=209° C.; DSC).

Preparation of Compound 185:

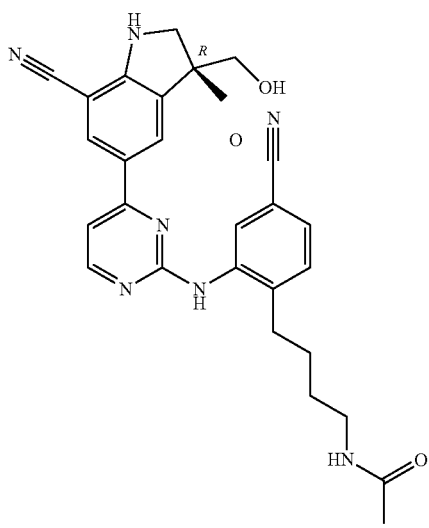

Compound 184 was synthesized by using an analogous method (solvent: DCM/THF) than the one used for the preparation of compound 172, starting from compound 184 (35 mg; 45%; MP=gum at 156° C.; Kofler).

Preparation of Compound 203:

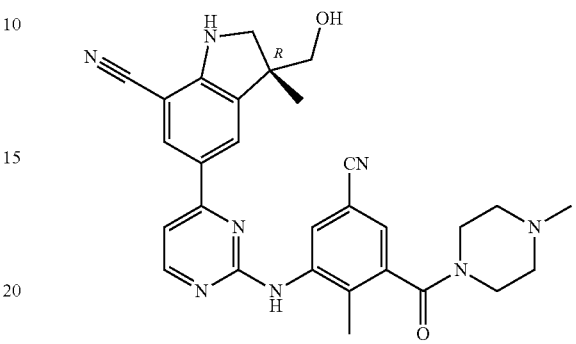

A mixture of compound 201 (260 mg; 0.38 mmol), 1-methylpiperazine (63 µL; 0.57 mmol), HATU (159 mg; 0.42 mmol) and DIEA (265 µL; 1.52 mmol) in DCM (10 mL) was stirred at room temperature for 18 hours. Water was added and the reaction mixture was extracted with DCM. The organic layer was filtered through Chromabond® and evaporated to dryness. The residue was purified (180 mg) by chromatography over silica gel (irregular SiOH, 10 g; mobile phase: gradient from 0.3% NH₄OH, 3% MeOH, 97% DCM to 1.5% NH₄OH, 15% MeOH, 85% DCM). The pure fractions were collected and evaporated to dryness. The residue was taken up with ACN and the precipitate was filtered and dried yielding 72 mg (36%) of compound 203. M.P.: 294° C. (DSC).

The compounds in the table below were prepared using an analogous method as described for the preparation of compound 203, starting from the respective starting materials.

| Compound number | Structure | Quantity | Yield |
|---|---|---|---|
| Compound 204 | From compound 201 and intermediate 524 | 78 mg | 40% |

-continued
| Compound number | Structure | Quantity | Yield |
|---|---|---|---|
| Compound 205 | 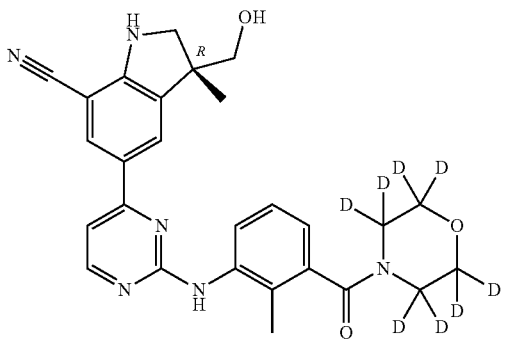<br>From compound 202 and morpholine-d8 | 331 mg | 38% |
| Compound 206 | 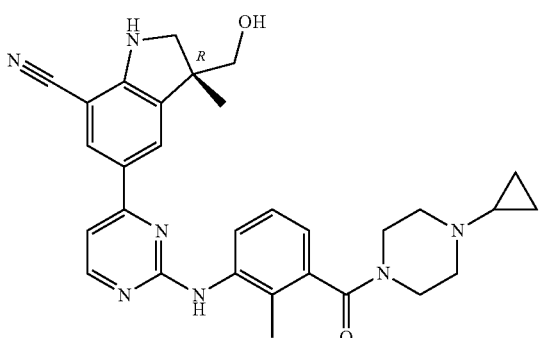<br>From compound 202 and 1-cyclopropylpiperazine | 205 mg | 71% |
| Compound 207 | 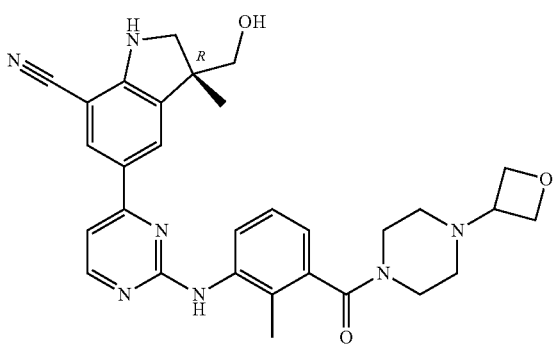<br>M.P.: 268° C. (DSC)<br>From compound 202 and 1-(oxetan-3-yl) piperazine | 200 mg | 67% |

Example C12

Preparation of Compound 178

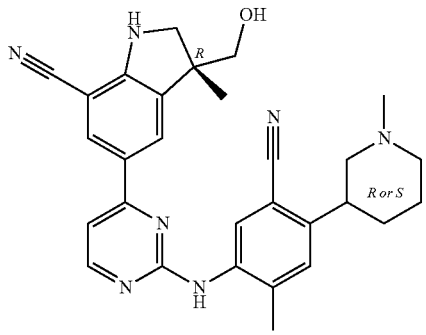

And Compound 179

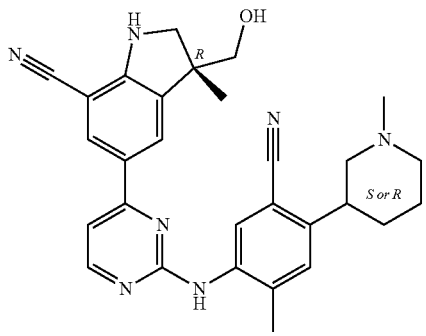

Compound 178 and compound 179 were obtained from an achiral SFC purification (stationary phase: Chiralpak IC 5 μm 250×20 mm, mobile phase: 50% $CO_2$, 50% EtOH (0.3% iPrNH$_2$)). The fractions containing the products were mixed and the solvent was evaporated to afford respectively 47 mg of compound 178 and 43 mg of compound 179.

Example C13

Preparation of Compound 201:

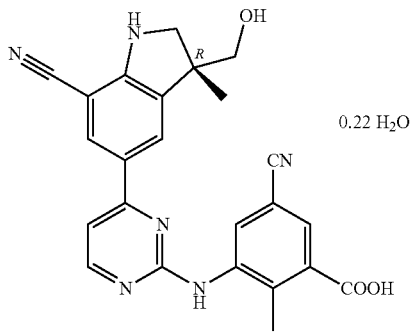

A solution of LiOH.H$_2$O (77 mg; 1.83 mmol) in distilled water (2 mL) was added to a solution of compound 8 (166 mg; 0.365 mmol) in THF (10 mL) and the reaction mixture was stirred for 18 hours. The reaction mixture was acidified with 6N aqueous HCl, diluted with ACN and concentrated. The residue was crystallized from water/ACN. The precipitate was filtered, washed with water and dried yielding 118 mg (72%) of compound 201. M.P.: 220° C. (gum, Kofler).

Preparation of Compound 202:

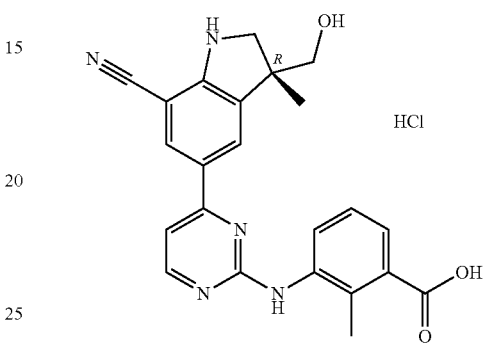

Compound 202 was prepared following an analogous method than the one used for the preparation of compound 501 starting from intermediate 522 (491 mg; 84%).

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). For molecules with multiple isotopic patterns (Br, Cl . . . ), the reported value is the one obtained for the lowest isotope mass. All results were obtained with experimental uncertainties that are commonly associated with the method used. Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| Method 1 | Waters: Acquity UPLC ®- DAD and Quattro Micro ™ | Waters: BEH C18 (1.7 µm, 2.1 × 100 mm) | A: 95% CH₃COONH₄ 7 mM/5% CH₃CN, B: CH₃CN | 84.2% A for 0.49 min, to 10.5% A in 2.18 min, held for 1.94 min, back to 84.2% A in 0.73 min, held for 0.73 min. | 0.343<br>40 | 6.2 |
| Method 2 | Waters: Acquity UPLC ® H-Class-DAD and SQD 2 | Waters: BEH C18 (1.7 µm, 2.1 × 100 mm) | A: 95% CH₃COONH₄ 7 mM/5% CH₃CN, B: CH₃CN | From 84.2% A to 10.5% A in 2.18 min, held for 1.94 min, back to 84.2% A in 0.73 min, held for 0.73 min. | 0.343<br>40 | 6.1 |
| Method 3 | Agilent 1200 equip with MSD 6110 | Agilent TC-C18 (5 µm, 2.1 × 50 mm) | A: H₂O (0.1% TFA), B: CH₃CN (0.05% TFA) | 90% A held for 0.80 min, then from 90% A to 20% A in 3.7 min, held for 3.00 min, back to 90% A in 2.00 min. | 0.8<br>50 | 10 |
| Method 4 | Waters: Acquity UPLC ® H-Class - DAD and QDa | BEH ®-C18 (1.7 µm, 2.1 × 1000 mm) | A:95% CH₃COONH₄ 7 mM/5% CH₃CN, B: CH₃CN | 95% A to 5% A in 1 min, held for 1.6 min, back to 95% A in 1.2 min, held for 0.5 min. | 0.5<br>40 | 3.3 |
| Method 5 | Agilent 1200 equip with MSD 6110 | XBridge Shield RP18 (5 µm, 2.1 × 50 mm) | A: H₂O (0.05% NH₃•H₂O), B: CH₃CN | 100% A held for 1.00 min, then from 100% A to 40% A in 4.00 min, then from 40% A to 5% A in 2.50 min, back to 100% A in 2.00 min. | 0.8<br>40 | 10 |
| Method 6 | Waters: Micromass ZQ2000-Waters Acquity UPLC system equipped with PDA detector | Acquity HST - C 18 (1.8 µM, 2.1 × 100 mm) | A:95% Water (with 0.1% CH₃COOH), B: CH₃CN (with 0.1% CH₃COOH) | 95% A held 0.4 min, then from 95% A to 5% A 5.2 min, held for 0.8 min. | 0.4<br>40 | 6.4 |
| Method 7 | Agilent 1100 | ACE C18 column (3 µM, 3.0 × 50 mm) | A: 95% Water (with 0.05% TFA), B: CH₃CN | 95% A to 0% A 5.2 min | 2.2<br>50 | 6.4 |
| Method 8 | Agilent 1200 equip with MSD 6110 | Phenomenex Luna-C18, 50 × 2 mm, 5 µm | A: H₂O (0.1% TFA), B: CH₃CN (0.05% TFA) | 100% A held for 1 mn then 100% A to 40% A in 4 mn then 40% A to 15% A in 2.5 mn then back to 100% A in 2 mn held for 0.5 min. | 0.8<br>50 | 10 |
| Method 9 | Agilent 1200 equip with MSD 6110 | Phenomenex Luna-C18, 50 × 2 mm, 5 µm | A: H₂O (0.1% TFA), B:CH₃CN (0.05% TFA) | 90% A held for 0.8 mn then 90% A to 20% A in 3.7 mn, held for 2 mn, back to 90% A in 2 mn held for 0.5 min. | 0.8<br>50 | 10 |
| Method 10 | Agilent 1290 Infinity DAD LC/MS G6110A | Phenomenex Kinetex C18 (50 × 2.1 mm, 1.7 µm) | A:0.1% HCOOH in H₂O B: CH₃CN | From 90% A to 10% A in 1.5 min, held for 0.4 min, to 90% A in 0.1 min. | 1.5<br>60 | 2.0 |
| Method 11 | Agilent 1100 Infinity DAD LC/MS G1956A | YMC-ODS-AQ C18 (50 × 4.6 mm, 3 µm) | A: 0.1% HCOOH in H₂O B: CH₃CN | From 95% A to 5% A in 4.8 min, held for 1.0 min, to 90% A in 0.2 min. | 2.6<br>35 | 6.0 |
| Method 12 | Agilent 1290 Infinity DAD TOF-LC/MS G6224A | YMC-pack ODS-AQ C18 (50 × 4.6 mm, 3 µm) | A: 0.1% HCOOH in H₂O B: CH₃CN | From 95% A to 5% A in 4.8 min, held for 1.0 min, to 95% A in 0.2 min. | 2.6<br>35 | 6.0 |

Melting Points

For a number of compounds, melting points (MP) were determined with a DSC1 (Mettler-Toledo). Melting points were measured with a temperature gradient of 10° C./minute. Maximum temperature was 350° C. Values are peak values. Indicated in the table as DSC.

For a number of compounds, melting points were obtained with a Kofler hot bench (indicated with (K) in the analytical table), consisting of a heated plate with linear temperature gradient, a sliding pointer and a temperature scale in degrees Celsius.

For a number of compounds, melting points were obtained with an automatic Melting Point Apparatus WRS-2A (indicated with WRS-2A in the analytical table). Melting points were measured with a temperature gradient of 5° C. per minute starting from room temperature to a maximum value of 320° C.

For a number of compounds, melting points were obtained with a Mettler Toledo MP50 apparatus (indicated with MP50 in the analytical table). Melting points were measured with a temperature gradient of 10° C. per minute starting from 50° C. (waiting time 10 second) to a maximum value of 300° C.

TABLE

| Co. No. | MP (° C.) | MP Method | Rt | [M + H]$^+$ | LCMS Method |
|---|---|---|---|---|---|
| 1 | 222 | DSC | 2.71 | 397 | 1 |
| 2 | — | — | 2.82 | 504 | 1 |
| 3 | — | — | 2.95 | 506 | 1 |
| 4 | 193 | DSC | 2.23 | 429 | 1 |
| 5 | 115 (gum) | K | 2.17 | 508 | 1 |
| 6 | 148 (gum) | K | 2.49 | 504 | 1 |
| 7 | 215 | DSC | 3.01 | 424 | 1 |
| 8 | 184 | K | 2.44 | 443 | 1 |
| 9 | 120 | K | 3.17 | 541 | 1 |
| 10 | 215 | K | 3.01 | 439 | 1 |
| 11 | 215 | DSC | 2.74 | 415 | 1 |
| 12 | 159 | K | 2.64 | 471 | 1 |
| 13 | 194 | K | 3.13 | 453 | 1 |
| 14 | 162 | K | 2.76 | 483 | 1 |
| 15 | 110 (gum) | K | 1.32 | 439 | 4 |
| 16 | 162 (gum) | K | 3.10 | 441 | 1 |
| 17 | 148 | K | 2.44 | 450 | 1 |
| 18 | 263 | DSC | 2.41 | 492 | 1 |
| 19 | 284 | DSC | 3.21 | 537 | 1 |
| 20 | — | — | 2.25 | 482 | 1 |
| 21 | — | — | 3.74 | 515 | 6 |
| 22 | — | — | 3.16 | 548 | 6 |
| 23 | >260 | K | 2.67 | 520 | 6 |
| 24 | — | — | 3.93 | 452 | 6 |
| 25 | — | — | 3.26 | 505 | 6 |
| 26 | 195 | DSC | 2.72 | 396 | 6 |
| 27 | 289 | DSC | 3.04 | 405 | 6 |
| 28 | — | — | 3.15 | 534 | 6 |
| 29 | 210 | DSC | 3.35 | 426 | 1 |
| 30 | 224 | DSC | 3.14 | 456 | 1 |
| 31 | 295 | DSC | 2.79 | 413 | 1 |
| 32 | 274 | DSC | 2.97 | 417 | 1 |
| 33 | 239 | DSC | 3.13 | 422 | 1 |
| 34 | 184 | K | 3.06 | 466 | 1 |
| 35 | 192 | K (gum) | 3.40 | 531 | 1 |
| 36 | 263 | K | 2.99 | 510 | 1 |
| 37 | 221 | K | 2.88 | 525 | 1 |
| 38 | 190 | K | 2.54 | 486 | 2 |
| 39 | 173 | K (gum) | 2.73 | 505 | 2 |
| 40 | 236 | K | 2.41 | 452 | 2 |
| 41 | >260 | K | 2.40 | 503 | 1 |
| 42 | 183 | K | 3.49 | 506 | 1 |
| 43 | 237 | K | 2.43 | 539 | 1 |
| 44 | 168 | K | 2.39 | 465 | 1 |
| 45 | 169 | K | 3.06 | 466 | 1 |
| 47 | >250 | K | 3.28 | 440 | 1 |
| 48 | >250 | K | 3.28 | 440 | 1 |
| 49 | 172 | K | 3.29 | 460 | 1 |
| 50 | 190 | K | 2.65 | 566 | 1 |
| 51 | 200 | K | 3.29 | 484 | 1 |
| 52 | 217 | K | 3.34 | 476 | 1 |
| 53 | 245 | K | 2.51 | 477 | 1 |
| 54 | 154 | K | 2.69 | 477 | 1 |
| 55 | 135 | K (gum) | 2.72 | 560 | 1 |
| 56 | 170 | K | 2.70 | 463 | 1 |
| 57 | 188 | K | 3.06 | 466 | 1 |
| 58 | 183 | K | 2.38 | 532 | 1 |
| 59 | 267 | DSC | 3.12 | 507 | 1 |
| 60 | 132 | K (gum) | 2.38 | 513 | 1 |
| 61 | — | — | 2.70 | 516 | 1 |
| 62 | 228 | DSC | 2.29 | 434 | 1 |
| 63 | 262 | K | 2.37 | 463 | 1 |
| 64 | 160 | DSC | 2.18 | 464 | 1 |
| 65 | 218 | K | 2.45 | 397 | |
| 66 | 165 | K | 2.74 | 457 | 1 |
| 67 | 188 | DSC | 2.19 | 508 | 1 |
| 68 | — | — | 2.19 | 546 | 1 |
| 69 | 157 | DSC | 2.87 | 450 | 1 |
| 70 | 237 | DSC | 2.97 | 451 | 1 |
| 71 | 210 | DSC | 2.97 | 423 | 1 |
| 72 | 189 | DSC | 3.20 | 464 | 1 |
| 73 | 201 | DSC | 2.55 | 466 | 1 |
| 74 | 124 | K | 2.86 | 455 | 1 |
| 75 | 228 | K | 2.75 | 481 | 1 |
| 76 | — | — | 3.37 | 484 | 2 |
| 77 | — | — | 2.85 | 484 | 2 |
| 78 | — | — | 4.15 | 483 | 6 |
| 78 | — | — | 4.15 | 483 | 6 |
| 79 | — | — | 5.55 | 491 | 6 |
| 80 | 192 | K | 3.81 | 489 | 6 |
| 81 | — | — | 3.67 | 518 | 6 |
| 82 | — | — | 4.68 | 507 | 6 |
| 83 | — | — | 3.69 | 532 | 6 |
| 84 | — | — | 4.82 | 436 | 6 |
| 85 | — | — | 5.10 | 484 | 6 |
| 87 | — | — | 3.71 | 532 | 6 |
| 88 | — | — | 5.83 | 450 | 6 |
| 89 | — | — | 3.72 | 548 | 6 |
| 90 | — | — | 5.47 | 454 | 6 |
| 91 | — | — | 3.46 | 502 | 6 |
| 92 | — | — | 5.91 | 519 | 6 |
| 93 | — | — | 3.77 | 532 | 6 |
| 94 | — | — | 3.62 | 527 | 6 |
| 95 | — | — | 3.50 | 548 | 6 |
| 96 | — | — | 4.97 | 468 | 6 |
| 97 | — | — | 4.59 | 491 | 6 |
| 98 | — | — | 3.77 | 530 | 6 |
| 99 | 120 | K (gum) | 4.15 | 515 | 1 |
| 100 | 171 | K | 3.61 | 450 | 1 |
| 101 | 104 | K (gum) | 3.76 | 489 | 1 |
| 102 | 112 | K (gum) | 4.01 | 434 | 1 |
| 103 | 126 | K (gum) | 3.66 | 476 | 1 |
| 104 | 176 | K | 3.12 | 420 | |
| 105 | >250 | K | 3.20 | 505 | 1 |
| 106 | 208 | K | 3.56 | 464 | 1 |
| 107 | 176 | K | 3.22 | 436 | 1 |
| 108 | >260 | K | 2.97 | 533 | 1 |
| 109 | 152 | K | 2.93 | 449 | 1 |
| 110 | — | — | 4.95 | 505 | |
| 111 | 219 | K | 2.65 | 455 | 1 |
| 112 | >260 | K | 2.77 | 507 | 1 |
| 113 | 178 | K | 2.62 | 558 | 1 |
| 114 | 206 | K (gum) | 2.54 | 558 | 1 |
| 115 | — | — | 5.04 | 533 | 5 |
| 116 | — | — | 5.10 | 533 | 5 |
| 117 | — | — | 5.01 | 545 | 5 |
| 118 | — | — | 5.65 | 539 | 5 |
| 119 | — | — | 5.07 | 547 | 5 |
| 120 | — | — | 5.19 | 545 | 5 |
| 121 | 193 | K | 5.03 | 543 | 5 |
| 122 | — | — | 3.22 | 544 | 3 |
| 123 | 287 | K | 3.62 | 545 | 3 |
| 124 | — | — | 5.07 | 534 | 5 |
| 125 | 213 | K | 2.98 | 439 | 1 |

TABLE-continued

| Co. No. | MP (° C.) | MP Method | Rt | [M + H]+ | LCMS Method |
|---|---|---|---|---|---|
| 126 | 200 | K | 3.25 | 467 | 1 |
| 127 | 158 | K | 3.01 | 499 | 1 |
| 128 | 156 | K (gum) | 3.37 | 495 | 1 |
| 129 | 190 | K | 2.70 | 397 | 1 |
| 130 | 264 | K | 2.71 | 397 | 1 |
| 131 | 174 | K | 2.71 | 397 | 1 |
| 132 | 234 | K | 2.70 | 397 | 1 |
| 133 | 262 | K | 2.71 | 397 | 1 |
| 134 | 190 | K | 2.71 | 397 | 1 |
| 135 | 166 | K (gum) | 2.91 | 425 | 1 |
| 136 | 219 | K | 2.76 | 397 | 1 |
| 137 | 290 | DSC | 2.60 | 454 | 1 |
| 138 | — | — | 2.67 | 468 | 1 |
| 139 | 202 | K (gum) | 2.90 | 496 | 1 |
| 140 | 180 | K (gum) | 3.01 | 544 | 1 |
| 141 | 212 | K (gum) | 2.57 | 468 | 2 |
| 142 a | 138 | DSC | 2.11 | 483 | 1 |
| 142 b | 214 | DSC | 2.18 | 483 | 1 |
| 143 | >270 | K | 2.18 | 477 | 1 |
| 144 | — | — | 2.17 | 477 | 1 |
| 145 | 216 (gum) | K | 2.61 | 573 | 1 |
| 146 | 186 (gum) | K | 2.85 | 524 | 1 |
| 147 | — | — | 1.32 | 415 | 7 |
| 148 | 231 | DSC | 2.43 | 422 | 1 |
| 149 | — | — | 3.27 | 444 | 9 |
| 150 | — | — | 3.67 | 404 | 8 |
| 151 | 122 | — | 2.75 | 430 | 9 |
| 152 | 229 | DSC | 2.43 | 420 | 1 |
| 153 | 144 (gum) | K | 2.38 | 413 | 1 |
| 154 | 250 | WRS-2A | 3.02 | 446 | 9 |
| 155 | 218 | DSC | 2.38 | 447 | 1 |
| 156 | 206 | DSC | 2.58 | 489 | 2 |
| 157 | 235 | DSC | 2.5 | 489 | 2 |
| 158 | — | — | 2.16 | 512 | 1 |
| 159 | 140 (gum) | K | 2.23 | 528 | 1 |
| 160 | 206 | K | 2.43 | 443 | 1 |
| 161 | 245 | DSC | 2.28 | 498 | 1 |
| 162 | 143 | DSC | 2.63 | 473 | 1 |
| 163 | 150 | K | 2.04 | 498 | 1 |
| 164 | 194 | K | 2.95 | 399 | 2 |
| 165 | 224 | DSC | 2.41 | 451 | 1 |
| 166 | 116 | DSC | 2.15 | 516 | 1 |
| 167 | 239 | DSC | 2.15 | 516 | 1 |
| 168 | 246 | DSC | 2.42 | 503 | 1 |
| 169 | 256 | DSC | 2.41 | 503 | 1 |
| 170 | 207 | K | 2.11 | 454 | 1 |
| 171 | 249 | K | 2.19 | 450 | |
| 172 | 193 | K | 2.49 | 510 | 1 |
| 173 | 183 | DSC | 2.57 | 510 | 1 |
| 174 | 211 | DSC | 2.66 | 498 | 1 |
| 175 | 226 | K | 2.24 | 494 | 1 |
| 176 | — | — | 2.56 | 506 | 1 |
| 177 | 222 | DSC | 2.38 | 494 | 1 |
| 178 | 230 | K | 2.27 | 494 | 2 |
| 179 | 188 (gum) | K | 2.26 | 494 | 2 |
| 180 | 194 (gum | K | 2.16 | 456 | 1 |
| 181 | — | — | 2.44 | 498 | 1 |
| 182 | — | — | 0.82 | 434 | 4 |
| 183 | 209 | DSC | 2.33 | 503 | 1 |
| 184 | 134 (gum) | K | 2.15 | 454 | 1 |
| 185 | 156 (gum) | K | 2.41 | 496 | 1 |
| 186 | 172 | DSC | 2.44 | 472 | 2 |
| 187 | 240 | DSC | 2.37 | 503 | 1 |
| 188 | 190 | K | 2.56 | 477 | 1 |
| 189 | 239 | K | 2.43 | 452 | 1 |
| 190 | 128 | K | 2.63 | 452 | 1 |
| 191 | 122 | WRS-2A | 2.42 | 438 | 9 |
| 192 | 250 | WRS-2A | 2.47 | 469 | 9 |
| 193 | 188 (gum) | K | 2.32 | 427 | 1 |
| 194 | 193 | DSC | 2.88 | 524 | 2 |
| 195 | 210 | K | 2.70 | 484 | 1 |
| 196 | 240 | K | 2.84 | 502 | 1 |
| 197 | 223 | DSC | 2.99 | 499 | 1 |
| 198 | 222 | DSC | 2.98 | 501 | 1 |
| 199 | 170 (gum) | K | 2.53 | 513 | 1 |
| 200 | 260 | K | 2.75 | 455 | 1 |
| 201 | 220 (gum) | K | 1.78 | 441 | 1 |
| 203 | 294 | DSC | 2.23 | 523 | 1 |
| 204 | 297 | DSC | 2.23 | 526 | 1 |
| 205 | 201 | K | 2.28 | 493 | 1 |
| 206 | 238 | DSC | 2.53 | 524 | 1 |
| 207 | 268 | DSC | 2.15 | 540 | 1 |
| 208 | 234 | DSC | 2.59 | 462 | 2 |
| 209 | 254 | DSC | 3.12 | 457 | 1 |
| 210 | | | 2.34 | 441 | 9 |
| 211 | 160 (gum) | K | 2.65 | 438 | 1 |
| 212 | 168 | K | 2.78 | 474 | 1 |
| 213 | 304 | WRS-2A | 4.66 | 398 | 8 |
| 214 | 252 | K | 4.08 | 430 | 8 |
| 215 | 225 | DSC | 2.38 | 402 | 1 |
| 216 | 108 (gum) | K | 2.25 | 455 | 1 |
| 217 | 151 | DSC | 2.18 | 459 | 1 |
| 218 | 115 (gum) | K | 2.49 | 441 | 1 |
| 219 | 181 | DSC | 2.86 | 477 | 1 |
| 220 | 140 | K | 2.65 | 459 | 1 |
| 221 | 181 | MP50 | 2.17 | 485 | 11 |
| 222 | — | — | 0.59 | 471 | 10 |
| 223 | 129 | DSC | 2.38 | 496 | 1 |
| 224 | 238 | K | 2.98 | 482 | 1 |
| 225 | 181 | MP50 | 2.17 | 452 | 11 |
| 226 | 298 | Y1P50 | 2.36 | 495 | 11 |
| 227 | 223 | MP50 | 3.64 | 488 | 11 |
| 228 | 170 | MP50 | 2.26 | 470 | 11 |
| 229 | 207 | DSC | 2.83 | 484 | 1 |
| 230 | | | 2.45 | 514 | 11 |
| 231 | | | 2.45 | 514 | 11 |
| 232 | 167 | DSC | 2.61 | 500 | 2 |
| 233 | 162 | DSC | 2.76 | 500 | 1 |
| 234 | 192 | DSC | 2.41 | 485 | 2 |
| 235 | 133 | MP50 | 2.36 | 471 | 12 |
| 236 | 249 | K | 2.39 | 499 | 1 |
| 237 | — | — | 2.12 | 427 | 1 |
| 238 | — | — | 2.12 | 427 | 1 |
| 239 | 116 (gum) | K | 2.05 | 415 | 1 |
| 240 | 259 | K | 2.57 | 479 | 1 |

Co. No. means compound number; Retention time (Rt) in min; MP means melting point (° C); dec means decomposition; n.d. means not determined.

OR

Optical Rotation is measured with a polarimeter such as e.g. 341 Perkin Elmer, an Autopol IV automatic polarimeter (Rodolph research analytical) or a P-2000 (Jasco).

Specific rotation (OR): $[\alpha]^{\theta}_{\lambda}=(100*\alpha)/(c*1)$

α (measured rotation) is the angle through which plane polarized light is rotated by a solution of mass concentration c and path length 1. Concentration is in grams per 100 mL; path length 1 is in decimeters and is 1.000 decimeter.
θ is the temperature (° C.) and λ the wavelength of the light used.

Unless otherwise indicated, temperature is 20° C., and the sodium D line is used (589 nanometer).

OR data: Solvent: DMF (unless otherwise indicated); temperature: 20° C. (unless otherwise indicated); wavelength: 589 nm (unless otherwise indicated); 'Conc.' means concentration of the sample in grams per 100 mL; 'OR' means optical rotation (specific rotation); 'Co. No.' means compound number

| Co. No. | OR (°) | Conc. |
|---|---|---|
| 1 | +48.33 | 0.3 |
| 2 | +21.17 | 0.227 |
| 3 | +17.21 | 0.215 |
| 4 | +8.89 | 0.225 |
| 7 | +27.2 | 0.261 |
| 8 | +21.43 | 0.28 |

-continued

| Co. No. | OR (°) | Conc. |
|---|---|---|
| 9 | +29.92 | 0.264 |
| 10 | +50 | 0.25 |
| 11 | +43.61 | 0.342 |
| 12 | +57.28 | 0.183 |
| 13 | +64.29 | 0.28 |
| 14 | +49.12 | 0.34 |
| 15 | +35.19 | 0.27 |
| 16 | +68.64 | 0.22 |
| 17 | +18.08 | 0.26 |
| 18 | +9.51 | 0.284 |
| 19 | +47.99 | 0.292 |
| 20 | +29.2 | 0.25 |
| 45 | +32.5 | 0.2 |
| 48 | +29.63 | 0.27 |
| 57 | −35.2 | 0.25 |
| 59 | +28.51 | 0.245 |
| 60 | +15.2 | 0.25 |
| 61 | +13.2 | 0.25 |
| 62 | +15.84 | 0.227 |
| 63 | +5.49 | 0.255 |
| 64 | +20.63 | 0.16 |
| 65 | −43.85 | 0.26 |
| 66 | +60.43 | 0.23 |
| 67 | +16.5 | 0.273 |
| 68 | +16.15 | 0.26 |
| 69 | +17.31 | 0.26 |
| 70 | +17.31 | 0.26 |
| 71 | +36.36 | 0.253 |
| 72 | +21.60 | 0.25 |
| 73 | +19.33 | 0.3 |
| 74 | +34.75 | 0.259 |
| 75 | +28.18 | 0.33 |
| 125 | +70.57 | 0.35 |
| 126 | +74.52 | 0.231 |
| 127 | +73 | 0.2 |
| 128 | +100 | 0.2 |
| 129 | +63.33 | 0.21 |
| 130 | +52.08 | 0.221 |
| 131 | +30.81 | 0.214 |
| 132 | +43.6 | 0.241 |
| 133 | +43.86 | 0.207 |
| 134 | +36.19 | 0.21 |
| 135 | +23.08 | 0.26 |
| 137 | +51.55 | 0.258 |
| 138 | +54.55 | 0.275 |
| 139 | +58.54 | 0.205 |
| 140 | +35.65 | 0.292 |
| 141 | +87.5 | 0.28 |
| 142a | +38.04 | 0.276 |
| 142b | +69.96 | 0.273 |
| 143 | +65.15 | 0.264 |
| 144 | −64.35 | 0.264 |
| 145 | +74.44 | 0.266 |
| 146 | +17.45 | 0.275 |
| 148 | +9.44 | 0.339 |
| 149 | +13.21 | 0.106(MeOH) |
| 150 | +11.67 | 0.3 |
| 151 | +8.33 | 0.3 (MeOH) |
| 152 | +13.01 | 0.269 |
| 153 | +61.94 | 0.258 |
| 154 | +8.08 | 0.099(MeOH) |
| 155 | +11.07 | 0.262 |
| 156 | +12.41 | 0.29 |
| 157 | +9.16 | 0.251 |
| 158 | +12 (at 436 nm) | 0.25 |
| 159 | +8.45 | 0.296 |
| 160 | +10.17 | 0.295 |
| 161 | +10.77 | 0.26 |
| 162 | +9.23 | 0.26 |
| 164 | +43.6 | 0.25 |
| 165 | +13.31 | 0.338 |
| 166 | +12 | 0.275 |
| 167 | +9.42 | 0.276 |
| 168 | +4.12 | 0.267 |
| 169 | +20.56 | 0.248 |
| 170 | +54 | 0.25 |
| 171 | +54.8 | 0.25 |
| 173 | +29.62 | 0.26 |
| 174 | +31.79 | 0.28 |
| 175 | +34.64 | 0.28 |
| 176 | +25.94 | 0.266 |
| 178 | +9.66 | 0.29 |
| 179 | +57.14 | 0.28 |
| 180 | +17.49 | 0.263 |
| 183 | +12.5 | 0.256 |
| 184 | +34.2 | 0.269 |
| 185 | +31.52 | 0.257 |
| 186 | +7.58 | 0.264 |
| 187 | +21.43 | 0.266 |
| 188 | +26.18 | 0.275 |
| 189 | +21.14 | 0.175 |
| 190 | +29.42 | 0.258 |
| 191 | +40 | 0.105(MeOH) |
| 192 | +28 | 0.1 (MeOH) |
| 193 | +34.58 | 0.24 |
| 194 | +22.91 | 0.227 |
| 195 | +21.05 | 0.285 |
| 196 | +28.46 | 0.26 |
| 200 | +31.37 | 0.271 |
| 201 | +29.44 | 0.248 |
| 203 | +27.89 | 0.251 |
| 204 | +27.09 | 0.251 |
| 205 | +10.04 | 0.259 |
| 206 | +9.73 | 0.298 |
| 207 | +10.76 | 0.288 |
| 208 | +18.29 | 0.257 |
| 209 | +47.92 | 0.288 |
| 211 | +80.43 | 0.281 |
| 212 | +58.7 | 0.23 |
| 213 | +31.11 | 0.135 T=24°C. |
| 214 | +14.29 | 0.238 |
| 215 | +14.62 | 0.26 |
| 216 | +10.07 | 0.278 |
| 217 | +11.54 | 0.26 |
| 218 | +12.69 | 0.26 |
| 219 | +8.63 | 0.255 |
| 220 | +10.94 | 0.256 |
| 221 | +13.72 | 0.277 |
| 222 | +18.39 | 0.261 |
| 223 | +46.55 | 0.29 |
| 224 | +44.17 | 0.24 |
| 225 | +34.16 | 0.322 |
| 226 | +34.2 | 0.2 (MeOH) |
| 227 | +39.3 | 0.23 (MeOH) |
| 228 | +44.2 | 0.16 (MeOH) |
| 229 | +50.33 | 0.302 |
| 232 | +40.15 | 0.269 |
| 233 | +46.85 | 0.254 |
| 234 | +15.75 | 0.254 |
| 235 | +20.27 | 0.301 |
| 236 | +12.4 | 0.258 |

SFC-MS Method:

General Procedure for SFC-MS Method

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE

Analytical SFC-MS Methods (Flow expressed in mL/min; column temperature (T) in ° C.; Run time in minutes, Backpressure (BPR) in bars.

| Method number | column | mobile phase | gradient | Flow Col T | Runtime BPR |
|---|---|---|---|---|---|
| 1 | Daicel Chiralpak ® AD-3 column (3 μm, 100 × 4.6 mm) | A: $CO_2$ B: MeOH (0.3% $iPrNH_2$) | 35% B hold 6 min | 3.5 35 | 6 103 |

TABLE

Analytical SFC-MS data - $R_t$ means retention time (in minutes), method refers to the method used for (SFC)MS analysis of enantiomerically pure compounds.

| Co. No. | Rt | Chiral purity UV Area % | Method number |
|---|---|---|---|
| 232 | 2.59 | 100 | 1 |
| 233 | 2.20 | 98.79 | 1 |

NMR

The NMR experiments were carried out using a Bruker Avance 500 III using internal deuterium lock and equipped with reverse triple-resonance ($^1H$, $^{13}C$, $^{15}N$ TXI) probe head or using a Bruker Avance DRX 400 spectrometer at ambient temperature, using internal deuterium lock and equipped with reverse double-resonance ($^1H$, $^{13}C$, SEI) probe head with z gradients and operating at 400 MHz for the proton and 100 MHz for carbon. Chemical shifts (δ) are reported in parts per million (ppm). J values are expressed in Hz.

Compound 1: $^1H$ NMR (500 MHz, DMSO-$d_6$): δ 8.92 (s, 1H), 8.40 (d, J=5.3 Hz, 1H), 8.17 (d, J=1.2 Hz, 1H), 8.07 (d, J=1.2 Hz, 1H), 7.92 (d, J=1.3 Hz, 1H), 7.48-7.40 (m, 3H), 7.36 (d, J=5.4 Hz, 1H), 4.98 (t, J=5.4 Hz, 1H), 3.69 (d, J=9.8 Hz, 1H), 3.44 (dd, J=10.7 Hz, 5.3 Hz, 1H), 3.34-3.39 (m, 1H, partially obscured by solvent peak), 3.29 (d, J=9.8 Hz, 1H), 2.37 (s, 3H), 1.27 (s, 3H).

Compound 4: $^1H$ NMR (500 MHz, DMSO-$d_6$): δ 8.80 (s, 1H), 8.33-8.37 (m, 2H), 8.20 (d, J=0.9 Hz, 1H), 8.04 (d, J=1.6 Hz, 1H), 7.91 (d, J=1.6 Hz, 1H), 7.52 (dd, J=7.9 Hz, 1.9 Hz, 1H), 7.36 (s, 1H), 7.30-7.22 (m, 2H), 4.95 (br s, 1H), 3.70 (d, J=9.1 Hz, 1H), 3.42 (dd, J=9.8 Hz, 1.8 Hz, 1H), 3.34-3.39 (m, 1H, partially obscured by solvent peak), 3.27 (d, J=9.1 Hz, 1H), 2.77 (d, J=4.4 Hz, 3H), 2.30 (s, 3H), 1.24 (s, 3H).

Compound 45: $^1H$ NMR (500 MHz, DMSO-$d_6$): δ 8.62 (d, J=2.5 Hz, 1H), 8.49 (d, J=5.4 Hz, 1H), 8.13 (d, J=1.6 Hz, 1H), 8.12 (s, 1H), 8.00 (d, J=1.3 Hz, 1H), 7.50 (s, 1H), 7.46 (d, J=5.4 Hz, 1H), 7.12 (d, J=8.5 Hz, 1H), 7.01 (dd, J=8.7 Hz, 2.7 Hz, 1H), 5.01 (t, J=5.4 Hz, 1H), 4.24-4.20 (m, 2H), 3.74-3.69 (m, 3H), 3.46 (dd, J=10.7 Hz, 5.3 Hz, 1H), 3.42-3.34 (m, 4H), 3.31-3.37 (m, 1H, partially obscured by solvent peak), 1.30 (s, 3H).

Compound 66: $^1H$ NMR (500 MHz, DMSO-$d_6$): δ 8.77 (d, J=1.9 Hz, 1H), 8.50 (d, J=5.4 Hz, 1H), 8.19 (s, 1H), 8.11 (d, J=1.9 Hz, 1H), 7.97 (d, J=1.6 Hz, 1H), 7.51-7.45 (m, 3H), 7.27 (d, J=8.5 Hz, 1H), 4.97 (t, J=5.5 Hz, 1H), 4.34-4.30 (m, 2H), 3.77-3.74 (m, 2H), 3.71 (d, J=9.8 Hz, 1H), 3.47 (dd, J=10.7 Hz, 5.3 Hz, 1H), 3.38 (dd, J=10.7 Hz, 5.7 Hz, 1H), 3.35 (s, 3H), 3.31 (d, J=10.1 Hz, 1H), 1.30 (s, 3H).

Compound 68: $^1H$ NMR (500 MHz, DMSO-$d_6$) δ ppm 9.39 (s, 1H) 8.90 (s, 1H) 8.36 (d, J=5.0 Hz, 1H) 8.07 (s, 1H) 7.93 (s, 1H) 7.62 (s, 1H) 7.39 (s, 1H) 7.32 (d, J=5.4 Hz, 1H) 7.22 (s, 1H) 4.99 (br t, J=5.2 Hz, 1H) 3.69 (br d, J=9.8 Hz, 1H) 3.50-3.35 (m, 2H, partially obscured by solvent peak) 3.29 (br d, J=10.1 Hz, 1H) 2.81 (br d, J=11.0 Hz, 2H) 2.31-2.40 (m, 1H) 2.16 (s, 3H) 2.07 (s, 3H) 1.87 (br t, J=11.2 Hz, 2H) 1.78 (br d, J=11.0 Hz, 2H) 1.58-1.73 (m, 2H) 1.27 (s, 3H).

Compound 73: $^1H$ NMR (500 MHz, DMSO-$d_6$): δ 8.67 (d, J=8.5 Hz, 1H), 8.51 (d, J=5.4 Hz, 1H), 8.33 (s, 1H), 8.16 (d, J=1.6 Hz, 1H), 8.03 (d, J=1.6 Hz, 1H), 7.54 (dd, J=8.5 Hz, 1.9 Hz, 1H), 7.46-7.50 (m, 3H), 5.04 (t, J=5.4 Hz, 1H), 4.01 (s, 3H), 3.68 (d, J=9.5 Hz, 1H), 3.47 (dd, J=10.7 Hz, 5.3 Hz, 1H), 3.40 (dd, J=10.4 Hz, 5.3 Hz, 1H), 3.29-3.33 (m, 1H, partially obscured by solvent peak), 3.21 (s, 3H), 1.30 (s, 3H).

Compound 74: $^1H$ NMR (500 MHz, DMSO-$d_6$): δ 8.92 (s, 1H), 8.38 (d, J=5.0 Hz, 1H), 8.16 (s, 1H), 8.05 (d, J=1.3 Hz, 1H), 7.91 (s, 1H), 7.51 (dd, J=7.9 Hz, 1.3 Hz, 1H), 7.38-7.45 (m, 2H), 7.35 (d, J=5.4 Hz, 1H), 4.97 (t, J=5.2 Hz, 1H), 3.69 (d, J=9.8 Hz, 1H), 3.44 (dd, J=10.4 Hz, 5.3 Hz, 1H), 3.33-3.38 (m, 1H, partially obscured by solvent peak), 3.27-3.31 (m, 3H), 3.21 (s, 3H), 2.79 (t, J=7.6 Hz, 2H), 1.78 (q, J=6.9 Hz, 2H), 1.27 (s, 3H).

Compound 110: $^1H$ NMR (400 MHz, DMSO-d6): δ 8.63 (s, 1H), 8.50 (d, J=5.5 Hz, 1H), 8.19 (br. s., 1H), 8.15 (d, J=1.5 Hz, 1H), 8.05 (d, J=1.5 Hz, 1H), 7.49 (m, 2H), 7.06 (s, 1H), 5.80 (br. s., 1H), 4.52 (m, 1H), 4.23 (m, 1H), 4.10 (m, 1H), 3.93 (s, 3H), 3.76 (m, 2H), 3.45 (s, 2H), 1.33 (s, 6H).

Compound 125:
$^1H$ NMR (400 MHz, DMSO-$d_6$): δ 8.90 (s, 1H), 8.42 (d, J=5.0 Hz, 1H), 8.18 (s, 1H), 8.12 (d, J=1.5 Hz, 1H), 8.02 (s, 1H), 7.51 (s, 1H), 7.41-7.49 (m, 2H), 7.38 (d, J=5.6 Hz, 1H), 4.00-4.14 (m, 2H), 3.62 (d, J=10.1 Hz, 1H), 3.39 (d, J=10.6 Hz, 1H), 2.36 (s, 3H), 1.94 (s, 3H), 1.35 (s, 3H).

Compound 138:
$^1H$ NMR (500 MHz, DMSO-$d_6$) δ ppm 9.47 (br s, 1H) 8.51 (br s, 2H) 8.47 (d, J=5.7 Hz, 1H) 8.22 (s, 1H) 8.20 (d, J=1.3 Hz, 1H) 8.08 (s, 1H) 7.57-8.03 (m, 1H) 7.46-7.56 (m, 3H) 5.20-7.15 (m, 1H) 4.35 (d, J=10.7 Hz, 1H) 4.14 (d, J=10.7 Hz, 1H) 3.95-4.09 (m, 1H) 3.73 (d, J=10.7 Hz, 1H) 3.47 (d, J=10.7 Hz, 1H) 2.39 (s, 3H) 1.40 (s, 3H) 1.25 (d, J=7.3 Hz, 3H)

Compound 137: $^1H$ NMR (400 MHz, DMSO-$d_6$) δ ppm 9.24 (br s, 1H) 8.45 (d, J=5.6 Hz, 1H) 8.36 (br s, 3H) 8.20 (s, 1H) 8.17 (d, J=1.5 Hz, 1H) 8.06 (d, J=1.5 Hz, 1H) 7.63 (br s, 1H) 7.48-7.53 (m, 1H) 7.42-7.48 (m, 2H) 6.34 (br s, 2H) 4.22 (s, 2H) 3.76-3.89 (m, 2H) 3.70 (d, J=10.6 Hz, 1H) 3.42 (d, J=10.6 Hz, 1H) 2.38 (s, 3H) 1.39 (s, 3H)

Compound 148:
$^1H$ NMR (500 MHz, DMSO-$d_6$) δ ppm 8.72 (s, 1H) 8.30 (br d, J=5.0 Hz, 1H) 8.03 (s, 1H) 7.91 (s, 1H) 7.57 (br d, J=7.3 Hz, 1H) 7.35 (s, 1H) 7.23 (br d, J=5.4 Hz, 1H) 7.02 (br d, J=10.7 Hz, 1H) 5.15 (s, 1H) 4.99 (br t, J=5.0 Hz, 1H) 3.67 (br d, J=9.8 Hz, 1H) 3.39-3.46 (m, 1H) 3.34-3.39 (m, 1H) 3.28 (br d, J=9.8 Hz, 1H) 2.21 (s, 3H) 1.26 (s, 3H)

Compound 155:
$^1H$ NMR (500 MHz, DMSO-$d_6$) δ ppm 8.86 (s, 1H) 8.40 (d, J=5.4 Hz, 1H) 8.12-8.20 (m, 1H) 8.10 (d, J=1.6 Hz, 1H) 8.01 (br d, J=7.3 Hz, 1H) 7.97 (d, J=1.3 Hz, 1H) 7.43 (s, 1H) 7.34 (d, J=5.4 Hz, 1H) 7.23 (d, J=11.3 Hz, 1H) 5.01 (t, J=5.4 Hz, 1H) 3.75 (d, J=9.5 Hz, 1H) 3.46-3.53 (m, 1H) 3.41 (dd, J=10.7, 5.7 Hz, 1H) 3.34 (d, J=9.5 Hz, 1H) 2.85 (d, J=4.4 Hz, 2H) 2.34 (s, 3H) 1.31 (s, 3H)

Compound 156:
$^1H$ NMR (500 MHz, DMSO-$d_6$) δ ppm 8.53 (br d, J=7.9 Hz, 1H) 8.39 (d, J=5.4 Hz, 1H) 8.06-8.13 (m, 2H) 7.93-8.06

(m, 2H) 7.40 (s, 1H) 7.36 (d, J=5.0 Hz, 1H) 7.25 (d, J=12.3 Hz, 1H) 4.93 (t, J=5.4 Hz, 1H) 3.99-4.07 (m, 1H) 3.72 (br d, J=9.8 Hz, 1H) 3.47-3.53 (m, 1H) 3.40 (br dd, J=10.6, 5.5 Hz, 1H) 3.29 (br d, J=9.8 Hz, 1H) 2.81 (d, J=4.4 Hz, 3H) 1.29 (s, 3H) 0.67-0.91 (m, 4H)

Compound 232: $^1$H NMR (500 MHz, DMSO-d$_6$) δ ppm 8.72 (s, 1H) 8.45-8.56 (m, 2H) 8.12 (s, 1H) 7.97 (s, 1H) 7.52 (br d, J=8.2 Hz, 1H) 7.43-7.48 (m, 2H) 7.22 (br d, J=8.5 Hz, 1H) 5.23-5.42 (m, 1H) 5.05-5.17 (m, 1H) 4.97 (br t, J=5.0 Hz, 1H) 3.71 (br d, J=9.8 Hz, 1H) 3.44-3.52 (m, 1H) 3.38 (br dd, J=10.6, 5.5 Hz, 1H) 3.28-3.33 (m, 2H, partially obscured by solvent peak) 3.25 (br dd, J=9.8, 6.6 Hz, 1H) 2.74-2.95 (m, 2H) 2.28 (s, 3H) 1.30 (s, 3H)

Pharmacological Part

Biological Assay A

Inhibition of Auto-Phosphorylation of Recombinant Human NF-kappaB-Inducing Kinase (NIK/MAP3K14) Activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. Final DMSO concentration was 1% (v/v) in assays. Assay buffer was 50 mM Tris pH 7.5 containing 1 mM EGTA (ethylene glycol tetraacetic acid), 1 mM DTT (dithiothreitol), 0.1 mM Na$_3$VO$_4$, 5 mM MgCl$_2$, 0.01% Tween® 20. Assays were carried out in 384 well Alphaplates (Perkin Elmer). Incubations consisted of compound, 25 microM Adenosine-5'-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and IC$_{50}$'s were determined by fitting a sigmoidal curve to % inhibition of control versus Log$_{10}$ compound concentration.

Biological Assay B

Effect of Compounds on P-IKKα Levels in L363 (NIK Translocated Multiple Myeloma) Cells All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of 0.2×10$^6$ cells per ml-1×10$^6$ cells per ml at 37° C. in a humidified 5% CO$_2$ atmosphere. Cells were passaged twice a week splitting back to obtain the low density. Cells were seeded in 96 well plates (Nunc 167008) at 2×10$^6$ per ml media in a volume of 75 μl per well plus 25 μl 1 μg/ml recombinant human B-cell activating factor (BAFF/BLyS/TNFSF13B). Seeded cells were incubated at 37° C. in a humidified 5% CO$_2$ atmosphere for 24 hr. Drugs and/or solvents were added (20 μl) to a final volume of 120 μl. Following 2 hr treatment plates were removed from the incubator and cell lysis was achieved by the addition of 30 μl 5× lysis buffer followed by shaking on a plate shaker at 4° C. for 10 min. At the end of this incubation lysed cells were centrifuged at 800×g for 20 min at 4° C. and the lysate was assessed for P-IKKα levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 10 μM ADS125117, a test concentration known to give full inhibition) were run in parallel. The blank incubation value was subtracted from all control and sample values. To determine the IC$_{50}$ a sigmoidal curve was fitted to the plot of % inhibition of control P-IKKα levels versus Log$_{10}$ compound concentration.

Note: Compounds 237 and 238 were tested at a maximum top concentration of 823 nM.

Biological Assay C

Determination of Antiproliferative Activity on JJN-3 (NIK Translocated) and KMS12-BM (NIK WT) Multiple Myeloma Cells All compounds tested were dissolved in DMSO and further dilutions were made in culture medium. Final DMSO concentration was 0.3% (v/v) in cell proliferation assays. Viability was assessed using CellTiter-Glo cell viability assay kit (Promega). The human JJN-3 and KMS12-BM cells (DSMZ) were cultured in RPMI 1640 medium supplemented with 2 mM L-glutamine, and 10% fetal calf serum (PAA). Cells were routinely kept as suspension cells at 37° C. in a humidified 5% CO$_2$ atmosphere. Cells were passaged at a seeding density of 0.2×10$^6$/ml twice a week. Cells were seeded in black tissue culture treated 96-well plates (Perkin Elmer). Densities used for plating ranged from 15000 (JJN3) to 20000 (KMS12BM) cells per well in a total volume of 135 μl medium. Drugs and/or solvents were added (15 μl) to a final volume of 150 μl. Following 96 hr of treatment, plates were removed from the incubator and allowed to equilibrate to room temperature for approx 10 min. 75 μl CellTiter-Glo reagent was added to each well that was then covered (Perkin Elmer Topseal) and shaken on plate shaker for 10 min. Luminescence was measured on a HTS Topcount (Perkin Elmer).

Within an experiment, the results for each treatment were the mean of 2 replicate wells. For initial screening purposes, compounds were tested using a 9 point dilution curve (serial 1:3 dilutions). For each experiment, controls (containing no drug) and a blank incubation (containing cells read at the time of compound addition) were run in parallel. The blank value was subtracted from all control and sample values. For each sample, the mean value for cell growth (in relative light units) was expressed as a percentage of the mean value for cell growth of the control.

Data for the compounds of the invention in the above assays are provided in Table A (the values in Table are averaged values over all measurements on all batches of a compound). ('n.c.' means not calculated)

TABLE A

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
| --- | --- | --- | --- | --- |
| 1 | 1.8 | 2.2 | 5188 | 85 |
| 2 | 4.3 | 4.8 | >10000 | 58 |
| 3 | 10.2 | 15.1 | >10000 | 115 |
| 4 | 4.2 | 20.9 | >10000 | 759 |
| 5 | 2511.9 | >10000 | n.d. | n.d. |
| 6 | 446.7 | >10000 | n.d. | n.d. |
| 7 | 5.8 | n.d. | 2512 | 148 |
| 8 | 1.3 | 32.4 | >10000 | 87 |
| 9 | 10.7 | 8.1 | 10233 | 162 |
| 10 | 7.4 | 11.5 | 1227 | 67 |
| 11 | 1.8 | 6.0 | >10000 | 617 |

TABLE A-continued

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
| --- | --- | --- | --- | --- |
| 12 | 4.1 | 25.7 | 4898 | 138 |
| 13 | 9.2 | 30.9 | >10000 | 146 |
| 14 | 5.5 | 21.4 | >10000 | 170 |
| 15 | 11.0 | ~269.1 | >10000 | 117 |
| 16 | 15.5 | 15.5 | 550 | 258 |
| 17 | 1.1 | 6.8 | 479 | 56 |
| 18 | 2.6 | 20.0 | ~8128 | 407 |
| 19 | 27.5 | 38.9 | >10000 | 1950 |
| 20 | 1.7 | 11.5 | ~1585 | 63 |
| 21 | 2.5 | 4.5 | 891 | 51 |
| 22 | 2.5 | 11.5 | 631 | 7 |
| 23 | 7.1 | 12.0 | >10000 | 71 |
| 24 | 4.5 | 6.0 | 2818 | 13 |
| 25 | 3.6 | 33.9 | 589 | 12 |
| 26 | 3.7 | n.d. | >10000 | 255 |
| 27 | 9.2 | n.d. | >10000 | 106 |
| 28 | n.d. | n.d. | n.d. | n.d. |
| 29 | 17.4 | n.d. | >10000 | 166 |
| 30 | 51.3 | n.d. | >10000 | >10000 |
| 31 | 5.3 | n.d. | >10000 | 2344 |
| 32 | 4.0 | n.d. | >10000 | 170 |
| 33 | 11.2 | n.d. | >10000 | 85 |
| 34 | 20.9 | n.d. | >10000 | 316 |
| 35 | 37.2 | n.d. | 7079 | 129 |
| 36 | 75.9 | n.d. | 6457 | 51 |
| 37 | 37.2 | n.d. | 4169 | 17 |
| 38 | 30.9 | n.d. | >10000 | 182 |
| 39 | 7.4 | n.d. | 2344 | 87 |
| 40 | 8.7 | n.d. | >10000 | 155 |
| 41 | 1.7 | n.d. | 110 | 13 |
| 42 | 309.0 | n.d. | >10000 | 4266 |
| 43 | 2.5 | n.d. | 251 | 9 |
| 44 | 8.3 | n.d. | >10000 | 219 |
| 45 | 9.1 | 37.2 | >10000 | 490 |
| 47 | 15.1 | n.d. | >10000 | 776 |
| 48 | 8.9 | n.d. | >10000 | 447 |
| 49 | 24.6 | n.d. | >10000 | 1622 |
| 50 | 3.0 | n.d. | 102 | 9 |
| 51 | 49.0 | n.d. | >10000 | 363 |
| 52 | 41.7 | n.d. | >10000 | 676 |
| 53 | 3.6 | n.d. | 1259 | 33 |
| 54 | 9.8 | n.d. | >10000 | 275 |
| 55 | 15.5 | n.d. | >10000 | 282 |
| 56 | 125.9 | n.d. | >10000 | 1738 |
| 57 | 50.1 | n.d. | >10000 | >10000 |
| 58 | 2.6 | n.d. | 6761 | 85 |
| 59 | 23.4 | n.d. | 4074 | 129 |
| 60 | 2754.2 | n.d. | n.d. | n.d. |
| 61 | 11.0 | n.d. | >10000 | 186 |
| 62 | 912.0 | n.d. | n.d. | n.d. |
| 63 | 1.7 | n.d. | ~5012 | 7 |
| 64 | 1.8 | 18.2 | 1230 | ~246 |
| 65 | 4.1 | 103.1 | >10000 | 1102 |
| 66 | 3.0 | 5.9 | 19 | 251 |
| 67 | 4.3 | n.d. | >10000 | ~1698 |
| 68 | 0.8 | 1.9 | 1479 | 16 |
| 69 | 4.9 | n.d. | >10000 | 1023 |
| 70 | 3.9 | n.d. | >10000 | 2188 |
| 71 | 7.2 | n.d. | >10000 | 148 |
| 72 | 11.0 | n.d. | >10000 | 123 |
| 73 | 2.2 | 1.4 | >10000 | 68 |
| 74 | 4.0 | 16.2 | ~1148 | 182 |
| 75 | 3.6 | n.d. | ~3311 | 105 |
| 76 | 186.2 | n.d. | >10000 | 2344 |
| 77 | 46.8 | n.d. | ~2455 | 126 |
| 78 | 2.7 | 7.9 | 2042 | 87 |
| 79 | 47.9 | 75.9 | ~5129 | 91 |
| 80 | 15.2 | 208.9 | 1000 | 124 |
| 81 | n.d. | n.d. | n.d. | n.d. |
| 82 | 7.6 | 5.3 | >10000 | 22 |
| 83 | n.d. | n.d. | n.d. | n.d. |
| 84 | 19.1 | 12.9 | ~7586 | 251 |
| 85 | 11.3 | 41.7 | >10000 | 57 |
| 87 | 7.1 | 93.3 | 1175 | 35 |
| 88 | 85.1 | n.d. | >10000 | 178 |
| 89 | 20.9 | n.d. | >10000 | ~100 |
| 90 | 218.8 | n.d. | >10000 | >10000 |
| 91 | 7.2 | n.d. | >10000 | ~107 |
| 92 | 138.0 | n.d. | >10000 | 389 |
| 93 | 11.5 | n.d. | >10000 | 83 |
| 94 | 9.8 | n.d. | >10000 | 166 |
| 95 | 9.3 | n.d. | >10000 | 129 |
| 96 | 9.1 | n.d. | >10000 | ~81 |
| 97 | 45.7 | n.d. | 4365 | 59 |
| 98 | 128.8 | n.d. | >10000 | 105 |
| 99 | 218.8 | n.d. | 8318 | 380 |
| 100 | 91.2 | n.d. | >10000 | 1413 |
| 101 | 49.0 | n.d. | 1349 | 447 |
| 102 | 403.3 | n.d. | >10000 | 3548 |
| 103 | 104.7 | n.d. | >10000 | 3715 |
| 104 | 12.0 | n.d. | >10000 | 2138 |
| 105 | 28.5 | 22.9 | ~6607 | 118 |
| 106 | 63.1 | 123.0 | >10000 | 1622 |
| 107 | 41.7 | n.d. | >10000 | 1023 |
| 108 | 11.0 | 3.8 | >3981 | 39 |
| 109 | 53.7 | n.d. | n.d. | 676 |
| 110 | 4.2 | n.d. | >10000 | 193 |
| 111 | 3548.1 | n.d. | >10000 | 3467 |
| 112 | 4.3 | n.d. | >10000 | 20 |
| 113 | 2.6 | n.d. | ~407 | 28 |
| 114 | 2.2 | n.d. | 490 | 19 |
| 115 | 4.9 | n.d. | >10000 | 166 |
| 116 | 6.8 | n.d. | >10000 | 162 |
| 117 | 4.7 | n.d. | 1549 | 19 |
| 118 | 25.7 | n.d. | >10000 | 933 |
| 119 | 7.1 | n.d. | 1380 | 28 |
| 120 | 15.5 | n.d. | >10000 | 25 |
| 121 | 8.5 | n.d. | 120 | 12 |
| 122 | 4.7 | n.d. | ~4467 | 35 |
| 123 | 8.5 | n.d. | 1047 | 14 |
| 124 | 1.6 | n.d. | 437 | 525 |
| 125 | 13.8 | 3.6 | ~6918 | 182 |
| 126 | 112.2 | ~6.9 | ~8913 | 151 |
| 127 | 128.8 | 11.5 | >10000 | 570 |
| 128 | 251.2 | 20.9 | >10000 | 407 |
| 129 | 1.4 | 3.2 | ~7943 | 330 |
| 130 | 1.5 | 2.2 | 9772 | 167 |
| 131 | 1.3 | 4.7 | >10000 | 324 |
| 132 | 1.3 | 2.2 | 5012 | 128 |
| 133 | 0.7 | 3.0 | 4365 | 170 |
| 134 | 0.9 | 2.8 | 5495 | 91 |
| 135 | 58.9 | 4365.2 | n.d. | n.d. |
| 136 | 1.7 | <0.66 | >10000 | 269 |
| 137 | 6.0 | 2.7 | ~10000 | 545 |
| 138 | 11.2 | 2.1 | ~4786 | 102 |
| 139 | 56.2 | 26.9 | ~8913 | 302 |
| 140 | 51.3 | 56.2 | ~9120 | 550 |
| 141 | 8.7 | 2.2 | >10000 | 33 |
| 142a | 12.0 | 2.2 | >10000 | 3631 |
| 142b | 17.0 | ~58.9 | >10000 | 977 |
| 143 | 6.5 | 12.3 | >10000 | 200 |
| 144 | 5.8 | ~1174.9 | >10000 | ~10000 |
| 145 | 17.4 | 436.5 | n.d. | n.d. |
| 146 | 19.9 | 5.2 | >10000 | 78 |
| 147 | 3.9 | 1.2 | >10000 | 302 |
| 148 | 4.7 | 8.9 | >10000 | 523 |
| 149 | 10.0 | 102.3 | n.d. | n.d. |
| 150 | 0.8 | 2.2 | >10000 | 91 |
| 151 | 22.4 | 426.6 | n.d. | n.d. |
| 152 | 2.3 | 7.8 | >10000 | 272 |
| 153 | 1.3 | 6.3 | >10000 | 240 |
| 154 | 1.4 | 6.6 | >10000 | 141 |
| 155 | 3.5 | 7.7 | >10000 | 467 |
| 156 | 4.8 | 7.8 | >10000 | 251 |
| 157 | 4.9 | 12.9 | ~7586 | 178 |
| 158 | 5.4 | 91.2 | >10000 | 1230 |
| 159 | 5.5 | 20.4 | >10000 | 4786 |
| 160 | 11.2 | 64.6 | >10000 | 4786 |

TABLE A-continued

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
|---|---|---|---|---|
| 161 | 20.4 | 407.4 | n.d. | n.d. |
| 162 | 5.5 | 19.5 | >10000 | 288 |
| 163 | 3.5 | 33.1 | >10000 | 437 |
| 164 | 26.9 | 288.4 | n.d. | n.d. |
| 165 | 3.6 | 6.0 | ~5248 | 1122 |
| 166 | 8.9 | 18.6 | >10000 | 955 |
| 167 | 7.6 | 19.1 | 6166 | 562 |
| 168 | 10.7 | 14.5 | >10000 | ~1413 |
| 169 | 8.7 | 8.3 | >10000 | ~1000 |
| 170 | 1.0 | 2.3 | ~4677 | 81 |
| 171 | 1.1 | 34.7 | >10000 | 955 |
| 172 | 4.8 | 2.4 | >10000 | 65 |
| 173 | 1.8 | 1.3 | >10000 | 29 |
| 174 | 3.5 | 2.0 | >10000 | 71 |
| 175 | 1.8 | 2.8 | ~191 | 27 |
| 176 | 3.8 | 5.9 | >10000 | 91 |
| 177 | 3.2 | 1.2 | ~246 | 14 |
| 178 | 2.0 | 2.6 | ~891 | 42 |
| 179 | 2.2 | 1.4 | 1288 | 58 |
| 180 | 3.7 | 44.7 | n.d. | n.d. |
| 181 | 5.1 | 7.8 | >10000 | 195 |
| 182 | n.d. | n.d. | n.d. | n.d. |
| 183 | 9.1 | 7.1 | >10000 | 501 |
| 184 | 2.8 | 19.1 | >10000 | 178 |
| 185 | 6.5 | 6.6 | n.d. | n.d. |
| 186 | 4.6 | n.d. | n.d. | n.d. |
| 187 | 3.2 | n.d. | 1097 | 39 |
| 188 | 2.6 | 5.4 | >10000 | 54 |
| 189 | 30.9 | 1621.8 | n.d. | n.d. |
| 190 | 34.7 | 2630.3 | n.d. | n.d. |
| 191 | 13.8 | 4073.8 | n.d. | n.d. |
| 192 | 72.4 | 2951.2 | 537 | 1175 |
| 193 | 1.6 | 1.7 | >10000 | 22 |
| 194 | 3.6 | 1.4 | 479 | 17 |
| 195 | 6.2 | 1.9 | ~3715 | 30 |
| 196 | 7.8 | 1.0 | >10000 | 14 |
| 197 | 6.0 | 4.8 | ~240 | 33 |
| 198 | 4.6 | 5.6 | ~550 | 63 |
| 199 | 6.9 | 7.4 | >10000 | 76 |
| 200 | 1.7 | ~0.66 | >10000 | 41 |
| 201 | 2.8 | ~1202.3 | n.d. | n.d. |
| 202 | n.d. | n.d. | n.d. | n.d. |
| 203 | 6.6 | 1.8 | ~5888 | 14 |
| 204 | 6.2 | 1.5 | ~3981 | 14 |
| 205 | 6.0 | 11.2 | >10000 | 162 |
| 206 | 5.3 | n.d. | ~7244 | 71 |
| 207 | 5.0 | 13.2 | ~9550 | 66 |
| 208 | 6.5 | 10.7 | >10000 | 389 |
| 209 | 14.5 | 14.8 | >10000 | 132 |
| 210 | 33.1 | >10000 | n.d. | n.d. |
| 211 | 16.2 | 3162.3 | n.d. | n.d. |
| 212 | 25.1 | ~4466.9 | n.d. | n.d. |
| 213 | 4.2 | 5.0 | >10000 | 1072 |
| 214 | 6.9 | n.d. | n.d. | n.d. |
| 215 | 1.5 | 2.9 | >10000 | 199 |
| 216 | 49.0 | 144.5 | n.d. | n.d. |
| 217 | 9.8 | 107.2 | ~7943 | 4266 |
| 218 | 3.6 | ~1230.3 | n.d. | n.d. |
| 219 | 15.5 | 5495.4 | n.d. | n.d. |
| 220 | 10.2 | 72.4 | >10000 | 4571 |
| 221 | 32.4 | 645.7 | n.d. | n.d. |
| 222 | 31.6 | 302.0 | n.d. | n.d. |
| 223 | 1.6 | 3.1 | ~851 | 23 |
| 224 | 14.1 | 83.2 | >10000 | 3236 |
| 225 | 20.0 | 19.5 | >10000 | 195 |
| 226 | 4.3 | 33.1 | >10000 | 74 |
| 227 | 7.9 | 32.4 | ~3162 | 96 |
| 228 | 5.4 | 19.5 | >10000 | 120 |
| 229 | 7.6 | 22.4 | >10000 | 251 |
| 230 | 6.3 | 7.7 | >10000 | 46 |
| 231 | 7.8 | 12.3 | >10000 | 89 |
| 232 | 5.5 | 11.5 | >10000 | 282 |
| 233 | 4.6 | 21.4 | >10000 | 741 |
| 234 | 3.5 | 5.9 | ~6607 | 20 |
| 235 | 3.9 | 60.3 | 2692 | 457 |
| 236 | 2.6 | 42.7 | 178 | 32 |
| 237 | 213.8 | >831.8 | n.d. | n.d. |
| 238 | 955.0 | >831.8 | n.d. | n.d. |
| 239 | 13.8 | 354.8 | n.d. | n.d. |
| 240 | 2.5 | 11.2 | 302 | 44 |

Prophetic Composition Examples

"Active ingredient" (a.i.) as used throughout these examples relates to a compound of Formula (I), including any tautomer or stereoisomeric form thereof, or a pharmaceutically acceptable addition salt, or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:
1. A compound of Formula (I):

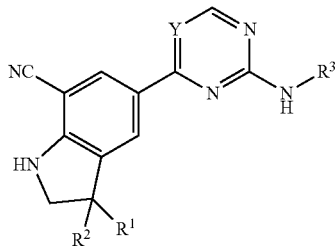

(I)

a tautomer or a stereoisomeric form thereof, wherein
$R^1$ represents $C_{1-4}$alkyl;
$R^2$ represents $C_{1-6}$alkyl, or $C_{1-6}$alkyl substituted with one $R^5$;
Y represents $CR^4$ or N;
$R^4$ represents hydrogen or halo;
$R^5$ represents halo, $Het^{3a}$, —$NR^{6a}R^{6b}$), or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —$NH_2$, —COOH, and $Het^6$;
$R^{16a}$ and $R^{16b}$ each independently represents hydrogen, $C_{1-4}$alkyl or $C_{3-6}$cycloalkyl;
$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; $C_{2-6}$alkenyl substituted with one $R^{13}$; $C_{2-6}$alkynyl; and $C_{2-6}$alkynyl substituted with one $R^{13}$;
$R^{10}$ represents —OH, —O—$C_{1-4}$alkyl, —$NR^{11a}R^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;
$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;
wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;
$Het^{1b}$, $Het^{1e}$, $Het^{1g}$, $Het^4$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^4$, $Het^7$ and $Het^8$ containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;
$Het^2$ represents a heterocyclyl of formula (b-1):

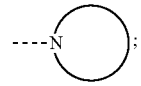

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; —$C_{1-4}$alkyl-$Het^5$; —$C_{1-4}$alkyl-$Het^8$; $C_{1-4}$alkyl substituted with one, two or three substituents each independently selected from the group consisting of halo, —OH and —O—$C_{1-4}$ alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, $Het^{1d}$, or —C(=O)—$Het^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, $Ar^2$, or $Het^{1c}$;

$Ar^1$ represents phenyl optionally substituted with one hydroxy;

$Ar^2$ represents phenyl optionally substituted with one $C_{1-4}$alkyl;

$Het^{3a}$, $Het^{3b}$, $Het^5$, $Het^6$ and $Het^{1f}$ each independently represents a heterocyclyl of formula (c-1):

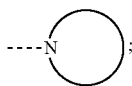

(c-1)

(c-1) represents a N-linked 4- to 7-membered monocyclic saturated heterocyclyl optionally containing one additional heteroatom selected from O, S, S(=O)$_p$ and N;

wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

or a pharmaceutically acceptable addition salt, or a solvate thereof.

2. The compound according to claim 1, wherein
Y represents $CR^4$;
$R^5$ represents $Het^{3a}$, —NR$^{6a}$R$^{6b}$, or —OR$^7$;
$R^3$ represents phenyl optionally substituted with one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=NR$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$Het^2$ represents a heterocyclyl of formula (b-1):

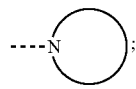

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; $C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl; and $R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl.

3. The compound according to claim 1, wherein
$R^5$ represents halo, —NR$^{6a}$R$^{6b}$, or —OR$^7$;
$R^{6a}$ represents hydrogen;
$R^{6b}$ represents —C(=O)—$C_{1-4}$alkyl; or —S(=O)$_2$—$C_{1-4}$alkyl;
$R^7$ represents hydrogen, —$C_{1-4}$alkyl-NR$^{8a}$R$^{8b}$, —C(=O)—R$^9$, —S(=O)$_2$—OH, or —(C=O)—CH(NH$_2$)—$C_{1-4}$alkyl-Ar$^1$;
$R^{8a}$ represents hydrogen;
$R^{8b}$ represents $C_{3-6}$cycloalkyl;
$R^3$ represents phenyl optionally substituted with one, two or three substituents each independently selected from the group consisting of halo; cyano; $C_{1-6}$alkyl;

—O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl substituted with one $R^{13}$; and $C_{2-6}$alkynyl substituted with one $R^{13}$;

$R^{18}$ represents a 5-membered aromatic ring containing one, two or three N-atoms; wherein said 5-membered aromatic ring may optionally be substituted with one substituent selected from the group consisting of $C_{1-4}$alkyl;

Het$^{1a}$, Het$^{1c}$ and Het$^{1d}$ each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, —O—$C_{1-4}$alkyl, and —N($C_{1-4}$alkyl)$_2$;

Het$^{1b}$, Het$^{1e}$, Het$^{1g}$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^7$ and Het$^8$ containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two substituents each independently selected from the group consisting of —OH, and halo;

Het$^2$ represents a heterocyclyl of formula (b-1):

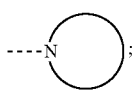

(b-1)

(b-1) represents a N-linked 4- to 7-membered monocyclic saturated heterocyclyl optionally containing one additional heteroatom selected from O and N, or a N-linked 6- to 11-membered bicyclic saturated heterocyclyl, including fused, spiro and bridged cycles, optionally containing one or two additional N-atoms;

wherein in case (b-1) contains one or two additional N-atoms, said one or two N-atoms may optionally be substituted with a substituent each independently selected from the group consisting of $C_{1-4}$alkyl, $C_{3-6}$cycloalkyl and Het$^7$; and wherein (b-1) may optionally be substituted on one, two or three ring C-atoms with one or two substituents each independently selected from the group consisting of —OH, cyano, $C_{1-4}$alkyl, and $C_{1-4}$alkyl-OH;

$R^{11b}$ represents Het$^{1e}$; $C_{1-4}$alkyl; —$C_{1-4}$alkyl-Het$^5$; —$C_{1-4}$alkyl-Het$^8$, $C_{1-4}$alkyl substituted with one, two or three OH substituents; or $C_{3-6}$cycloalkyl substituted with one, two or three substituents each independently selected from the group consisting of halo and —OH;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, $C_{3-6}$cycloalkyl, Ar$^2$, or Het$^{1c}$;

Ar$^1$ represents phenyl;

Het$^5$, Het$^6$ and Het$^{1f}$ each independently represents a heterocyclyl of formula (c-1):

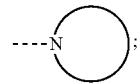

(c-1)

(c-1) represents a N-linked 4- to 7-membered monocyclic saturated heterocyclyl optionally containing one additional heteroatom selected from O and N;

wherein in case (c-1) contains one additional N-atom, said additional N-atom may optionally be substituted with $C_{1-4}$alkyl; and $R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of —OH and —O—$C_{1-4}$alkyl; or —S(=O)$_2$—$C_{1-4}$alkyl.

4. The compound according to claim 1 or 2, wherein $R^5$ represents —NR$^{6a}$R$^{6b}$ or —OR$^7$;

$R^{6a}$ represents hydrogen;

$R^{6b}$ represents —C(=O)—$C_{1-4}$alkyl; or —S(=O)$_2$—$C_{1-4}$ alkyl;

$R^7$ represents hydrogen, —C(=O)—$R^9$, —S(=O)$_2$—OH, or —(C=O)—CH(NH$_2$)—$C_{1-4}$alkyl-Ar$^1$;

$R^9$ represents $C_{1-4}$alkyl, or $C_{1-4}$alkyl substituted with one substituent selected from the group consisting of —NH$_2$, —COOH, and Het$^6$;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^{1g}$; $C_{1-4}$alkyl substituted with one, two or three halo atoms; $C_{1-4}$alkyl substituted with one, two or three —OH substituents; and $C_{1-4}$alkyl substituted with one $R^{13}$;

$R^{10}$ represents —OH, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl;

Het$^{1a}$, Het$^{1c}$ and Het$^{1d}$ each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, —O—$C_{1-4}$alkyl, and —N($C_{1-4}$ alkyl)$_2$;

$Het^{1b}$, $Het^{1e}$, and $Het^{1g}$ each independently represents a 4- to 7-membered monocyclic saturated heterocyclyl, attached to the remainder of the molecule of Formula (I) through any available ring carbon atom, said $Het^{1b}$, $Het^{1e}$ and $Het^{1g}$ containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two —OH substituents;

$Het^2$ represents a heterocyclyl of formula (b-1):

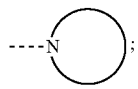
(b-1)

(b-1) represents a N-linked 4- to 7-membered monocyclic saturated heterocyclyl optionally containing one additional N-atom, or a N-linked 6- to 11-membered bicyclic saturated heterocyclyl, including fused, spiro and bridged cycles, optionally containing one or two additional N-atoms;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of —OH, cyano, and $C_{1-4}$alkyl-OH;

$R^{11b}$ represents $Het^{1e}$; $C_{1-4}$alkyl; $C_{1-4}$alkyl-$Het^5$; $C_{1-4}$alkyl substituted with one, two or three OH substituents; or $C_{3-6}$cycloalkyl substituted with one, two or three substituents each independently selected from the group consisting of halo and —OH;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;

$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, $C_{3-6}$cycloalkyl, $Ar^2$, or $Het^{1c}$;

$Ar^1$ represents phenyl;

$Ar^2$ represents phenyl optionally substituted with one $C_{1-4}$alkyl;

$Het^5$, $Het^6$ and $Het^{1f}$ each independently represents a heterocyclyl of formula (c-1):

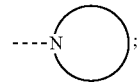
(c-1)

(c-1) represents a N-linked 4- to 7-membered monocyclic saturated heterocyclyl optionally containing one additional heteroatom selected from O and N;

wherein in case (c-1) contains one additional N-atom, said additional N-atom may optionally be substituted with $C_{1-4}$alkyl;

$R^{11a}$, $R^{14a}$, $R^{14c}$, $R^{15a}$ and $R^{19a}$ each independently represents hydrogen or $C_{1-4}$alkyl;

$R^{14b}$, $R^{14d}$, $R^{15b}$, and $R^{19b}$ each independently represents hydrogen; $C_{1-4}$alkyl; $C_{3-6}$cycloalkyl; or $C_{1-4}$alkyl substituted with one —O—$C_{1-4}$alkyl.

5. The compound according to claim 1 or 2, wherein
Y represents $CR^4$;
$R^4$ represents hydrogen;
$R^5$ represents —$OR^7$;
$R^7$ represents hydrogen or —C(=O)—$R^9$;
$R^9$ represents $C_{1-4}$alkyl;
$R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; —O—$C_{3-6}$cycloalkyl; —O-$Het^{1b}$; —NH—C(=O)—$Het^{1g}$; and $C_{1-4}$alkyl substituted with one $R^{13}$;

$R^{10}$ represents —$NR^{11a}R^{11b}$ or $Het^2$;

$Het^{1g}$ represents a 4- to 7-membered monocyclic saturated heterocyclyl, attached to the remainder of the molecule of Formula (I) through any available ring carbon atom, said $Het^{1g}$ containing one or two N-atoms;

wherein said 4- to 7-membered monocyclic saturated heterocyclyl may optionally be substituted, where possible, on one or two ring N-atoms with a $C_{1-4}$alkyl substituent;

$Het^{1b}$ represents a 4- to 7-membered monocyclic saturated heterocyclyl, attached to the remainder of the molecule of Formula (I) through any available ring carbon atom, said $Het^{1b}$ containing one or two N-atoms;

wherein said 4- to 7-membered monocyclic saturated heterocyclyl may optionally be substituted, where possible, on one or two ring N-atoms with a $C_{1-4}$alkyl substituent; and wherein said 4- to 7-membered monocyclic saturated heterocyclyl may optionally be substituted on one ring C-atom with one halo substituent;

$Het^2$ represents a heterocyclyl of formula (b-1):

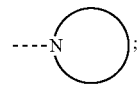
(b-1)

(b-1) represents a N-linked 4- to 7-membered monocyclic saturated heterocyclyl wherein (b-1) may optionally be substituted on one C-atom with one —OH substituent;

$R^{11b}$ represents $C_{1-4}$alkyl;

$R^{13}$ represents —O—$C_{1-4}$alkyl;

$R^{12}$ represents —O—$C_{1-4}$alkyl; and
$R^{11a}$ represents hydrogen.

6. The compound according to claim 1 or 2, wherein
$R^4$ represents hydrogen;
$R^5$ represents —$OR^7$;
$R^7$ represents hydrogen or —C(=O)—$R^9$;
$R^9$ represents $C_{1-4}$alkyl;
$R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; —NH—C(=O)—$Het^{1g}$; and $C_{1-4}$alkyl substituted with one $R^{13}$;
$R^{10}$ represents —$NR^{11a}R^{11b}$ or $Het^2$;
$Het^{1g}$ represents a 4- to 7-membered monocyclic saturated heterocyclyl, attached to the remainder of the molecule of Formula (I) through any available ring carbon atom, said $Het^{1g}$ containing one or two N-atoms;
wherein said 4- to 7-membered monocyclic saturated heterocyclyl may optionally be substituted, where possible, on one or two ring N-atoms with a $C_{1-4}$alkyl substituent;
$Het^2$ represents a heterocyclyl of formula (b-1):

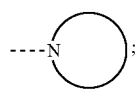
(b-1)

(b-1) represents a N-linked 4- to 7-membered monocyclic saturated heterocyclyl wherein (b-1) may optionally be substituted on one C-atom with one —OH substituent;
$R^{11b}$ represents $C_{1-4}$alkyl;
$R^{13}$ represents —O—$C_{1-4}$alkyl,
$R^{12}$ represents —O—$C_{1-4}$alkyl; and
$R^{11a}$ represents hydrogen.

7. The compound according to claim 1 or 2, wherein
$R^2$ represents $C_{1-6}$alkyl substituted with one $R^5$;
$R^4$ represents hydrogen;
$R^5$ represents —$OR^7$;
$R^7$ represents hydrogen; and
$R^3$ represents phenyl substituted with one, two or three substituents each independently selected from the group consisting of halo; cyano; and $C_{1-6}$alkyl.

8. The compound according to any one of claims 1 to 6, wherein
$R^1$ represents methyl;
$R^2$ represents methyl or —$CH_2$—OH.

9. The compound according to any one of claims 1 to 4, wherein
$R^4$ is hydrogen.

10. The compound according to any one of claims 1 to 6, wherein
$R^5$ represents —$OR^7$; and
$R^7$ represents hydrogen.

11. The compound according to claim 1 or 2, wherein
$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$.

12. The compound according claim 1 or 2, wherein
$Het^2$ represents a heterocyclyl of formula (b-1):

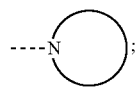
(b-1)

(b-1) represents a N-linked 4- to 7-membered monocyclic saturated heterocyclyl optionally containing one additional heteroatom selected from O, S, S(=O)$_p$ and N;
wherein in case (b-1) contains one additional N-atom, said N-atom may optionally be substituted with $C_{1-4}$alkyl; and
wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —$NH_2$, —NR($C_{1-4}$alkyl), —N($C_{1-4}$alkyl)$_2$, and $C_{1-4}$alkyl-OH.

13. The compound according to claim 1, wherein the compound is selected from

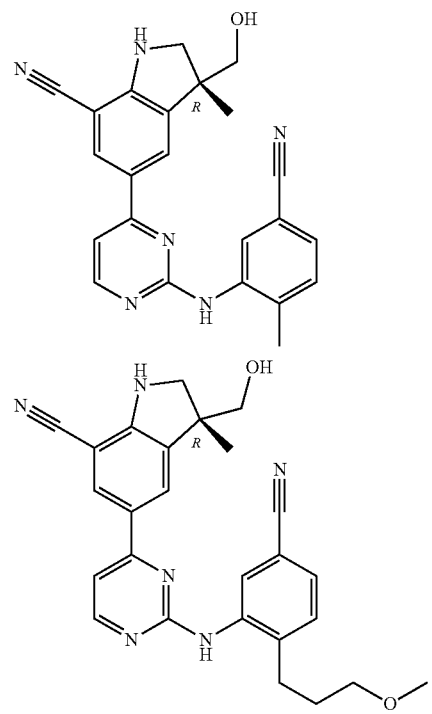

601
-continued
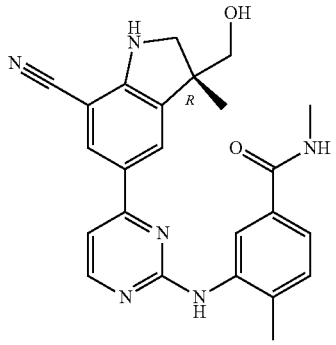
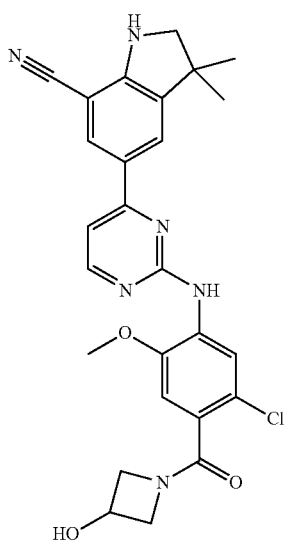
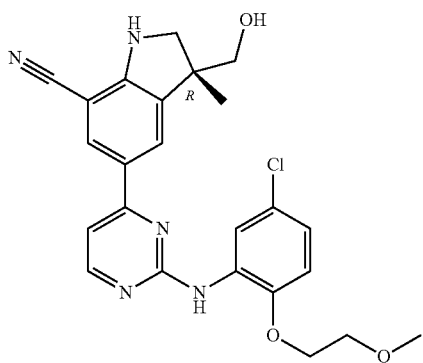
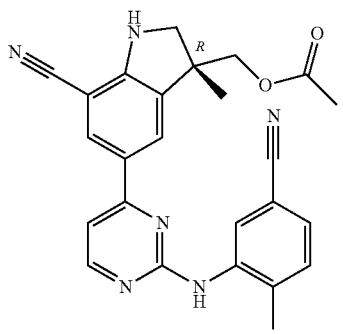
602
-continued
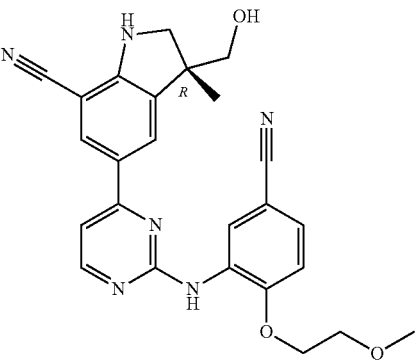
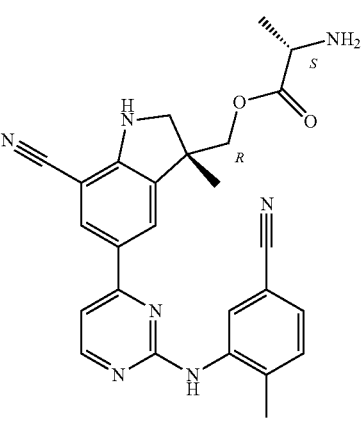
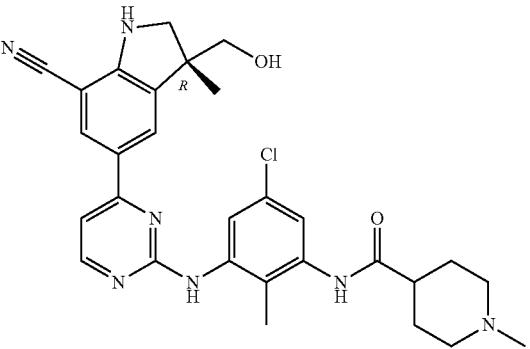
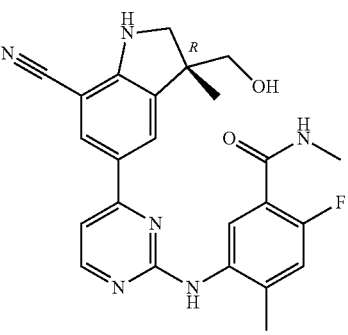

-continued

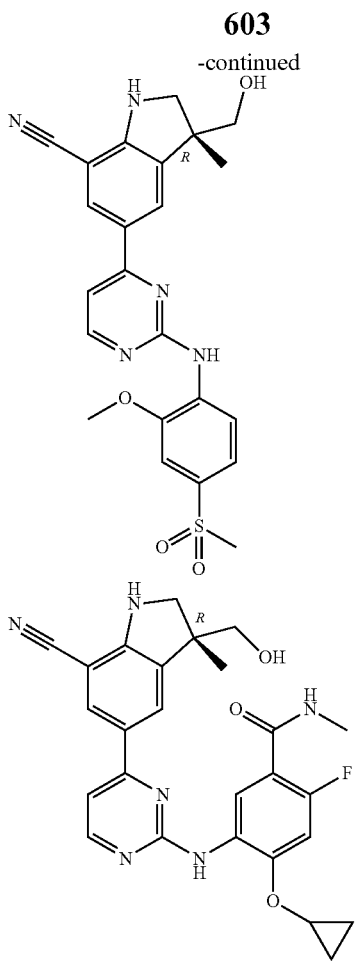

-continued

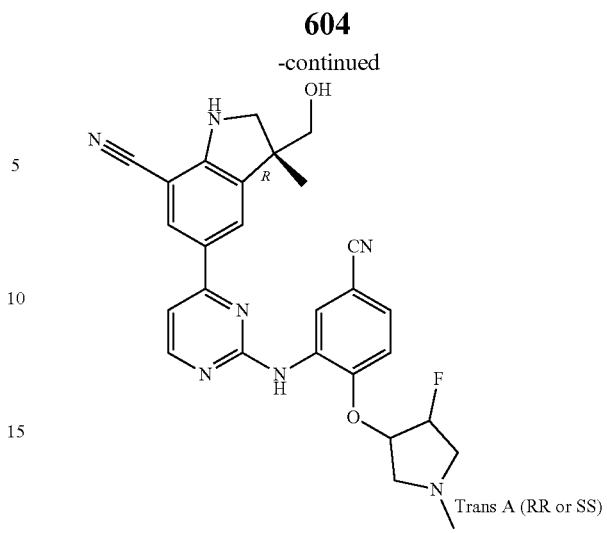

tautomers and stereoisomeric forms thereof, and the pharmaceutically acceptable addition salts, and the solvates thereof.

14. A pharmaceutical composition comprising a compound as claimed in any one of claims 1 to 10 and 13 and a pharmaceutically acceptable carrier or diluent.

15. A method of treating a cell proliferative disease in a warm-blooded animal which comprises administering to the said animal an effective amount of a compound as claimed in any one of claims 1 to 10 and 13.

\* \* \* \* \*